US010662193B2

(12) United States Patent
Kroth et al.

(10) Patent No.: US 10,662,193 B2
(45) Date of Patent: May 26, 2020

(54) CARBAZOLE AND CARBOLINE COMPOUNDS FOR USE IN THE DIAGNOSIS, TREATMENT, ALLEVIATION OR PREVENTION OF DISORDERS ASSOCIATED WITH AMYLOID OR AMYLOID-LIKE PROTEINS

(71) Applicants: AC IMMUNE SA, Lausanne (CH); LIFE MOLECULAR IMAGING SA, Matran (CH)

(72) Inventors: Heiko Kroth, Ecublens (CH); Sreenivasachary Nampally, Ecublens (CH); Jérŏme Molette, Prevessin Moens (FR); Emanuele Gabellieri, Lausanne (CH); Pascal André René Benderitter, Apolinaire (FR); Wolfgang Froestl; Hanno Schieferstein, Berlin (DE); Andre Mueller, Berlin (DE); Heribert Schmitt-Willich, Berlin (DE); Mathias Berndt, Berlin (DE)

(73) Assignees: AC IMMUNE SA, Lausanne (CH); LIFE MOLECULAR IMAGING SA, Matran (CH)

( * ) Notice: Subject to any disclaimer, the term of this patent is extended or adjusted under 35 U.S.C. 154(b) by 0 days.

(21) Appl. No.: 15/112,672

(22) PCT Filed: Jan. 21, 2015

(86) PCT No.: PCT/EP2015/000107
§ 371 (c)(1),
(2) Date: Jul. 19, 2016

(87) PCT Pub. No.: WO2015/110263
PCT Pub. Date: Jul. 30, 2015

(65) Prior Publication Data

US 2017/0002005 A1 Jan. 5, 2017

(30) Foreign Application Priority Data

Jan. 21, 2014 (EP) .................................... 14151986

(51) Int. Cl.

| | |
|---|---|
| *C07D 471/14* | (2006.01) |
| *A61K 49/10* | (2006.01) |
| *A61K 49/00* | (2006.01) |
| *A61K 51/04* | (2006.01) |
| *C07D 519/00* | (2006.01) |

(52) U.S. Cl.
CPC .......... *C07D 471/14* (2013.01); *A61K 49/006* (2013.01); *A61K 49/0052* (2013.01); *A61K 49/10* (2013.01); *A61K 51/0455* (2013.01); *A61K 51/0459* (2013.01); *A61K 51/0463* (2013.01); *C07D 519/00* (2013.01)

(58) Field of Classification Search
CPC .......................... C07D 471/14; C07D 519/00; A61K 49/0052; A61K 51/0455
USPC .......................................................... 546/82
See application file for complete search history.

(56) References Cited

U.S. PATENT DOCUMENTS

2012/0302755 A1* 11/2012 Szardenings ......... C07B 59/002
546/82

FOREIGN PATENT DOCUMENTS

| | | | | |
|---|---|---|---|---|
| CH | 143704 A | 11/1930 | | |
| EP | 2527334 A1 | 11/2012 | | |
| GB | 1268772 A | 3/1972 | | |
| WO | WO-2006040451 A2 * | 4/2006 | .......... | C07D 471/04 |
| WO | 2008077631 A1 | 7/2008 | | |
| WO | 2008132454 A1 | 11/2008 | | |
| WO | 2009085185 A1 | 7/2009 | | |
| WO | 2009102498 A1 | 8/2009 | | |
| WO | 2010080481 A1 | 7/2010 | | |
| WO | 2011119565 A1 | 9/2011 | | |
| WO | 2011128455 A1 | 10/2011 | | |
| WO | 2012088124 A2 | 6/2012 | | |
| WO | 2013176698 A1 | 11/2013 | | |
| WO | WO-2013176698 A1 * | 11/2013 | .......... | C07D 209/80 |

OTHER PUBLICATIONS

Vrinda Shanbaug et al . Amide and ester prodrugs of Ibuprofen and Naproxen . . . (Year: 1992).*
New Research findings from Princeton University, Tien Nguyen (Year: 2014).*
International Search Report and Written Opinion for PCT/EP2015/000107, dated May 12, 2015, 22.
Hubschwerlen, et al., "Pyrimido [1,6-a]benzimidazoles: A New Class of DNA Gyrase Inhibitors", Journal of Medicinal Chemistry. vol. 35, No. 8, Jan. 1, 1992, 1385-1392.
Kovtonyuk, et al., "Photochemical Cyclization of Polyfluorinated Aryloxo-1, 2-Dihydronaphthalanes and 6-Phenyl-3-phenoxy-2,4-cyclohexadienon", Journal of Fluorine Chemistry, vol. 66, No. 3, Mar. 1, 1994, 219-221.

(Continued)

*Primary Examiner* — Rita J Desai

(74) *Attorney, Agent, or Firm* — F. Brent Nix, Esq.; Johnson, Marcou, Isaacs & Nix, LLC

(57) ABSTRACT

The present invention relates to novel compounds that can be employed in the diagnosis, treatment, alleviation or prevention of a group of disorders and abnormalities associated with amyloid proteins and amyloid-like proteins, such as Alzheimer's disease. Precursors for the preparation of the compounds according to the present invention are also provided.

14 Claims, 13 Drawing Sheets

(56) References Cited

OTHER PUBLICATIONS

Song, et al., “beta-Carbolines as Specific Inhibitors of Cyclin-Dependent Kinases”, Bioorganic & Medicinal Chemistry Letters, vol. 12, No. 7, Apr. 8, 2002, 1129-1132.
Zall, et al., “NSAID-Derived-Secretase Modulation Requires an Acidic Moiety on the Carbazole Scaffold”, Biogranic & Medicinal Chemistry, vol. 19, No. 16, Jun. 22, 2011, 4903-4909.

* cited by examiner a)

b)

CARBAZOLE AND CARBOLINE COMPOUNDS FOR USE IN THE DIAGNOSIS, TREATMENT, ALLEVIATION OR PREVENTION OF DISORDERS ASSOCIATED WITH AMYLOID OR AMYLOID-LIKE PROTEINS

CROSS REFERENCE TO RELATED APPLICATIONS

This application is a 35 U.S.C. § 371 national stage of International Application No. PCT/EP2015/000107 filed on Jan. 21, 2015, and published in English under PCT Article 21(2), which claims the benefit of European Patent Application No. 14151986.8 filed Jan. 21, 2014. The entire contents of the above-identified priority applications are hereby fully incorporated herein by reference.

FIELD OF THE INVENTION

The present invention relates to novel compounds that can be employed in the diagnosis, treatment, alleviation or prevention of a group of disorders and abnormalities associated with amyloid proteins and amyloid-like proteins, such as Alzheimer's disease. Precursors which can be used in the preparation of the compounds of the present invention are also disclosed.

BACKGROUND OF THE INVENTION

Many aging diseases are based on or associated with extracellular or intracellular deposits of amyloid or amyloid-like proteins that contribute to the pathogenesis as well as to the progression of the disease. The best characterized amyloid protein that forms extracellular aggregates is amyloid beta (Aβ). Diseases involving Abeta (Aβ) aggregates are generally listed as amyloidosis and this includes, but is not limited to, Alzheimer's disease, Lewy body dementia (LBD), hereditary cerebral hemorrhage with amyloidosis (Dutch type), mild cognitive impairment (MCI), progressive supranuclear palsy, multiple sclerosis, inclusion-body myositis (IBM), Creutzfeldt-Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystropy.

Other examples of amyloid proteins that form extracellular aggregates are prion, ATTR (transthyretin) or ADan (ADanPP). Diseases associated with the amyloid-like proteins that form extracellular aggregates include, but are not limited to, Creutzfeldt-Jakob disease, associated to prion aggregates, familial senile systemic tenosynovium, associated to ATTR aggregates, and familial dementia (Danish type), associated to ADan aggregates (Sipe et al., Amyloid, 2010, 17, 101-4).

Amyloid-like proteins, that form mainly intracellular aggregates, include, but are not limited to tau, alpha-synuclein, and huntingtin (htt). Diseases involving tau aggregates are generally listed as tauopathies or tauopathies and this includes, but is not limited to, Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, familial British dementia, Hallervorden-Spatz disease, chronic traumatic encephalopathy, familial Danish dementia, frontotemporal lobar degeneration, Guadeloupean Parkinsonism, neurodegeneration with brain iron accumulation, SLC9A6-related mental retardation, and white matter tauopathy with globular glial inclusions etc. (Williams et al., Intern. Med. J., 2006, 36, 652-60).

Amyloid or amyloid-like deposits result from misfolding of proteins followed by aggregation to give β-sheet assemblies in which multiple peptides or proteins are held together by inter-molecular hydrogen-bonds. While amyloid or amyloid-like proteins have different primary amino acid sequences, their deposits often contain many shared molecular constituents, in particular the presence of β-sheet quaternary structures. The reasons for amyloid association with diseases remain largely unclear. A diverse range of protein aggregates, including both those associated and not associated with disease pathologies, have been found to be toxic suggesting that the common molecular features of amyloid are implicated or responsible for disease on-set (Bucciantini et al., Nature, 2002, 416, 507-11). Various multimers of β-sheet aggregated peptides or proteins have also been associated with toxicity for different peptides or proteins ranging from dimers, through to soluble low molecular weight oligomers, protofibrils or insoluble fibrillar deposits.

In AD, some studies suggest that Aβ deposits physically disrupt tissue architecture (Demuro et al., J. Biol. Chem., 2005, 280, 17294-300). However, an emerging consensus implicates prefibrillar intermediates, rather than mature amyloid fibers, in causing cell death (Ferreira et al., IUBMB Life, 2007, 59, 332-45). Other studies have shown that amyloid deposition is associated with mitochondrial dysfunction and a resulting generation of reactive oxygen species (ROS), which can initiate a signaling pathway leading to apoptosis (Kadowaki et al., Cell Death Differ., 2005, 12, 19-24). In addition, local activation of pro-inflammatory pathways thereby leading to the concurrent deposition of activated complement components, acute phase reactants, immune modulators, and other inflammatory mediators seem to play an important role.

Determining the load of amyloid or amyloid-like deposits in living subjects is therefore important in order to help identify subjects at potential risk of developing disease, before disease progression or on-set of symptoms. Knowledge of the amyloid or amyloid-like load in subjects can thus help determine potential measures to prevent or reverse disease progression. Advanced diagnostic techniques are required which are non-invasive and show high sensitivity and selectivity in order to detect and quantify amyloid or amyloid-like load in human tissue or body fluids. For detection of amyloid or amyloid-like deposits, techniques such as those based upon magnetic resonance imaging (MRI) are commonly used. For imaging of amyloid associated with neurological diseases, molecular imaging techniques such as positron emission tomography (PET) (Kadir et al., J. Nucl. Med., 2010, 51, 1418-30, Politis et al., J. Neurol., 2012, 259, 1769-80), single photon emission computed tomography (SPECT) (Ono et al., Int. J. Mol. Imaging, 2011, 543267) or contrast-enhanced magnetic resonance imaging (MRI) (Poduslo et al., Neurobiol. Dis., 2002, 11, 315-29) have been described and enable visualization of amyloid biomarkers.

In order to achieve high target selectivity, molecular probes have been used which recognize and bind to the pathological target. Selectivity for binding to pathological amyloid over other biological entities is therefore a basic requirement of an imaging probe. In order to reduce background signal interference resulting from non-specific off-target binding, and to reduce dosing requirements, imaging compounds should bind with high affinity to their target. Since amyloid or amyloid-like deposits formed from proteins of diverse primary amino acid sequences share a common β-sheet quaternary conformation, molecular probes are required that can differentiate such structures in order to avoid detection of false-positives and mis-diagnosis. In addition, molecular probes must also be designed such that upon administration they can distribute within the body and reach their target. For imaging of amyloid or amyloid-like aggregates associated with neurological disorders such as Alzheimer's disease, Huntington's disease or Parkinson's disease, imaging compounds are required that can penetrate the blood brain barrier and pass into the relevant regions of the brain. For targeting intracellular amyloid-like inclusions, cell permeability is a further requirement of imaging compounds. A further prerequisite in order to avoid unnecessary accumulation of compound which may result in increased risk of unwanted side-effects, is a fast compound wash-out from the brain (or other targeting organ).

Alzheimer's disease (AD) is a neurological disorder primarily thought to be caused by amyloid plaques, an extracellular accumulation of abnormal deposit of Aβ aggregates in the brain. The other major neuropathological hallmarks in AD are the intracellular neurofibrillary tangles (NFT) that originate by the aggregation of the hyperphosphorylated tau protein, phosphorylated tau or pathological tau and its conformers. AD shares this pathology with many neurodegenerative tauopathies, in particular with specified types of frontotemporal dementia (FTD). The tau protein is a freely soluble, "naturally unfolded" protein that binds avidly to microtubuli (MT) to promote their assembly and stability. MT are of major importance for the cytoskeletal integrity of neurons—and thereby for the proper formation and functioning of neuronal circuits, hence for learning and memory. The binding of tau to MT is controlled by dynamic phosphorylation and de-phosphorylation, as demonstrated mainly in vitro and in non-neuronal cells. In AD brain, tau pathology (tauopathy) develops later than, and therefore probably in response to, amyloid pathology, which constitutes the essence of the amyloid cascade hypothesis (Lewis et al., Science, 2001, 293, 1487-1491; Oddo et al., Neuron., 2004, 43, 321-332; Ribe et al., Neurobiol. Dis., 2005, 20(3), 814-22; Muyllaert et al., Rev. Neurol. (Paris), 2006 162, 903-7; Muyllaert et al., Genes Brain and Behav., 2008, Suppl 1, 57-66; Terwel et al., Am. J. Pathol., 2007, 172, 786-798). The exact mechanisms that link amyloid to tau pathology remain largely unknown, but are proposed to involve activation of neuronal signaling pathways that act on or by GSK3 and cdk5 as the major "tau-kinases" (reviewed by Muyllaert et al., Rev. Neurol. (Paris), 2006, 162, 903-7, Muyllaert et al., Genes Brain and Behav. 2008, Suppl 1, 57-66). Even if the tauopathy develops later than amyloid, it is not just an innocent side-effect but a major pathological executer in AD. In experimental mouse models the cognitive defects caused by amyloid pathology are nearly completely alleviated by the absence of protein tau (Roberson et al., Science, 2007, 316(5825), 750-4) and the severity of cognitive dysfunction and dementia correlates with the tauopathy, not with amyloid pathology. Presently, the only definite way to diagnose AD is to identify plaques and tangles in brain tissue in an autopsy after the death of the individual. Therefore, physicians can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid can provide some further information.

Diagnostic approaches to AD are also challenging due to the knowledge that underlying pathology starts 10 to 20 years before clinical signs of dementia appear (Holtzman et al., Sci. Transl. Med., 2011, 3, 77). In AD, several PET radiopharmaceuticals target Aβ plaques including the FDA-approved tracers [F-18] flutemetamol (Vizamyl®), [F-18] florbetapir (Amyvid®) and $^{11}$C-labelled Pittsburgh compound B (PiB). Aβ burden, as measured by PET with these tracers, matches histopathological reports of Aβ distribution in aging and dementia. Indeed, post-mortem analysis of AD patients who had undergone [$^{11}$C]PiB PET imaging before death suggested a strong correlation between in vivo PiB binding and regional distribution of Aβ plaques (Ikonomovic et al., Brain, 2008, 131, 1630-45). These agents enable the in vivo assessment of brain Aβ pathology and its changes over time, and provide highly accurate, reliable, and reproducible quantitative statements of regional or global Aβ burden in the brain, essential for therapeutic trial recruitment and for the evaluation of anti-Aβ treatments.

Aβ plaques have also been found in the retina of post-mortem eyes from AD patients. Furthermore, non-invasive live optical imaging of Aβ plaques in retina of APP/PS1 transgenic mice was reported following systemic administration of the Aβ-targeting compound curcumin (Koronyo-Hamaoui et al., Neuroimage, 2011, 54 Suppl. 1, S204-S217).

Nevertheless, in humans, Aβ burden does not strongly correlate with cognitive impairment in AD and therefore imaging compounds against other AD biomarkers are needed. The formation of tau aggregates is thought to precede the cognitive symptoms of AD (Lee et al., Trends Mol. Med., 2005, 11, 164-9), hence they represent an additional attractive potential pre-symptomatic marker of AD. Moreover, as NFT load correlates well with the degree of cognitive impairment in AD patients (Arriagada et al., Neurology, 1992, 42, 631-9), imaging agents selective for tau aggregates would provide important information on the tau pathophysiological features in AD and support the development of therapeutic agents targeting tau aggregates. Since Aβ plaques and NFTs colocalize with each other in the neocortex of AD brain, and moreover since the concentrations of Aβ in AD brain are typically 5 to 20 times higher than that of tau (Näslund et al., JAMA, 2000, 283, 1571-7 and Mukactova-Ladinska et al., Am. J. Pathol., 1993, 143, 565-78), imaging probes with high selectivity for NFT are important. This challenge is particularly evident when considering imaging probes such as 2-(1-(6-[2-$^{18}$F-fluoroethyl)(methyl)amino]-2-naphthyl)ethylidene)malonitrile ($^{18}$F-

FDDNP) which shows equal binding to both AB plaques and NFTs (Shoghi-Jadid et al., Am. J. Geriatr. Psychiatry, 2002, 10, 24-35).

Tau imaging PET probes based on quinoline derivatives, such as [$^{18}$F]THK-523 (Harada et al., Eur. J. Nucl. Med. Mol. Imaging, 2013, 40, 125-32), hydroxyquinoline derivatives such as [$^{11}$C]THK-951 (Tago et al., J. Labelled Comp. Radiopharm., 2013, doi: 10.1002/jlcr.3133), and arylquinoline derivatives such as THK-5105 and THK-5117 (Okamura et al., J. Nucl. Med., 2013, 54, 1420) have been described that show high binding affinity for tau pathology in human AD brain sections. Other compounds such as T-807 (Chien et al., J, Alzheimers Dis., 2013, 34, 457-68) and T-808 (Zhang et al., J. Alzheimers Dis., 2012, 31, 601-12, Chien et al., J. Alzheimers Dis., 2014, 38, 171-184) have also been described.

In addition, there is also a need to develop imaging agents suitable for selectively detecting and quantifying the load of amyloid-like deposits associated with other neurodegenerative conditions such as Parkinson's disease (PD) and Huntington's disease (HD).

Parkinson's disease (PD) is the most common neurodegenerative motor disorder. PD is mainly an idiopathic disease, although in at least 5% of the PD patients the pathology is linked to mutations in one or several specific genes (Lesage et al., Hum. Mol. Genet., 2009, 18, R48-59). The pathogenesis of PD remains elusive, however, growing evidence suggests a role for the pathogenic folding of the alpha-synuclein protein that leads to the formation of amyloid-like fibrils. Indeed, the hallmarks of PD are the presence of intracellular alpha-synuclein aggregate structures called Lewy Bodies in the nigral neurons, as well as the death of dopaminergic neurons in the substantia nigra. Alpha-synuclein is a natively unfolded presynaptic protein that can misfold and aggregate into larger oligomeric and fibrillar forms which are linked to the pathogenesis of PD. Recent studies have implicated small soluble oligomeric and protofibrillar forms of alpha-synuclein as the most neurotoxic species (Lashuel et al., J. Mol. Biol., 2002, 322, 1089-102), however the precise role of alpha-synuclein in the neuronal cell toxicity remains to be clarified (review: Cookson, Annu. Rev. Biochem., 2005, 74, 29-52). The PD diagnosis is still solely based on the appearance of symptoms such as tremor, rigidity, and bradykinesia.

Huntington's disease (HD) is a neurodegenerative disorder caused by a mutation in the huntingtin gene (HTT). Typical clinical features of HD include chorea (ancient Greek for "dance"), progressive motor dysfunction, cognitive decline, psychiatric disturbance, and lethality. These debilitating symptoms are thought to be caused by neuronal dysfunction and wide-spread neurodegeneration (Walker et al., Lancet, 2007, 369, 218-28; Ross et al., Medicine (Baltimore), 1997, 76, 305-38). The pathogenesis of HD has been extensively studied and involves the proteolytic cleavage of the HTT protein (Wellington et al., J. Biol. Chem., 1998, 273, 9158-67). HTT cleavage is increased in the mutant HTT and gives rise to N-terminal fragments that acquire abnormal conformations in the cytoplasm or nucleus, and eventually form multimeric assemblies and insoluble high-molecular weight aggregates (Lathrop et al., Proc. Int. Conf. Intell. Syst. Mol. Biol., 1998, 6, 105-14). Post-translational modifications might also affect the mutant HTT conformation, its propensity to aggregate, its cellular localization and clearance, and thus, influence toxicity (Ehrnhoefer et al., Neuroscientist, 2011, 17, 475-492). Misfolding and aggregation initiate a cascade of cytotoxic events. Formal diagnosis of HD onset in an individual at risk, i.e. carrying the mutated HTT gene (Huntington Study Group, Mov. Disord., 1996, 11, 136-42) is made on the motor signs like bradykinesia, chorea, dystonia, or incoordination (Marder et al., Neurology, 2000, 54, 452-58).

WO 2011/128455 refers to specific compounds which are suitable for treating disorders associated with amyloid proteins or amyloid-like proteins. US 2012/0302755 relates to certain imaging agents for detecting neurological dysfunction. Further compounds for the diagnosis of neurodegenerative disorders on the olfactory epithelium are discussed in WO 2012/037928.

SUMMARY OF THE INVENTION

Figure 1:
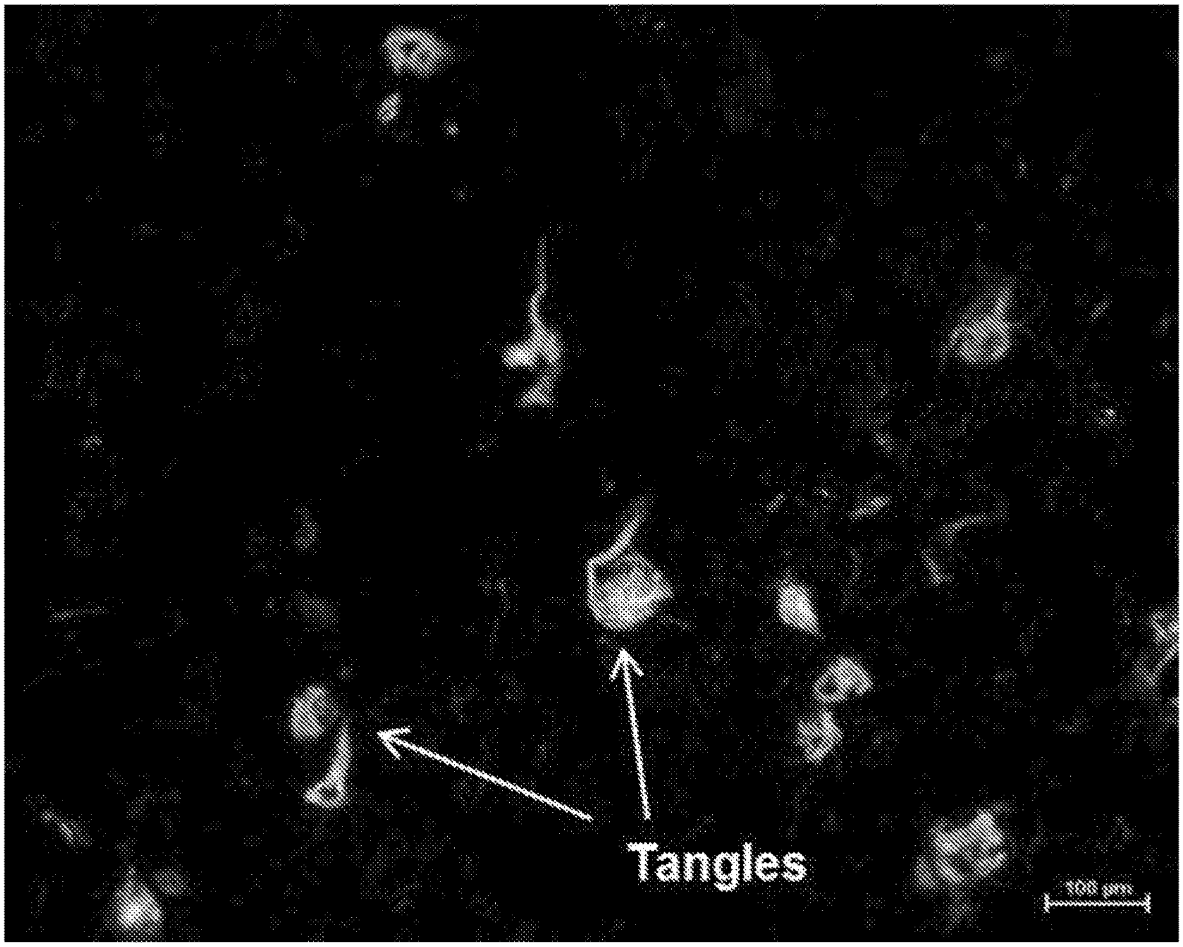
FIG. 1 shows direct staining of tau tangles on AD brain section by RefA at a concentration of 100 μM (green, here presented by white color).

It was an object of the present invention to provide compounds that can be employed in the diagnosis, treatment, alleviation or prevention of a group of disorders and abnormalities associated with amyloid proteins and amyloid-like proteins, such as Alzheimer's disease. Furthermore, there exists a need in the art for compounds which can be used as imaging agents for tau aggregates/NFTs. In particular, it was an object of the present invention to provide compounds that are suitable as a diagnostic composition for positron emission tomography imaging of tauopathies, e.g., wherein the compounds are detectably labeled with $^{18}F$. The present inventors have surprisingly found that these objects can be achieved by the compounds of formulae (I) and (II) as described hereinafter.

Due to the close structural similarities that are observed between amyloid or amyloid-like deposits formed from proteins having different primary amino acid sequences, the design of imaging probes that can bind selectively to one particular amyloid or amyloid-like deposit is very challenging. The compounds of formulae (I) and (II) display high binding affinity and selectivity to different amyloid or amyloid-like deposits in human tissues. Due to their unique design features, these compounds display properties such as appropriate lipophilicity and molecular weight, brain uptake and pharmacokinetics, cell permeability, solubility and metabolic stability, in order to be successful imaging probes for detection and quantification of amyloid or amyloid-like load in vivo, ex vivo and in vitro.

The present invention discloses novel compounds of formulae (I) and (II) having enhanced binding properties to amyloid and/or amyloid-like protein aggregates, particularly to tau aggregates/PHFs derived from human Alzheimer's disease brains ex-vivo. The compounds of this invention may be radiolabeled so that they may be used for ex vivo and in vivo imaging to detect amyloid and/or amyloid-like protein aggregates, particularly tau aggregates or NFTs. The present invention provides methods for the detection of amyloid and/or amyloid-like protein aggregates, particularly tau aggregates/PHFs, ex vivo using a compound of formulae (I) and (II) or a pharmaceutical composition thereof. The present invention provides compounds of formulae (I) and (II) for use as diagnostic imaging agents, particularly for presymptomatic detection of Alzheimer's disease and/or other tauopathies, e.g., using positron emission tomography (PET). The present invention further provides a pharmaceutical composition comprising a compound of formula (I) or (II) and a pharmaceutically acceptable carrier or excipient.

The present invention is summarized in the following items:

1. A compound of formula (I):

(I)

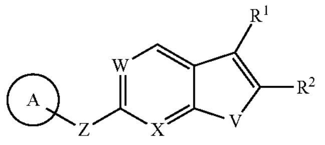

and all detectably labeled derivatives, stereoisomers, racemic mixtures, pharmaceutically acceptable salts, hydrates, solvates and polymorphs thereof;

wherein

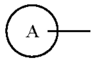

is selected from the group consisting of a pyridine ring, a phenyl ring, an azole ring and a thiazole ring, wherein the pyridine ring, the phenyl ring, the azole ring and the thiazole ring can be attached at any available position of the respective ring to the moiety Z, and wherein

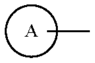

can be optionally substituted by one or more substituents $R^3$;

V is selected from the group consisting of $NR^b$, O and S;

W is selected from the group consisting of $CR^c$ and N;

X is selected from the group consisting of $CR^c$ and N;

Z is selected from the group consisting of —N($R^a$)— and —O—;

$R^a$ is selected from the group consisting of hydrogen, and alkyl, wherein alkyl can be optionally substituted;

$R^b$ is selected from the group consisting of hydrogen, alkyl, —($CH_2CH_2$—O)$_n$—H and —($CH_2CH_2$—O)$_n$-alkyl, wherein alkyl can be optionally substituted;

$R^c$ is selected from the group consisting of hydrogen, alkyl, and halogen, wherein alkyl can be optionally substituted;

$R^d$ is selected from the group consisting of halogen, H, OH and O-alkyl, wherein alkyl can be optionally substituted;

$R^f$ is selected from the group consisting of H or alkyl;

$R^1$ and $R^2$ together form a 6-membered aromatic ring containing carbon atoms and optionally one or more N atoms or $R^1$ and $R^2$ together form a 6-membered ring containing an amide moiety —C(O)—N($R^{13}$)—, wherein the 6-membered aromatic ring or the 6-membered ring containing an amide moiety formed by $R^1$ and $R^2$ can be optionally substituted by $R^{12}$;

for each occurrence, $R^3$ is independently selected from the group consisting of halogen, —CN, —O—$R^{10}$, —S—$R^{10}$, —$NO_2$, —$NR^{10}R^{11}$, —$CONR^{10}R^{11}$, —N($R^{10}$)—C(O)—$R^{11}$, —C(O)O—$R^{10}$, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —N($R^{10}$)—C(O)—$R^{11}$, —C(O)O—$R^{10}$, —($CH_2CH_2$—O)$_n$—$R^f$, —($CH_2CH_2$—O)$_n$—($CH_2CH_2$)—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —($CH_2CH_2$—O)$_n$—$R^f$, —($CH_2CH_2$—O)$_n$—($CH_2CH_2$)—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 5.

2. A compound of formula (I):

(I)

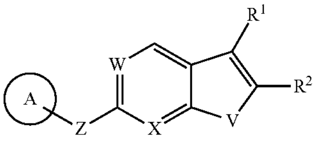

and all detectably labeled derivatives, stereoisomers, racemic mixtures, pharmaceutically acceptable salts, hydrates, solvates and polymorphs thereof;

wherein

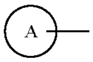

is selected from the group consisting of

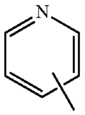
and
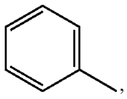
, wherein the pyridine ring

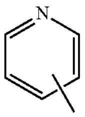

can be attached at any available position of the pyridine ring to the moiety Z, and wherein

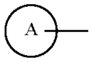

can be optionally substituted by one or more substituents $R^3$;

V is selected from the group consisting of $NR^b$, O and S;

W is selected from the group consisting of $CR^c$ and N;

X is selected from the group consisting of $CR^c$ and N;

Z is selected from the group consisting of —$N(R^a)$— and —O—;

$R^a$ is selected from the group consisting of hydrogen, alkyl, and haloalkyl;

$R^b$ is selected from the group consisting of hydrogen, alkyl, and haloalkyl;

$R^c$ is selected from the group consisting of hydrogen, alkyl, haloalkyl, and halogen;

$R^d$ is selected from the group consisting of halogen or H;

$R^f$ is selected from the group consisting of halogen or H;

$R^1$ and $R^2$ together form a 6-membered aromatic ring containing carbon atoms and optionally one or more N atoms or $R^1$ and $R^2$ together form a 6-membered ring containing an amide moiety —C(O)—$N(R^{13})$—, wherein the 6-membered aromatic ring or the 6-membered ring containing an amide moiety formed by $R^1$ and $R^2$ can be optionally substituted by $R^{12}$;

for each occurrence, $R^3$ is independently selected from the group consisting of halogen, —CN, —O—$R^{10}$, —$NR^{10}R^{11}$, —$CONR^{10}R^{11}$)C(O)—$R^{11}$, —C(O)O—$R^{10}$, —(O—$CH_2CH_2)_n$—$R^d$, —$(CH_2CH_2$—$O)_n$—$(CH_2CH_2)$—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —$N(R^{10})$—C(O)—$R^{11}$, —C(O)O—$R^{10}$, $(CH_2CH_2$—$O)_n$—$R^f$, —$(CH_2CH_2$—$O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —$(CH_2CH_2$—$O)_n$—$R^f$, —$(CH_2CH_2$—$O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 5.

3. The compound according to item 1 or 2, which is selected from:

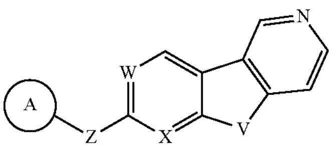

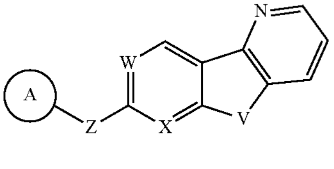

wherein A, V, W, X, and Z are as defined in item 1 or 2.

4. The compound according to item 1 or 2, which is a compound of the formula

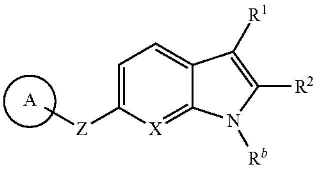

wherein $R^1$, $R^2$, $R^b$, A, X and Z are as defined in item 1 or 2.

5. The compound according to item 1 or 2, which is a compound of the formula

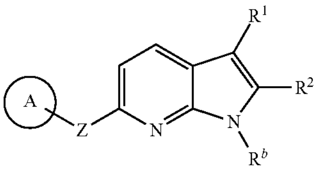

wherein $R^1$, $R^2$, $R^b$, A, and Z are as defined in item 1 or 2.

6. The compound according to item 1 or 2, which is a compound of the formula

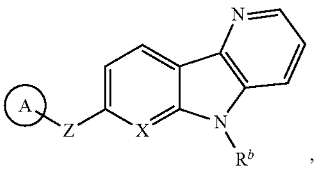,

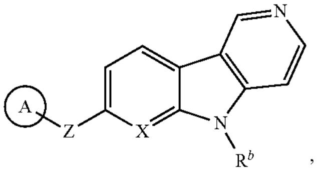,

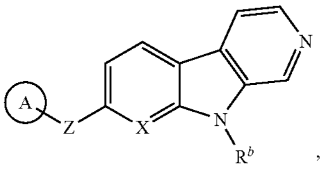,

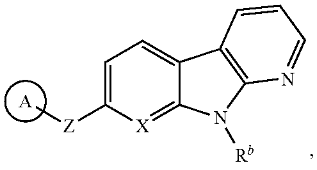, wherein A, $R^b$, X and Z are as defined in item 1 or 2.

7. The compound according to item 1 or 2, which is a compound of the formula:

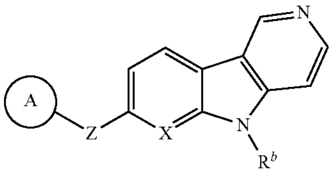

wherein A, $R^b$, X and Z are as defined in item 1 or 2.

8. The compound according to item 1 or 2, which is a compound selected from:

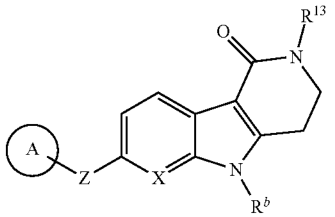

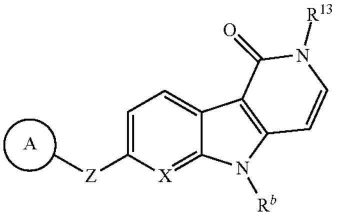

wherein A, $R^b$, $R^{13}$, X and Z are as defined in item 1 or 2.

9. The compound according to any one of items 1 to 3, wherein W is $CR^c$, preferably CH.

10. The compound according to any one of items 1 to 3, wherein V is $NR^b$, preferably —$N(CH_3)$—.

11. The compound according to any one of items 1 to 10, wherein Z is —$N(R^a)$—, preferably —NH—.

12. The compound according to any one of items 1 to 11, wherein for each occurrence, $R^3$ is independently selected from the group consisting of halogen, —CN, —O—$R^{10}$, —S—$R^{10}$, —$NO_2$, —$NR^{10}R^{11}$, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl and heterocyclyl, wherein alkyl and heterocyclyl can be optionally substituted, and wherein $R^{10}$, $R^{11}$, n, $R^d$ and $R^f$ are as defined in item 1 or 2.

13. The compound according to item 12, wherein for each occurrence, $R^3$ is independently selected from the group consisting of halogen, —CN, —O—$R^{10}$, —$NR^{10}R^{11}$, —(O—$CH_2CH_2$)$_n$—$R^d$, —($CH_2CH_2$—O)$_n$—($CH_2CH_2$)—$R^d$, alkyl and heterocyclyl, wherein alkyl and heterocyclyl can be optionally substituted, and wherein $R^{10}$, $R^{11}$, n, $R^d$ and $R^f$ are as defined in item 1 or 2.

14. The compound according to item 13, wherein for each occurrence, $R^3$ is independently selected from the group consisting of —F, —$^{18}F$, —CN, —O-alkylene-F, —O-alkylene-$^{18}F$, alkyl, —(O-alkylene)$_n$-F, —(O-alkylene)$_n$-$^{18}F$, wherein alkylene is a $C_{1-6}$ alkylene and n is as defined in item 1 or 2.

15. The compound according to any one of items 1 to 11, wherein two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted.

16. The compound according to any one of items 1 to 15, wherein, for each occurrence, $R^{10}$ and $R^{11}$ are each independently selected from the group consisting of hydrogen and alkyl, wherein alkyl can be optionally substituted.

17. The compound according to any one of items 1 to 16, wherein, for each occurrence, $R^{12}$ is independently selected from the group consisting of hydrogen, halogen, $-(CH_2CH_2-O)_n-R^f$, $-(CH_2CH_2-O)_n-(CH_2CH_2)-R^d$, and alkyl, wherein alkyl can be optionally substituted, and wherein n and $R^f$ are as defined in item 1 or 2.

18. The compound according to any one of items 1 to 17, wherein, for each occurrence, $R^{13}$ is independently selected from the group consisting of hydrogen, $-(CH_2CH_2-O)_n-R^f$, $-(CH_2CH_2-O)_n-(CH_2CH_2)-R^d$ and alkyl, wherein alkyl can be optionally substituted, and wherein n, $R^d$ and $R^f$ are as defined in item 1 or 2.

19. The compound according to item 18, wherein, for each occurrence, $R^{13}$ is independently selected from the group consisting of hydrogen, methyl and ethyl.

20. The compound according to any one of items 1 to 19, wherein X is N.

21. The compound according to any one of items 1 to 20, wherein $R^a$ is hydrogen and/or $R^b$ is alkyl or hydrogen.

22. The compound according to item 21, wherein $R^b$ is methyl.

23. The compound according to any one of items 1 to 22, wherein

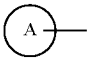

is selected from the group consisting of

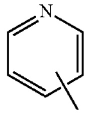 and 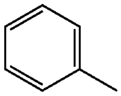 , wherein

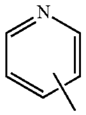

can be attached at any available position of the ring to the moiety Z, and wherein

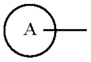

can be optionally substituted by one or more substituents $R^3$.

24. The compound according to any one of items 1, and 3 to 17, wherein

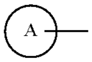

is selected from the group consisting of

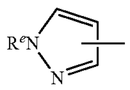 and 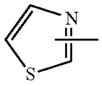 , wherein

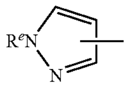 , and 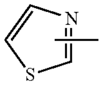

can be attached at any available position of the respective ring to the moiety Z, wherein

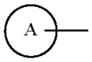

can be optionally substituted by one or more substituents $R^3$, and $R^e$ is selected from the group consisting of hydrogen, $-(CH_2CH_2-O)_n-R^f$, $-(CH_2CH_2-O)_n-(CH_2CH_2)-R^d$, alkyl, carbocyclyl and heterocyclyl, wherein alkyl, carbocyclyl and heterocyclyl can be optionally substituted. Preferably, $R^e$ is hydrogen or alkyl which can be optionally substituted (most preferably optionally substituted by Hal).

25. A compound of formula (II):

(II)

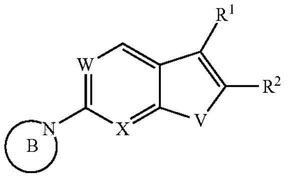

and all detectably labeled derivatives, stereoisomers, racemic mixtures, pharmaceutically acceptable salts, hydrates, solvates and polymorphs thereof;

wherein

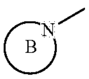

is a 4 to 10-membered ring system containing carbon atoms and optionally one or more heteroatoms selected from O, S, or N or optionally one or more heteroatom (e.g., N, O and/or S)-containing moieties and wherein the 4- to 10-membered ring system may be optionally substituted by one or more $R^3$;

V is selected from the group consisting of $NR^b$, O and S;

W is selected from the group consisting of $CR^c$ and N;

X is selected from the group consisting of $CR^c$ and N;

$R^b$ is selected from the group consisting of hydrogen, alkyl, —$(CH_2CH_2—O)_n$—H and —$(CH_2CH_2—O)_n$-alkyl, wherein alkyl can be optionally substituted;

$R^c$ is selected from the group consisting of hydrogen, alkyl, halogen, wherein alkyl can be optionally substituted;

$R^d$ is selected from the group consisting of halogen, H, OH and O-alkyl, wherein alkyl can be optionally substituted;

$R^f$ is selected from the group consisting of H and alkyl;

$R^1$ and $R^2$ together form a 6-membered aromatic ring containing carbon atoms and optionally one or more N atoms or $R^1$ and $R^2$ together form a 6-membered saturated or unsaturated ring containing an amide moiety —C(O)—N($R^{13}$)—, wherein the 6-membered aromatic ring or the 6-membered saturated or unsaturated ring containing an amide moiety formed by $R^1$ and $R^2$ can be optionally substituted by $R^{12}$;

for each occurrence, $R^3$ is independently selected from the group consisting of halogen, —CN, —O—$R^{10}$, —S—$R^{10}$, —$NO_2$, —$NR^{10}R^{11}$, —$CONR^{10}R^{11}$, —N($R^{10}$)—C(O)—$R^{11}$, —C(O)O—$R^{10}$, —(O—$CH_2CH_2)_n$—$R^d$, —$(CH_2CH_2—O)_n$—$R^f$, —$(CH_2CH_2—O)_n$—$(CH_2CH_2)$—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —N($R^{10}$)—C(O)—$R^{11}$, —C(O)O—$R^{10}$, —$(CH_2CH_2—O)_n$—$R^f$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —$(CH_2CH_2—O)_n$—$R^f$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 5.

26. A compound of formula (II):

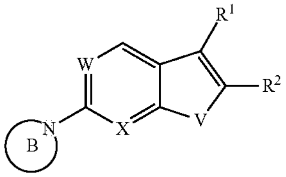
(II)

and all detectably labeled derivatives, stereoisomers, racemic mixtures, pharmaceutically acceptable salts, hydrates, solvates and polymorphs thereof;

wherein

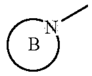

is a 5 to 8-membered ring containing carbon atoms and optionally one or more heteroatoms selected from O, S, or N or optionally one or more heteroatom (e.g., N, O and/or S)-containing moieties and wherein the 5- to 8-membered ring may be optionally substituted by one or more $R^3$;

V is selected from the group consisting of $NR^b$, O and S;

W is selected from the group consisting of $CR^c$ and N;

X is selected from the group consisting of $CR^c$ and N;

$R^b$ is selected from the group consisting of hydrogen, alkyl, and haloalkyl;

$R^c$ is selected from the group consisting of hydrogen, alkyl, haloalkyl, and halogen;

$R^d$ is selected from the group consisting of halogen or H;

$R^f$ is selected from the group consisting of halogen or H;

$R^1$ and $R^2$ together form a 6-membered aromatic ring containing carbon atoms and optionally one or more N atoms or $R^1$ and $R^2$ together form a 6-membered saturated or unsaturated ring containing an amide moiety —C(O)—N($R^{13}$)—, wherein the 6-membered aromatic ring or the 6-membered saturated or unsaturated ring containing an amide moiety formed by $R^1$ and $R^2$ can be optionally substituted by $R^{12}$;

for each occurrence, $R^3$ is independently selected from the group consisting of halogen, —CN, —O—$R^{10}$, —$NR^{10}R^{11}$, —$CONR^{10}R^{11}$, —N($R^{10}$)—C(O)—$R^{11}$, —C(O)O—$R^{10}$, —(O—$CH_2CH_2)_n$—$R^d$, —$(CH_2CH_2—O)_n$—$(CH_2CH_2)$—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —$N(R^{10})$—C(O)—$R^{11}$, —C(O)O—$R^{10}$, —$(CH_2CH_2—O)_n$—$R^f$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —$(CH_2CH_2—O)_n$—$R^f$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 5.

27. The compound according to item 25 or 26, which is a compound of the formula

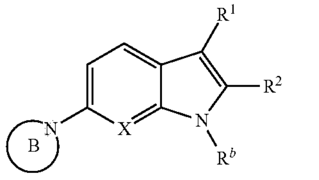

wherein $R^1$, $R^2$, $R^b$, B, and X are as defined in item 25 or 26.

28. The compound according to item 25 or 26, which is a compound of the formula:

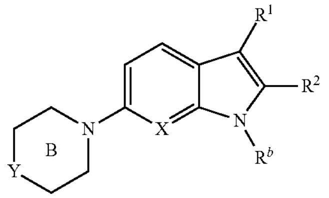

wherein Y is $NR^{14}$, O or $CHR^{15}$;

$R^{14}$ is selected from the group consisting of hydrogen, —$(CH_2CH_2—O)_n$—$R^f$, —$(CH_2CH_2—O)_n$—$(CH_2CH_2)$—$R^d$, alkyl, carbocyclyl and heterocyclyl, wherein alkyl, carbocyclyl and heterocyclyl can be optionally substituted;

$R^{15}$ is independently selected from the group consisting of hydrogen and $R^3$, preferably $R^{15}$ is independently selected from the group consisting of hydrogen, halogen, —$(O—CH_2CH_2)_n$—$R^d$, —$(CH_2CH_2—O)_n$—$R^f$, —$(CH_2CH_2—O)_n$—$(CH_2CH_2)$—$R^d$, alkyl, carbocyclyl and heterocyclyl, wherein alkyl, carbocyclyl and heterocyclyl can be optionally substituted, more preferably $R^{15}$ is halogen, alkyl which can be optionally substituted by Hal, —$(O—CH_2CH_2)_n$—$R^d$, —$(CH_2CH_2—O)_n$—$R^f$, or —$(CH_2CH_2—O)_n$—$(CH_2CH_2)$—$R^d$;

the ring system B can be optionally substituted by one or more $R^3$;

$R^1$, $R^2$, $R^3$, $R^{10}$, $R^{11}$, $R^b$, $R^d$, $R^f$, n and X are as defined in item 25 or 26.

29. The compound according to item 25 or 26, which is a compound of the formula:

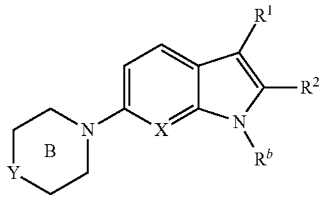

wherein Y is $NR^{14}$, O or $C(R^{15})_2$;

$R^{14}$ is selected from the group consisting of hydrogen, —$(CH_2CH_2—O)_n$—$R^f$, —$(CH_2CH_2—O)_n$—$(CH_2CH_2)$—$R^d$, alkyl, carbocyclyl and heterocyclyl, wherein alkyl, carbocyclyl and heterocyclyl can be optionally substituted;

$R^{15}$ is independently selected from the group consisting of hydrogen, halogen, —$(CH_2CH_2—O)_n$—$R^f$, —$(CH_2CH_2—O)_n$—$(CH_2CH_2)$—$R^d$, alkyl, carbocyclyl and heterocyclyl, wherein alkyl, carbocyclyl and heterocyclyl can be optionally substituted;

the ring B can be optionally substituted by one or more $R^3$; and $R^1$, $R^2$, $R^3$, $R^b$, $R^d$, $R^f$, n and X are as defined in item 25 or 26.

30. The compound according to item 25, wherein

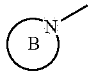

is selected from the group consisting of

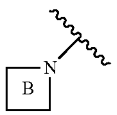, 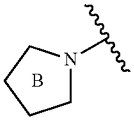, 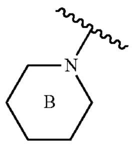,

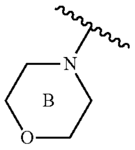, 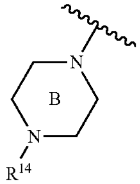, 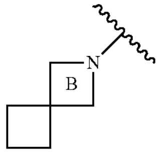,

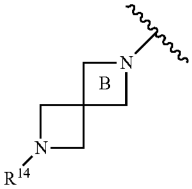, 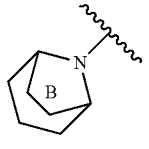, and

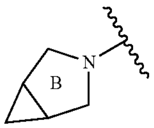;

wherein the ring system B can be optionally substituted in any available position of any of its rings by one or more $R^3$; and $R^{14}$ is as defined in item 28 or 29.

31. The compound according to any one of items 25 to 30, wherein W is $CR^c$, preferably CH.

32. The compound according to any one of items 25 to 31, wherein V is —N($R^b$)—.

33. The compound according to item 32, wherein V is —N($CH_3$)—.

34. The compound according to any one of items 25 to 33, wherein for each occurrence, $R^3$ is independently selected from the group consisting of halogen, —CN, —$NR^{10}R^{11}$, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl, carbocyclyl and heterocyclyl, wherein alkyl, carbocyclyl and heterocyclyl can be optionally substituted, and wherein $R^{10}$, $R^{11}$, n, $R^d$ and $R^f$ are as defined in item 25 or 26.

35. The compound according to item 34, wherein for each occurrence, $R^3$ is independently selected from the group consisting of halogen, —CN, —O—$R^{10}$, —$NR^{10}R^{11}$, —(O—$CH_2CH_2$)$_n$—$R^d$, —($CH_2CH_2$—O)$_n$—($CH_2CH_2$)—$R^d$, and alkyl, wherein alkyl can be optionally substituted, and wherein $R^{10}$, $R^{11}$, n, $R^d$ and $R^f$ are as defined in item 25 or 26.

36. The compound according to item 35, wherein for each occurrence, $R^3$ is independently selected from the group consisting of —F, —$^{18}F$, -alkylene-F, -alkylene-$^{18}F$, —O— alkylene-F, —O— alkylene-$^{18}F$, —(O-alkylene)$_n$-F, —(O-alkylene)$_n$-$^{18}F$, wherein alkylene is a $C_{1-6}$ alkylene and n is as defined in item 25 or 26.

37. The compound according to any one of items 25 to 33, wherein two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted.

38. The compound according to any one of items 25 to 37, wherein, for each occurrence, $R^{10}$ and $R^{11}$ are each independently selected from the group consisting of hydrogen and alkyl, wherein alkyl can be optionally substituted.

39. The compound according to any one of items 25 to 38, wherein, for each occurrence, $R^{12}$ is independently selected from the group consisting of hydrogen, halogen, —($CH_2CH_2$—O)$_n$—$R^f$, —($CH_2CH_2$—O)$_n$—($CH_2CH_2$)—$R^d$, and alkyl, wherein alkyl can be optionally substituted, and wherein n, $R^d$ and $R^f$ are as defined in item 25 or 26.

40. The compound according to any one of items 25 to 39, wherein, for each occurrence, $R^{13}$ is independently selected from the group consisting of hydrogen, —($CH_2CH_2$—O)$_n$—$R^f$, —($CH_2CH_2$—O)$_n$—($CH_2CH_2$)—$R^d$ and alkyl, wherein alkyl can be optionally substituted, and wherein n, $R^d$ and $R^f$ are as defined in item 25 or 26.

41. The compound according to item 40, wherein, for each occurrence, $R^{13}$ is independently selected from the group consisting of hydrogen, methyl and ethyl.

42. The compound according to any one of items 25 to 41, wherein X is N.

43. The compound according to any one of items 25 to 42, wherein $R^b$ is alkyl or hydrogen.

44. The compound according to item 43, wherein $R^b$ is methyl.

45. The compound according to any one of items 1 to 44 which is detectably labeled.

46. The compound according to item 45, wherein the detectable label is selected from the group consisting of a radionuclide, a positron emitter, a gamma emitter, or a fluorescent label.

47. The compound according to item 45 or 46, wherein the detectable label is selected from the group consisting of $^{2}H$, $^{3}H$, $^{18}F$, $^{123}I$, $^{124}I$, $^{125}I$, $^{131}I$, $^{11}C$, $^{13}N$, $^{15}O$, and $^{77}Br$.

48. The compound according to item 47, wherein the detectable label is $^{18}F$.

49. The compound according to item 48, which is selected from the group comprising

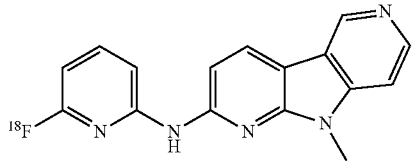
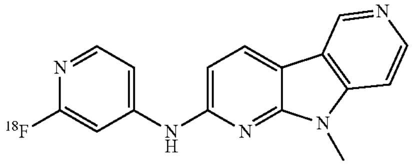
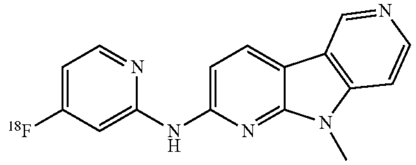
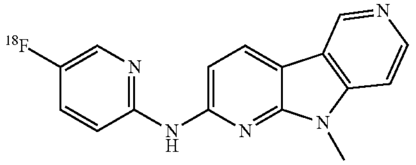
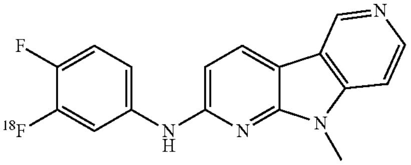
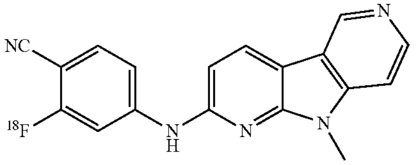
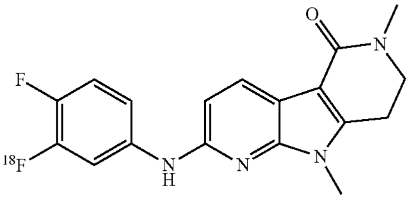
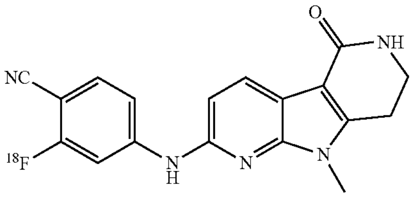

-continued
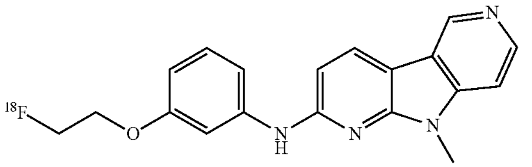
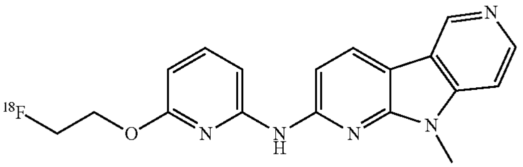
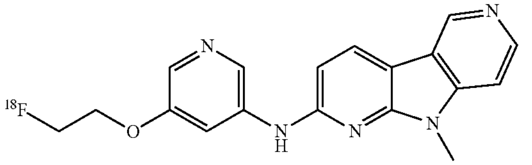
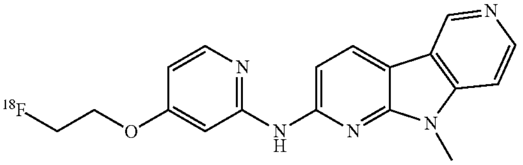
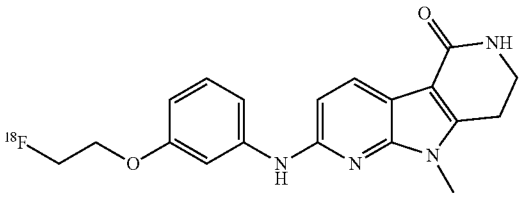
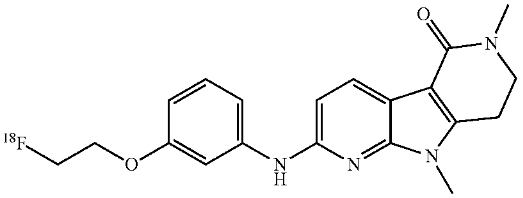
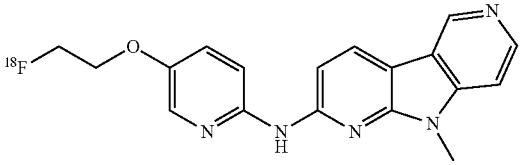
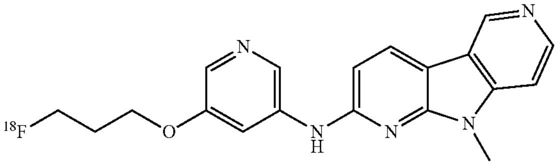
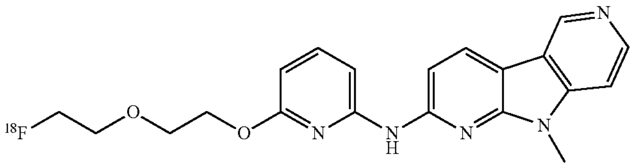
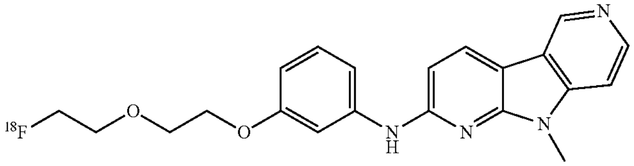
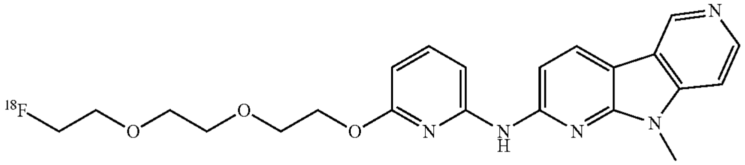
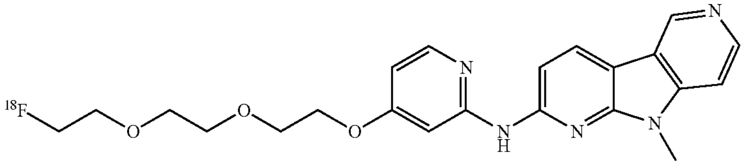
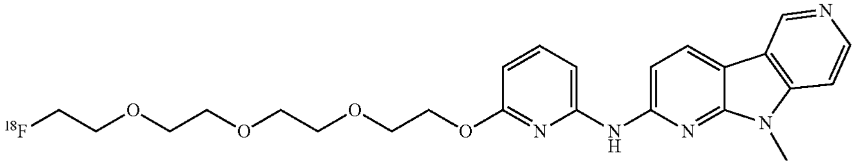

-continued
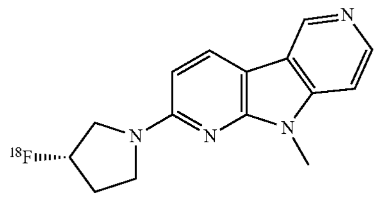
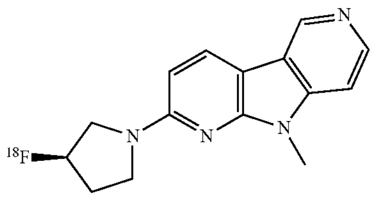
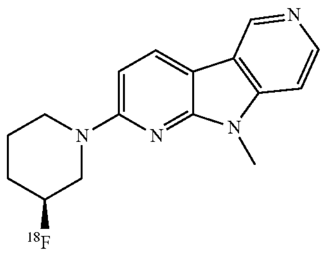
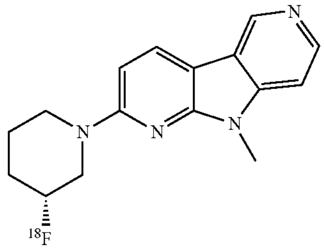
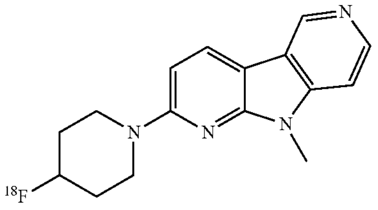
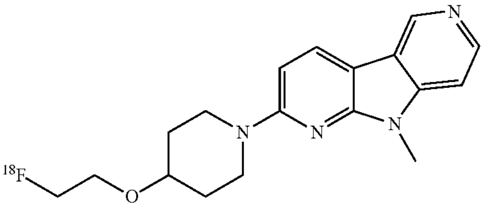
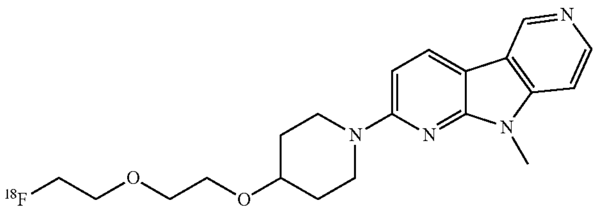
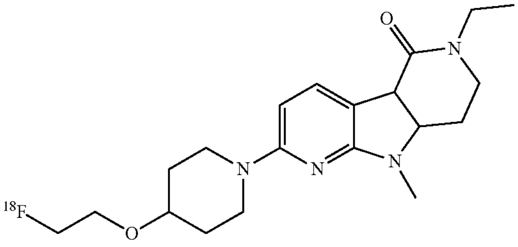
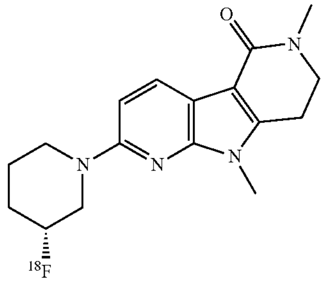
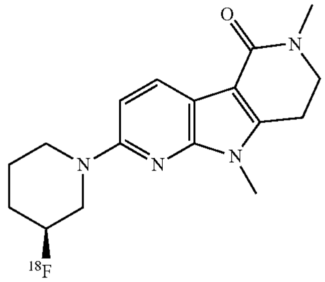
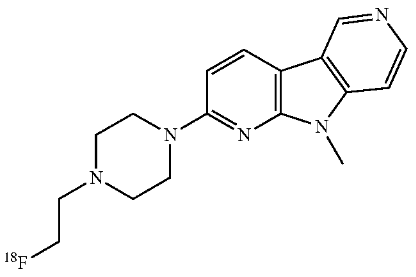
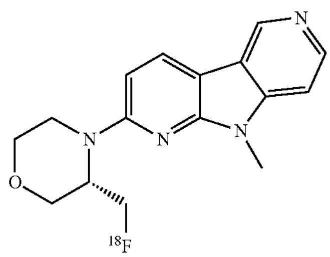
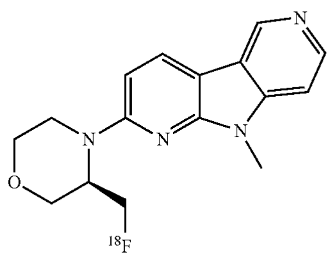
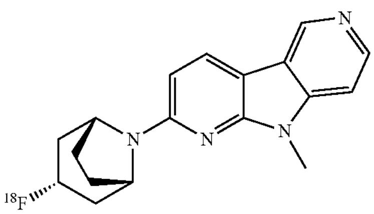
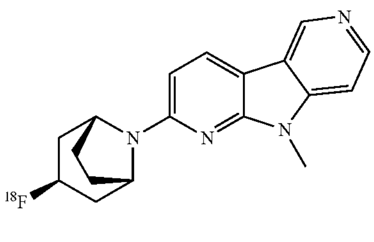
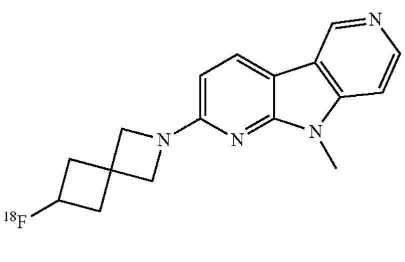

-continued

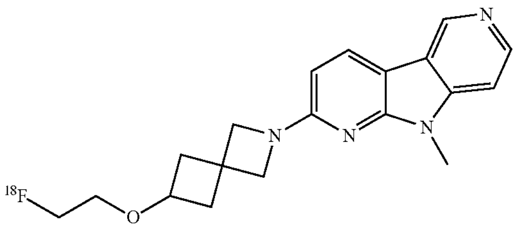

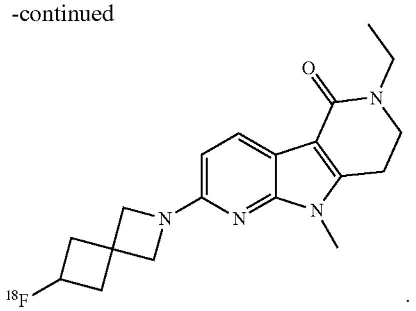

50. The compound according to item 47, wherein the detectable label is $^3H$ or $^2H$.
51. The compound according to item 46, wherein the detectable label is a fluorescent label.
52. A diagnostic composition comprising the compound according to any one of items 45 to
51 and optionally a pharmaceutically acceptable carrier or excipient.
53. The compound according to any one of items 45 to 51 for use in diagnostics, preferably wherein the detectable label is $^{18}F$ and the compound is for use in positron emission tomography.
54. The compound according to any one of items 45 to 51 for use in the imaging of amyloid and/or amyloid-like protein aggregates, preferably wherein the detectable label is $^{18}F$ and the imaging is positron emission tomography.
55. The compound according to any one of items 45 to 51 for use in the imaging of amyloid and/or amyloid-like protein aggregates in the brain or in the eye, preferably wherein the detectable label is $^{18}F$ and the imaging is positron emission tomography.
56. The compound according to any one of items 45 to 51 for use in the diagnostics of a disorder associated with amyloid and/or amyloid-like protein aggregates, preferably wherein the detectable label is $^{18}F$ and the diagnostics is positron emission tomography.
57. The compound according to any one of items 45 to 51 for use in the diagnostics of a tauopathy, preferably wherein the detectable label is $^{18}F$ and the diagnostics is positron emission tomography.
58. The compound according to any one of items 54 to 56, wherein the amyloid and/or amyloid-like protein is an extracellular and/or an intracellular amyloid-like protein.
59. The compound according to any one of items 54 to 56, wherein the amyloid-like protein is selected from the group consisting of tau, Abeta, alpha-synuclein, Huntingtin, prion, ATTR (transthyretin) or ADan (ADanPP), preferably wherein the amyloid-like protein is tau.
60. The compound according to any one of items 56 to 59, wherein the disorder is a neurological disorder.
61. The compound according to any one of items 56 to 59, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, Pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy.
62. The compound according to any one of items 56 to 59, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, and white matter tauopathy with globular glial inclusions.
63. The compound according to any one of items 56 to 59, wherein the disorder is selected from the group consisting of Alzheimer's disease, Lewy body dementia (LBD), hereditary cerebral hemorrhage with amyloidosis (Dutch type), mild cognitive impairment (MCI), progressive supranuclear palsy, multiple sclerosis, inclusion-body myositis (IBM), Creutzfeldt-Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystropy.

64. The compound according to any one of items 56 to 59, wherein the disorder is selected from the group consisting of Parkinson's disease (PD), Huntington's disease, Creutzfeldt-Jakob disease, familial senile systemic tenosynovium, and familial dementia (Danish type).

65. A method of imaging amyloid and/or amyloid-like protein aggregates comprising administering an effective amount of a compound according to any one of items 45 to 51 to a patient in need thereof, preferably wherein the detectable label is $^{18}F$ and the imaging is positron emission tomography.

66. The method according to item 65, wherein the amyloid and/or amyloid-like protein aggregates are imaged in the brain or in the eye, preferably wherein the detectable label is $^{18}F$ and the imaging is positron emission tomography.

67. A method of diagnosing a disorder associated with amyloid and/or amyloid-like protein aggregates comprising administering an effective amount of a compound according to any one of items 45 to 51 to a patient in need thereof, preferably wherein the detectable label is $^{18}F$ and the method of diagnosing is positron emission tomography.

68. A method of diagnosing a tauopathy comprising administering an effective amount of a compound according to any one of items 45 to 51 to a patient in need thereof, preferably wherein the detectable label is $^{18}F$ and the method of diagnosing is positron emission tomography.

69. The method according to any one of items 65 to 68, wherein the amyloid and/or amyloid-like protein is an extracellular and/or an intracellular amyloid-like protein.

70. The method according to any one of items 65 to 69, wherein the amyloid-like protein is selected from the group consisting of tau, Abeta, alpha-synuclein, Huntingtin, prion, ATTR (transthyretin) or ADan (ADanPP), preferably wherein the amyloid-like protein is tau.

71. The method according to any one of items 68 to 70, wherein the disorder is a neurological disorder.

72. The method according to any one of items 68 to 70, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, familial British dementia, Hallervorden-Spatz disease, chronic traumatic encephalopathy, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy.

73. The method according to any one of items 68 to 70, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, and white matter tauopathy with globular glial inclusions.

74. The method according to any one of items 68 to 70, wherein the disorder is selected from the group consisting of Alzheimer's disease, Lewy body dementia (LBD), hereditary cerebral hemorrhage with amyloidosis (Dutch type), mild cognitive impairment (MCI), progressive supranuclear palsy, multiple sclerosis, inclusion-body myositis (IBM), Creutzfeldt-Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystropy.

75. The method according to any one of items 68 to 70, wherein the disorder is selected from the group consisting of Parkinson's disease (PD), Huntington's disease, Creutzfeldt-Jakob disease, familial senile systemic tenosynovium, and familial dementia (Danish type).

76. Use of a compound according to any one of items 45 to 51 for the manufacture of a composition for imaging amyloid and/or amyloid-like protein aggregates, preferably wherein the detectable label is $^{18}F$ and the imaging is positron emission tomography.

77. The use according to item 76, wherein the amyloid and/or amyloid-like protein aggregates are imaged in the brain or in the eye.
78. Use of a compound according to any one of items 45 to 51 for the manufacture of a composition for diagnosing a disorder associated with amyloid and/or amyloid-like protein aggregates, preferably wherein the detectable label is $^{18}F$ and the diagnosing is positron emission tomography.
79. Use of a compound according to any one of items 45 to 51 for the manufacture of a composition for diagnosing a tauopathy, preferably wherein the detectable label is $^{18}F$ and the diagnosing is positron emission tomography.
80. The use according to any one of items 76 to 79, wherein the amyloid and/or amyloid-like protein is extracellular and/or intracellular amyloid-like protein.
81. The use according to any one of items 76 to 80, wherein the amyloid-like protein is selected from the group consisting of tau, Abeta, alpha-synuclein, Huntingtin, prion, ATTR (transthyretin) or ADan (ADanPP), wherein the amyloid-like protein is tau.
82. The use according to any one of items 76 to 81, wherein the disorder is a neurological disorder.
83. The use according to any one of items 76 to 81, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy.
84. The use according to any one of items 76 to 81, wherein the disorder is selected from the group consisting of Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, and white matter tauopathy with globular glial inclusions.
85. The use according to any one of items 76 to 81, wherein the disorder is selected from the group consisting of Alzheimer's disease, Lewy body dementia (LBD), hereditary cerebral hemorrhage with amyloidosis (Dutch type), mild cognitive impairment (MCI), progressive supranuclear palsy, multiple sclerosis, inclusion-body myositis (IBM), Creutzfeldt-Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystropy.
86. The use according to any one of items 76 to 81, wherein the disorder is selected from the group consisting of Parkinson's disease (PD), Huntington's disease, Creutzfeldt-Jakob disease, familial senile systemic tenosynovium, and familial dementia (Danish type).
87. A method of collecting data for the diagnosis of a disorder associated with amyloid and/or amyloid-like protein aggregates in a sample or a patient comprising:
(a) bringing a sample or a specific body part or body area suspected to contain an amyloid and/or amyloid-like protein aggregate into contact with a compound as defined in any one of items 45 to 51;
(b) allowing the compound to bind to the amyloid and/or amyloid-like protein aggregate;
(c) detecting the compound bound to the amyloid and/or amyloid-like protein aggregate; and
(d) optionally correlating the presence or absence of compound binding with the amyloid and/or amyloid-like protein aggregate with the presence or absence of amyloid and/or amyloid-like protein aggregate in the sample or specific body part or body area.
88. A method of determining the amount of amyloid and/or amyloid-like protein aggregate in a tissue and/or a body fluid comprising:
(a) providing a sample representative of the tissue and/or body fluid under investigation;
(b) testing the sample for the presence of amyloid and/or amyloid-like protein aggregate with a compound as defined in any one of items 45 to 51;
(c) determining the amount of compound bound to the amyloid and/or amyloid-like protein aggregate; and
(d) calculating the amount of amyloid and/or amyloid-like protein aggregate in the tissue and/or body fluid.
89. The method according to item 88, wherein the determination in step (c) is conducted such that presence or absence of the compound binding with the amyloid and/or amyloid-like protein aggregate correlates with presence or absence of amyloid and/or amyloid-like protein aggregate.

90. A method of collecting data for determining a predisposition to a disorder associated with amyloid and/or amyloid-like protein aggregates in a patient comprising detecting the specific binding of a compound as defined in any one of items 45 to 51 to an amyloid and/or amyloid-like protein aggregate in a sample or in situ which comprises the steps of:
  (a) bringing the sample or a specific body part or body area suspected to contain the amyloid and/or amyloid-like protein aggregate into contact with the compound as defined in any one of items 45 to 51, which compound specifically binds to the amyloid and/or amyloid-like protein aggregate;
  (b) allowing the compound to bind to the amyloid and/or amyloid-like protein aggregate to form a compound/amyloid and/or amyloid-like protein aggregate complex;
  (c) detecting the formation of the compound/amyloid and/or amyloid-like protein aggregate complex;
  (d) optionally correlating the presence or absence of the compound/amyloid and/or amyloid-like protein aggregate complex with the presence or absence of amyloid and/or amyloid-like protein aggregate in the sample or specific body part or body area; and
  (e) optionally comparing the amount of the compound/amyloid and/or amyloid-like protein aggregate to a normal control value.

91. A method of collecting data for monitoring residual disorder in a patient suffering from a disorder associated with amyloid and/or amyloid-like protein aggregates who has been treated with a medicament, wherein the method comprises:
  (a) bringing a sample or a specific body part or body area suspected to contain an amyloid and/or amyloid-like protein aggregate into contact with a compound as defined in any one of items 45 to 51, which compound specifically binds to the amyloid and/or amyloid-like protein aggregate;
  (b) allowing the compound to bind to the amyloid and/or amyloid-like protein aggregate to form a compound/amyloid and/or amyloid-like protein aggregate complex;
(c) detecting the formation of the compound/amyloid and/or amyloid-like protein aggregate complex;
  (d) optionally correlating the presence or absence of the compound/amyloid and/or amyloid-like protein aggregate complex with the presence or absence of amyloid and/or amyloid-like protein in the sample or specific body part or body area; and
(e) optionally comparing the amount of the compound/amyloid and/or amyloid-like protein aggregate to a normal control value.

92. A method of collecting data for predicting responsiveness of a patient suffering from a disorder associated with amyloid and/or amyloid-like protein aggregates and being treated with a medicament comprising:
  (a) bringing a sample or a specific body part or body area suspected to contain an amyloid and/or amyloid-like protein aggregate into contact with a compound as defined in any one of items 45 to 51, which compound specifically binds to the amyloid and/or amyloid-like protein aggregate;
  (b) allowing the compound to bind to the amyloid and/or amyloid-like protein aggregate to form a compound/amyloid and/or amyloid-like protein aggregate complex;
  (c) detecting the formation of the compound/amyloid and/or amyloid-like protein aggregate complex;
  (d) optionally correlating the presence or absence of the compound/amyloid and/or amyloid-like protein aggregate complex with the presence or absence of amyloid and/or amyloid-like protein in the sample or specific body part or body area; and
  (e) optionally comparing the amount of the compound/amyloid and/or amyloid-like protein aggregate to a normal control value.

93. A pharmaceutical composition comprising a compound as defined in any one of items 1 to 51 and optionally a pharmaceutically acceptable carrier or excipient.

94. The compound as defined in any one of items 1 to 51 for use as a medicament.

95. Use of the compound as defined in any one of items 1 to 51 for the preparation of a medicament for treating, preventing or alleviating a disorder associated with amyloid and/or amyloid-like protein aggregates.

96. A method of treating, preventing or alleviating a disorder associated with amyloid and/or amyloid-like protein aggregates, the method comprising administering to a subject in need of such treatment an effective amount of a compound as defined in any one of items 1 to 51.

97. The compound as defined in any one of items 1 to 51 for use in the treatment, prevention or alleviation of a disorder associated with amyloid and/or amyloid-like protein aggregates.

98. A compound of formula (I*):

(I*)

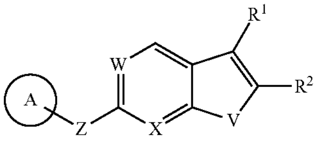

and all stereoisomers, racemic mixtures, pharmaceutically acceptable salts, hydrates, solvates and polymorphs thereof;
wherein

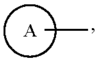,

V, W, X, Z, $R^b$, $R^c$, $R^d$, $R^f$, $R^1$, $R^2$, $R^3$, $R^{10}$, $R^{11}$, $R^{12}$, $R^{13}$, and n are as defined in any of items 1 to 44,
wherein

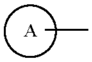

is substituted by $R^{3*}$ which comprises a leaving group selected from the group consisting of halogen (e.g., Br, I, or Cl), nitro, tri($C_{1-4}$ alkyl)ammonium (e.g., trimethylammonium), iodonium-aryl ($I^+$-aryl), or $—OSO_2—R$, with R being selected from the group consisting of $C_{1-4}$ alkyl, perfluoro($C_{1-4}$)alkyl, and aryl which can be optionally substituted by $C_{1-4}$ alkyl, halogen or nitro (e.g., $—OSO_2—CH_3$, $—OSO_2—C_6H_4—CH_3$, or $—OSO_2—CF_3$); and wherein $R^a$ is selected from the group consisting of hydrogen, an amine protecting group PG and alkyl, wherein alkyl can be optionally substituted.

99. The compound according to item 98, wherein $R^{3*}$ is halogen, $—NO_2$, tri($C_{1-4}$ alkyl)ammonium, alkyl substituted with halogen or $—OSO_2—R$, —O—($C_{2-5}$ alkyl), wherein the alkyl group is substituted with halogen or $—OSO_2—R$, or $—(O—CH_2CH_2)_n$-L, wherein L is selected from halogen or $—OSO_2—R$ and n is 2 to 5; and wherein R is as defined in item 98, preferably R is methyl or tolyl.

100. The compound according to item 99, wherein $R^{3*}$ is halogen or $—NO_2$.

101. The compound according to item 100, wherein $R^{3*}$ is $—NO_2$.

102. The compound according to item 99, wherein $R^{3*}$ is -alkyl, —O—($C_{2-5}$ alkyl) or $—(O—CH_2CH_2)_n$ (with n=1 to 6) wherein -alkyl, —O—($C_{2-5}$ alkyl) or $—(O—CH_2CH_2)_n$ is substituted with a leaving group selected from halogen and $—OSO_2—R$, with R being selected from the group consisting of $C_{1-4}$ alkyl, perfluoro($C_{1-4}$) alkyl, and aryl which can be optionally substituted by $C_{1-4}$ alkyl, halogen or nitro (e.g., $—OSO_2—CH_3$, $—OSO_2—C_6H_4—CH_3$, or $—OSO_2—CF_3$).

103. The compound according to item 102, wherein $R^{3*}$ comprises a leaving group selected from the group consisting of $—OSO_2—CH_3$ and $—OSO_2—C_6H_4—CH_3$.

104. A compound of formula (II*):

(II*)

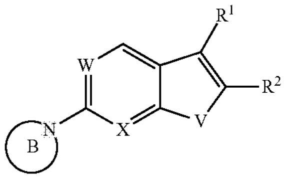

and all stereoisomers, racemic mixtures, pharmaceutically acceptable salts, hydrates, solvates and polymorphs thereof;

wherein

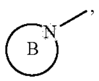

V, W, X, $R^b$, $R^c$, $R^d$, $R^f$, $R^1$, $R^2$, $R^3$, $R^{10}$, $R^{11}$, $R^{12}$, $R^{13}$, and n are as defined in any of items 1 to 44, wherein

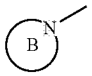

is substituted by $R^{3*}$ which comprises a leaving group selected from the group consisting of halogen (e.g., Br, I, or Cl) or $—OSO_2—R$, with R being selected from the group consisting of $C_{1-4}$ alkyl, perfluoro($C_{1-4}$)alkyl, and aryl which can be optionally substituted by $C_{1-4}$ alkyl, halogen or nitro (e.g., $—OSO_2—CH_3$, $—OSO_2—CF_3$ or $—OSO_2—C_6H_4—CH_3$).

105. The compound according to item 104, wherein $R^{3*}$ is halogen, $—OSO_2—R$, alkyl substituted with halogen or $—OSO_2—R$, —O-alkyl, wherein the alkyl group is substituted with halogen or $—OSO_2—R$, or $—(O—CH_2CH_2)_n$-L, wherein L is selected from halogen or $—OSO_2—R$ and n is 2 to 5; and wherein R is as defined in item 104, preferably R is methyl or tolyl.

106. The compound according to item 105, wherein $R^{3*}$ comprises a leaving group selected from the group consisting of $—OSO_2—CH_3$ and $—OSO_2—C_6H_4—CH_3$.

107. The compound according to any one of items 98 to 106, wherein the compound is selected from the group consisting of

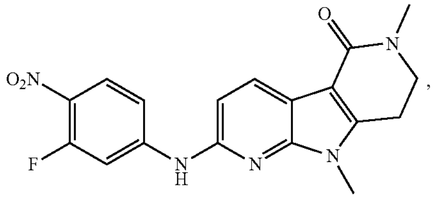

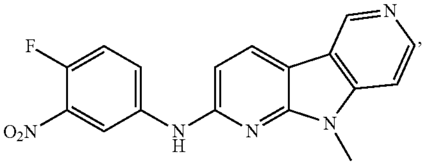

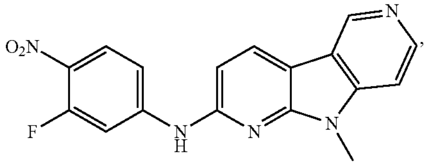

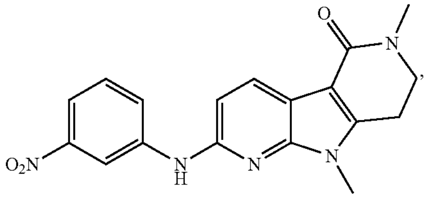

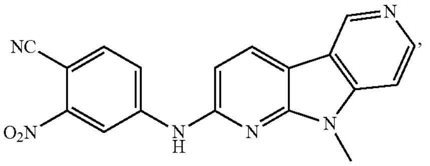

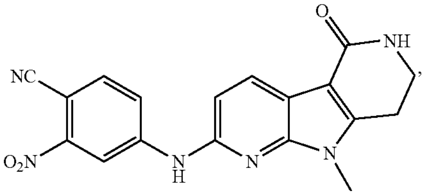

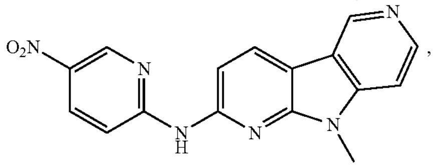

-continued
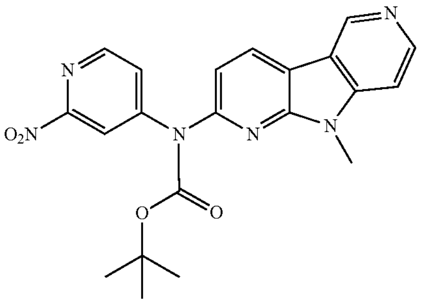,
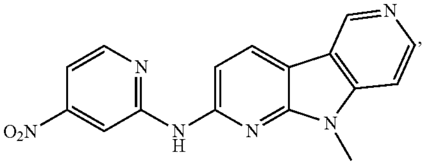,
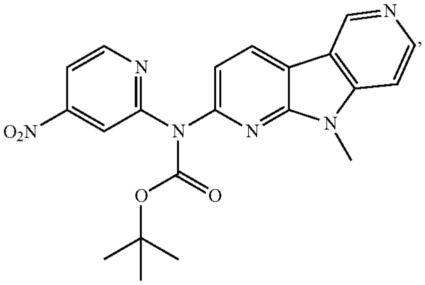,
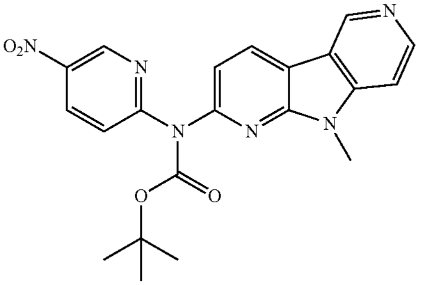,
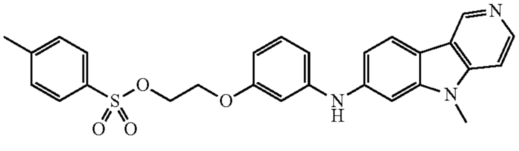,
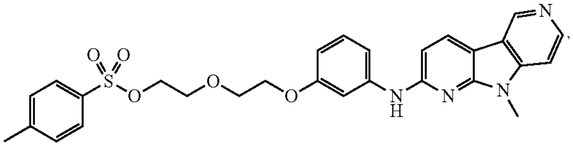,
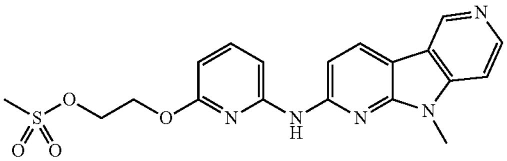,
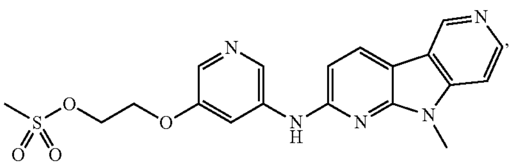,
-continued
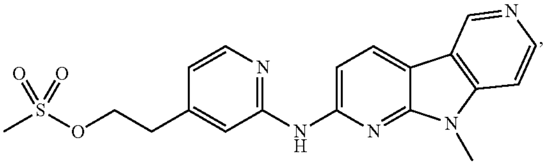,
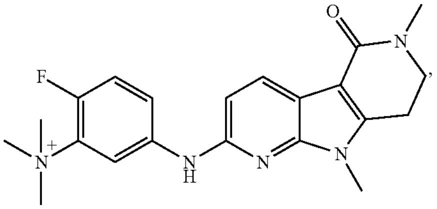,
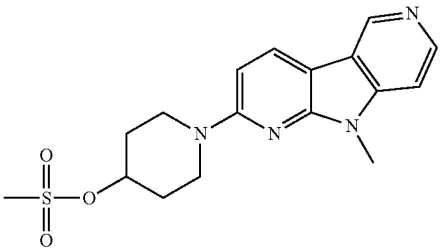,
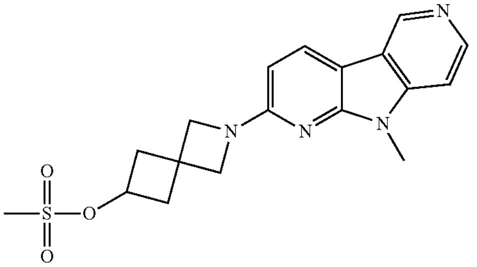,
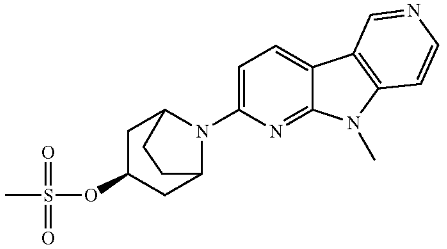,
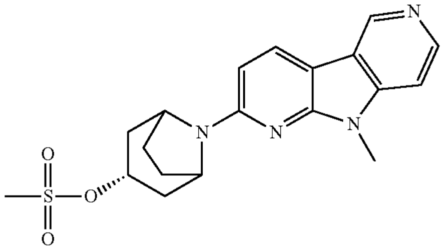,
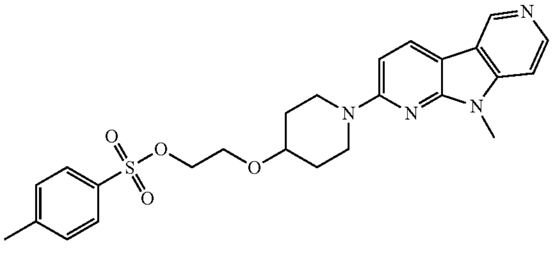, -continued
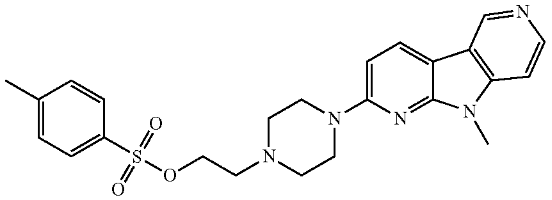
,
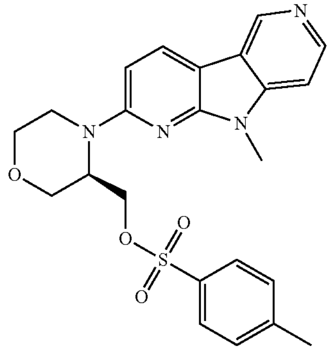
,
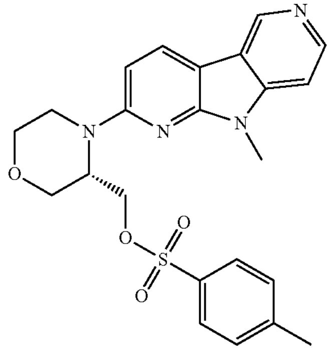
,
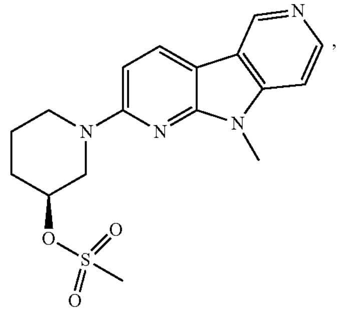
,
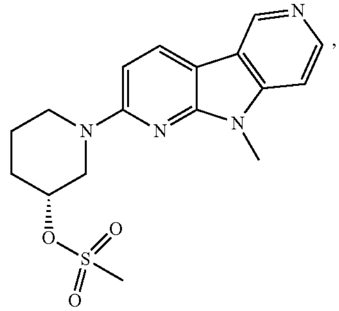
,
-continued
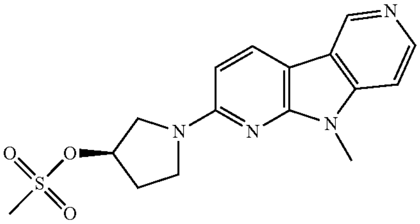
,
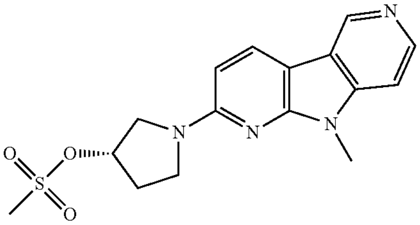
,
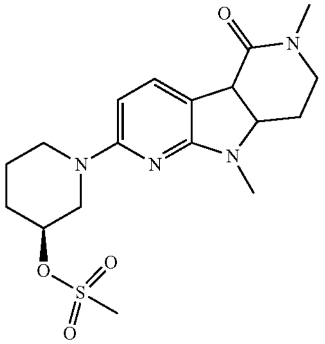
,
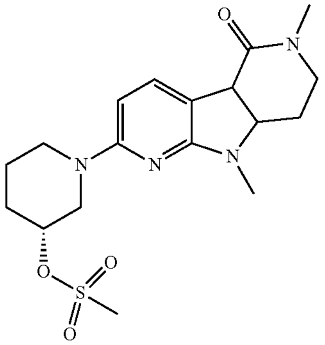
,
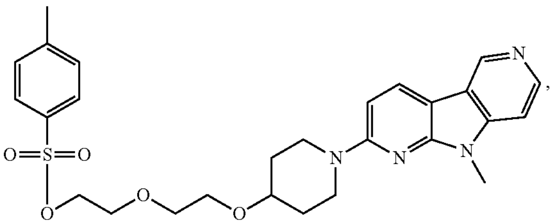
,
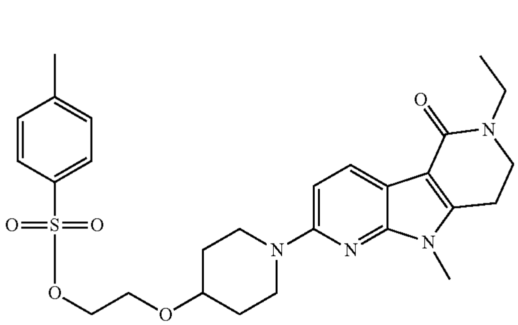
, -continued

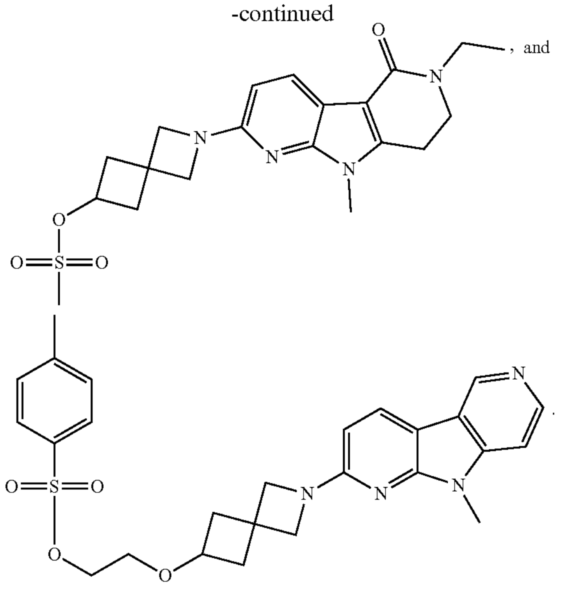

108. A method of preparing a compound according to any one of items 1 to 51, which is labeled by $^{18}F$, wherein the method comprises the steps of:
   (a) reacting a compound of formula (I*) or (II*) as defined in any one of items 98 to 106 with an $^{18}F$-fluorinating agent, so that the leaving group comprised in $R^{3*}$ is replaced by $^{18}F$; and
   (b) optionally removing the amine protecting group, if present.
109. The method according to item 108, wherein the $^{18}F$-fluorinating agent is selected from the group consisting of $H^{18}F$, alkali $^{18}F$-fluoride, alkaline earth $^{18}F$-fluoride, a tetraalkylammonium salt of $^{18}F$ and a tetraalkylphosphonium salt of $^{18}F$, preferably wherein the $^{18}F$-fluorinating agent is selected from the group consisting of $Cs^{18}F$, $K^{18}F$, and tetrabutylammonium [$^{18}F$]fluoride.
110. The method according to item 108 or 109, wherein the $^{18}F$-fluorinating agent is used in combination with a chelating agent.
111. The compound according to any one of items 1 to 44 which comprises $^{19}F$.
112. Use of the compound according to item 111 as an analytical standard or reference during manufacturing, quality control, release and clinical use of the corresponding $^{18}F$-analog.

Definitions

Within the meaning of the present application the following definitions apply:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl and isobutyl.

"Alkylene" refers to a divalent saturated, linear or branched organic moiety consisting of carbon and hydrogen atoms. Examples of suitable alkylene groups have 1 to 6 carbon atoms, preferably 1 to 4 carbon atoms, and include methylene, ethylene, propylene, isopropylene, n-butylene, t-butylene and isobutylene.

"Carbocyclyl" refers to a cyclic organic moiety consisting of carbon and hydrogen atoms. Examples of suitable carbocyclyl groups have 3 to 10 carbon atoms, preferably 3, 4, 5 or 6 carbon atoms. The carbocyclyl group can be unsaturated or saturated. The term "carbocyclyl" also covers aromatic cyclic organic moiety consisting of carbon and hydrogen atoms. Examples of the carbocyclyl group include cyclopentyl, cyclohexyl and phenyl.

"Heterocyclyl" refers to a carbocyclyl group as defined above in which at least one of the carbon atoms has been replaced by a heteroatom which is, e.g., selected from N, O or S, or heteroatom (e.g., N, O and/or S)-containing moiety. The heterocyclyl group can be unsaturated or saturated. It covers both heteroalkyl groups and heteroaryl groups. Examples include azetidine, pyrrolidine, pyrrole, tetrahydrofuran, furan, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, triazole, furazan, oxadiazoles, thiadiazole, dithiazole, tetrazole, piperidine, oxane, thiane, pyridine, pyran, thiopyran, piperazine, diazine (including pyrazine and pyrimidine), morpholine, oxazine, thiomorpholine, thiazine, dioxane, dioxine, dithiane, dithiine, triazine, trioxane, tetrazine, azepane, azepine, oxepane, oxepine, thiepane, thiepine.

Examples of possible heterocyclyl groups include azetidine, morpholine, piperazine, pyrrolidine, tetrahydrofuran, piperidine, etc. Examples of possible heteroaryl groups include pyridine, etc.

"Alkenyl" refers to an organic moiety consisting of carbon and hydrogen atoms which includes at least one double bond. Examples of suitable alkenyl groups have 2 to 6 carbon atoms, preferably 2 to 4 carbon atoms, and include propenyl and butenyl.

"Alkynyl" refers to an organic moiety consisting of carbon and hydrogen atoms which includes at least one triple bond. Examples of suitable alkynyl groups have 2 to 6 carbon atoms, preferably 2 to 4 carbon atoms, and include propinyl and butinyl.

"Aryl" refers to homocyclic aromatic organic moieties containing 1 or 2 rings consisting of carbon and hydrogen atoms which preferably have 6 to 12 carbon atoms, more preferably 5 or 6 carbon atoms. Examples are, but not limited to, phenyl, biphenyl, and naphthyl.

"Alkoxy" refers to the group —O-alkyl.

"Hal" or "halogen" refers to F, Cl, Br, and I. With respect to diagnostic and pharmaceutical applications, F (e.g., $^{19}F$ and $^{18}F$) is particularly preferred.

"Arylalkyl" refers to a group aryl-alkyl-.

"Carbocyclylalkyl" refers to a group carbocyclyl-alkyl-.

"Heterocyclylalkyl" refers to a group heterocyclyl-alkyl-.

"4- to 10-Membered ring system containing carbon atoms and optionally one or more heteroatoms selected from O, S, or N or optionally one or more heteroatom (e.g., N, O and/or S)-containing moieties" refers to ring system having 4 to 10 carbon atoms and optionally one or more heteroatoms selected from O, S, or N or optionally one or more heteroatom (e.g., N, O and/or S)-containing moieties in addition to the nitrogen atom which is shown in the ring system B. The term is also meant to include monocyclic, bicyclic, and polycyclic versions thereof. If more than one ring is present, the rings can be annelated, connected in a bridged manner or connected in a spiro manner. The ring(s) can be either carbocyclic or heterocyclic and can be saturated, unsaturated or aromatic. Examples of these groups include, but are not restricted to, azetidine (azacyclobutane), pyrrolidine (azacyclopentane), pyrrole, imidazolidine, pyrazolidine, imidazole, pyrazole, oxazolidine, isoxazolidine, oxazole, isoxazole, thiazolidine, isothiazolidine, thiazole, isothiazole, triazole, furazan, oxadiazoles, thiadiazole, dithiazole, tetrazole, imidazoline, piperidine (azacyclohexane), pyridine, piperazine, pyrrolidine, diazine (including pyrazine and pyrimidine), morpholine, thiomorpholine, thiazine, triazine, tetrazine, azepane, and azepine. Preferably the 4- to 10-membered ring containing carbon atoms and optionally one or more heteroatoms selected from O, S, or N or optionally one or more heteroatom (e.g., N, O and/or S)-containing moieties is selected from, imidazoline, dioxolane, piperidine, piperazine, pyrrolidine, tetrahydrofuran, dioxane, phenyl, pyridine, thiazole, diazines (including pyrazine and pyrimidine), and oxadiazoles, more preferably imidazoline, dioxolane, piperidine, piperazine, pyrrolidine, phenyl and pyridine. The 4- to 10-membered ring containing carbon atoms and optionally one or more heteroatoms selected from O, S, or N or optionally one or more heteroatom (e.g., N, O and/or S)-containing moieties can be attached at any available position. Preferably, the "4- to 10-membered ring system containing carbon atoms and optionally one or more heteroatoms selected from O, S, or N or optionally one or more heteroatom (e.g., N, O and/or S)-containing moieties" is a "5- to 8-membered ring containing carbon atoms and optionally one or more heteroatoms selected from O, S, or N or optionally one or more heteroatom (e.g., N, O and/or S)-containing moieties", more preferably it is a 4-, 5- or 6-membered (preferably saturated) ring containing carbon atoms and optionally one or more heteroatoms selected from O, S, or N. Specific examples are the 5- or 6-membered rings containing carbon atoms and optionally one or more heteroatoms selected from O, S, or N given in the above list. Even more preferably, it is a 6-membered, saturated ring containing carbon atoms and optionally one or more heteroatoms selected from O, S, or N. In a further embodiment, 6-membered bicyclic rings (such as 3-azabicyclo[3.1.0]hexane) or 7-membered spirocyclic rings (such as azaspiro[3.3]heptane, diazaspiro[3.3]heptane) or 8-membered bicyclic rings (such as azabicyclo[3.2.1]octane, diazabicyclo[3.2.1]octane) are preferred.

It is understood that in the case of ring B the ring must contain at least the nitrogen atom indicated in the general formula.

If more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties. In this embodiment, the 5- to 8-membered ring can be any 5- to 8-membered ring containing carbon atoms and optionally one or more heteroatoms selected from O, S, or N or optionally one or more heteroatom (e.g., N, O and/or S)-containing moieties. Examples thereof can be found in the list of examples given for the "4- to 10-membered ring system containing carbon atoms and optionally one or more heteroatoms selected from O, S, or N or optionally one or more heteroatom (e.g., N, O and/or S)-containing moieties", as well as in the lists of examples of the carbocyclyl, aryl, and heterocyclyl groups. The ring formed by two adjacent groups $R^3$ is preferably a 5- or 6-membered, saturated or unsaturated ring containing carbon atoms and optionally one or more heteroatoms selected from O, S, or N or optionally one or more heteroatom (e.g., N, O and/or S)-containing moieties. Specific examples of the 5- or 6-membered, saturated or unsaturated rings containing carbon atoms and optionally one or more heteroatoms selected from O, S, or N or optionally one or more heteroatom (e.g., N, O and/or S)-containing moieties are given in the above list. In all of these embodiments, the heteroatom is preferably N and/or O. In all of these embodiments, the ring preferably contains 0, 1, 2 or 3 heteroatom(s). In all of these embodiments, the ring preferably contains 0 or 1 heteroatom (e.g., N, O and/or S)-containing moieties.

Specific examples of the "5- to 8-membered ring containing carbon atoms and optionally one or more heteroatoms selected from O, S, or N or optionally one or more heteroatom (e.g., N, O and/or S)-containing moieties" include the 5- to 8-membered rings containing carbon atoms and optionally one or more heteroatoms selected from O, S, or N given in the above list. The 5- to 8-membered ring containing carbon atoms and optionally one or more heteroatoms selected from O, S, or N or optionally one or more heteroatom (e.g., N, O and/or S)-containing moieties can be attached at any available position. Preferably, the "5- to 8-membered ring containing carbon atoms and optionally one or more heteroatoms selected from O, S, or N or optionally one or more heteroatom (e.g., N, O and/or S)-containing moieties" is a 5- or 6-membered ring containing carbon atoms and optionally one or more heteroatoms selected from O, S, or N. Specific examples are the 5- or 6-membered rings containing carbon atoms and optionally one or more heteroatoms selected from O, S, or N given in the above list. More preferably, with respect to the ring B the "5- to 8-membered ring containing carbon atoms and optionally one or more heteroatoms selected from O, S, or N or optionally one or more heteroatom (e.g., N, O and/or S)-containing moieties" is a 6-membered, saturated ring containing carbon atoms and optionally one or more heteroatoms selected from O, S, or N. It is understood that in the case of ring B the ring must contain at least the nitrogen atom indicated in the general formula. Specific examples of the 6-membered, saturated rings containing carbon atoms and optionally one or more heteroatoms selected from O, S, or N are given in the above list. More preferably, with respect to the ring formed by two adjacent groups $R^3$ the "5- to 8-membered ring containing carbon atoms and optionally one or more heteroatoms selected from O, S, or N or optionally one or more heteroatom (e.g., N, O and/or S)-containing moieties" is a 5- or 6-membered, saturated or unsaturated ring containing carbon atoms and optionally one or more heteroatoms selected from O, S, or N or optionally one or more heteroatom (e.g., N, O and/or S)-containing moieties. Specific examples of the 5- or 6-membered, saturated or unsaturated rings containing carbon atoms and optionally one or more heteroatoms selected from O, S, or N or optionally one or more heteroatom (e.g., N, O and/or S)-containing moieties are given in the above list. In all of these embodiments, the heteroatom is preferably N and/or O. In all of these embodiments, the ring preferably contains 0, 1, 2 or 3 heteroatom(s). In all of these embodiments, the ring preferably contains 0 or 1 heteroatom (e.g., N, O and/or S)-containing moieties.

"Heteroatom-containing moieties" are moieties which contain e.g., N, O and/or S. Examples of such moieties include —C(O)—, —C(O)O— and —N($R^{50}$)— in which $R^{50}$ is, for each occurrence, independently selected from the group consisting of $R^{51}$, $S(O)_tNR^{51}R^{52}$, $S(O)_tR^{51}$, $C(O)OR^{51}$, $C(O)R^{51}C(=NR^{53})NR^{51}R^{52}$, $C(=NR^{51})NR^{52}R^{53}$, $C(=NOR^{51})R^{52}$ and $C(O)NR^{51}R^{52}$. Specific examples include —C(O)—, —O(O)O— and —N($R^{50}$)— in which $R^{50}$ is, for each occurrence, independently selected from the group consisting of H or $C_{1-4}$ alkyl.

For each occurrence, $R^{51}$ is each independently selected from the group consisting of: hydrogen, alkyl, carbocyclyl, carbocyclylalkyl, heterocyclyl, haloalkyl, heterocyclylalkyl, alkenyl, and alkynyl, wherein alkyl, carbocyclyl, carbocyclylalkyl, heterocyclyl, haloalkyl, heterocyclylalkyl, alkenyl, and alkynyl can be optionally substituted. In a preferred embodiment $R^{51}$ is hydrogen or alkyl.

For each occurrence, $R^{52}$ is each independently selected from the group consisting of: hydrogen, alkyl, carbocyclyl, carbocyclylalkyl, heterocyclyl, haloalkyl, heterocyclylalkyl, alkenyl, and alkynyl, wherein alkyl, carbocyclyl, carbocyclylalkyl, heterocyclyl, haloalkyl, heterocyclylalkyl, alkenyl, and alkynyl can be optionally substituted. In a preferred embodiment $R^{52}$ is hydrogen or alkyl.

For each occurrence, $R^{53}$ is each independently selected from the group consisting of: hydrogen and alkyl.

For each occurrence, t is 1, 2 or 3.

An "amine protecting group" is any protecting group which suitable for protecting an amine group during an envisaged chemical reaction. Examples of suitable protecting groups are well-known to a person skilled in the art. Examples thereof include but are not limited to carbamates, amides, imides, N-alkyl amines, N-aryl amines, imines and enamines. Suitable protecting groups are discussed, e.g., in the textbook Greene and Wuts, Protecting groups in Organic Synthesis, third edition, page 494-653, which is included herein by reference. Specific preferred examples of the amine-protecting groups include tert-butyloxycarbonyl (Boc), trimethylsilylethoxycarbonyl (Teoc), carbobenzyloxy (Cbz), p-methoxybenzyl carbonyl (Moz or MeOZ), 9-fluorenylmethyloxycarbonyl (Fmoc), acetyl (Ac), or trifluoroacetyl. Examples of possible positions of the amine protecting group for precursor compounds are shown in the following scheme:

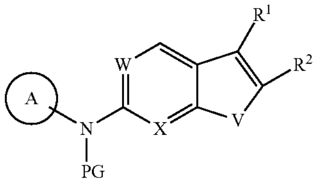

PG (amine protecting group)

Figure 7:
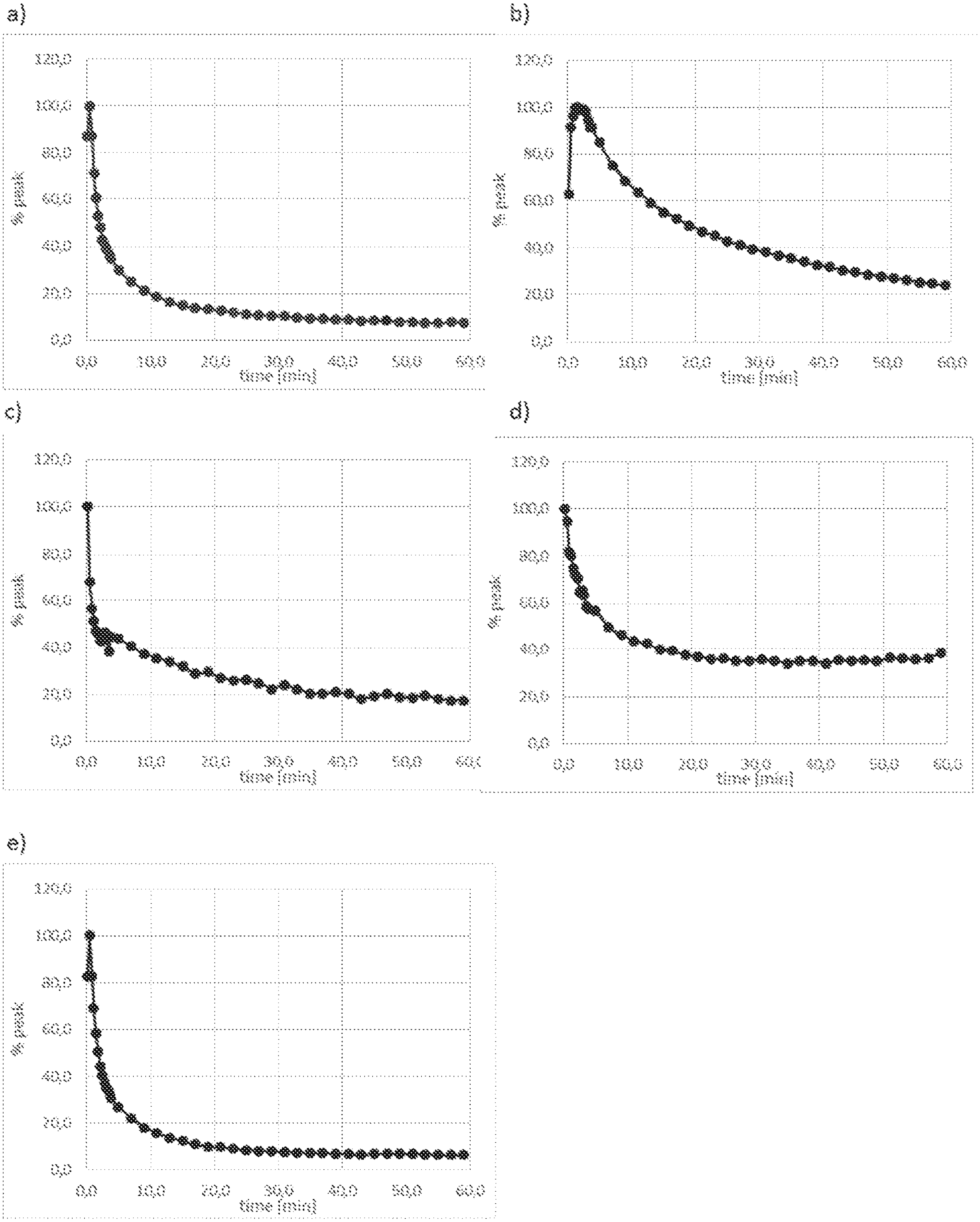
FIG. 7 shows the washout kinetics of the compounds: a) $^{18}$F-196, b) $^{18}$F-159, c) $^{18}$F-178, d) $^{18}$F-189, and e) $^{18}$F-54.
Figure 8:
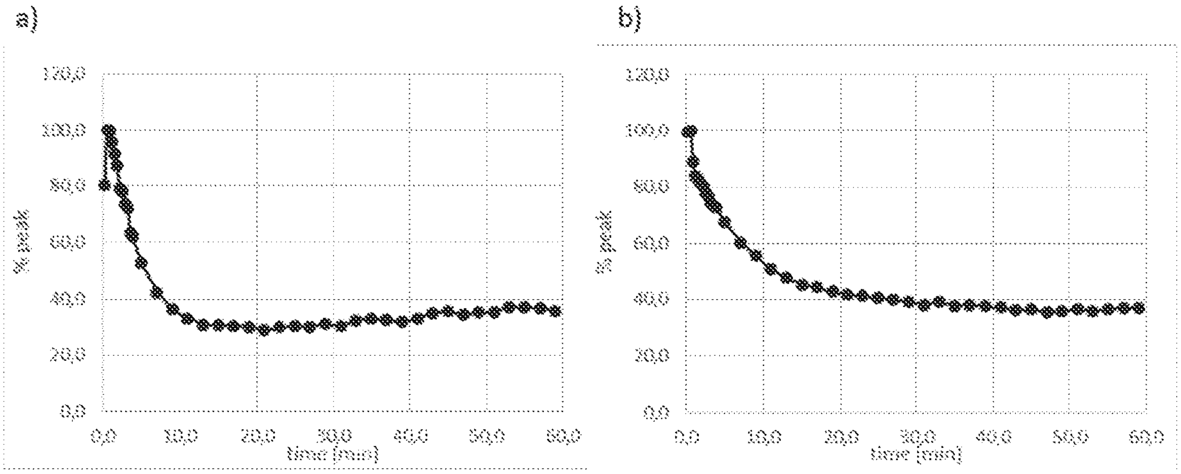
FIG. 8 shows the washout kinetics of the compounds: a) $^{18}$F-62, and b) $^{18}$F-157.
Figure 9:
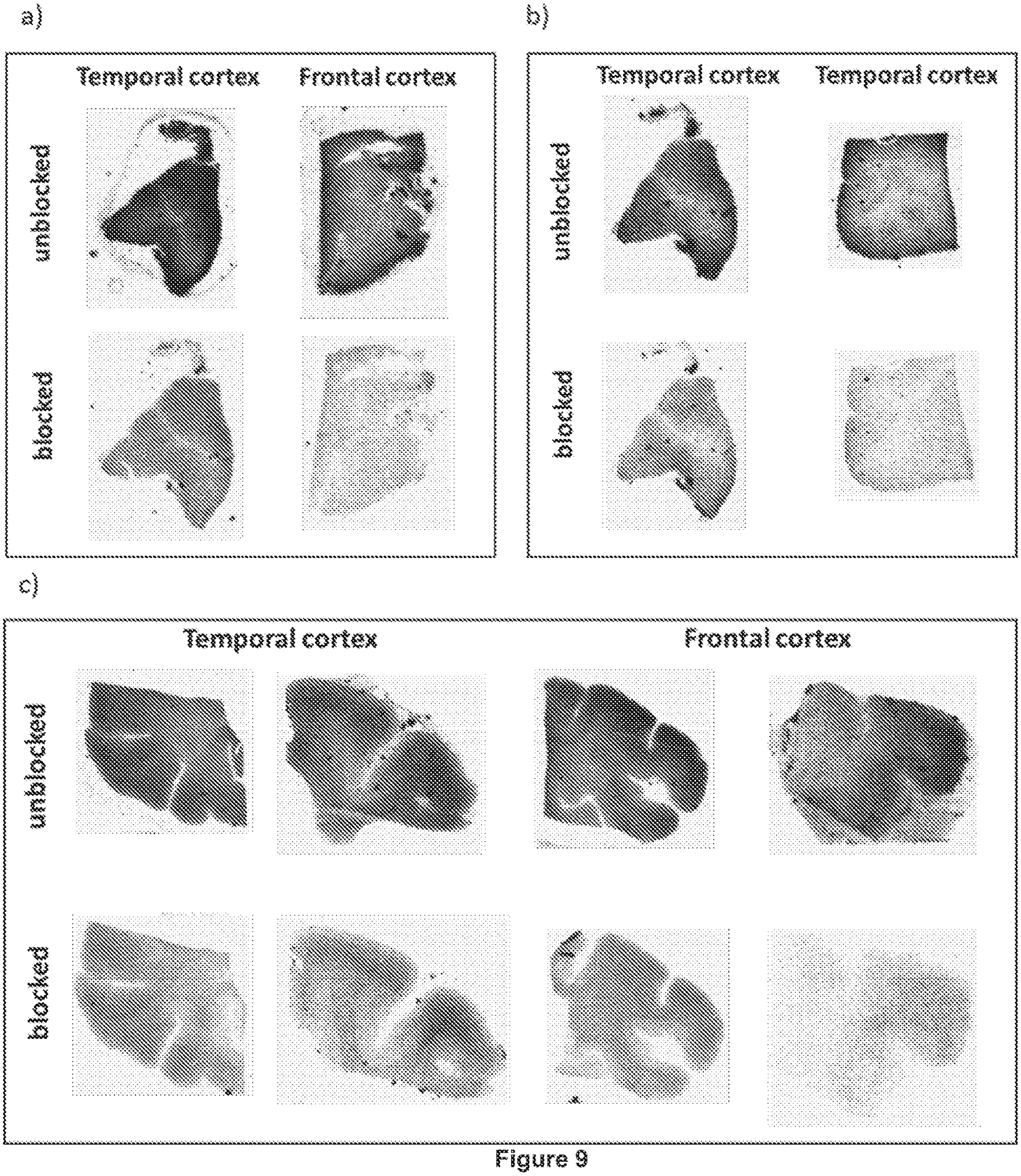
FIG. 9 shows the ex vivo autoradiograph on human brain sections. a) $^{18}$F-178, b) $^{18}$F-189, and c) $^{18}$F-161.
Figure 10:
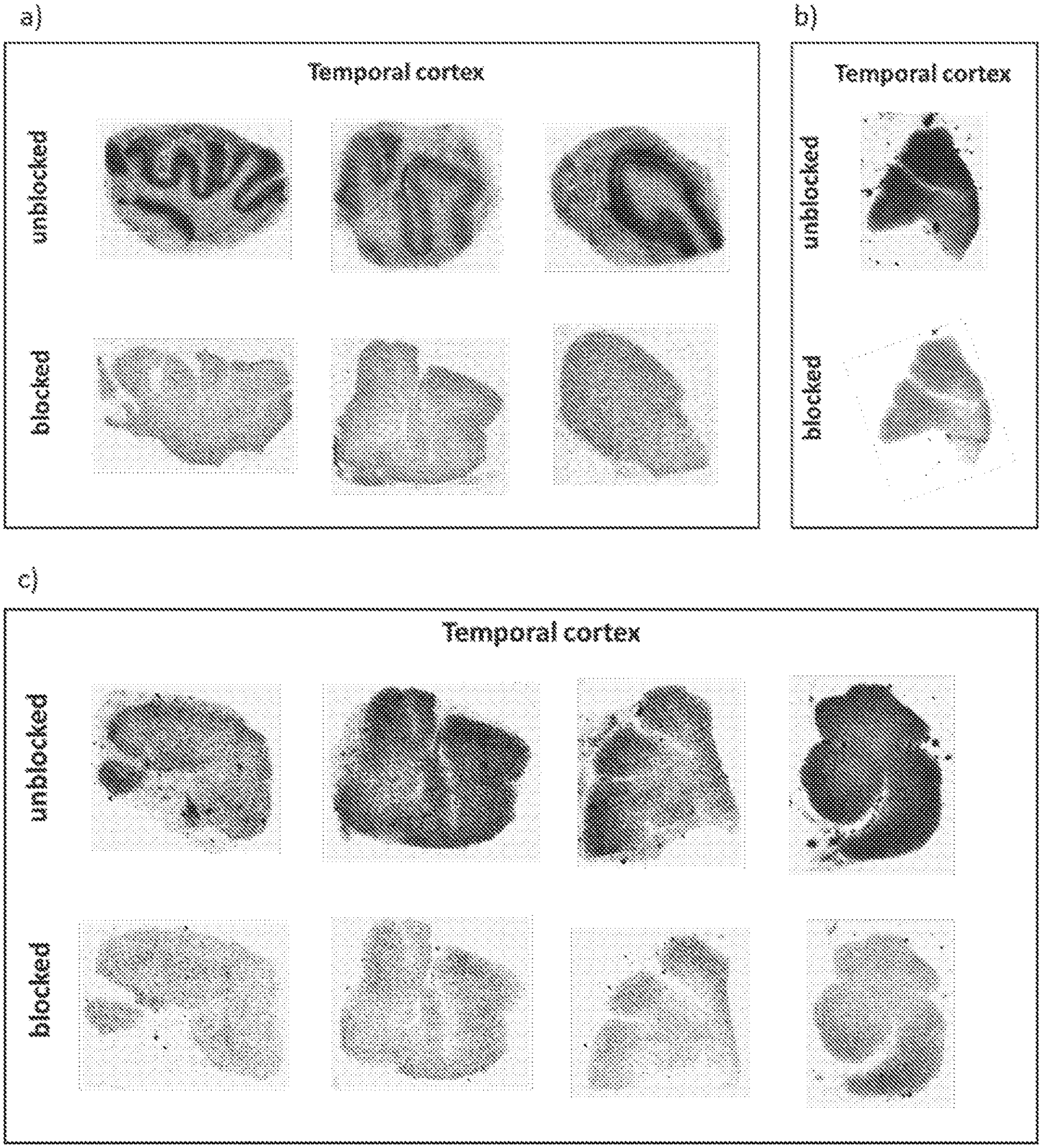
FIG. 10 shows the ex vivo autoradiograph on human brain sections. a) $^{18}$F-95, b) $^{18}$F-168, and c) $^{18}$F-146.
Figure 11:
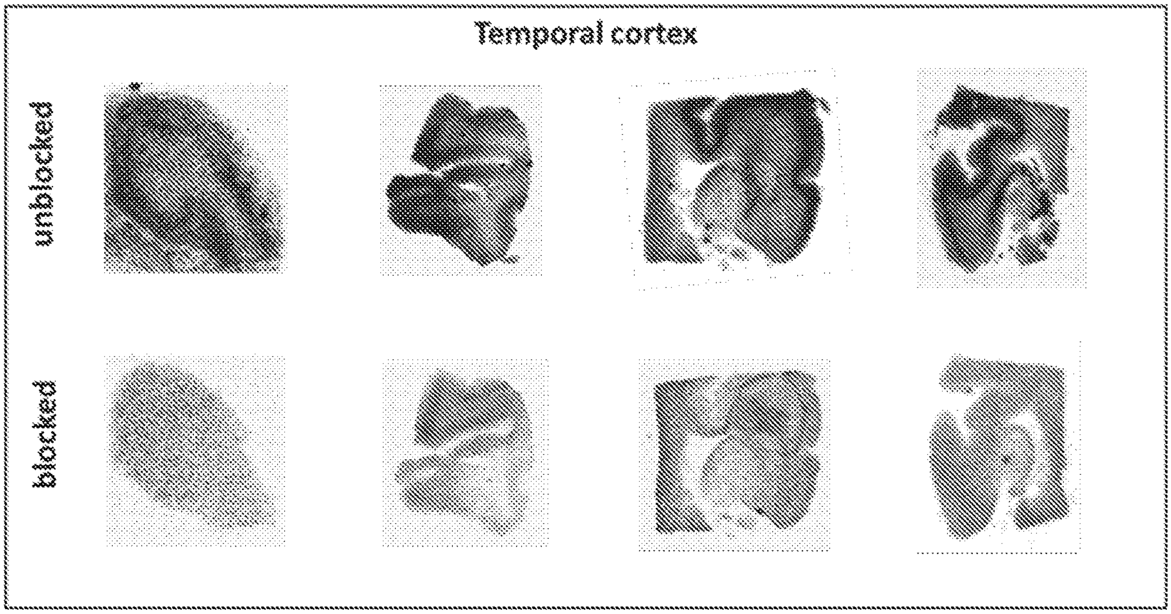
FIG. 11 shows the ex vivo autoradiograph on human brain sections. a) $^{18}$F-156, and b) $^{18}$F-159.
Figure 11:
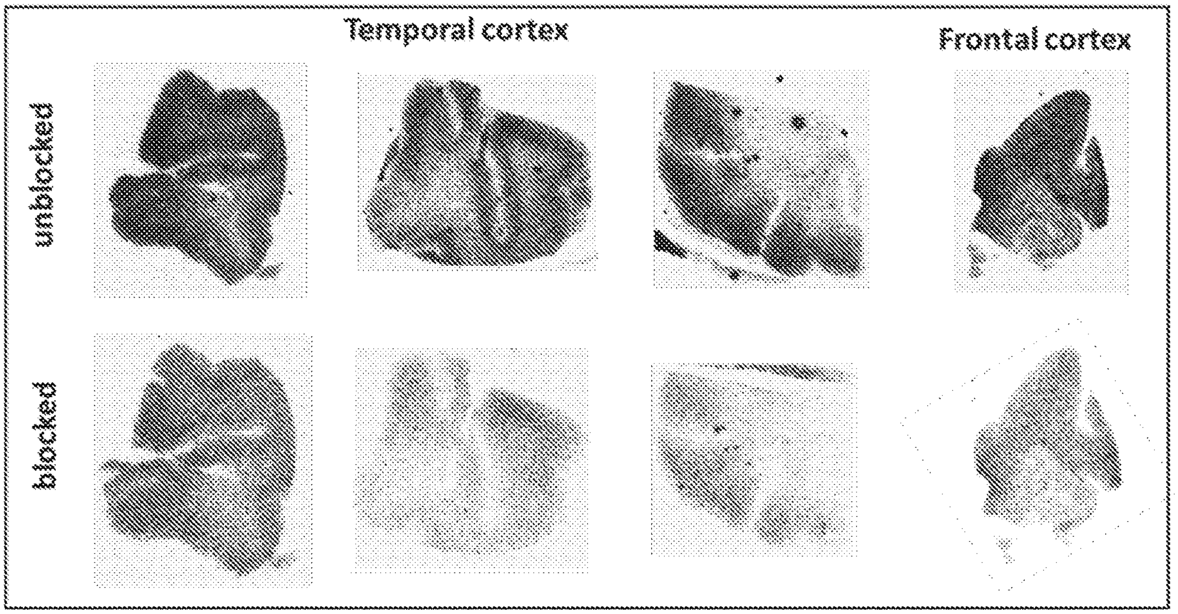
Figure 12:
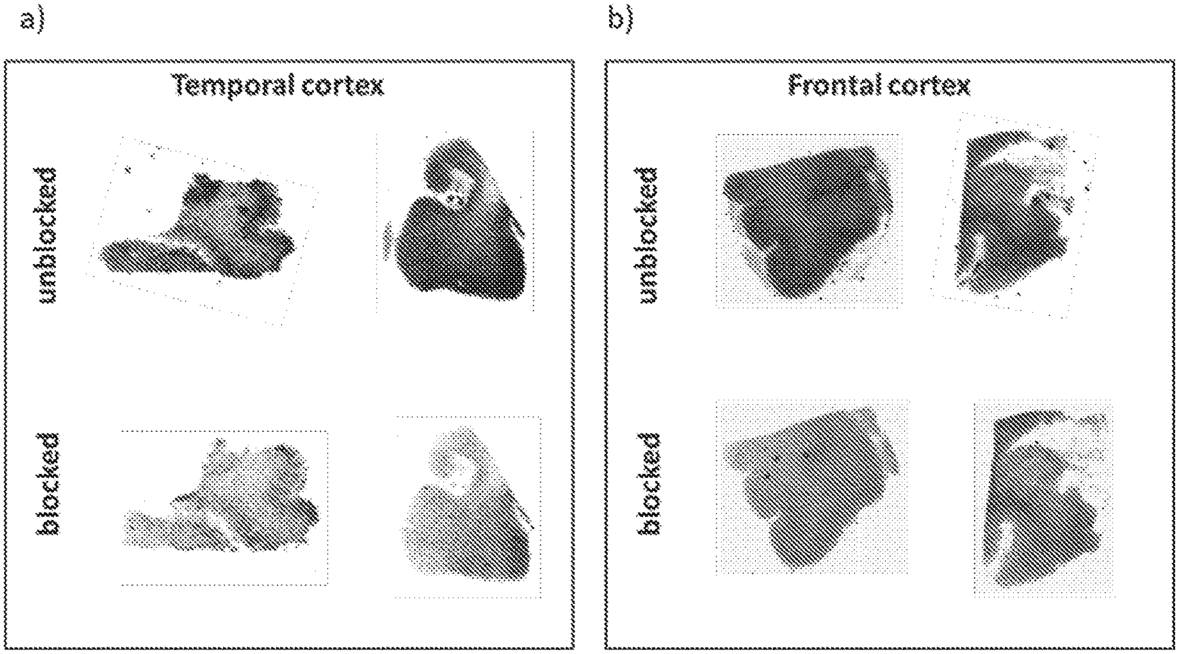
FIG. 12 shows the ex vivo autoradiograph on human brain sections. a) $^{18}$F-152, and b) $^{18}$F-160.

A "leaving group at a saturated carbon atom" (also referred to as $LG^2$) is any leaving group which can be attached to a saturated carbon atom and means an atom or group of atoms can be replaced by another atom or group of atoms. Examples are given e.g. in Synthesis (1982), pages 85 to 125, table 2 (p. 86; (the last entry of this table 2 needs to be corrected: "n-$C_4F_9S(O)_2$—O— nonaflat" instead of "n-$C_4H_9S(O)_2$—O— nonaflat"), Carey and Sundberg, Organische Synthese, (1995), pages 279 to 281, table 5.8; or Netscher, Recent Res. Dev. Org. Chem., 2003, 7, 71-83, schemes 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pages 15 to 50, particularly scheme 4 page 25, scheme 5 page 28, table 4 page 30, FIG. 7 page 33). Preferably, the "leaving group at a saturated carbon atom" is halogen (e.g., Br, I, Cl), an alkyl sulfonate leaving group, or an aryl sulfonate leaving group.

An "alkyl sulfonate leaving group" includes any group which comprises a —$OSO_2$—R group, with R being selected from the group consisting of $C_{1-4}$ alkyl and perfluoro($C_{1-4}$)alkyl. This includes but is not limited to methyl sulfonyloxy, trifluoromethyl sulfonyloxy and nonafluorobutyl sulfonyloxy.

An "aryl sulfonate leaving group" includes any group which comprises a —$OSO_2$—R group, with R being selected from the group consisting of aryl which can be optionally substituted by $C_{1-4}$ alkyl, halogen and nitro. This includes but is not limited to (4-methylphenyl) sulfonyloxy, (4-bromo-phenyl)sulfonyloxy, (4-nitro-phenyl) sulfonyloxy, (2-nitro-phenyl) sulfonyloxy, (4-isopropyl-phenyl) sulfonyloxy, (2,4,6-tri-isopropyl-phenyl) sulfonyloxy, (2,4,6-trimethyl-phenyl) sulfonyloxy, (4-tert-butyl-phenyl) sulfonyloxy and (4-methoxy-phenyl) sulfonyloxy.

In a more preferred embodiment, $LG^2$ is halogen or —$OSO_2$—R. In an even more preferred embodiment, $LG^2$ is —$OSO_2$—R, particularly, methyl sulfonyloxy, (4-methylphenyl) sulfonyloxy, or trifluoromethyl sulfonyloxy.

The term "leaving group suitable for aromatic radiofluorination" (also referred to as $LG^1$) refers to is any leaving group which is suitable for aromatic radiofluorination. Examples include halogen (e.g. Br, I or Cl), iodonium-aryl ($I^+$-aryl), tri($C_{1-4}$ alkyl)ammonium (preferably trimethylammonium), and nitro. In a preferred embodiment, $LG^1$ is selected from halogen, $NO_2$, and tri($C_{1-4}$ alkyl)ammonium.

In a more preferred embodiment $LG^1$ is nitro.

If a group is defined as being "optionally substituted" (unless defined otherwise), as chemically appropriate, it can have one or more substituents selected from -Hal, —CN, —OH, —(O—$CH_2CH_2$)$_n$—R, —($CH_2CH_2$—O)$_n$—R*, —($CH_2CH_2$—O)$_n$—($CH_2CH_2$)—R (with R═H or Hal and R*═H, $CHal_3$ or $CH_3$), —$C_{1-6}$ alkyl, —$C_{1-6}$ alkoxy, —$SO_2$-alkyl, —$NH_2$, —NH($C_{1-6}$ alkyl) or —N($C_{1-6}$ alkyl)$_2$, preferably -Hal, —CN, —OH, —(O—$CH_2CH_2$)$_n$—R, —($CH_2CH_2$—O)$_n$—R*, or —($CH_2CH_2$—O)$_n$—($CH_2CH_2$)—R, more preferably -Hal or —OH. In addition, typical substituents of the aryl groups include one or more alkyl groups, e.g. 1 or 2 alkyl groups, particularly 1 or 2 methyl groups.

Compounds of the present invention having one or more optically active carbons can exist as racemates and racemic mixtures, stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all salt forms, polymorphs, hydrates and solvates.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph. Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional nontoxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, 18$^{th}$ ed., Mack Publishing Company, Easton, Pa., 1990, p. 1445, the disclosure of which is hereby incorporated by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

Amyloid or amyloid-like proteins as used herein refers to proteins naturally present in the body or acquired during an infection that when, inappropriately folded, can start to erroneously interact with one another or with other cell components forming insoluble fibrils.

Amyloid or amyloid-like aggregates as used herein refer to insoluble fibrous aggregates sharing specific structural traits, e.g. containing β-sheet structures. They arise from inappropriately folded amyloid or amyloid-like proteins and play a role in various neurodegenerative disorders. Amyloid aggregates as used herein refer to extracellular aggregates. Amyloid-like aggregates as used herein refer to intracellular inclusions.

Tau as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitiriation, sumoylation and oxidation.

Neurofibrillary Tangles (NFTs) as used herein refer to insoluble aggregates of the hyperphosphorylated tau protein containing paired helical filaments and straight filaments. Their presence is a hallmark of AD and other diseases known as tauopathies.

The preferred definitions given in the "Definition"-section apply to all of the embodiments described below unless stated otherwise.

DETAILED DESCRIPTION OF THE INVENTION

The compounds of the present invention will be described in the following. It is to be understood that all possible combinations of the following definitions are also envisaged.

In one embodiment, the present invention relates to a compound of formula (I):

(I)

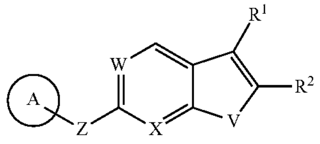

and all detectably labeled derivatives, stereoisomers, racemic mixtures, pharmaceutically acceptable salts, hydrates, solvates and polymorphs thereof.

A preferred embodiment of the compound of formula (I) is

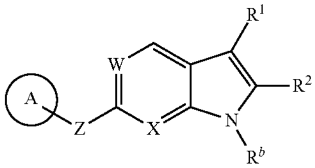

Another preferred embodiment of the compound of formula (I) is selected from

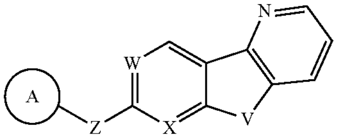

,

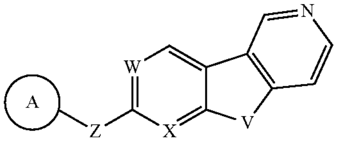

,

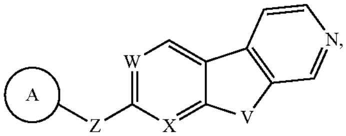

,

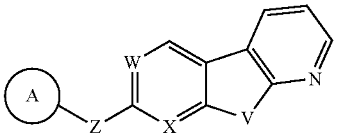

.

A further preferred embodiment of the compound of formula (I) is

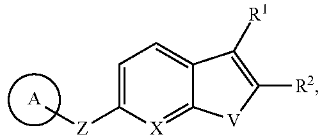

, such as

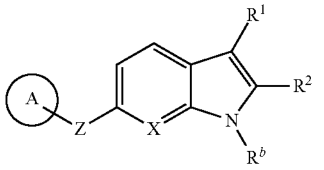

Examples thereof include

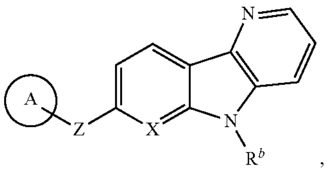

,

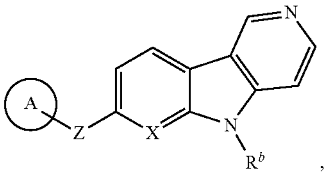

,

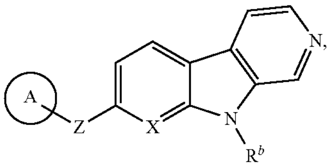

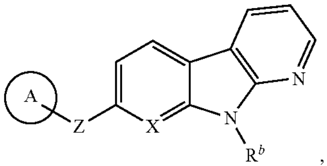

,

In one preferred embodiment, the compound of formula (I) is

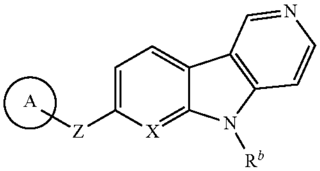

In a further preferred embodiment, the compound of formula (I) is selected from

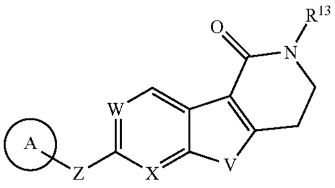

-continued

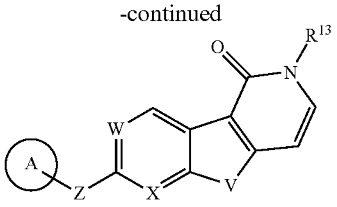

In a further preferred embodiment, the compound of formula (I) is selected from

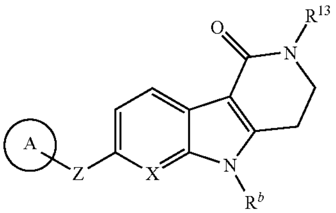

or

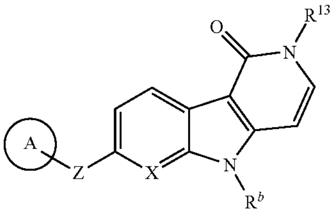

In a further preferred embodiment, the compound of formula (I) is

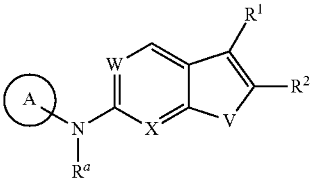

Examples thereof include

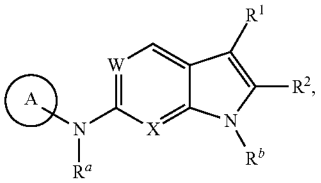

such as

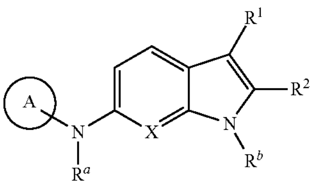

In a further preferred embodiment, the compound of formula (I) is selected from

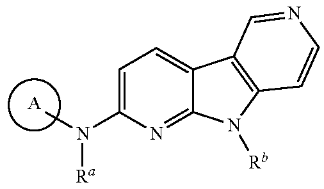

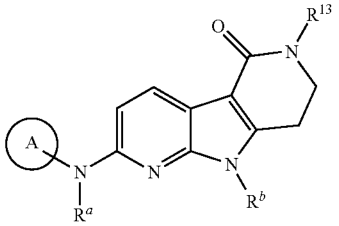

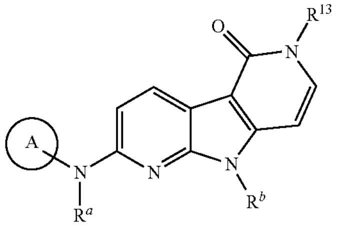

The following definitions of

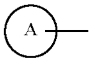

apply to the compounds of formula (I) and its preferred embodiments.

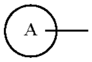

is selected from the group consisting of a pyridine ring, a phenyl ring, an azole ring and a thiazole ring, wherein the pyridine ring, the phenyl ring, the azole ring and the thiazole ring can be attached at any available position of the respective ring to the moiety Z, and wherein

can be optionally substituted by one or more substituents $R^3$.

In one embodiment,

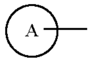

is selected from the group consisting of a pyridine ring

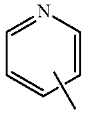

and a phenyl ring

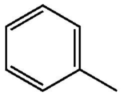, wherein the pyridine ring

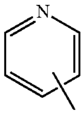

can be attached at any available position of the pyridine ring to the moiety Z, and wherein

can be optionally substituted by one or more substituents $R^3$.

In a further embodiment,

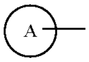

is selected from the group consisting of an azole ring and a thiazole ring, wherein the azole ring and the thiazole ring can be attached at any available position of the respective ring to the moiety Z and

can be optionally substituted by one or more substituents $R^3$.

In one preferred embodiment,

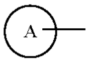

is a pyridine ring

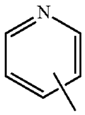, wherein

can be optionally substituted by one or more substituents $R^3$. This pyridine ring can be attached at any available position to Z, including

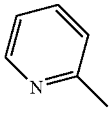, 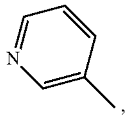, and 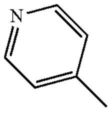, and wherein

can be optionally substituted by one or more substituents $R^3$.

In a further preferred embodiment,

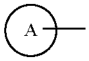

is a phenyl ring

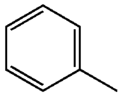, and wherein

can be optionally substituted by one or more substituents $R^3$.

In one preferred embodiment,

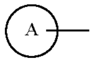

is an azole ring, wherein

can be optionally substituted by one or more substituents $R^3$. The azole ring can be either a pyrazole ring

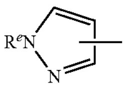

or an imidazole ring

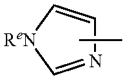.

The pyrazole ring can be attached at any available position to Z, including

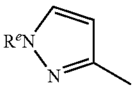, 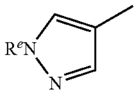, and 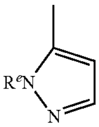, and wherein

can be optionally substituted by one or more substituents $R^3$. The imidazole ring can be attached at any available position to Z, including

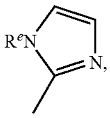, 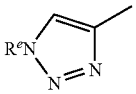, and 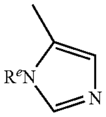, and wherein

can be optionally substituted by one or more substituents $R^3$.

In one preferred embodiment,

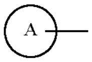

is a thiazole group

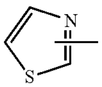, wherein

can be optionally substituted by one or more substituents $R^3$. This thiazole ring can be attached at any available position to Z, including

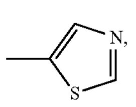

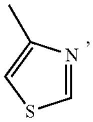

and

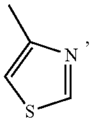

and wherein

can be optionally substituted by one or more substituents $R^3$.

In a further embodiment, the present invention refers to a compound of formula (II):

(II)

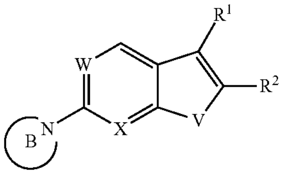

and all detectably labeled derivatives, stereoisomers, racemic mixtures, pharmaceutically acceptable salts, hydrates, solvates and polymorphs thereof.

A preferred embodiment of the compound of formula (II) is

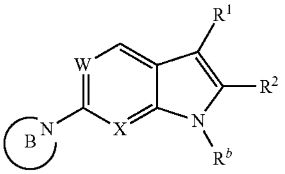

In another preferred embodiment, the compound of formula (II) is selected from

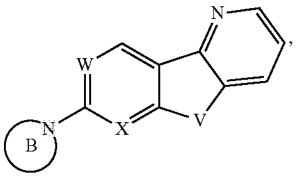

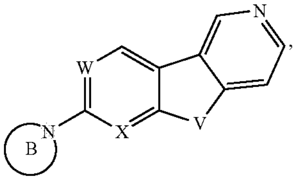

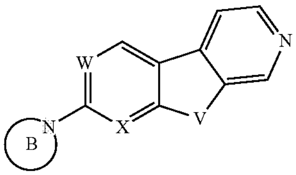

and

-continued

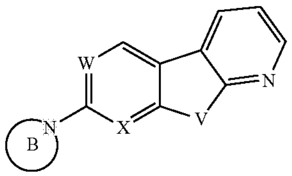

In one preferred embodiment, the compound of formula (II) is

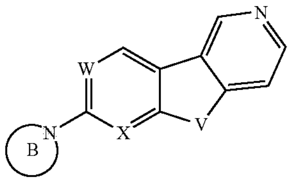

In one preferred embodiment, the compound of formula (II) is selected from:

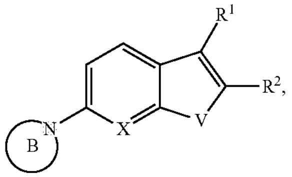

such as

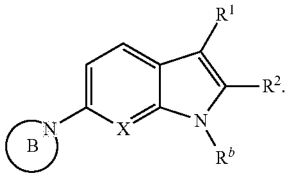

Examples thereof include

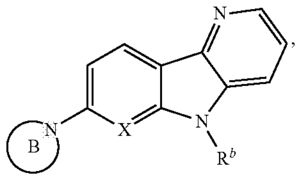

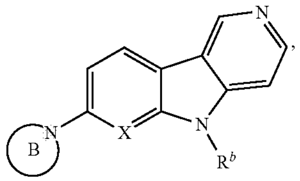

-continued

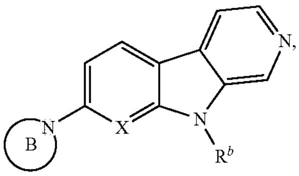

and

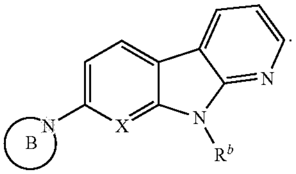

In one preferred embodiment, the compound of formula (II) is preferably

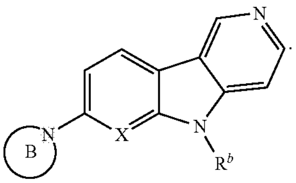

In a further preferred embodiment, the compound of formula (II) is selected from

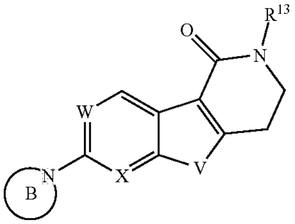

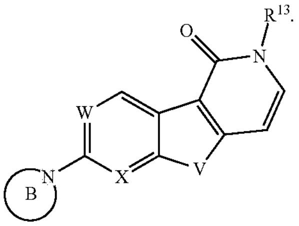

In yet a further preferred embodiment, the compound of formula (II) is a compound of the formula.

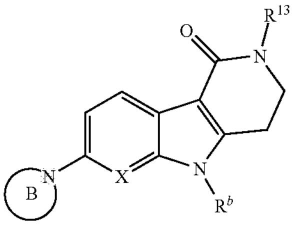

or

-continued

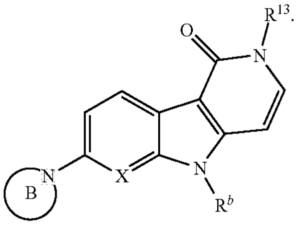

In one preferred embodiment, the compound of formula (II) is selected from

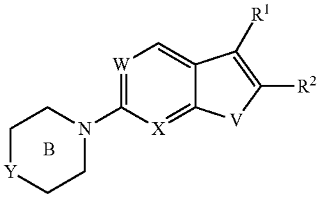

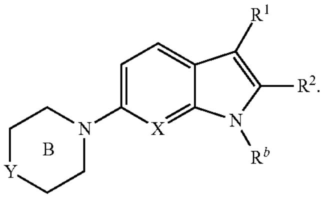

In a further preferred embodiment, the compound of formula (II) is selected from:

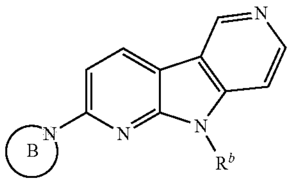

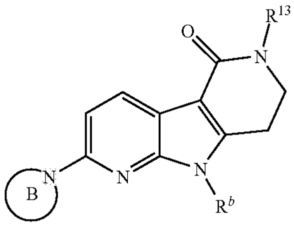

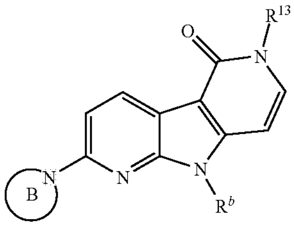

The following definitions of

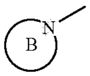

apply to the compounds of formula (II) and its preferred embodiments.

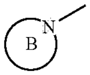

is a 4 to 10-membered ring system containing carbon atoms and optionally one or more heteroatoms selected from O, S, or N or optionally one or more heteroatom (e.g., N, O and/or S)-containing moieties and wherein the 4- to 10-membered ring system may be optionally substituted by one or more $R^3$. Preferably

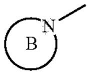

is a 4- to 8-membered ring system containing carbon atoms and optionally one or more heteroatoms selected from O, S, or N or optionally one or more heteroatom (e.g., N, O and/or S)-containing moieties, wherein the 4- to 8-membered ring system may be optionally substituted by one or more $R^3$. More preferably,

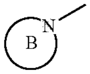

is a 4- to 8-membered saturated ring system containing carbon atoms, wherein the 4- to 8-membered ring system may be optionally substituted by one or more $R^3$. In a further preferred embodiment,

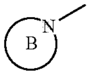

is a 5- to 8-membered bicyclic or spirocyclic ring system containing carbon atoms and optionally one or more heteroatoms selected from O or N and wherein the bicyclic or spirocyclic ring may be optionally substituted by one or more $R^3$.

In these definitions, the ring system can be monocyclic, bicyclic, and polycyclic. If more than one ring is present, the rings can be annelated, connected in a bridged manner or connected in a spiro manner.

In one embodiment,

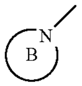

is a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be optionally substituted by one or more $R^3$. In a preferred embodiment,

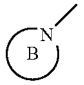

is a 6-membered ring containing carbon atoms and optionally one or more heteroatoms selected from O, S, or N or optionally one or more heteroatom (e.g., N, O and/or S)-containing moieties and wherein the 6-membered ring may be optionally substituted by one or more $R^3$. One example of

 is 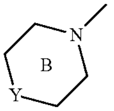, which may be optionally substituted by one or more $R^3$. A more preferred embodiment of

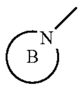 is 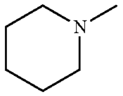,

In a further embodiment,

is selected from the group consisting of

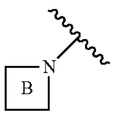, 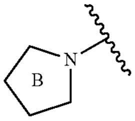, 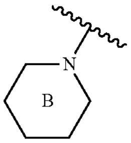,

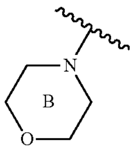, 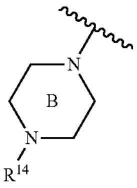, 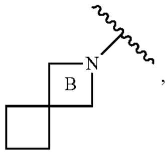,

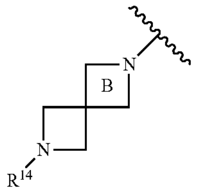, 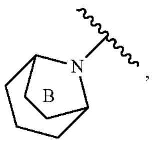,

-continued

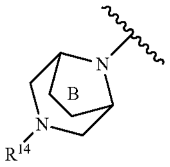

, and

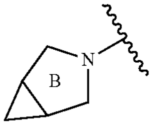

;

wherein $R^{14}$ is as defined herein and the ring system B can be optionally substituted in any available position of any of its rings by one or more $R^3$. In these embodiments, $R^3$ can be, for instance, F, $^{18}F$, optionally substituted alkyl, optionally substituted —O— alkyl, —(O—$CH_2CH_2$)$_n$—$R^d$, or —$NR^{10}R^{11}$, where the optional substituents are, e.g., selected from Hal (e.g., F, $^{18}F$) and OH, more preferably $R^3$ comprises or is F or $^{18}F$.

The following definitions apply to the formulae (I) and (II) and their preferred embodiments, as appropriate.

V is selected from the group consisting of $NR^b$, O and S, preferably V is —N($R^b$)—, more preferably —N(alkyl)-, most preferably —N($CH_3$)—.

W is selected from the group consisting of $CR^c$ and N, preferably W is $CR^c$, more preferably W is CH.

X is selected from the group consisting of $CR^c$ and N, preferably X is N.

Y is $NR^{14}$, O or $CHR^{15}$, preferably Y is $CHR^{15}$.

As appropriate, W is preferably $CR^c$ (more preferably CH), X is preferably N, V is preferably $NR^b$ (more preferably N-alkyl) and Z is preferably —N($R^a$)—.

$R^{14}$ is selected from the group consisting of hydrogen, —($CH_2CH_2$—O)$_n$—$R^f$, —($CH_2CH_2$—O)$_n$—($CH_2CH_2$)—$R^d$, alkyl, carbocyclyl and heterocyclyl, wherein alkyl, carbocyclyl and heterocyclyl can be optionally substituted. Preferably $R^{14}$ is selected from the group consisting of hydrogen, alkyl and aryl, wherein alkyl and aryl can be optionally substituted (particularly with Hal), more preferably $R^{14}$ is hydrogen or alkyl which can be optionally substituted (particularly with Hal (e.g., $^{18}F$ or $^{19}F$).

$R^{15}$ is independently selected from the group consisting of hydrogen and $R^3$, preferably $R^{15}$ is independently selected from the group consisting of hydrogen, halogen, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl, carbocyclyl and heterocyclyl, wherein alkyl, carbocyclyl and heterocyclyl can be optionally substituted, more preferably $R^{15}$ is halogen, alkyl which can be optionally substituted by Hal, —(O—$CH_2CH_2$)$_n$—$R^d$, —($CH_2CH_2$—O)$_n$—$R^f$, or —($CH_2CH_2$—O)$_n$—($CH_2CH_2$)—$R^d$.

Z is selected from the group consisting of —N($R^a$)— and —O—, preferably Z is —N($R^a$)—, more preferably —NH—.

$R^a$ is selected from the group consisting of hydrogen, and alkyl, preferably $R^a$ is hydrogen or alkyl, more preferably $R^a$ is hydrogen. The alkyl group can be optionally substituted as indicated in the definitions section above. Preferred substituents include Hal (e.g., $^{18}F$ or $^{19}F$).

$R^b$ is selected from the group consisting of hydrogen, alkyl, —($CH_2CH_2$—O)$_n$—H and —($CH_2CH_2$—O)$_n$-alkyl, preferably $R^b$ is selected from the group consisting of hydrogen, alkyl, and haloalkyl, more preferably $R^b$ is hydrogen or alkyl, more preferably $R^b$ is alkyl such as methyl. The alkyl group can be optionally substituted as indicated in the definitions section above. Preferred substituents include Hal (e.g., $^{18}F$ or $^{19}F$).

$R^c$ is selected from the group consisting of hydrogen, alkyl, and halogen, preferably $R^c$ is selected from the group consisting of hydrogen, alkyl, haloalkyl and halogen, more preferably $R^c$ is hydrogen or halogen, more preferably $R^c$ is hydrogen. The alkyl group can be optionally substituted as indicated in the definitions section above. Preferred substituents include Hal (e.g., $^{18}F$ or $^{19}F$).

$R^d$ is selected from the group consisting of halogen, H, OH and O-alkyl, preferably $R^d$ is H or halogen, more preferably $R^d$ is H or F. The alkyl group can be optionally substituted as indicated in the definitions section above. Preferred substituents include Hal (e.g., $^{18}F$ or $^{19}F$).

$R^e$ is selected from the group consisting of hydrogen, —($CH_2CH_2$—O)$_n$—$R^f$, —($CH_2CH_2$—O)$_n$—($CH_2CH_2$)—$R^d$, alkyl, carbocyclyl and heterocyclyl, wherein alkyl, carbocyclyl and heterocyclyl can be optionally substituted. Preferably, $R^e$ is hydrogen or alkyl which can be optionally substituted (most preferably optionally substituted by Hal (e.g., $^{18}F$ or $^{19}F$)).

$R^f$ is selected from the group consisting of H and alkyl.

$R^1$ and $R^2$ together form a 6-membered aromatic ring containing carbon atoms and optionally one or more N atoms or $R^1$ and $R^2$ together form a 6-membered ring containing an amide moiety —C(O)—N($R^{13}$)—, wherein the 6-membered aromatic ring or the 6-membered ring containing an amide moiety formed by $R^1$ and $R^2$ can be optionally substituted by $R^{12}$. Examples are also evident from preferred embodiments shown above.

For each occurrence, $R^3$ is independently selected from the group consisting of halogen, —CN, —O—$R^{10}$, —S—$R^{10}$, —$NO_2$, —$NR^{10}R^{11}$, —$CONR^{10}R^{11}$, —N($R^{10}$)—C(O)—$R^{11}$, —C(O)O—$R^{10}$, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted. Preferably, for each occurrence, $R^3$ is independently selected from the group consisting of halogen, —CN, —O—$R^{10}$, —$NR^{10}R^{11}$, —(O—$CH_2CH_2$)$_n$—$R^d$, —($CH_2CH_2$—O)$_n$—$R^f$, —($CH_2CH_2$—O)$_n$—($CH_2CH_2$)—$R^d$, alkyl and heterocyclyl, wherein alkyl and heterocyclyl can be optionally substituted. In these definitions, the indicated groups can be optionally substituted as specified in the definitions section above. Preferred substituents include halogen (e.g., $^{18}F$ or $^{19}F$), OH, —(O—$CH_2CH_2$)$_n$—$R^d$ and alkyl.

In a more preferred embodiment, for each occurrence, $R^3$ is independently selected from the group consisting of halogen (e.g., $^{18}F$ or $^{19}F$)), —CN, —O-alkyl, —OH, —NH— alkyl, —N-(alkyl)$_2$, —(O—$CH_2CH_2$)$_n$—$R^d$ (with n=1 to 3 and $R^d$=H or halogen, preferably F), —($CH_2CH_2$—O)$_n$—$R^f$ (with n=1 to 3 and $R^f$=H), —($CH_2CH_2$—O)$_n$—($CH_2CH_2$)—$R^d$ (with n=1 to 3 and $R^d$=H or halogen, preferably $^{18}F$ or $^{19}F$), alkyl and heterocyclyl (preferably morpholino), wherein alkyl and heterocyclyl can be optionally substituted by halogen (preferably F), OH and —(O—$CH_2CH_2$)$_n$—$R^d$, most preferably by halogen (e.g., $^{18}F$ or $^{19}F$).

In another embodiment, for each occurrence, $R^3$ is independently selected from the group consisting of halogen, CN, —O—$R^{10}$, —$NR^{10}R^{11}$, —$CONR^{10}R^{11}$, —N($R^{10}$)—C(O)—$R^{11}$, —C(O)O—$R^{10}$, —(O—$CH_2CH_2$)$_n$—$R^d$, —($CH_2CH_2$—O)$_n$—($CH_2CH_2$)—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted. Preferably, for each occurrence, $R^3$ is independently selected from the group consisting of halogen, —CN, —O—$R^{10}$, —$NR^{10}R^{11}$, —(O—$CH_2CH_2$)$_n$—

$R^d$, —$(CH_2CH_2$—$O)_n$—$(CH_2CH_2)$—$R^d$, alkyl and heterocyclyl, wherein alkyl and heterocyclyl can be optionally substituted. In a more preferred embodiment, for each occurrence, $R^3$ is independently selected from the group consisting of halogen (preferably $^{18}F$ or $^{19}F$), —CN, —O—alkyl, —NH— alkyl, —N-$(alkyl)_2$, —(O—$CH_2CH_2)_n$—$R^d$, —$(CH_2CH_2$—$O)_n$—$(CH_2CH_2)$—$R^d$ (with n=1 to 3 and $R^f$=H or halogen, preferably $^{18}F$ or $^{19}F$), alkyl and heterocyclyl (preferably morpholino), wherein alkyl and heterocyclyl can be optionally substituted by halogen (preferably $^{18}F$ or $^{19}F$).

In preferred a embodiment, $R^3$ comprises or is $^{19}F$ or $^{18}F$.

If more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted. In a preferred embodiment, two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted. In one preferred embodiment, the heteroatom is O. In a further preferred embodiment, the heteroatom is N. Examples of the ring A with two adjacent groups $R^3$ which form a 5-membered ring include but are not limited to:

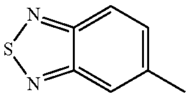
,
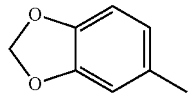
and
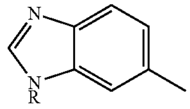

wherein R is H or alkyl. In a preferred embodiment, the ring B does not have two adjacent groups $R^3$.

With respect to

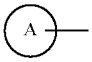
, $R^3$ is preferably —F, —$^{18}F$, —CN, —O-alkylene-F, —O-alkylene-$^{18}F$, alkyl, —$(O\text{-alkylene})_n F$, and —$(O\text{-alkylene})_n$-$^{18}F$, wherein alkylene is a $C_{1-6}$ alkylene and n is as defined above.

In a preferred embodiment

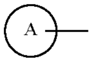

is substituted and is selected from the group consisting of

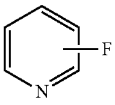
,
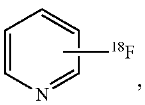
,
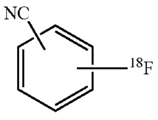
,

-continued

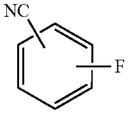
,
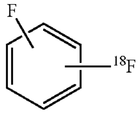
,
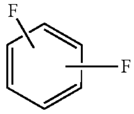
,
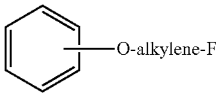
,
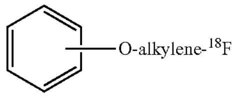
,
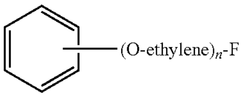
,
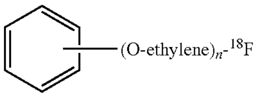
,
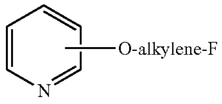
,
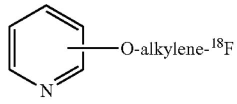
,
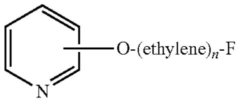
,
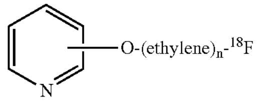
,
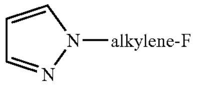
,
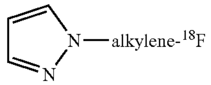
, and
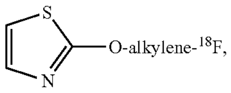

wherein n=2 to 5, preferably 2 to 3 and wherein the respective rings can be attached at any available position to the moiety Z.

In a preferred embodiment,

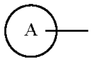

is selected from the group consisting of

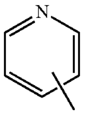
, and
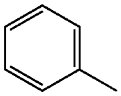
, which is preferably at least substituted by $^{18}F$—, F—, $^{18}F$-alkylene-O—, F-alkylene-O— (wherein alkylene is preferably a $C_{1-6}$ alkylene such as ethylene), $^{18}F$—$(CH_2CH_2$—$O)_n$— or $^{18}F$—$(CH_2CH_2$—$O)_n$— (wherein n is 1 to 5).

With respect to

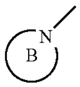
, $R^3$ is preferably —F, —$^{18}F$, -alkylene-F, -alkylene-$^{18}F$, —O-alkylene-F, —O— alkylene-$^{18}F$, —$(O\text{-alkylene})_n$-F, and —$(O\text{-alkylene})_n$-$^{18}F$, wherein alkylene is a $C_{1-6}$ alkylene and n is as defined above.

In a preferred embodiment

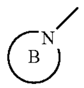

is substituted and is selected from the group consisting of:

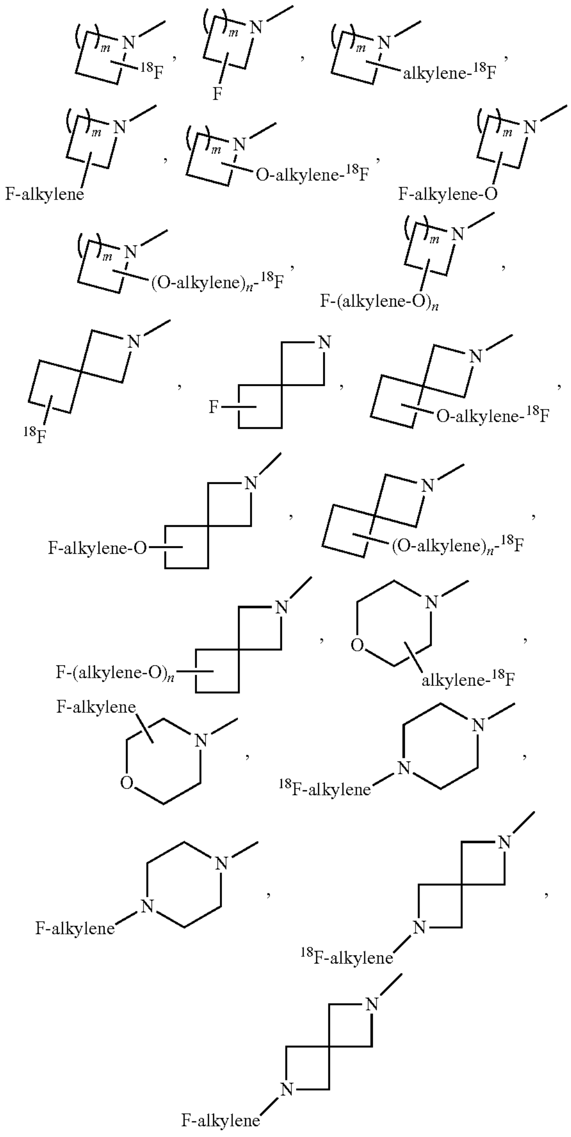

wherein m is preferably 1 to 3, more preferably 2 or 3, and n is preferably 2 to 5, more preferably 2 or 3 and alkylene is preferably ethylene.

In a further preferred embodiment,

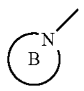

is selected from the group consisting of

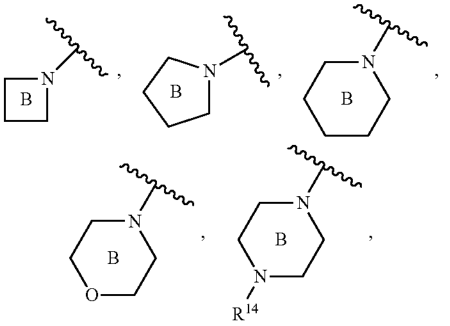

which is preferably at least substituted by $^{18}F$—, F—, $^{18}F$-alkylene-, F-alkylene-, $^{18}F$-alkylene-O—, F-alkylene-O— (wherein alkylene is preferably a $C_{1-6}$ alkylene such as ethylene), $^{18}F—(CH_2CH_2—O)_n—$ or $^{18}F—(CH_2CH_2—O)_n—$ (wherein n is 1 to 5)

For each occurrence, $R^{10}$ and $R^{11}$ are each independently selected from the group consisting of: hydrogen, alkyl, carbocyclyl, carbocyclylalkyl, heterocyclyl, heterocyclylalkyl, wherein alkyl, carbocyclyl, carbocyclylalkyl, heterocyclyl, heterocyclylalkyl, can be optionally substituted. In a preferred embodiment, for each occurrence, $R^{10}$ and $R^{11}$ are each independently selected from the group consisting of hydrogen and alkyl, wherein alkyl can be optionally substituted. The indicated groups can be optionally substituted as specified in the definitions section above. Preferred substituents include Hal (e.g., $^{18}F$ or $^{19}F$), and OH.

For each occurrence, $R^{12}$ is independently selected from the group consisting of halogen, CN, —O—$R^{10}$, —$NR^{10}R^{11}$, —$CONR^{10}R^{11}$, —$N(R^{10})$—C(O)—$R^{11}$, —C(O)O—$R^{10}$, $—(CH_2CH_2—O)_n—R^1$, $—(CH_2CH_2—O)_n—(CH_2CH_2)—R^d$, alkyl, carbocyclyl, carbocyclylalkyl, heterocyclyl, heterocyclylalkyl, wherein alkyl, carbocyclyl, carbocyclylalkyl, heterocyclyl, heterocyclylalkyl, can be optionally substituted. In a preferred embodiment, for each occurrence, $R^{12}$ is independently selected from the group consisting of hydrogen, halogen, $—(CH_2CH_2—O)_n—R^f$, $—(CH_2CH_2—O)_n—(CH_2CH_2)—R^d$ and alkyl, wherein alkyl can be optionally substituted. The indicated groups can be optionally substituted as specified in the definitions section above. Preferred substituents include Hal (e.g., $^{18}F$ or $^{19}F$), and OH.

For each occurrence, $R^{13}$ is independently selected from the group consisting of hydrogen, —$CONR^{10}R^{11}$, —C(O)O—$R^{10}$, $—(CH_2CH_2—O)_n—R^f$, $—(CH_2CH_2—O)_n—(CH_2CH_2)—R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted. In a preferred embodiment, for each occurrence, $R^{13}$ is independently selected from the group consisting of hydrogen, $—(CH_2CH_2—O)_n—R^f$, $—(CH_2CH_2—O)_n—(CH_2CH_2)—R^d$, and optionally substituted alkyl. The indicated groups can be optionally substituted as specified in the definitions section above. Preferred substituents include Hal (e.g., $^{18}F$ or $^{19}F$), and OH.

For each occurrence, n is 1, 2, 3 4 or 5, preferably n is 1, 2, 3, or 4, more preferably n is 2 or 3.

Examples of possible optional substituents for the alkyl, carbocyclyl, carbocyclylalkyl, heterocyclyl, heterocyclylalkyl, alkenyl, and alkynyl include, but are not limited to, -Hal, —CN, —OH, $—(O—CH_2CH_2)_n—R$, $—(CH_2CH_2—O)_n—R^*$, $—(CH_2CH_2—O)_n—(CH_2CH_2)—R$ (with R═H or Hal and R*═H, $CHal_3$ or $CH_3$), —$C_{1-6}$ alkyl, —$C_{1-6}$ alkoxy, —$SO_2$-alkyl, —$NH_2$, —$NH(C_{1-6}$ alkyl) or —$N(C_{1-6}$ alkyl$)_2$, preferably -Hal, —CN, —OH, —$(O—CH_2CH_2)_n$—R, —$(CH_2CH_2—O)_n$—R*, or —$(CH_2CH_2—O)_n$—$(CH_2CH_2)$—R, more preferably -Hal or —OH. In this context, Hal is preferably $^{18}F$ or $^{19}F$. In addition, typical substituents of the aryl groups include one or more alkyl groups, e.g. 1 or 2 alkyl groups, particularly 1 or 2 methyl groups.

Some preferred compounds of formula (I) include

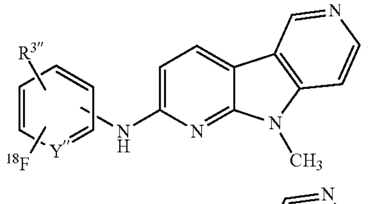
,

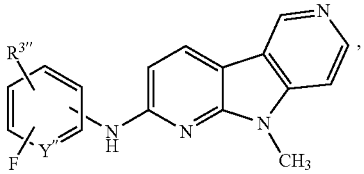
,

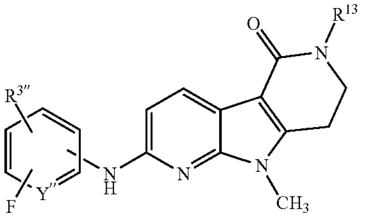
,

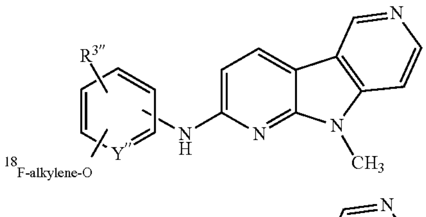
,

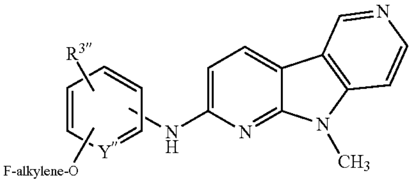
,

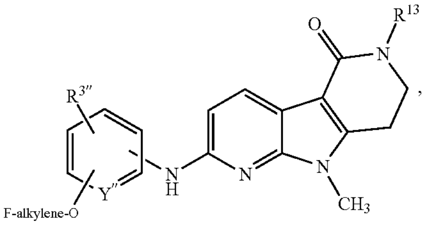
,

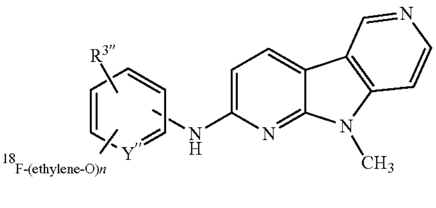
,

-continued

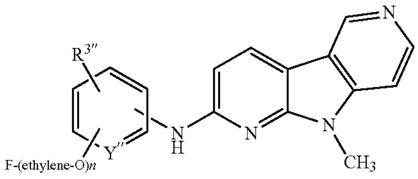
,

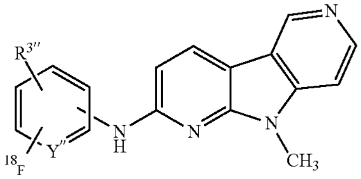
,

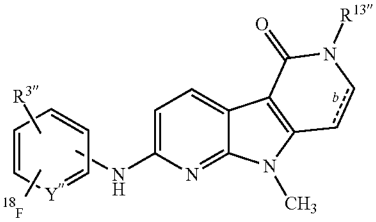
,

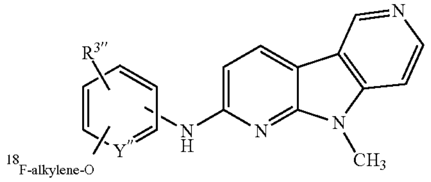
,

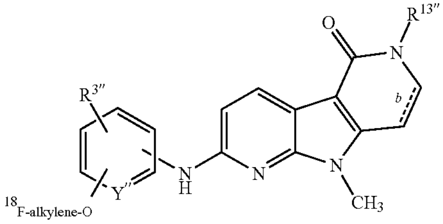
,

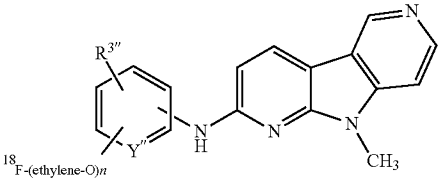
,

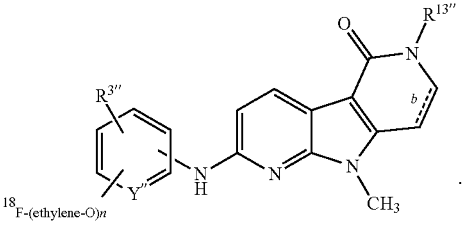
.

In these formulae, $\overset{b}{\cdots\cdots}$ is a double or single bond;

Y" is N or CH;

$R^{3''}$ is $R^3$ or hydrogen, preferably $R^{3''}$ is hydrogen, halogen, hydroxy, methoxy, difluoromethoxy, morpholino, alkyl, cyano, nitro, trifluoromethyl, optionally substituted alkyl, optionally substituted —O-alkyl, —$(O—CH_2CH_2)_n$—$R^d$, or —$NR^{10}R^{11}$, in which the optional substituents are preferably selected from the group consisting of F and $^{18}F$; more preferably $R^{3''}$ is hydrogen, fluorine or cyano
$R^{13''}$ is $R^{13}$, preferably $R^{13''}$ is hydrogen, methyl, or ethyl;
n is 2 to 5;
m is 1 to 3;
alkylene is a $C_{1-6}$ alkylene group, preferably alkylene is ethylene; and
$R^3$, $R^d$, $R^{10}$, $R^{11}$ and $R^{13}$ are as defined above.
Preferred compounds of formula (I) are
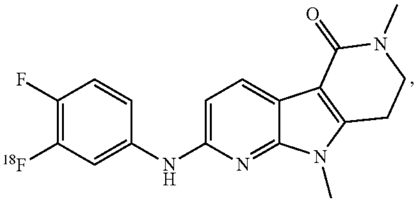
,
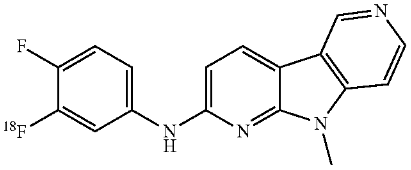
,
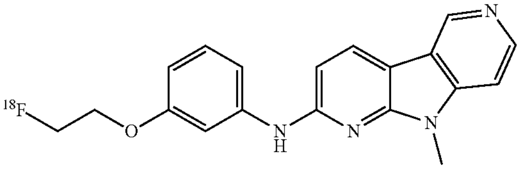
,
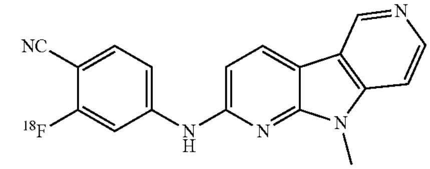
,
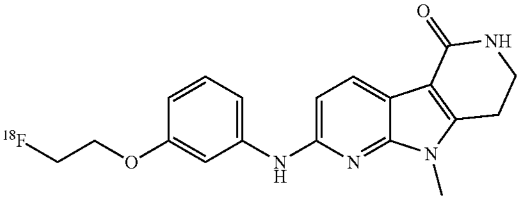
,
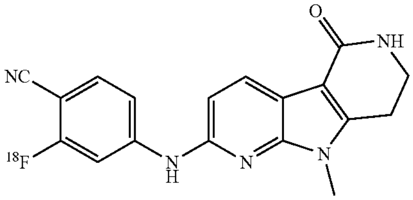
,
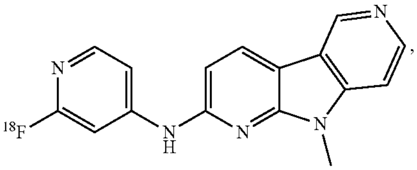
,
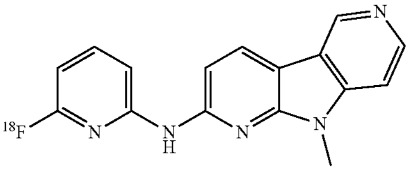
,
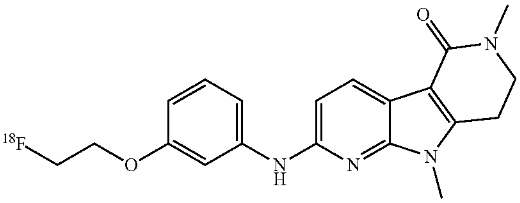
,
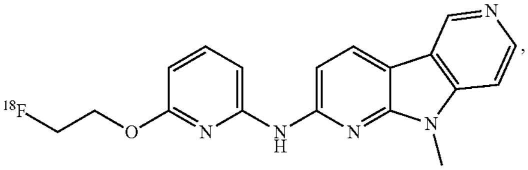
,
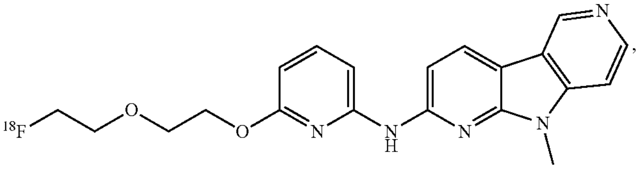
,
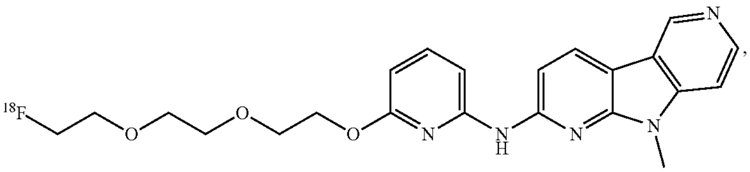
,
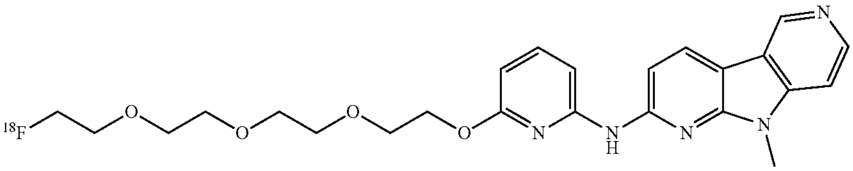
, -continued
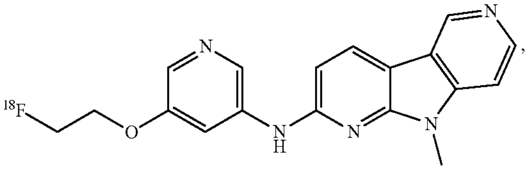
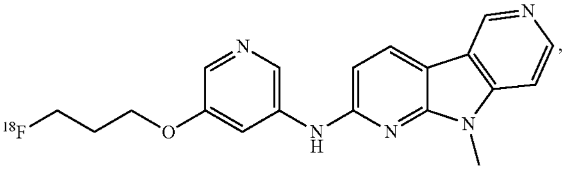
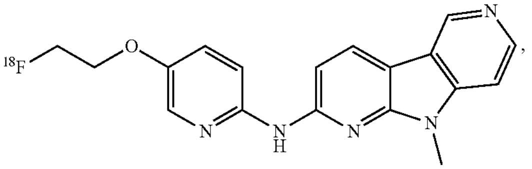
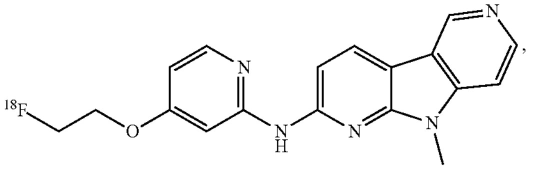
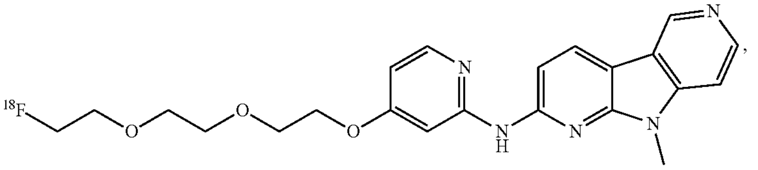
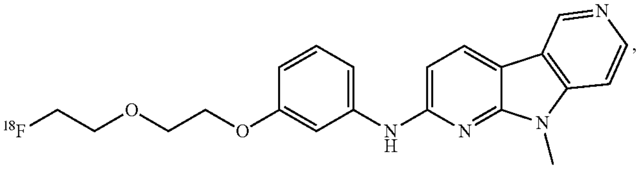
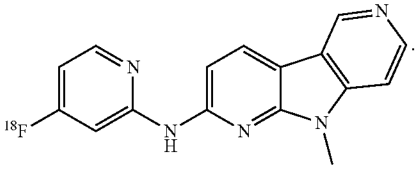
The corresponding $^{19}F$ analogs are also preferred.
Some preferred compounds of formula (II) include
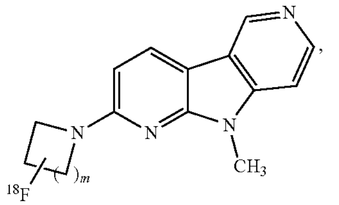
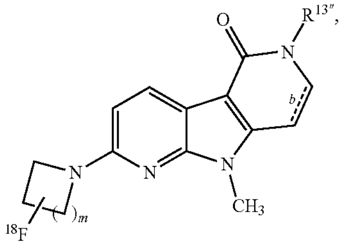
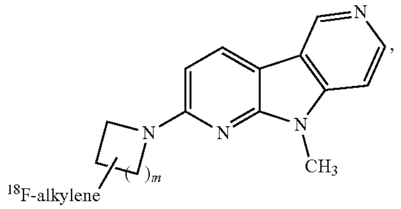
-continued
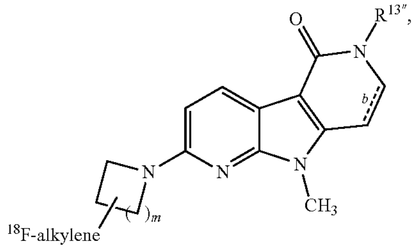
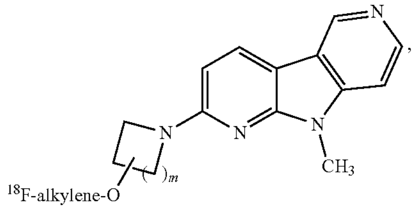
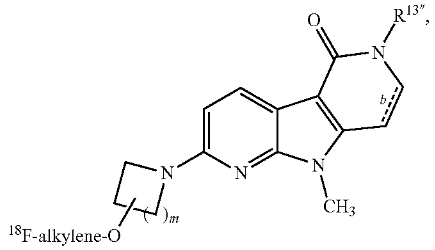
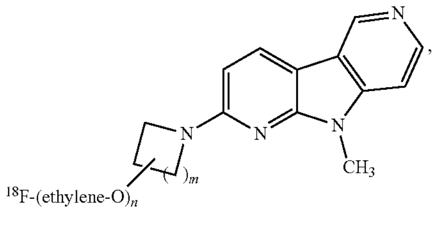

-continued
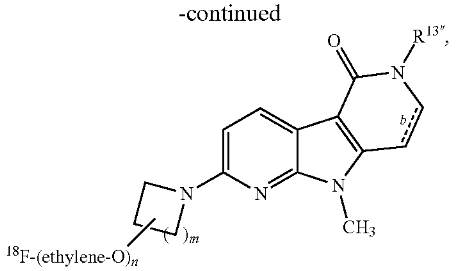
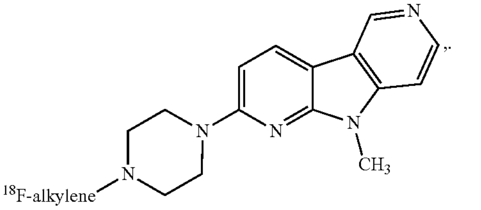
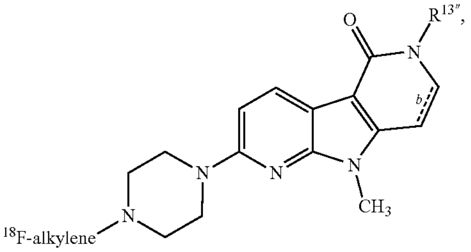
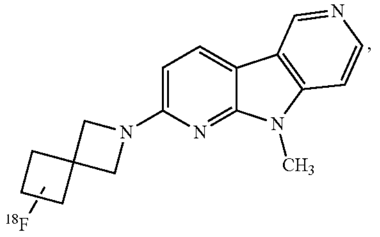
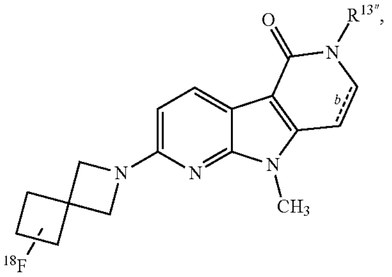
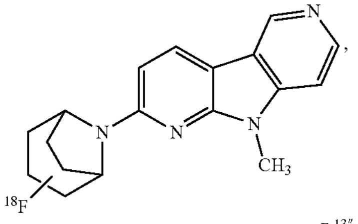
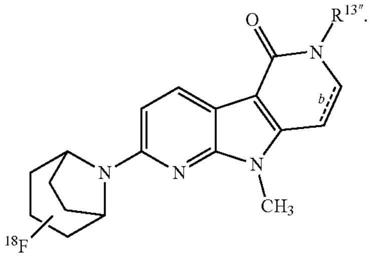
The corresponding $^{19}F$ analogs are also preferred.
In these formulae,
$R^{13''}$ is $R^{13}$, preferably $R^{13''}$ is hydrogen, methyl, or ethyl;
n is 2 to 5;
m is 1 to 3;
$\overset{b}{\cdots}$ is a single bond or a double bond;
alkylene is a $C_{1-6}$ alkylene group, preferably alkylene is methylene or ethylene.
Preferred compounds of formula (II) are
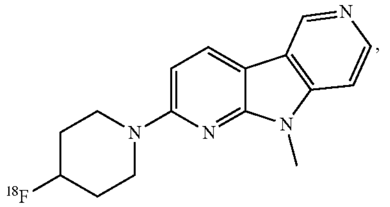
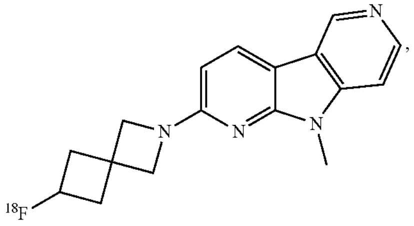
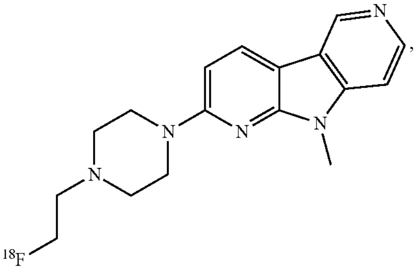
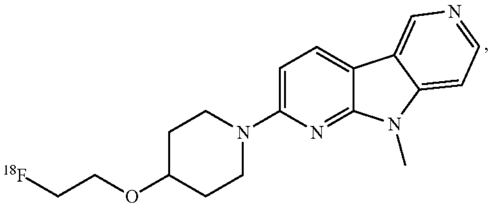
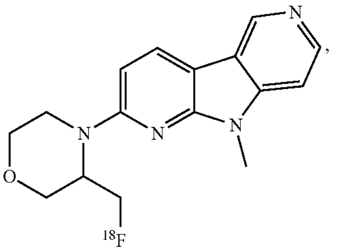
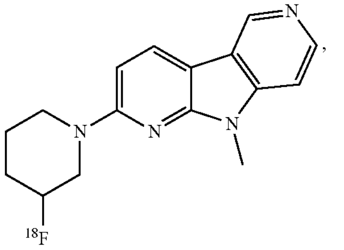

-continued

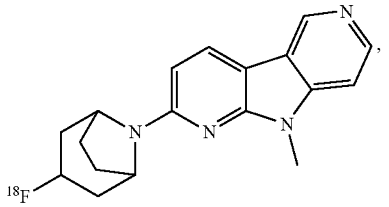

,

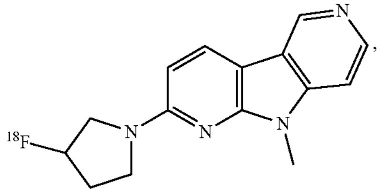

,

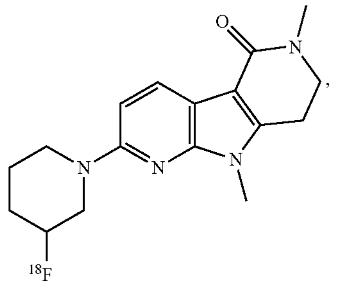

,

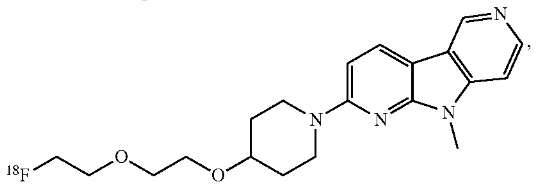

,

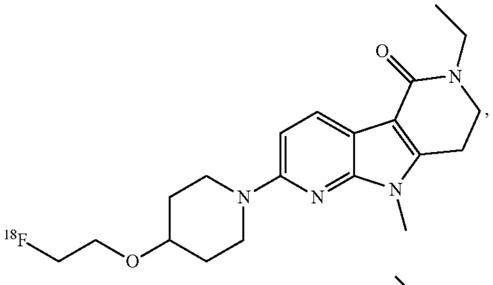

,

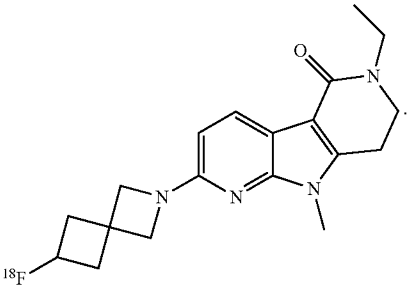

.

The corresponding $^{19}F$ analogs are also preferred.

The compounds of the present invention can be detectably labeled. The type of the label is not specifically limited and will depend on the detection method chosen. Examples of possible labels include isotopes such as radionuclides, positron emitters, gamma emitters, as well as fluorescent, luminescent and chromogenic labels. With respect to the detectably labeled compounds of the present invention which include a radioisotope, a positron emitter, or a gamma emitter, it is to be understood that the radioisotope, positron emitter, or gamma emitter is to be present in an amount which is not identical to the natural amount of the respective radioisotope, positron emitter, or gamma emitter. Furthermore, the employed amount should allow detection thereof by the chosen detection method.

Examples of suitable isotopes such as radionuclides, positron emitters and gamma emitters include $^{2}H$, $^{3}H$, $^{18}F$, $^{123}I$, $^{124}I$, $^{125}I$, $^{131}I$, $^{11}C$, $^{13}N$, $^{15}O$, and $^{77}Br$, preferably $^{2}H$, $^{3}H$, $^{11}C$, $^{13}N$, $^{15}O$, and $^{18}F$, more preferably $^{2}H$, $^{3}H$ and $^{18}F$, even more preferably $^{18}F$.

$^{18}F$-labeled compounds are particularly suitable for imaging applications such as PET. The corresponding compounds which include fluorine having a natural $^{19}F$ isotope are also of particular interest as they can be used as analytical standards and references during manufacturing, quality control, release and clinical use of their $^{18}F$-analogs.

Any combination of the embodiments, preferred embodiments and more preferred embodiments disclosed herein is also envisaged in the present invention.

Radionuclides, positron emitters and gamma emitters can be included into the compounds of the present invention by methods which are usual in the field of organic synthesis. Typically, they will be introduced by using a correspondingly labeled starting material when the desired compound of the present invention is prepared. Illustrative methods of introducing detectable labels are described, for instance, in US 2012/0302755.

Alternatively, fluorescent, luminescent and chromogenic labels can be used to detectably label the compounds of the present invention. The labels should be relatively nonpolar and the chromophore should be electrically neutral, have high peak intensity, a small Stokes shift, and high, environment-independent fluorescence quantum yields. More preferred labels should have longer-wavelength absorption to allow the measurement of fluorescence spectra that span the visible spectrum.

The fluorescent, luminescent and chromogenic labels are not particularly limited and can be chosen from any fluorescent, luminescent and chromogenic labels which are known in the art. One example of a possible fluorescent label is

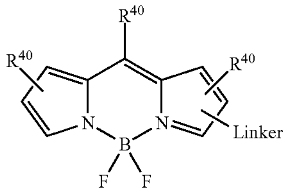

For each occurrence, $R^{40}$ is independently selected from the group consisting of hydrogen, alkyl,

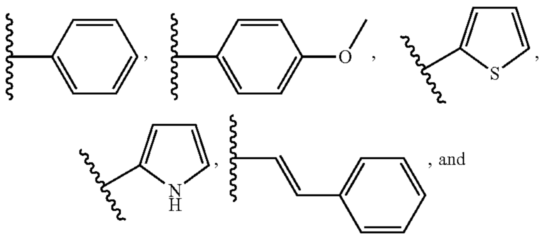

, , , , and

-continued

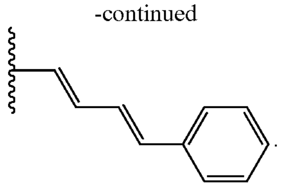

whereby the fluorescent label can contain one or more than one $R^{40}$, for instance, 1, 2 or 3 $R^{40}$.

To allow a more efficient coupling of the label to the compounds of this invention, an acid moiety of the label-linker can be activated by an active ester moiety such as, but are not limited to, 4-nitrophenyl ester, 2,4,5-trichlorophenyl ester, pentachiorophenyl ester, pentafluorophenyl ester, succinimido ester, and 4-oxo-3,4-dihydrobenzotriazin-3-yl ester. Although an active ester moiety is sufficient for efficient coupling of the label to the compounds of the present invention, other methods for the covalent attachment of the label to the compounds of the present invention may be applied as described in de Rezende and da Silva Emery, Orbital Elec. J. Chem., 2013, 5, 62-83.

The fluorescent, luminescent and chromogenic labels can be either directly attached to the compounds of the present invention or be attached via a linker. The linker is not particularly limited and can, for example, have a chain length of 1 to 20, preferably 5 to 18, more preferably 6 to 15 atoms. The linker can be a hydrocarbon chain or additionally contain an aryl moiety or heteroatoms (such as S, N and O) or heteroatom-containing moieties such as ester or amide moieties. Examples of possible linkers include, but are not limited to, $-(CH_2)_p-Y-(CH_2)_q-$ (p=1 to 6, q=1 to 6, Y=—C(O)—NR— or —NR—C(O)—; R=H or $C_{1-4}$ alkyl) or $-(CH_2)_r-Y-(CH_2)_q-Y-(CH_2)_t-$ (r=1 to 6, s=1 to 6, t=1 to 6, Y=—C(O)—NR— or —NR—C(O)—; R=H or $C_{1-4}$ alkyl).

Other examples of linkers include those selected from the group consisting of $-(CH_2)_m-X-$ (m=1 to 6; X=—C(O)O— or —OC(O)—), $-(CH_2)_p-Y-(CH_2)_q-X-$ (p=1 to 6; q=1 to 6; X=—C(O)O— or —OC(O)—; Y=—C(O)—NR— or —NR—C(O)—; R=H or $C_{1-4}$ alkyl),

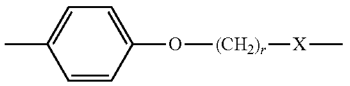

(r=1 to 6; X=—C(O)O— or —OC(O)—) and

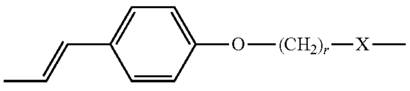

(r=1 to 6; X=—C(O)O— or —OC(O)—).

The position at which the detectable label is to be attached to the compounds of the present invention is not particularly limited.

The radionuclides, positron emitters and gamma emitters, for example, can be attached at any position where the corresponding non-emitting atom can also be attached. For instance, $^{18}F$ can be attached at any position which is suitable for attaching F. The same applies to the other radionuclides, positron emitters and gamma emitters. Due to the ease of synthesis, it is preferred to attach $^{18}F$, $^{123}I$, $^{124}I$, $^{125}I$, $^{131}I$, and $^{77}Br$ as $R^3$ or part of $R^3$. If $^3H$ is employed as a detectable label it is preferably attached in the form of $-C(^3H)_3$ at any position at which a methyl group can be attached. If $^2H$ is employed as a detectable label it is preferably attached in the form of $-C(^2H)_3$ at any position at which a methyl group can be attached. Easily available positions include $R^a$, $R^b$ and $R^{13}$. $^{11}C$, $^{13}N$, and $^{15}O$ can be incorporated into the compounds of the present invention at any position where C, N and O appear.

The fluorescent, luminescent and chromogenic labels can be attached (either directly or via a linker) to any position of the compounds of the present invention. In view of the ease of synthesis, the fluorescent, luminescent and chromogenic labels are preferably attached to $R^a$, $R^b$ or a nitrogen atom which is present in the ring formed by $R^1$ and $R^2$. More preferably, the fluorescent, luminescent and chromogenic labels are attached to the nitrogen atom of the amide bond present in the ring formed by $R^1$ and $R^2$.

Preferred compounds are also illustrated in the examples.

The present invention also refers to precursors from which detectably labeled compounds of the present invention can be prepared.

In one embodiment, the precursor is a compound of formula (I*):

(I*)

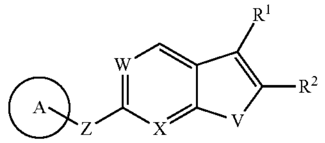

and all stereoisomers, racemic mixtures, pharmaceutically acceptable salts, hydrates, solvates and polymorphs thereof; wherein

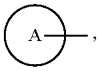,

V, W, X, Z, $R^b$, $R^c$, $R^d$, $R^f$, $R^1$, $R^2$, $R^3$, $R^{10}$, $R^{11}$, $R^{12}$, $R^{13}$, and n are as defined in as set out in any of the definitions above, wherein

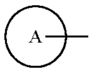

is substituted by $R^{3*}$ which comprises a leaving group $LG^1$ or $LG^2$. Preferably $R^{3*}$ comprises a leaving group selected from the group consisting of halogen (e.g., Br, I, or Cl), nitro, tri($C_{1-4}$ alkyl)ammonium (e.g., trimethylammonium), or $-OSO_2-R$, with R being selected from the group consisting of $C_{1-4}$ alkyl, perfluoro($C_{1-4}$)alkyl, and aryl which can be optionally substituted by $C_{1-4}$ alkyl, halogen or nitro (e.g., $-OSO_2-CH_3$, $-OSO_2-C_6H_4-CH_3$, or $-OSO_2-CF_3$); and wherein $R^a$ is selected from the group consisting of hydrogen, an amine protecting group PG and alkyl, wherein alkyl can be optionally substituted, preferably $R^a$ is hydrogen or a tert.-butyloxycarbonyl group (Boc).

In one embodiment, $R^{3*}$ is halogen, —$NO_2$, tri($C_{1-4}$ alkyl)ammonium, alkyl substituted with halogen or —$OSO_2$—R, —O—($C_{2-5}$ alkyl), wherein the alkyl group is substituted with halogen or —$OSO_2$—R, or —(O—$CH_2CH_2$)$_n$-L, wherein L is selected from halogen or —$OSO_2$—R and n is 2 to 5; and wherein R is as defined above, preferably R is methyl or tolyl.

In one preferred embodiment, $R^{3*}$ is halogen or —$NO_2$. In another preferred embodiment, $R^{3*}$ is —$NO_2$. In a further preferred embodiment, $R^{3*}$ is -alkyl, —O-alkyl or —(O—$CH_2CH_2$)$_n$ (with n=1 to 6), wherein -alkyl, —O-alkyl or —(O—$CH_2CH_2$)$_n$ is substituted with a leaving group selected from halogen and —$OSO_2$—R, with R being selected from the group consisting of $C_1$ alkyl, perfluoro($C_{1-4}$)alkyl, and aryl which can be optionally substituted by $C_{1-4}$ alkyl, perfluoro($C_{1-4}$)alkyl, halogen or nitro (e.g., —$OSO_2$—$CH_3$, —$OSO_2$—$C_6H_4$—$CH_3$, or —$OSO_2$—$CF_3$). Most preferably, $R^{3*}$ comprises a leaving group selected from the group consisting of —$OSO_2$—$CH_3$ and —$OSO_2$—$C_6H_4$—$CH_3$.

In a preferred embodiment of the precursors of formula (I*),

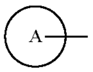

is substituted and is selected from the group consisting of

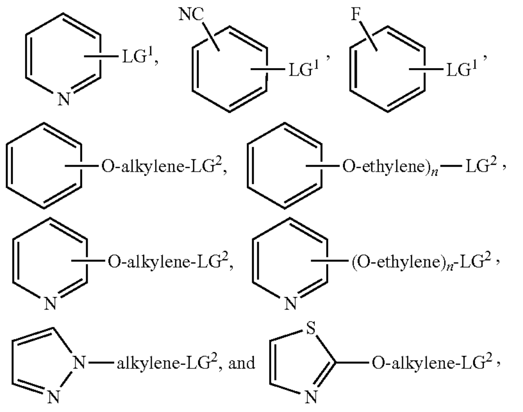

wherein the respective rings can be attached at any available position to the moiety Z.

Some preferred compounds of formula (I*) include

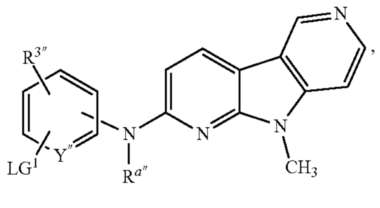

-continued

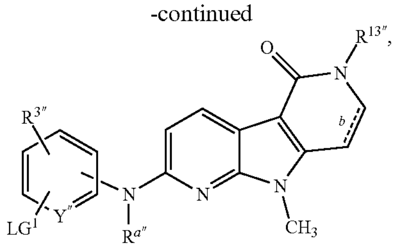

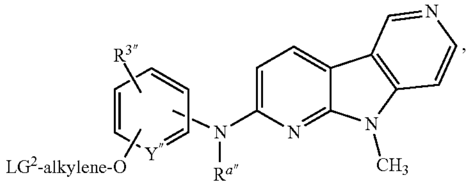

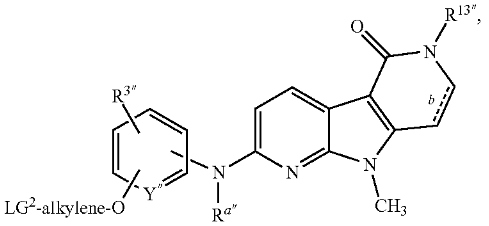

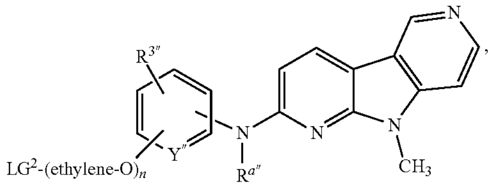

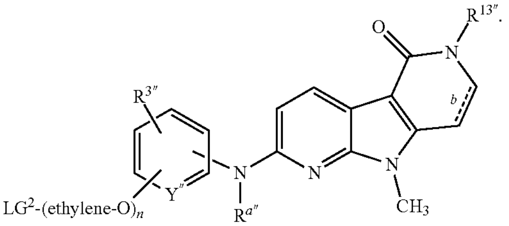

In these formulae,

 is a single or double bond;

$LG^1$ is defined above, preferably $LG^1$ is nitro;

$LG^2$ is defined above, preferably $LG^2$ is —O—$SO_2$—$CH_3$ or —O—$SO_2$—$C_6H_4$—$CH_3$;

$R^{a''}$ is hydrogen or Pert-butyloxycarbonyl (Boc);

Y" is N or CH;

$R^{3''}$ is $R^3$ or hydrogen, preferably $R^{3''}$ is hydrogen, halogen, hydroxy, methoxy, difluoromethoxy, morpholino, alkyl, cyano, nitro, trifluoromethyl, optionally substituted alkyl, optionally substituted —O-alkyl, —(O—$CH_2CH_2$)$_n$—$R^d$, or —$NR^{10}R^{11}$. More preferably $R^{3''}$ is hydrogen, fluorine or cyano;

$R^{13''}$ is hydrogen, methyl, or ethyl;

n is 2 to 5;

alkylene is a $C_{1-6}$ alkylene group, preferably alkylene is ethylene; and $R^3$, $R^{10}$ and $R^{11}$ are as defined above.

Preferred compounds of formula (I*) are

Preferred precursor compounds of the present invention include

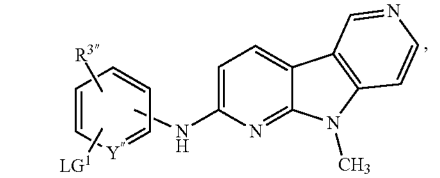

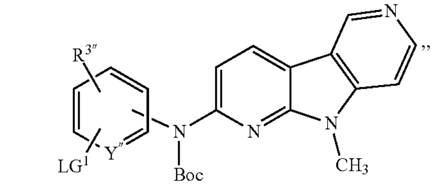

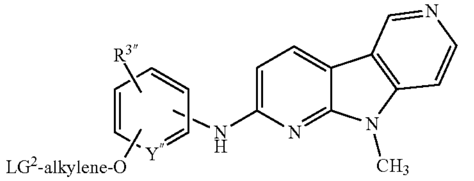

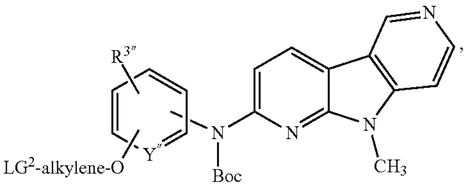

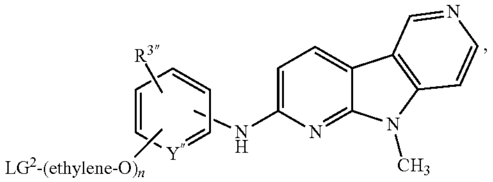

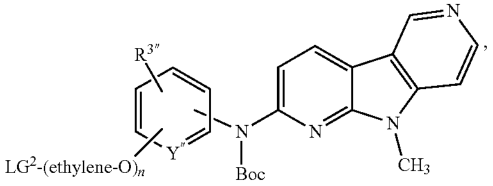

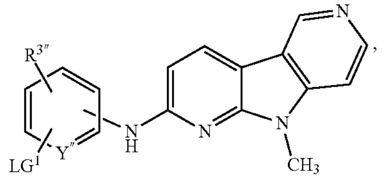

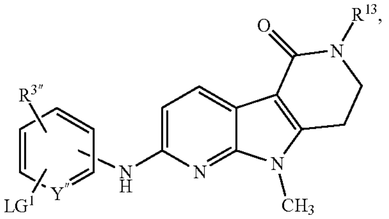

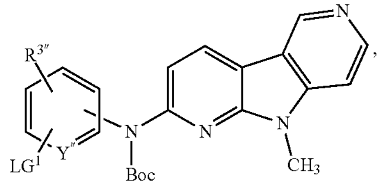

-continued

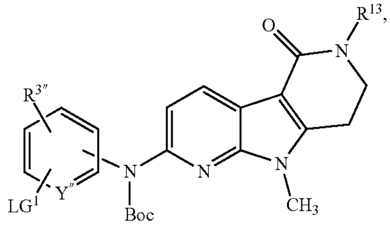

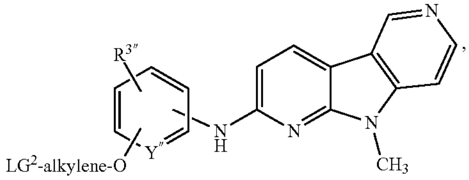

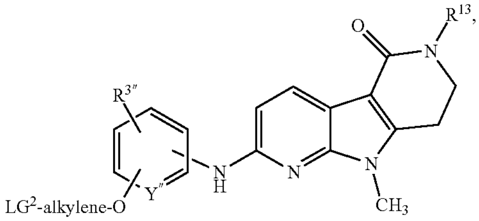

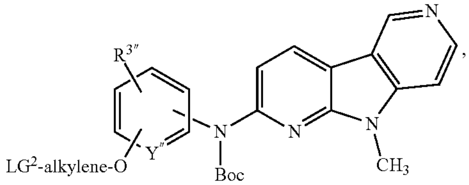

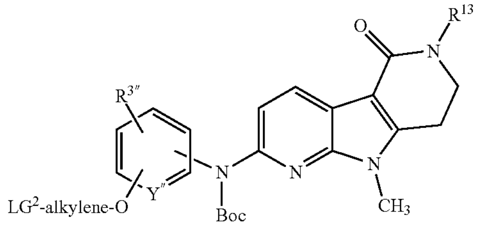

In these formulae,

Y" is N or CH;

$R^{3''}$ is $R^3$ or hydrogen, preferably $R^{3''}$ is hydrogen, halogen, hydroxy, methoxy, difluoromethoxy, morpholino, alkyl, cyano, nitro, trifluoromethyl, $LG^1$, optionally substituted alkyl, optionally substituted —O-alkyl, —(O—$CH_2CH_2)_n$—$R^d$, or —$NR^{10}R^{11}$, in which the optional substituents are preferably selected from the group consisting of $LG^2$, F and $^{18}F$;

n is 2 to 5;

m is 1 to 3;

$LG^1$ and $LG^2$ are as defined above;

alkylene is a $C_{1-6}$ alkylene group;

Boc is a tert-butyloxycarbonyl group, and $R^3$, $R^d$, $R^{10}$, $R^{11}$ an $R^{13}$ are as defined above.

More preferred precursor compounds of the present invention include

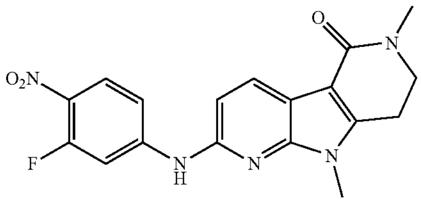
,
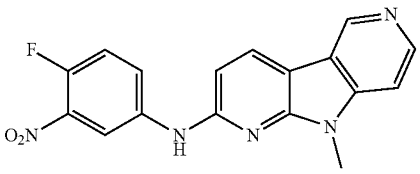
,
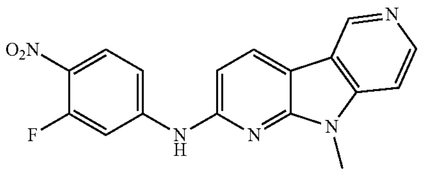
,
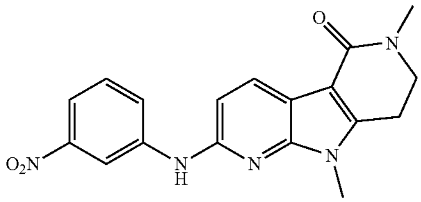
,
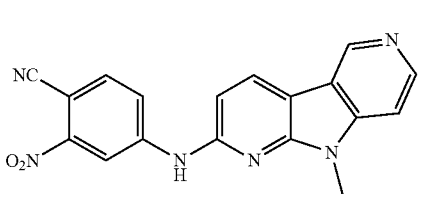
,
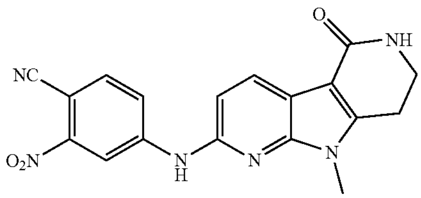
,
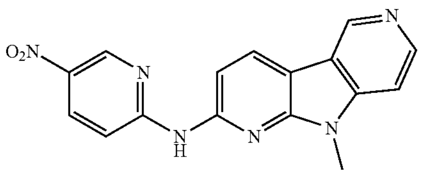
,
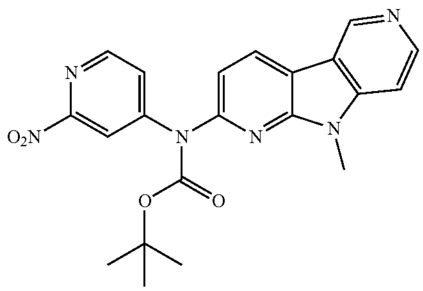
,
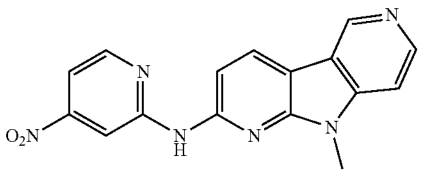
,
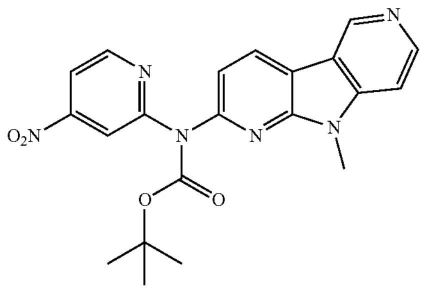
,
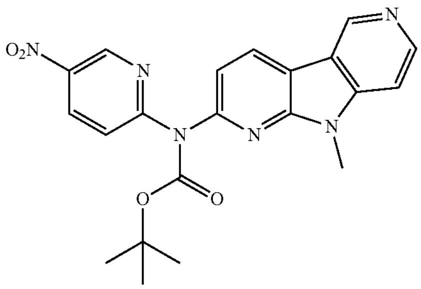
,
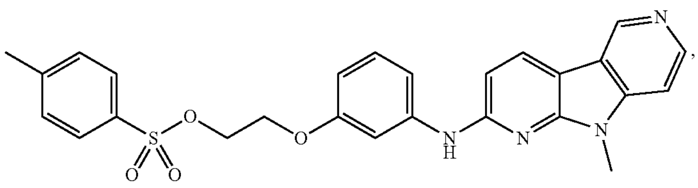
, -continued

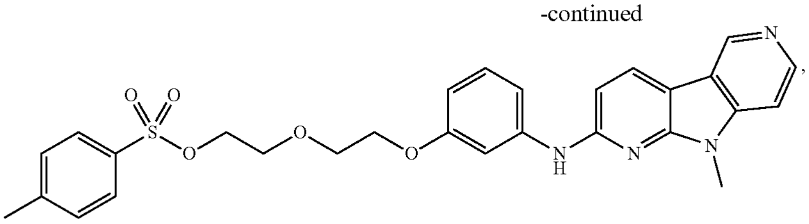

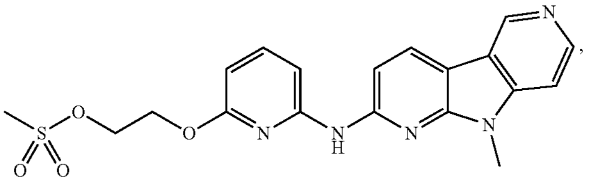

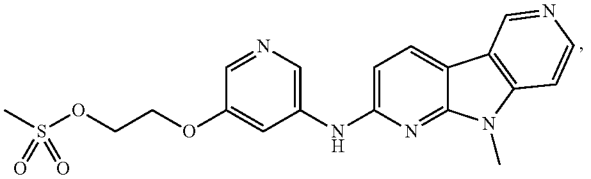

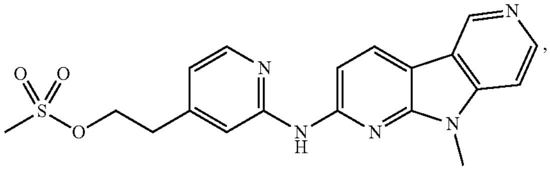

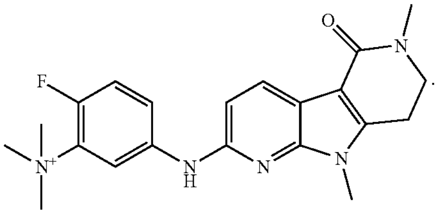

In a further embodiment, the precursors are a compound of formula (II*):

(II*)

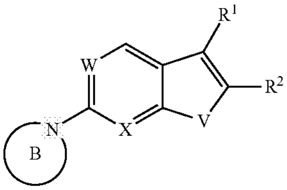

and all stereoisomers, racemic mixtures, pharmaceutically acceptable salts, hydrates, solvates and polymorphs thereof; wherein

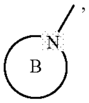

V, W, X, $R^b$, $R^c$, $R^d$, $R^f$, $R^1$, $R^2$, $R^3$, $R^{10}$, $R^{11}$, $R^{12}$, $R^{13}$, and n are as defined in as set out in any of the definitions above, wherein

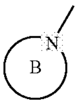

is substituted by $R^{3*}$ which comprises a leaving group $LG^2$. Preferably $R^{3*}$ comprises a leaving group comprising halogen (e.g., Br, I, or Cl) or $—OSO_2—R$, with R being selected from the group consisting of $C_{1-4}$ alkyl, perfluoro($C_{1-4}$)alkyl, and aryl which can be optionally substituted by $C_{1-4}$ alkyl, halogen or nitro (e.g., $—OSO_2—CH_3$, $—OSO_2—CF_3$ or $—OSO_2—C_6H_4—CH_3$).

With respect to the formula (II*), preferably $R^{3*}$ is halogen, $—OSO_2—R$, alkyl substituted with halogen or $—OSO_2—R$, $—O—(C_{2-5}$ alkyl), wherein the alkyl group is substituted with halogen or $—OSO_2—R$, or $—(O—CH_2CH_2)_n$-L, wherein L is selected from halogen or $—OSO_2—R$ and n is 2 to 5; and wherein R is as defined above, preferably R is methyl or tolyl.

In a preferred embodiment, $R^{3*}$ comprises a leaving group selected from the group consisting of $—OSO_2—CH_3$ and $—OSO_2—C_6H_4—CH_3$.

In a preferred embodiment of the precursors of formula (II*),

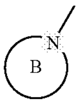

is substituted and is selected from the group consisting of

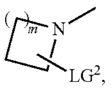

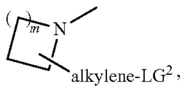

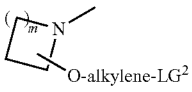

-continued
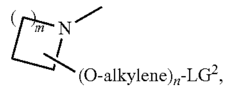
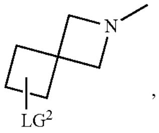
,
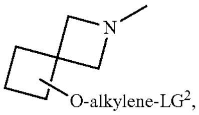
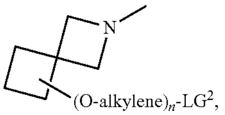
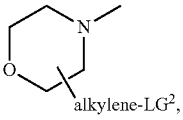
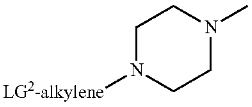
,
wherein m is preferably 1 to 3, more preferably 2 or 3, and n is preferably 2 to 5, more preferably 2 or 3 and alkylene is preferably ethylene.
Some preferred compounds of formula (II*) include
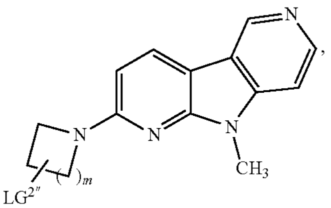
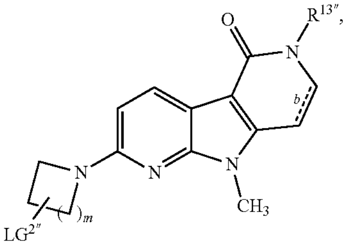
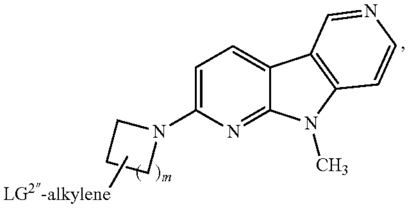
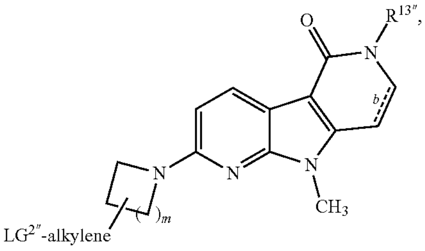
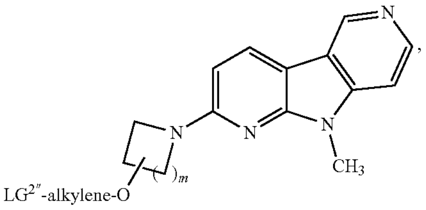
-continued
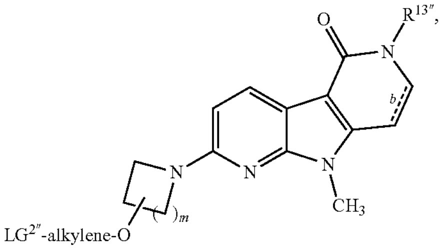
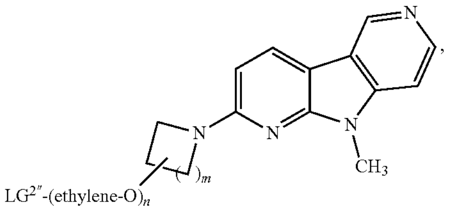
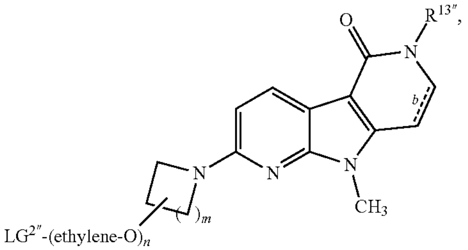
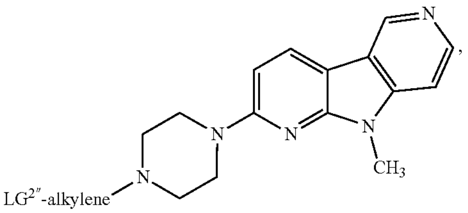
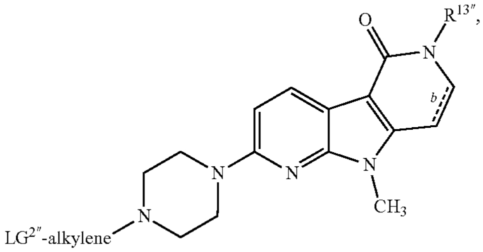
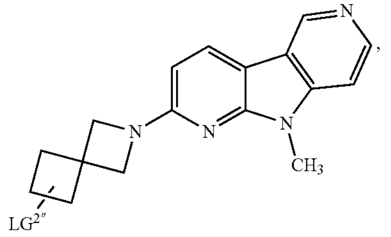
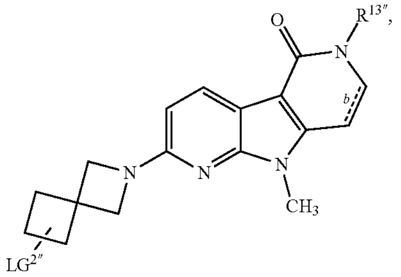

-continued
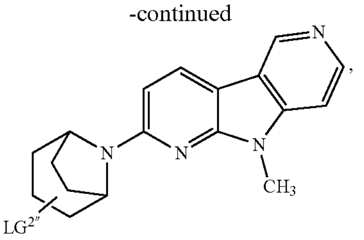
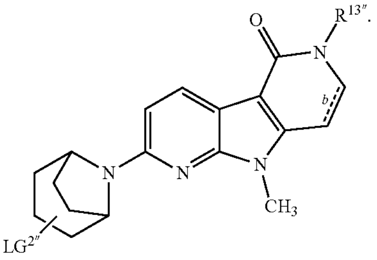
In these formulae,
$\overset{b}{\cdots}$ is a single or double bond;
n is 2 to 5;
$R^{13''}$ is hydrogen, methyl, or ethyl;
m is 1 to 3;
$LG^{2''}$ is $LG^2$ as defined above, preferably $LG^{2''}$ is $—O—SO_2—CH_3$ or $—O—SO_2—C_6H_4—CH_3$;
alkylene is a $C_{1-6}$ alkylene group, preferably alkylene is methylene or ethylene.
Preferred compounds of formula (II*) include
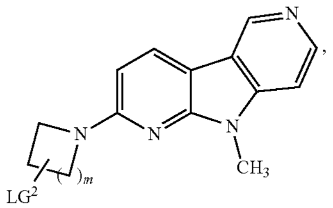
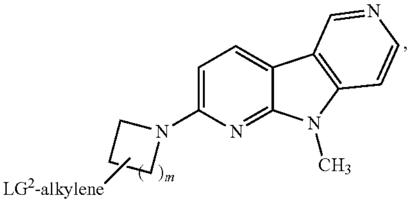
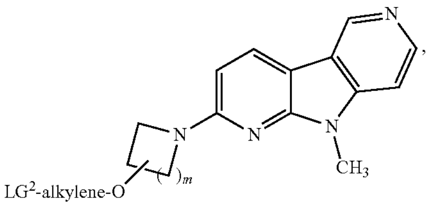
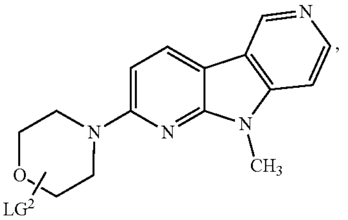
-continued
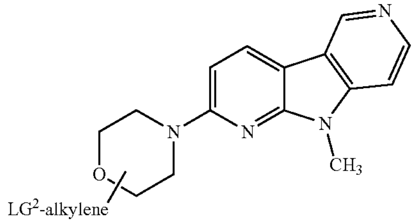
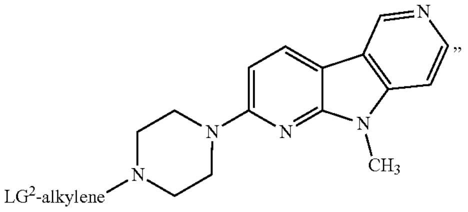
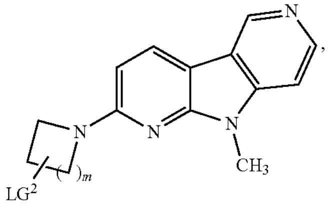
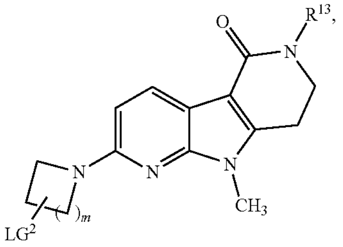
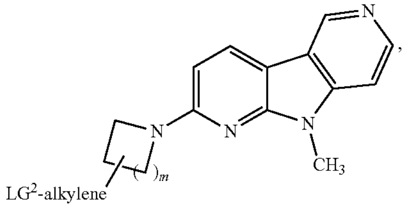
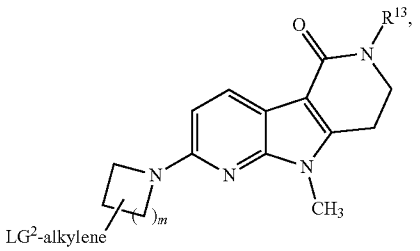
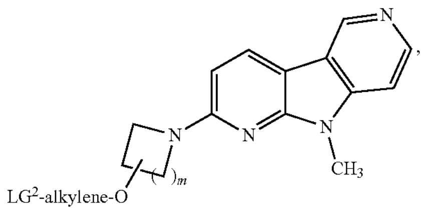

-continued
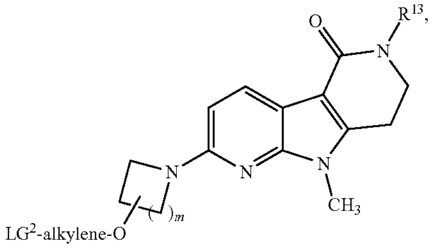
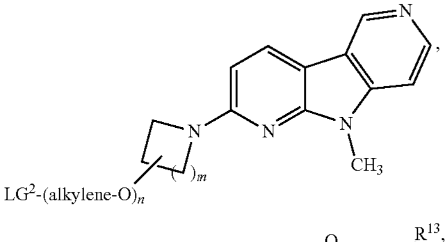
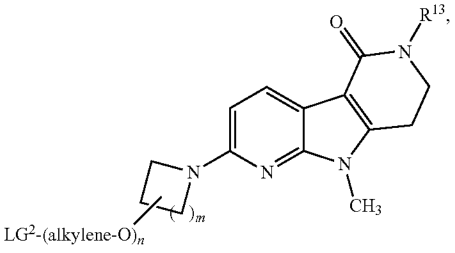
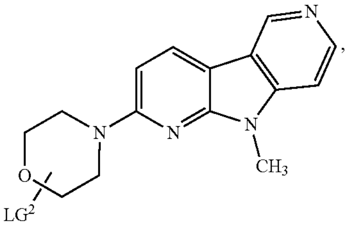
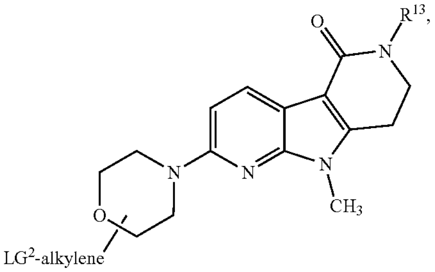
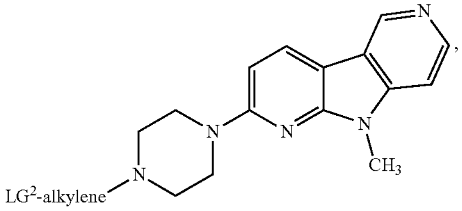
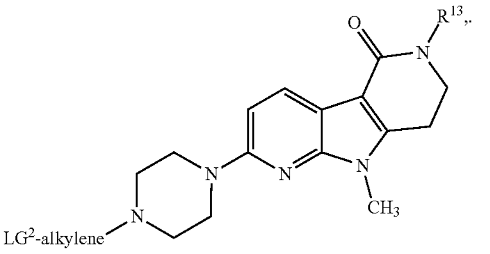
-continued
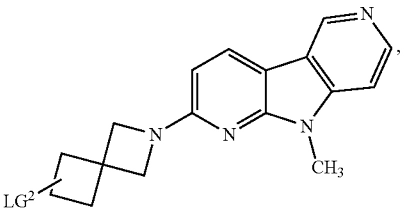
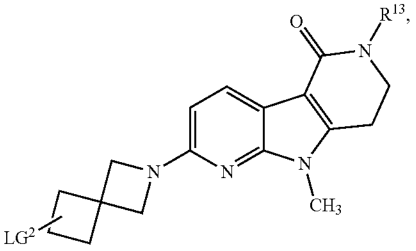
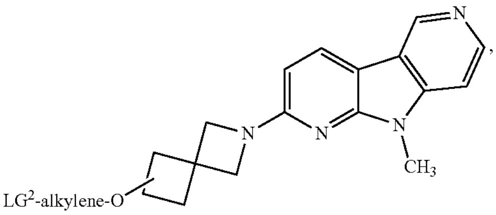
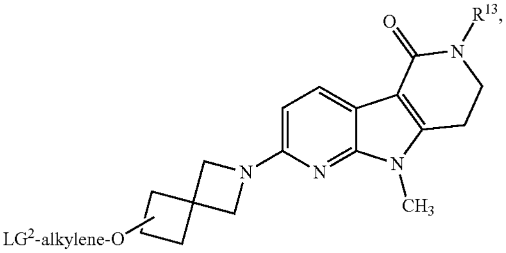
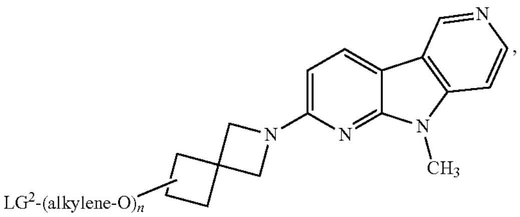
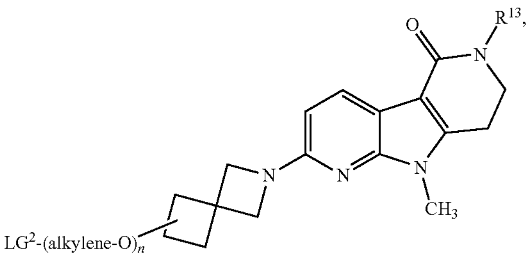

-continued

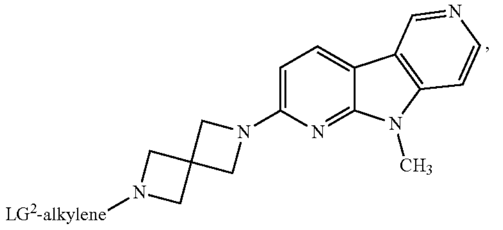

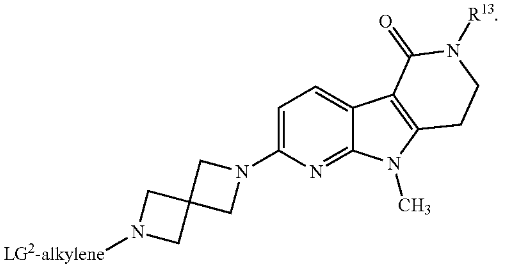

In these formulae,

Y" is N or CH;

$R^{3''}$ is $R^3$ or hydrogen, preferably $R^{3''}$ is hydrogen, halogen, hydroxy, methoxy, difluoromethoxy, morpholino, alkyl, cyano, nitro, trifluoromethyl, $LG^1$, optionally substituted alkyl, optionally substituted —O-alkyl, —(O—$CH_2CH_2)_n$—$R^d$, or —$NR^{10}R^{11}$, in which the optional substituents are preferably selected from the group consisting of $LG^2$, F and $^{18}F$;

n is 2 to 5;

m is 1 to 3;

$LG^1$ and $LG^2$ are as defined above;

alkylene is a $C_{1-6}$ alkylene group;

Boc is a Pert-butyloxycarbonyl group, and $R^3$, $R^d$, $R^{10}$, $R^{11}$ and $R^{13}$ are as defined above.

Preferred compounds of formula (II*) include

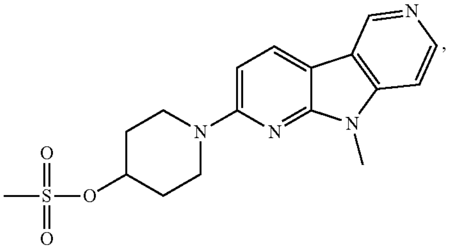

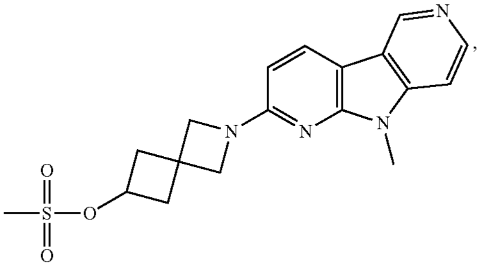

-continued

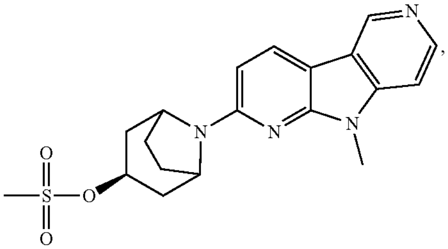

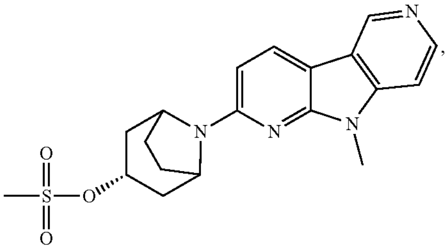

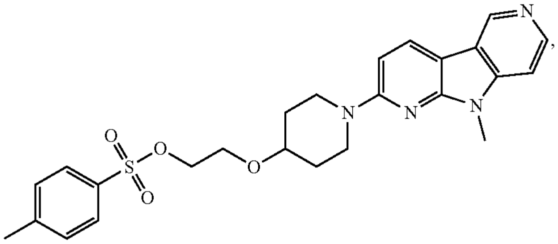

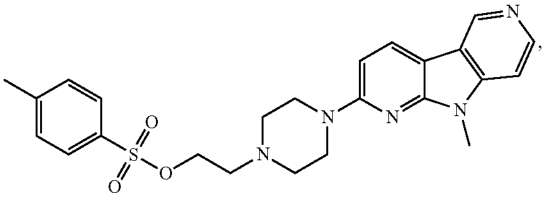

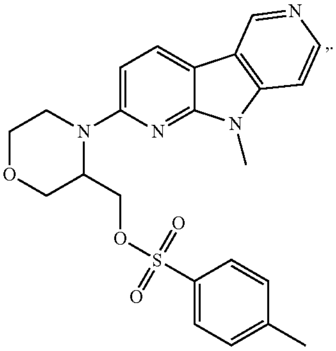

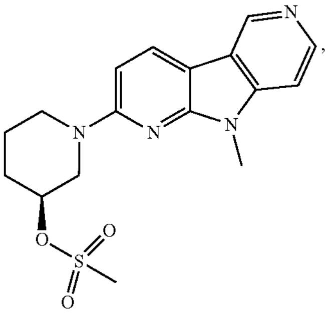

-continued

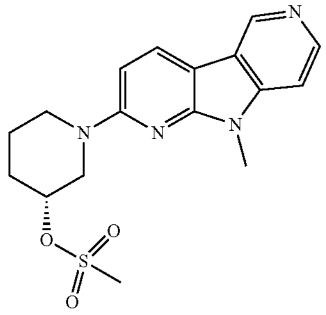,

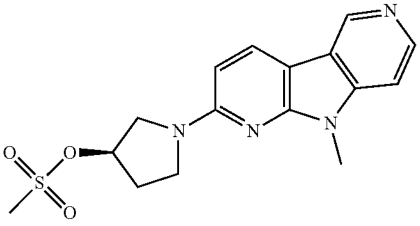,

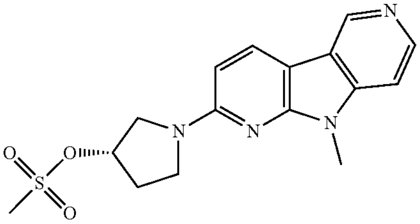,

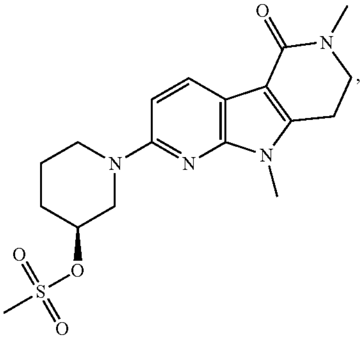,

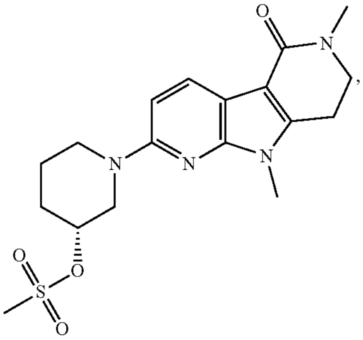,

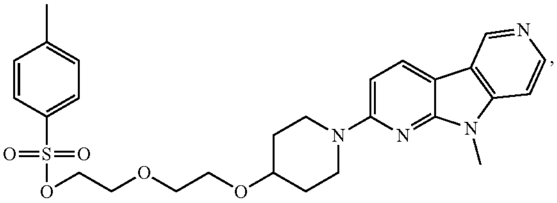,

-continued

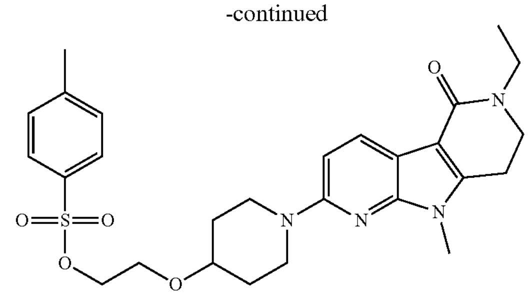,

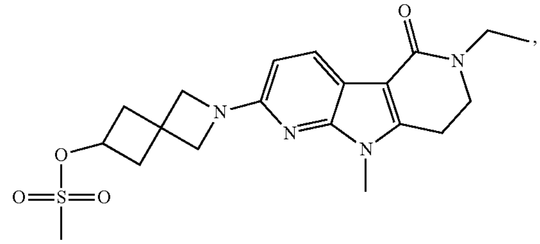,

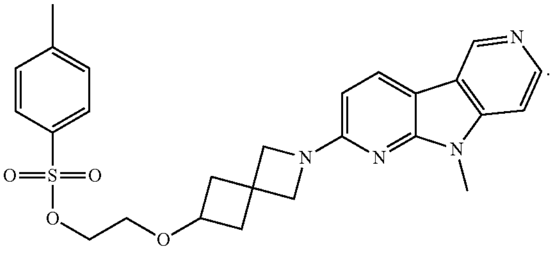.

General Synthesis of $^{18}$F-Labeled Compounds of the Present Invention

Compounds having the formula (I) which are labeled by $^{18}$F can be prepared by reacting a compound of formula (I*) with an $^{18}$F-fluorinating agent, so that the leaving group comprised in $R^{3}$* is replaced by $^{18}$F. The preparation optionally includes the cleavage of a protecting group. Compounds having the formula (II) which are labeled by $^{18}$F can be prepared by reacting a compound of formula (II*) with an $^{18}$F-fluorinating agent, so that the leaving group comprised in $R^{3}$* is replaced by $^{18}$F. The preparation optionally includes the cleavage of a protecting group.

Any suitable $^{18}$F-fluorinating agent can be employed. Typical examples include $H^{18}F$, alkali or alkaline earth $^{18}$F-fluorides (e.g., $K^{18}F$, $Rb^{18}F$, $Cs^{18}F$, and $Na^{18}F$). Optionally, the $^{18}$F-fluorination agent can be used in combination with a chelating agent such as a cryptand (e.g.: 4,7,13,16,21,24-hexaoxa-1,10-diazabicyclo[8.8.8]-hexacosane—Kryptofix®) or a crown ether (e.g.: 18-crown-6). Alternatively, the $^{18}$F-fluorinating agent can be a tetraalkylammonium salt of $^{18}$F or a tetraalkylphosphonium salt of $^{18}$F. Examples thereof include tetrabutylammonium [$^{18}$F]fluoride and tetrabutylphosphonium [$^{18}$F]fluoride. Preferably, the $^{18}$F-fluorination agent is $Cs^{18}F$, $K^{18}F$, or tetrabutylammonium [$^{18}$F]fluoride.

The reagents, solvents and conditions which can be used for the $^{18}$F-fluorination are well-known to a skilled person in the field (L. Cai, S. Lu, V. Pike, Eur. J. Org. Chem 2008, 2853-2873; J. Fluorine Chem., 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the $^{18}$F-fluorination are DMF, DMSO, acetonitrile, DMA, or mixtures thereof, preferably the solvent is acetonitrile, DMSO.

If desired, the compound having the formula (I*) can contain an amine protecting group in order to protect the group Z during the $^{18}F$ fluorination reaction. This amine protecting group can be subsequently removed. Methods for removing the amine protecting group are known in the art and include, but are not limited to, acid cleavage.

If desired, the compound of formula (I) or formula (II) can be isolated and/or purified further before use. Corresponding procedures are well-known in the art.

The precursor compounds (I*) or (II*) of the present invention can be provided in a kit which is suitable for producing the compounds of the formula (I) or (II) by reaction with a $^{18}F$-fluorinating agent. In one embodiment the kit comprises a sealed vial containing a predetermined quantity of the precursor compound (I*) or (II*) of the present invention. For instance, the kit can contain 1.5 to 75 μmol, preferably 7.5 to 50 μmol, more preferably 10 to 30 μmol of a precursor compound (I*) or (II*) of the present invention. Optionally, the kit can contain further components, such as solvents, solid-phase extraction cartridges, components of the $^{18}F$-fluorinating agent, reagent for cleaving protecting groups, solvent or solvent mixtures for purification, solvents and excipients for formulation.

Diagnostic Compositions

The compounds of the present invention are particularly suitable for imaging of amyloid and/or amyloid-like protein aggregates, including extracellular and/or intracellular amyloid and amyloid-like protein. Examples of amyloid-like protein include tau, Aβ, alpha-synuclein, Huntingtin, prion, ATTR (transthyretin) or ADan (ADanPP). Illustrative examples of the amyloid-like protein aggregates are pathologically aggregated tau, hyperphosphorylated tau, neurofibrillary tangles (NFT), paired helical filaments, Aβ oligomers, polymers and fibrils, Aβ plaques, neurotoxic soluble oligomers in brain, alpha-synuclein aggregates, and Lewy bodies. With respect to tau protein, the compounds of the present invention are able to bind to pathologically aggregated tau, hyperphosphorylated tau, neurofibrillary tangles, paired helical filaments, straight filaments, neurotoxic soluble oligomers, polymers and fibrils. The compounds of the present invention are particularly suitable for binding to various types of tau aggregates.

Due to the above binding characteristics, the compounds of the present invention are suitable for use in the diagnosis of disorders associated with amyloid and/or amyloid-like protein aggregates. The compounds of the present invention are particularly suitable for positron emission tomography imaging of tau deposits.

Diseases involving tau aggregates are generally listed as tauopathies and these include, but are not limited to, Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, and white matter tauopathy with globular glial inclusions, etc (Williams et al., Intern. Med. J., 2006, 36, 652-60).

Diseases involving Abeta aggregates are generally listed as amyloidosis and this includes, but is not limited to, Alzheimer's disease, Lewy body dementia (LBD), hereditary cerebral hemorrhage with amyloidosis (Dutch type), mild cognitive impairment (MCI), progressive supranuclear palsy, multiple sclerosis, inclusion-body myositis (IBM), Creutzfeldt-Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystropy.

Other diseases which are based on or associated with amyloid-like proteins include, but are not limited to, Parkinson's disease (PD), Huntington's disease, Creutzfeldt-Jakob disease, familial senile systemic tenosynovium, and familial dementia (Danish type) (Sipe et al., Amyloid, 2010, 17, 101-4).

Due to their design the compounds of the present invention are particularly suitable for use in the diagnosis of Alzheimer's disease, as well as other neurodegenerative tauopathies such as Creutzfeldt-Jacob disease, dementia pugilistica, amyotrophic lateral sclerosis, argyrophilic grain disease, corticobasal degeneration, frontotemporal dementia with Parkinsonism linked to chromosome 17, Pick's disease, progressive supranuclear palsy (PSP), tangle only dementia, Parkinson dementia complex of Guam, Hallervorden-Spatz disease and fronto-temporal lobar degeneration.

In the methods of diagnosing a disorder associated with amyloid and/or amyloid-like protein aggregates such as Alzheimer's disease, or a predisposition therefor in a subject, the method comprising:

a) administering to the mammal a diagnostically effective amount of a compound of the present invention;
b) allowing the compound of the present invention to distribute into the tissue of interest (such as brain tissue, the eye or body fluids such as cerebrospinal fluid (CSF)); and
c) imaging the tissue of interest, wherein an increase in binding of the compound of the present invention to the tissue of interest compared to a normal control level of binding indicates that the subject is suffering from or is at risk of developing a disorder associated with amyloid and/or amyloid-like protein aggregates.

The compounds of the present invention can be used for imaging of amyloid and/or amyloid-like protein aggregates in any sample or a specific body part or body area of a patient which suspected to contain an amyloid and/or amyloid-like protein aggregate. The compounds of the present invention are able to pass the blood-brain barrier and to pass into the eye. Consequently, they are particularly suitable for imaging of amyloid and/or amyloid-like protein aggregates in the brain, in the eye (ophthalmic and/or retinal imaging) as well as in body fluids such as cerebrospinal fluid (CSF).

In diagnostic applications, the compound of the present invention is preferably administered in a diagnostic composition comprising the compound of the invention. A "diagnostic composition" is defined in the present invention as a composition comprising compounds of the present invention in a form suitable for administration to mammals such as humans. Preferably a diagnostic composition further comprises a physiologically acceptable carrier, diluent, adjuvant or excipient. Administration is preferably carried out by injection of the composition as an aqueous solution. Such a composition may optionally contain further ingredients such as buffers; pharmaceutically acceptable solubilisers (e.g., cyclodextrins or surfactants such as Pluronic, Tween or phospholipids); and pharmaceutically acceptable stabilisers or antioxidants (such as ascorbic acid, gentisic acid or para-aminobenzoic acid). The dose of the compound of the present invention will vary depending on the exact compound to be administered, the weight of the patient, and other variables as would be apparent to a physician skilled in the art. Generally, the dose could preferably lie in the range 0.001 μg/kg to 10 μg/kg, preferably 0.01 μg/kg to 1.0 μg/kg.

Diagnosis of an amyloid-associated disorder or of a predisposition to an amyloid-associated disorder in a patient may be achieved by detecting the specific binding of a compound according to the invention to the amyloid and/or amyloid-like protein aggregates in a sample or in situ, which includes:

(a) bringing the sample or a specific body part or body area suspected to contain the amyloid and/or amyloid-like protein aggregate into contact with a compound of the invention which binds the amyloid and/or amyloid-like protein aggregate,
(b) allowing the compound of the invention to bind to the amyloid and/or amyloid-like protein aggregate to form a compound/amyloid and/or amyloid-like protein aggregate complex (hereinafter "compound/amyloid and/or amyloid-like protein aggregate complex" will be abbreviated as "compound/protein aggregate complex"),
(c) detecting the formation of the compound/protein complex,
(d) optionally correlating the presence or absence of the compound/protein complex with the presence or absence of amyloid and/or amyloid-like protein aggregates in the sample or specific body part or area, and
(e) optionally comparing the amount of the compound/protein to a normal control value, wherein an increase in the amount of the compound/protein compared to a normal control value may indicate that the patient is suffering from or is at risk of developing an amyloid-associated disorder.

The compound of the present invention can be brought into contact with the sample or the specific body part or body area suspected to contain the amyloid and/or amyloid-like protein aggregate by a suitable method. In in vitro methods the compound of the present invention and a liquid sample can be simply mixed. In in vivo tests the compound of the present invention is typically administered to the patient by any suitable means such as the routes for administration (delivery) described below with respect to the pharmaceutical compositions. These routes of administration include, but are not limited to, one or more of: oral (e. g. as a tablet, capsule, or as an ingestible solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. In some instances, parenteral administration can be preferred.

After the sample or a specific body part or body area has been brought into contact with the compound of the present invention, the compound is allowed to bind to the amyloid and/or amyloid-like protein aggregate. The amount of time required for binding will depend on the type of test (e.g., in vitro or in vivo) and can be determined by a person skilled in the field by routine experiments.

The compound which has bound to the amyloid and/or amyloid-like protein aggregate can be subsequently detected by any appropriate method. The specific method chosen will depend on the detectable label which has been chosen. Examples of possible methods include, but are not limited to, a fluorescence imaging technique or a nuclear imaging technique such as positron emission tomography (PET), single photon emission computed tomography (SPECT), magnetic resonance imaging (MRI), and contrast-enhanced magnetic resonance imaging (MRI). These have been described and enable visualization of amyloid biomarkers. The fluorescence imaging technique and/or nuclear imaging technique can be employed for monitoring and/or visualizing the distribution of the detectably labeled compound within the sample or a specific body part or body area.

The presence or absence of the compound/protein is then optionally correlated with the presence or absence of amyloid and/or amyloid-like protein aggregates in the sample or specific body part or area. Finally, the amount of the compound/protein can be compared to a normal control value which has been determined in a sample or a specific body part or body area of a healthy subject, wherein an increase in the amount of the compound/protein compared to a normal control value may indicate that the patient is suffering from or is at risk of developing an amyloid-associated disorder.

The present invention also relates to a method of determining the amount of amyloid and/or amyloid-like protein aggregate in a tissue and/or a body fluid. This method comprises the steps of:

(a) providing a sample representative of the tissue and/or body fluid under investigation;
(b) testing the sample for the presence of amyloid and/or amyloid-like protein aggregate with a compound of the present invention;
(c) determining the amount of compound bound to the amyloid and/or amyloid-like protein aggregate; and
(d) calculating the amount of amyloid and/or amyloid-like protein aggregate in the tissue and/or body fluid.

The sample can be tested for the presence of amyloid and/or amyloid-like protein aggregate with a compound of the present invention by bringing the sample into contact with a compound of the invention, allowing the compound of the invention to bind to the amyloid and/or amyloid-like protein aggregate to form a compound/protein aggregate complex and detecting the formation of the compound/protein complex as explained above.

Monitoring minimal residual disorder in a patient suffering from a disorder associated with amyloid and/or amyloid-like protein aggregates who has been treated with a medicament with a compound according to the invention may be achieved by (a) bringing a sample or a specific body part or body area suspected to contain an amyloid and/or amyloid-like protein aggregate into contact with a compound of the present invention;

(b) allowing the compound to bind to the amyloid and/or amyloid-like protein aggregate to form a compound/protein aggregate complex;

(c) detecting the formation of the compound/protein aggregate complex;

(d) optionally correlating the presence or absence of the compound/protein aggregate complex with the presence or absence of amyloid and/or amyloid-like protein aggregate in the sample or specific body part or body area; and (e) optionally comparing the amount of the compound/protein aggregate to a normal control value, wherein an increase in the amount of the aggregate compared to a normal control value may indicate that the patient may still suffer from a minimal residual disease.

How steps (a) to (e) can be conducted has already been explained above.

Predicting responsiveness of a patient suffering from a disorder associated with amyloid and/or amyloid-like protein aggregates and being treated with a medicament can be achieved by (a) bringing a sample or a specific body part or body area suspected to contain an amyloid and/or amyloid-like protein aggregate into contact with a compound of the present invention;

(b) allowing the compound to bind to the amyloid and/or amyloid-like protein aggregate to form a compound/protein aggregate complex;

(c) detecting the formation of the compound/protein aggregate complex;

(d) optionally correlating the presence or absence of the compound/protein aggregate complex with the presence or absence of amyloid and/or amyloid-like protein aggregate in the sample or specific body part or body area; and (e) optionally comparing the amount of the compound/protein aggregate to a normal control value.

How steps (a) to (e) can be conducted has already been explained above.

The medicament with which the patient is being treated can be any medicament which is suitable for treating a disorder associated with amyloid and/or amyloid-like protein aggregates. It includes an antibody, a vaccine composition and a small molecule. In one embodiment, the medicament can comprise a compound of the present invention.

In the method for predicting responsiveness the amount of the compound/protein complex can be optionally compared at various points of time during the treatment, for instance, before and after onset of the treatment or at various points of time after the onset of the treatment. A change, especially a decrease, in the amount of the compound/protein complex may indicate that the patient has a high potential of being responsive to the respective treatment.

A compound according to the present invention can also be incorporated into a test kit for detecting an amyloid and/or amyloid-like protein. The test kit typically comprises a container holding one or more compounds according to the present invention and instructions for using the compound for the purpose of binding to an amyloid protein to form a compound/protein complex and detecting the formation of the compound/protein complex such that presence or absence of the compound/protein complex correlates with the presence or absence of the amyloid protein.

The term "test kit" refers in general to any diagnostic kit known in the art. More specifically, the latter term refers to a diagnostic kit as described in Zrein et al., Clin. Diagn. Lab. Immunol., 1998, 5, 45-49.

Pharmaceutical Compositions

The compounds of the present invention cannot only be used in diagnosis of disorders associated with amyloid and/or amyloid-like protein aggregates, but also in treating, preventing or alleviating such disorders.

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formulae (I) or (II) in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, $15^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e. g. as a tablet, capsule, or as an ingestible solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e. g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e. g. using a mixture of ethanol and the propellant as the solvent, which may additionally contain a lubricant, e. g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, $15^{th}$ Ed., Mack Publishing Co., New Jersey (1975).

Diseases that can be treated, alleviated or prevented with the compounds of the present invention can be associated with the formation of abnormal protein structures, in particular abnormal β-sheet structures. In the context of the present invention, an abnormal protein structure is a protein structure that arises when a protein or peptide refolds from its natural occurring conformation in healthy individuals, into a β-sheet three-dimensional structure, which is associated with a pathological condition. Likewise, an abnormal β-sheet structure in the context of the present invention is a β-sheet structure that arises when a protein or peptide refolds from its natural occurring conformation in healthy individuals, into a different β-sheet structure, which is associated with a pathological condition.

In particular, in one embodiment diseases or disorders that can be treated, alleviated or prevented with the compounds of the present invention are diseases or conditions associated with amyloid or amyloid-like proteins.

The diseases or conditions that can be treated, alleviated or prevented with the compounds of the present invention include neurodegenerative disorders such as tauopathies. Examples of diseases and conditions which can be treated, alleviated or prevented are caused by or associated with the formation of neurofibrillary lesions. This is the predominant brain pathology in tauopathy. The diseases and conditions comprise a heterogeneous group of neurodegenerative diseases or conditions including diseases or conditions which show co-existence of tau and amyloid pathologies. Examples of the diseases and conditions which can be treated, alleviated or prevented include Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GSS with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, lattice dystrophy. Preferably the diseases and conditions which can be treated, alleviated or prevented include Alzheimer's disease, as well as other neurodegenerative tauopathies such as Alzheimer's disease (AD), Creutzfeldt-Jacob disease, dementia pugilistica, amyotrophic lateral sclerosis, argyrophilic grain disease, corticobasal degeneration, frontotemporal dementia with Parkinsonism linked to chromosome 17, Pick's disease, progressive supranuclear palsy (PSP), tangle only dementia, Parkinson dementia complex of Guam, Hallervorden-Spatz disease and fronto-temporal lobar degeneration.

It is also possible to use the compounds of the present invention to treat, alleviate or prevent diseases or conditions which include diseases or conditions associated with an amyloid and/or amyloid-like protein which are characterized by a loss of cognitive memory capacity and wherein preferably the treatment or alleviation leads to an increase in the retention of cognitive memory capacity and/or wherein preferably the treatment or alleviation leads to a complete restoration of cognitive memory capacity. In a preferred embodiment, the compounds of the present invention can be used for treating, alleviating or preventing a cognitive deficit, wherein preferably the alleviation leads to an arrest in the progression of the cognitive deficit and/or wherein preferably the alleviation leads to an increase in the retention, particularly a complete restoration of cognitive memory capacity. Preferably the compounds of the present invention retain or increase cognitive memory capacity in a subject suffering from memory impairment.

The compounds of the present invention can also be employed to inhibit protein aggregation, in particular to inhibit Aβ aggregation, tau aggregation, alpha-synuclein aggregation, Huntingtin (htt) aggregation, prion aggregation, ATTR (transthyretin) or ADan (ADanPP). The ability of a compound to inhibit the aggregation of Aβ can, for example, be determined using fluorescence correlation spectroscopy as described in Rzepecki et al., J. Biol. Chem., 2004, 279(46), 47497-47505 or by using the thioflavin T spectrofluorescence assay. The ability of a compound to inhibit the aggregation of Aβ, tau, alpha-synuclein, ADan and ATTR can, for example, be determined using the ThT assay (Hudson et al., FEBS J., 2009, 5960-72). The ability of a compound to inhibit the aggregation of htt can, for example, be determined using filter trap assay (Heiser et al., PNAS, 2000, 6739-44).

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholineesterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidosis, compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or tau modifying drug and nutritive supplements, an antibody, including any functionally equivalent antibody or functional parts thereof.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 93) and prodrugs (pages 93 and 94), which document is incorporated herein by reference.

The compounds of the present invention can be synthesized by one of the general methods shown in the following schemes. These methods are only given for illustrative purposes and should not to be construed as limiting.

General Synthetic Schemes for the Preparation of Tricyclic Building Blocks of this Invention:

SCHEME 1

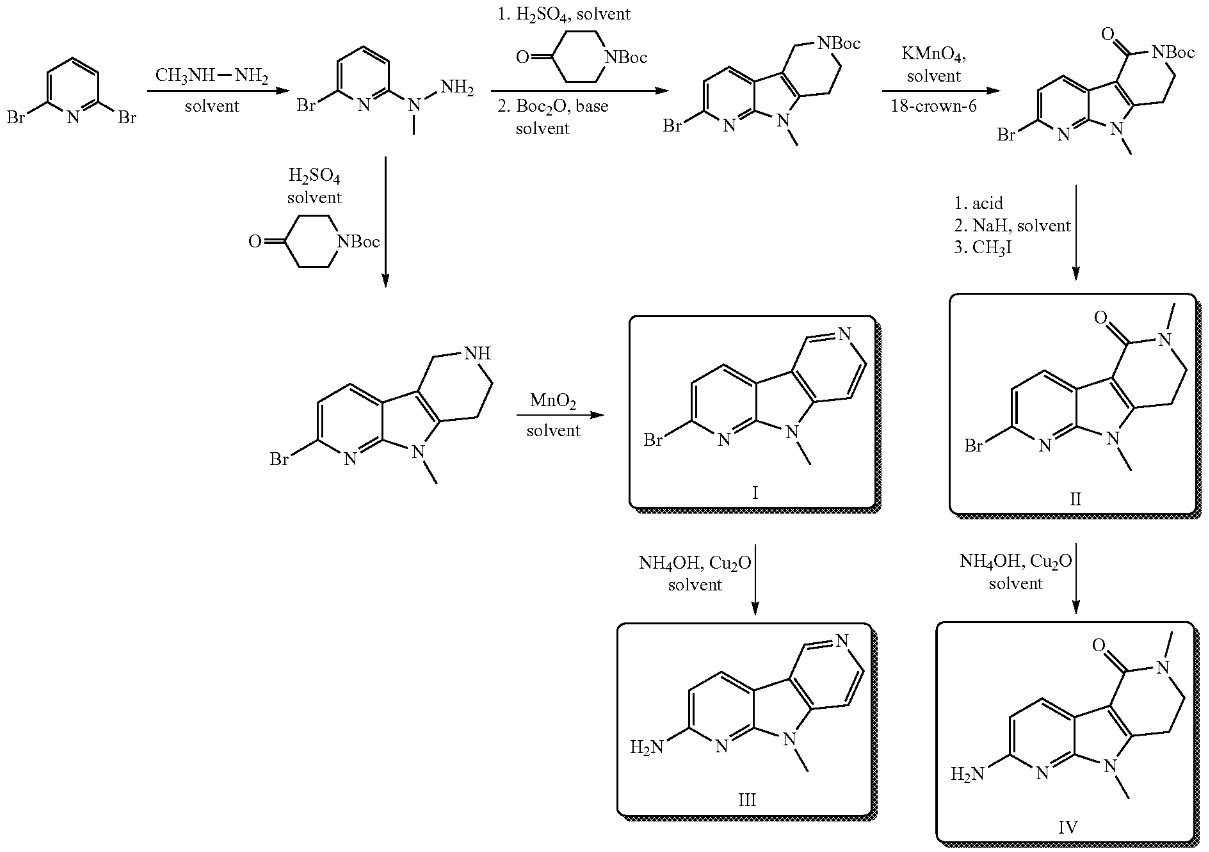

Commercially available 2,6-dibromopyridine was heated under reflux with N-methylhydrazine in a solvent to afford the desired N-methylhydrazine-pyridine derivative after purification. The N-methylhydrazine-pyridine derivative was then treated with commercially available N-Boc-piperidone under the conditions of a Fischer-indole synthesis to afford the corresponding azaindole derivative as a free base after purification. Oxidation of the azaindole derivative with manganese dioxide in a solvent afforded the desired tricyclic building block I after purification. In order to prepare tricyclic building block II, the crude product from the Fischer-indole synthesis was treated with commercially available di-tert.-butyl dicarbonate and base in a solvent. The N-Boc-protected derivative was obtained after purification and then oxidized with potassium permanganate using a crown ether and solvent. The N-Boc-protected amide derivative was obtained after purification. The Boc-protecting group was removed by acid treatment in a solvent. The obtained compound was treated with sodium hydride in a solvent followed by methyl iodide to afford the desired tricyclic building block II after purification. Nucleophilic displacement of the bromo moiety of building block I or building block II with aqueous ammonia using a copper catalyst in a solvent afforded building block III and building block IV after purification, respectively.

afforded building blocks of type VI. Oxidation of building block VI using a suitable oxidation reagent (2,3-dichloro-5,6-dicyano-1,4-benzoquinone, etc:) in a solvent afforded building blocks of type VII after purification. Boc-protection of the amide moiety of building block V afforded the

SCHEME 2

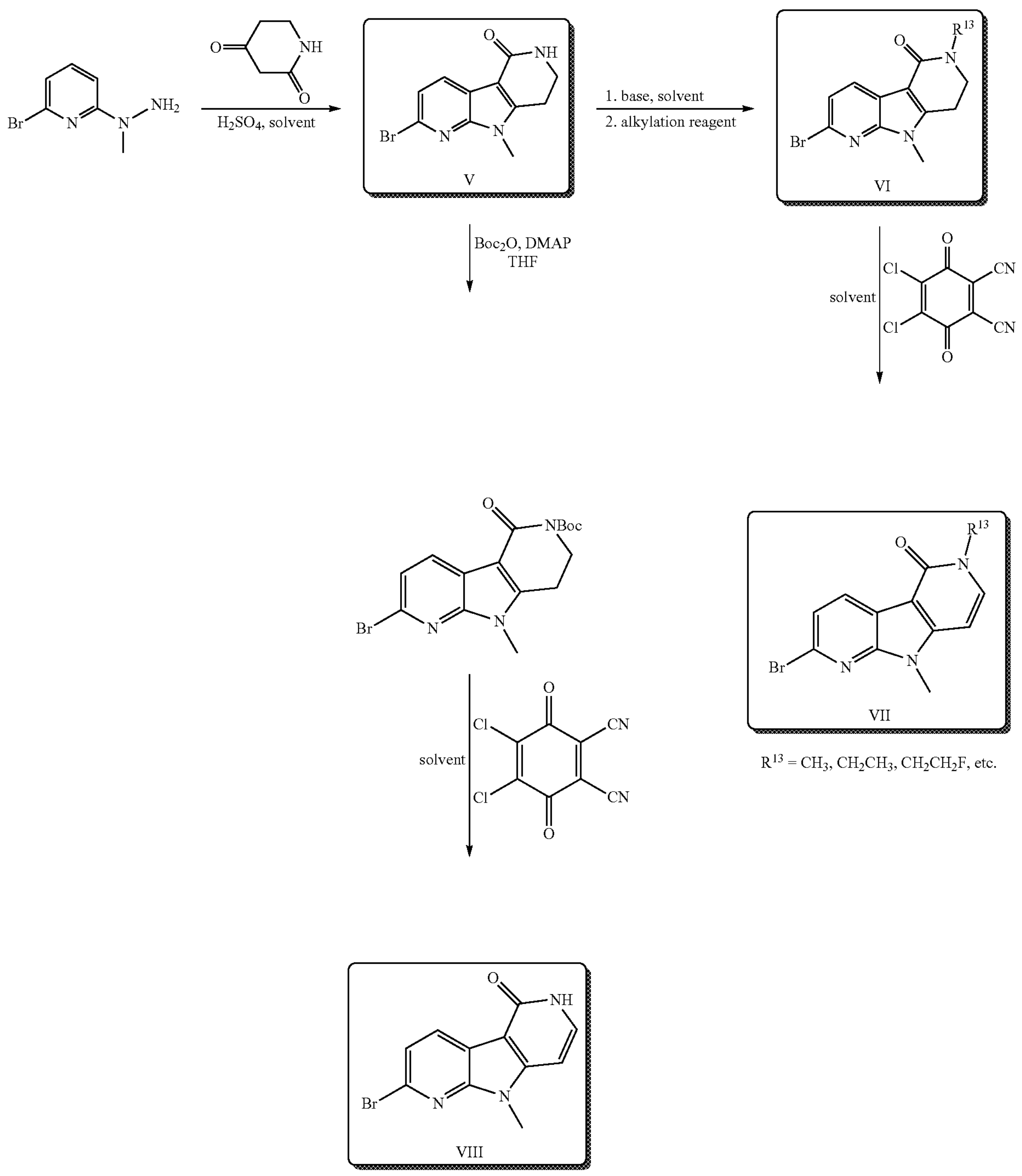

$R^{13}$ = $CH_3$, $CH_2CH_3$, $CH_2CH_2F$, etc.

The N-methylhydrazine-pyridine derivative was treated with commercially available piperidine-2,4-dione under the conditions of a Fischer-indole synthesis to afford building block V after purification. Alkylation of building block V with suitable alkylation reagents ($CH_3J$, $CH_3CH_2$—Br, etc.) corresponding Boc-protected derivative after purification. Oxidation of the Boc-protected derivative using a suitable oxidation reagent (2,3-dichloro-5,6-dicyano-1,4-benzoquinone, etc.: in a solvent afforded building block VIII after purification.

SCHEME 3

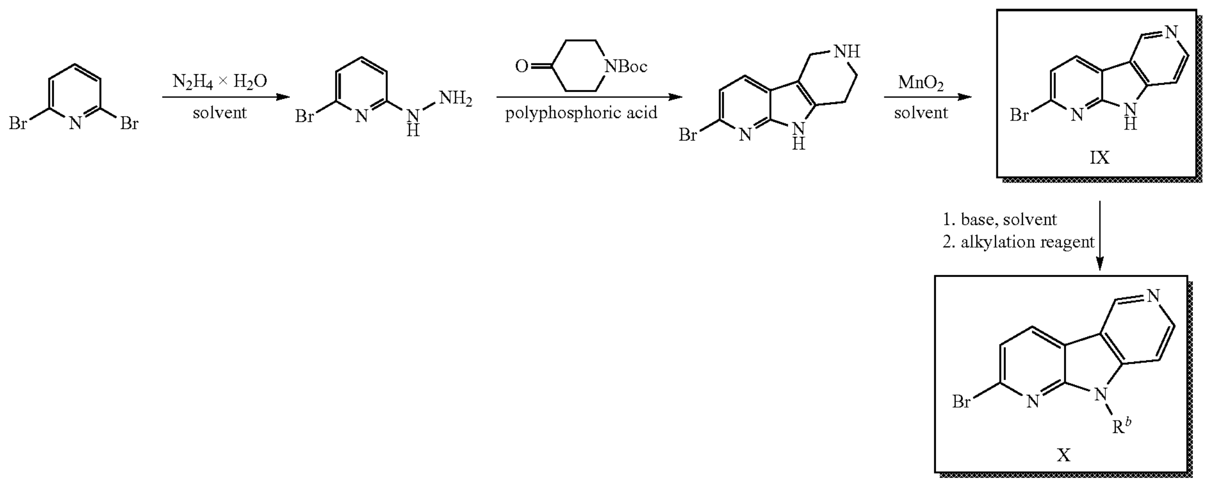

IX

X $R^b$ = $CH_3$, $CH_2CH_2OTBDMS$
$CH_2CH_2OH$
$CH_2CH_2F$
$CH_2CH_2OCH_2CH_2OCH_3$

Commercially available 2,6-dibromopyridine was heated under reflux with hydrazine hydrate in a solvent to afford the desired hydrazine-pyridine derivative after purification. The hydrazine-pyridine derivative was then treated with commercially available N-Boc-piperidone under the conditions of a Fischer-indole synthesis using polyphosphoric acid to afford the corresponding azaindole derivative as a free base after purification. Oxidation of the azaindole derivative with manganese dioxide in a solvent afforded the desired tricyclic building block IX after purification. Alkylation of building block IX with suitable alkylation reagents in a solvent affords building blocks of type X after purification. In case the alkylation product of building block IX contains a silyl-protecting group, the silyl-group is cleaved with tetrabutylammonium fluoride to afford building block X after purification.

SCHEME 4

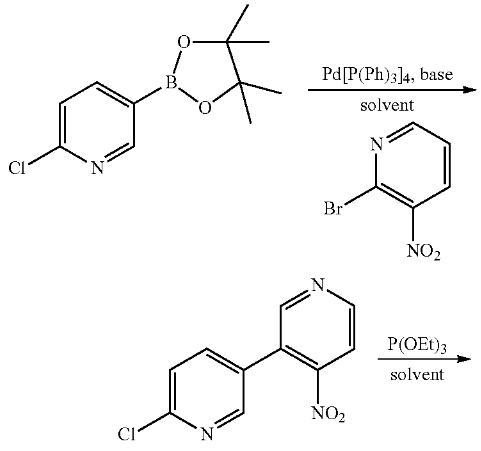

-continued

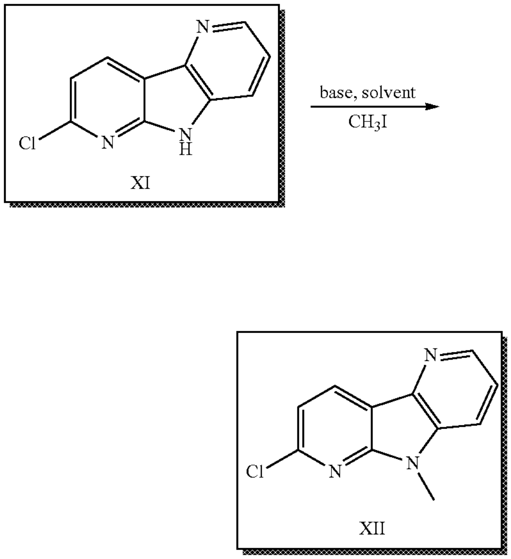

XI

XII

A suitable chloro-pyridine boronic ester derivative was treated with 2-bromo-3-nitropyridine under Suzuki conditions to afford the corresponding crosscoupling product after purification. Reduction of the nitro moiety with triethylphosphite in a solvent resulted in subsequent ring closure to afford building block XI after purification. Alkylation of the building block XI with methyl iodide in a solvent afforded the corresponding building block XII after purification.

22General Synthetic Schemes for the Preparation of Building Blocks of this Invention:

SCHEME 5

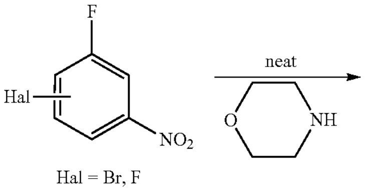

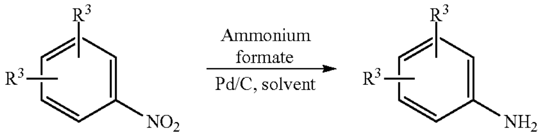

Nitrobenzene derivatives were heated with morpholine to afford the desired nucleophilic substitution product. Reduction of the nitro group using ammonium formate and palladium on charcoal in a solvent afforded the desired building blocks after purification.

SCHEME 6

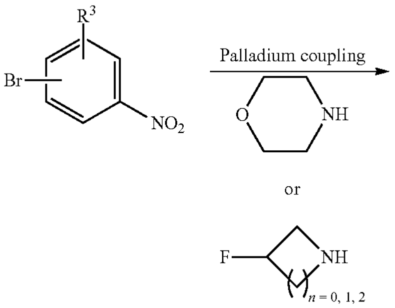

-continued

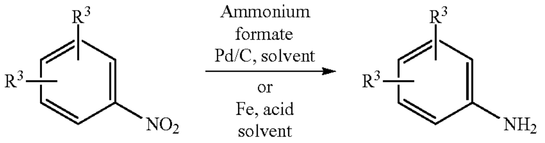

Bromo-nitrobenzene derivatives were treated with amine derivatives in a solvent via palladium-catalyzed crosscoupling (Buchwald-Hartwig amination) conditions to afford the desired coupling products after purification. Reduction of the nitro group using ammonium formate and palladium on charcoal in a solvent or iron and acid in a solvent afforded the desired building blocks after purification.

SCHEME 7

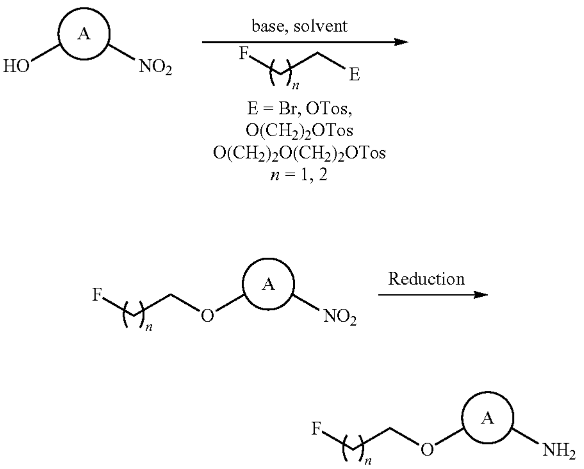

Aromatic or six-membered heteroaromatic hydroxy-nitro derivatives were treated with an alkylating agent in a solvent using a base to afford the desired ether derivatives after purification. Reduction of the nitro group using ammonium formate and palladium on charcoal in a solvent afforded the desired building blocks after purification.

SCHEME 8

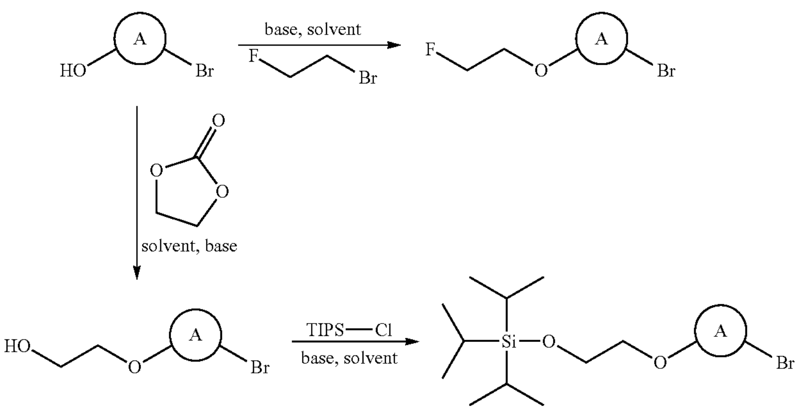

Aromatic or six-membered heteroaromatic hydroxy-bromo derivatives were treated with 1-bromo-2-fluoroethane in a solvent using a base to afford the desired building blocks after purification. Aromatic or six-membered heteroaromatic hydroxy-bromo derivatives were treated with diethylcarbonate in a solvent to afford the corresponding aryloxy/hetaryloxy-ethanol derivatives after purification. The free hydroxyl moiety was then protected by a suitable silyl-protecting group to afford the desired building blocks after purification.

SCHEME 9

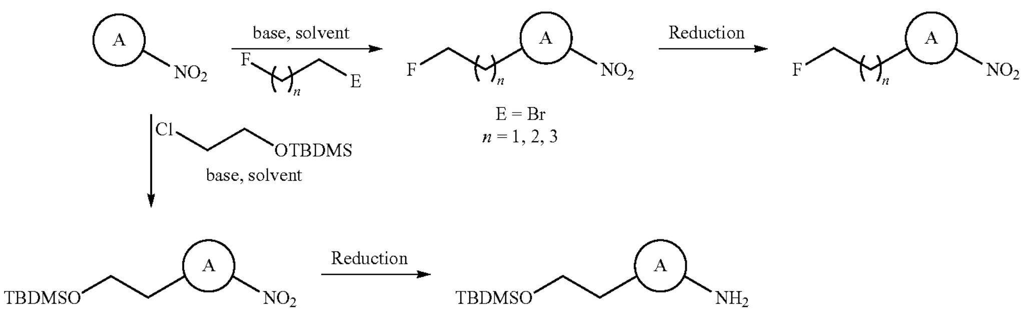

Five-membered heteroaromatic nitro derivatives containing basic nitrogen atoms (pyrazole, imidazole, thiazole, etc.) were treated with a suitable alkylating agent in a solvent using a base to afford the desired N-alkyl derivatives after purification. Reduction of the nitro group using ammonium formate and palladium on charcoal in a solvent afforded the desired building blocks after purification.

SCHEME 10

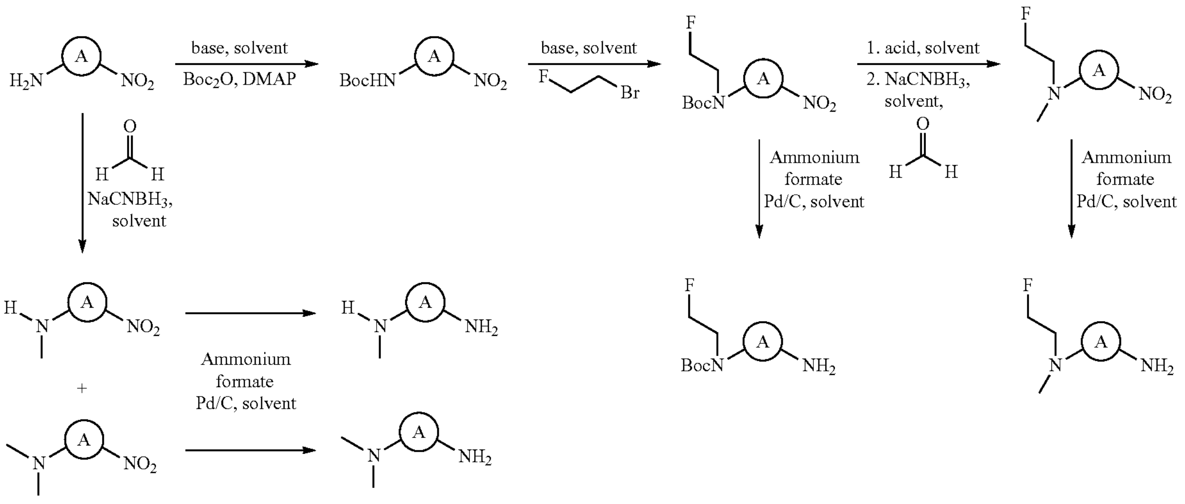

Aromatic or six-membered heteroaromatic nitro-aniline derivatives were treated with di-tert.-butyl dicarbonate, 4-(dimethylamino)-pyridine and base in a solvent to afford the N-Boc protected derivatives after purification. The N-Boc protected derivatives were treated with an alkylating agent in a solvent using a base to afford the desired N-Boc-alkylated amine derivatives after purification. Reduction of the nitro group using ammonium formate and palladium on charcoal in a solvent afforded the desired building blocks after purification. Cleavage of the Boc-protected group from the N-Boc-alkylated amine derivatives, followed by reductive amination afforded the N-dialkylated nitro derivatives after purification. Reduction of the nitro group using ammonium formate and palladium on charcoal in a solvent afforded the desired building blocks after purification. Reductive amination of aromatic or six-membered heteroaromatic nitro-aniline derivatives afforded a mixture of mono- and dialkylated nitro derivatives. Separation of the mixture by chromatography followed by reduction of the nitro group using ammonium formate and palladium on charcoal in a solvent afforded the desired mono- and dialkylated amine building blocks after purification.

General Synthetic Scheme for the Preparation of Compounds of this Invention:

SCHEME 11

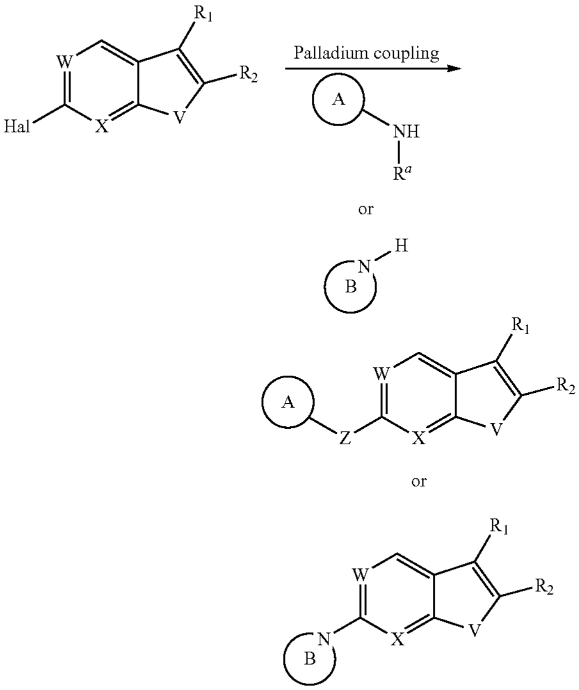

Tricyclic building blocks (Hal=Br, Cl) were treated with aromatic/heteroaromatic amine derivatives containing a fluoro moiety or cycloamine/bicycloamine/spirocycloamine derivatives containing a fluoro moiety in a solvent via palladium-catalyzed crosscoupling (Buchwald-Hartwig amination) conditions to afford the desired final compounds as solids after purification. In case the palladium coupling products contained an acid labile protecting group, the coupling products were treated with acid in a solvent to afford the desired final compounds after purification.

SCHEME 12

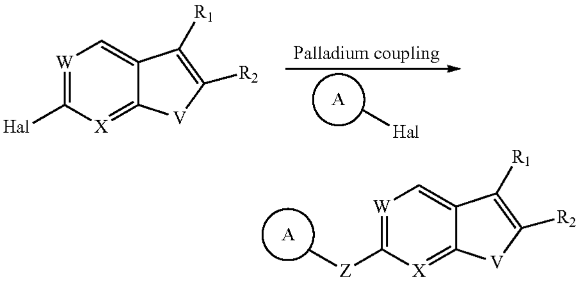

In a suitable solvent tricyclic building blocks containing an amine moiety (Hal=Br, Cl) were treated with aromatic/heteroaromatic derivatives containing a fluoro moiety and containing a halogen moiety (Hal=Br, Cl) suitable for palladium-catalyzed crosscoupling (Buchwald-Hartwig amination) reactions to afford the desired final compounds as solids after purification. In case the palladium coupling products contained an acid labile protecting group, the coupling products were treated with acid in a solvent to afford the desired final compounds as salts.

SCHEME 13
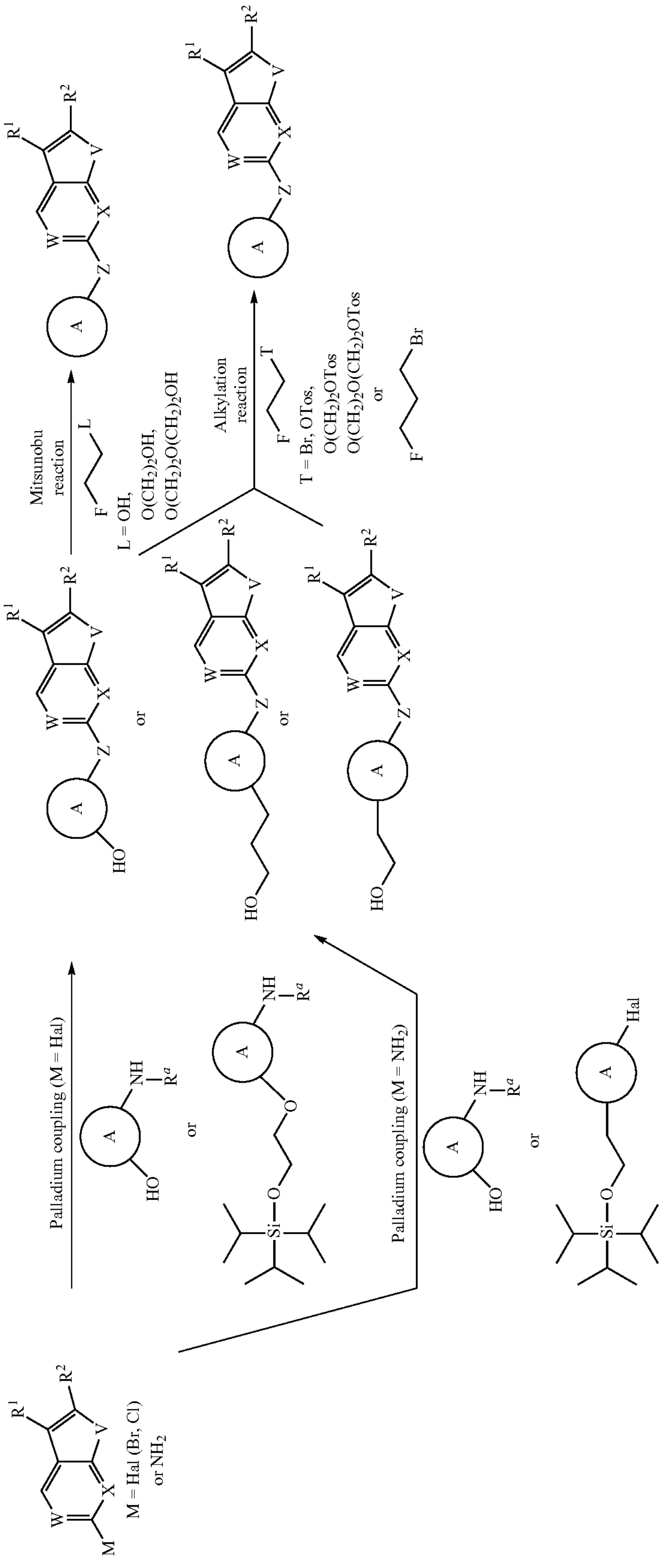

Tricyclic building blocks (M=Hal (Br, Cl) were treated with aromatic/heteroaromatic amine derivatives containing a phenolic hydroxyl moiety or a silyl-protected alcohol moiety. In a solvent via palladium-catalyzed crosscoupling (Buchwald-Hartwig amination) conditions to afford the corresponding coupling products after purification. In case a silyl-protecting group is present, the silyl group is cleaved by treatment with tetrabutylammonium fluoride to afford the alcohol derivatives. Tricyclic building blocks ($M=NH_2$) were treated with aromatic/heteroaromatic halogen (Br, Cl) derivatives containing a phenolic hydroxyl moiety or a silyl-protected alcohol moiety in a solvent via palladium-catalyzed crosscoupling (Buchwald-Hartwig amination) conditions to afford the corresponding coupling products after purification. In case a silyl-protecting group is present, the silyl group is cleaved by treatment with tetrabutylammonium fluoride to afford the alcohol derivatives. Alkylation of the phenolic or aliphatic hydroxyl moieties with a fluoroalkyl derivative having a suitable leaving group (Br, Tos, etc.) in a solvent affords the desired final compounds after purification. Treatment of the phenolic palladium-coupling products with suitable fluoroalcohol derivatives employing Mitsunobu conditions affords the desired final compounds after purification.

SCHEME 14

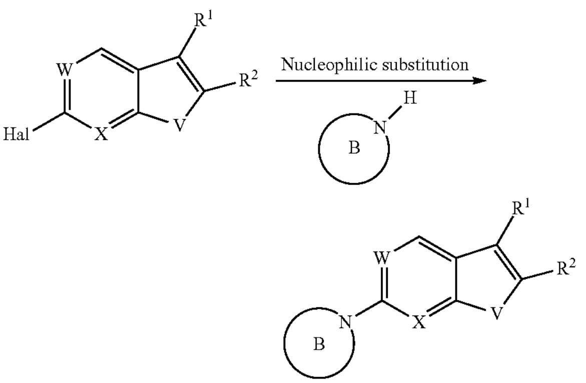

Tricyclic building blocks (Hal=Br, Cl) were treated with cycloamine/bicycloamine/spirocycloamine derivatives containing a fluoro moiety in a solvent using a microwave to enable a nucleophilic substitution reaction to afford the desired final compounds after purification.

SCHEME 15

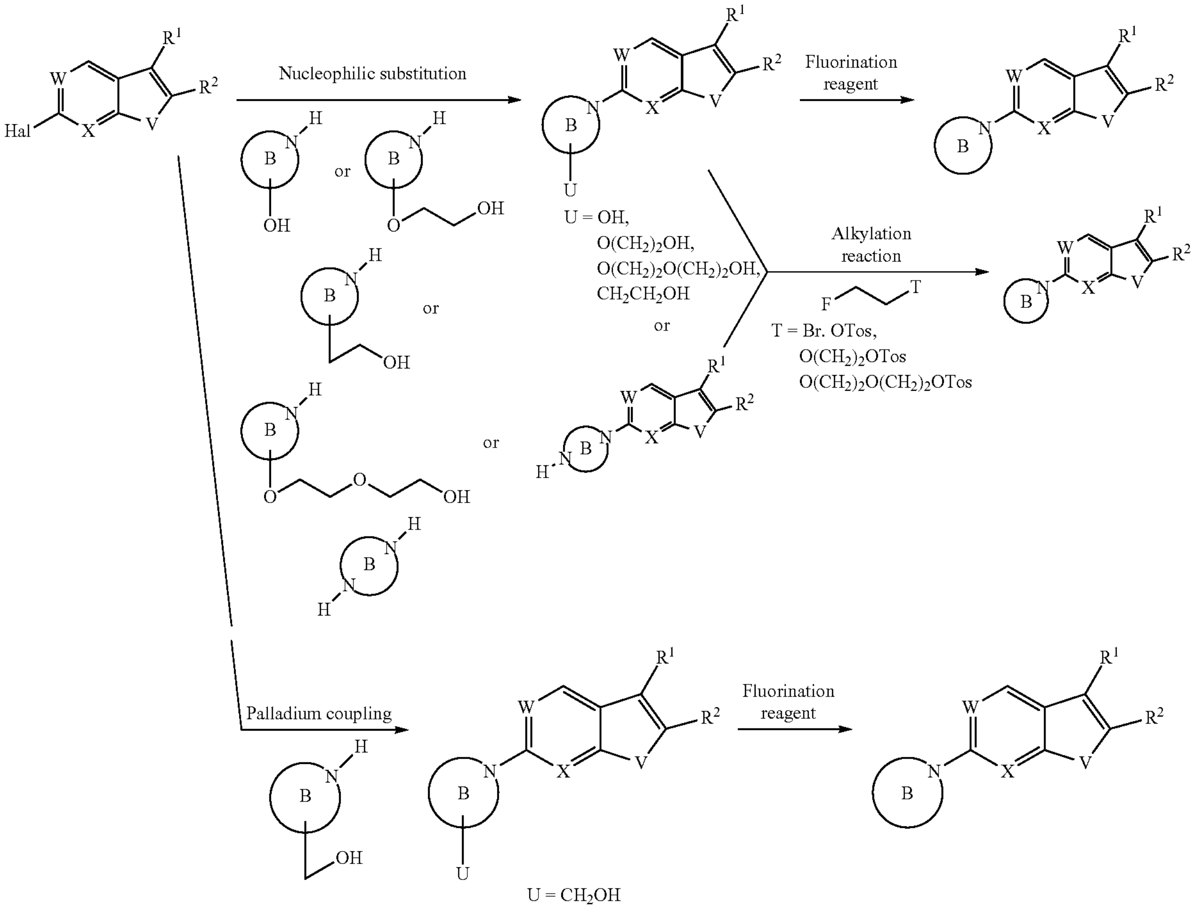

Tricyclic building blocks (Hal=Br, Cl) were treated with cycloamine/bicycloamine/spirocycloamine derivatives containing a hydroxyl- or amino-moiety in a solvent using a microwave to enable a nucleophilic substitution reaction to afford the desired intermediates after purification. Treatment of intermediates with U=OH, $CH_2OH$, $O(CH_2)_2OH$, $O(CH_2)_2O(CH_2)_2OH$ and $CH_2CH_2OH$ with a fluorination reagent (Deoxo-Fluor, etc.) in a solvent afforded the desired final compounds after purification. Alkylation of intermediates with U=OH and $CH_2CH_2OH$ with a fluoroalkyl reagent having a suitable leaving group (Br, Tos, etc.) in a solvent afforded the desired final compounds after purification. The alkylation reaction of piperazine derivatives with a fluoroalkyl reagent having a suitable leaving group (Br, Tos, etc.) in a solvent afforded the desired final compounds after purification. Tricyclic building blocks (Hal=Br, Cl) were treated with cycloamine derivatives containing an unprotected hydroxyl moiety in a solvent via palladium-catalyzed crosscoupling (Buchwald-Hartwig amination) conditions to afford the desired compounds after purification. The alcohol derivatives with U=$CH_2OH$ were treated with a fluorination reagent (Deoxo-Fluor, etc.) in a solvent which afforded the desired final compounds after purification.

General Synthetic Scheme for the Preparation of Precursor Compounds of this Invention:

SCHEME 16

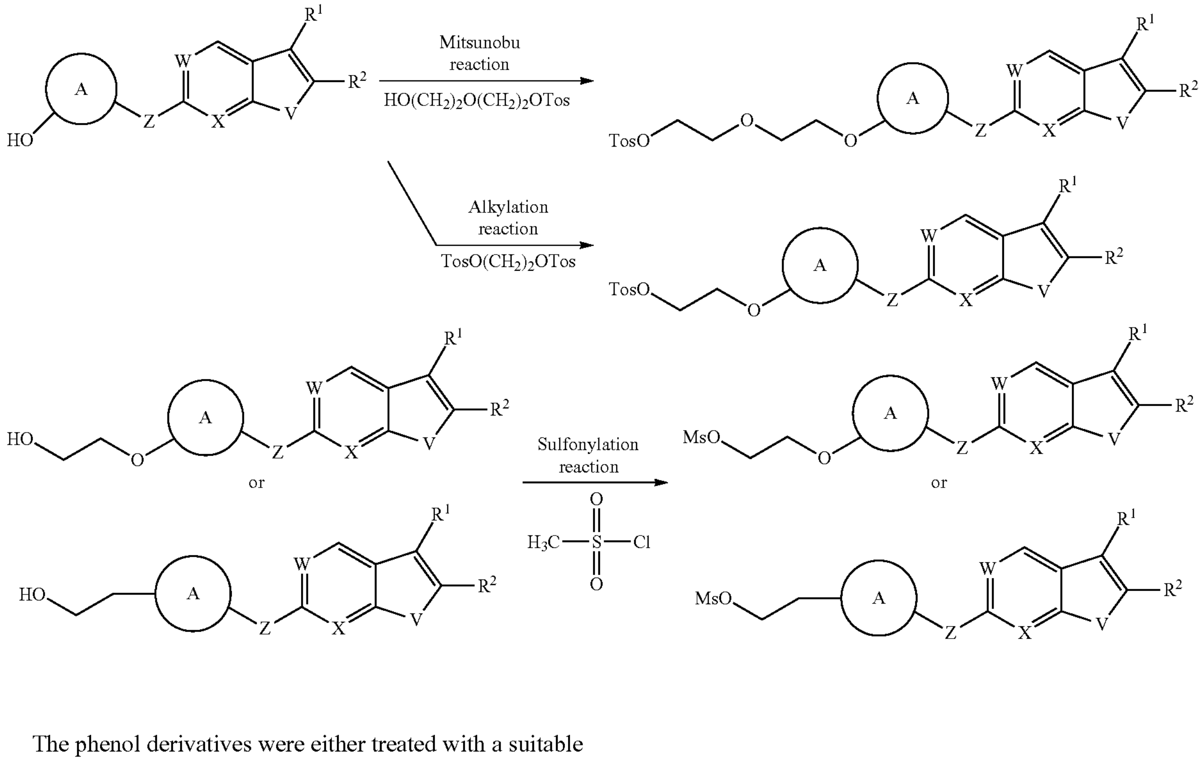

The phenol derivatives were either treated with a suitable alcohol derivative employing Mitsunobu conditions or alkylated using a suitable alkylation reagent to afford the corresponding sulfonyl derivatives. The desired precursor compounds to allow the introduction of the $^{18}F$-label in the following step were obtained after purification. The alcohol derivatives were treated with a suitable sulfonylation reagent ($CH_3SO_2Cl$) in a solvent to afford the desired precursor compounds to allow the introduction of the $^{18}F$-label in the following step.

SCHEME 17

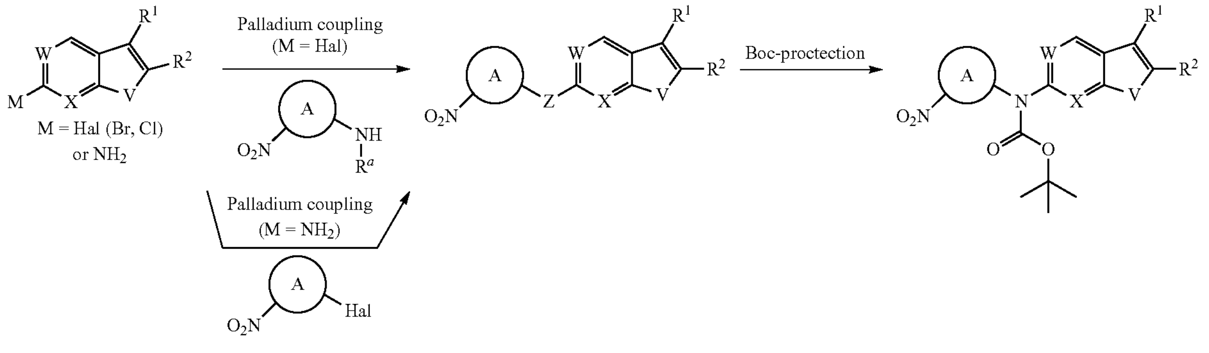

Tricyclic building blocks (M=Hal (Br, Cl) were treated with aromatic/heteroaromatic amine derivatives containing a nitro moiety in a solvent via palladium-catalyzed cross-coupling (Buchwald-Hartwig amination) conditions to afford the corresponding coupling products after purification. Tricyclic building blocks ($M=NH_2$) were treated with aromatic/heteroaromatic halogen (Br, Cl) derivatives containing a nitro moiety in a solvent via palladium-catalyzed crosscoupling (Buchwald-Hartwig amination) conditions to afford the corresponding coupling products after purification. The nitro derivatives are precursor compounds to allow the introduction of the $^{18}F$-label in the following step. In case of very poor solubility of the nitro derivatives in organic solvents and poor radiochemical yield during $^{18}F$-labeling, the nitro derivatives were treated with di-tert.-butyl dicarbonate in a solvent to afford the Boc-protected aniline compounds after purification. The Boc-nitro derivatives are precursor compounds to allow the introduction of the $^{18}F$-label in the following step.

Tricyclic building blocks (Hal=Br, Cl) were treated with cycloamine/bicycloamine/spirocycloamine derivatives containing a protected hydroxyl moiety or a protected amino moiety in a solvent via palladium-catalyzed crosscoupling (Buchwald-Hartwig amination) conditions to afford the desired compounds after purification. In case the palladium-coupling products contained silyl-protecting groups, the coupling products were treated with tetrabutylammonium fluoride to afford the desired hydroxyl precursor compounds after purification. In case the palladium coupling products contained an acid labile protecting group, the coupling products were treated with acid in a solvent to afford the desired amino precursor compounds after purification. The hydroxyl and amino precursor compounds were used to introduce a $^{18}F$-label in the following step.

SCHEME 18

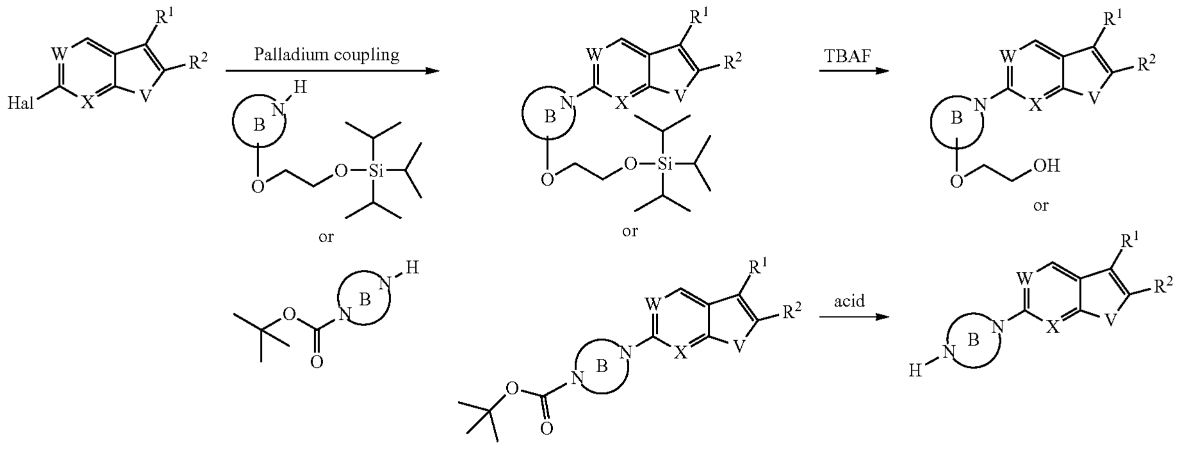

SCHEME 19

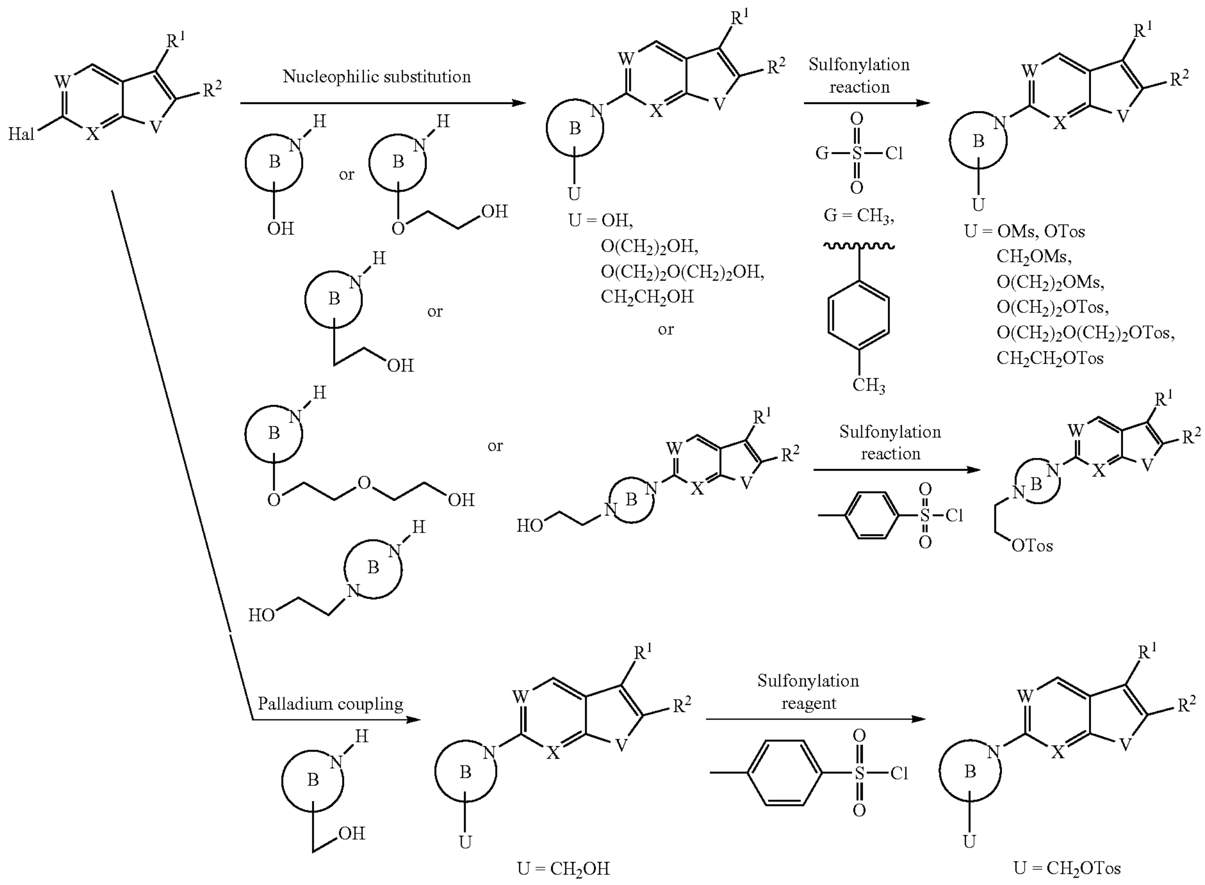

Tricyclic building blocks (Hal=Br, Cl) were treated with cycloamine/bicycloamine/spirocycloamine derivatives containing a hydroxyl-moiety in a solvent using a microwave to enable a nucleophilic substitution reaction to afford the desired alcohol derivatives after purification. The alcohol derivatives with U═OH, $CH_2OH$, $O(CH_2)_2OH$, $O(CH_2)_2O(CH_2)_2OH$ and $CH_2CHOH$ were treated with a suitable sulfonylation reagent ($CH_3SO_2Cl$, p-Tos-Cl) in a solvent to afford the desired precursor compounds to allow the introduction of the $^{18}F$-label in the following step. Tricyclic building blocks (Hal=Br, Cl) were treated with piperazine derivatives containing an alkylhydroxy moiety in a solvent via palladium-catalyzed crosscoupling (Buchwald-Hartwig amination) conditions to afford the desired compounds after purification. The piperazine alkylhydroxy coupling products were treated with a suitable sulfonylation reagent (p-Tos-Cl) in a solvent to afford the desired precursor compounds to allow the direct introduction of the $^{18}F$-label in the following step.

EXAMPLES

All reagents and solvents were obtained from commercial sources and used without further purification. Proton ($^1H$) spectra were recorded on a Bruker DRX-400 MHz NMR spectrometer or on a Bruker AV-400 MHz NMR spectrometer in deuterated solvents. Mass spectra (MS) were recorded on an Advion CMS mass spectrometer. Chromatography was performed using silica gel (Fluka: Silica gel 60, 0.063-0.2 mm) and suitable solvents as indicated in the specific examples. Flash purification was conducted with a Biotage Isolera One flash purification system using HP-Sil or KP-NH SNAP cartridges (Biotage) and the solvent gradient indicated in the specific examples. Thin layer chromatography (TLC) was carried out on silica gel plates with UV detection.

Although some of the present examples do not indicate that the respective compounds were detectably labeled, it is understood that corresponding detectably labeled compounds are intended and can be easily prepared, e.g., by using detectably labeled starting materials, such as starting materials containing $C(^3H)_3$, $(^{11}C)H_3$ or $^{18}F$.

Preparative Example 1

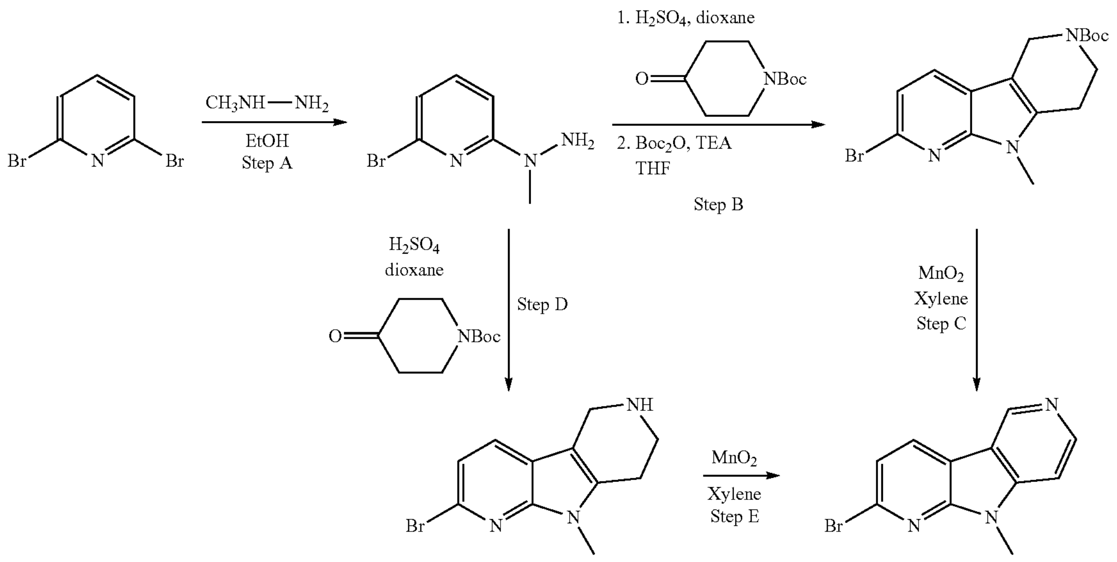

Step A

To a suspension of commercially available 2,6-dibromopyridine (10 g, 42.2 mmol) in ethanol (50 mL) was added commercially available N-methylhydrazine (11.11 mL, 211 mmol). The mixture was heated at 80° C. (reaction mixture temperature) for 48 h. The reaction mixture was concentrated to dryness and the residue was purified by chromatography on HP-Sil SNAP cartridges using a Biotage Isolera One purification system employing an ethyl acetate/n-heptane gradient (15/75->35/65) to afford the title compound as a reddish oil which became a solid by standing at room temperature (7.6 g, 89%)

$^1$H-NMR (400 MHz, $CDCl_3$): δ=3.23 (s, 3H), 4.00 (br-s, 2H), 6.70 (d, 1H), 6.82 (d, 1H), 7.27 (t, 1H).

Step B

A suspension of N-Boc-piperidone (10 g, 56 mmol) and the title compound from Step A above (10.1 g, 50 mmol) in 1,4-dioxane (100 mL) was placed in an ice-bath. To the stirred suspension concentrated sulfuric acid (15 mL) was slowly added (exotherm, gas evolution). After the addition was completed, the reaction mixture was heated at reflux temperature for 7 h using a sand-bath (~140° C.). The reaction mixture was cooled to room temperature, the dioxane layer was discarded, and ice-water (150 mL) was added. The mixture was stirred until the gummy material was dissolved. Then the pH of the reaction mixture was adjusted to pH=12-13 by adding solid NaOH. The aqueous layer was extracted with dichloromethane (3×100 mL) and the organic phase was washed with water and brine. The organic phase was separated, dried over $Na_2SO_4$ and the solvent was removed under reduced pressure to afford the crude free base. The residue was dissolved in THF (100 mL) and triethylamine (10 mL) and di-tert-butyl dicarbonate (20 g, 91.6 mmol) were added. The reaction mixture was stirred at room temperature overnight. Then, the reaction mixture was concentrated and the residue was dissolved in dichloromethane (200 mL). The organic phase was washed with water as well as brine, dried over $Na_2SO_4$ and filtered. The solvent was removed under reduced pressure and the residue was dissolved in dichloromethane (200 mL) and water (50 mL). The organic phase was separated, dried over $Na_2SO_4$, filtered and the solvent was removed under reduced pressure. The dark residue was purified by chromatography on silica gel employing EtOAc/n-heptane (20/80) as a mobile phase to afford the title compound as an off-white solid (3.8 g, 20% for 2 steps).

$^1$H-NMR (400 MHz, $CDCl_3$): δ=1.53 (s, 9H), 2.84 (t, 2H), 3.73 (s, 3H), 3.87 (t, 2H), 4.58-4.62 (br-s, 2H), 7.17 (d, 1H), 7.62 (d, 1H).

Step C

The title compound from Step B above (1.8 g, 4.92 mmol) was dissolved in xylene (100 mL) and activated $MnO_2$ (4.7 g, 54 mmol) was added at room temperature. The mixture was then heated at ~160° C. in a sand-bath for 3 days. The reaction mixture was cooled to room temperature, filtered through paper filters and the filter was washed with xylene (20 mL). The combined filtrates were evaporated under reduced pressure and the dark residue was purified by chromatography on HP-Sil SNAP cartridges using a Biotage Isolera One purification system employing a dichloromethane/methanol gradient (100/0->90/10). Fractions containing the product were collected and the solvents were removed under reduced pressure. The dark residue was again purified by chromatography on HP-Sil SNAP cartridges using a Biotage Isolera One purification system employing an EtOAc/n-heptane gradient (5/95->100/0) to separate unreacted starting material and nonpolar by-products. Then the gradient was changed to dichloromethane/methanol (90/10) to afford the title compound as a dark-yellow solid (0.48 g, 37%).

$^1$H-NMR (400 MHz, DMSO-$d_6$): S=3.90 (s, 3H), 7.57 (d, 1H), 7.74 (d, 1H), 8.60-8.63 (m, 2H), 9.42 (s, 1H).

Step D

A suspension of N-Boc-piperidone (10 g, 56 mmol) and the title compound from Step A above (10.1 g, 50 mmol) in 1,4-dioxane (100 mL) was placed in an ice-bath. To the stirred suspension concentrated sulfuric acid (15 mL) was slowly added (exotherm, gas evolution). After the addition was completed, the reaction mixture was heated at reflux temperature for 7 h using a sand-bath (~140° C.). The reaction mixture was cooled to room temperature, the dioxane layer was discarded, and ice-water (150 mL) was added.

The mixture was stirred until the gummy material was dissolved. Then the pH of the reaction mixture was adjusted to pH=12-13 by adding solid NaOH. After adjusting the pH, the reaction mixture was stirred at 0° C. for 30 minutes, the precipitate was collected by filtration and washed with water (15 mL). The precipitate was suspended in propan-2-ol (80 mL) and heated at reflux for 10 minutes. The reaction mixture was filtered, the precipitate was washed with propan-2-ol (10 mL) and the combined filtrate was evaporated. The dark residue was purified by chromatography on a 100 g KP-NH column using a Biotage Isolera One purification system employing a dichloromethane/methanol gradient (100/0->80/20) to afford the title compound as a grey solid (3.14 g, 23%).

$^1$H-NMR (400 MHz, $CDCl_3$): δ=2.74-2.78 (m, 2H), 3.26 (t, 2H), 3.70 (s, 3H), 4.02 (t, 2H), 7.13 (d, 1H), 7.52 (d, 1H).

Step E

The title compound from Step D above (3.0 g, 11.28 mmol) was dissolved in xylene (230 mL) and activated $MnO_2$ (10.8 g, 124 mmol) was added at room temperature. The mixture was then heated at ~160° C. in a sand-bath for 24 hours. The reaction mixture was cooled to room temperature, filtered through paper filters and the filter was washed with xylene (40 mL). The combined filtrates were evaporated under reduced pressure and the dark residue was purified by chromatography on HP-Sil SNAP cartridges using a Biotage Isolera One purification system employing an EtOAc/n-heptane gradient (5/95->100/0) to elute nonpolar by-products. Then the gradient was changed to dichloromethane/methanol (90/10) to afford the title compound as a dark-yellow solid (2.0 g, 64%).

$^1$H-NMR (400 MHz, DMSO-$d_6$): δ=3.90 (s, 3H), 7.57 (d, 1H), 7.74 (d, 1H), 8.60-8.63 (m, 2H), 9.42 (s, 1H).

Preparative Example 2

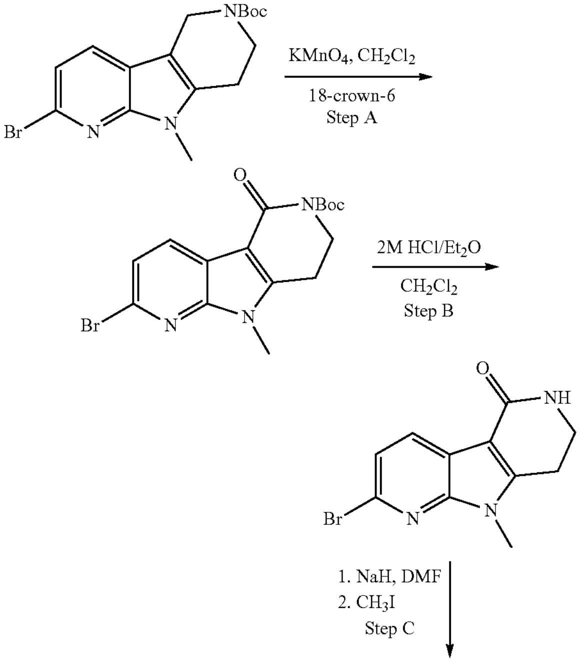

-continued

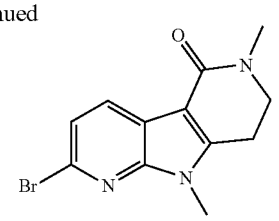

Step A

To a solution of the title compound from Preparative Example 1 Step B (0.95 g, 2.6 mmol) in dichloromethane (20 mL) was added 18-crown-6 (026 g, 0.98 mmol) followed by portionwise addition of $KMnO_4$ (0.65 g, 4.0 mmol). The resulting reaction mixture was stirred for 3 h at room temperature. Then the reaction mixture was quenched with saturated sodium metabisulfite solution and stirred for 30 min, and extracted with more dichloromethane (100 mL). The organic layer was washed with water, brine, and dried over $Na_2SO_4$. The solvent was removed, the crude product was purified on a silica gel column using a Biotage Isolera One purification system employing an EtOAc/heptane gradient (50/50->100/0) to afford the title compound (0.25 g, 34%).

Step B

To a solution of the title compound from Step A above (0.5 g, 1.3 mmol) in dichloromethane (15 mL) was added 2M HCl in diethyl ether (5 mL). The reaction mixture was stirred overnight. The reaction mixture was diluted with more dichloromethane (50 mL) and washed with sodium hydroxide solution, water, as well as brine, and dried over $Na_2SO_4$. The solvent was removed to give the title compound (0.3 g, 83%).

$^1$H-NMR (400 MHz, $CDCl_3$) δ=8.24 (d, 1H), 7.34 (d, 1H), 3.81 (s, 3H), 3.78-3.71 (m, 2H), 3.10-3.00 (m, 2H).

Step C

To solution of the title compound from Step B above (0.2 g, 0.7 mmol) in N,N'-dimethylformamide (5 mL) was added sodium hydride (0.025 g, 1 mmol), followed by addition of methyl iodide (0.15 g, 1 mmol). The reaction mixture was stirred at room temperature overnight. Then the reaction mixture was dissolved in ethyl acetate (200 ml) and washed with water as well as brine, and dried over $Na_2SO_4$. The solvent was removed under reduced pressure and the residue was purified on silica gel column on a Biotage Isolera One purification system by employing a gradient dichloromethane/methanol (100/0->80/20) to afford the title compound (0.15 g, 73%)).

$^1$H-NMR (400 MHz, $CDCl_3$) δ=8.26 (d, 1H), 7.32 (d, 1H), 3.78 (s, 3H), 3.70 (t, 2H), 3.14-3.01 (m, 5H).

Preparative Example 3

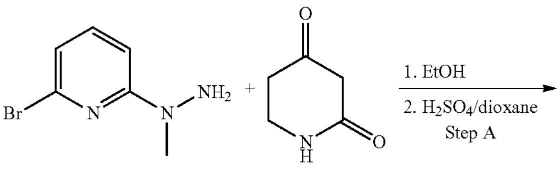

-continued

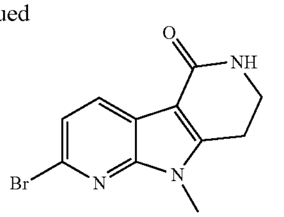

To mixture of the title compound from Preparative Example 1 Step A (4.3 g, 11 mmol) and piperidine-2,4-dione (2.41 g, 11 mmol) was added EtOH (50 mL). The reaction mixture was stirred for 3 hours. The solvent was removed, the residue was distributed in a 3 microwavable vials and diethylene glycol was added. The vials were sealed and heated at 245° C. for 30 minutes. The combined reaction mixture was poured into water and extracted with ethyl acetate (200 mL). The organic phase was washed with water as well as brine solution, and dried over $Na_2SO_4$. The solvent was removed under reduced pressure. The compound, which crystallized while concentrating the solvent, was filtered off and dried to afford the title compound (1.2 g, 20%).

$^1$H-NMR (400 MHz, $CDCl_3$) δ=8.24 (d, 1H), 7.34 (d, 1H), 3.81 (s, 3H), 3.78-3.71 (m, 2H), 3.10-3.00 (m, 2H).

Preparative Example 4

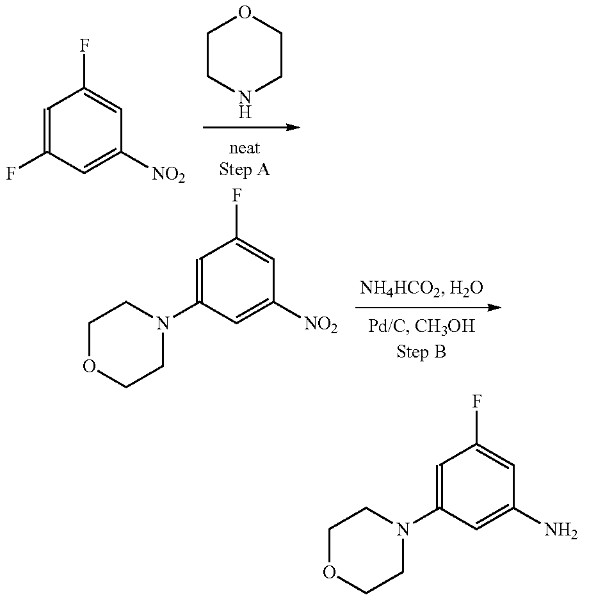

Step A

A solution of commercially available 3,5-difluoroaniline (2.5 g, 15.7 mmol) and morpholine (15 mL) was heated for 2 h at 130° C. using a Biotage Initiator microwave. The mixture was diluted with water (100 mL), the precipitate a EtOAc collected by filtration, washed with water (15 mL) and air dried to afford the title compound as a yellow solid (3.55 g, 99%)

$^1$H-NMR (400 MHz, $CDCl_3$): δ=3.25-3.28 (m, 4H), 3.86-3.90 (m, 4H), 6.85 (dt, 1H), 7.36 (dt, 1H), 7.53 (s, 1H).

Step B

The title compound from Step A above (3.55 g, 15.7 mmol) was suspended in methanol (55 mL) and ammonium formate (4.95 g, 78.7 mmol) a EtOAc added. After the addition of 10% palladium on charcoal (0.49 g) in water (5 mL), the mixture was stirred at room temperature for 18 h. A slight exotherm was observed after adding the suspension of the catalyst. The mixture was filtered, the catalyst a EtOAc washed with methanol (5 mL) and the combined filtrate a EtOAc evaporated under reduced pressure. The residue was dissolved in ethyl acetate (100 mL) and water (25 mL). The organic phase was separated, dried over $Na_2SO_4$, filtered and the solvent a EtOAc removed under reduced pressure to afford the title compound as a tan solid (2.56 g, 83%).

$^1$H-NMR (400 MHz, $CDCl_3$): δ=3.13-3.17 (m, 4H), 3.72 (br-s, 2H), 3.83-3.87 (m, 4H), 5.96 (dt, 1H), 6.00 (s, 1H), 6.06 (dt, 1H).

Preparative Example 5

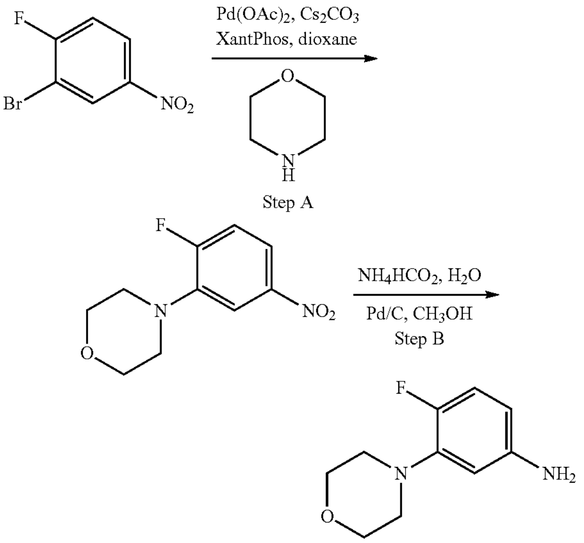

Step A

Commercially available 2-bromo-1-fluoro-4-nitro-benzene (1.5 g, 6.82 mmol) was combined with palladium(II) acetate (0.16 g, 0.8 mmol), 4,5-bis(diphenylphosphino)-9,9-dimethylxanthene (0.62 g, 0.8 mmol) and cesium carbonate (4.44 g, 13.64 mmol). To the mixture was then added degassed 1,4-dioxane (15 mL) and morpholine (0.84 g, 9.6 mmol). The reaction mixture was heated at ~110° C. in a sand-bath for 8 h. The reaction mixture was cooled to room temperature and diluted with ethyl acetate (150 mL), water, (20 mL) and brine (20 mL). The organic phase was separated, dried over $Na_2SO_4$, filtered and the solvents were removed under reduced pressure. The residue was purified on HP-Sil SNAP cartridges using a Biotage Isolera One purification system employing an EtOAc/n-heptane gradient (5/95->40/60) to afford the title compound as a yellow solid (0.77 g, 50%).

$^1$H-NMR (400 MHz, $CDCl_3$): δ=3.15-3.18 (m, 4H), 3.87-3.92 (m, 4H), 7.15 (dd, 1H), 7.81 (dd, 1H), 7.86 (dt, 1H).

Step B

The title compound from Step A above (0.77 g, 3.41 mmol) was dissolved in methanol (15 mL) and ammonium formate was added (0.86 g, 13.4 mmol). After the addition of a suspension of 10% palladium on charcoal (0.085 g) in water (1 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure to afford the title compound as an off-white solid (0.57 g, 85%).

$^1$H-NMR (400 MHz, $CDCl_3$): δ=3.03-3.07 (m, 4H), 3.51 (br-s, 2H), 3.84-3.88 (m, 4H), 6.21-6.28 (m, 2H), 6.82 (dd, 1H).

Preparative Example 6

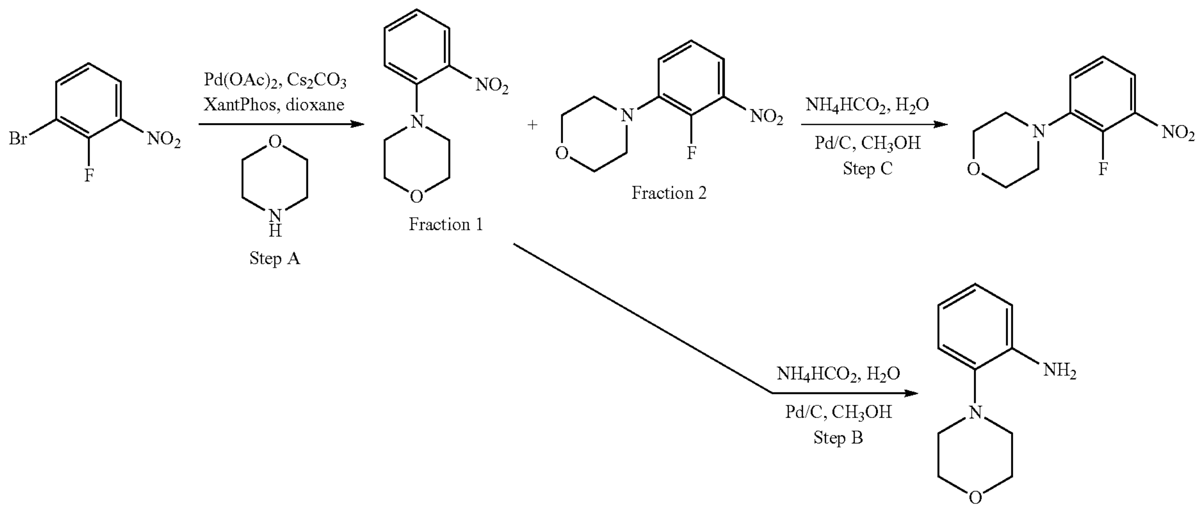 [SMILES: O=[N+]([O-])c1cccc(Br)c1F ; C1COCCN1 ; O=[N+]([O-])c1ccccc1N1CCOCC1 ; O=[N+]([O-])c1cccc(N2CCOCC2)c1F ; O=[N+]([O-])c1cccc(N2CCOCC2)c1F ; Nc1ccccc1N1CCOCC1]

Step A

Commercially available 1-bromo-2-fluoro-3-nitro-benzene (1.5 g, 6.82 mmol) was combined with palladium(II) acetate (0.16 g, 0.8 mmol), 4,5-bis(diphenylphosphino)-9,9-dimethylxanthene (0.62 g, 0.8 mmol) and cesium carbonate (4.44 g, 13.64 mmol). To the mixture was then added degassed 1,4-dioxane (15 mL) and morpholine (0.84 g, 9.6 mmol). The reaction mixture was heated at ~110° C. in a sand-bath for 8 h. The reaction mixture was cooled to room temperature and diluted with ethyl acetate (150 mL), water, (20 mL) and brine (20 mL). The organic phase was separated, dried over $Na_2SO_4$, filtered and the solvents were removed under reduced pressure. The residue was purified on HP-Sil SNAP cartridges using a Biotage Isolera One purification system employing an EtOAc/n-heptane gradient (5/95->40/60) to afford the title compound as a reddish oil (Fraction 1: 0.13 g, 9%) and a yellow solid (Fraction 2: 0.65 g, 42%), respectively.

Fraction 1:

$^1$H-NMR (400 MHz, $CDCl_3$): δ=3.05-3.09 (m, 4H), 3.84-3.87 (m, 4H), 7.08 (dt, 1H), 7.16 (dd, 1H), 7.52 (dt, 1H), 7.77 (dd, 1H).

Fraction 2:

$^1$H-NMR (400 MHz, $CDCl_3$): δ=3.13-3.17 (m, 4H), 3.87-3.92 (m, 4H), 7.16-7.22 (m, 2H), 7.58 (m, 1H).

Step B

The title compound from Step A above (Fraction 1; 0.13 g, 0.615 mmol) was dissolved in methanol (2.5 mL) and ammonium formate solvents were removed added (0.16 g, 2.42 mmol). After the addition of a suspension of 10% palladium on charcoal (0.016 g) in water (0.2 mL), the mixture was stirred at room temperature overnight. The reaction mixture was filtered and the catalyst was washed with methanol (1 mL). The filtrate was evaporated under reduced pressure and the residue was re-dissolved in ethyl acetate (25 mL) and water (10 mL). The organic phase was separated, dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->40/60) to afford the title compound as a dark oil which became a solid by standing at room temperature (0.066 g, 60%).

$^1$H-NMR (400 MHz, DMSO-$d_6$): δ=2.75-2.78 (m, 4H), 3.70-3.74 (m, 4H), 4.74 (br-s, 2H), 6.53 (dt, 1H), 6.66 (dd, 1H), 6.79 (dt, 1H), 6.87 (dd, 1H).

Step C

The title compound from Step A above (Fraction 2: 0.65 g, 2.87 mmol) was dissolved in methanol (10 mL) and ammonium formate was added (0.72 g, 11.3 mmol). After the addition of a suspension of 10% palladium on charcoal (0.072 g) in water (1 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure to afford the title compound as an off-white solid (0.46 g, 81%).

$^1$H-NMR (400 MHz, DMSO-$d_6$): δ=2.90-2.93 (m, 4H), 3.69-3.73 (m, 4H), 4.80 (br-s, 2H), 6.16 (dt, 1H), 6.40 (dt, 1H), 6.74 (dt, 1H).

Preparative Example 7

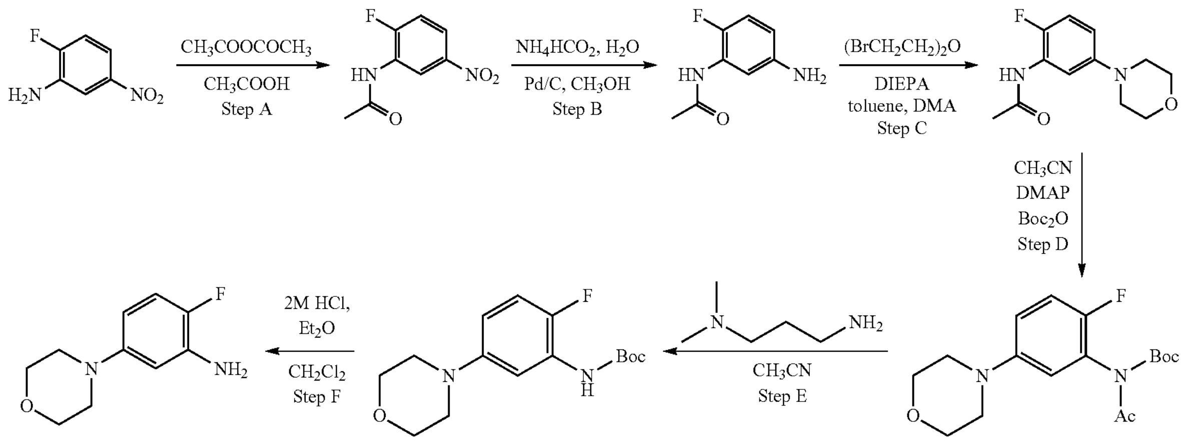

Step A

Commercially available 2-fluoro-5-nitrophenylamine (7.8 g, 50 mmol) was suspended in acetic acid (50 mL) and heated to reflux. Then acetic acid anhydride (8 mL) was added over a period of 10 minutes. After the addition was completed, the mixture was heated at reflux for another 30 minutes. The mixture was allowed to cool to ~40° C. and poured into ice-water (800 mL). The precipitate was collected by filtration, washed with water (50 mL) and air-dried to afford the title compound as a beige solid (8.9 g, 89%).

$^1$H-NMR (400 MHz, $CDCl_3$): δ=2.27 (s, 3H), 7.23-7.26 (m, 1H), 7.50 (br-s, 1H), 7.97-8.01 (m, 1H), 9.31 (s, 1H).

Step B

The title compound from Step A above (4.45 g, 22.5 mmol) was dissolved in methanol (80 mL) and ammonium formate was added (7.08 g, 112.5 mmol). After the addition of a suspension of 10% palladium on charcoal (0.71 g) in water (7 mL), the mixture was stirred at room temperature overnight. The reaction mixture was filtered and the catalyst was washed with methanol (15 mL). The filtrate was evaporated under reduced pressure and the residue was re-dissolved in ethyl acetate (200 mL) and water (50 mL). The organic phase was separated, dried over $Na_2SO_4$, filtered and the solvent was removed under reduced pressure to afford the title compound as an off-white solid (3.77 g, 99%).

$^1$H-NMR (400 MHz, $CDCl_3$): δ=2.23 (s, 3H), 3.63 (br-s, 2H), 6.33-6.37 (m, 1H), 6.88 (t, 1H), 7.34 (br-s, 1H), 7.76-7.78 (m, 1H).

Step C

The title compound from Step B above (3.77 g, 22.5 mmol) was dissolved in N,N-dimethylacetamide (17 ml) and toluene (350 mL). After the addition of bis(2-bromoethyl) ether (5 g, 22.5 mmol) and diisopropylethyl-amine (15.8 mL, 33.8 mmol), the reaction mixture was heated to reflux for 4 days (~160° C. in a sand-bath). The cooled reaction mixture was concentrated to ~30 mL and diluted with ethyl acetate (150 mL) and water (40 mL). The organic phase was separated, dried over $Na_2SO_4$, filtered and the solvents were removed under reduced pressure. The residue was purified by chromatography on silica using ethyl acetate as a mobile phase to afford the title compound as an off-white solid (2.72 g, 50%).

$^1$H-NMR (400 MHz, $CDCl_3$): δ=2.24 (s, 3H), 3.11-3.16 (m, 4H), 3.82-3.87 (m, 4H); 6.55-6.59 (m, 1H), 7.00 (t, 1H), 7.36 (br-s, 1H), 8.03-8.06 (m, 1H).

Step D

The title compound from Step C above (2.72 g, 11.4 mmol) was dissolved in acetonitrile (25 mL) and 4-(dimethylamino)-pyridine (0.14 g, 1.14 mmol) was added. To the clear solution was then added a solution of di-tert-butyl dicarbonate (3 g, 13.5 mmol) in acetonitrile (6 mL) in one portion. The reaction mixture was stirred at room temperature overnight. The reaction mixture was concentrated and the residue was purified on HP-Sil SNAP cartridges using a Biotage Isolera One purification system employing an EtOAc/n-heptane gradient (5/95->100/0) to afford the title compound as a white solid (3 g, 77%).

$^1$H-NMR (400 MHz, $CDCl_3$): δ=1.44 (s, 9H), 2.63 (s, 3H), 3.09-3.12 (m, 4H), 3.85-3.89 (m, 4H); 6.66 (dd, 1H), 6.85-6.90 (m, 1H), 7.07 (dd, 1H).

Step E

The title compound from Step D above (3 g, 8.87 mmol) was dissolved in acetonitrile (45 mL) and 3-dimethylamino-1-propylamine (2.23 mL, 17.74 mmol) was added. The reaction mixture was stirred at room temperature for 20 h and the solvents were evaporated under reduced pressure. The residue was dissolved in ethyl acetate (150 mL) and water (45 mL). After the addition of a 10% aqueous citric acid solution (25 mL), the organic phase was separated, washed with water (25 mL) and brine (25 mL). The organic phase was dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->100/0) to afford the title compound as a white solid (2.38 g, 90%).

$^1$H-NMR (400 MHz, $CDCl_3$): δ=1.55 (s, 9H), 3.11-3.15 (m, 4H), 3.85-3.89 (m, 4H); 6.46-6.54 (m, 1H), 6.73 (br-s, 1H), 6.97 (dd, 1H), 7.78-7.82 (m, 1H).

Step F

The title compound from Step E above (2.38 g, 7.08 mmol) was dissolved in dichloromethane (70 mL) and the mixture was cooled to 0° C. At 0° C. a 2 M solution of hydrochloric acid in diethylether (70 mL) was added. The reaction mixture was stirred overnight and allowed to warm to room temperature. The precipitate was collected by filtration and then dissolved in water (100 mL). Solid sodium hydroxide was added until pH-10 and the aqueous layer was extracted with dichloromethane (3×100 mL). The combined organic phase was dried over $Na_2SO_4$, filtered and the solvent was removed under reduced pressure to afford the title compound as an off-white solid (1.43 g, 90%).

$^1H$-NMR (400 MHz, $CDCl_3$): δ=3.05-3.09 (m, 4H), 3.70 (br-s, 2H), 3.84-3.88 (m, 4H); 6.27 (dt, 1H), 6.36 (dd, 1H), 6.93 (dd, 1H).

Preparative Example 8

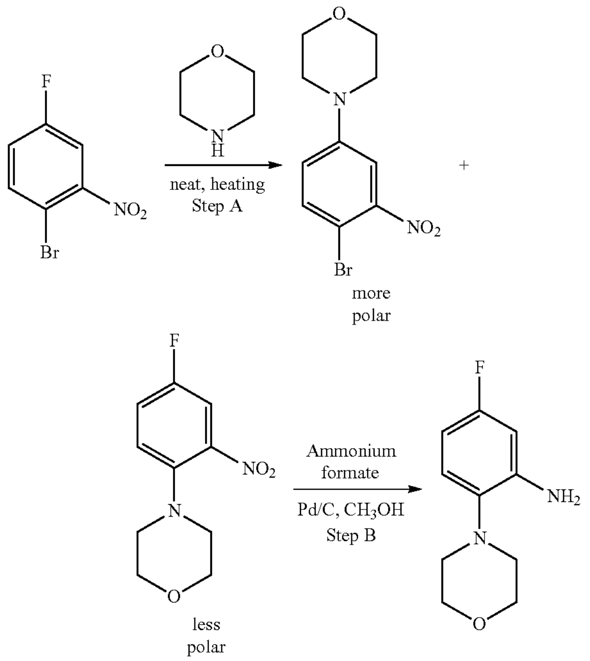

Step A

A solution of commercially available 2-bromo-5-fluoronitrobenzene (1.78 g, 8.09 mmol) and morpholine (2.12 mL, 24.3 mmol) was heated for 2 h at 120° C. using a Biotage Initiator microwave. The mixture was dissolved in dichloromethane (50 mL) and water (20 mL). The organic phase was separated, dried over $Na_2SO_4$, filtered and the solvents were removed under reduced pressure. The residue was purified by chromatography on HP-Sil SNAP cartridges using a Biotage Isolera system employing an ethyl acetate/n-heptane gradient (5/95->40/60) to afford the less polar title compound as a bright orange oil which became a solid by standing at room temperature (1.41 g, 77%). The more polar by-product was isolated as a yellow solid (0.064 g, 3.5%).

Less polar title compound: $^1H$-NMR (400 MHz, $CDCl_3$): δ=3.00-3.04 (m, 4H), 3.82-3.86 (m, 4H), 7.18-7.22 (m, 1H), 7.25-7.30 (m, 1H), 7.53 (dd, 1H).

More polar by-product: $^1H$-NMR (400 MHz, $CDCl_3$): δ=3.18-3.22 (m, 4H), 3.86-3.90 (m, 4H), 6.93 (dd, 1H), 7.31 (d, 1H), 7.55 (d, 1H).

Step B

The less polar title compound from Step A above (1.41 g, 6.24 mmol) was dissolved in methanol (30 mL) and ammonium formate (1.57 g, 24.5 mmol) was added. After the addition of 10% palladium on charcoal (0.15 g) in water (2 mL), the mixture was stirred at room temperature for 18 h. A slight exotherm was observed after adding the suspension of the catalyst. The mixture was filtered, the catalyst was washed with methanol (3 mL) and the combined filtrate was evaporated under reduced pressure. The residue was dissolved in ethyl acetate (100 mL) and water (25 mL). The organic phase was separated, dried over $Na_2SO_4$, filtered and the solvent was removed under reduced pressure. The residue was purified by chromatography on HP-Sil SNAP cartridges using a Biotage Isolera system employing an ethyl acetate/n-heptane gradient (5/95->40/60) to afford the title compound as an off-white solid (1.00 g, 81%).

$^1H$-NMR (400 MHz, DMSO-$d_6$): δ=2.70-2.74 (m, 4H), 3.68-3.72 (m, 4H), 5.11 (br-s, 2H), 6.26 (dt, 1H), 6.43 (dd, 1H), 6.87 (dd, 1H).

Preparative Example 9

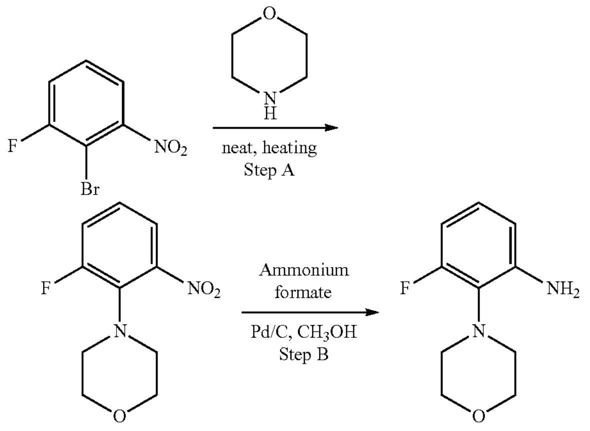

Step A

A solution of commercially available 2-bromo-3-fluoronitrobenzene (1.78 g, 8.09 mmol) and morpholine (2.12 mL, 24.3 mmol) was heated for 2 h at 120° C. using a Biotage Initiator microwave. The mixture was dissolved in dichloromethane (50 mL) and water (20 mL). The organic phase was separated, dried over $Na_2SO_4$, filtered and the solvents were removed under reduced pressure. The residue was purified by chromatography on HP-Sil SNAP cartridges using a Biotage Isolera system employing an ethyl acetate/n-heptane gradient (5/95->40160) to afford the title compound as a bright orange oil (1.39 g, 76%).

$^1H$-NMR (400 MHz, $CDCl_3$): δ=3.13-3.17 (m, 4H), 3.76-3.80 (m, 4H), 7.15-7.22 (m, 1H), 7.23-7.28 (m, 1H), 7.43 (dt, 1H).

Step B

The title compound from Step A above (1.39 g, 6.15 mmol) was dissolved in methanol (30 mL) and ammonium formate (1.57 g, 24.5 mmol) was added. After the addition of 10% palladium on charcoal (0.15 g) in water (2 mL), the mixture was stirred at room temperature for 18 h. A slight exotherm was observed after adding the suspension of the catalyst. The mixture was filtered, the catalyst was washed with methanol (3 mL) and the combined filtrate was evaporated under reduced pressure. The residue was dissolved in ethyl acetate (100 mL) and water (25 mL). The organic phase was separated, dried over $Na_2SO_4$, filtered and the solvent was removed under reduced pressure to afford the title compound as an off-white solid (1.17 g, 97%).

$^1H$-NMR (400 MHz, DMSO-$d_6$): δ=2.62-3.15 (br-m, 4H), 3.70 (br-s, 4H), 5.26 (br-s, 2H), 6.26 (ddd, 1H), 6.47 (d, 1H), 6.80-6.86 (m, 1H).

Preparative Example 10

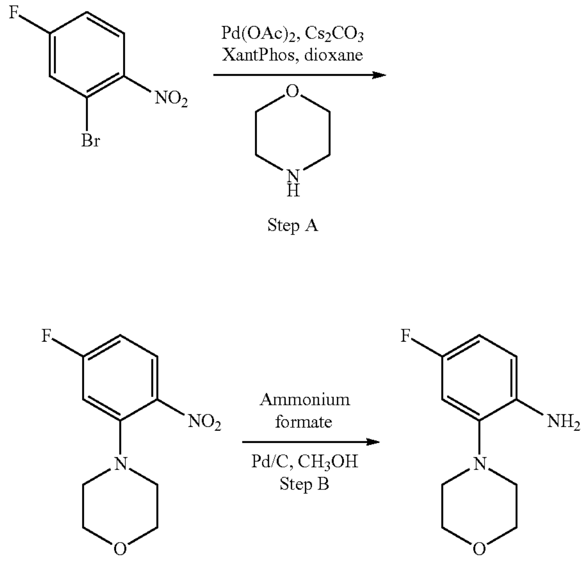

Step A

Commercially available 2-bromo-4-fluoro-nitrobenzene (1.5 g, 6.82 mmol) was combined with palladium(II) acetate (0.16 g, 0.8 mmol), 4,5-bis(diphenylphosphino)-9,9-dimethylxanthene (0.62 g, 0.8 mmol) and cesium carbonate (4.44 g, 13.64 mmol). To the mixture was then added degassed 1,4-dioxane (15 mL) and morpholine (0.84 g, 9.6 mmol). The reaction mixture was heated at ~110° C. in a sand-bath for 8 h. The reaction mixture was cooled to room temperature and diluted with ethyl acetate (150 mL), water, (20 mL) and brine (20 mL). The organic phase was separated, dried over $Na_2SO_4$, filtered and the solvents were removed under reduced pressure. The residue was purified on HP-Sil SNAP cartridges using a Biotage Isolera One purification system employing an EtOAc/n-heptane gradient (5/95->40/60) to afford the title compound as a yellow oil (0.59 g, 38%).

$^1$H-NMR (400 MHz, $CDCl_3$): δ=3.05-3.09 (m, 4H), 3.84-3.88 (m, 4H), 6.72-6.77 (m, 1H), 6.78 (dd, 1H), 7.91 (dd, 1H).

Step B

The title compound from Step A above (0.59 g, 2.59 mmol) was dissolved in methanol (15 mL) and ammonium formate was added (0.65 g, 10.17 mmol). After the addition of a suspension of 10% palladium on charcoal (0.065 g) in water (1 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->60/40) to afford the title compound as an off-white solid (0.35 g, 68%).

$^1$H-NMR (400 MHz, DMSO-$d_6$): δ=2.76-2.80 (m, 4H), 3.70-3.74 (m, 4H), 4.62 (br-s, 2H), 6.62-6.65 (m, 2H), 6.72 (dt, 1H).

Preparative Example 11

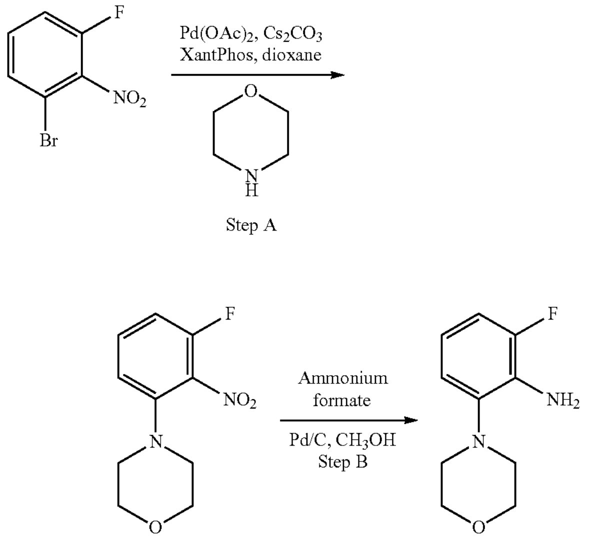

Step A

Commercially available 2-bromo-6-fluoro-nitrobenzene (1.5 g, 6.82 mmol) was combined with palladium(II) acetate (0.16 g, 0.8 mmol), 4,5-bis(diphenylphosphino)-9,9-dimethylxanthene (0.62 g, 0.8 mmol) and cesium carbonate (4.44 g, 13.64 mmol). To the mixture was then added degassed 1,4-dioxane (15 mL) and morpholine (0.84 g, 9.6 mmol). The reaction mixture was heated at ~110° C. in a sand-bath for 8 h. The reaction mixture was cooled to room temperature and diluted with ethyl acetate (150 mL), water, (20 mL) and brine (20 mL). The organic phase was separated, dried over $Na_2SO_4$, filtered and the solvents were removed under reduced pressure. The residue was purified on HP-Sil SNAP cartridges using a Biotage Isolera One purification system employing an EtOAc/n-heptane gradient (5/95->40/60) to afford the title compound as a yellow oil (0.65 g, 42%).

$^1$H-NMR (400 MHz, $CDCl_3$): δ=3.02-3.06 (m, 4H), 3.77-3.81 (m, 4H), 6.91-6.97 (m, 2H), 7.36-7.44 (m, 1H).

Step B

The title compound from Step A above (0.65 g, 2.88 mmol) was dissolved in methanol (15 mL) and ammonium formate was added (0.73 g, 11.3 mmol). After the addition of a suspension of 10% palladium on charcoal (0.070 g) in water (1 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->40/60) to afford the title compound as a pale yellow oil which became an off-white solid by standing at room temperature (0.35 g, 62%).

$^1$H-NMR (400 MHz, DMSO-$d_6$): δ=2.76-2.80 (m, 4H), 3.72-3.76 (m, 4H), 4.65 (br-s, 2H), 6.52-6.57 (m, 1H), 6.75-6.85 (m, 2H).

Preparative Example 12

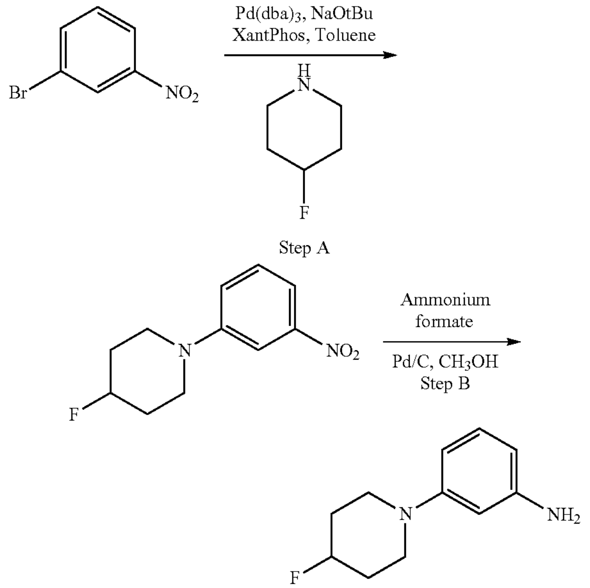

Step A

A solution of 1-bromo-3-nitrobenzene (0.323 g, 1.6 mmol), 4-fluoropiperidine hydrochloride (0.268 g, 1.92 mmol), tris(dibenzylideneacetone)dipalladium(0) ($Pd_2(dba)_3$, 0.073 g, 0.080 mmol), 4,5-bis(diphenylphosphino)-9,9-dimethylxanthene (XantPhos, 0.139 g, 0.240 mmol) and NaOtBu (0.369 g, 3.84 mmol) in toluene (3 mL) was degassed by bubbling argon and the mixture was stirred under microwave irradiation at 80° C. for 60 minutes. The crude reaction mixture was diluted with ethyl acetate, the solids were removed by filtration through a short plug of silica gel and the filtrate was concentrated by evaporation. The residue was purified on HP-Sil SNAP cartridges using a Biotage Isolera One purification system employing an EtOAc/n-heptane gradient (5/95->40/60) to afford the title compound (0.359 g, 22%).

$^1$H-NMR (400 MHz, $CDCl_3$): δ=1.99-2.11 (m, 4H), 3.32-3.50 (m, 4H), 4.81-4.96 (m, 1H), 7.23 (d, 1H), 7.39 (t, 1H), 7.65 (d, 1H), 7.75 (s, 1H).

MS (ESI); m/z=225.17 $[M+H]^+$.

Step B

4-Fluoro-1-(3-nitrophenyl)piperidine (0.08 g, 0.35 mmol) was dissolved in methanol (5 mL) and ammonium formate was added (0.112 g, 1.78 mmol). After the addition of a suspension of 10% palladium on charcoal (0.064 g) in water (0.5 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->40/60) to afford the title compound as a pale yellow oil which became an off-white solid by standing at room temperature (0.067 g, 96%).

$^1$H-NMR (400 MHz, $CDCl_3$): δ=1.98-2.07 (m, 4H), 3.14-3.20 (m, 2H), 3.37 (m, 2H), 3.65 (br-s, 1H), 4.77-4.90 (m, 1H), 6.26 (d, 1H), 6.33 (s, 1H), 6.42 (d, 1H), 7.08 (t, 1H), 7.29 (s, 1H).

MS (ESI); m/z=195.27 $[M+H]^+$.

Preparative Example 13

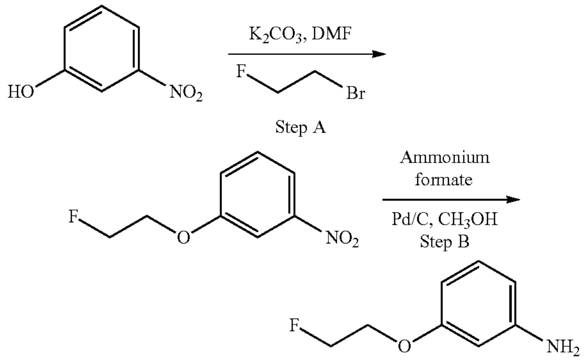

Step A

To a solution of 3-nitrophenol (5.0 g, 35.9 mmol) in N,N-dimethylformamide (40 mL), $K_2CO_3$ (14.8 g, 107 mmol) was added and the mixture was stirred at room temperature for 10 min. Then 1-bromo-2-fluoroethane (6.8 g, 53.8 mmol) was added dropwise. The mixture was heated at 100° C. overnight. To the cooled reaction mixture $H_2O$ (150 ml) was added. The mixture was extracted with ethyl acetate (2×50 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound (5.93 g, 90%).

$^1$H-NMR (400 MHz, $CDCl_3$) δ=7.87 (ddd, 1H), 7.76 (t, 1H), 7.46 (t, 1H), 7.28 (ddd, 1H), 4.93-4.81 (m, 1H), 4.81-4.70 (m, 1H), 4.40-4.30 (m, 1H), 4.31-4.22 (m, 1H).

Step B

The title compound from Step A above (5.93 g, 32.4 mmol) was dissolved in methanol (100 mL) and ammonium formate was added (7.4 g, 162 mmol). After the addition of a suspension of 10% palladium on charcoal (3.0 g) in water (10 mL), the mixture was stirred at room temperature overnight. The reaction mixture was filtered and the catalyst was washed with methanol (20 mL). The filtrate was evaporated under reduced pressure and the residue was re-dissolved in ethyl acetate (60 mL) and water (50 mL). The organic phase was separated, dried over $Na_2SO_4$, filtered and the solvent was removed under reduced pressure. The residue was purified on a HP-Sil column using a Biotage Isolera One purification system employing an EtOAc/n-heptane gradient (5/95->40/60) to afford the title compound as a brown solid (3.7 g, 73%).

$^1$H-NMR (400 MHz, DMSO-$d_6$) δ=6.92 (t, 1H), 6.23-6.03 (m, 3H), 5.06 (s, 2H), 4.85-4.72 (m, 1H), 4.70-4.61 (m, 1H), 4.19-4.11 (m, 1H), 4.12-4.00 (m, 1H).

MS (ESI); m/z=156.20 $[M+H]^+$.

Preparative Example 14

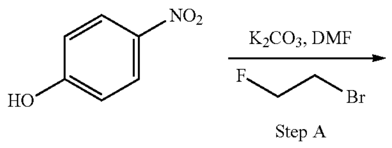

-continued

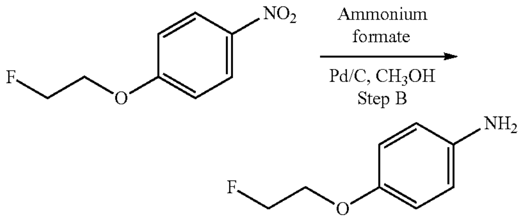

Step A

To a solution of 4-nitrophenol (3.23 g, 23 mmol) in N,N'-dimethylformamide (30 mL), $K_2CO_3$ (9.5 g, 69 mmol) was added and the mixture was stirred at room temperature for 10 min. Then 1-bromo-2-fluoroethane (4.4 g, 34 mmol) was added dropwise. The mixture was heated at 100° C. overnight. To the cooled reaction mixture $H_2O$ (100 ml) was added. The mixture was extracted with ethyl acetate (2×50 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound (3.85 g, 87%).

$^1$H-NMR (400 MHz, DMSO-$d_6$) δ=8.28-8.12 (m, 2H), 7.29-6.98 (m, 2H), 4.94-4.77 (m, 1H), 4.77-4.65 (m, 1H), 4.49-4.39 (m, 1H), 4.42-4.30 (m, 1H).

Step B

The title compound from Step A above (3.85 g, 20 mmol) was dissolved in methanol (100 mL) and ammonium formate was added (2.3 g, 100 mmol). After the addition of a suspension of 10 palladium on charcoal (2.3 g) in water (10 mL), the mixture was stirred at room temperature overnight. The reaction mixture was filtered and the catalyst was washed with methanol (20 mL). The filtrate was evaporated under reduced pressure and the residue was re-dissolved in ethyl acetate (50 mL) and water (40 mL). The organic phase was separated, dried over $Na_2SO_4$, filtered and the solvent was removed under reduced pressure. The residue was purified on a HP-Sil column using a Biotage Isolera One purification system employing an EtOAc/n-heptane gradient (5/95->40/60) to afford the title compound (3.0 g, 97%).

$^1$H-NMR (400 MHz, DMSO-$d_6$) δ=6.74-6.58 (m, 2H), 6.55-6.41 (m, 2H), 4.80-4.66 (m, 1H), 4.66-4.50 (m, 3H), 4.16-4.05 (m, 1H), 4.05-3.95 (m, 1H).

MS (ESI); m/z=156.07 $[M+H]^+$.

Preparative Example 15

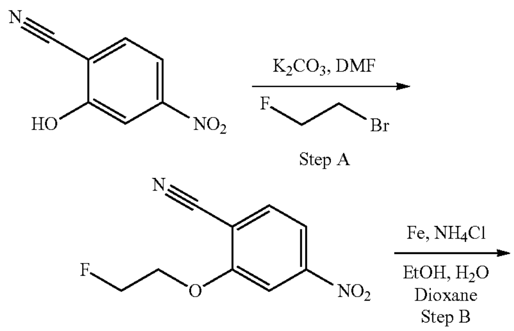

-continued

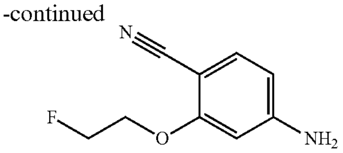

Step A

To a solution of 2-hydroxy-4-nitrobenzonitrile (1.0 g, 6.1 mmol) in N,N'-dimethylformamide (10 mL), $K_2CO_3$ (2.5 g, 18.3 mmol) was added and the mixture was stirred at room temperature for 10 min. Then 1-bromo-2-fluoroethane (1.1 g, 9.1 mmol) was added dropwise. The mixture was heated at 100° C. overnight. To the cooled reaction mixture $H_2O$ (50 ml) was added. The mixture was extracted with ethyl acetate (2×30 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound (0.89 g, 70%).

$^1$H-NMR (400 MHz, DMSO-$d_6$) δ=8.11 (d, 1H), 8.04 (s, 1H), 7.95 (d, 1H), 4.97-4.79 (m, 1H), 4.84-4.71 (m, 1H), 4.74-4.62 (m, 1H), 4.63-4.52 (m, 1H).

Step B

A stirred solution of the title compound from Step A above (0.89 g, 4.2 mmol) in 1,4-dioxane (20 ml), ethanol (16 ml) and $H_2O$ (5 ml) was stirred at room temperature and $NH_4Cl$ (0.91 g, 16.9 mmol) was added, followed by addition of iron powder (1.1 g, 21.15 mmol). The mixture was heated at 80° C. overnight. The mixture was filtered through a cellulose pad and the residue was concentrated and portioned between $H_2O$ (50 ml) and ethyl acetate (50 mL). The organic phase was separated, dried over $Na_2SO_4$ and the solvent was removed under reduced pressure. The residue was purified on a HP-Sil column using a Biotage Isolera One purification system employing an EtOAc/n-heptane gradient (5/95->40/60) to afford the title compound (0.55 g, 72%).

$^1$H-NMR (400 MHz, DMSO-$d_6$) δ=7.25 (d, 1H), 6.30-6.02 (m, 4H), 4.86-4.73 (m, 1H), 4.74-4.64 (m, 1H), 4.34-4.21 (m, 1H), 4.23-4.10 (m, 1H).

MS (ESI); m/z=181.05 $[M+H]^+$.

Preparative Example 16

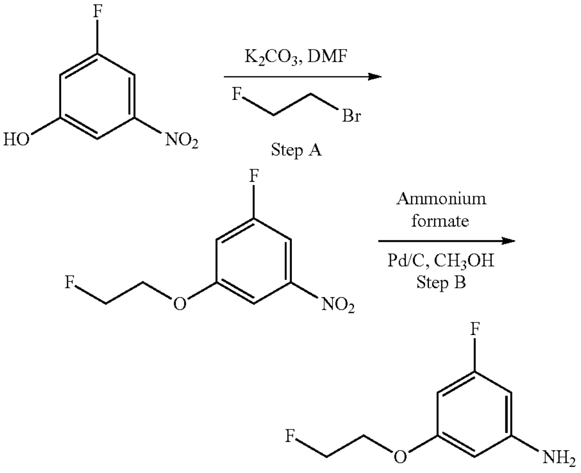

Step A

To a solution of 3-fluoro-5-nitrophenol (1.0 g, 6.3 mmol) in N,N'-dimethylformamide (10 mL), $K_2CO_3$ (2.6 g, 18.9 mmol) was added and the mixture was stirred at room temperature for 10 min. Then 1-bromo-2-fluoroethane (1.2 g, 9.5 mmol) was added dropwise. The mixture was heated at 100° C. overnight. To the cooled reaction mixture $H_2O$ (50 ml) was added. The mixture was extracted with ethyl acetate (2×30 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound which was used in the next step without further purification.

$^1$H-NMR (400 MHz, DMSO-$d_6$) δ=7.72 (dt, 1H), 7.71-7.59 (m, 1H), 7.46 (dt, 1H), 4.93-4.78 (m, 1H), 4.81-4.61 (m, 1H), 4.55-4.43 (m, 1H), 4.44-4.31 (m, 1H).

Step B

The crude title compound from Step A above (2.0 g, 10 mmol) was dissolved in methanol (30 mL) and ammonium formate was added (2.4 g, 50 mmol). After the addition of a suspension of 10% palladium on charcoal (1.5 g) in water (5 mL), the mixture was stirred at room temperature overnight. The reaction mixture was filtered and the catalyst was washed with methanol (20 mL). The filtrate was evaporated under reduced pressure and the residue was re-dissolved in ethyl acetate (50 mL) and water (40 mL). The organic phase was separated, dried over $Na_2SO_4$, filtered and the solvent was removed under reduced pressure. The residue was purified on a HP-Sil column using a Biotage Isolera One purification system employing an EtOAc/n-heptane gradient (5/95->40/60) to the title compound (0.98 g, 56%).

$^1$H-NMR (400 MHz, DMSO-$d_6$) δ=6.01-5.84 (m, 3H), 5.40 (s, 2H), 4.8-4.68 (m, 1H), 4.68-4.56 (m, 1H), 4.21-4.09 (m, 1H), 4.11-4.00 (m, 1H).

Preparative Example 17

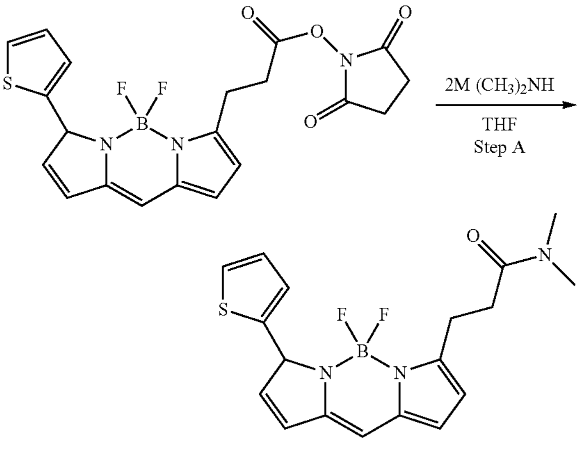

To a solution of commercially available BODIPY® 558/568 D2219 ester (0.005 g, 0.008 mmol) in THF (1 mL) was added a solution of 2 M dimethylamine in THF (0.3 mL). The reaction mixture was stirred for 2 hours at room temperature and the solvent was removed under reduced pressure to afford the crude title compound (quantitative).

Preparative Example 18

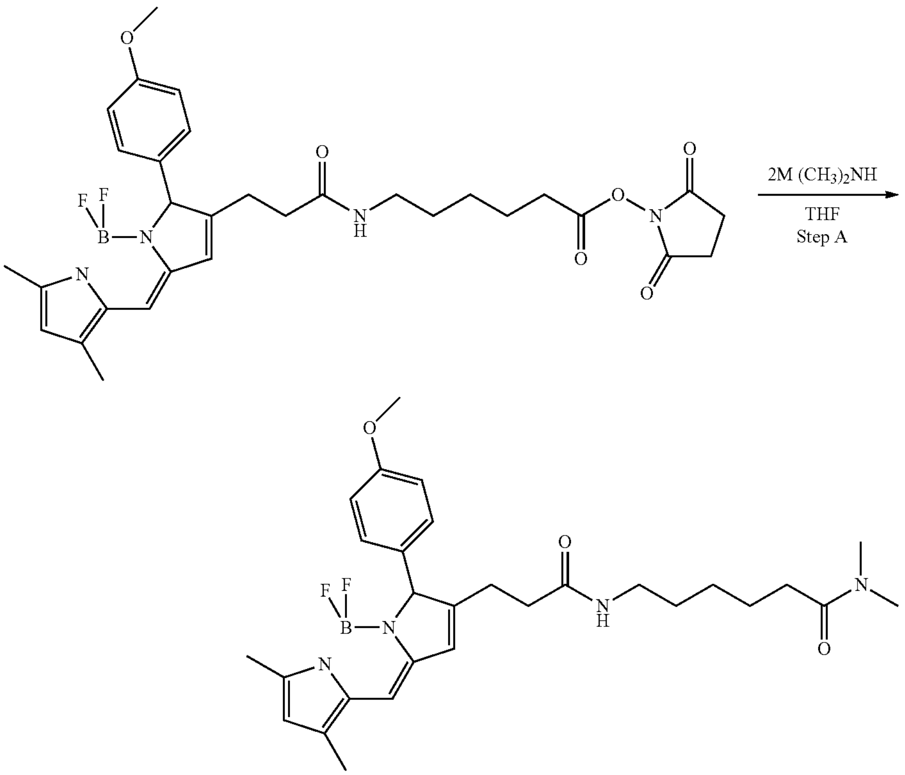

To a solution of commercially available BODIPY® TMR-X D6117 ester (0.005 g, 0.008 mmol) in THF (1 mL) was added a solution of 2 M dimethylamine in THF (0.3 mL). The reaction mixture was stirred for 2 hours at room temperature and the solvent was removed under reduced pressure to afford the crude title compound (quantitative).

Preparative Example 19

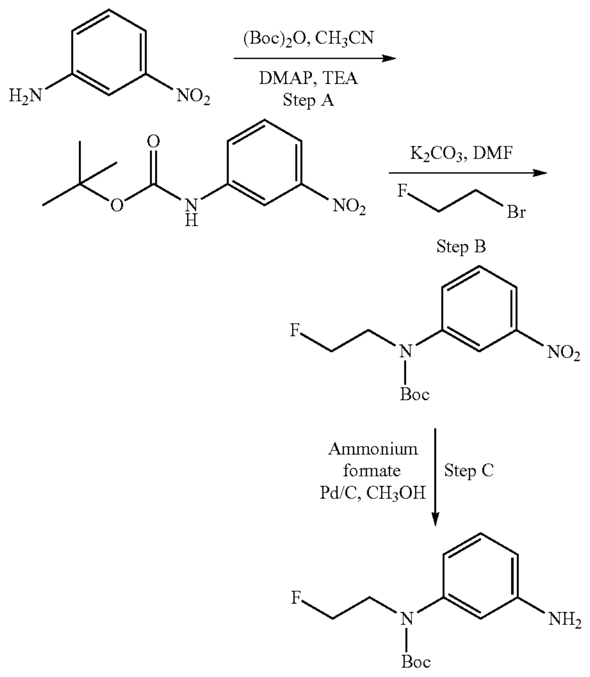

Step A

To a solution of 3-nitroaniline (4.0 g, 28 mmol) in acetonitrile (100 mL) were added di-tert-butyldicarbonat ($(Boc)_2O$, 15 g, 70 mmol), triethylamine (6 ml, 42 mmol) and 4-(dimethylamino)-pyridine (DMAP, 0.34 g) and the mixture was stirred at room temperature overnight. The reaction mixture was concentrated and 100 ml of a methanol/tetrahydrofuran (1:1) solution was added followed by potassium carbonate (8 g). The mixture was then heated at 60° C. for 1 hour. To the cooled reaction mixture water (100 ml) and ethyl acetate (100 ml) were added and the organic phases were separated. The organic layer was washed with brine (50 mL), dried over $Na_2SO_4$ and evaporated under reduced pressure. The residue was purified on HP-Sil SNAP cartridges using a Biotage Isolera One purification system employing an ethyl acetate/n-heptane gradient (5/95->40/60) to afford the title compound (5.37 g, 79%)).

$^1$H-NMR (400 MHz, DMSO-$d_6$) δ=9.90 (s, 1H), 8.47 (s, 1H), 7.92-7.66 (m, 2H), 7.53 (t, 1H), 1.49 (s, 9H).

Step B

To a solution of the title compound from Step A above (2.0 g, 8.4 mmol) in N,N'-dimethylformamide (20 mL), potassium carbonate (8.1 g, 25 mmol) was added and the mixture was stirred at room temperature for 10 minutes. Then 1-bromo-2-fluoroethane (1.6 g, 12.5 mmol) was added dropwise. The mixture was heated at 100° C. overnight. To the cooled reaction mixture, water (200 mL) was added and the mixture was extracted with ethyl acetate (2×50 mL). The organic layers were combined, dried over $Na_2SO_4$ and evaporated under reduced pressure. The residue was purified on HP-Sil SNAP cartridges using a Biotage Isolera One purification system employing an ethyl acetate/n-heptane gradient (5/95->40/60) to afford the title compound (2.37 g, 98%).

$^1$H-NMR (400 MHz, DMSO-$d_6$) δ=8.22-7.98 (m, 2H), 7.88-7.70 (m, 1H), 7.66 (t, 1H), 4.63 (t, 1H), 4.51 (t, 1H), 4.00 (t, 1H), 3.94 (t, 1H), 1.41 (s, 9H).

Step C

The title compound from Step B above (2.37 g, 8.3 mmol) was dissolved in methanol (30 mL) and ammonium formate was added (1.9 g, 41.5 mmol). After the addition of a suspension of 10% palladium on charcoal (1.2 g) in water (5 mL), the mixture was stirred at room temperature overnight. The reaction mixture was filtered and the catalyst was washed with methanol (20 mL). The filtrate was evaporated under reduced pressure and the residue was re-dissolved in ethyl acetate (60 mL) and water (50 mL). The organic phase was separated, dried over $Na_2SO_4$, filtered and the solvent was removed under reduced pressure. The residue was purified on a HP-Sil column using a Biotage Isolera One purification system employing an ethyl acetate/n-heptane gradient (5/95->40/60) to afford the title compound (1.6 g, 76%).

$^1$H-NMR (400 MHz, DMSO-$d_6$) δ=6.99 (t, 1H), 6.50-6.25 (m, 3H), 5.12 (s, 2H), 4.54 (t, 1H), 4.42 (t, 1H), 3.82 (t, 1H), 3.76 (t, 1H), 1.38 (s, 9H).

MS (ESI); m/z=155.11 $[M-Boc+H]^+$.

Preparative Example 20

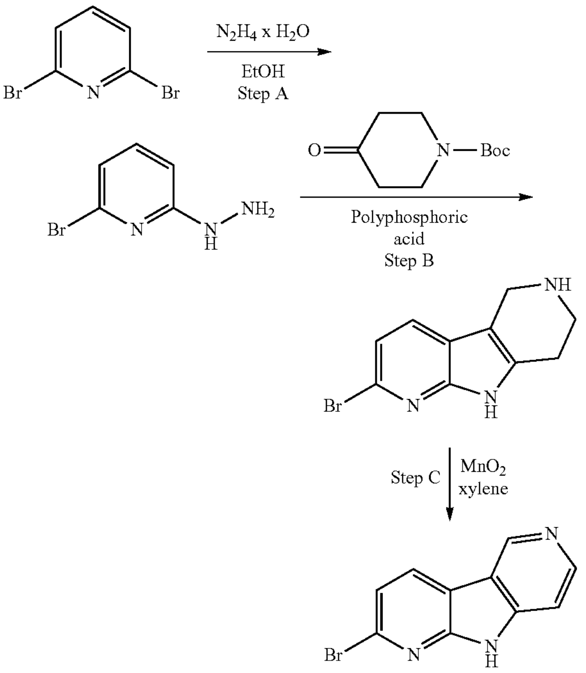

Step A

Commercially available 2,6-dibromopyridine (4.12 g, 16.6 mmol) was suspended in ethanol (40 mL) and hydrazine hydrate (10 mL, 97.6 mmol) in water (~50-60%) was added. The mixture was heated in a sand-bath at ~115° C. for 18 hours. The solvent was removed and the residue was purified by chromatography on silica using ethyl acetate/n-heptane (60/40) to afford the title compound as an off-white solid (3.05 g, 93%).

$^1$H-NMR (400 MHz, $CDCl_3$): δ=7.33 (t, 1H), 6.83 (d, 1H), 6.67 (d, 1H), 6.00 (br-s, 1H), 3.33-3.00 (br-s, 2H).

Step B

The title compound from Step A above (5 g, 26.59 mmol) was mixed with commercially available N-(tert-butoxycarbonyl)-4-piperidone (5.3 g, 26.6 mmol) in a 250 mL flask. Then polyphosphoric acid (40 g) was added and the mixture was heated at ~160° C. in a sand-bath for 20 hours with stirring. Cleavage of the Boc-protection group was observed (foaming) during the initial stages of the reaction. The black reaction mixture was cooled to ~40° C. and ice-water (200 mL) was added. The reaction mixture was then stirred at room temperature until the gummy mass was dissolved. The reaction mixture was placed in an ice-bath and made alkaline (pH~12) by the addition of solid sodium hydroxide (exotherm). The reaction mixture was diluted with water (300 mL) to dissolve phosphate salts and extracted with a mixture of dichloromethane/methanol (9/1; 3×200 mL). The organic phase was separated, dried over $Na_2SO_4$, filtered and the solvents were removed under reduced pressure. The dark residue was purified on a HP-Sil column using a Biotage Isolera One purification system employing a dichloromethane/methanol gradient (100/0->50/50) to afford the crude title compound as a beige solid. The beige solid was treated with dichloromethane (30 mL), sonicated for 5 minutes and filtered. The solid material was washed with dichloromethane (5 mL) and air-dried to afford the title compound as an off-white solid (1.84 g, 27%).

$^1$H-NMR (400 MHz, DMSO-$d_6$): δ=11.50 (br-s, 1H), 7.68 (d, 1H), 7.12 (d, 1H), 3.81 (s, 2H), 3.81 (s, 2H), 3.03-2.97 (t, 2H), 2.68-2.62 (m, 2H).

Step C,

The title compound from Step B above (1.387 g, 5.5 mmol) was suspended in xylene (300 mL) and activated $MnO_2$ (5.3 g, 60.95 mmol) was added at room temperature. The mixture was then heated at ~160° C. in a sand-bath for 36 hours. The reaction mixture was evaporated, the residue was treated with dichloromethane/methanol (1/1; 300 mL), stirred at room temperature for 30 minutes, filtered and the solid material was washed with methanol (30 mL). The filtrate was evaporated under reduced pressure and the residue was purified by chromatography on HP-Sil SNAP cartridges using a Biotage Isolera One purification system employing an EtOAc/n-heptane gradient (5/95->100/0) to elute nonpolar by-products. Then the gradient was changed to dichloromethane/methanol (9/1->4/1) to afford the title compound as a pale-yellow solid (0.52 g, 38%).

$^1$H-NMR (400 MHz, DMSO-$d_6$): δ=9.40 (br-s, 1H), 8.58 (d, 1H), 8.52 (d, 1H), 7.55-7.49 (m, 2H).

Preparative Example 21

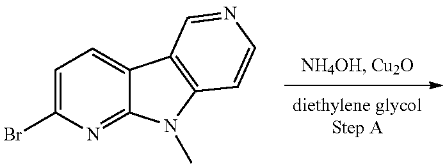

-continued

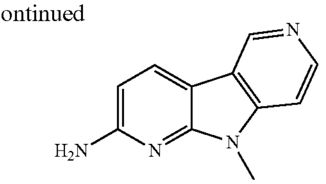

Step A

A suspension of the title compound from Preparative Example 1 (1 g, 3.8 mmol), diethylene glycol (10 mL), 28-30% aqueous ammonium hydroxide solution (5 mL) and copper(I)-oxide (0.005 g, 0.034 mmol) was sealed in a microwave glass tube. The sealed tube was heated 140° C. for 90 minutes, using a Biotage Initiator microwave. The reaction mixture was cooled to room temperature, the reaction mixture was poured in ethyl acetate (150 mL), washed with water as well as brine and dried over $Na_2SO_4$. The solvent was removed to afford the title compound as an off white solid (0.62 g, 80%).

$^1$H-NMR (400 MHz, $CDCl_3$) δ=9.09 (s, 1H), 8.49 (d, 1H), 8.11 (d, 1H), 7.49-7.04 (m, 2H), 6.47 (d, 1H), 3.82 (d, 3H).

Preparative Example 22

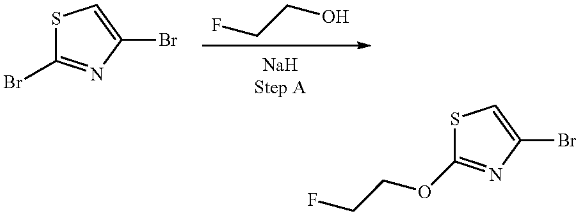

Step A

To a solution of 2-fluoroethanol (0.158 g, 2.470 mmol) in THF (5 mL) was added at 0° C. NaH (0.053 g, 1.976 mmol). After 30 min at room temperature, 2,4-dibromothiazole (0.4 g, 1.647 mmol) was added and the suspension was degased with argon for 2 min. Then, the reaction mixture was heated under microwave irradiation at 150° C. for 30 min. Water was added, which was then extracted several times with EtOAc. The combined organics were dried over $Na_2SO_4$, filtered and concentrated under reduced pressure. The residue was purified on HP-Sil SNAP cartridges using a Biotage Isolera One purification system employing an EtOAc/n-heptane gradient (2/98->5/95) to afford the title compound as a yellow solid (0.287 g, 77%).

1H NMR (400 MHz, DMSO-$d_6$) δ=7.20 (s, 0.5H), 4.84-4.77 (m, 1H), 4.72-4.63 (m, 2H), 4.61-4.55 (m, 1H).

Preparative Example 23

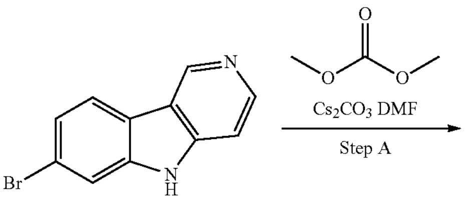

-continued

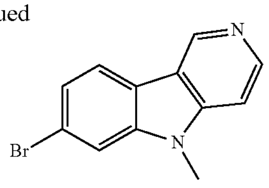

Step A

To a solution of custom made 7-bromo-5H-pyrido[4,3-b]indole (0.49 g, 1.98 mmol) in N,N'-dimethylformamide (5 mL) was added cesium carbonate (0.32 g, 0.99 mmol) and the mixture was stirred at room temperature for 10 minutes and dimethylcarbonate was added dropwise (334 μL, 3.96 mmol). The reaction mixture was heated at 160° C. for 3 hours and after cooling, water (20 mL) and ethyl acetate (20 mL) were added to the mixture. The phases were separated and the aqueous phase was extracted with ethyl acetate (2×20 mL). The organic phases were combined and dried over $Na_2SO_4$. The solvent was removed under reduced pressure and the residue was purified on a HP-Sil column using a Biotage Isolera One purification system employing a dichloromethane/methanol gradient (100/0->90/10) to afford the crude title compound (0.36 g, 69%).

$^1$H NMR (400 MHz, DMSO-$d_6$) δ=9.36 (s, 1H), 8.52 (d, 1H), 8.21 (d, 1H), 7.95 (d, 1H), 7.62 (d, 1H), 7.45 (dd, 1H), 3.88 (s, 3H).

MS (ESI): m/z=263.95 [M+H]$^+$.

Preparative Example 24

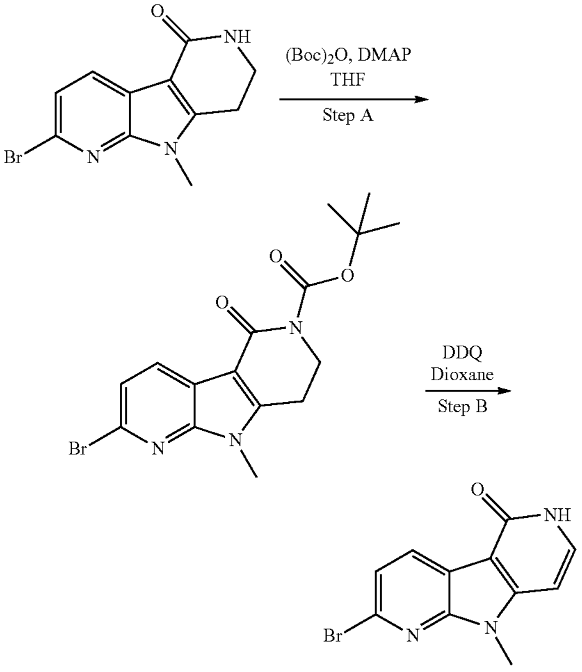

Step A

To a solution of the title compound from Preparative Example 2, Step B (0.40 g, 1.4 mmol) in tetrahydrofuran (20 mL) were added di-tert-butyldicarbonate (0.467 g, 2.1 mmol), and 4-(dimethylamino)-pyridine (0.05 g) and the mixture was stirred at room temperature overnight. The reaction mixture was concentrated and the residue was purified on HP-Sil SNAP cartridges using a Biotage Isolera One purification system employing an ethyl acetate/n-heptane gradient (5/95->40/60) to afford the title compound (0.42 g, 78%)

$^1$H-NMR (400 MHz, DMSO-$d_6$) δ=8.18 (d, 1H), 7.45 (d, 1H), 4.06 (t, 2H), 3.73 (s, 3H), 3.16 (t, 2H), 1.48 (s, 9H).

MS (ESI): m/z=324.09 [M+H]$^+$.

Step B

The title compound from Step A above (0.10 g, 0.26 mmol) and 2,3-dichloro-5,6-dicyano-1,4-benzoquinone (0.29 g, 1.30 mmol) in 1,4-dioxane (2 mL) were heated at 110° C. overnight in a sealed tube. The solvent was removed and the residue was purified by chromatography on HP-Sil SNAP cartridges using a Biotage Isolera One purification system employing an dichloromethane/methanol gradient (100/0->90/10) to afford the title compound (0.05 g, 69%).

$^1$H-NMR (400 MHz, DMSO-$d_6$) δ=11.51 (s, 1H), 8.28 (d, 1H), 7.53 (t, 1H), 7.46 (d, 1H), 6.78 (d, 1H), 3.85 (s, 3H).

MS (ESI): m/z=280.28 [M+H]$^+$.

Preparative Example 25

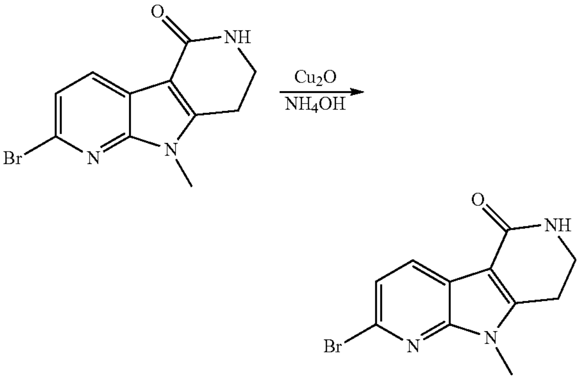

Step A

To a suspension of the title compound from Preparative Example 3 (0.05 g, 0.19 mmol) in a 28-30% aqueous ammonium hydroxide solution (5 mL) was added copper (I)-oxide. The reaction mixture was heated in a sealed microwave tube using a Biotage Initiator microwave at 135° C. for 60 minutes. After cooling the reaction mixture, the solid was filtered off, washed with cold water and dried under vacuum to afford the title compound (0.025 g, 66%).

$^1$H-NMR (400 MHz, DMSO-$d_6$) δ=7.78 (d, 1H), 6.92 (t, 1H), 6.32 (d, 1H), 5.80 (s, 2H), 5.75 (s, OH), 3.56 (s, 3H), 3.43 (tt, 2H), 2.90 (t, 2H).

Preparative Example 26

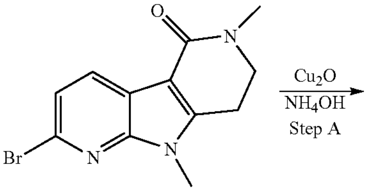

-continued

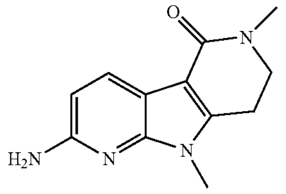

Step A

To a suspension of the title compound from Preparative Example 2 (0.68 g, 2.31 mmol) in a 28-30% aqueous ammonium hydroxide solution (12 mL) was added copper (I)-oxide. The reaction mixture was heated in a sealed microwave tube using a Biotage Initiator microwave at 135° C. for 90 minutes. After cooling the reaction mixture, the solid was filtered off, washed with cold water and dried under vacuum to afford the title compound as an off-white solid (0.415 g, 80%).

$^1$H-NMR (400 MHz, DMSO-$d_6$) δ=7.83 (d, 1H), 6.35 (d, 1H), 5.82 (s, 2H), 3.58 (d, 5H), 3.02 (t, 2H), 2.92 (s, 3H).

Preparative Example 27

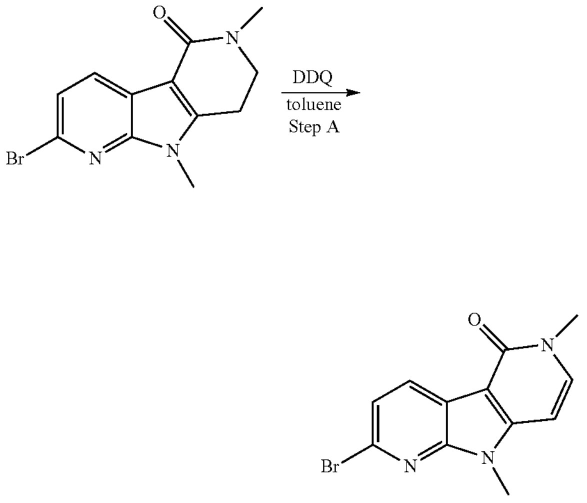

Step A

A mixture of the title compound from Preparative Example 2 (0.110 g, 0.37 mmol) and 2,3-dichloro-5,6-dicyano-1,4-benzoquinone (0.13 g, 0.57 mmol) in toluene was heated at 160° C. overnight in a sealed tube. The solvent was removed and the residue was purified by chromatography on HP-Sil SNAP cartridges using a Biotage Isolera One purification system employing an ethyl acetate/methanol gradient (100/0->90/10). The fractions containing the polar product were combined and the solvents were evaporated under reduced pressure. The polar compound was crystalized from an ethyl acetate/n-heptane mixture (90/10). The solid was filtered off and dried under vacuum to afford the title compound (0.076 g, 70%)

$^1$H-NMR (400 MHz, DMSO-$d_6$) δ=8.29 (d, 1H), 7.85 (d, 1H), 7.46 (d, 1H), 6.82 (d, 1H), 3.83 (s, 3H), 3.56 (s, 3H).

Preparative Example 28

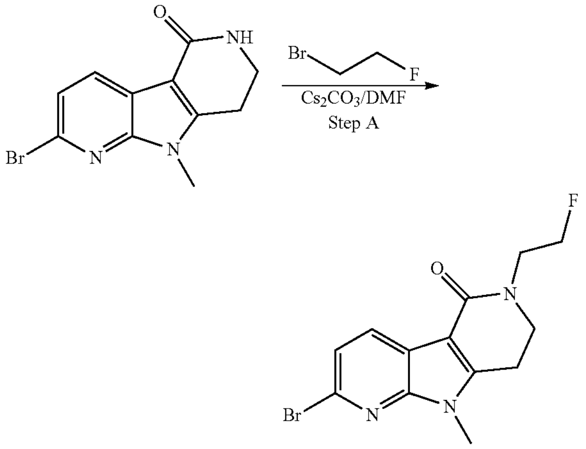

Step A

To the title compound from Preparative Example 3 (0.5 g, 1.79 mmol) in N,N'-dimethylformamide (10 mL) was added cesium carbonate (1.7 g, 5.3 mmol), followed by the addition of 1-bromo-2-fluoroethane (0.8 g, 6.4 mmol). Then the reaction mixture was stirred at 90° C. overnight. The solid was filtered off and the filtrate was diluted with ethyl acetate. The organic phase was washed with water as well as brine, dried over $Na_2SO_4$ and filtered. The solvent was removed and the crude residue was purified on HP-Sil SNAP cartridges using a Biotage Isolera One purification system employing an ethyl acetate/MeOH gradient (100/0->80/20) to afford the title compound (0.180 g, 30%).

1H-NMR (400 MHz, $CDCl_3$) δ=8.17 (d, 1H), 7.28 (dd, 1H), 4.80-4.62 (m, 1H), 4.58 (t, 1H), 3.88-3.74 (m, 4H), 3.73 (d, 3H), 3.03 (t, 2H).

Preparative Example 29

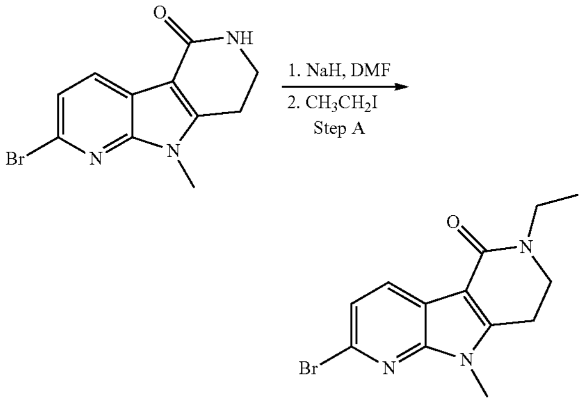

Step A

To a suspension of the title compound from Preparative Example 3 (1.5 g, 5.3 mmol) in N,N'-dimethylformamide (20 mL) was added sodium hydride (255 mg, 10.6 mmol) at 0° C. Then the reaction mixture was stirred at room temperature for 10 minutes. After the addition of ethyl iodide (1.2 g, 7.9 mmol), the reaction mixture was stirred at room temperature for 3 hours. The reaction mixture was quenched by the careful addition of water and extracted with ethyl acetate (200 mL). The organic phase was washed with water as well as brine, dried over $Na_2SO_4$ and filtered The solvent was evaporated and the residue was purified on HP-Sil SNAP cartridges using a Biotage Isolera One purification system employing an ethyl acetate/methanol gradient (100/0->90/10) to afford the title compound (1.5 g, 93%).

$^1$H-NMR (400 MHz, DMSO-$d_6$) δ=8.11 (d, 1H), 7.37 (d, 1H), 3.71 (s, 3H), 3.66 (t, 2H), 3.45 (q, 2H), 3.12 (t, 2H), 1.09 (t, 3H).

Preparative Example 30

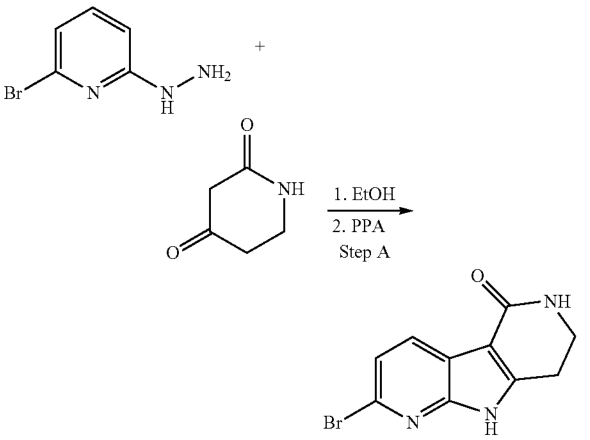

Step A

The title compound from Preparative Example 20, Step A (0.65 g, 3.46 mmol) was dissolved in ethanol (40 mL) and piperidine-2,4-dione (0.39 g, 3.46 mmol) was added. The reaction mixture was stirred at room temperature for 2 hours and the solvent was evaporated under reduced pressure. The residue was treated with polyphosphoric acid (12 ml) and the reaction mixture was heated at 190° C. in a sand-bath overnight with stirring The resulting thick brown mixture was cooled to room temperature. Then a 1 M sodium hydroxide solution was slowly added and the pH was adjusted to ~8. The precipitate was collected by filtration, the filtrate was extracted with dichloromethane (200 mL) and evaporated to afford additional solid. The solids were combined, triturated with an ethyl acetate/acetone mixture and filtered. The solid was then air-dried to afford the title compound (0.59 g, 64%).

$^1$H NMR (400 MHz, DMSO-$d_6$) δ=11.72 (s, 1H), 8.08 (s, 1H), 7.82 (d, 1H), 7.21 (d, 1H), 4.49-4.38 (m, 2H), 3.53 (t, 2H).

Preparative Example 31

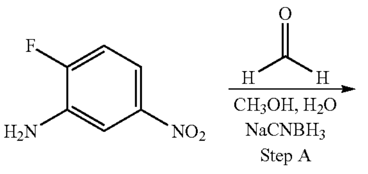

-continued

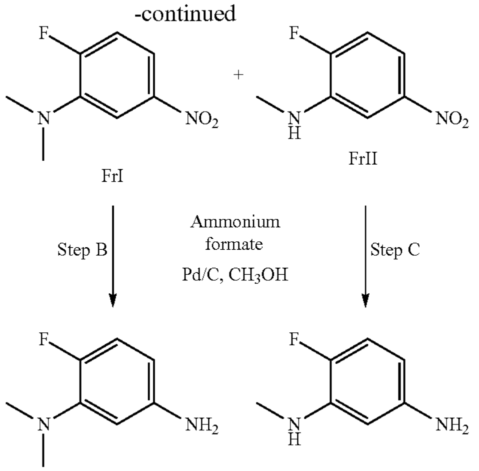

Step A

Commercially available 2-fluoro-5-nitro-aniline (2 g, 12.8 mmol) was dissolved in methanol (100 mL) and a 37% aqueous formaldehyde solution (10 mL, 128 mmol) was added. After the addition of sodium cyanoborohydride (4.2 g, 68 mmol) and acetic acid (15 mL) an exotherm was observed and the reaction mixture was stirred at room temperature for 18 hours. The solvents were evaporated under reduced pressure and the residue was dissolved in dichloromethane (150 mL) and water (50 mL). The pH was adjusted to pH~10/11 by the addition of solid sodium hydroxide. The organic phase was separated and the aqueous layer was extracted with dichloromethane (75 mL). The combined organic phase was dried over $Na_2SO_4$, filtered and the solvent was removed under reduced pressure. The residue was purified by chromatography on HP-Sil SNAP cartridges using a Biotage Isolera One purification system employing an ethyl acetate/n-heptane gradient (5/95->30/70) to afford the less polar title compound FrI as a yellow oil (2.09 g, 88%) and the more polar title compound FrII as a yellow solid (0.2 g, 9%).

Less polar FrI: $^1$H-NMR (400 MHz, DMSO-$d_6$): δ=2.88 (s, 6H), 7.36 (dd, 1H), 7.65 (dd, 1H), 7.73 (dt, 1H).

More polar FrII: $^1$H-NMR (400 MHz, DMSO-$d_6$): δ=2.78 (d, 3H), 6.27-6.31 (br-s, 1H), 7.26 (dd, 1H), 7.35 (dd, 1H), 7.44 (dt, 1H).

Step B

The less polar title compound from Step A above (2.09 g, 11.35 mmol) was dissolved in methanol (60 mL) and ammonium formate was added (2.86 g, 44.6 mmol). After the addition of a suspension of 10% palladium on charcoal (0.2 g) in water (6 mL), the mixture was stirred at room temperature overnight. As the reaction mixture was not completed, another batch of ammonium formate (2.86 g, 44.6 mmol) and 10% palladium on charcoal (0.2 g) in water (6 mL) was added. After additional 6 hours at room temperature, the reaction mixture was filtered and the catalyst was washed with methanol (15 mL). The filtrate was evaporated under reduced pressure and the residue was re-dissolved in ethyl acetate (150 mL) and water (40 mL). The organic phase was separated, dried over $Na_2SO_4$, filtered and the solvent was removed under reduced pressure. The black residue was purified on HP-Sil SNAP cartridges using a Biotage Isolera One purification system employing an EtOAc/n-heptane gradient (5/95->40/60) to afford the title compound as a dark oil (1.176 g, 67%).

$^1$H-NMR (400 MHz, DMSO-$d_6$): δ=2.66 (s, 6H), 4.75-4.78 (br-s, 2H), 6.02 (dt, 1H), 6.16 (dd, 1H), 6.70 (dd, 1H).

Step C

The more polar title compound from Step A above (0.2 g, 1.17 mmol) was dissolved in methanol (10 mL) and ammonium formate was added (0.295 g, 4.59 mmol). After the addition of a suspension of 10% palladium on charcoal (0.02 g) in water (1 mL), the mixture was stirred at room temperature overnight. As the reaction mixture was not completed, another batch of ammonium formate (0.295 g, 4.59 mmol) and 10% palladium on charcoal (0.02 g) in water (1 mL) was added. After additional 6 hours at room temperature, the reaction mixture was filtered and the catalyst was washed with methanol (2 mL). The filtrate was evaporated under reduced pressure and the residue was re-dissolved in ethyl acetate (25 mL) and water (10 mL). The organic phase was separated, dried over $Na_2SO_4$, filtered and the solvent was removed under reduced pressure. The black residue was purified on HP-Sil SNAP cartridges using a Biotage Isolera One purification system employing an EtOAc/n-heptane gradient (5/95->40/60) to afford the title compound as a dark oil (0.0734 g, 44%).

$^1$H-NMR (400 MHz, DMSO-$d_6$): δ=2.62 (d, 3H), 4.60-4.65 (br-s, 2H), 5.58 (dt, 1H), 5.87 (dd, 1H), 6.630 (dd, 1H).

Preparative Example 32 in a sand-bath for 30 minutes. The reaction mixture was cooled to ~50° C. and poured into ice-water (300 mL). The mixture was stirred for 30 minutes, the precipitate was collected by filtration, washed with water (30 mL) and air-dried to afford the title compound as an off-white solid (5.5 g, 92%).

$^1$H-NMR (400 MHz, $CDCl_3$): δ=2.50 (s, 3H), 7.55 (br-s, 1H), 7.61-7.67 (m, 2H), 8.13 (d, 2H).

Step B

The title compound from Step A above (1.5 g, 5.8 mmol) was dissolved in degassed N,N'-dimethylacetamide (20 mL) and zinc cyanide (1.368 g, 11.65 mmol) and tetrakis-(triphenylphosphane)palladium(0) (0.684 g, 0.59 mmol) was added. The reaction mixture was heated at ~110° C. in a sand-bath for 16 hours. The reaction mixture was diluted with ethyl acetate (300 mL) and water (100 mL). The organic phase was separated and the aqueous layer was extracted with ethyl acetate (100 mL). The combined organic phase was dried over $Na_2SO_4$, filtered and the solvents were removed. The black residue was purified by chromatography on HP-Sil SNAP cartridges using a Biotage Isolera One purification system employing an ethyl acetate/n-heptane gradient (5/95->100/0) to afford the crude title compound as a pale yellow solid (1.5 g, >100%). The crude title compound was used for the next step.

Step C

The crude title compound from Step B above (~5.8 mmol) was dissolved in acetonitrile (13 mL) and a solution of

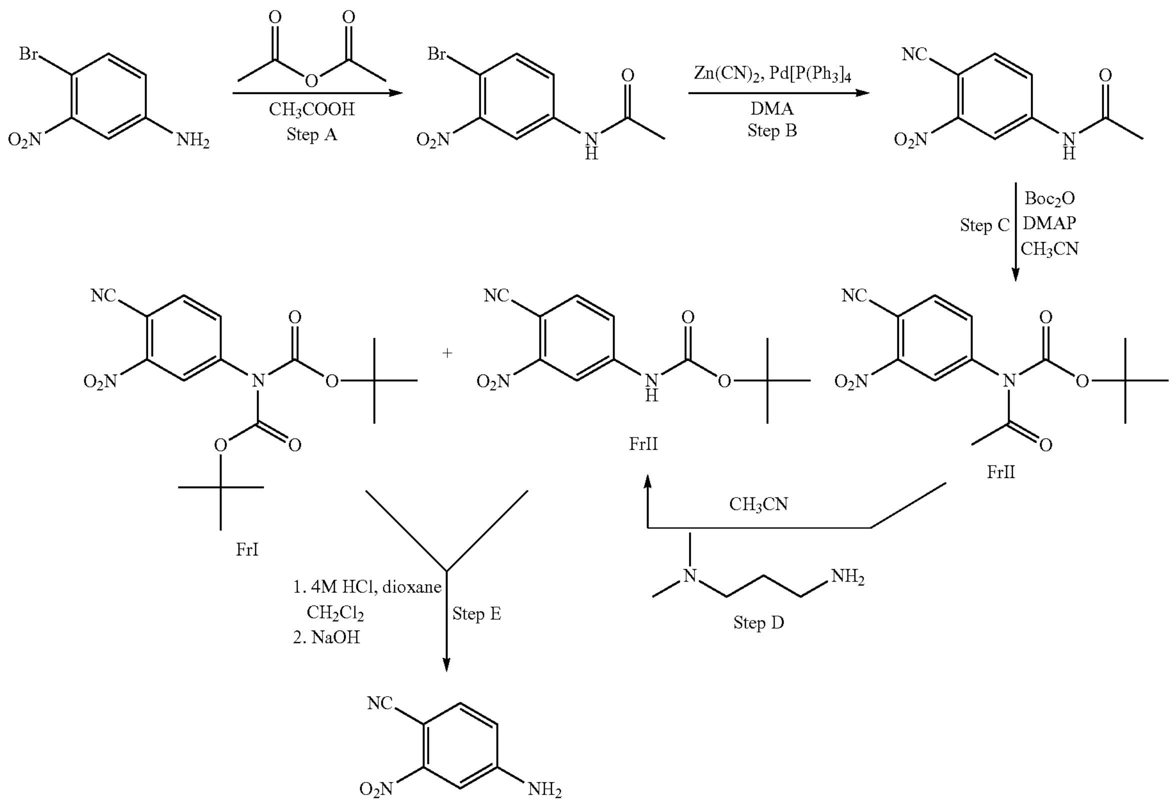

Step A

Commercially available 4-bromo-3-nitro-aniline (5 g, 23.25 mmol) was suspended in acetic acid (23 mL). The mixture was heated at ~160° C. in a sand-bath until a clear solution was obtained. The acetic acid anhydride (3.7 mL) was added and the reaction mixture was heated at ~160° C.

di-tert.-butyl dicarbonate (1.53 g, 6.87 mmol) in acetonitrile (3 mL) was added. After the addition of 4-(dimethylamino)-pyridine (0.072 g, 0.58 mmol), the reaction mixture was stirred at room temperature for 18 hours. Since TLC indicated the presence of a lot of starting material, another batch of di-tert.-butyl dicarbonate (3 g, 13.47 mmol) and 4-(dimethylamino)-pyridine (0.15 g, 1.2 mmol) was added and stirring at room temperature was continued for another 8 hours. The solvent was removed under reduced pressure and the residue was purified by chromatography on HP-Sil SNAP cartridges using a Biotage Isolera One purification system employing an ethyl acetate/n-heptane gradient (5/95->100/0) to afford the less polar bis-Boc-protected title compound (FrI) as an off-white solid (0.487 g, 23%) and the more polar FrII-mixture as a pale orange semisolid (0.792 g).

Less polar FrI (bis-Boc): $^1$H-NMR (400 MHz, $CDCl_3$): δ=1.47 (s, 18H), 7.63 (dd, 1H), 7.91 (d, 1H), 8.17 (d, 1H).

Step D

The more polar FrII-mixture from Step C above (0.792 g, ~2.9 mmol) was dissolved in acetonitrile (15 mL) and treated with $N^1$,$N^1$-dimethylpropane-1,3-diamine (0.654 mL, 5.2 mmol). The reaction mixture was stirred at room temperature for 30 hours and the solvent was evaporated under reduced pressure. The oily residue was purified by chromatography on HP-Sil SNAP cartridges using a Biotage Isolera One purification system employing an ethyl acetate/n-heptane gradient (5/95->80/20) to afford the mono-Boc-protected title compound as an off-white solid (0.692 g, 90%).

$^1$H-NMR (400 MHz, $CDCl_3$): δ=1.56 (s, 9H), 7.02 (br-s, 1H), 7.79-7.83 (br-s, 1H), 8.43-8.46 (br-s, 1H).

Step E

The less polar title compound from Step C above (0.487 g, 1.34 mmol) and the title compound from Step D above (0.692 g, 2.63 mmol) were dissolved in dichloromethane (15 mL) and a 4 M solution of hydrogen chloride in 1,4-dioxane (30 mL) was added. The reaction mixture was stirred at room temperature for 3 days. The solvents were evaporated under reduced pressure and the residue was dissolved in dichloromethane (100 mL) and water (35 mL). Then solid sodium hydroxide was added under cooling until the aqueous layer was alkaline (pH~12). The organic phase was separated, dried over $Na_2SO_4$, filtered and the solvent was removed under reduced pressure. The residue was purified by chromatography on HP-Sil SNAP cartridges using a Biotage Isolera One purification system employing an ethyl acetate/n-heptane gradient (5/95->100/0) to afford the title compound as an orange solid (0.538 g, 83%).

$^1$H-NMR (400 MHz, DMSO-$d_6$): δ=6.87 (br-s, 2H), 6.93 (dd, 1H), 7.45 (d, 1H), 7.67 (d, 1H).

Preparative Example 33

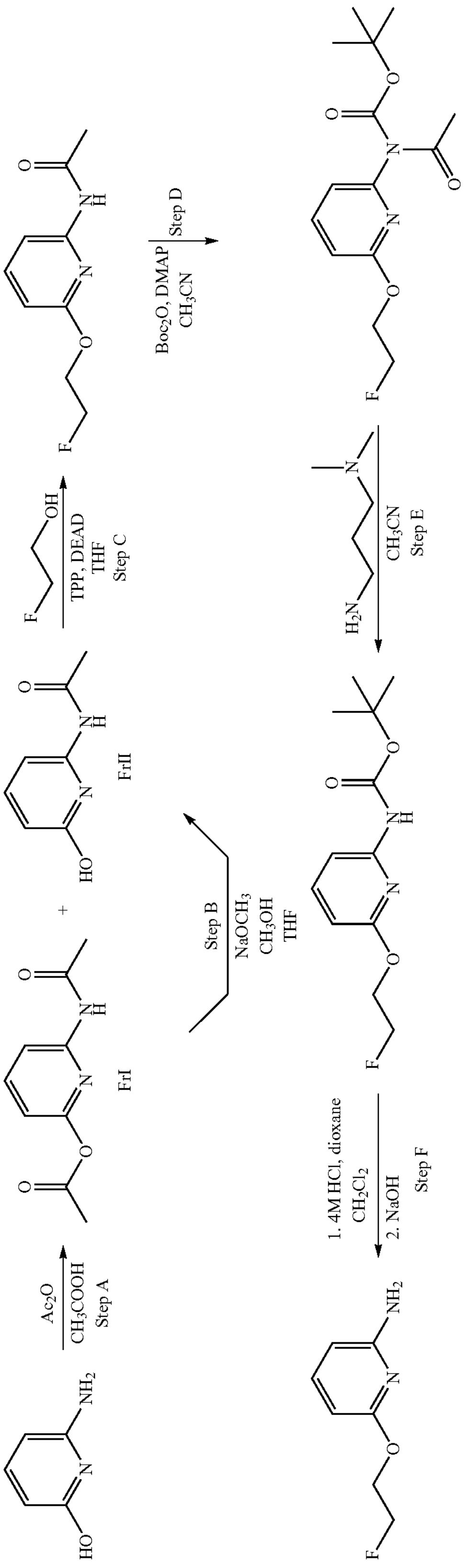
FrI
FrII

Step A

Commercially available 2-amino-6-hydroxypyridine (1 g, 9.09 mmol) was suspended in acetic acid (9 mL) and the reaction mixture was heated to reflux (~125° C. in a sand-bath). Then acetic acid anhydride (2.3 mL) was added and the reaction mixture was heated at reflux for 1 hour. The reaction mixture was poured into ice-water (150 mL) and the mixture was stirred for 30 minutes. The precipitate was collected by filtration, washed with water (30 mL) and air-dried to afford the less polar title compound FrI as a grey solid (0.716 g, 40%). The filtrate was evaporated under reduced pressure and the residue was purified by chromatography on HP-Sil SNAP cartridges using a Biotage Isolera One purification system employing an ethyl acetate/n-heptane gradient (5/95->100/0) to afford additional title compound FrI (0.415 g, 23%). The gradient was then changed to dichloromethane/methanol (100/0->80/20) to afford the more polar title compound FrII as an off-white solid (0.292 g, 21%).

Less polar FrI: $^1$H-NMR (400 MHz, DMSO-$d_6$): δ=2.07 (s, 3H), 2.28 (s, 3H), 6.86 (d, 1H), 7.90 (t, 1H), 8.02 (d, 1H), 10.65 (br-s, 1H).

More polar FrII: $^1$H-NMR (400 MHz, DMSO-$d_6$): δ=2.06 (s, 3H), 6.20 (d, 1H), 6.90-7.00 (br-s, 1H), 7.49 (t, 1H), 10.27-10.32 (br-s, 1H), 10.75-10.85 (br-s, 1H).

Step B

The less polar title compound FrI from Step A above (0.207 g, 1.067 mmol) was dissolved in tetrahydrofuran (5 mL) and a 25%-solution of sodium methylate in methanol (0.35 mL, 1.53 mmol) was added. The reaction mixture was stirred at room temperature for 1 hour. After the addition of methanol (5 mL), the reaction mixture was concentrated under reduced pressure and the residue was purified by chromatography on HP-Sil SNAP cartridges using a Biotage Isolera One purification system employing a dichloromethane/methanol (100/0->80/20) to afford the title compound as an off-white solid (0.159 g, 98%).

Step C

The more polar title compound FrI from Step A or the title compound from Step B above (0.529 g, 3.48 mmol) was dissolved in tetrahydrofuran (45 mL) and triphenylphosphine (1.608 g, 6.09 mmol) and 2-fluoroethanol (0.179 mL, 3.05 mmol) were added. After the addition of a solution of diethyl diazodicarboxylate in tetrahydrofuran (2.519 mL, 6.09 mmol), the reaction mixture was stirred at room temperature for 3 days. The reaction mixture was concentrated under reduced pressure and the residue was purified by chromatography on HP-Sil SNAP cartridges using a Biotage Isolera One purification system employing an ethyl acetate/n-heptane gradient (5/95->100/0) to afford the title compound as a white solid (0.624 g) which was contaminated with diethyl hydrazine-1,2-dicarboxylate. The gradient was then changed to dichloromethane/methanol (100/0->80/20) to recover the starting material as an off-white solid (0.208 g, 39%).

$^1$H-NMR (400 MHz, DMSO-$d_6$): δ=1.15 (t; diethyl hydrazine-1,2-dicarboxylate), 2.07 (s, 3H), 2.28 (s, 3H), 4.01 (q, diethyl hydrazine-1,2-dicarboxylate), 4.40-4.42 (m, 1H), 4.48-4.51 (m, 1H), 4.66-4.69 (m, 1H), 4.78-4.81 (m, 1H), 6.52 (d, 1H), 7.63-7.68 (m, 2H), 8.97 (br-s, 1H).

Step D

The crude title compound from Step C above (0.624 g) was dissolved in acetonitrile (10 mL) and a solution of di-tert.-butyl dicarbonate (0.8 g, 3.55 mmol) in acetonitrile (2 mL) was added. After the addition of 4-(dimethylamino)-pyridine (0.037 g, 0.3 mmol), the reaction mixture was stirred at room temperature for 16 hours. Since TLC indicated the presence of a lot of starting material, another batch of di-tert.-butyl dicarbonate (1.6 g, 7.1 mmol) and 4-(dimethylamino)-pyridine (0.037 g, 0.3 mmol) was added and stirring at room temperature was continued for another 4 hours. The solvent was removed under reduced pressure and the residue was purified by chromatography on HP-Sil SNAP cartridges using a Biotage Isolera One purification system employing an ethyl acetate/n-heptane gradient (5/95->60/40) to afford the title compound as a colorless oil (0.982 g) contaminated with 1,2-di-tert-butyl 1,2-diethyl hydrazine-1,1,2,2-tetracarboxylate.

$^1$H-NMR (400 MHz, DMSO-$d_6$): δ=1.23 (t; 1,2-di-tert-butyl 1,2-diethyl hydrazine-1,1,2,2-tetracarboxylate), 1.35 (s, 9H), 1.45 (s, 1,2-di-tert-butyl 1,2-diethyl hydrazine-1,1,2,2-tetracarboxylate), 2.46 (s, 3H), 2.28 (s, 3H), 4.24 (q, 1,2-di-tert-butyl 1,2-diethyl hydrazine-1,1,2,2-tetracarboxylate), 4.37-4.41 (m, 1H), 4.46-4.48 (m, 1H), 4.66-4.69 (m, 1H), 4.78-4.81 (m, 1H), 6.87 (d, 1H), 6.95 (d, 1H), 7.84 (t, 1H).

Step E

The crude title compound from Step D above (0.982 g) was dissolved in acetonitrile (20 mL) and treated with $N^1$,$N^1$-dimethylpropane-1,3-diamine (0.83 mL, 6.59 mmol). The reaction mixture was stirred at room temperature for 16 hours and the solvent was evaporated under reduced pressure. The oily residue was purified by chromatography on HP-Sil SNAP cartridges using a Biotage Isolera One purification system employing an ethyl acetate/n-heptane gradient (5/95->60/40) to afford the title compound as a colorless oil (0.359 g, 40% for 3 steps).

$^1$H-NMR (400 MHz, DMSO-$d_6$): δ=1.45 (s, 3H), 0.4.37-4.41 (m, 1H), 4.46-4.48 (m, 1H), 4.66-4.69 (m, 1H), 4.77-4.80 (m, 1H), 6.45 (d, 1H), 7.33 (d, 1H), 7.62 (t, 1H), 9.55 (s, 1H).

Step F

The title compound from Step E above (0.359 g, 1.4 mmol) was dissolved in dichloromethane (6 mL) and a 4 M solution of hydrogen chloride in 1,4-dioxane (12 mL) was added. The reaction mixture was stirred at room temperature for 18 hours. The solvents were evaporated under reduced pressure and the residue was dissolved in water (20 mL). Then solid sodium hydroxide was added under cooling until the aqueous layer was alkaline (pH~12). The aqueous layer was extracted with dichloromethane (2×50 mL), the combined organic phase was dried over $Na_2SO_4$ and filtered and the solvent was removed under reduced pressure. The residue was purified by chromatography on HP-Sil SNAP cartridges using a Biotage Isolera One purification system employing an ethyl acetate/n-heptane gradient (5/95->60/40) to afford the title compound as a pale yellow oil (0.202 g, 92%).

$^1$H-NMR (400 MHz, DMSO-$d_6$): δ=4.33-4.36 (m, 1H), 4.41-4.43 (m, 1H), 4.63-4.66 (m, 1H), 4.74-4.77 (m, 1H), 5.85 (br-s, 2H), 5.91 (d, 1H), 6.02 (d, 1H), 7.30 (t, 1H).

Preparative Example 34

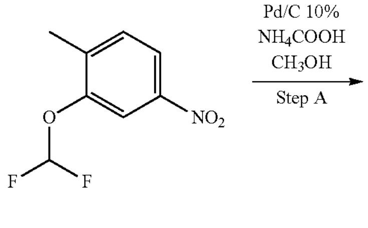

-continued

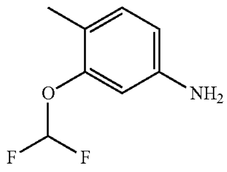

Step A

Commercially available 2-(difluoromethoxy)-1-methyl-4-nitrobenzene (0.06 g, 0.29 mmol) was dissolved in methanol (5 mL) and ammonium formate was added (0.068 g, 1.45 mmol). After the addition of a suspension of 10% palladium on charcoal (0.026 g) in water (500 μL), the mixture was stirred at room temperature overnight. The reaction mixture was filtered and the catalyst was washed with methanol (10 mL). The filtrate was evaporated under reduced pressure and the residue was purified by chromatography on HP-Sil SNAP cartridges using a Biotage Isolera One purification system employing an ethyl acetate/n-heptane gradient (5/95->60/40) to afford the title compound (0.043 g, 79%).

$^1$H-NMR (400 MHz, DMSO-$d_6$) δ=6.86 (t, 1H), 6.79 (d, 1H), 6.43 (s, 1H), 6.37 (d, 1H), 4.98 (s, 2H), 2.09 (s, 3H).

Preparative Example 35

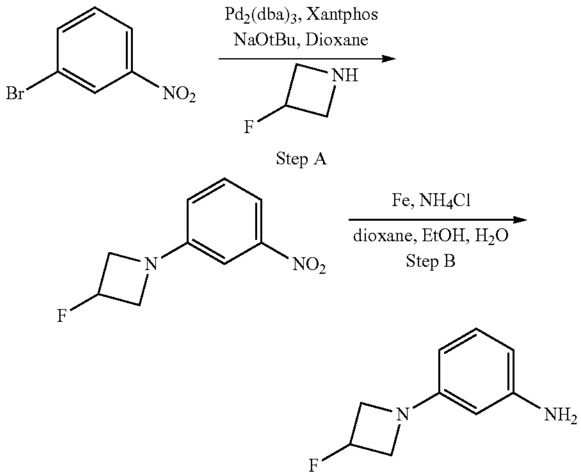

Step A

An oven dried Schlenk flask was evacuated and back filled with argon gas. The procedure was repeated 3-4 times and the flask was cooled to room temperature. Then commercially available 1-bromo-3-nitrobenzene (0.48 g, 2.39 mmol), commercially available 3-fluoroazetidine hydrochloride (0.30 g, 2.62 mmol), tris(dibenzylideneacetone) dipalladium(0) (0.098 g, 0.26 mmol), 4,5-bis(diphenylphosphino)-9,9-dimethylxanthene (0.60 g, 1.04 mmol), sodium tert.-butoxide (0.600 g, 5.97 mmol) and 1,4-dioxane (5 mL) were added and the reaction mixture was heated at 90° C. in a sand-bath for 12 h. The reaction mixture was diluted with ethyl acetate (50 mL) and water (30 mL), the phases were separated and the aqueous layer was extracted with ethyl acetate (2×20 mL). The combined organic phase was dried over $Na_2SO_4$ and filtered and the solvents were removed. The black residue was purified by chromatography on HP-Sil SNAP cartridges using a Biotage Isolera One purification system employing an ethyl acetate/n-heptane gradient (0/100->40/60) to afford the title compound as a pale yellow solid (0.07 g, 15%).

$^1$H-NMR (400 MHz, $CDCl_3$) δ=7.61 (d, 1H), 7.35 (t, 1H), 7.31-7.21 (m, 1H), 6.73 (d, 1H), 5.62-5.32 (m, 1H), 4.43-4.17 (m, 2H), 4.16-3.89 (m, 2H).

Step B

To a solution of the title compound from Step A above (0.07 g, 0.38 mmol) in ethanol (8 mL), 1,4-dioxane (10 mL) and water (2.5 mL) was added ammonium chloride (0.082 g, 1.54 mmol). The mixture was stirred at room temperature for 15 minutes and iron powder (0.107 g, 1.94 mmol) was added. The heterogeneous mixture was heated at 85° C. in a sand-bath for 12 h, cooled at room temperature and filtered. The solvents were removed under reduced pressure, the crude product was dissolved with ethyl acetate (10 mL), washed with water (10 mL) and brine (10 mL), dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->40/60) to afford the title compound as a pale yellow solid (0.03 g, 47%).

$^1$H-NMR (400 MHz, DMSO-$d_6$) δ=6.82 (t, 1H), 6.05-5.87 (m, 1H), 5.67 (dq, 2H), 5.44 (ddt, 1H), 4.89 (s, 2H), 4.04 (dddd, 2H), 3.74 (dddd, 2H).

Preparative Example 36

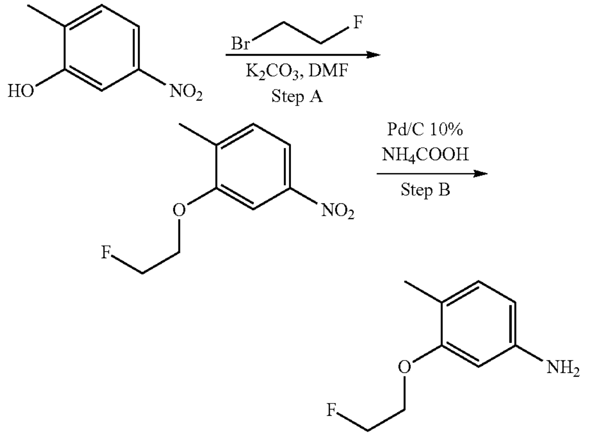

Step A

To 2-methyl-5-nitrophenol (2.0 g, 12.9 mmol) in N,N'-dimethylformamide (10 mL) was added potassium carbonate (0.53 g, 38.7 mmol), followed by the addition of 1-bromo-2-fluoroethane (2.4 g, 19.3 mmol). The reaction mixture was stirred at 100° C. overnight. Ethyl acetate (50 mL) and water (100 mL) were added to the cooled mixture, the phases were separated and the aqueous layer was extracted with ethyl acetate (2×20 mL). The combined organic phase was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->10/90) to afford the title compound (0.719 g, 33%).

$^1$H-NMR (400 MHz, DMSO-$d_6$) δ=8.23-8.01 (m, 2H), 7.38-6.97 (m, 1H), 4.94-4.80 (m, 1H), 4.80-4.66 (m, 1H), 4.52-4.42 (m, 1H), 4.42-4.33 (m, 1H), 2.26 (s, 3H).

Step B

Following the procedure as described in Preparative Example 34, the title compound from Step B was prepared (0.51 mg, 69%).

$^1$H-NMR (400 MHz, DMSO-$d_6$) δ=6.63 (d, 1H), 6.38 (d, 1H), 6.33 (dd, 1H), 4.75-4.66 (m, 1H), 4.66-4.58 (m, 1H), 4.56 (s, 2H), 4.16-4.04 (m, 1H), 4.04-3.93 (m, 1H), 2.04 (s, 3H).

Preparative Example 37

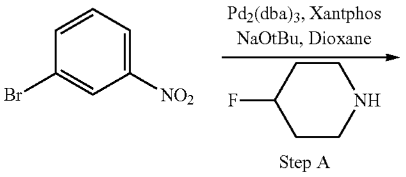

Step B

Following the procedure as described in Preparative Example 35 Step B, the title compound from Step B was prepared (0.06 g, 43%).

$^1$H-NMR (400 MHz, DMSO-$d_6$) δ=6.84 (t, 1H), 6.23-6.07 (m, 2H), 6.07-5.92 (m, 1H), 4.90-4.66 (m, 3H), 3.29-3.18 (m, 2H), 3.12-2.90 (m, 2H), 2.15-1.85 (m, 2H), 1.85-1.64 (m, 2H).

Preparative Example 38

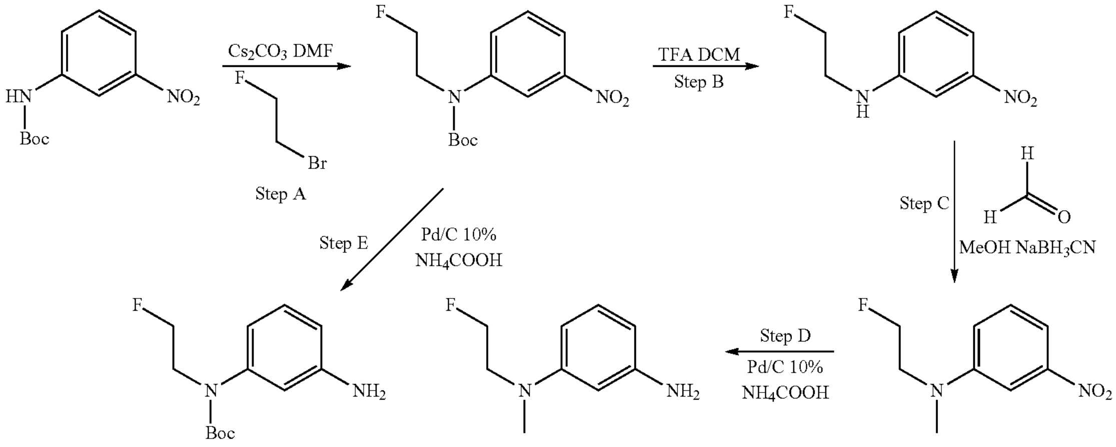

-continued

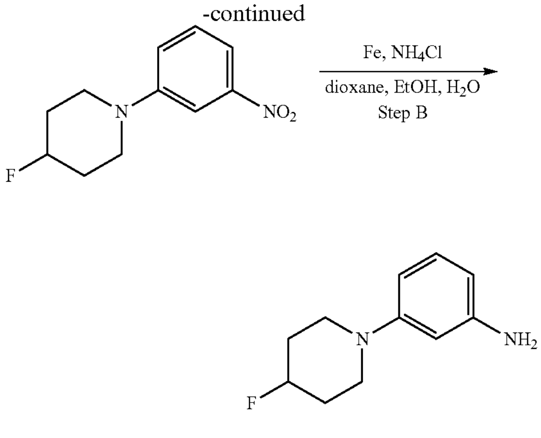

Step A

Following the procedure as described in Preparative Example 35 Step A, the title compound from Step A was prepared (0.28 g, 30%).

$^1$H-NMR (400 MHz, $CDCl_3$) δ=7.72 (s, 1H), 7.63 (d, 1H), 7.36 (t, 1H), 7.20 (d, 1H), 5.03-4.63 (m, 1H), 3.53-3.39 (m, 2H), 3.38-3.21 (m, 2H), 2.28-1.75 (m, 4H).

Step A

To a commercially available tert-butyl (3-nitrophenyl) carbamate (2.0 g, 8.43 mmol) in N,N'-dimethylformamide (20 mL) was added cesium carbonate (8.1 g, 25 mmol), followed by the addition of 1-bromo-2-fluoroethane (1.6 g, 12.5 mmol). The reaction mixture was stirred at 100° C. overnight. Water (200 mL) and ethyl acetate (100 mL) were added to the cooled mixture, the phases were separated and the aqueous layer was extracted with ethyl acetate (2×20 mL). The combined organic phase was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->40/60) to afford the title compound (2.37 g, 98%).

$^1$H-NMR (400 MHz, DMSO-$d_6$) δ=8.14 (t, 1H), 8.08 (d, 1H), 7.76 (d, 1H), 7.66 (t, 1H), 4.63 (t, 1H), 4.51 (t, 1H), 4.00 (t, 1H), 3.94 (t, 1H), 1.40 (s, 9H).

Step B

To compound from Step A above (2.0 g, 8.4 mmol) was added dichloromethane (27 mL) and trifluoroacetic acid (3 mL) and the solution was stirred at room temperature overnight. The reaction mixture was concentrated under reduced pressure and dichloromethane (20 mL) was added and the solution was washed with an aqueous solution (1N) of sodium hydroxide (2×20 mL), dried over $Na_2SO_4$, filtered and the solvents was removed under reduced pressure. The residue was purified by chromatography on HP-Sil SNAP cartridges using a Biotage Isolera One purification system employing an ethyl acetate/n-heptane gradient (0/100->60/40) to afford the title compound (1.29 g, 83%).

$^1$H-NMR (400 MHz, DMSO-$d_6$) δ=7.49-7.18 (m, 3H), 7.17-6.94 (m, 1H), 6.60 (t, 1H), 4.63 (t, 1H), 4.51 (t, 1H), 3.46 (q, 1H), 3.39 (q, 1H).

Step C

The title compound from Step B above (1.29 g, 7.0 mmol) was dissolved in methanol (10 mL). A 37%-aqueous formaldehyde solution (0.42 g, 210 mmol) was added and the mixture was stirred at room temperature for 10 minutes. Then sodium cyanoborohydride (2.2 g, 35 mmol) was added and the mixture was stirred at room temperature overnight. A water solution (1 N) of sodium hydroxide was added dropwise (30 mL) and the mixture was stirred at room temperature for 10 minutes. The reaction mixture was concentrated under reduced pressure and the aqueous layer was extracted with ethyl acetate (3×20 mL). The combined organic phase was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->10/90) to afford the title compound (0.1 g, 7%).

$^1$H-NMR (400 MHz, $CDCl_3$) δ=7.73-7.42 (m, 2H), 7.33 (t, 1H), 6.98 (dd, 1H), 4.68 (t, 1H), 4.57 (t, 1H), 3.74 (t, 1H), 3.68 (t, 1H), 3.08 (s, 3H).

Step D

Following the hydrogenation procedure as described in Preparative Example 34, the title compound of Step D was prepared (0.08 g, 95%).

$^1$H-NMR (400 MHz, $CD_3OD$) δ=6.99 (t, 1H), 6.22-6.14 (m, 3H), 4.64 (t, 1H), 4.52 (t, 1H), 3.61 (t, 1H), 3.58 (t, 1H), 2.97 (s, sH).

MS (ESI); m/z=169.08 ($MH^+$).

Step E

Following the hydrogenation procedure as described in Preparative Example 34, the title compound of Step E was prepared (1.6 g, 76%).

$^1$H-NMR (400 MHz, DMSO-$d_6$) δ=6.99 (t, 1H), 6.50-6.25 (m, 3H), 5.12 (s, 2H), 4.54 (t, 1H), 4.42 (t, 1H), 3.82 (t, 1H), 3.76 (t, 1H), 1.38 (s, 9H).

Preparative Example 39

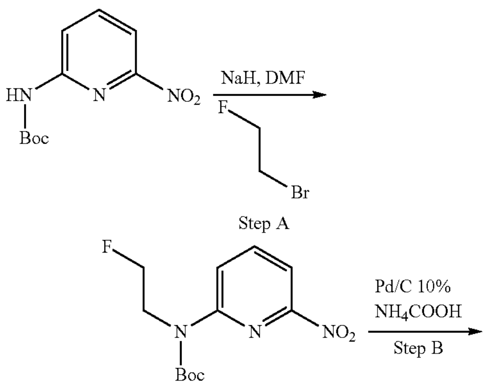

-continued

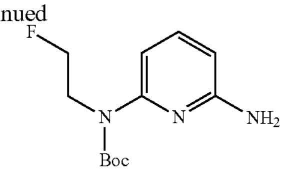

Step A

To a commercially available tert-butyl (6-nitropyridin-2-yl)carbamate (0.58 g, 2.43 mmol) in DMF (15 mL) was added NaH 60% (in mineral oil) (0.45 g, 4.37 mmol) portionwise. The suspension was stirred at room temperature for 30 minutes and 1-bromo-2-fluoroethane (719 μL g, 3.4 mmol) was added. The reaction mixture was stirred at room temperature overnight. Then a saturated solution of ammonium chloride (15 mL) was added and extracted with ethyl acetate (3×50 mL). The combined organic phase was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->10/90) to afford the title compound (0.4 g, 57%).

$^1$H NMR (400 MHz, DMSO-$d_6$) δ 8.23-8.16 (m, 1H), 8.12 (d, 1H), 8.05 (dd, 1H), 4.74 (t, 1H), 4.62 (t, 1H), 4.30 (t, 1H), 4.24 (t, 1H), 1.49 (s, 9H).

Step B

Following the hydrogenation procedure as described in Preparative Example 34, the crude title compound from Step B was prepared (0.1 g, 28%). The residue was purified by chromatography on HP-Sil SNAP cartridges using a Biotage Isolera One purification system employing an Dichloromethane/methanol gradient (100/0->0/100) to afford the title compound (0.1 g, 28%).

$^1$H NMR (400 MHz, DMSO-$d_6$) δ 7.37-7.17 (m, 1H), 6.47-6.30 (m, 1H), 6.20 (d, 1H), 4.03 (s, 4H), 1.51 (s, 9H).

Preparative Example 40

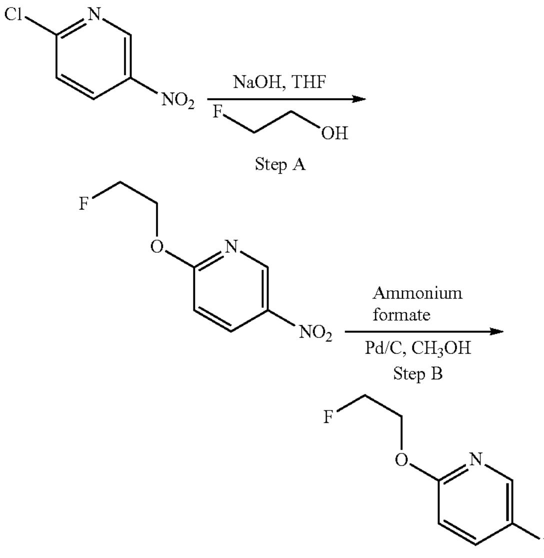

Step A

To a suspension of sodium hydroxide (0.375 g, 9.08 mmol) in tetrahydrofuran (5 mL), 2-fluoroethanol (0.50 g, 7.57 mmol) was added and the mixture was stirred at room temperature for 1 h. Then commercially available 2-chloro-5-nitropyridine (1.2 g, 7.57 mmol) in tetrahydrofuran (10 mL) was added to the above suspension. The reaction mixture was heated at 60° C. overnight and cooled at room temperature. Water (10 mL) and ethyl acetate (20 mL) were added, the phases were separated and organic layer was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->10/90) to afford the title compound (0.53 g, 38%).

$^1$H-NMR (400 MHz, DMSO-$d_6$) δ 9.10 (d, 1H), 8.52 (d, 1H), 7.12 (d, 1H), 4.98-4.80 (m, 1H), 4.77-4.69 (m, 2H), 4.66-4.47 (m, 1H).

Step B

Following the hydrogenation procedure as described in Preparative Example 34, the title compound from Step B was prepared (0.23 g, 51%).

$^1$H-NMR (400 MHz, DMSO-$d_6$) δ=7.48 (d, 1H), 7.01 (dd, 1H), 6.58 (d, 1H), 4.81-4.66 (m, 3H), 4.66-4.55 (m, 1H), 4.49-4.33 (m, 1H), 4.33-4.18 (m, 1H).

Preparative Example 41

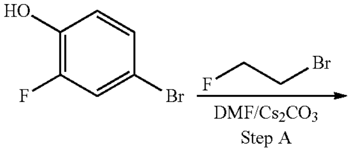

-continued

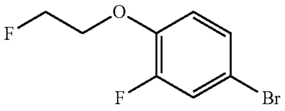

Step A

To 4-bromo-2-fluorophenol (0.760 g, 4.3 mmol) in N,N'-dimethylformamide (20 mL) was added cesium carbonate (6.8 g, 21 mmol), followed by the addition of 1-bromo-2-fluoroethane (2.7 g, 21 mmol). The reaction mixture was stirred at 90° C. overnight. The solid was filtered off and the filtrate was diluted with ethyl acetate. The organic phase was washed with water as well as brine, dried over $Na_2SO_4$ and filtered. The solvent was removed and the residue was purified on HP-Sil SNAP cartridges using a Biotage Isolera One purification system employing an ethyl acetate/n-heptane gradient (20/80->80/20) to afford the title compound (1.6 g, 64%).

$^1$H-NMR (400 MHz, $CDCl_3$) δ=7.28 (dd, 1H), 7.22 (dt, 1H), 6.91 (t, 1H), 4.88-4.80 (m, 1H), 4.79-4.69 (m, 1H), 4.33 (dd, 1H), 4.29-4.22 (m, 1H).

Preparative Examples 42 to 46

Following the procedure as described in Preparative Example 41, except using the phenol-derivatives and fluoroalkyl derivatives indicated in the table below, the following compounds were prepared. Cesium carbonate can be substituted by potassium carbonate as a base.

TABLE 1

| Phenol derivative | Fluoroalkyl derivative | Product Preparative Example | 1. Yield 2. $^1$H-NMR 3. $MH^+$ (ESI) |
|---|---|---|---|
| 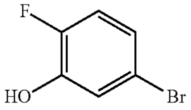 | 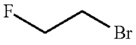 | 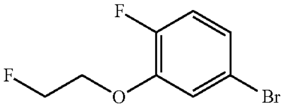 42 | 1. 68% 2. $^1$H-NMR (400 MHz, $CDCl_3$) δ = 7.27 (s, 0H), 7.13 (dd, 1H), 7.07 (ddd, 1H), 6.98 (dd, 1H), 4.90-4.76 (m, 1H), 4.76-4.67 (m, 1H), 4.38-4.28 (m, 1H), 4.29-4.14 (m, 1H) |
| 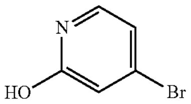 | 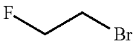 | 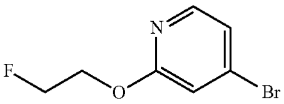 43 | 1. 26% 2. $^1$H-NMR (400 MHz, $CD_3OD$) δ = 7.56 (d, 1H), 6.84 (d, 1H), 6.57 (d, 1H), 4.76 (t, 1H), 4.64 (t, 1H), 4.33 (t, 1H), 4.26 (t, 1H) |
| 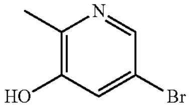 | 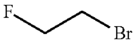 | 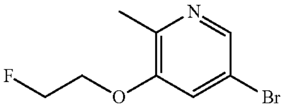 44 | 1. 51% 2. $^1$H-NMR (400 MHz, DMSO-$d_6$) δ = 8.14 (s, 1H), 7.65 (s, 1H), 4.93-4.78 (m, 1H), 4.78-4.59 (m, 1H), 4.45-4.33 (m, 1H), 4.33-4.24 (m, 1H), 2.33 (d, 3H) |
| 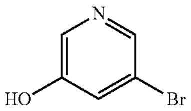 | 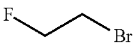 | 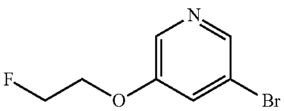 45 | 1. 50% 2. $^1$H-NMR (400 MHz, DMSO-$d_6$) δ = 8.33 (dd, 2H), 7.77 (t, 1H), 4.97-4.76 (m, 1H), 4.76-4.61 (m, 1H), 4.51-4.37 (m, 1H), 4.37-4.25 (m, 1H) |

TABLE 1-continued

| Phenol derivative | Fluoroalkyl derivative | Product Preparative Example | 1. Yield 2. $^1$H-NMR 3. $MH^+$ (ESI) |
|---|---|---|---|
| 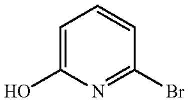 | 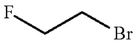 | 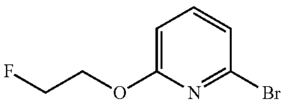 46 | 1. 43% 2. $^1$H-NMR (400 MHz, DMSO-$d_6$) δ = 7.70 (t, 1H), 7.25 (d, 1H), 6.81 (d, 1H), 4.80 (m, 1H), 4.45 (m, 1H), 4.50 (m, 1H), 4.43 (m, 1H) |

Preparative Example 47

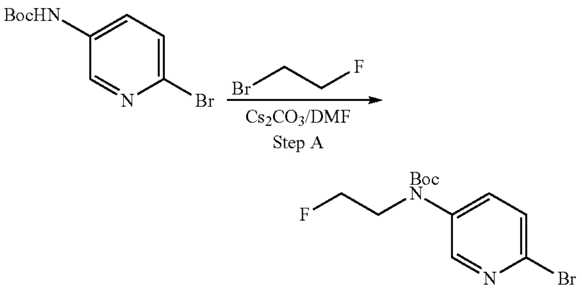

Step A

To a solution of commercially available tert-butyl (6-bromopyridin-3-yl)carbamate (0.68 g, 2.5 mmol) was added cesium carbonate (2.6 g, 8 mmol), followed by 2-fluoroethyl bromide (0.95 g, 7.5 mmol). Then the reaction mixture was stirred at 90° C. overnight. At the conclusion of the reaction, the reaction mixture was poured in ethyl acetate (200 mL) and washed with water as well as brine solution and dried over $Na_2SO_4$. The solvent was evaporated and the residue was purified on HP-Sil SNAP cartridges using a Biotage Isolera One purification system employing an ethyl acetate/n-heptane gradient (40/60->80/20) to afford the title compound (0.58 g, 72%).

$^1$H-NMR (400 MHz, DMSO-$d_6$) δ=8.31 (d, 1H), 7.62-7.40 (m, 2H), 7.27 (s, OH), 4.69 (t, 1H), 4.57 (t, 1H), 3.92 (t, 1H), 3.85 (t, 1H), 1.45 (s, 9H).

Preparative Example 48

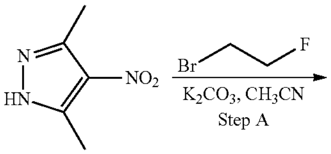

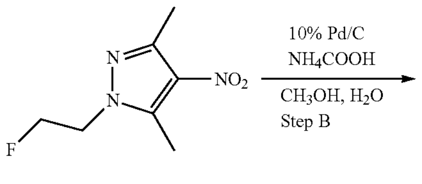

-continued

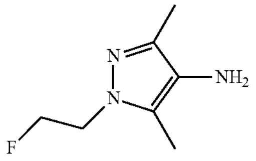

Step A

To a solution of 3,5-dimethyl-4-nitro-1H-pyrazole (0.5 g, 3.54 mmol) in acetonitrile (10 mL), $K_2CO_3$ (1.4 g, 10.62 mmol) was added and the mixture was stirred at room temperature for 30 minutes. Then 1-bromo-2-fluoroethane (0.67 g, 5.31 mmol) was added dropwise. The mixture was heated at reflux overnight. To the cooled reaction mixture $H_2O$ (20 ml) was added. The mixture was extracted with ethyl acetate (3×50 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound which was used in the next step without further purification (0.515 g, 77%).

$^1$H-NMR (400 MHz, DMSO-$d_6$) δ=4.80 (t, 1H), 4.68 (t, 1H), 4.48 (t, 1H), 4.41 (t, 1H), 2.57 (s, 3H), 2.40 (s, 3H).

Step B

The crude title compound from Step A above (0.45 g, 2.4 mmol) was dissolved in methanol (10 mL) and ammonium formate was added (0.55 g, 12 mmol). After the addition of a suspension of 10% palladium on charcoal (0.22 g) in water (1 mL), the mixture was stirred at room temperature overnight. The reaction mixture was filtered and the catalyst was washed with methanol (20 mL). The filtrate was evaporated under reduced pressure and the residue was re-dissolved in ethyl acetate (50 mL) and water (40 mL). The organic phase was separated, dried over $Na_2SO_4$, filtered and the solvent was removed under reduced pressure. The residue was purified on a HP-Sil column using a Biotage Isolera One purification system employing an EtOAc/n-heptane gradient (5/95->40/60) to the title compound (0.236 g, 62%).

$^1$H-NMR (400 MHz, DMSO-$d_6$) δ=4.66 (t, 1H), 4.54 (t, 1H), 4.14 (t, 1H), 4.08 (t, 1H), 3.72 (s, 2H), 2.04 (s, 3H), 1.97 (s, 3H).

MS (ESI); m/z=157.66 $[M+H]^+$.

Preparative Examples 49 to 53

Following the procedure as described in Preparative Example 48 Step A, except using the nitro-derivatives and fluoroalkyl derivatives indicated in the table below, the following compounds were prepared.

TABLE 2

| Nitro derivative | Fluoroalkyl derivative | Product Preparative Example | 1. Yield 2. ¹H-NMR 3. $MH^+$ (ESI) |
|---|---|---|---|
| 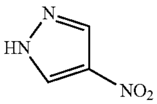 | 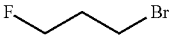 | 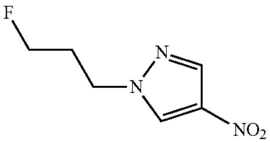 49 | 1. 52% 2. ¹H-NMR (400 MHz, DMSO-$d_6$) δ = 8.93 (s, 1H), 8.27 (s, 1H), 4.52 (t, 1H), 4.40 (t, 1H), 4.29 (t, 2H), 2.30-2.12 (m, 2H) |
| 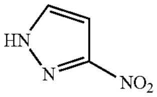 | 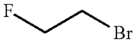 | 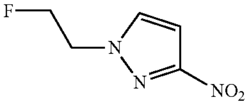 50 | 1. 35% 2. ¹H-NMR (400 MHz, DMSO-$d_6$) δ = 8.08 (d, 1H), 7.08 (d, 1H), 4.91-4.84 (m, 1H), 4.79-4.72 (m, 1H), 4.62 (t, 1H), 4.55 (t, 1H) |
| 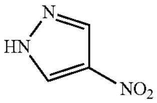 | 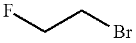 | 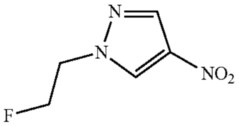 51 | 1. 70% 2. ¹H-NMR (400 MHz, DMSO-$d_6$) δ = 8.95 (s, 1H), 8.32 (s, 1H), 4.89 (t, 1H), 4.77 (t, 1H), 4.66-4.52 (m, 1H), 4.50 (t, 1H). |
| 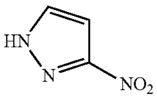 | 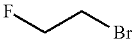 | 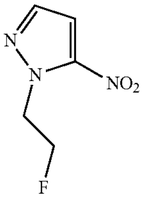 52 | 1. 11% 2. ¹H-NMR (400 MHz, DMSO-$d_6$) δ = 7.75 (d, 1H), 7.31 (d, 1H), 4.81-4.71 (m, 1H), 4.71-4.62 (m, 1H), 4.59-4.48 (m, 1H), 4.47-4.39 (m, 1H). |
| 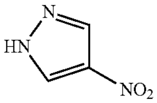 | 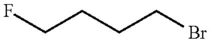 | 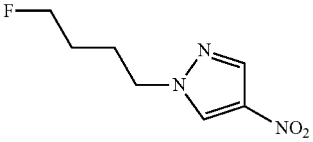 53 | 1. 66% 2. ¹H-NMR (400 MHz, DMSO-$d_6$) δ = 8.92 (s, 1H), 8.27 (s, 1H), 4.51 (t, 1H), 4.39 (t, 1H), 4.23 (t, 2H), 1.90 (p, 2H), 1.72-1.47 (m, 2H). |

Preparative Examples 54 to 58

Following the procedure as described in Preparative Example 48 Step B, except using the nitro-derivatives indicated in the table below, the following compounds were prepared.

TABLE 3

| Nitro derivative | Product Preparative Example | 1. Yield 2. ¹H-NMR 3. $MH^+$ (ESI) |
|---|---|---|
| 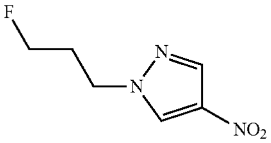 [SMILES: O=[N+]([O-])c1cnn(CCCF)c1] | 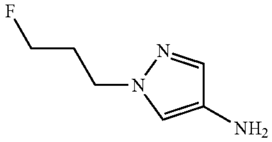 54 | 1. 81% 2. ¹H-NMR (400 MHz, DMSO-$d_6$) δ = 7.03 (s, 1H), 6.91 (s, 1H), 4.44 (t, 1H), 4.33 (t, 1H), 4.01 (t, 2H), 3.83 (bs, 2H), 2.23-1.94 (m, 2H). |

TABLE 3-continued

| Nitro derivative | Product Preparative Example | 1. Yield<br>2. $^1$H-NMR<br>3. MH$^+$ (ESI) |
|---|---|---|
| 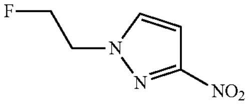 | 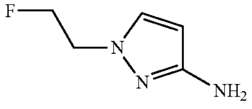 [SMILES: O=[N+]([O-])c1ccn(CCF)n1]<br>55 | 1. 83%<br>2. $^1$H-NMR (400 MHz, DMSO-d$_6$) δ = 7.32 (d, 1H), 5.39 (d, 1H), 4.71 (t, 1H), 4.68-4.42 (m, 3H), 4.15 (t, 1H), 4.08 (t, 1H).<br>3. 129.43 |
| 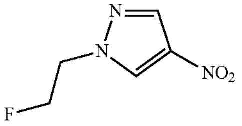 [SMILES: O=[N+]([O-])c1cnn(CCF)c1] | 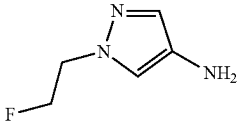<br>56 | 1. 86%<br>2. $^1$H-NMR (400 MHz, DMSO-d$_6$) δ 7.14-6.99 (m, 1H), 6.93 (d, 1H), 4.71 (t, 1H), 4.59 (t, 1H), 4.24 (t, 1H), 4.17 (t, 1H), 3.81 (s, 2H). |
| 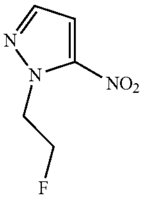 [SMILES: O=[N+]([O-])c1ccnn1CCF] | 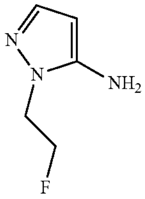<br>57 | 1. 50%<br>2. $^1$H-NMR (400 MHz, DMSO-d$_6$) δ = 7.07 (d, 1H), 5.27 (d, 1H), 5.16 (s, 2H), 4.73 (t, 1H), 4.62 (t, 1H), 4.29-4.16 (m, 1H), 4.13 (t, 1H).<br>3. 129.41 |
| 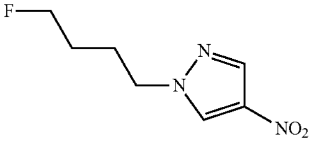 | 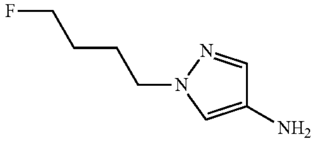 [SMILES: O=[N+]([O-])c1cnn(CCCCF)c1]<br>58 | 1. 70%<br>2. $^1$H-NMR (400 MHz, DMSO-d$_6$) δ = 7.01 (s, 1H), 6.88 (s, 1H), 4.45 (t, 1H), 4.33 (t, 1H), 3.92 (t, 2H), 1.83-1.66 (m, 2H), 1.62-1.40 (m, 2H). |

Preparative Example 59

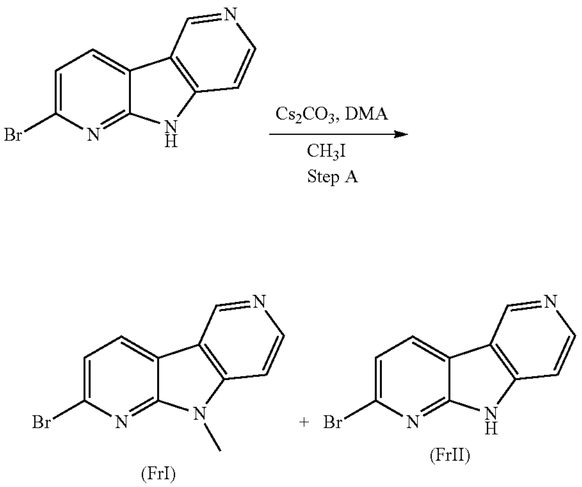

(FrI) (FrII)

Step A

The title compound from Preparative Example 20 (0.05 g, 0.2 mmol) was dissolved in N,N'-dimethylacetamide (1 mL) and cesium carbonate (0.098 g, 0.3 mmol) was added. After the addition of methyl iodide (0.018 mL, 0.3 mmol), the reaction mixture was stirred at room temperature for 16 hours. The reaction mixture was diluted with dichloromethane (30 mL) and brine (10 mL). The organic phase was separated, dried over $Na_2SO_4$, filtered and the solvents were evaporated. The residue was purified by chromatography on silica (10 g HP-SIL) using a Biotage Isolera system employing the following gradient:

| Time [Min] | dichloromethane | methanol |
|---|---|---|
| t = 0 | 100 | 0 |
| t = 3 | 99 | 1 |
| t = 6 | 98 | 2 |
| t = 9 | 97 | 3 |
| t = 12 | 96 | 4 |
| t = 15 | 95 | 5 |
| t = 18 | 90 | 10 |
| t = 27 | 90 | 10 |

Evaporation of the solvents from the less polar fraction (FrI) afforded the alkylation product as an off-white solid (0.0258 g, 49%) whereas the more polar fraction (FrII) afforded unreacted starting material (0.0013 g, 3%).

Less polar FrI: $^1$H-NMR (400 MHz, DMSO-d$_6$): δ=9.42 (s, 1H), 8.62-8.58 (m, 2H), 7.74 (d, 1H), 7.56 (d, 1H), 3.89 (s, 3H).

Preparative Example 60

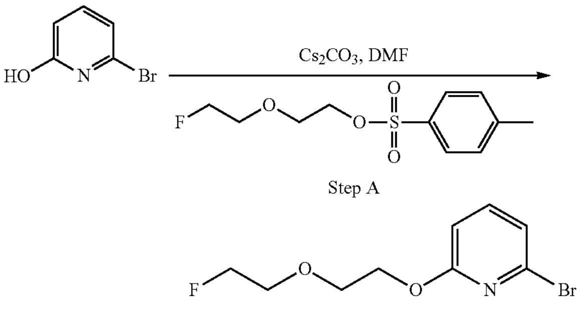

Step A

To a suspension of 6-bromopyridin-2-ol (0.4 g, 2.3 mmol) and cesium carbonate (0.95 g, 2.9 mmol) in N,N'-dimethylformamide (5 mL) was added the custom made tosyl derivative (0.78 g, 2.9 mmol). The reaction mixture was heated at 80° C. overnight. The reaction mixture was cooled to room temperature and dissolved in ethyl acetate (150 mL) and washed with water as well as brine, and dried over $Na_2SO_4$. The solvent was removed. The residue was purified on HP-Sil SNAP cartridges using a Biotage Isolera One purification system employing an ethyl acetate/n-heptane gradient (20/80->80/20) to afford the title compound (0.35 g, 58%).

$^1$H NMR (400 MHz, $CDCl_3$) δ=7.42 (t, 1H), 7.06 (d, 1H), 6.74 (d, 1H), 4.71-4.61 (m, 1H), 4.57-4.41 (m, 3H), 3.92-3.81 (m, 3H), 3.82-3.71 (m, 1H).

Preparative Example 61

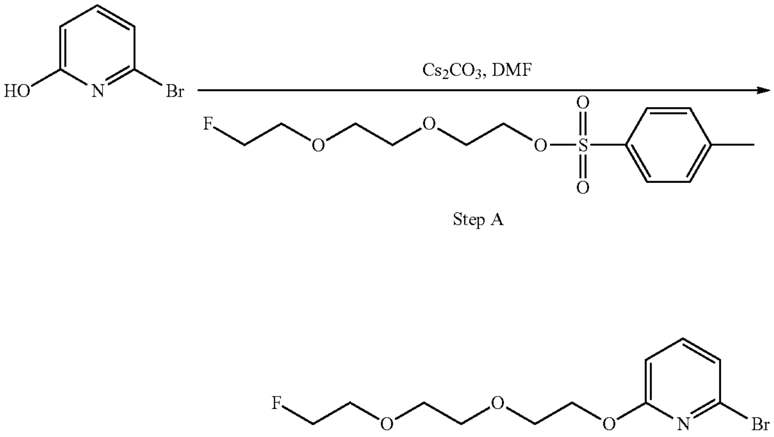

Step A

To a suspension of 6-bromopyridin-2-ol (0.6 g, 3.4 mmol) and cesium carbonate (1.4 g, 4.3) in N,N'-dimethylformamide (5 mL) was added the custom made tosyl derivative (1.29 g, 4.3 mmol). The reaction mixture was heated at 80° C. overnight. The reaction mixture was cooled to room temperature and dissolved in ethyl acetate (150 mL) and washed with water as well as brine, and dried over $Na_2SO_4$. The solvent was removed. The residue was purified on HP-Sil SNAP cartridges using a Biotage Isolera One purification system employing an ethyl acetate/n-heptane gradient (30/70->100/0) to afford the title compound (0.71 g, 69%).

$^1$H NMR (400 MHz, $CDCl_3$) δ=7.41 (t, 1H), 7.05 (d, 1H), 6.72 (d, 1H), 4.70-4.57 (m, 1H), 4.56-4.40 (m, 2H), 3.84 (t, 2H), 3.81-3.76 (m, 1H), 3.75-3.63 (m, 6H).

Preparative Example 62

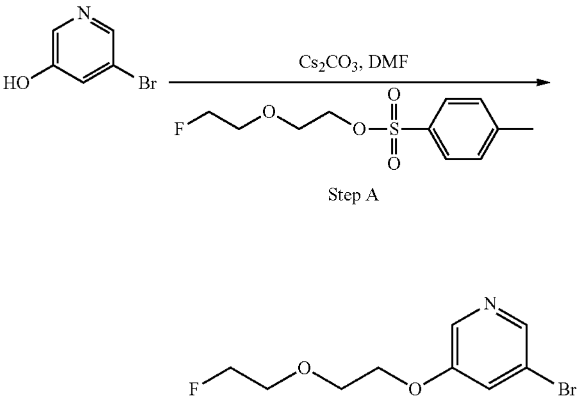

Step A

To a solution of 5-bromopyridin-3-ol (0.12 g, 0.69 mmol) in DMF (3 mL) was added $Cs_2CO_3$ (0.68 g, 2.09 mmol) and tosyl derivative (0.36 g, 1.38 mmol). The reaction mixture was heated at 70° C. overnight. Then the reaction mixture was cooled to room temperature, and dissolved in ethyl acetate (100 mL) and washed with water as well as brine solution. The organic phase was separated, dried over $Na_2SO_4$, filtered and the solvent was evaporated under reduced pressure. The residue was purified on HP-Sil Silica gel cartridges using a Biotage Isolera One purification system employing an ethyl acetate/n-heptane gradient (50/50->90/10) to afford the title compound (0.098 g, 54%).

$^1$H-NMR (400 MHz, $CDCl_3$) δ 8.27 (m, 2H), 7.40 (d, 1H), 4.59 (dt, 2H), 4.26-4.12 (m, 2H), 3.90 (t, 2H), 3.81 (dt, 2H).

Preparative Example 63

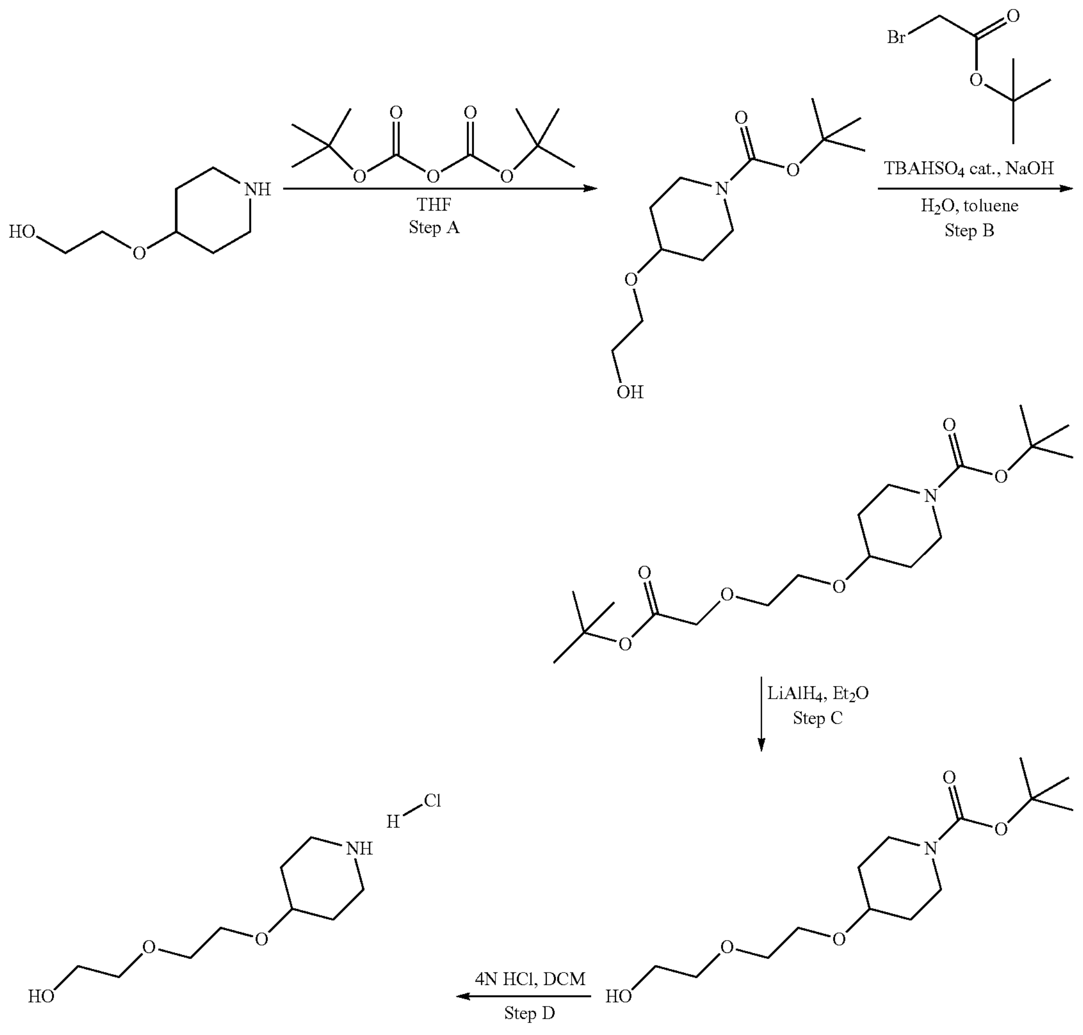

Step A

To a suspension of commercially available 2-(piperidin-4-yloxy)ethanol (0.702 g, 4.83 mmol) in THF (20 mL) was added di-tert-butyldicarbonate (1.26 g, 5.80 mmol). The reaction mixture was stirred at room temperature for 6 hours. The reaction mixture was concentrated in vacuo to afford the title compound (1.2 g, 100%).

$^1$H-NMR (400 MHz, DMSO-$d_6$) δ=4.58-4.50 (m, 1H), 3.62 (m, 3H), 3.45 (m, 4H), 3.09-2.89 (m, 2H), 1.83-1.71 (m, 2H), 1.39 (s, 9H), 1.31 (m, 2H).

Step B

To a solution of the title compound from Step A above (1.2 g, 4.89 mmol), tetra-butylammonium hydrogen sulfate (0.083 g, 0.25 mmol) and tert-butyl 2-bromoacetate (1.431 g, 7.34 mmol) in water (1 mL) and toluene (20 mL) was added over a period of 1 hour a solution of NaOH (6.98 g, 175 mmol) in water (10 mL). Then, the reaction mixture was stirred at room temperature for 5 hours. Water was added and the toluene phase was removed under reduced pressure. The aqueous phase was further extracted with toluene. The combined organics were dried over $Na_2SO_4$, filtered and concentrated in vacuo. The residue was purified on HP-Sil SNAP cartridges using a Biotage Isolera One purification system employing an n-heptane/EtOAc gradient (90/10->60/40) to afford the title compound (1.07 g, 61%).

$^1$H-NMR (400 MHz, DMSO-$d_6$) δ=3.99 (s, 2H), 3.67-3.52 (m, 6H), 3.51-3.41 (m, 1H), 3.08-2.92 (m, 2H), 1.83-1.72 (m, 2H), 1.42 (s, 9H), 1.38 (s, 9H), 1.30 (m, 2H).

Step C

To a suspension of lithium aluminum hydride (0.136 g, 3.57 mmol) in diethyl ether (20 mL) at 0° C. was added a solution of the title compound from Step B above (1.07 g, 2.98 mmol) in diethyl ether (10 mL) over 30 min. Then, the reaction mixture was stirred at 0° C. for 2 hours. Then, water (0.13 mL), 15% NaOH (0.13 mL) and water (0.39 mL) were sequentially added at 0° C. to the reaction mixture. The crude product was then allowed to warm to room temperature. After 30 min, the solid was filtered and the mother liquor was concentrated under reduced pressure to afford the title compound (0.882 g, 100%).

$^1$H-NMR (400 MHz, DMSO-$d_6$) δ=4.60-4.50 (m, 1H), 3.69-3.56 (m, 2H), 3.56-3.37 (m, 9H), 2.99 (t, 2H), 1.77 (ddt, 2H), 1.39 (s, 9H), 1.30 (dtd, 2H).

Step D

A solution of the title compound from Step C above (0.882 g, 3.05 mmol) in 4 N HCl (5 mL) and dichloromethane (10 mL) was stirred at room temperature for 18 hours. The reaction mixture was concentrated in vacuo to dryness to afford the title compound as a HCl salt (0.680 g, 99%).

$^1$H-NMR (400 MHz, DMSO-$d_6$) δ=8.82 (s, 2H), 4.64-4.55 (m, 1H), 3.62-3.45 (m, 7H), 3.45-3.40 (m, 2H), 3.12 (ddd, 2H), 2.99-2.85 (m, 2H), 1.99-1.85 (m, 2H), 1.75-1.60 (m, 2H).

MS (ESI); m/z=190.1 ($MH^+$).

Preparative Example 64

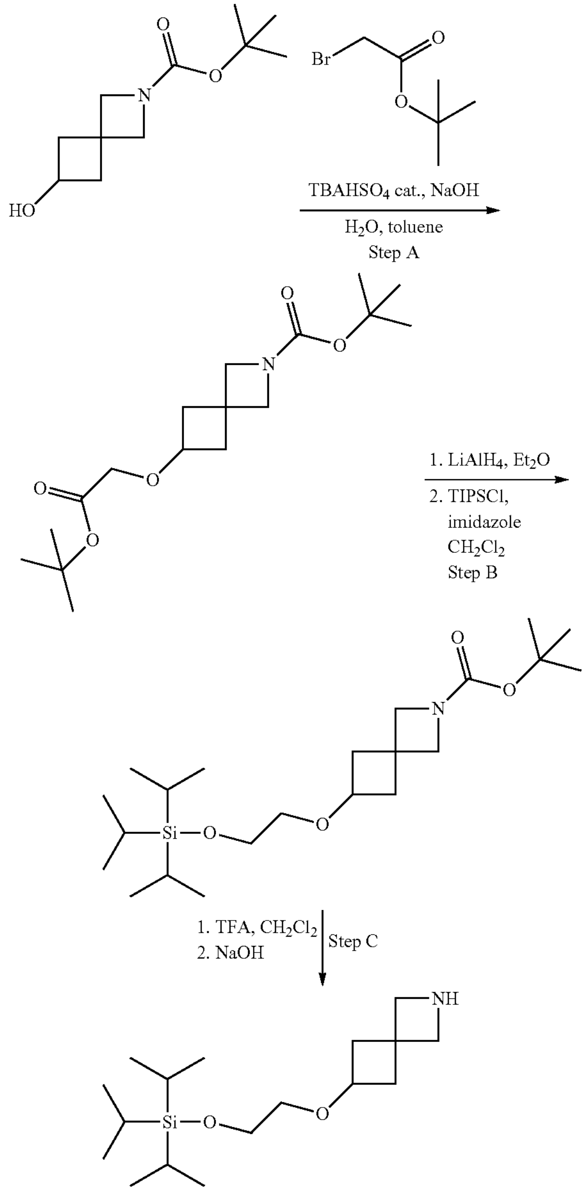

Step A

To a solution of commercially available tert-butyl 6-hydroxy-2-azaspiro[3.3]heptane-2-carboxylate (2.0 g, 9.38 mmol), tetrabutylammonium hydrogen sulfate (159 mg, 0.47 mmol) and tert-butyl 2-bromoacetate (2.74 g, 14.07 mmol) in water (1 mL) and toluene (40 mL) were added over 1 hour a solution of NaOH (13.13 g, 328 mmol) in water (20 mL). Then, the reaction mixture was stirred at room temperature for 18 hours. Water was added and the toluene phase was removed. The aqueous phase was further extracted with toluene. The combined organics were dried over $Na_2SO_4$, filtered and concentrated under reduced pressure. The residue was purified on HP-Sil SNAP cartridges using a Biotage Isolera One purification system employing an EtOAc/n-heptane gradient (2/98->50/50) to afford the title compound (2.80 g, 91%).

$^1$H-NMR (400 MHz, $CDCl_3$) δ=3.94 (p, 1H), 3.88 (s, 2H), 3.86 (d, 4H), 2.48 (ddd, 2H), 2.18 (ddd, 2H), 1.47 (s, 9H), 1.42 (s, 9H).

Step B

To a suspension of lithium aluminum hydride (0.398 g, 10.50 mmol) in diethyl ether (40 mL) at 0° C. was added a solution of the title compound from Step A above (2.75 g, 8.40 mmol) in diethyl ether (20 mL) over 30 minutes. Then, the reaction mixture was stirred at 0° C. for 2 hours. Then, water (0.4 mL), 15% NaOH (0.4 mL) and water (1.2 mL) were sequentially added at 0° C. to the reaction mixture. The crude product was then allowed to warm to room temperature. After 30 minutes, the solid was filtered and the mother liquor was concentrated under reduced pressure to afford the alcohol. Then, dichloromethane (40 mL) was added and the reaction mixture was cooled to 0° C. Imidazole (1.14 g, 16.80 mmol), followed by triisopropylsilyl chloride (2.67 mL, 12.60 mmol) were added and the reaction mixture was allowed to warm to room temperature. After 2 hours at room temperature, 1N NaOH was added and the aqueous phase was extracted with dichloromethane several times. The combined organics were dried over $Na_2SO_4$, filtered and dried under reduced pressure. The residue was purified on HP-Sil SNAP cartridges using a Biotage Isolera One purification system employing an EtOAc/n-heptane gradient (2/98->30/70) to afford the title compound (2.50 g, 72% over two steps).

$^1$H-NMR (400 MHz, $CDCl_3$) δ=3.96-3.83 (m, 5H), 3.79 (t, 2H), 3.42 (t, 2H), 2.53-2.40 (m, 2H), 2.08 (ddd, 2H), 1.42 (s, 9H), 1.16-1.00 (m, 21H).

Step C

To a solution of the title compound from Step B above (2.5 g, 6.04 mmol) in dichloromethane (15 mL) was added at 0° C. trifluoroacetic acid (4.66 mL, 60.4 mmol). Then, the reaction mixture was stirred at room temperature for 4 hours. The reaction mixture was carefully made alkaline to pH 10 using 1 N NaOH and the aqueous phase was extracted several times with dichloromethane. The combined organics were dried over $Na_2SO_4$, filtered and dried to afford the title compound (1.61 g, 85%).

$^1$H-NMR (400 MHz, DMSO-$d_6$) δ=3.81 (q, 1H), 3.71 (t, 2H), 3.45 (s, 2H), 3.40 (s, 2H), 3.32 (t, 2H), 2.37 (ddd, 2H), 1.94-1.83 (m, 2H), 1.11-0.88 (m, 21H).

Preparative Example 65

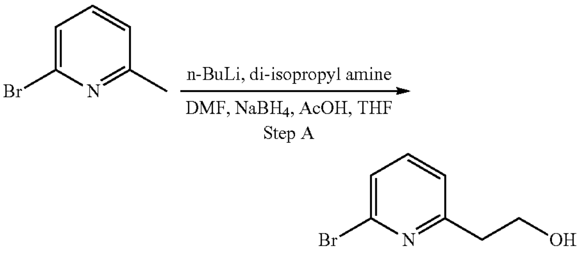

Step A

To a stirred solution of n-butyllithium (1 L, 1.6 M in hexane) in tetrahydrofuran was added diisopropylamine (600 mL) dropwise through a dropping funnel at −10° C. under an $N_2$ atmosphere for 30 minutes. The ice bath was removed and the reaction mixture was cooled to −78° C. A solution of 2-bromo-6-methyl pyridine (100 g, 0.58 mol) in THF (1.6 L) was added and the color changed pale yellow to dark brown. The mixture was stirred for 1 hour at the same temperature and then N,N'-dimethylformamide (200 mL, 2.147 mol) was added. After 60 minutes at −78° C., methanol (1.6 L) and acetic acid (160 mL, 2.49 mol) were added. Then sodium borohydride (28 g, 0.557 mol) was added at −78° C. and the mixture was allowed to come to room temperature and was stirred overnight. The color changed dark brown to yellow color. The reaction mixture was diluted with ethyl acetate (3.0 L) and 10% citric acid solution (1.5 L) and was extracted with EtOAc (2×2 L), and washed with brine (1 L). The combined organic extracts were dried over $Na_2SO_4$ and solvents were removed under reduced pressure. The residue was purified by column chromatography on silica gel (60-120 mesh) using ethyl acetate/n-heptane (30/70) to afford the title compound as a pale yellow oil (90 g, 76.5%).

$^1$H-NMR (400 MHz, $CDCl_3$): δ=7.43 (t, 1H), 7.34 (d, 1H), 7.16 (d, 1H), 4.02 (q, 2H), 3.09 (t, 1H), 3.01 (t, 2H).

Preparative Example 66

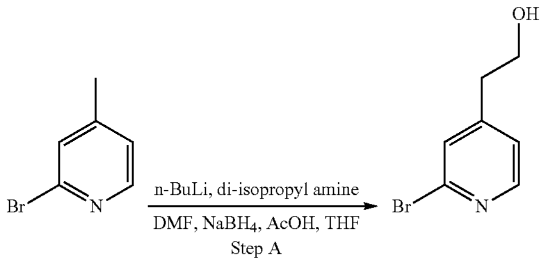

To a stirred solution of diisopropylamine in THF (30 mL) was added n-butyllithium (7.3 mL, 1.6M in hexane) at 0° C. dropwise. The solution was stirred at 0° C. for 20 min, then cooled to −70° C. Then 2-bromo-4-methylpyridine (2 g, 11.7 mmol) was added slowly at −70° C. over a period of 5 minutes. During addition, the reaction mixture changed to a red colored solution, and the reaction mixture was kept stirring at −70° C. for another 25 minutes. Then N,N'-dimethylformamide (0.939 g, 12.8 mmol) was added slowly, and the reaction mixture was stirred for another 15 minutes. The reaction mixture was quenched with methanol (5 mL). Then sodium borohydride (1.g, 29 mmol) was added in one portion, followed by acetic acid (0.350 g, 5.8 mmol) and the reaction mixture was added overnight. The reaction mixture was concentrated. The residue was dissolved in ethyl acetate (200 mL) and washed with water, citric acid solution and brine solution. The solvent was evaporated and the crude product was purified on silica gel column using ethyl acetate/n-heptane (50/50) to afford the title compound (0.580 g 25%) as yellow oil.

$^1$H-NMR (400 MHz, $CDCl_3$) δ=8.28 (d, 1H), 7.42 (s, 1H), 7.28 (s, 1H), 7.17 (dd, 1H), 3.94 (dd, 2H), 2.86 (t, 2H).

Example 1

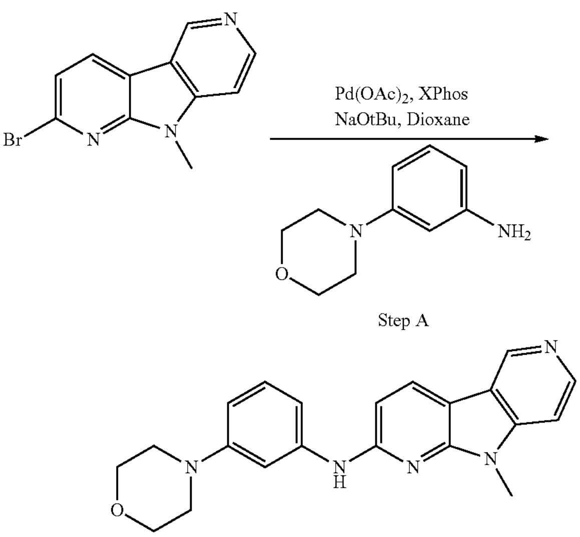

Step A

An oven dried Schlenk flask was evacuated and back filled with argon gas. The procedure was repeated 3-4 times and the flask was cooled to room temperature. Then dicyclohexyl-(2',4',6'-triisopropyl-[1,1'-biphenyl]-2-yl)phosphine (0.027 g, 0.057 mmol) and palladium(II)-acetate (0.0043 g, 0.019 mmol) were added and the flask was flushed with argon). 1,4-Dioxane (4 mL) was added by syringe and the mixture was heated at 110° C. for 1 minute to become a clear red solution, indicating the formation of the Pd-catalyst. Then commercially available 3-morpholinoaniline (0.04 g, 0.225 mmol), the title compound from Preparative Example 1 (0.05 g, 0.191 mmol) and sodium tert.-butoxide (0.06 g, 0.630 mmol) were added under an argon atmosphere. The reaction mixture was heated at 110° C. in a sand-bath for 4 h, cooled to room temperature and the solvents were removed under reduced pressure. The residue was purified on HP-Sil SNAP cartridges using a Biotage Isolera One purification system employing a dichloromethane/methanol gradient (100/0->90/10) to afford the title compound as a white solid (0.02 g, 31%).

1H NMR (400 MHz, DMSO-$d_6$) δ=9.35 (s, 1H), 9.14 (s, 1H), 8.40 (d, 1H), 8.33 (d, 1H), 7.77 (s, 1H), 7.56 (d, 1H), 7.18-7.14 (m, 2H), 6.79 (d, 1H), 6.58-6.56 (m, 1H), 3.88 (s, 3H), 3.79-3.76 (m, 4H), 3.17-3.15 (m, 4H).

MS (ESI); m/z=360.33 ($MH^+$).

Examples 2 to 55

Following the Pd-coupling procedure as described in Example 1, except using the bromo-derivatives and amines indicated in the table below, the following compounds were prepared. The ligand dicyclohexyl-(2',4',6'-triisopropyl-[1,1'-biphenyl]-2-yl)phosphine (XPhos) can be replaced by 4,5-bis(diphenylphosphino)-9,9-dimethylxanthene (XantPhos) or 2-(dicyclohexylphosphino)3,6-dimethoxy-2',4',6'-triisopropyl-1,1'-biphenyl (BrettPhos) and the base sodium tert.-butoxide can be replaced by cesium carbonate. For Examples 29 and 39 lithium-bis(trimethylsilyl)amide was used as a base.

TABLE 4

| Bromo derivative | Amine | Product Example | 1. Yield<br>2. $^1$H-NMR<br>3. $MH^+$ (ESI) |
|---|---|---|---|
| 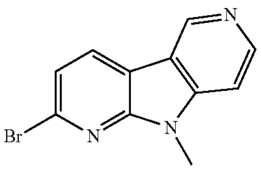 | 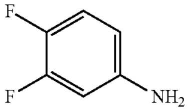 | 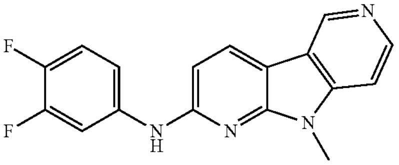<br>2 | 1. 10%<br>2. $^1$H-NMR (400 MHz, DMSO-$d_6$) δ = 9.68 (s, 1H), 9.17 (s, 1H), 8.44-3.37 (m, 2H), 8.26-8.20 (m, 1H), 7.59-7.58 (m, 1H), 7.51-7.34 (m, 2H), 6.78 (d, 1H), 3.89 (s, 3H)<br>3. 311.60 |
| 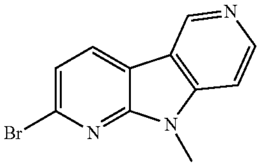 | 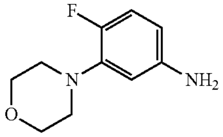 [SMILES: Nc1ccc(F)c(N2CCOCC2)c1] | 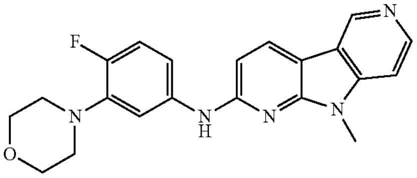<br>3 | 1. 30%<br>2. $^1$H NMR (400 MHz, DMSO-$d_6$) δ = 9.44 (s, 1H), 9.15 (s, 1H), 8.49-8.23 (m, 2H), 7.91 (dd, 1H), 7.58 (d, 1H), 7.36-7.25 (m, 1H), 7.11 (dd, 1H), 6.77 (d, 1H), 3.90 (s, 3H), 3.85-3.74 (m, 4H), 3.17-3.03 (m, 4H)<br>3. 378.07 |
| 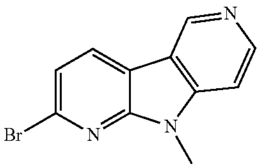 | 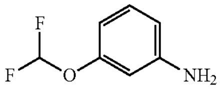 | 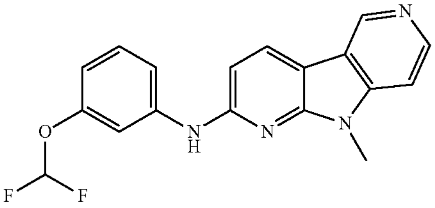<br>4 | 1. 40%<br>2. $^1$H NMR (400 MHz, $CD_3OD$) δ = 9.05 (s, 1H), 8.37 (d, 1H), 8.28 (d, 1H), 8.19 (s, 1H), 7.55 (dd, 1H), 7.48-7.39 (m, 1H), 7.31 (t, 1H), 6.96 (t, 1H), 6.78 (d, 1H), 6.75-6.70 (m, 1H), 3.95 (s, 3H)<br>3. 341.39 |
| 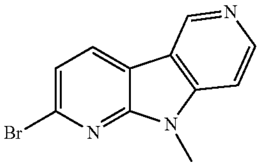 | 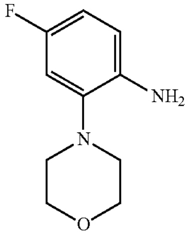 | 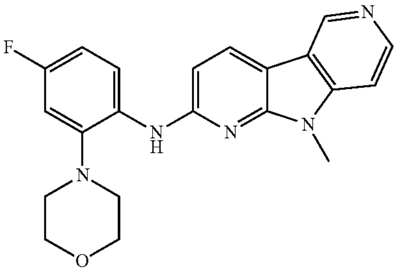<br>5 | 1. 25%<br>2. $^1$H NMR (400 MHz, DMSO-$d_6$) δ = 9.50 (s, 1H), 8.77 (s, 1H), 8.64 (d, 1H), 8.51 (d, 1H), 8.13 (d, 1H), 8.10-8.01 (m, 1H), 7.11-6.87 (m, 3H), 3.95 (s, 3H), 3.75-3.65 (m, 4H), 2.88 (m, 4H)<br>3. 378.48 |
| 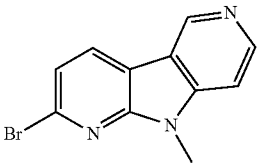 | 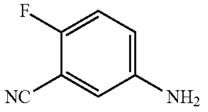 | 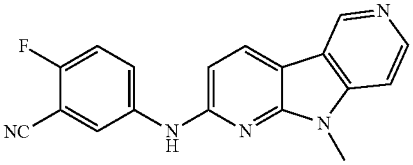<br>6 | 1. 5%<br>2. $^1$H NMR (400 MHz, DMSO-$d_6$) δ = 9.67 (s, 1H), 9.20 (s, 1H), 8.58-8.28 (m, 3H), 8.21-8.02 (m, 1H), 7.71-7.55 (m, 1H), 7.56-7.40 (m, 1H), 7.01-6.65 (m, 1H), 3.91 (s, 3H)<br>3. 318.27 |
| 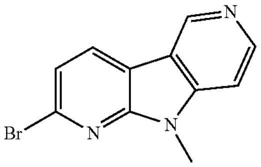 | 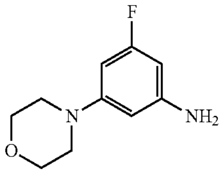 [SMILES: Nc1cc(F)cc(N2CCOCC2)c1] | 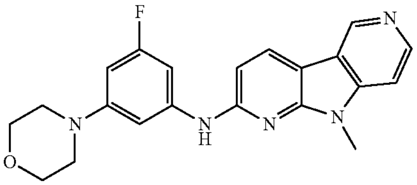<br>7 | 1. 11%<br>2. $^1$H NMR (400 MHz, DMSO-$d_6$) δ = 9.53 (s, 1H), 9.16 (s, 1H), 8.42 (d, 1H), 8.36 (d, 1H), 7.59 (d, 1H), 7.35 (t, 1H), 7.24 (dt, 1H), 6.79 (d, 1H), 6.39 (dt, 1H), 3.88 (s, 3H), 3.75 (dd, 4H), 3.22-2.99 (m, 4H)<br>3. 378.36 |

TABLE 4-continued

| Bromo derivative | Amine | Product Example | 1. Yield<br>2. $^1$H-NMR<br>3. $MH^+$ (ESI) |
|---|---|---|---|
| 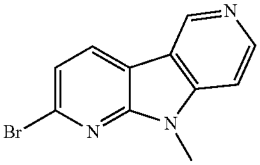 | 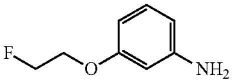 | 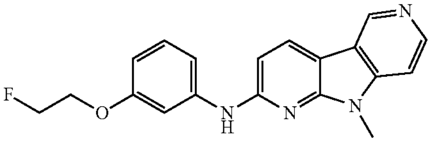<br>8 | 1. 14%<br>2. $^1$H NMR (400 MHz, DMSO-$d_6$) δ = 9.48 (s, 1H), 9.17 (s, 1H), 8.50-8.27 (m, 2H), 7.79 (s, 1H), 7.59 (d, 1H), 7.42-7.32 (m, 1H), 7.25 (t, 1H), 6.82 (d, 1H), 6.62-6.46 (m, 1H), 4.92-4.78 (m, 1H), 4.78-4.69 (m, 1H), 4.39-4.29 (m, 1H), 4.29-4.20 (m, 1H), 3.91 (s, 3H)<br>3. 337.07 |
| 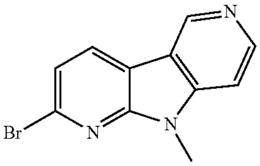 | 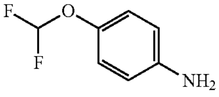 | 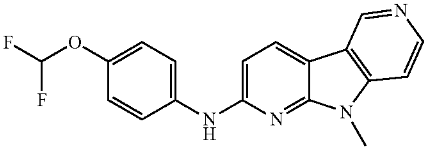<br>9 | 1. 30%<br>2. $^1$H NMR (400 MHz, DMSO-$d_6$) δ = 9.53 (s, 1H), 9.16 (s, 1H), 8.48-8.25 (m, 2H), 8.03-7.88 (m, 2H), 7.59 (d, 1H), 7.19 (d, 2H), 7.06 (t, 1H), 6.80 (d, 1H), 3.90 (s, 3H)<br>3. 341.04 |
| 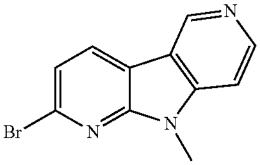 | 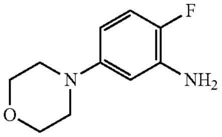 [SMILES: Nc1cc(N2CCOCC2)ccc1F] | 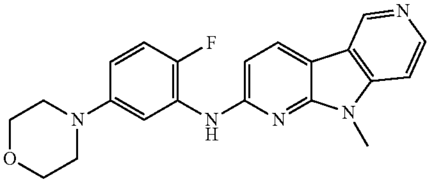<br>10 | 1. 48%<br>2. $^1$H NMR (400 MHz, DMSO-$d_6$) δ = 9.17 (s, 1H), 9.07-8.92 (m, 1H), 8.43 (d, 1H), 8.38 (d, 1H), 8.28 (dd, 1H), 7.67-7.53 (m, 1H), 7.13 (dd, 1H), 7.02 (d, 1H), 6.66-6.53 (m, 1H), 3.86 (s, 3H), 3.83-3.72 (m, 4H), 3.19-3.09 (m, 4H)<br>3. 378.07 |
| 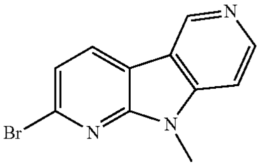 | 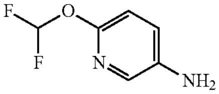 | 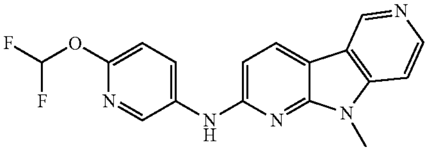<br>11 | 1. 46%<br>2. $^1$H NMR (400 MHz, DMSO-$d_6$) δ = 9.67 (s, 1H), 9.19 (s, 1H), 8.85 (d, 1H), 8.53-8.30 (m, 3H), 7.66 (t, 1H), 7.60 (d, 1H), 7.12 (d, 1H), 6.81 (d, 1H), 3.89 (s, 3H)<br>3. 342.03 |
| 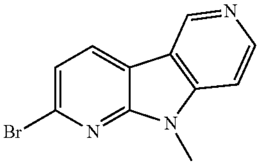 | 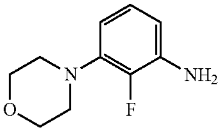 [SMILES: Nc1cccc(N2CCOCC2)c1F] | 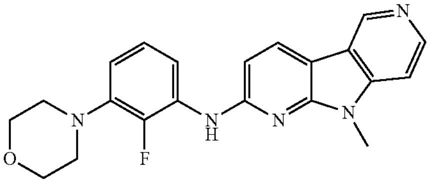<br>12 | 1. 21%<br>2. $^1$H NMR (400 MHz, DMSO-$d_6$) δ = 9.16 (s, 1H), 9.06-8.93 (m, 1H), 8.48-8.30 (m, 2H), 8.04-7.89 (m, 1H), 7.56 (d, 1H), 7.16-7.05 (m, 1H), 6.94 (d, 1H), 6.82-6.66 (m, 1H), 3.88-3.65 (m, 7H), 3.12-2.93 (m, 4H)<br>3. 378.07 |
| 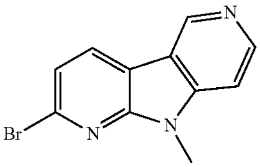 | 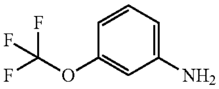 | 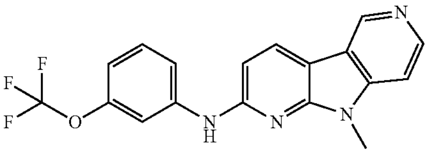<br>13 | 1. 27%<br>2. $^1$H NMR (400 MHz, DMSO-$d_6$) δ = 9.80 (s, 1H), 9.20 (s, 1H), 8.56-8.18 (m, 3H), 7.71-7.55 (m, 2H), 7.44 (t, 1H), 6.98-6.76 (m, 2H), 3.90 (s, 3H)<br>3. 359.03 |

TABLE 4-continued
| Bromo derivative | Amine | Product Example | 1. Yield 2. $^1$H-NMR 3. $MH^+$ (ESI) |
|---|---|---|---|
| 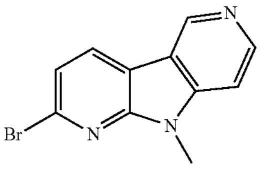 | 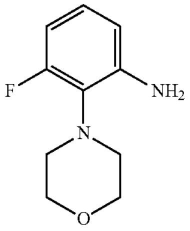 | 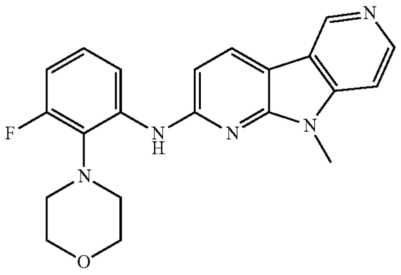 14 | 1. 37% 2. $^1$H NMR (400 MHz, DMSO-$d_6$) δ = 9.44 (s, 1H), 9.15 (s, 1H), 8.42 (d, 1H), 8.35 (d, 1H), 7.95-7.84 (m, 1H), 7.58 (d, 1H), 7.38-7.24 (m, 1H), 7.17-7.00 (m, 1H), 6.78 (d, 1H), 3.90 (s, 3H), 3.87-3.73 (m, 4H), 3.16-3.02 (m, 4H) 3. 378.07 |
| 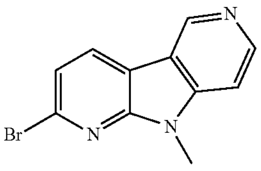 | 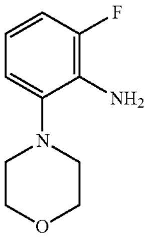 [SMILES: Nc1c(F)cccc1N1CCOCC1] | 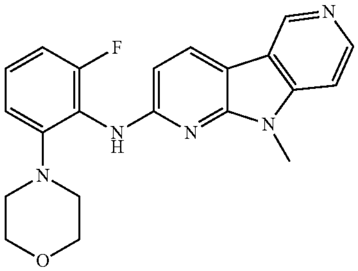 15 | 1. 16% 2. $^1$H NMR (400 MHz, DMSO-$d_6$) δ = 9.12 (s, 1H), 8.45-8.18 (m, 3H), 7.52 (d, 1H), 7.33-7.14 (m, 1H), 7.09-6.80 (m, 2H), 6.61 (s, 1H), 3.72 (s, 3H), 3.53 (m, 4H), 3.04-2.81 (m, 4H) 3. 378.02 |
| 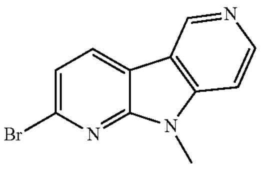 | 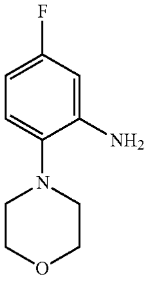 [SMILES: Nc1cc(F)ccc1N1CCOCC1] | 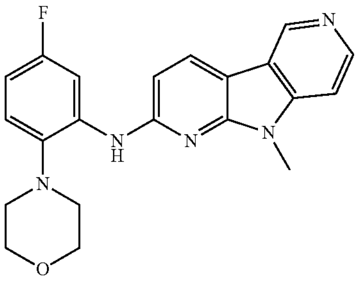 16 | 1. 26% 2. $^1$H NMR (400 MHz, DMSO-$d_6$) δ = 9.21 (s, 1H), 8.70-8.52 (m, 2H), 8.52-8.37 (m, 2H), 7.66-7.55 (m, 1H), 7.28 (dd, 1H), 7.13 (d, 1H), 6.79 (td, 1H), 3.98-3.77 (m, 7H), 2.93-2.71 (m, 4H) 3. 378.08 |
| 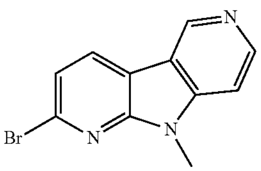 | 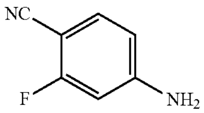 | 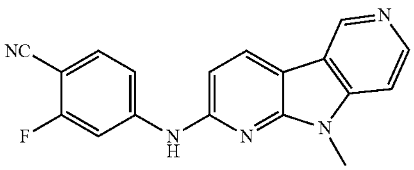 17 | 1. 16% 2. $^1$H NMR (400 MHz, DMSO-$d_6$) δ = 10.30 (s, 1H), 9.26 (s, 1H), 8.52 (d, 2H), 8.39-8.23 (m, 1H), 7.80 (t, 1H), 7.73-7.53 (m, 2H), 6.93 (d, 1H), 3.94 (s, 3H) 3. 318.00 |
| 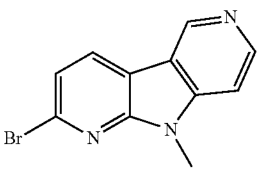 | 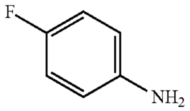 | 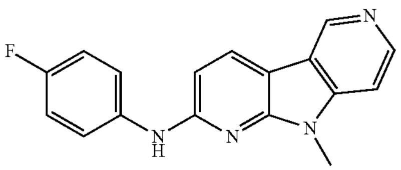 18 | 1. 16% 2. $^1$H NMR (400 MHz, DMSO-$d_6$) δ = 9.47 (s, 1H), 9.16 (s, 1H), 8.49-8.27 (m, 2H), 8.06-7.82 (m, 2H), 7.58 (d, 1H), 7.19 (t, 2H), 6.78 (d, 1H), 3.89 (s, 3H) 3. 292.97 |

TABLE 4-continued

| Bromo derivative | Amine | Product Example | 1. Yield<br>2. $^1$H-NMR<br>3. $MH^+$ (ESI) |
|---|---|---|---|
| 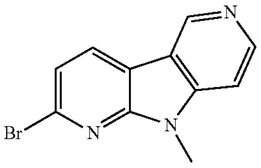 | 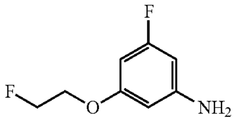 | 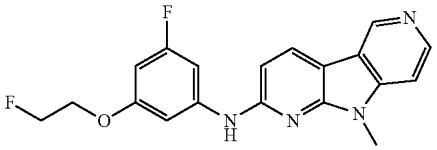<br>19 | 1. 14%<br>2. $^1$H NMR (400 MHz, DMSO-$d_6$) δ = 9.66 (s, 1H), 9.17 (s, 1H), 8.51-8.33 (m, 2H), 7.58 (d, 1H), 7.47 (d, 1H), 7.35 (s, 1H), 6.80 (d, 1H), 6.42 (d, 1H), 4.90-4.76 (m, 1H), 4.77-4.64 (m, 1H), 4.40-4.28 (m, 1H), 4.29-4.17 (m, 1H), 3.89 (s, 3H)<br>3. 355.00 |
| 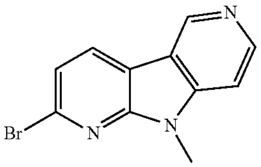 | 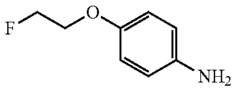 [SMILES: Nc1ccc(OCCF)cc1] | 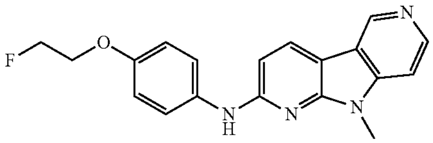<br>20 | 1. 22%<br>2. $^1$H NMR (400 MHz, DMSO-$d_6$) δ = 9.26 (s, 1H), 9.11 (s, 1H), 8.38 (d, 1H), 8.29 (d, 1H), 7.87-7.70 (m, 2H), 7.53 (d, 1H), 7.03-6.91 (m, 2H), 6.72 (d, 1H), 4.86-4.72 (m, 1H), 4.73-4.62 (m, 1H), 4.30-4.20 (m, 1H), 4.22-4.12 (m, 1H), 3.85 (s, 3H)<br>3. 337.02 |
| 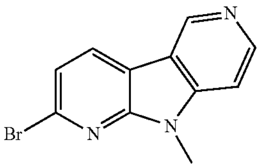 | 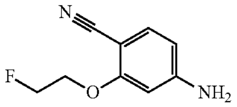 [SMILES: N#Cc1ccc(N)cc1OCCF] | 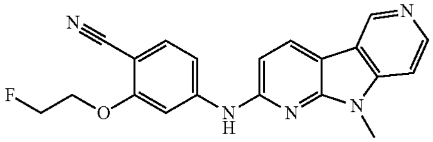<br>21 | 1. 24%<br>2. $^1$H NMR (400 MHz, DMSO-$d_6$) δ = 10.03 (s, 1H), 9.21 (s, 1H), 8.55-8.35 (m, 2H), 8.25 (s, 1H), 7.72-7.51 (m, 2H), 7.29 (d, 1H), 6.89 (d, 1H), 4.98-4.83 (m, 1H), 4.83-4.67 (m, 1H), 4.62-4.47 (m, 1H), 4.48-4.38 (m, 1H), 3.92 (s, 3H).<br>3. 362.01 |
| 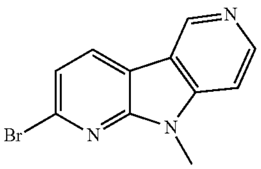 | 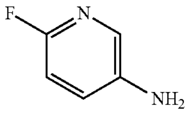 | 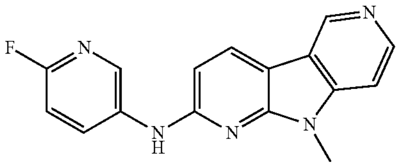<br>22 | 1. 60%<br>2. $^1$H NMR (400 MHz, DMSO-$d_6$) δ = 9.68 (s, 1H), 9.17 (s, 1H), 8.44-3.37 (m, 2H), 8.26-8.20 (m, 1H), 7.59-7.58 (m, 1H), 7.51-7.34 (m, 2H), 6.78 (d, 1H), 3.89 (s, 3H)<br>3. 293.91 |
| 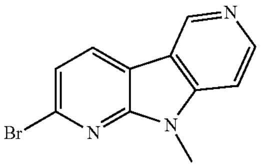 | 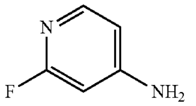 | 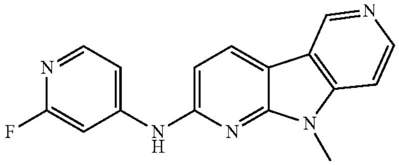<br>23 | 1. 75%<br>2. $^1$H NMR (400 MHz, DMSO-$d_6$) δ = 10.26 (s, 1H), 9.23 (s, 1H), 8.51-8.46 (m, 2H), 8.02 (d, 1H), 7.82 (s, 1H), 7.62 (d, 1H), 7.53 (d, 1H), 6.93 (d, 1H), 3.89 (s, 3H)<br>3. 362.01 |
| 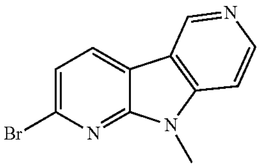 | 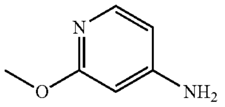 | 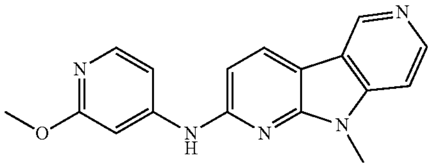<br>24 | 1. 45%<br>2. $^1$H NMR (400 MHz, DMSO-$d_6$) δ = 10.42 (s, 1H), 9.21 (s, 1H), 8.54-8.38 (m, 4H), 7.78 (s, 1H), 7.68-7.56 (m, 1H), 7.31 (d, 1H), 3.92 (s, 3H), 3.89 (s, 3H) |

TABLE 4-continued

| Bromo derivative | Amine | Product Example | 1. Yield<br>2. $^1$H-NMR<br>3. $MH^+$ (ESI) |
|---|---|---|---|
| 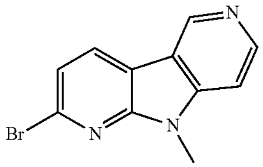 | 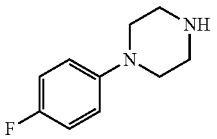 [SMILES: Fc1ccc(N2CCNCC2)cc1] | 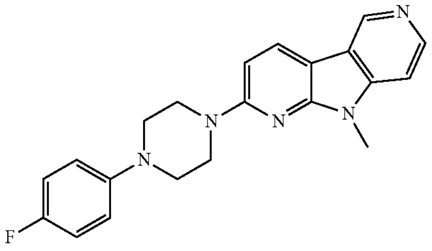<br>25 | 1. 36%<br>2. $^1$H-NMR (400 MHz, DMSO-$d_6$) δ = 9.13 (s, 1H), 8.46-8.25 (m, 2H), 7.53 (d, 1H), 7.16-6.98 (m, 4H), 6.90 (d, 1H), 3.90-3.76 (m, 7H), 3.24 (t, 4H).<br>362.17 |
| 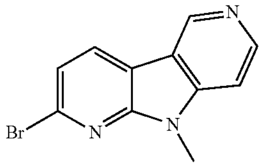 | 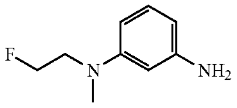 | 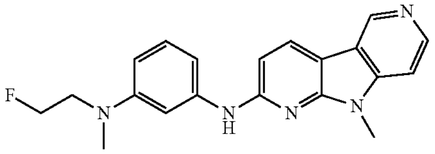<br>26 | 1. 37%<br>2. $^1$H NMR (400 MHz, DMSO-$d_6$) δ = 9.27 (s, 1H), 9.12 (s, 1H), 8.39 (s, 1H), 8.31 (d, 1H), 7.62 (t, 1H), 7.55 (d, 1H), 7.11 (t, 1H), 6.99 (d, 1H), 6.79 (d, 1H), 6.36 (d, 1H), 4.69 (t, 1H), 4.57 (t, 1H), 3.87 (s, 3H), 3.72 (t, 1H), 3.66 (t, 1H), 3.00 (s, 3H).<br>3. 350.17 |
| 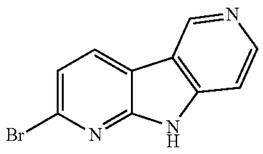 [SMILES: Brc1ccc2c(n1)[nH]c1ccncc12] | 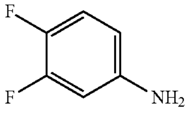 | 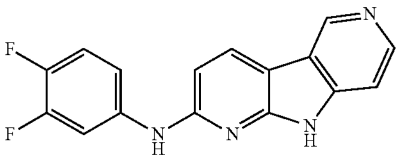<br>27 | 1. 59%<br>2. $^1$H-NMR (400 MHz, DMSO-$d_6$) δ 12.05 (br-s, 1H), 9.59 (s, 1H), 9.14 (s, 1H), 8.37-8.25 (m, 3H), 7.38-7.34 (m, 3H), 6.75 (d, 1H).<br>3. 297.01 |
| 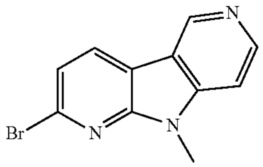 | 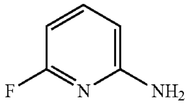 | 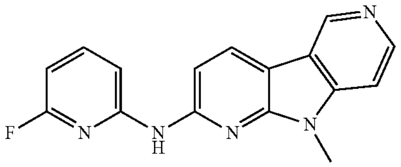<br>28 | 1. 46%<br>2. $^1$H-NMR (400 MHz, DMSO-$d_6$) δ = 10.27 (s, 1H), 9.21 (s, 1H), 8.59-8.32 (m, 2H), 8.20 (dd, 1H), 7.93 (q, 1H), 7.62 (dd, 1H), 7.37 (d, 1H), 6.64 (dd, 1H), 3.92 (s, 3H)<br>3. 294.13 |
| 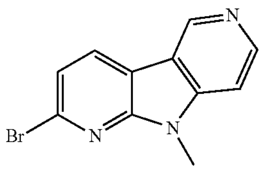 | 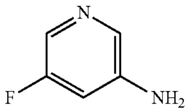 | 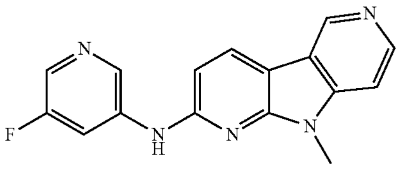<br>29 | 1. 55%<br>2. $^1$H-NMR (400 MHz, DMSO-$d_6$) δ = 9.96 (s, 1H), 9.21 (s, 1H), 8.70 (s, 1H), 8.56 (d, 1H), 8.53-8.35 (m, 2H), 8.13 (d, 1H), 7.62 (d, 1H), 6.87 (d, 1H), 3.91 (s, 3H)<br>3. 294.13 |
| 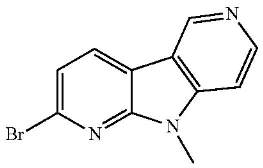 | 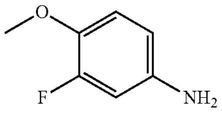 | 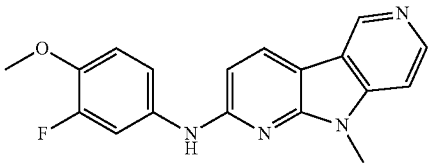<br>30 | 1. 76%<br>2. $^1$H-NMR (400 MHz, DMSO-$d_6$) δ = 9.42 (s, 1H), 9.14 (s, 1H), 8.40 (d, 1H), 8.33 (d, 1H), 7.96 (d, 1H), 7.56 (d, 1H), 7.48 (d, 1H), 7.15 (t, 1H), 6.74 (d, 1H), 3.87 (s, 3H), 3.82 (s, 3H)<br>3. 323.13 |

TABLE 4-continued

| Bromo derivative | Amine | Product<br>Example | 1. Yield<br>2. $^1$H-NMR<br>3. $MH^+$ (ESI) |
|---|---|---|---|
| 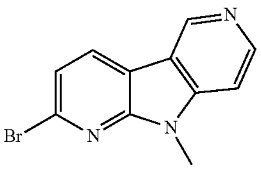 | 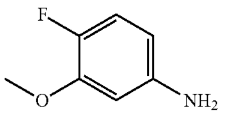 | 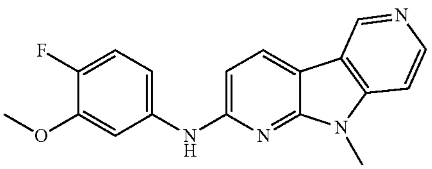<br>31 | 1. 68%<br>2. $^1$H-NMR (400 MHz, DMSO-$d_6$) $\delta$ = 9.56 (s, 1H), 9.21 (s, 1H), 8.45 (d, 1H), 8.37 (d, 1H), 8.08 (dd, 1H), 7.69 (d, 1H), 7.33-7.00 (m, 2H), 6.81 (d, 1H), 3.91 (s, 6H)<br>3. 323.12 |
| 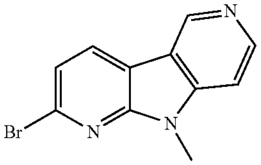 | 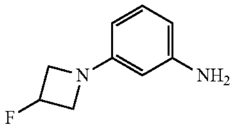 [SMILES: Nc1cccc(N2CC(F)C2)c1] | 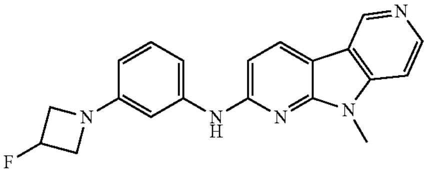<br>32 | 1. 21%<br>2. $^1$H-NMR (400 MHz, DMSO-$d_6$) $\delta$ = 9.35 (s, 1H), 9.13 (s, 1H), 8.40 (d, 1H), 8.32 (d, 1H), 7.56 (d, 1H), 7.49 (t, 1H), 7.12 (t, 1H), 7.06-6.94 (m, 1H), 6.78 (d, 1H), 6.09 (dd, 1H), 5.68-5.33 (m, 1H), 4.30-4.05 (m, 2H), 3.99-3.90 (m, 2H), 3.88 (s, 3H)<br>3. 348.13 |
| 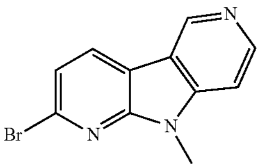 | 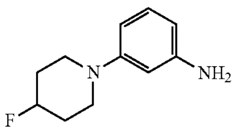 [SMILES: Nc1cccc(N2CCC(F)CC2)c1] | 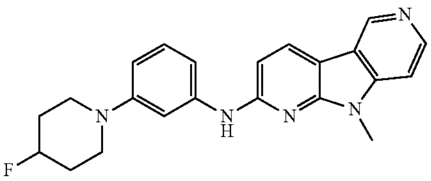<br>33 | 1. 77%<br>2. $^1$H-NMR (400 MHz, DMSO-$d_6$) $\delta$ = 9.32 (s, 1H), 9.14 (s, 1H), 8.40 (d, 1H), 8.33 (d, 1H), 7.82 (d, 1H), 7.56 (d, 1H), 7.15 (d, 2H), 6.79 (d, 1H), 6.67-6.51 (m, 1H), 5.02-4.70 (m, 1H), 3.88 (s, 3H), 3.53-3.37 (m, 2H), 3.24-3.07 (m, 2H), 2.14-1.70 (m, 4H)<br>3. 376.18 |
| 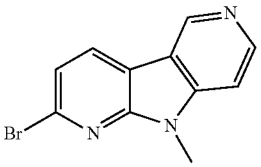 | 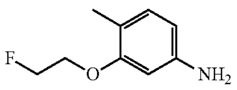 | 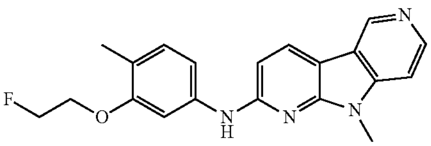<br>34 | 1. 12%<br>2. $^1$H-NMR (400 MHz, DMSO-$d_6$) $\delta$ = 9.19 (s, 1H), 9.10 (s, 1H), 8.38 (d, 1H), 8.28 (d, 1H), 7.69 (dd, 1H), 7.62 (d, 1H), 7.53 (d, 1H), 6.95 (d, 1H), 6.71 (d, 1H), 4.89-4.75 (m, 1H), 4.75-4.57 (m, 1H), 4.32-4.21 (m, 1H), 4.21-4.09 (m, 1H), 3.85 (s, 3H), 2.21 (s, 3H)<br>3. 351.14 |
| 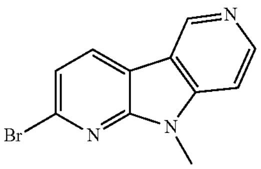 | 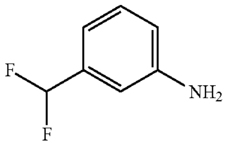 | 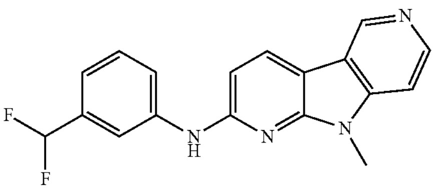<br>35 | 1. 48%<br>2. $^1$H-NMR (400 MHz, DMSO-$d_6$) $\delta$ = 9.67 (s, 1H), 9.16 (s, 1H), 8.46-8.11 (m, 3H), 7.97-7.77 (m, 1H), 7.57 (d, 1H), 7.46 (t, 1H), 7.11 (d, 1H), 7.05 (t, 1H), 6.82 (d, 1H), 3.89 (s, 3H)<br>3. 325.14 |

TABLE 4-continued

| Bromo derivative | Amine | Product<br>Example | 1. Yield<br>2. $^1$H-NMR<br>3. $MH^+$ (ESI) |
|---|---|---|---|
| 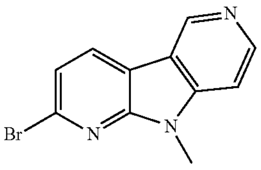 | 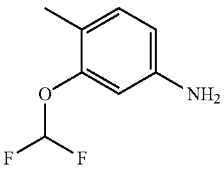 | 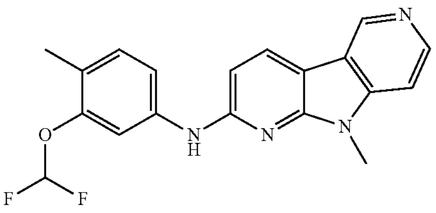<br>36 | 1. 15%<br>2. $^1$H-NMR (400 MHz, DMSO-$d_6$) δ = 9.46 (s, 1H), 9.16 (s, 1H), 8.39 (dd, 2H), 7.95-7.73 (m, 2H), 7.59 (d, 1H), 7.14 (d, 1H), 7.10 (t, 1H), 6.79 (d, 1H), 3.90 (s, 3H), 2.29 (s, 3H)<br>2. 355.15 |
| 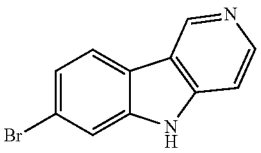 [SMILES: Brc1ccc2c(c1)[nH]c1ccncc12] | 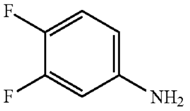 | 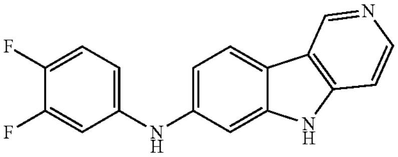<br>37 | 1. 45%<br>2. $^1$H-NMR (400 MHz, DMSO-$d_6$) δ = 11.51 (s, 1H), 9.18 (s, 1H), 8.56 (s, 1H), 8.33 (s, 1H), 8.06 (d, 1H), 7.40 (d, 1H), 7.32 (q, 1H), 7.22 (s, 1H), 7.12 (ddd, 1H), 7.05-6.86 (m, 2H)<br>3. 296.18 |
| 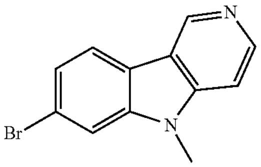 | 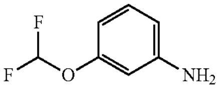 | 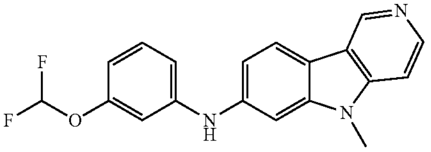<br>38 | 1. 24%<br>2. $^1$H-NMR (400 MHz, $CD_3OD$) δ = 8.99 (s, 1H), 8.29 (s, 1H), 7.95 (d, 1H), 7.37 (d, 1H), 7.24 (t, 1H), 7.18 (d, 1H), 7.11-6.99 (m, 2H), 6.99-6.90 (m, 1H), 6.78 (t, 1H), 6.71-6.45 (m, 1H), 3.71 (s, 3H)<br>3. 340.17 |
| 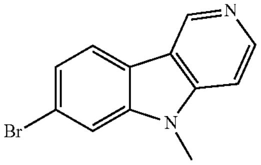 | 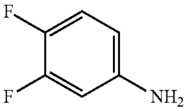 | 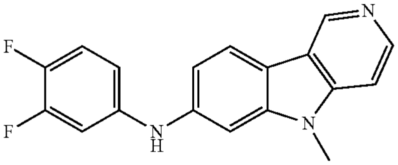<br>39 | 1. 43%<br>2. $^1$H-NMR (400 MHz, DMSO-$d_6$) δ = 9.19 (s, 1H), 8.61 (s, 1H), 8.40 (d, 1H), 8.10 (d, 1H), 7.54 (d, 1H), 7.43-7.24 (m, 2H), 7.16 (ddd, 1H), 7.09-6.90 (m, 2H), 3.82 (s, 3H)<br>3. 310.18 |
| 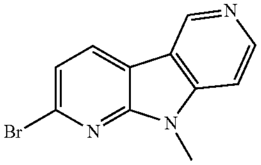 | 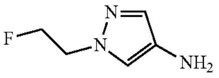 | 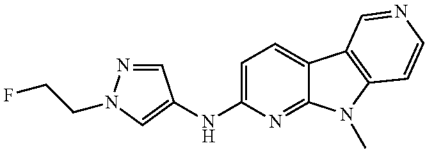<br>40 | 1. 25%<br>2. $^1$H-NMR (400 MHz, DMSO-$d_6$) δ = 9.37 (s, 1H), 9.12 (s, 1H), 8.39 (d, 1H), 8.27 (d, 2H), 7.67 (s, 1H), 7.57 (d, 1H), 6.66 (d, 1H), 4.87 (t, 1H), 4.75 (t, 1H), 4.51 (t, 1H), 4.44 (t, 1H), 3.91 (s, 3H)<br>3. 311.20 |
| 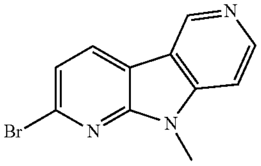 | 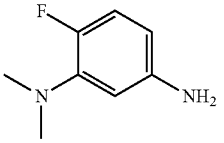 | 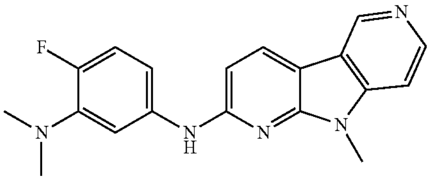<br>41 | 1. 98%<br>2. $^1$H NMR (400 MHz, DMSO-$d_6$) δ = 9.38 (s, 1H), 9.15 (s, 1H), 8.41 (d, 1H), 8.33 (d, 1H), 7.85-7.82 (m, 1H), 7.56 (d, 1H), 7.24-7.20 (m, 1H), 7.08-7.02 (m, 1H), 6.77 (d, 1H), 3.90 (s, 3H), 2.85 (s, 6H) |

TABLE 4-continued

| Bromo derivative | Amine | Product Example | 1. Yield 2. $^1$H-NMR 3. $MH^+$ (ESI) |
|---|---|---|---|
| 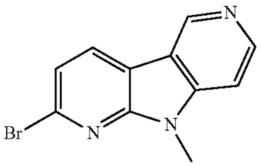 | 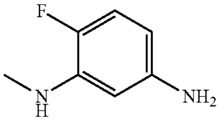 | 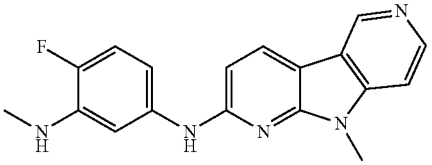 42 | 1. 82% 2. $^1$H NMR (400 MHz, DMSO-$d_6$) δ = 9.28 (s, 1H), 9.12 (s, 1H), 8.40 (d, 1H), 8.30 (d, 1H), 7.55 (d, 1H), 7.54-7.49 (m, 1H), 6.97-6.87 (m, 2H), 6.74 (d, 1H), 5.51-5.48 (br-s, 1H), 3.87 (s, 3H), 2.80 (d, 3H) |
| 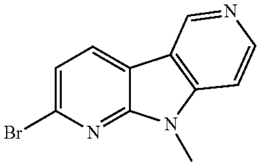 | 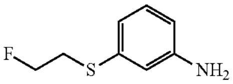 | 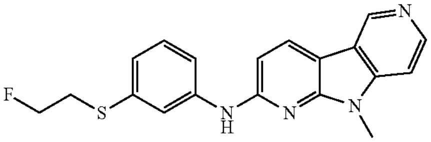 43 | 1. 5% 2. $^1$H-NMR (400 MHz, $CD_3OD$) δ = 9.19 (s, 1H), 8.48 (s, 1H), 8.34 (d, 1H), 8.14 (d, 1H), 7.83 (s, 1H), 7.76-7.67 (m, 1H), 7.67-7.53 (m, 2H), 7.32 (t, 1H), 7.08 (d, 1H), 6.87 (d, 1H), 4.70 (t, 1H), 4.59 (t, 1H), 4.02 (s, 3H), 3.36-3.20 (m, 2H) 3. 353.49 |
| 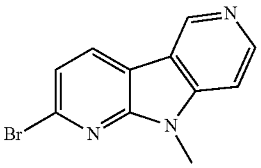 | 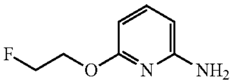 | 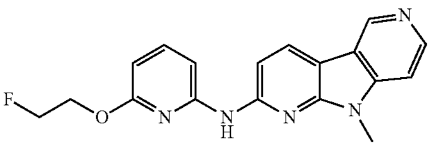 44 | 1. 49% 2. $^1$H NMR (400 MHz, DMSO-$d_6$) δ = 9.87 (s, 1H), 9.18 (s, 1H), 8.44 (d, 1H), 8.42 (s, 1H), 7.66-7.73 (m, 2H), 7.59 (d, 1H), 7.50 (d, 1H), 6.38 (d, 1H), 4.85-4.82 (m, 1H), 4.73-4.71 (m, 1H). 4.60-4.57 (m, 1H), 4.52-4.49 (m, 1H), 3.89 (s, 3H), |
| 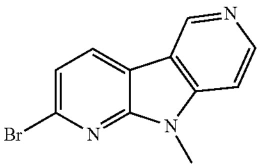 | 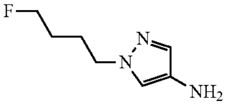 | 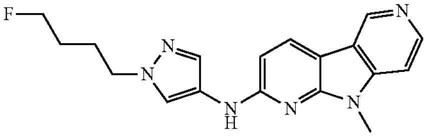 45 | 1. 26% 2. $^1$H-NMR (400 MHz, DMSO-$d_6$) δ = 9.30 (s, 1H), 9.09 (s, 1H), 8.36 (d, 1H), 8.24 (d, 1H), 8.17 (s, 1H), 7.61 (s, 1H), 7.54 (d, 1H), 6.63 (d, 1H), 4.52 (t, 1H), 4.40 (t, 1H), 4.17 (t, 2H), 3.88 (s, 3H), 1.94-1.75 (m, 2H), 1.73-1.47 (m, 2H) 3. 338.77 |
| 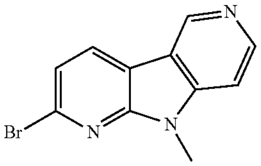 | 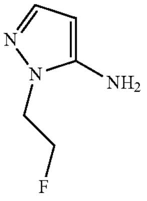 | 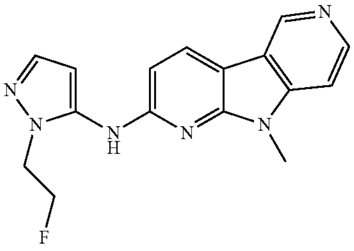 46 | 1. 53% 2. $^1$H-NMR (400 MHz, DMSO-$d_6$) δ = 9.15 (s, 2H), 8.49-8.18 (m, 2H), 7.56 (d, 1H), 7.48 (s, 1H), 6.78 (d, 1H), 6.56 (s, 1H), 4.83 (t, 1H), 4.71 (t, 1H), 4.45 (t, 1H), 4.39 (t, 1H), 3.81 (s, 3H) 3. 310.71 |
| 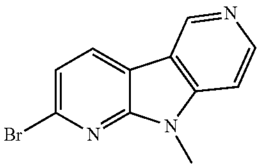 | 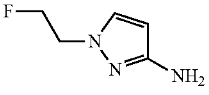 | 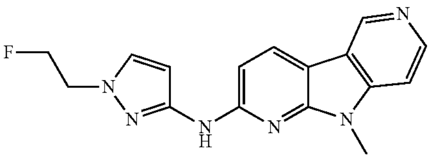 47 | 1. 40% 2. $^1$H-NMR (400 MHz, DMSO-$d_6$) δ = 9.81 (s, 1H), 9.11 (s, 1H), 8.39 (d, 1H), 8.31 (d, 1H), 7.68 (d, 1H), 7.55 (d, 1H), 7.01 (d, 1H), 6.81 (d, 1H), 4.83 (t, 1H), 4.71 (t, 1H), 4.47-4.36 (m, 1H), 4.32 (t, 1H), |

TABLE 4-continued

| Bromo derivative | Amine | Product Example | 1. Yield<br>2. $^1$H-NMR<br>3. $MH^+$ (ESI) |
|---|---|---|---|
| | | | 3.86 (s, 3H)<br>3. 310.71 |
| 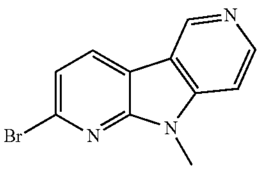 | 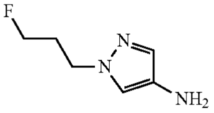 | 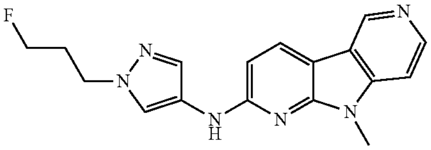<br>48 | 1. 47%<br>2. $^1$H-NMR (400 MHz, DMSO-$d_6$) δ = 9.32 (s, 1H), 9.09 (s, 1H), 8.44-8.32 (m, 1H), 8.32-8.14 (m, 2H), 7.70-7.61 (m, 1H), 7.61-7.49 (m, 1H), 6.72-6.51 (m, 1H), 4.63-4.49 (m, 1H), 4.49-4.35 (m, 1H), 4.35-4.06 (m, 2H), 4.04-3.85 (m, 3H), 2.32-2.04 (m, 2H)<br>3. 324.74 |
| 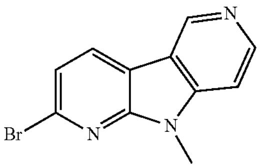 | 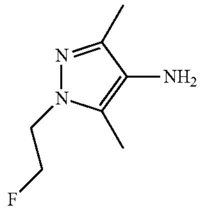 | 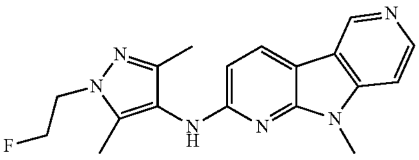<br>49 | 1. 69%<br>2. $^1$H-NMR (400 MHz, DMSO-$d_6$) δ 9.06 (s, 1H), 8.36 (d, 1H), 8.20 (d, 2H), 7.51 (d, 1H), 6.27 (d, 1H), 4.81 (t, 1H), 4.69 (t, 1H), 4.35 (t, 1H), 4.28 (t, 1H), 3.75 (s, 3H), 2.11 (s, 3H), 2.03 (s, 3H)<br>3. 339.2 |
| 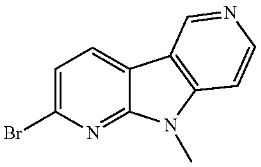 | 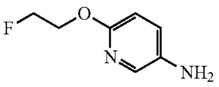 | 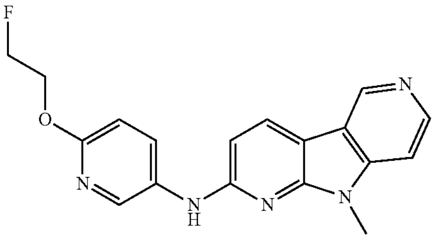<br>50 | 1. 16%<br>2. $^1$H-NMR (400 MHz, DMSO-$d_6$) δ = 9.40 (s, 1H), 9.15 (s, 1H), 8.72 (d, 1H), 8.41 (d, 1H), 8.35 (d, 1H), 8.19 (d, 1H), 7.57 (d, 1H), 6.91 (d, 1H), 6.75 (d, 1H), 4.94-4.78 (m, 1H), 4.78-4.63 (m, 1H), 4.62-4.50 (m, 1H), 4.50-4.39 (m, 1H), 3.87 (s, 3H)<br>3. 338.13 |
| 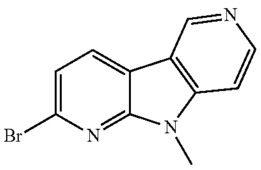 | 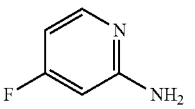 | 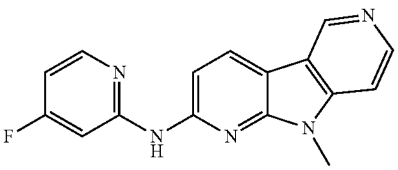<br>51 | 1. 62%<br>2. $^1$H-NMR (400 MHz, DMSO-$d_6$) δ = 10.33 (s, 1H), 9.20 (s, 1H), 8.58-8.36 (m, 2H), 8.30 (dd, 1H), 8.16 (dd, 1H), 7.61 (d, 1H), 7.39 (d, 1H), 6.86 (ddt, 1H), 3.90 (s, 3H) |
| 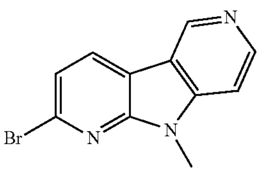 | 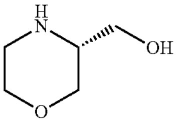 | 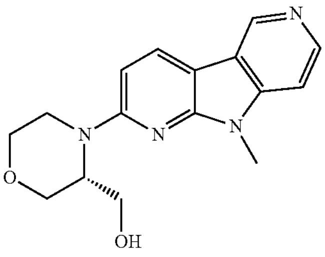<br>52 | 1. 40%<br>2. $^1$H-NMR (400 MHz, $CDCl_3$) δ = 9.17 (s, 1H), 8.54 (d, 1H), 8.25 (d, 1H), 7.33 (d, 1H), 6.72 (d, 1H), 4.39 (qd, 2H), 3.98 (dd, 1H), 3.89 (s, 3H), 3.84 (s, 1H), 3.71 (s, 1H), 3.69-3.57 (m, 1H), 3.55-3.41 (m, 1H), 3.36 (dq, J = 6.8, 3.0, 2.2 Hz, 1H), 3.10-2.94 (m, 2H) |

TABLE 4-continued

| Bromo derivative | Amine | Product Example | 1. Yield 2. $^1$H-NMR 3. MH$^+$ (ESI) |
|---|---|---|---|
| 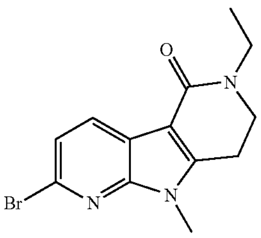 [SMILES: CCN1CCc2c(c3ccc(Br)nc3n2C)C1=O] | 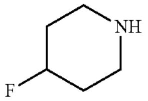 | 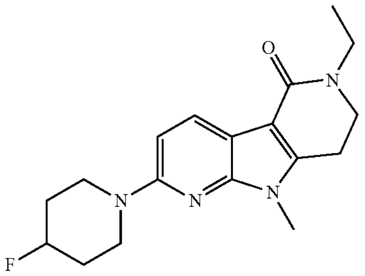 53 | 1. 17% $^1$H NMR (400 MHz, $CDCl_3$) δ 8.21 (d, 1H), 6.67 (d, 1H), 5.03-4.72 (m, 1H), 3.86-3.75 (m, 3H), 3.70-3.64 (m, 6H), 3.64-3.55 (m, 4H), 3.00 (t, 2H), 2.11-2.00 (m, 1H), 2.00-1.87 (m, 2H), 1.21 (t, 2H). |
| 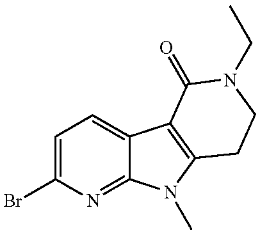 [SMILES: CCN1CCc2c(c3ccc(Br)nc3n2C)C1=O] | 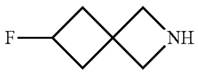 | 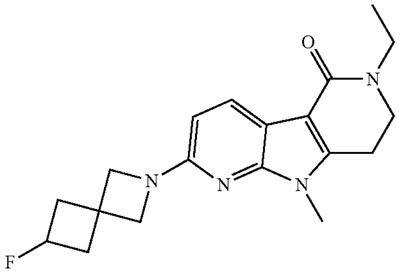 54 | 1. 73% 2. $^1$H NMR (400 MHz, DMSO-$d_6$) δ 8.18 (d, 1H), 6.23 (d, 1H), 5.00 (dp, , 1H), 4.06 (s, 2H), 4.02 (s, 2H), 3.70-3.63 (m, 5H), 3.59 (q, 2H), 2.99 (t, 2H), 2.79-2.59 (m, 2H), 2.57-2.29 (m, 2H), 1.21 (t, 3H). |
| 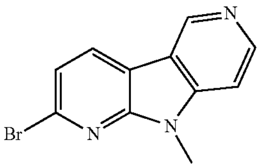 | 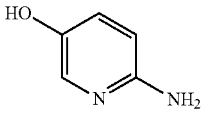 | 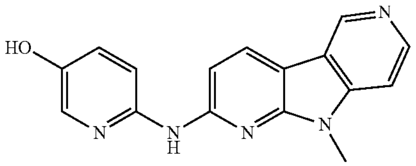 55 | 1. 57% 2. $^1$H NMR (400 MHz, DMSO-$d_6$) δ 9.68 (s, 1H), 9.13 (s, 1H), 8.40 (d, 1H), 8.34 (d, 1H), 8.09 (d, 1H), 7.85 (d, 1H), 7.55 (d, 1H), 7.31 (d, 1H), 7.24 (dd, 1H), 3.87 (s, 3H). |

Example-56

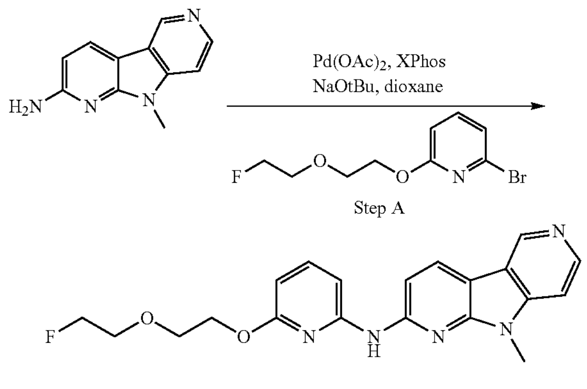

An oven dried Schlenk flask was evacuated and back filled with argon gas. The procedure was repeated 3-4 times and the flask was cooled to room temperature. Then dicyclohexyl-(2',4',6'-triisopropyl-[1,1'-biphenyl]-2-yl)phosphine (0.053 g, 0.1 mmol) and palladium(II)-acetate (0.008 g, 0.03 mmol) were dissolved in 1,4-dioxane (4 mL) and heated at 110° C. for 1 minute to become a clear red solution. Then the title compound from Preparative Example 21 (0.040 g, 0.2 mmol), the title compound from Preparative Example 60 (0.054 g, 0.2 mmol), and sodium tert.-butoxide (0.066 g, 0.69 mmol) were added. The reaction mixture was heated at 110° C. in a sand-bath for 4 hours, cooled to room temperature and the solvents were removed under reduced pressure. The residue was purified on HP-Sil SNAP cartridges using a Biotage Isolera One purification system employing an ethyl acetate/methanol gradient (100/0->90/10) to afford the title compound (0.018 g, 23%).

$^1$H-NMR (400 MHz, DMSO-$d_6$) δ=9.86 (s, 1H), 9.18 (s, 1H), 8.44 (d, 2H), 7.73-7.61 (m, 2H), 7.59 (d, 1H), 7.54 (d, 1H), 6.35 (dd, 1H), 4.64-4.58 (m, 1H), 4.52-4.47 (m, 1H), 4.48-4.40 (m, 2H), 3.89 (s, 3H), 3.85-3.79 (m, 2H), 3.79-3.74 (m, 1H), 3.72-3.64 (m, 1H).

Examples 57 to 70

Following the Pd-coupling procedure as described in Example 56, except using the amino-derivatives and bromo-derivatives indicated in the table below, the following compounds were prepared. The ligand dicyclohexyl-(2',4',6'-triisopropyl-[1,1'-biphenyl]-2-yl)phosphine (XPhos) can be replaced by 4,5-bis(diphenylphosphino)-9,9-dimethylxanthene (XantPhos) or 2-(dicyclohexylphosphino)3,6-dimethoxy-2',4',6'-triisopropyl-1,1'-biphenyl (BrettPhos) and the base sodium tert.-butoxide can be replaced by cesium carbonate.

TABLE 5
| Amine derivative | Bromo derivative | Product Example | 1. Yield 2. $^{1}$H-NMR 3. $MH^+$ (ESI) |
|---|---|---|---|
| 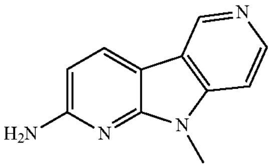 | 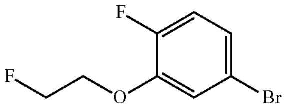 [SMILES: FCCOc1cc(Br)ccc1F] | 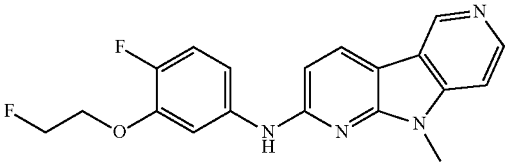 57 | 1. 31% 2. $^{1}$H-NMR (400 MHz, DMSO-$d_6$) δ = 9.49 (s, 1H), 9.15 (s, 1H), 8.41 (d, 1H), 8.35 (d, 1H), 8.05 (d, 1H), 7.58 (d, 1H), 7.28-7.04 (m, 2H), 6.77 (d, 1H), 4.98-4.82 (m, 1H), 4.75 (t, 1H), 4.49-4.40 (m, 1H), 4.34 (t, 1H), 3.88 (s, 3H) 3. 355.29 |
| 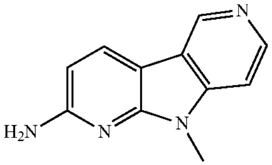 | 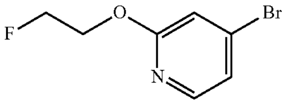 | 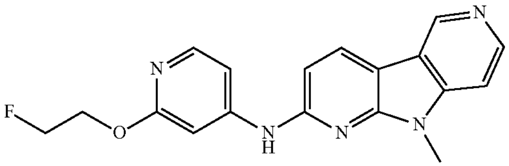 58 | 1. 13% 2. $^{1}$H-NMR (400 MHz, DMSO-$d_6$) δ = 9.73 (s, 1H), 9.24 (s, 1H), 8.73-8.26 (m, 2H), 7.65 (d, 1H), 7.51 (d, 1H), 7.29 (d, 1H), 6.91 (d, 1H), 6.46 (d, 1H), 4.71 (t, 1H), 4.59 (t, 1H), 4.17 (t, 1H), 4.10 (t, 1H), 3.91 (s, 3H) 3. 338.26 |
| 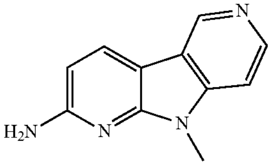 | 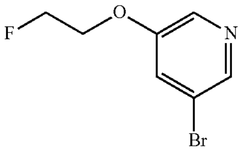 | 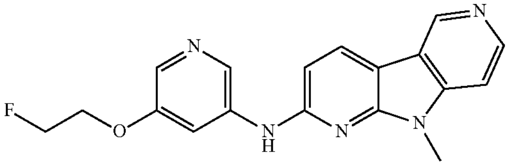 59 | 1. 44% 2. $^{1}$H-NMR (400 MHz, DMSO-$d_6$) δ = 9.71 (s, 1H), 9.18 (s, 1H), 8.50 (d, 1H), 8.47-8.35 (m, 2H), 8.31 (s, 1H), 7.91 (s, 1H), 7.59 (d, 1H), 6.84 (d, 1H), 4.91-4.79 (m, 1H), 4.80-4.63 (m, 1H), 4.54-4.38 (m, 1H), 4.38-4.27 (m, 1H), 3.89 (s, 3H) 3. 337.96 |

TABLE 5-continued
| Amine derivative | Bromo derivative | Product Example | 1. Yield<br>2. $^1$H-NMR<br>3. MH$^+$ (ESI) |
|---|---|---|---|
| 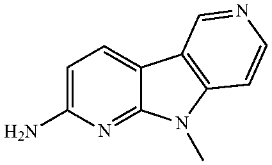 | 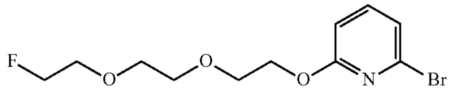 [SMILES: FCCOCCOCCOc1cccc(Br)n1] | 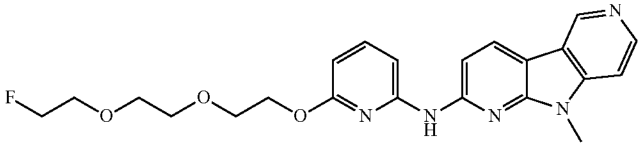<br>60 | 1. 28%<br>2. $^1$H-NMR (400 MHz, $CD_3OD$) δ = 9.05 (s, 1H), 8.37 (d, 1H), 8.31 (d, 1H), 7.71-7.55 (m, 2H), 7.52 (d, 1H), 7.40 (d, 1H), 6.34 (dd, 1H), 4.61 (s, 2H), 4.52-4.41 (m, 3H), 3.96-3.84 (m, 5H), 3.82-3.64 (m, 6H) |
| 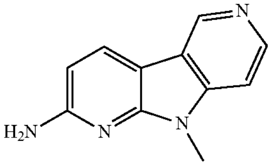 | 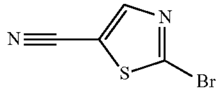 | 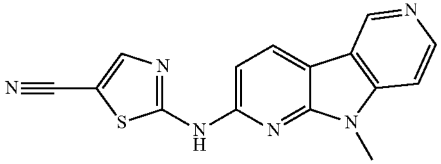<br>61 | 1. 84%<br>2. $^1$H-NMR (400 MHz, DMSO-$d_6$) δ = 9.10 (s, 1H), 8.37 (d, 1H), 8.26 (d, 1H), 8.01 (s, 1H), 7.54 (d, 1H), 7.44-7.30 (m, 1H), 6.80 (d, 1H), 4.00 (s, 3H) |
| 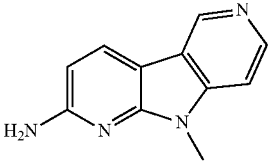 | 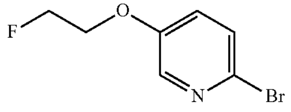 | 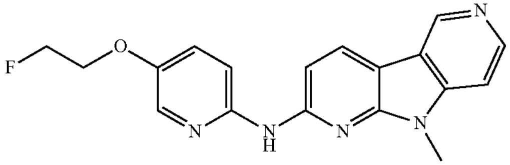<br>62 | 1. 42%<br>2. $^1$H-NMR (400 MHz, $CDCl_3$) δ = 9.15 (s, 1H), 8.53 (d, 1H), 8.22 (d, 1H), 8.15 (d, 1H), 8.05 (d, 1H), 7.48 (s, 1H), 7.38 (dd, 1H), 7.32 (d, 1H), 7.03 (d, 1H), 4.88-4.80 (m, 1H), 4.76-4.69 (m, 1H), 4.35-4.30 (m, 1H), 4.28-4.21 (m, 1H), 3.92 (s, 3H) |
| 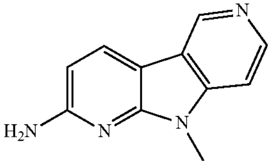 | 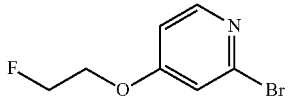 | 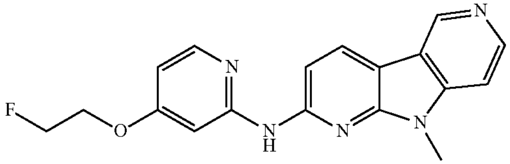<br>63 | 1. 50%<br>2. $^1$H-NMR (400 MHz, DMSO-$d_6$) δ = 10.03 (s, 1H), 9.20 (s, 1H), 8.50-8.39 (m, 2H), 8.10 (d, 1H), 7.98 (d, 1H), 7.64 (d, 1H), 7.43 (d, 1H), 6.60 (dd, 1H), 4.90-4.84 (m, 1H), 4.77-4.72 (m, 1H), 4.48- |

TABLE 5-continued
| Amine derivative | Bromo derivative | Product Example | 1. Yield<br>2. $^{1}$H-NMR<br>3. $MH^{+}$ (ESI) |
|---|---|---|---|
| | | | 4.40 (m, 1H), 4.40-4.30 (m, 1H), 3.91 (s, 3H) |
| 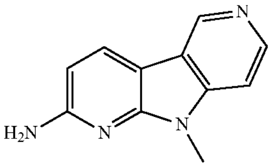 | 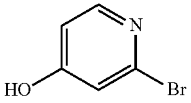 | 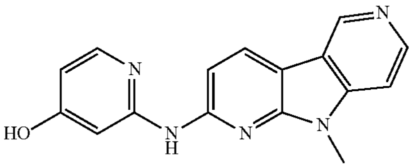<br>64 | 1. 73%<br>2. $^{1}$H-NMR (400 MHz, DMSO-$d_6$) δ = 9.93 (s, 1H), 9.24 (s, 1H), 8.48 (d, 1H), 8.43 (d, 1H), 7.97 (d, 1H), 7.70 (d, 2H), 7.40 (d, 1H), 6.38 (dd, 1H), 3.96 (s, 3H) |
| 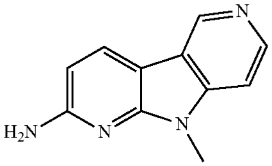 | 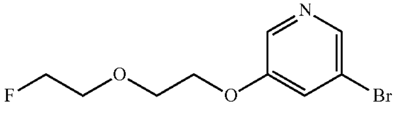 [SMILES: FCCOCCOc1cncc(Br)c1] | 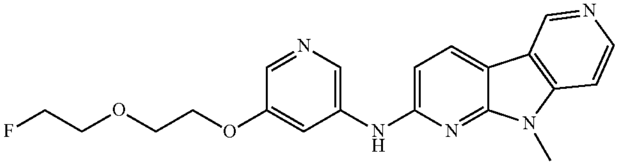<br>65 | 1. 28%<br>3. 382.2 |
| 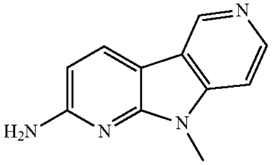 | 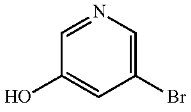 | 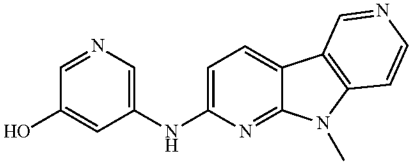<br>66 | 1. 97%<br>2. $^{1}$H-NMR (400 MHz, DMSO-$d_6$) δ = 9.54 (s, 1H), 9.15 (s, 1H), 8.49-8.29 (m, 3H), 8.08 (t, 1H), 7.71 (d, 1H), 7.57 (d, 1H), 6.81 (d, 1H), 3.91 (s, 3H), 2.08 (s, 2H) |
| 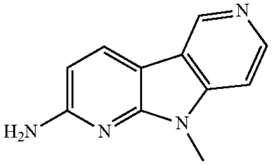 | 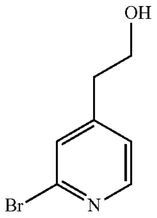 | 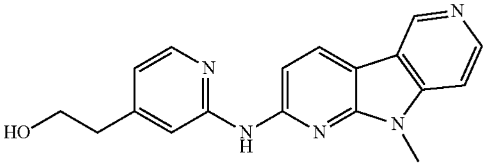<br>67 | 1. 26%<br>2. $^{1}$H-NMR (400 MHz, $CDCl_3$) δ = 9.15 (s, 1H), 8.52 (s, 1H), 8.33-8.10 (m, 3H), 7.32 (d, 1H), 7.09 (d, 1H), 6.83 (d, 1H), 4.02 (t, 2H), 3.91 (s, 3H), 2.95 (t, 2H) |

TABLE 5-continued
| Amine derivative | Bromo derivative | Product Example | 1. Yield<br>2. $^1$H-NMR<br>3. $MH^+$ (ESI) |
|---|---|---|---|
| 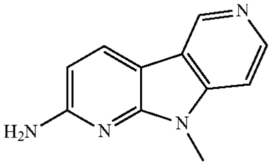 | 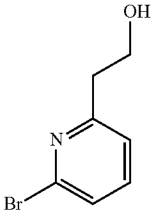 | 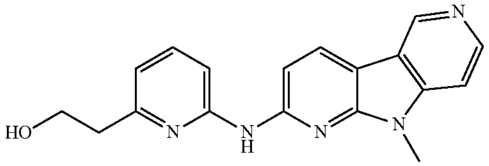<br>68 | 1. 52%<br>2. $^1$H-NMR (400 MHz, $CDCl_3$) δ = 9.18 (s, 1H), 8.55 (s, 1H), 8.27 (d, 1H), 8.02 (d, 1H), 7.65 (dd, 1H), 7.46 (s, 1H), 7.34 (d, 1H), 7.06 (d, 1H), 6.81 (d, 1H), 4.21-3.99 (m, 2H), 3.94 (d, 3H), 2.99 (t, 2H) |
| 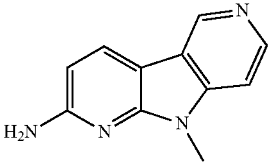 | 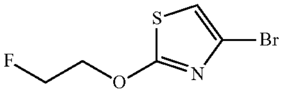 | 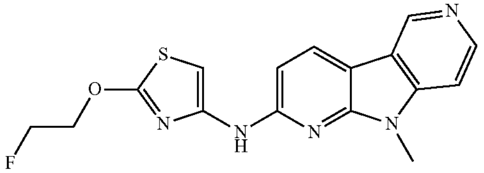<br>69 | 1. 44%<br>2. $^1$H-NMR (400 MHz, DMSO-$d_6$) δ = 10.22 (s, 1H), 9.15 (s, 1H), 8.41 (d, 1H), 8.34 (d, 1H), 7.59 (d, 1H), 7.34 (s, 1H), 6.92 (d, 1H), 4.92-4.81 (m, 1H), 4.78-4.72 (m, 1H), 4.72-4.65 (m, 1H), 4.65-4.57 (m, 1H), 3.91 (s, 3H).<br>3. 343.83 |
| 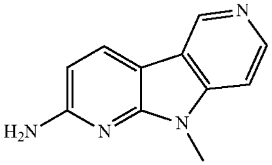 | 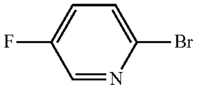 | 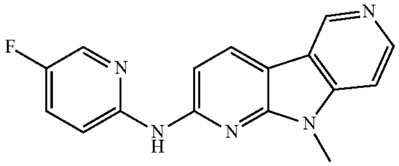<br>70 | 1. 71%<br>2. $^1$H-NMR (400 MHz, $CDCl_3$) δ = 9.18 (s, 1H), 8.55 (d, 1H), 8.33-8.19 (m, 2H), 8.17 (d, 1H), 7.56 (s, 1H), 7.48 (ddd, 1H), 7.33 (d, 1H), 7.03 (d, 1H), 3.93 (d, 3H). |

Example 71

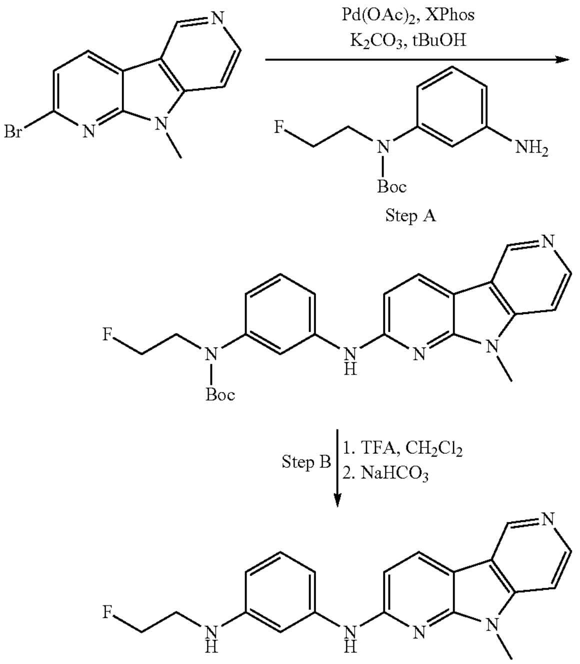

Step A

An oven dried Schlenk flask was evacuated and back filled with argon gas. The procedure was repeated 3-4 times and the flask was cooled to room temperature. Then dicyclohexyl-(2',4',6'-triisopropyl-[1,1-biphenyl]-2-yl)phosphine (0.054 g, 0.114 mmol) and palladium(II)-acetate (0.008 g, 0.038 mmol) were added and degassed (argon) 1,4-dioxane (4 mL) was added by syringe and the mixture was heated at 110° C. for 1 minute to become a clear red solution, indicating the formation of the Pd-catalyst. Then the title compound from Preparative Example 19 (0.116 g, 0.46 mmol), the title compound from Preparative Example 1 (0.1 g, 0.38 mmol) and sodium tert.-butoxide (0.12 g, 1.26 mmol) were added under an argon atmosphere. The reaction mixture was heated at 110° C. in a sand-bath for 4 h, cooled to room temperature and the solvents were removed under reduced pressure. The residue was purified on HP-Sil SNAP cartridges using a Biotage Isolera One purification system employing a dichloromethane/methanol gradient (100/0->90/10) to afford the title compound as a solid (0.11 g, 66%).

$^1$H NMR (400 MHz, $CD_3OD$) δ=8.71 (s, 1H), 8.15 (d, 1H), 7.98-7.73 (m, 2H), 7.55-7.44 (m, 1H), 7.24 (t, 1H), 7.16 (d, 1H), 6.81 (dd, 1H), 6.45 (d, 1H), 4.62 (t, 1H), 4.50 (t, 1H), 4.07-3.75 (m, 2H), 3.56 (s, 3H), 1.47 (s, 9H).

MS (ESI); m/z=436.24 $[M+H]^+$.

Step B

To a solution of the title compound from Step A above (0.11 g, 0.23 mmol) in dichloromethane (4 mL) was added trifluoroacetic acid (0.4 mL). The reaction mixture was stirred at room temperature overnight and then concentrated under reduced pressure. NaOH 1N (10 mL) was added to the crude mixture and the basic solution was extracted with dichloromethane (2×20 ml) and the combined organic fractions were washed with brine (20 mL) and concentrated in vacuo. The residue was purified on HP-Sil SNAP cartridges using a Biotage Isolera One purification system employing an dichloromethane/methanol gradient (100/0->90/10) to afford the title compound as a solid (0.027 g, 32%).

$^1$H NMR (400 MHz, DMSO-$d_6$) δ=9.19 (s, 1H), 9.12 (d, 1H), 8.39 (d, 1H), 8.29 (d, 1H), 7.63-7.49 (m, 1H), 7.37 (t, 1H), 7.10-6.86 (m, 2H), 6.78 (d, 1H), 6.38-6.14 (m, 1H), 5.79 (t, 1H), 4.65 (t, 1H), 4.53 (t, 1H), 3.87 (s, 3H), 3.40 (dd, 2H).

MS (ESI); m/z=335.93 $[M+H]^+$.

Examples 72 to 77

Following the palladium coupling procedure as described in Example 71, Step A, except using the bromo derivatives and anilines indicated in the table below, the following compounds were prepared.

TABLE 6

| Bromo derivative | Aniline | Product Example | 1. Yield 2. $^1$H-NMR 3. $MH^+$ (ESI) |
|---|---|---|---|
| 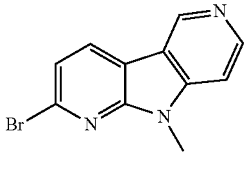 | 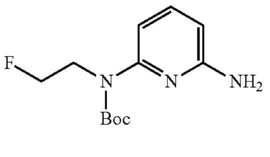 [SMILES: CC(C)(C)OC(=O)N(CCF)c1cccc(N)n1] | 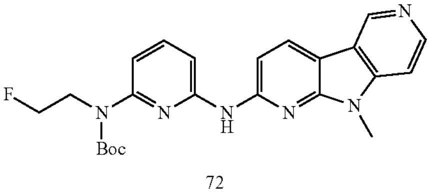 [SMILES: Cn1c2ccncc2c2ccc(Nc3cccc(N(CCF)C(=O)OC(C)(C)C)n3)nc21] 72 | 1. 14% 2. $^1$H-NMR (400 MHz, $CD_3OD$) δ = 9.10 (s, 1H), 8.55-8.13 (m, 2H), 7.54 (d, 1H), 7.44-7.23 (m, 1H), 7.02 (d, 1H), 6.94 (d, 1H), 6.64 (s, 1H), 4.45-4.23 (m, 2H), 4.23-4.03 (m, 2H), 3.90 (s, 3H), 1.60 (s, 9H) |
| 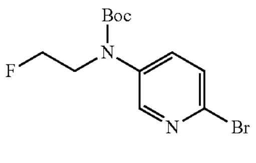 [SMILES: CC(C)(C)OC(=O)N(CCF)c1ccc(Br)nc1] | 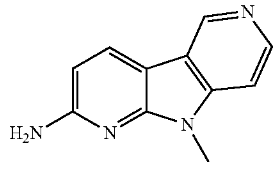 | 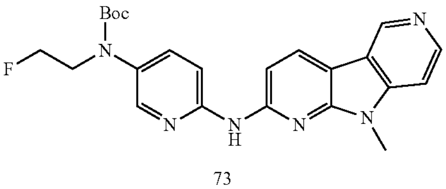 [SMILES: Cn1c2ccncc2c2ccc(Nc3ccc(N(CCF)C(=O)OC(C)(C)C)cn3)nc21] 73 | 1. 63% 2. $^1$H-NMR (400 MHz, $CDCl_3$) δ = 9.17 (s, 1H), 8.54 (d, 1H), 8.39-8.29 (m, 2H), 8.24 (d, 1H), 8.16 (s, 1H), 7.63 (s, 1H), 7.34 |

TABLE 6-continued

| Bromo derivative | Aniline | Product Example | 1. Yield<br>2. $^1$H-NMR<br>3. MH$^+$ (ESI) |
|---|---|---|---|
| | | | (d, 1H), 7.08 (d, 1H), 4.70 (t, 1H), 4.58 (t,, 1H), 3.93 (d, 3H), 3.77 (dd, 1H), 3.67-3.59 (m, 1H), 1.45 (d, 9H) |
| 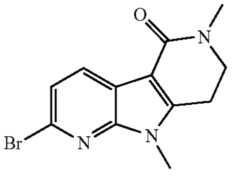 [SMILES: CN1CCc2c(c3ccc(Br)nc3n2C)C1=O] | 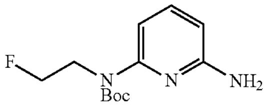 [SMILES: CC(C)(C)OC(=O)N(CCF)c1cccc(N)n1] | 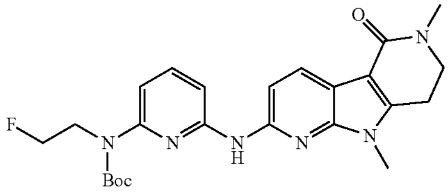<br>74 | 1. 64%<br>2. $^1$H.NMR (400 MHz, $CDCl_3$) δ = 8.24 (d, 1H), 7.60 (s, 1H), 7.38-7.19 (m, 1H), 6.85 (dlH), 6.70 (d, 1H), 6.51 (s, 1H), 4.72-4.58 (m, 1H), 4.58-4.46 (m, 1H), 4.04-3.92 (m, 1H), 3.94-3.83 (m, 1H), 3.77-3.59 (m, 5H), 3.10 (s, 3H), 3.09-2.95 (m, 2H), 1.46 (s, 9H) |
| 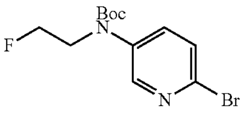 [SMILES: CC(C)(C)OC(=O)N(CCF)c1ccc(Br)nc1] | 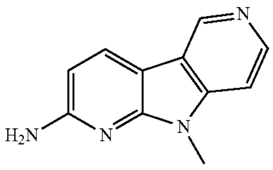 | 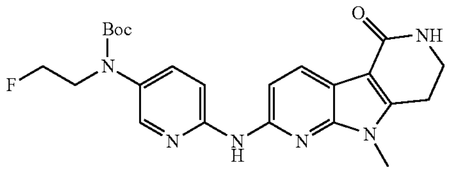<br>75 | 1. 23%<br>2. $^1$H-NMR (400 MHz, $CDCl_3$) δ = 8.30 (d, 1H), 8.18 (d, 1H), 7.96 (d, 1H), 7.56 (d, 1H) 6.48 (d, 1H), 4.67 (t, 1H), 4.55 (t, 1H), 4.51-4.39 (m, 3H), 3.93 (t, 1H), 3.86 (t, , 1H), 3.71 (s, 3H), 3.10 (t, 2H), 1.45 (s, 9H) |
| 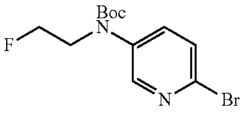 [SMILES: CC(C)(C)OC(=O)N(CCF)c1ccc(Br)nc1] | 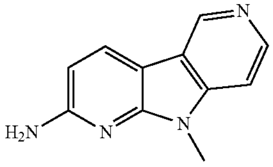 | 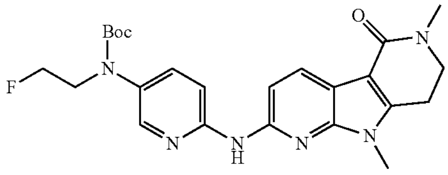<br>76 | 1. 70%<br>2. $^1$H-NMR (400 MHz, DMSO-$d_6$) δ = 9.77 (s, 1H), 8.14 (d, 1H), 8.09 (d, 1H), 8.04 (d, 1H), 7.57 (dd, 1H), 7.31 (d, 1H), 4.59 (t, 1H), 4.47 (t, 1H), 3.88 (t, 1H), 3.82 (t, 1H), 3.72 (s, 3H), 3.62 (t, 2H), 3.09 (t, 2H), 2.93 (s, 3H), 1.37 (s, 9H) |
| 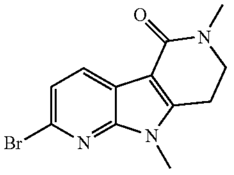 [SMILES: CN1CCc2c(c3ccc(Br)nc3n2C)C1=O] | 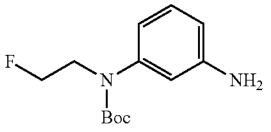 [SMILES: CC(C)(C)OC(=O)N(CCF)c1cccc(N)c1] | 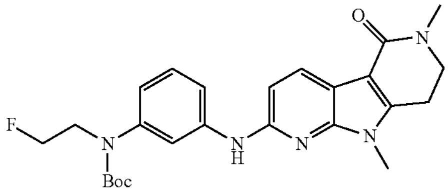<br>77 | 1. 41%<br>2. $^1$H-NMR (400 MHz, DMSO-$d_6$) δ = 9.15 (s, 1H), 7.99 (d, 1H), 7.87 (s, 1H), 7.65-7.51 (m, 1H), 7.24 (t, , 1H), 6.75-6.72 (m, 1H), 6.70 (d, 1H), 4.58 (t, 1H), 4.47 (t, 1H), 3.91 (t, |

TABLE 6-continued

| Bromo derivative | Aniline | Product Example | 1. Yield 2. $^1$H-NMR 3. MH$^+$ (ESI) |
|---|---|---|---|
| | | | 1H), 3.84 (t, 1H), 3.68 (s, 3H), 3.60 (t, 2H), 33.07 (t, 2H), 2.92 (s, 3H), 1.38 (s, 9H) |

Examples 78 to 84

Following the procedure as described in Example 71, Step B, except using the Boc-protected derivatives indicated in the table below, the following compounds were prepared. The acid to cleave the Boc-protecting group can be trifluroacetic acid or a 2 M solution of hydrogen chloride in diethylether or a 4 M solution of hydrogen chloride in 1,4-dioxane.

TABLE 7

| Boc-protected derivative | Product Example | 1. Yield 2. $^1$H-NMR 3. MH$^+$ (ESI) |
|---|---|---|
| 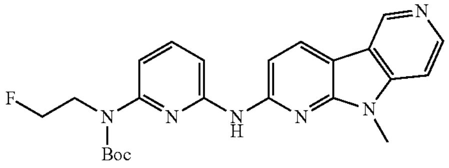 [SMILES: Cn1c2ccncc2c2ccc(Nc3cccc(N(CCF)C(=O)OC(C)(C)C)n3)nc21] | 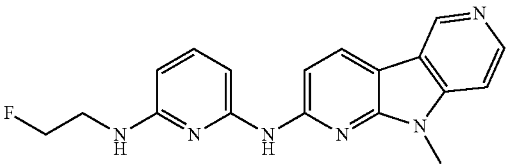 78 | 1. 32% 2· $^1$H-NMR (400 MHz, $CD_3OD$) δ 9.10 (s, 1H), 8.44-8.21 (m, 2H), 7.55 (d, 1H), 7.28 (t, 1H), 6.98 (d, 1H), 6.77 (d, 1H), 5.67 (d, 1H), 4.39 (t, 2H), 3.91 (s, 3H), 3.82 (t, 2H) |
| 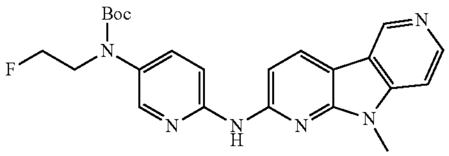 [SMILES: Cn1c2ccncc2c2ccc(Nc3ccc(N(CCF)C(=O)OC(C)(C)C)cn3)nc21] | 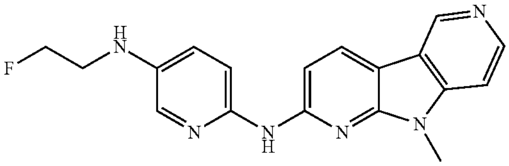 79 | 1. 20% 2. $^1$H-NMR (400 MHz, DMSO-$d_6$) δ = 9.64 (s, 1H), 8.79 (d, 1H), 8.72 (d, 1H), 8.24 (d, 2H), 7.82 (dd, 2H), 7.58 (d, 1H), 7.24 (d, 1H), 4.68 (t, 1H), 4.56 (t, 1H), 4.14 (s, 3H), 3.49-3.43 (m, 1H), 3.40 (t, 1H) |
| 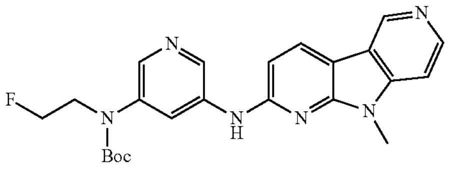 [SMILES: Cn1c2ccncc2c2ccc(Nc3cncc(N(CCF)C(=O)OC(C)(C)C)c3)nc21] | 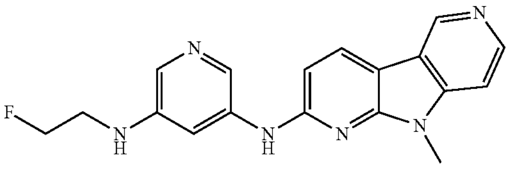 80 | 1. 78% 2. $^1$H-NMR (400 MHz, DMSO-$d_6$) δ 10.94 (s, 1H), 9.64 (s, 1H), 8.77 (s, 1H), 8.73 (d, 1H), 8.68 (d, 1H), 8.24 (d, 1H), 8.15 (s, 1H), 7.84 (d, 1H), 7.46 (s, 1H), 7.18 (d, 1H), 4.71 (t, 1H), 4.59 (t, 1H), 4.09 (s, 3H), 3.61-3.56 (m, 1H), 3.55-3.48 (m, 1H) |

TABLE 7-continued
| Boc-protected derivative | Product Example | 1. Yield 2. $^1$H-NMR 3. $MH^+$ (ESI) |
| --- | --- | --- |
| 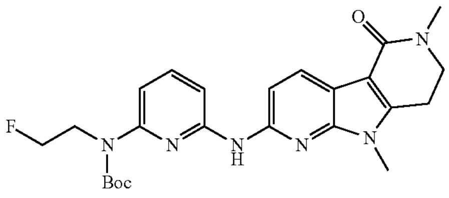 [SMILES: CN1CCc2c(c3ccc(Nc4cccc(N(CCF)C(=O)OC(C)(C)C)n4)nc3n2C)C1=O] | 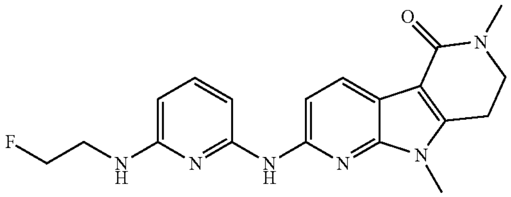 81 | 1. 36% 2. $^1$H-NMR (400 MHz, DMSO-$d_6$) δ = 9.72 (s, 1H), 8.75 (s, 1H), 8.24 (d, 1H), 7.75 (t, 1H), 7.45 (d, 1H), 7.22 (d, 1H), 6.33 (d, 1H), 4.70-4.61 (m, 2H), 3.92 (t, 2H), 3.75-3.70 (m, 3H), 3.67-3.60 (m, 2H), 3.20-3.10 (m, 2H), 2.95 (s, 3H) |
| 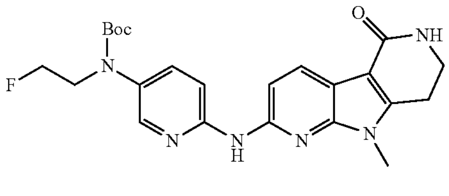 [SMILES: Cn1c2c(c3ccc(Nc4ccc(N(CCF)C(=O)OC(C)(C)C)cn4)nc31)C(=O)NCC2] | 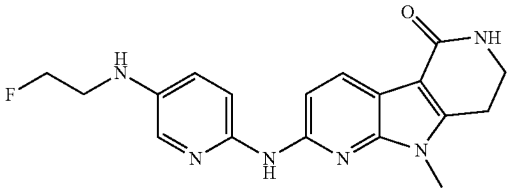 82 | 1. 82% 2. $^1$H-NMR (400 MHz, DMSO-$d_6$) δ = 8.02 (d, 1H), 7.89 (s, 1H), 7.65-7.54 (m, 2H), 6.61 (d, 1H), 4.66 (t, 1H), 4.54 (t, 1H), 4.16 (t, 2H), 3.71 (s, 3H), 3.52 (t, 1H), 3.45 (t, 1H), 3.22 (t, 2H) |
| 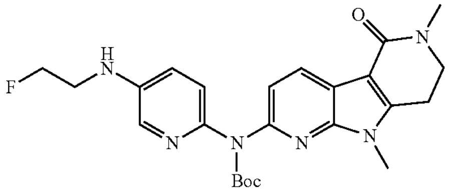 [SMILES: CN1CCc2c(c3ccc(N(C(=O)OC(C)(C)C)c4ccc(NCCF)cn4)nc3n2C)C1=O] | 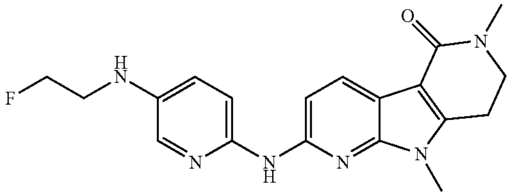 83 | 1. 52% 2. $^1$H-NMR (400 MHz, DMSO-$d_6$) δ = 11.75 (s, 1H), 8.25 (d, 1H), 7.80 (dd, 1H), 7.70 (d, 1H), 7.47 (d, 1H), 7.01 (d, 1H), 4.68 (t, 1H), 4.57 (t, 1H), 3.85 (s, 3H), 3.65 (t, 2H), 3.43 (t, 1H), 3.36 (t, 1H), 3.16 (t, 2H), 2.95 (s, 3H) |
| 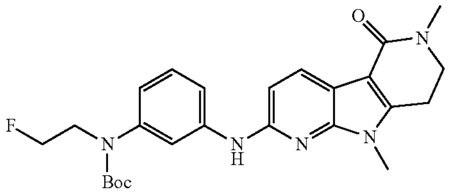 [SMILES: CN1CCc2c(c3ccc(Nc4cccc(N(CCF)C(=O)OC(C)(C)C)c4)nc3n2C)C1=O] | 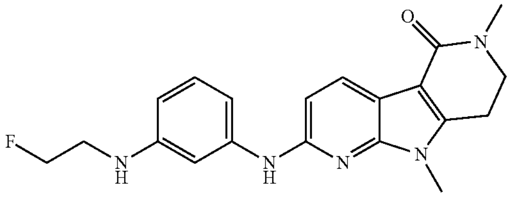 84 | 1. 87% 2. $^1$H-NMR (400 MHz, $CDCl_3$) δ = 8.22 (d, 1H), 7.14 (t, 1H), 6.95 (t, 1H), 6.80 (d, 1H), 6.76 (d, 1H), 6.43 (s, 1H), 6.36-6.22 (m, 1H), 4.71 (t, 1H), 4.59 (t, 1H), 3.72 (s, 3H), 3.67 (t, 2H), 3.51 (t, 1H), 3.45 (t, 1H), 3.10 (s, 3H), 3.05 (t, 2H) |

Example 85

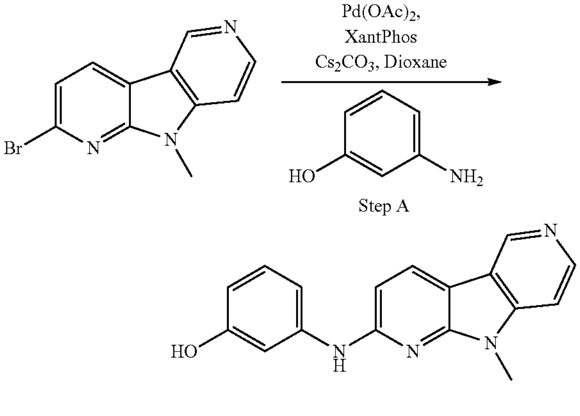

Step A

An oven dried Schlenk flask was evacuated and back filled with argon gas. The procedure was repeated 3-4 times and the flask was cooled to room temperature. Then the title compound from Preparative Example 1 (0.3 g, 1.14 mmol), commercially available 3-amino-phenol (0.137 g, 1.26 mmol), palladium(II)-acetate (0.027 g, 0.138 mmol), 4,5-bis(diphenylphosphino)-9,9-dimethylxanthene (0.21 g, 0.27 mmol), cesium carbonate (0.744 g, 2.28 mmol) and 1,4-dioxane (10 mL) were added and the reaction mixture was heated at 110° C. in a sand-bath for 3 h. The reaction mixture was diluted with dichloromethane (25 mL) and 1:1 mixture of water and brine (50 mL). Then a 1:1 mixture of methanol and acetone (40 mL) was added and the mixture was shaken in a separation funnel. The organic phase was separated and the aqueous phase was extracted with the 1:1 mixture of methanol and acetone two more times. The combined organic phase was dried over $Na_2SO_4$, filtered and the solvents were evaporated under reduced pressure. The residue was suspended in dichloromethane (10 mL) and sonicated for 5 minutes.

The precipitate was collected by filtration, washed with dichloromethane (3 mL) and air-dried to afford the title compound as a beige solid (0.246 g, 74%).

$^1$H-NMR (400 MHz, DMSO-$d_6$) δ=9.35 (s, 1H), 9.30 (s, 1H), 9.19 (s, 1H), 8.44 (d, 1H), 8.35 (d, 1H), 7.65 (d, 1H), 7.52 (t, 1H), 7.27-7.15 (m, 1H), 7.10 (t, 1H), 6.82 (d, 1H), 6.38 (dd, 1H), 3.93 (s, 3H).

Examples 86 to 94

Following the Pd-coupling procedure as described in Example 85, except using the bromo-derivatives and amine-derivatives indicated in the table below, the following compounds were prepared. The ligand 4,5-bis(diphenylphosphino)-9,9-dimethylxanthene (XantPhos) can be replaced by 2-(dicyclohexylphosphino)3,6-dimethoxy-2',4',6'-triisopropyl-1,1'-biphenyl (BrettPhos).

TABLE 8

| Bromo derivative | Amine derivative | Product Example | 1. Yield<br>2. $^1$H-NMR<br>3. $MH^+$ (ESI) |
|---|---|---|---|
| 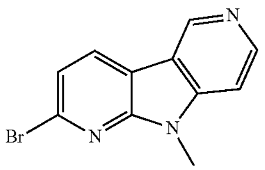 | 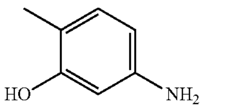 | 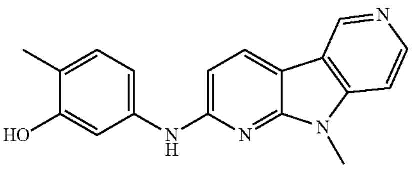<br>86 | 1. 66%<br>2. $^1$H-NMR (400 MHz, DMSO-$d_6$) δ = 9.32 (s, 1H), 9.11 (s, 1H), 8.38 (d, 1H), 8.28 (d, 1H), 7.55 (s, 2H), 7.20-7.04 (m, 1H), 6.95 (d, 1H), 6.81 (d, 1H), 3.90 (s, 3H), 2.08 (s, 3H)<br>3. 304.71 |
| 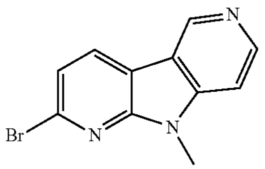 | 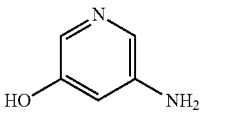 | 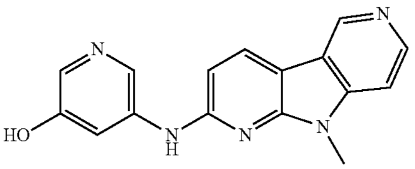<br>87 | 1. 97%<br>2. $^1$H-NMR (400 MHz, DMSO-$d_6$) δ = 9.54 (s, 1H), 9.15 (s, 1H), 8.49-8.29 (m, 3H), 8.08 (t, 1H), 7.71 (d, 1H), 7.57 (d, 1H), 6.81 (d, 1H), 3.91 (s, 3H), 2.08 (s, 2H). |
| 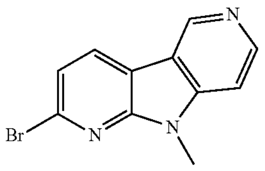 | 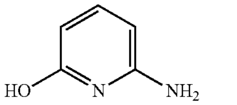 | 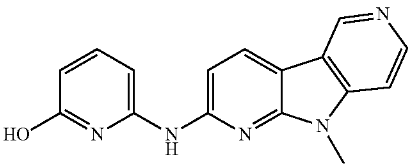<br>88 | 1. 60%<br>2. $^1$H-NMR (400 MHz, $CD_3OD$) δ = 9.13 (s, 1H), 8.45 (dd, 2H), 7.61 (d, 1H), 7.55 (t, 1H), 6.85 (d, 1H), 6.05 (d, 1H), 5.97 (d, 1H), 4.00 (s, 3H)<br>3. 291.81 |

TABLE 8-continued

| Bromo derivative | Amine derivative | Product Example | 1. Yield<br>2. $^{1}$H-NMR<br>3. MH$^{+}$ (ESI) |
|---|---|---|---|
| 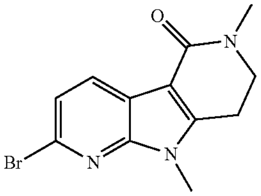 [SMILES: CN1CCc2c(c3ccc(Br)nc3n2C)C1=O] | 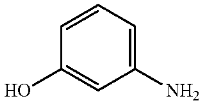 | 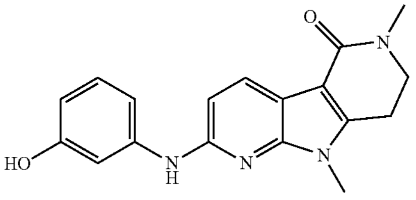<br>89 | 1.<br>2. $^{1}$H-NMR (400 MHz, DMSO-$d_6$) δ = 10.81 (s, 1H), 9.46 (s, 1H), 8.06 (d, 1H), 7.18 (d, 1H), 7.13 (s, 1H), 6.80 (d, 1H), 6.28 (d, 1H), 3.71 (s, 3H), 3.62 (t, 2H), 3.10 (t, 2H), 2.91 (d, 3H) |
| 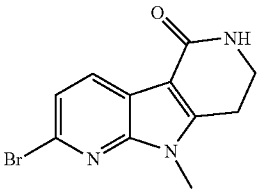 | 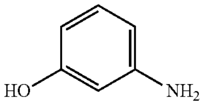 | 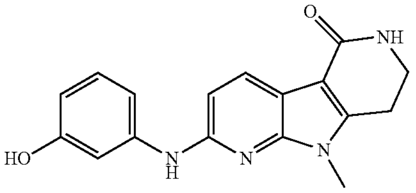<br>90 | 1. 34%<br>3. 309.2 |
| 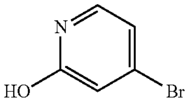 | 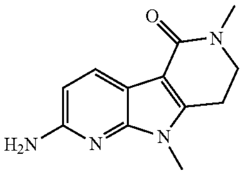 [SMILES: CN1CCc2c(c3ccc(N)nc3n2C)C1=O] | 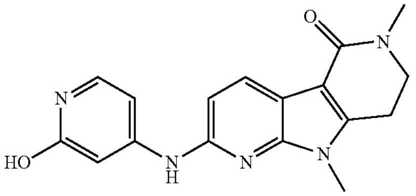<br>91 | 1. 72%<br>2. $^{1}$H-NMR (400 MHz, DMSO-$d_6$) δ = 10.81 (s, 1H), 9.46 (s, 1H), 8.06 (d, 1H), 7.18 (d, , 1H), 7.13 (s, 1H), 6.80 (d, , 1H), 6.28 (d, , 1H), 3.71 (s, 3H), 3.62 (t, 2H), 3.10 (t, 2H), 2.91 (d, 3H) |
| 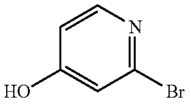 | 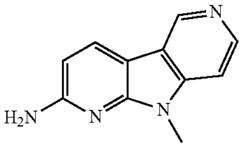 | 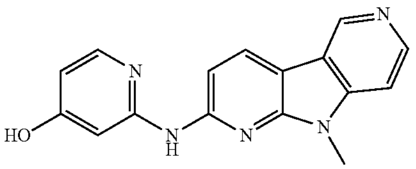<br>92 | 1. 73%<br>2. $^{1}$H-NMR (400 MHz, DMSO-$d_6$) δ = 9.93 (s, 1H), 9.24 (s, 1H), 8.48 (d, 1H), 8.43 (d, 1H), 7.97 (d, 1H), 7.70 (d, 2H), 7.40 (d, 1H), 6.38 (dd, 1H), 3.96 (s, 3H) |
| 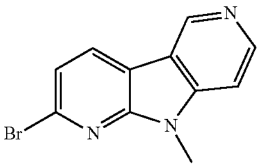 | 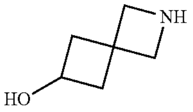 | 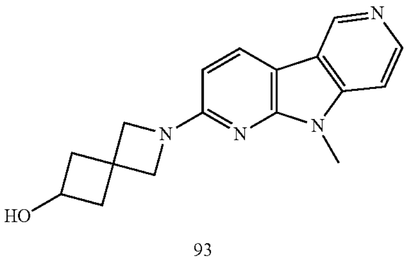 [SMILES: Cn1c2ccncc2c2ccc(N3CC4(CC(O)C4)C3)nc21]<br>93 | 1. 35%<br>2. $^{1}$H-NMR (400 MHz, DMSO-$d_6$) δ = 9.09 (s, 1H), 8.37 (d, 1H), 8.27 (d, 1H), 7.51 (d, 1H), 6.28 (d, 1H), 5.07 (d, 1H), 4.09-3.95 (m, 5H), 3.77 (s, 3H), 2.49-2.41 (m, 2H), 2.11-1.98 (m, 2H)<br>3. 294.82 |
| 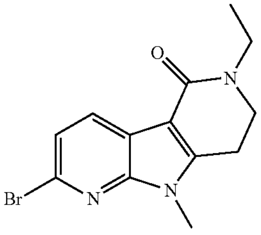 [SMILES: CCN1CCc2c(c3ccc(Br)nc3n2C)C1=O] | 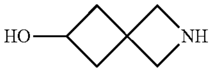<br>TFA salt | 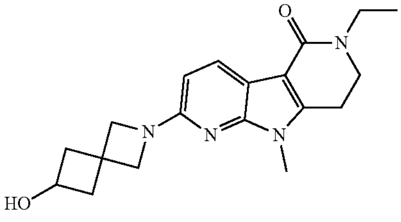<br>94 | 1. 52%<br>2. $^{1}$H-NMR (400 MHz, $CDCl_3$) δ = 8.17 (d, 1H), 6.22 (d, 1H), 4.29 (t, 1H), 4.02 (s, 2H), 4.00 (s, 2H), 3.66 (d, 5H), 3.58 (q, 2H), 2.99 (t, 2H), 2.63 (ddd, 2H), 2.17 (ddd, 2H), 1.21 (t, 3H) |

Example 95

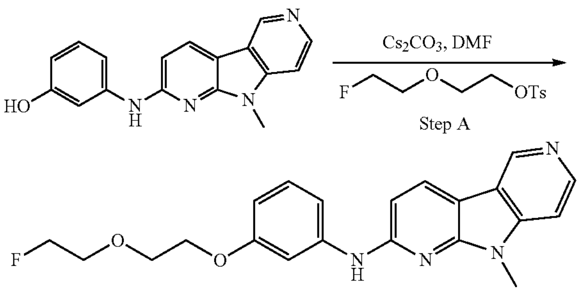

Step A

The title compound from Example 85 (0.075 g, 0.259 mmol) was suspended in N,N'-dimethylformamide (2 mL) and cesium carbonate (0.093 g, 0.285 mmol) was added. The reaction mixture was stirred at room temperature for 10 minutes and then custom made 2-(2-fluoroethoxy)ethyl 4-methylbenzenesulfonate (0.075 g, 0.337 mmol) was added. The reaction mixture was heated at ~80° C. in a sand-bath for 5 hours. The reaction mixture was diluted with dichloromethane (100 mL) and water (30 mL). Then methanol was added until all solid material was dissolved by shaking the reaction mixture in a separation funnel. The organic phase was separated, dried over $Na_2SO_4$, filtered and the solvents were evaporated under reduced pressure. The residue was purified on HP-Sil SNAP cartridges using a Biotage Isolera One purification system employing an dichloromethane/methanol gradient (100/0->90/10) to afford the title compound as a beige solid/glass (0.041 g, 41%).

$^1$H-NMR (400 MHz, DMSO-$d_6$) δ=9.46 (s, 1H), 9.16 (s, 1H), 8.43 (d, 1H), 8.35 (d, 1H), 7.78 (s, 1H), 7.58 (d, 1H), 7.35-7.32 (m, 1H), 7.22 (t, 1H), 6.81 (d, 1H), 6.55-6.52 (m, 1H), 4.65-4.63 (m 1H), 4.54-4.50 (m, 1H), 4.20-4.15 (m, 2H), 3.90 (s, 3H), 3.86-3.80 (m, 3H), 3.74-3.71 (m, 1H).

Examples 96 to 97

Following the alkylation procedure as described in Example 95, except using the phenol-derivatives and alkylation reagents indicated in the table below, the following compounds were prepared.

TABLE 9
| Phenol derivative | Alkylation reagent | Product Example | 1. Yield<br>2. $^1$H-NMR<br>3. MH$^+$ (ESI) |
| --- | --- | --- | --- |
| 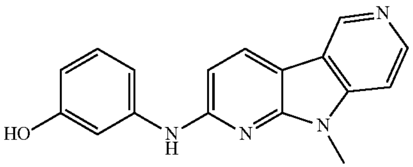 [SMILES: Cn1c2ccncc2c2ccc(Nc3cccc(O)c3)nc21] | 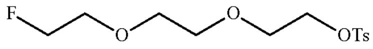 [SMILES: Cc1ccc(S(=O)(=O)OCCOCCOCCF)cc1] | 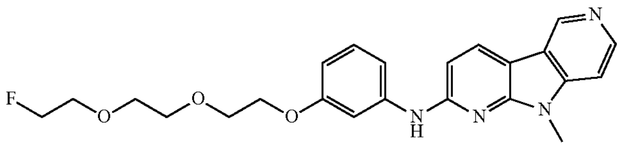<br>96 | 1. 16%<br>2. $^1$H-NMR (400 MHz, DMSO-$d_6$) δ = 9.45 (s, 1H), 9.14 (s, 1H), 8.40 (d, 1H), 8.33 (d, 1H), 7.75 (s, 1H), 7.56 (d, 1H), 7.32-7.29 (m, 1H), 7.20 (t, 1H), 6.80 (d, 1H), 6.57-6.55 (m, 1H), 4.57-4.55 (m, 1H), 4.46-4.43 (m, 1H), 4.17-4.12 (m, 2H), 3.88 (s, 3H), 3.81-3.74 (m, 2H), 3.71-3.68 (m, 1H), 3.65-3.58 (m, 5H) |
| 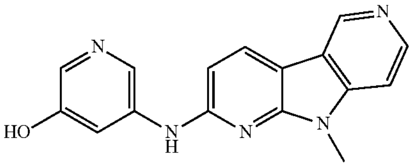 [SMILES: Cn1c2ccncc2c2ccc(Nc3cncc(O)c3)nc21] | 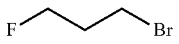 | 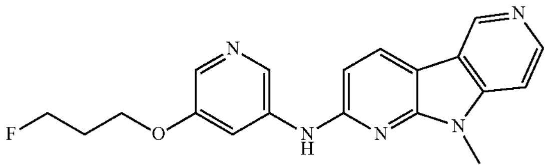<br>97 | 1. 41%<br>2. $^1$H-NMR (400 MHz, DMSO-$d_6$) δ = 9.74 (s, 1H), 9.20 (s, 1H), 8.53-8.30 (m, 4H), 7.89 (d, 1H), 7.64 (d, 1H), 6.85 (d, 1H), 4.71 (t, 1H), 4.59 (t, 1H), 4.22 (t, 2H), 3.90 (s, 3H), 2.18 (dt, 2H)<br>3. 351.81 |

Example 98

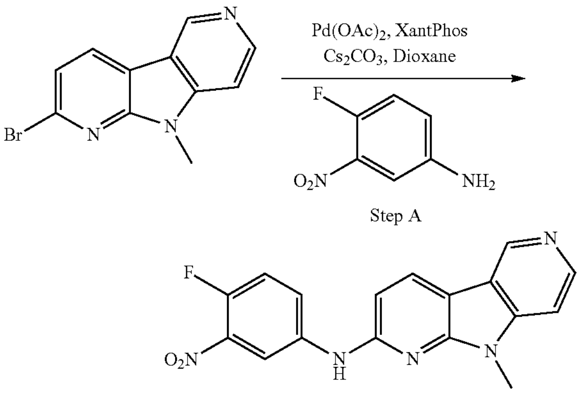

Step A

An oven dried Schlenk flask was evacuated and back filled with argon gas. The procedure was repeated 3-4 times and the flask was cooled to room temperature. Then the title compound from Preparative Example 1 (0.5 g, 1.9 mmol), commercially available 4-fluoro-3-nitro-aniline (0.415 g, 2.1 mmol), palladium(II)-acetate (0.045 g, 0.225 mmol), 4,5-bis(diphenylphosphino)-9,9-dimethylxanthene (0.35 g, 0.45 mmol), cesium carbonate (1.24 g, 3.8 mmol) and 1,4-dioxane (25 mL) were added and the reaction mixture was heated at 110° C. in a sand-bath for 6 h. The cooled reaction mixture was diluted with ethyl acetate (350 mL), acetone (150 mL) and methanol (70 mL). After the addition of brine (150 mL), the organic phase was separated, dried over $Na_2SO_4$, filtered and the solvents were evaporated under reduced pressure. The residue was treated with methanol (30 mL), sonicated for 10 minutes and the precipitate was collected by filtration. The solid material was washed with methanol (10 mL) and air dried to afford the title compound as a reddish solid (0.558 g, 86%).

$^1$H NMR (400 MHz, DMSO-$d_6$) δ=9.95 (s, 1H), 9.26-9.23 (d, 1H), 9.17 (s, 1H), 8.46-8.40 (m, 2H), 7.98-7.93 (m, 1H), 7.63 (d, 1H), 7.57-7.51 (m, 1H), 6.81 (d, 1H), 3.94 (s, 3H).

Examples 99 to 101

Following the Pd-coupling procedure as described in Example 98, except using the bromo-derivatives and amines indicated in the table below, the following compounds were prepared.

TABLE 10

| Bromo derivative | Amine | Product Example | Yield 2. $^1$H-NMR 3. $MH^+$ (ESI) |
|---|---|---|---|
| 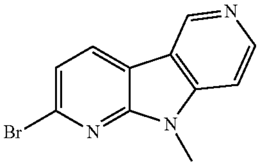 | 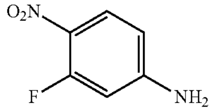 [SMILES: Nc1ccc([N+](=O)[O-])c(F)c1] | 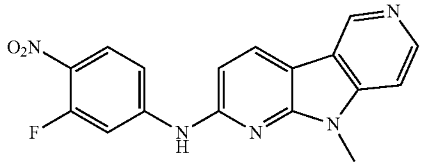 99 | 1. 67% 2. $^1$H NMR (400 MHz, DMSO-$d_6$) δ = 9.23 (s, 1H), 8.52 (d, 1H), 8.47 (d, 1H), 8.28-8.24 (m, 1H), 8.16 (t, 1H), 7.64-7.59 (m, 2H), 6.93 (d, 1H), 3.94 (s, 3H) |
| 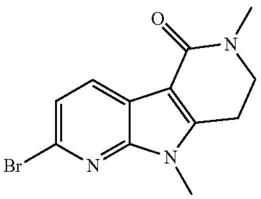 [SMILES: CN1CCc2c(c3ccc(Br)nc3n2C)C1=O] | 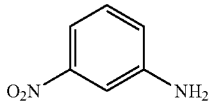 | 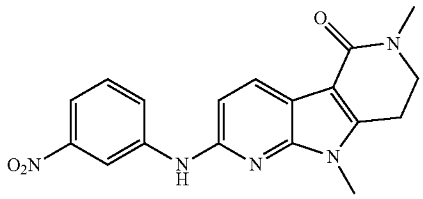 100 | 1. 23% 2. $^1$H-NMR (400 MHz, $CDCl_3$) δ = 9.22 (t, 1H), 8.30 (d, 1H), 7.86-7.75 (m, 1H), 7.62-7.51 (m, 1H), 7.42 (t, 1H), 6.81-6.74 (m, 1H), 6.65 (d, 1H), 3.81 (s, 3H), 3.70 (t, 2H), 3.10 (d, 5H) |
| 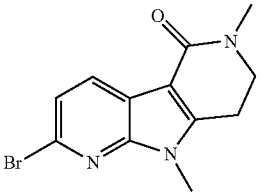 [SMILES: CN1CCc2c(c3ccc(Br)nc3n2C)C1=O] | 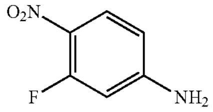 | 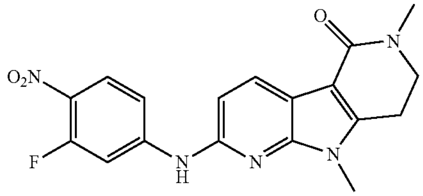 101 | 1. 90% 2. $^1$H-NMR (400 MHz, DMSO-$d_6$) δ = 8.21-7.95 (m, 3H), 7.54-7.34 (m, 1H), 6.85 (d, 1H), 3.73 (s, 3H), 3.70-3.56 (m, 3H), 3.11 (t, 2H), 2.93 (s, 3H) |

Example 102

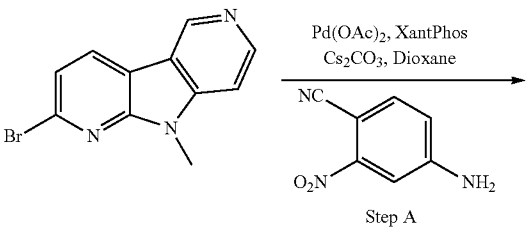

-continued

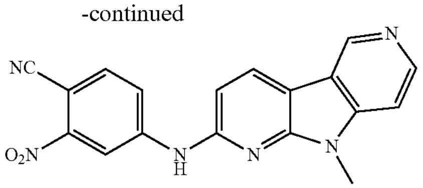

Step A

An oven dried Schlenk flask was evacuated and back filled with argon gas. The procedure was repeated 3-4 times and the flask was cooled to room temperature. Then the title compound from Preparative Example 1 (0.15 g, 0.572 mmol), the title compound from Preparative Example 32 (0.13 g, 0.795 mmol), palladium(II)-acetate (0.0135 g, 0.069 mmol), 4,5-bis(diphenylphosphino)-9,9-dimethylxanthene (0.105 g, 0.135 mmol), cesium carbonate (0.372 g, 1.14 mmol) and 1,4-dioxane (7.5 mL) were added and the reaction mixture was heated at 110° C. in a sand-bath for 6 h. The cooled reaction mixture was diluted with dichloromethane (100 mL), water (15 mL) and brine (15 mL). The organic phase was separated and discarded. The insoluble, reddish material in the aqueous phase was collected by filtration. The solid material was suspended in water (15 mL) by sonication and filtered again. The solid material was washed with methanol (10 mL), dichloromethane (10 mL) and methanol (10 ml). The solid material was then air-dried to afford the title compound as a red solid (0.126 g, 64%) which is hardly soluble in organic solvents.

$^1H$ NMR (400 MHz, DMSO-$d_6$) δ=10.55 (s, 1H), 9.40 (s, 1H), 9.25 (s, 1H), 8.54 (d, 1H), 8.49 (d, 1H), 8.14-8.10 (m, 1H), 8.05-8.02 (m, 1H), 7.65 (d, 1H), 6.93 (d, 1H), 3.96 (s, 3H).

Examples 103 and 104

Following the Pd-coupling procedure as described in Example 102, except using the bromo-derivatives and amines indicated in the table below, the following compounds were prepared.

TABLE 11

| Bromo derivative | Amine | Product Example | 1. Yield<br>2. $^1H$-NMR<br>3. $MH^+$ (ESI) |
|---|---|---|---|
| 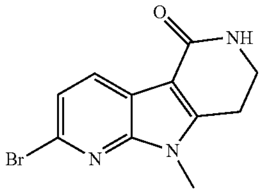 [SMILES: Cn1c2c(c3ccc(Br)nc31)C(=O)NCC2] | 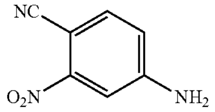 [SMILES: N#Cc1ccc(N)cc1[N+](=O)[O-]] | 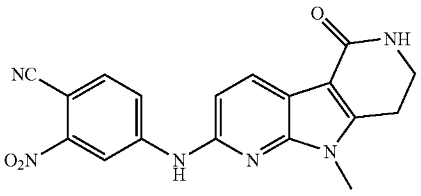<br>103 | 1. 97%<br>2. $^1H$ NMR (400 MHz, DMSO-$d_6$) δ = 10.26 (s, 1H), 9.28 (s, 1H), 8.12 (d, 1H), 8.00-7.93 (m, 2H), 7.13 (s, 1H), 6.82 (d, 1H) 3.77 (s, 3H), 3.52-3.47 (m, 2H), 3.03-2.98 (m, 2H) |
| 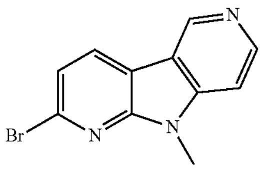 | 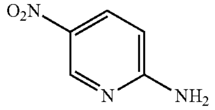 | 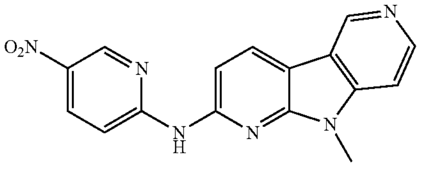<br>104 | 1. 86%<br>2. $^1H$-NMR (400 MHz, DMSO-$d_6$) δ = 9.28 (s, 1H), 9.17 (d, 1H), 8.75-8.47 (m, 3H), 8.40 (d, 1H), 7.68 (d, 1H), 7.61 (d, 1H), 3.97 (s, 3H) |

Example 105

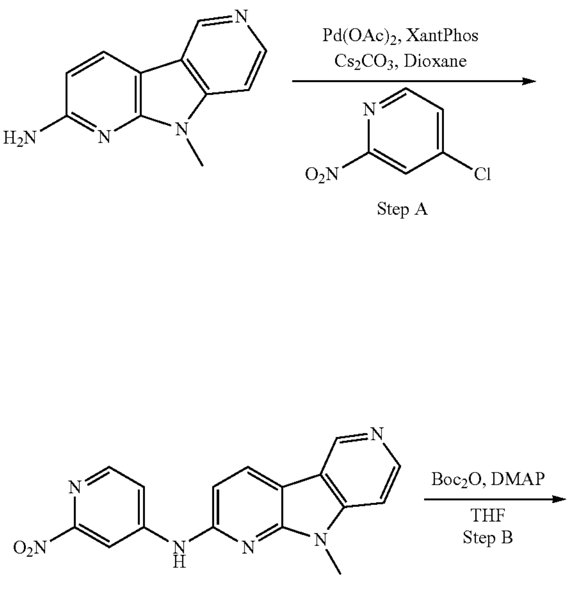

-continued

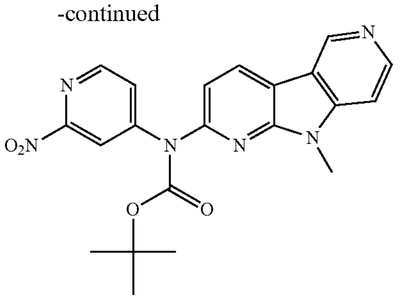

Step A 1,4-Dioxane (20 mL) was degassed for 10 minutes with argon. Then palladium(II)-acetate (0.017 g, 0.076 mmol) and 4,5-bis(diphenylphosphino)-9,9-dimethylxanthene (0.131 g, 0.227 mmol) were added. The suspension was then heated at 110° C. for 2 minutes. Then the title compound from Preparative Example 21 (0.150 g, 0.757 mmol), 4-chloro-2-nitropyridine (0.168 g, 1.059 mmol) and cesium carbonate (0.740 g, 2.270 mmol) were added and the stirring was continued at 120° C. for 4 hours. Water was added and the solid was filtered. The solid was washed with water and dried to afford the title compound (0.246 g, quant.).

MS (ESI); m/z=320.81 $[M+H]^+$.

Step B

A suspension of the title compound from Step A above (0.246.g, 0.770 mmol), di-tert.-butyl dicarbonate (0.252 g, 1.155 mmol) and 4-dimethylamino-pyridine (0.019.g, 0.154 mmol) in tetrahydrofuran (20 mL) was stirred at 60° C. for 4 hours. The reaction mixture was concentrated in vacuo and the crude product was purified on HP-Sil SNAP cartridges using a Biotage Isolera One purification system employing a dichloromethane/methanol gradient (98/2->90/10). Fractions containing the product were collected and the solvents were removed under reduced pressure. The smallest volume of ethyl acetate was added to solubilize the oily residue and a large volume of n-heptane was added. The suspension was dried under vacuum to dryness to afford the title compound as a beige solid (0.22 g, 70% over 2 steps).

$^1H$ NMR (400 MHz, DMSO-$d_6$) δ=9.45 (s, 1H), 8.85 (d, 1H), 8.60 (d, 1H), 8.48 (d, 1H), 8.23 (d, 1H), 7.73 (d, 1H), 7.51 (d, 1H), 7.41 (dd, 1H), 3.82 (s, 3H), 1.41 (s, 9H).

MS (ESI); m/z=421.11 $[M+H]^+$.

Example 106

Following the Pd-coupling procedure as described in Example 105, Step A, except using the amine derivatives and halogen derivatives indicated in the table below, the following compounds were prepared.

TABLE 12

| Amine derivative | Halogen derivative | Product Example | 1. Yield<br>2. $^1H$-NMR<br>3. $MH^+$ (ESI) |
|---|---|---|---|
| 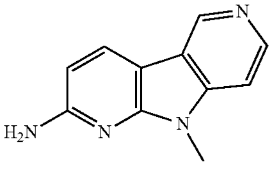 | 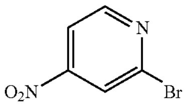 | 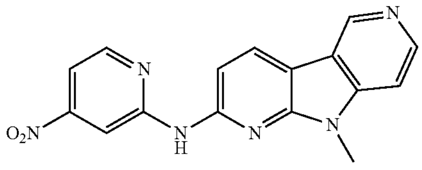 [SMILES: Cn1c2ccncc2c2ccc(Nc3cc([N+](=O)[O-])ccn3)nc21]<br>106 | 1. 65%<br>2. $^1H$ NMR (400 MHz, DMSO-$d_6$) δ = 10.74 (s, 1H), 9.27 (d, 2H), 8.61 (d, 1H), 8.51 (dd, 2H), 7.77-7.54 (m, 2H), 7.38 (d, 1H), 3.98 (s, 3H) |

Examples 107 to 109

Following the Boc-protection procedure as described in Example 105, Step B, except using the starting materials indicated in the table below, the following compounds were prepared. In case of Examples 108 and 109 the crude reaction products by following the procedure described in Example 105, Step A were directly used for Boc-protection as described in Example 105, Step B.

TABLE 13

| Starting material | Product Example | 1. Yield<br>2. $^1H$-NMR<br>3. $MH^+$ (ESI) |
|---|---|---|
| 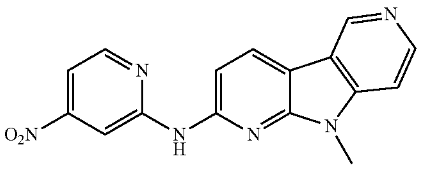 | 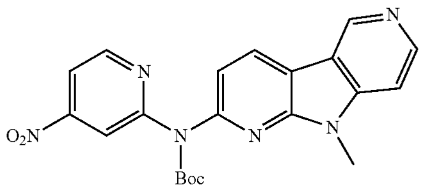<br>107 | 1. 85%<br>2. $^1H$ NMR (400 MHz, DMSO-$d_6$) δ = 9.42 (s, 1H), 8.76 (d, 1H), 8.59 (dd, 2H), 8.49 (d, 1H), 7.93 (dd, 1H), 7.70 (d, 1H), 7.44 (d, 1H), 3.79 (s, 3H), 1.44 (s, 9H) |

TABLE 13-continued

| Starting material | Product Example | 1. Yield<br>2. $^1$H-NMR<br>3. $MH^+$ (ESI) |
|---|---|---|
| 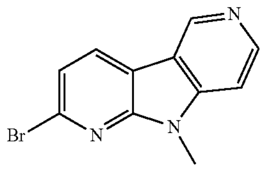 + 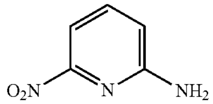 | 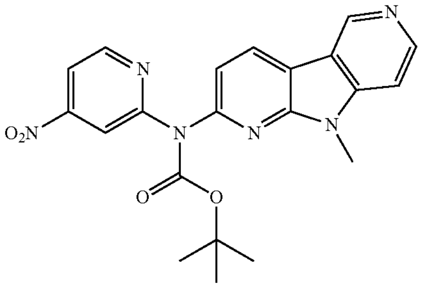<br>108 | 1. 60% (2 steps)<br>2. $^1$H NMR (400 MHz, DMSO-$d_6$) δ = 9.40 (s, 1H), 8.75 (d, 1H), 8.56 (d, 1H), 8.33 (t, 1H), 8.18 (d, 1H), 8.07 (d, 1H), 7.65 (d, 1H), 7.48 (d, 1H), 3.74 (s, 3H), 1.45 (s, 9H) |
| 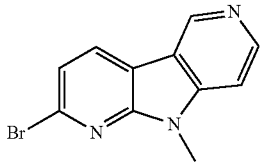 + 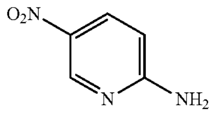 | 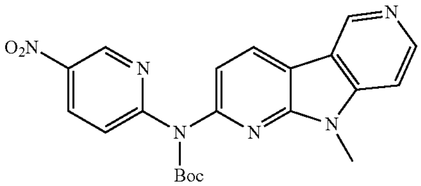<br>109 | 1. 77% (2 steps)<br>2. $^1$H-NMR (400 MHz, $CDCl_3$) δ = 9.36 (s, 1H), 9.05 (d, 1H), 8.68 (d, 1H), 8.61-8.47 (m, 2H), 8.15 (d, 1H), 7.41 (d, 1H), 7.29 (s, 1H), 3.89 (s, 3H), 1.48 (s, 9H) |

Example 110

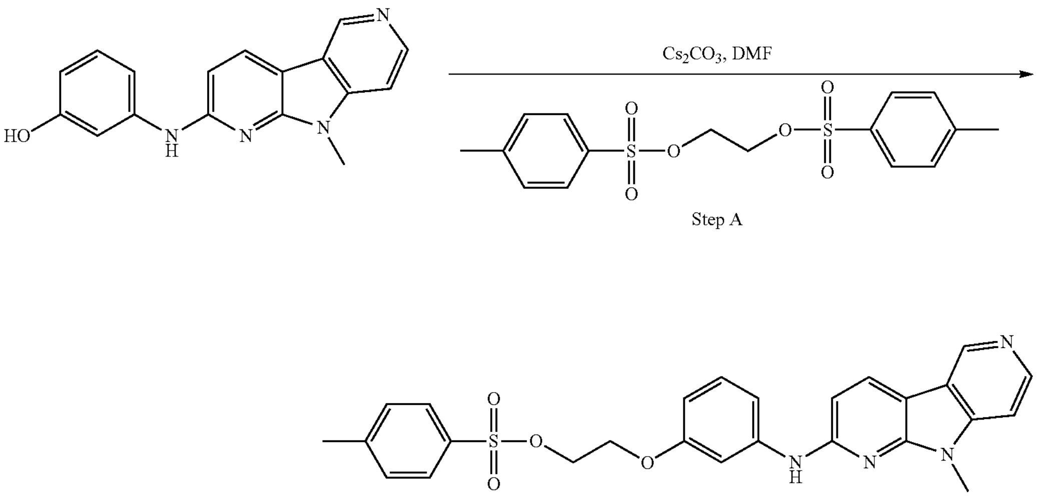

Step A

The title compound from Example 85 (0.3 g, 1.03 mmol) was suspended in N,N'-dimethylformamide (5 mL) and cesium carbonate (0.37 g, 1.13 mmol) was added. The reaction mixture was stirred at room temperature for 1 h and then commercially available ethane-1,2-diyl bis(4-methylbenzenesulfonate (0.5 g, 1.34 mmol) was added. The reaction mixture was heated at ~80° C. in a sand-bath for 5 hours. The reaction mixture was diluted with dichloromethane (60 mL) and water (30 mL). The organic phase was separated, dried over $Na_2SO_4$, filtered and the solvents were evaporated under reduced pressure. The residue was purified on HP-Sil SNAP cartridges using a Biotage Isolera One purification system employing an dichloromethane/methanol gradient (100/0->90/10) to afford the title compound as a beige solid/glass (0.1 g, 20%).

$^1$H-NMR (400 MHz, $CD_3OD$) δ=8.94 (d, 1H), 8.30 (d, 1H), 8.12 (d, 1H), 7.84-7.76 (m, 2H), 7.65 (s, 1H), 7.42 (d, 1H), 7.37 (d, 2H), 7.17-7.11 (m, 2H), 6.66 (d, 1H), 6.45-6.38 (m, 1H), 4.43-4.31 (m, 2H), 4.21-4.12 (m, 2H), 3.78 (s, 3H), 2.38 (s, 3H).

MS (ESI); m/z=489.15 $[M+H]^+$.

Example 111

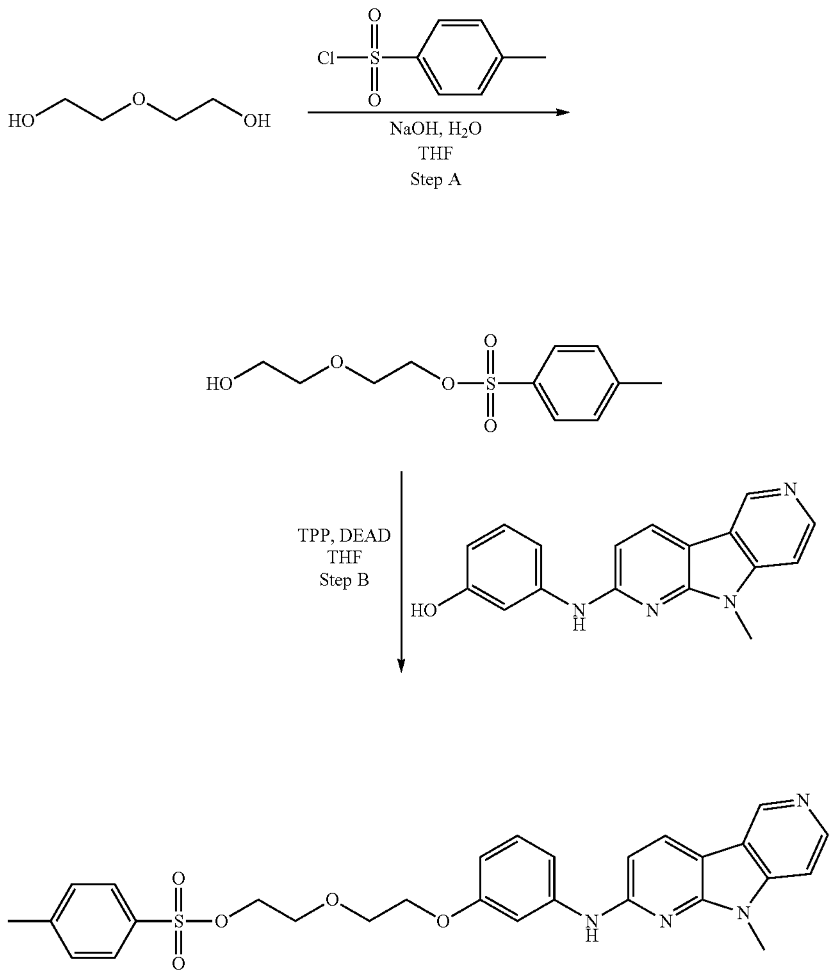

Step A

Diethyleneglycol (1.25 g, 11.8 mmol) was dissolved in water (3.5 mL) and sodium hydroxide (0.768 g, 19.2 mmol) was added. The mixture was stirred at room temperature until a clear solution was obtained. The mixture was cooled to 0° C. and a solution of 4-toluene sulfonylchloride (2.27 g, 11.9 mmol) in tetrahydrofuran (30 mL) was dropwise added over a period of 20 minutes. After the addition was completed, the reaction mixture was stirred at 0° C. for 1 hour. The reaction mixture was diluted with ethyl acetate (150 mL) and water (40 mL). The organic phase was separated, dried over $Na_2SO_4$, filtered and the solvents were evaporated under reduced pressure. The residue was purified on HP-Sil SNAP cartridges using a Biotage Isolera One purification system employing an dichloromethane/methanol gradient (100/0->100/0) to afford the more polar title compound as a colorless oil (1.47 g, 47%). The less polar bis-tosyl derivative was discarded.

$^1$H-NMR (400 MHz, $CDCl_3$) δ=7.80 (d, 2H), 7.35 (d, 2H), 4.22-4.18 (m, 2H), 3.72-3.66 (m, 4H), 3.55-3.51 (m, 2H), 2.45 (s, 3H).

Step B

The title compound from Example 85 (0.08 g, 0.276 mmol) was suspended in tetrahydrofuran (5 mL) and triphenylphosphine (0.178 g, 0.69 mmol) and the title compound from Step A above (0.085 g, 0.345 mmol) was added. After the addition of a solution of diethyl diazodicarboxylate in tetrahydrofuran (0.285 mL, 0.69 mmol), the reaction mixture was stirred at room temperature for 18 hours. The reaction mixture was concentrated under reduced pressure without heating and the residue was purified by chromatography on HP-Sil SNAP cartridges using a Biotage Isolera One purification system employing a dichloromethane/methanol gradient (100/0->50/50). The solvents of the fraction containing the less polar title compound were evaporated under reduced pressure without heating to afford the title compound as a pale yellow glass (0.032 g, 22%). The more polar phenol starting material was isolated as a beige solid (0.013 g, 16%).

$^1$H-NMR (400 MHz, DMSO-$d_6$): δ=9.45 (s, 1H), 9.15 (s, 1H), 8.41 (d, 1H), 8.34 (d, 1H), 7.79-7.76 (m, 3H), 7.55 (d, 1H), 7.40 (d, 2H), 7.33-7.30 (m, 1H), 7.20 (t, 1H), 6.80 (d, 1H), 6.52-6.48 (m, 1H), 4.17-4.15 (m, 2H), 4.08-4.05 (m, 2H), 3.86 (s, 3H), 3.73-3.67 (m, 4H), 2.34 (s, 3H).

Example 112

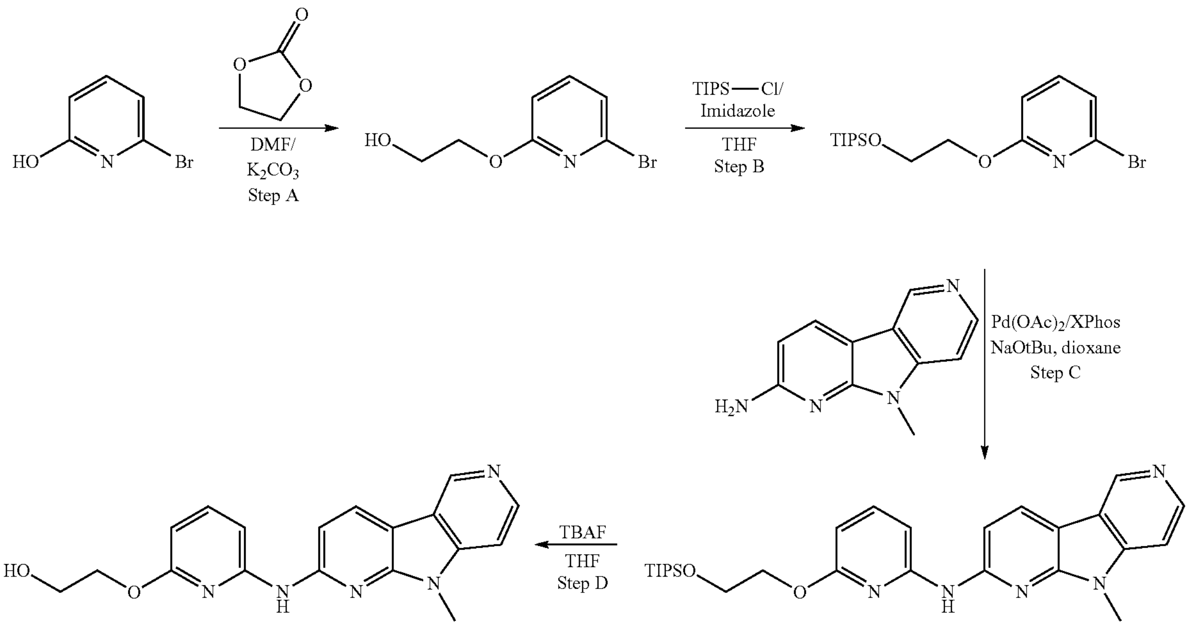

Step A

To a solution of commercially available 6-bromopyridin-2-ol (1 g, 5.7 mmol) in N,N'-dimethylformamide (10 mL) was added diethylcarbonate (1 g, 11.3 mmol) and potassium carbonate (1.19 g, 8.6 mmol). The reaction mixture was heated at 86° C. overnight. The reaction mixture was poured in ethyl acetate (20 mL) and washed with water (20 mL) and brine (20 mL) solution. The organic phase was separated, dried over $Na_2SO_4$ and filtered. The solvent was removed under reduced pressure and the residue was purified on HP-Sil SNAP cartridges using a Biotage Isolera One purification system employing a dichloromethane/methanol gradient (100/0->80/20) to afford the title compound (0.7 g, 56%).

$^1$H-NMR (400 MHz, DMSO-$d_6$) δ 7.65 (t, 1H), 7.21 (d, 1H), 6.86 (d, 1H), 4.84 (t, 1H), 4.23 (t, 2H), 3.69 (q, 2H).

Step B

To a solution of imidazole (0.48 g, 7.12 mmol), triisopropylsilyl chloride (915 μL, 4.27 mmol) in tetrahydrofuran (10 mL) at 0° C. was added dropwise a solution of the title compound from Step A above (0.623 g, 2.85 mmol) in tetrahydrofuran (5 mL). The reaction mixture was stirred at room temperature for 1 hour and was poured into water (20 mL), the mixture was stirred for 30 minutes and extracted with ethyl acetate (2×50 mL). The organic phases were combined, dried over $Na_2SO_4$ and filtered. The solvent was removed under reduced pressure and the residue was purified on HP-Sil SNAP cartridges using a Biotage Isolera One purification system employing a n-heptane/ethyl acetate gradient (100/0->60/40) to afford the title compound (0.72 g, 67%).

$^1$H-NMR (400 MHz, DMSO-$d_6$) δ=7.65 (t, 1H), 7.21 (d, 1H), 6.82 (d, 1H), 4.34 (dd, 2H), 4.08-3.89 (m, 2H), 1.35-0.75 (m, 21H).

Step C

An oven dried Schlenk flask was evacuated and back filled with argon gas. The procedure was repeated 3-4 times and the flask was cooled to room temperature. Then the title compound from Step B above (0.566 g, 1.51 mmol), the title compound from Preparative Example 21 (0.25 g, 1.26 mmol), palladium(II)-acetate (0.0028 g, 0.126 mmol), 4,5-bis(diphenylphosphino)-9,9-dimethylxanthene (0.218 g, 0.378 mmol), cesium carbonate (1.23 g, 3.78 mmol) and 1,4-dioxane (10 mL) were added and the reaction mixture was heated at 110° C. in a sand-bath for 4 h. The solvent was removed under reduced pressure and the residue was purified on HP-Sil SNAP cartridges using a Biotage Isolera One purification system employing a dichloromethane/methanol gradient (100/00->90/10) to afford the title compound (0.39 g 63%).

$^1$H-NMR (400 MHz, DMSO-$d_6$) δ=9.82 (s, 1H), 9.18 (s, 1H), 8.68-8.29 (m, 2H), 7.74-7.46 (m, 4H), 6.31 (dd, 1H), 4.39 (dd, 2H), 4.02 (dd, 2H), 3.89 (s, 3H), 1.37-0.79 (m, 21H).

MS (ESI); m/z=493.18 $[M+H]^+$.

Step D To a cooled (0° C.) solution of the title compound from Step C above (0.390 g, 0.79 mmol) in tetrahydrofuran (10 mL) was added a 1 M solution of tetrabutylammonium fluoride in tetrahydrofuran (2.37 mL, 2.37 mmol). The reaction mixture was then stirred at room temperature overnight. The solvent was removed and the residue was purified on HP-Sil SNAP cartridges using a Biotage Isolera One purification system employing a dichloromethane/methanol gradient (100/0->80/20) to afford the title compound (0.235 g, 95%).

$^1$H-NMR (400 MHz, DMSO-$d_6$) δ=9.83 (s, 1H), 9.19 (s, 1H), 8.53-8.30 (m, 2H), 7.79-7.62 (m, 2H), 7.63-7.49 (m, 2H), 6.34 (dd, 1H), 4.85 (t, 1H), 4.32 (t, 2H), 3.90 (s, 3H), 3.83-3.65 (m, 2H).

MS (ESI); m/z=336.42 $[M+H]^+$.

Example 113

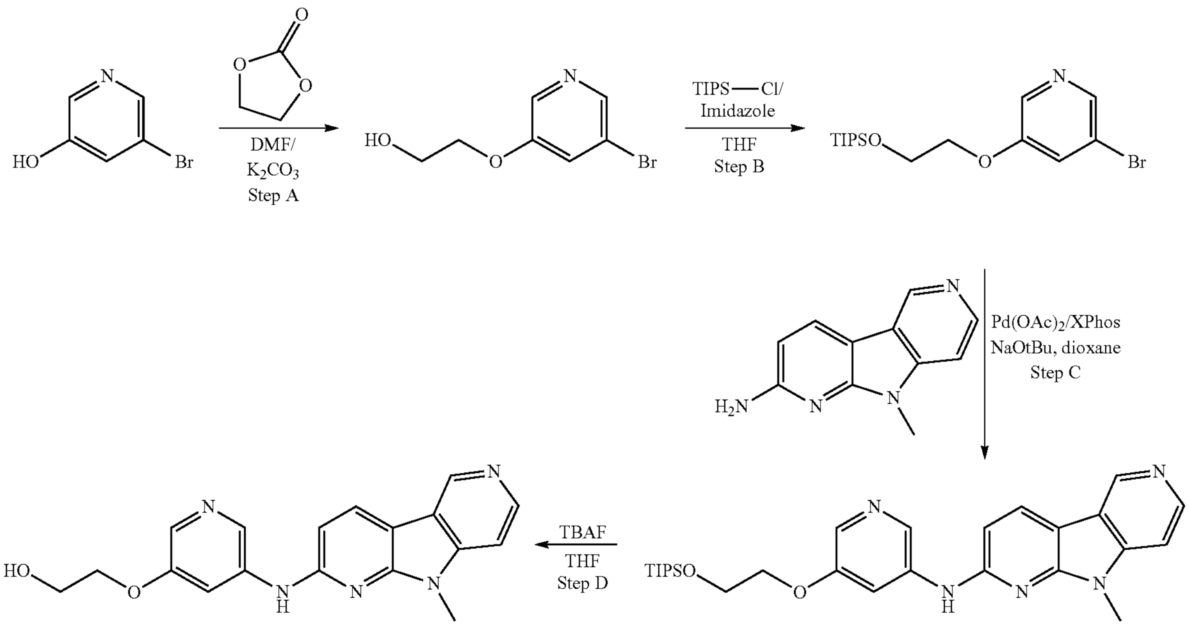

Step A

To a solution of commercially available 5-bromopyridin-3-ol (2 g, 11.62 mmol) in N,N'-dimethylformamide (10 mL) was added diethylcarbonate (2.5 g, 28 mmol) and potassium carbonate (3 g, 21 mmol). The reaction mixture was heated at 110° C. overnight. The reaction mixture was poured in ethyl acetate and the mixture was washed with water and brine solution. The organic phase was separated, dried over $Na_2SO_4$ and filtered. The solvent was removed under reduced pressure and the residue was purified on HP-Sil SNAP cartridges using a Biotage Isolera One purification system employing a dichloromethane/methanol gradient (100/0->80/20) to afford the title compound (2.31 g, 92%).

$^1$H-NMR (400 MHz, $CDCl_3$) δ=8.33-8.28 (m, 1H), 8.27-8.23 (m, 1H), 7.40 (d, 1H), 4.17-4.09 (m, 2H), 4.05-3.96 (m, 2H).

Step B

To a solution of the title compound from Step A above (1 g, 4.6 mmol) in tetrahydrofuran (5 mL) was added imidazole (0.78 g, 11.5 mmol), followed by triisopropylsilyl chloride (1.6 g, 9.2 mmol). The reaction mixture was stirred at room temperature for 1 hour. The reaction mixture was poured in ethyl acetate (200 mL) and washed with water and brine solution. The organic phase was separated, dried over $Na_2SO_4$ and filtered. The solvent was removed under reduced pressure and the residue was purified on HP-Sil SNAP cartridges using a Biotage Isolera One purification system employing a n-heptane/ethyl acetate gradient (80/20->20/80) to afford the title compound (1.2 g 70%).

Step C

An oven dried Schlenk flask was evacuated and back filled with argon gas. The procedure was repeated 3-4 times and the flask was cooled to room temperature. Then dicyclohexyl-(2',4',6'-triisopropyl-[1,1'-biphenyl]-2-yl)phosphine (0.05 mg, 0.1 mmol) and palladium(II)-acetate (0.008 g, 0.03 mmol) were heated at 110° C. for 1 minute to become a clear red solution. Then the title compound from Preparative Example 21 (0.155 g, 0.79 mmol), the title compound from Step B above (bromo) (0.294 g, 0.0.79 mmol), and sodium tert.-butoxide (0.1 g, 1.04 mmol) were added. The reaction mixture was heated at 110° C. in a sand-bath for 3 hours, cooled to room temperature and the solvents were removed under reduced pressure. The residue was purified on HP-Sil SNAP cartridges using a Biotage Isolera One purification system employing a dichloromethane/methanol gradient (100/0->90/10) to afford the title compound (0.195 g, 50%).

$^1$H-NMR (400 MHz, DMSO-$d_6$) δ=9.72 (s, 1H), 9.19 (s, 1H), 8.54-8.32 (m, 4H), 7.88 (d, 1H), 7.62 (d, 1H), 6.84 (s, 1H), 4.31-4.06 (m, 2H), 4.11-3.95 (m, 2H), 3.89 (s, 3H), 3.58-3.46 (m, 2H), 3.46-3.42 (m, 1H), 1.04 (d, 18H).

Step D

To a solution of the title compound from Step C above (0.195 g, 0.397 mmol) in tetrahydrofuran (5 mL) was added a 1 M solution of tetrabutylammonium fluoride in tetrahydrofuran (4 mL). The reaction mixture was then stirred at room temperature overnight. The solvent was removed and the residue was purified on HP-Sil SNAP cartridges using a Biotage Isolera One purification system employing a dichloromethane/methanol gradient (100/0->80/20) to afford the title compound (0.060 g, 45%).

$^1$H-NMR (400 MHz, DMSO-$d_6$) δ=9.74 (s, 1H), 9.20 (s, 1H), 8.50 (d, 1H), 8.50-8.40 (m, 3H), 8.33 (t, 1H), 7.90 (d, 1H), 7.63 (d, 1H), 6.87 (d1H), 5.04-4.92 (m, 1H), 4.21-4.10 (m, 2H), 3.92 (s, 3H), 3.86-3.74 (m, 2H).

Example 114

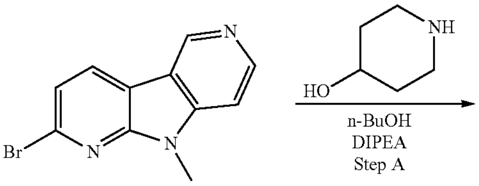

-continued

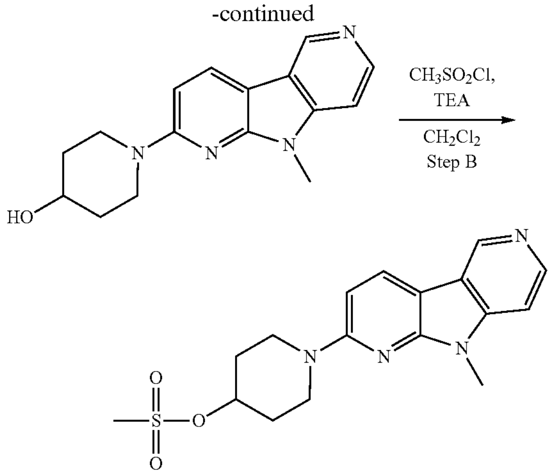

Step A

To a microwave tube were added the title compound from Preparative Example 1 (0.3 g, 1.14 mmol), piperidin-4-ol (0.347 g, 3.42 mmol), n-butanol (4 mL), followed by N,N'-diisopropylethylamine (1.1 mL, 6.84 mmol). The tube was sealed and heated at 200° C. for 2 hours using a Biotage Initiator microwave. The solvents were removed under reduced pressure and the residue was purified on HP-Sil SNAP cartridges using a Biotage Isolera One purification system employing a methanol/dichloromethane gradient (0/100->10/90) to afford the title compound (0.28 g, 86%).

$^1$H NMR (400 MHz, DMSO-$d_6$) δ=9.11 (s, 1H), 8.39 (d, 1H), 8.30 (d, 1H), 7.54 (d, 1H), 6.85 (d, 1H), 4.75 (d, 1H), 4.20 (dt, 2H), 4.11 (d, 1H), 3.81 (s, 4H), 3.32-3.11 (m, 3H), 1.86 (dt, 2H), 1.44 (dt, 2H).

Step-B

To a solution of the title compound from Step A above (0.2 g, 0.73 mmol) in dichloromethane (10 mL) triethylamine (0.122 mL, 0.876 mmol) was added and the mixture was cooled at 0° C. Then methanesulfonyl chloride (0.067 mL, 0.876 mmol) was added and the mixture was stirred at 0° C. for 30 minutes and at room temperature for 2 hours. Another equivalent of triethylamine, followed by another equivalent of methanesulfonyl chloride was added to the reaction mixture at room temperature in order to get complete conversion of the starting material. A saturated ammonium chloride solution (20 mL) was added to the mixture, followed by dichloromethane (10 mL). The phases were separated and the organic layer was washed with saturated ammonium chloride solution (20 mL) and water (20 mL). The organic phase was dried over $Na_2SO_4$ and the solvent was removed under reduced pressure. The residue was triturated with ethyl acetate (10 mL), the precipitate was collected by filtration and dried under reduced pressure to afford the title compound (0.045 g). The collected aqueous phases were extracted twice with a solution of dichloromethane (20 mL) and methanol (1 mL). The organic layers were collected, dried over $Na_2SO_4$ and the solvents were removed under reduced pressure. The residue was purified on HP-Sil SNAP cartridges using a Biotage Isolera One purification system employing a dichloromethane/methanol gradient (100/0->90/10) to afford more of the title compound (0.02 g) to total yield of 0.065 g (25%).

$^1$H NMR (400 MHz, DMSO-$d_6$) δ 9.25 (s, 1H), 8.49 (d, 1H), 8.39 (d, 1H), 7.78 (d, 1H), 6.98 (d, 1H), 4.97 (dt, 1H), 4.13 (d, 2H), 3.86 (s, 3H), 3.54 (t, 1H), 3.24 (m, 2H), 2.06 (m, 2H), 1.77 (m, 2H).

MS (ESI); m/z=361.23 [M+H]$^+$.

Examples 115 to 126

Following the coupling procedure as described in Example 114, Step A, except using the bromo and amino-alcohol derivatives indicated in the table below, the following compounds were prepared.

TABLE 14

| Bromo derivative | Amino-alcohol derivative | Product Example | 1. Yield<br>2. $^1$H-NMR<br>3. MH$^+$ (ESI) |
|---|---|---|---|
| 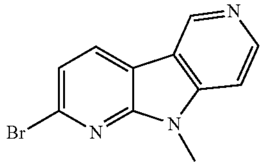 | 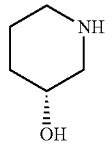 | 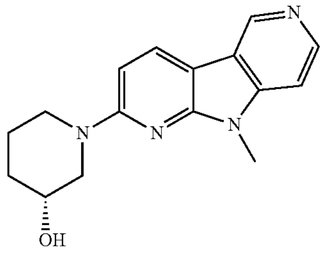<br>115 | 1. 28%<br>2. $^1$H-NMR (400 MHz, DMSO-$d_6$) δ = 9.08 (s, 1H), 8.36 (d, 1H), 8.26 (d, 1H), 7.50 (d, 1H), 6.78 (d, 1H), 5.02-4.73 (m, 1H), 4.34 (dd, 1H), 4.16 (d, 1H), 3.79 (s, 3H), 3.66-3.45 (m, 1H), 3.12-2.96 (m, 1H), 2.94-2.78 (m, 1H), 2.04- 1.88 (m, 1H), 1.88-1.73 (m, 1H), 1.55-1.33 (m, 2H)<br>3. 282.85 |

TABLE 14-continued

| Bromo derivative | Amino-alcohol derivative | Product Example | 1. Yield<br>2. $^{1}H$-NMR<br>3. $MH^{+}$ (ESI) |
|---|---|---|---|
| 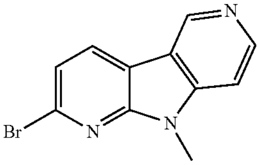 | 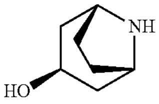 | 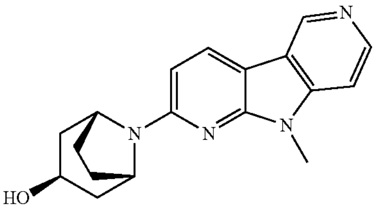<br>116 | 1. 43%<br>2. $^{1}H$-NMR (400 MHz, DMSO-$d_6$) δ 9.06 (s, 1H), 8.34 (d, 1H), 8.25 (d, 1H), 7.48 (d, 1H), 6.66 (d, 1H), 4.69-4.54 (m, 3H), 3.84 (s, 1H), 3.77 (s, 3H), 2.32 (q, 2H), 2.06 (dt, 2H), 2.00-1.87 (m, 2H), 1.66 (d, 2H).<br>3. 309.02 |
| 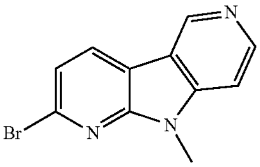 | 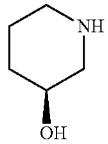 | 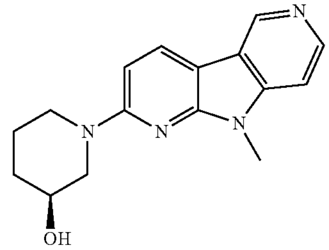<br>117 | 1. 67%<br>2. $^{1}H$-NMR (400 MHz, DMSO-$d_6$) δ 9.39 (s, 1H), 8.59 (d, 1H), 8.43 (d, 1H), 8.06 (d, 1H), 6.95-6.79 (m, 1H), 4.69 (s, 3H), 3.92 (s, 3H), 3.85 (s, 1H), 2.35 (q, 2H), 2.12-1.90 (m, 4H), 1.73 (d, 2H).<br>3. 308.92 |
| 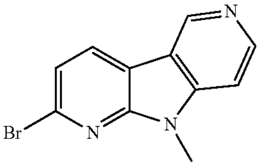 | 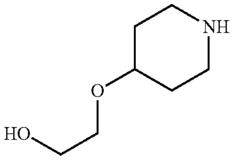 | 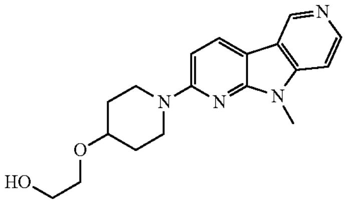<br>118 | 1. 40%<br>2. $^{1}H$.NMR (400 MHz, DMSO-$d_6$) δ = 9.16-9.02 (m, 1H), 8.36 (d, 1H), 8.28 (d, 1H), 7.49 (dd, 1H), 6.82 (d, 1H), 4.58 (t, 1H), 4.15 (dt, 2H), 3.78 (s, 3H), 3.58 (dt, 1H), 3.49 (q, 4H), 3.30-3.20 (m, 2H), 1.95 (d, J = 13.0 Hz, 2H), 1.49 (dq, 2H)<br>327.05 |
| 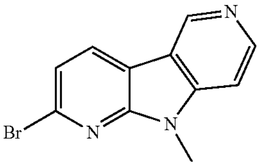 | 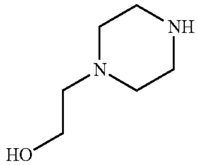 | 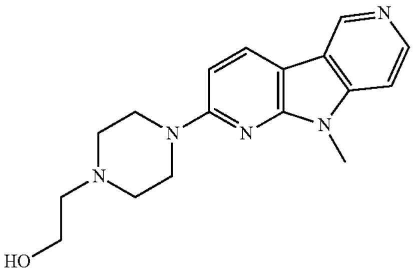<br>119 | 1. 96%<br>2. $^{1}H$-NMR (400 MHz, DMSO-$d_6$) δ = 9.13 (s, 1H), 8.40 (d, 1H), 8.33 (d, 1H), 7.56 (d, 1H), 6.84 (d, 1H), 4.78-4.41 (m, 1H), 3.80 (s, 3H), 3.76-3.66 (m, 4H), 3.60 (t, 2H), 2.77-2.64 (m, 4H), 2.58 (t, 2H). |
| 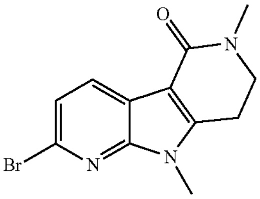 [SMILES: CN1CCc2c(c3ccc(Br)nc3n2C)C1=O] | 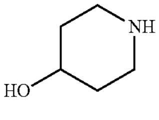 | 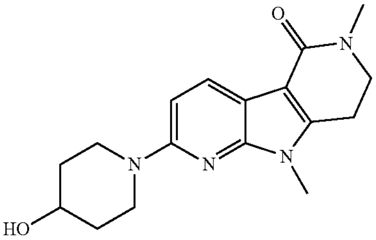<br>120 | 1. 26%<br>2. 329.3 |

TABLE 14-continued

| Bromo derivative | Amino-alcohol derivative | Product Example | 1. Yield<br>2. $^{1}$H-NMR<br>3. $MH^{+}$ (ESI) |
|---|---|---|---|
| 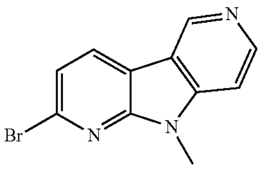 | 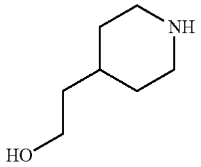 | 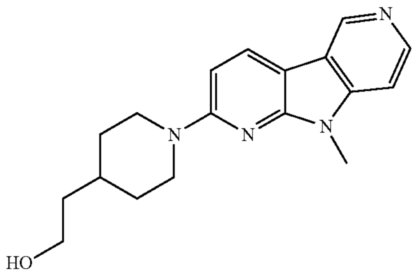<br>121 | 1. 91%<br>2. $^{1}$H-NMR (400 MHz, DMSO-$d_6$) δ = 9.08 (d, 1H), 8.37 (d, 1H), 8.27 (d, 1H), 7.50 (dd, 1H), 6.81 (d, 1H), 4.49 (d, 2H), 4.39 (s, 1H), 3.79 (s, 3H), 3.49 (t, 2H), 2.90 (td, 2H), 1.86-1.63 (m, 3H), 1.40 (q, 2H), 1.29-1.10 (m, 2H)<br>3. 311.23 |
| 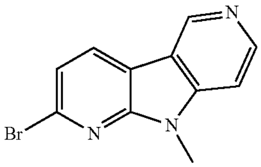 | 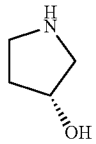 | 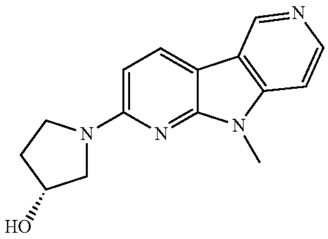<br>122 | 1. 23%<br>2. $^{1}$H-NMR (400 MHz, DMSO-$d_6$) δ = 9.24 (s, 1H), 8.48 (d, 1H), 8.35 (d, 1H), 7.78 (d, 1H), 6.54 (d, 1H), 5.05 (s, 1H), 4.55-4.42 (m, 1H), 3.87 (s, 3H), 3.74-3.45 (m, 4H), 2.20-2.03 (m, 1H), 2.03-1.80 (m, 1H). |
| 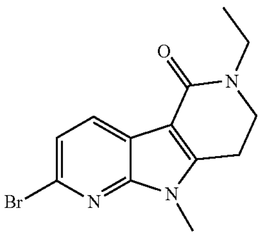 [SMILES: CCN1CCc2c(c3ccc(Br)nc3n2C)C1=O] | 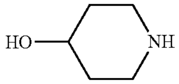 | 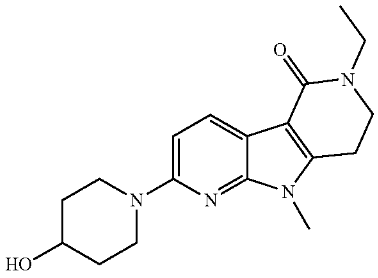<br>123 | 1. 55%<br>2. $^{1}$H NMR (400 MHz, DMSO-$d_6$) δ 7.94 (d, 1H), 6.74 (d, 1H), 4.71 (d, 1H), 4.07 (dt, 2H), 3.70 (dq, 1H), 3.62 (d, 5H), 3.44 (q, 2H), 3.17-2.92 (m, 4H), 1.82 (dq, 2H), 1.41 (dtd, 2H), 1.10 (t, 3H). |
| 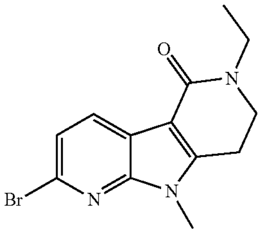 [SMILES: CCN1CCc2c(c3ccc(Br)nc3n2C)C1=O] | 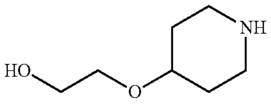 | 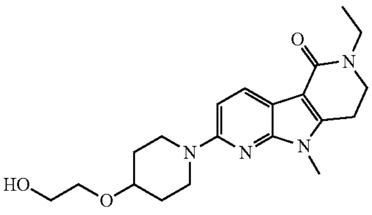<br>124 | 1. 32%<br>3. 373.3 |
| 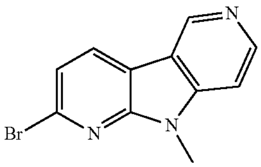 | 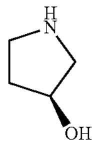 | 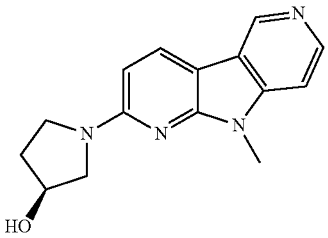<br>125 | 1. 88%<br>2. $^{1}$H-NMR (400 MHz, DMSO-$d_6$) δ = 9.22 (s, 1H), 8.46 (d, 1H), 8.33 (d, 1H), 7.76 (d, 1H), 6.53 (d, 1H), 5.02 (s, 1H), 4.51-4.37 (m, 1H), 3.86 (s, 3H), 3.70-3.43 (m, 4H), 2.20-2.01 (m, 1H), 2.01-1.87 (m, 1H<br>3. 269.29 |

TABLE 14-continued

| Bromo derivative | Amino-alcohol derivative | Product Example | 1. Yield 2. $^{1}$H-NMR 3. MH$^{+}$ (ESI) |
|---|---|---|---|
| 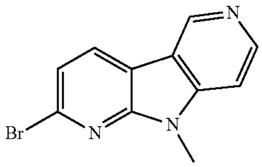 | 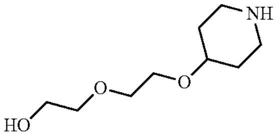 [SMILES: OCCOCCOC1CCNCC1] | 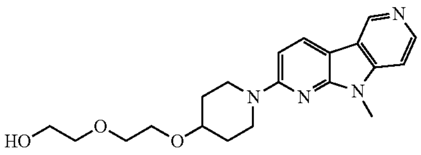 126 | 1. 78% 2. $^{1}$H-NMR (400 MHz, DMSO-d$_6$) δ = 9.09 (s, 1H), 8.37 (d, 1H), 8.28 (d, 1H), 7.50 (d, 1H), 6.83 (d, 1H), 4.57 (t, 1H), 4.14 (dd, 2H), 3.79 (s, 3H), 3.51 (ddt, 9H), 3.30-3.22 (m, 2H), 2.05-1.88 (m, 2H), 1.57-1.40 (m, 2H). 3. 371.0 |

Example 127

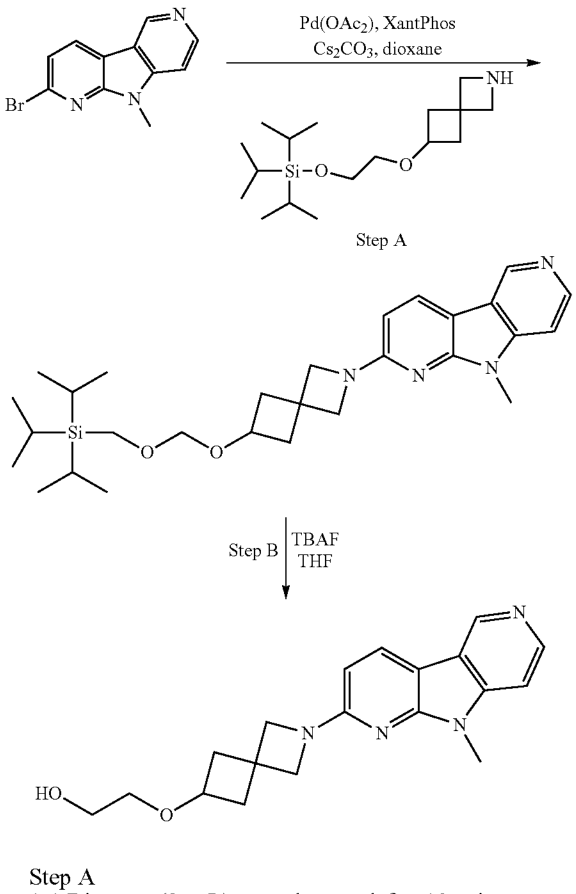

Step A 1,4-Dioxane (8 mL) was degassed for 10 minutes and palladium(II)-acetate (0.0173 g, 0.076 mmol) and 5-bis (diphenylphosphino)-9,9-dimethylxanthene (0.132 g, 0.229 mmol) were added. The suspension was heated at ~110° C. in a sand-bath for 2 minutes. Then the title compound from Preparative Example 1 (0.2 g, 0-763 mmol), the title compound from Preparative Example 64 (0.339 g, 3.05 mmol) and cesium carbonate (0.994 g, 3.05 mmol) were added and heating was continued at ~120° C. for 30 minutes. The reaction mixture was concentrated in vacuo and the residue was purified by chromatography on silica using dichloromethane/methanol (93/7) as a mobile phase to afford the title compound (0.275 g, 73%).

$^{1}$H-NMR (400 MHz, DMSO-d$_6$) δ=9.09 (s, 1H), 8.36 (d, 1H), 8.27 (d, 1H), 7.50 (d, 1H), 6.28 (d, 1H), 4.09-3.92 (m, 5H), 3.79-3.71 (m, 5H), 3.38 (t, 2H), 2.58-2.52 (m, 2H), 2.09 (ddd, 2H), 1.04 (d, 21H).

Step B

To a solution of the title compound from Step A above (0.188 g, 0.380 mmol) in dichloromethane (20 mL) was added at 0° C. a 1 M solution of tetrabutylammonium fluoride in tetrahydrofuran (1.140 mL, 1.140 mmol). The reaction mixture was stirred at room temperature for 18 hours. Then 1 N NaOH was added until pH 10 was reached and the aqueous phase was extracted several times with dichloromethane. The combined organics were dried over $Na_2SO_4$, filtered and dried under reduced pressure. The residue was purified on HP-Sil SNAP cartridges using a Biotage Isolera One purification system employing a dichloromethane/methanol gradient (98/2->85/15) to afford the title compound contaminated with tetrabultylammonium salt (0.3 g, >100%).

$^{1}$H-NMR (400 MHz, DMSO-d$_6$) δ=9.19 (s, 1H), 8.43 (d, 1H), 8.33 (d, 1H), 7.66 (d, 1H), 6.34 (d, 1H), 4.63 (s, 1H), 4.08 (s, 2H), 4.03 (s, 2H), 3.93 (p, 1H), 3.81 (s, 3H), 3.51-3.43 (m, 2H), 3.30 (m, 2H), 2.57-2.51 (m, 2H), 2.11 (ddd, 2H).

MS (ESI); m/z=339.14 [M+H]$^{+}$.

Examples 128 to 144

Following the alkylation procedure as described in Example 114, Step B, except using the alcohol derivatives and alkylation reagents indicated in the table below, the following compounds were prepared. Reactions using tosyl chloride can also be performed in tetrahydrofuran using aqueous sodium hydroxide as a base.

TABLE 15
| Alcohol derivative | Alkylation reagent | Product Example | 1. Yield 2. $^{1}$H-NMR 3. $MH^+$ (ESI) |
|---|---|---|---|
| 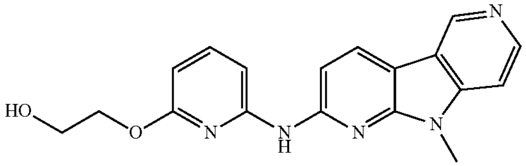 [SMILES: Cn1c2ccncc2c2ccc(Nc3cccc(OCCO)n3)nc21] | 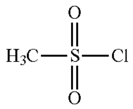 | 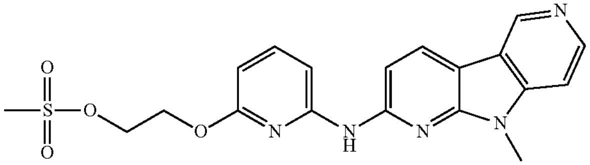 128 | 1. 38% 2. $^{1}$H-NMR (400 MHz, DMSO-$d_6$) δ = 9.91 (s, 1H), 9.64 (s, 1H), 8.80 (d, 1H), 8.72 (d, 1H), 8.25 (d, 1H), 8.22-8.08 (m, 2H), 7.63 (d, 1H), 6.86 (d, 1H), 5.12-4.80 (m, 4H), 4.02 (s, 3H), 2.33 (s, 3H) 3. 317.73 |
| 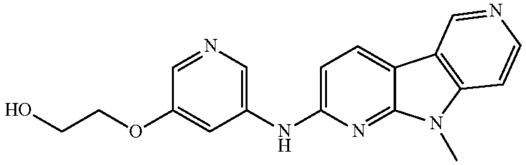 [SMILES: Cn1c2ccncc2c2ccc(Nc3cncc(OCCO)c3)nc21] | 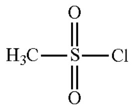 | 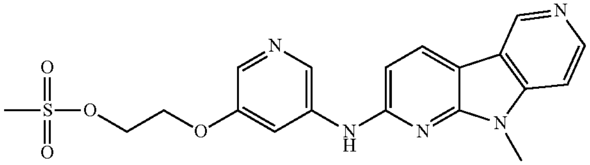 129 | 1. 77% |
| 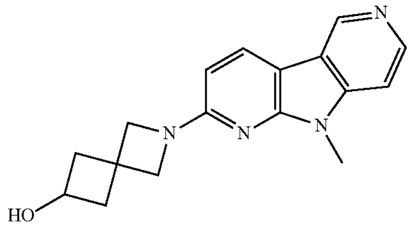 [SMILES: Cn1c2ccncc2c2ccc(N3CC4(CC(O)C4)C3)nc21] | 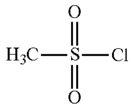 | 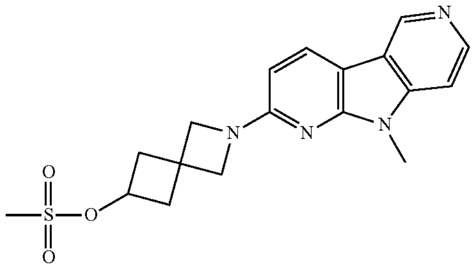 130 | 1. 87% 2. $^{1}$H-NMR (400 MHz, DMSO-$d_6$) δ = 9.44 (s, 1H), 8.61 (d, 1H), 8.46 (d, 1H), 8.09 (d, 1H), 6.51 (d, 1H), 5.10-4.90 (m, 1H), 4.16 (d, 4H), 3.92 (s, 3H), 3.17 (s, 3H), 2.76 (ddd, 2H), 2.57-2.51 (m, 2H). 3. 373.12 |

TABLE 15-continued
| Alcohol derivative | Alkylation reagent | Product Example | 1. Yield<br>2. $^1$H-NMR<br>3. $MH^+$ (ESI) |
|---|---|---|---|
| 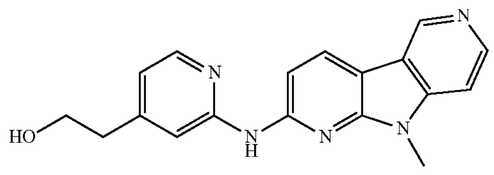 [SMILES: Cn1c2ccncc2c2ccc(Nc3cc(CCO)ccn3)nc21] | 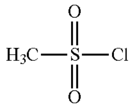 | 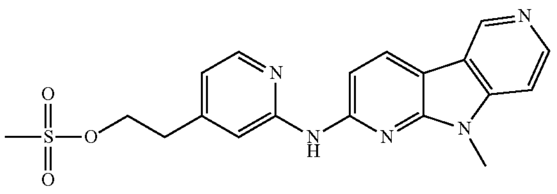<br>131 | 1. >100% (contains TEA × HCl)<br>3. 398.1 |
| 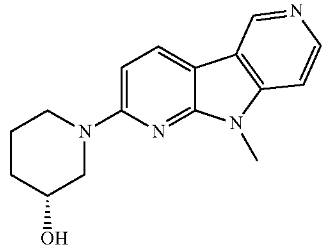 [SMILES: Cn1c2ccncc2c2ccc(N3CCC[C@@H](O)C3)nc21] | 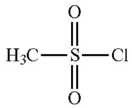 | 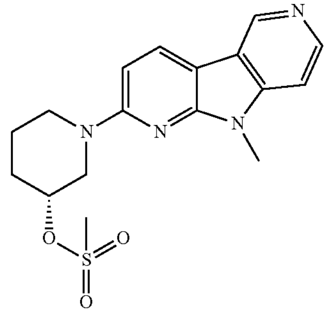<br>132 | 1. 56%<br>2. $^1$H NMR (400 MHz, DMSO-$d_6$) δ = 9.46 (s, 1H), 8.64 (d, 1H), 8.50 (d, 1H), 8.11 (d, 1H), 7.09 (d, 1H), 4.91-4.67 (m, 1H), 4.13 (d, 6H), 3.95 (s, 3H), 3.91-3.77 (m, 1H), 3.79-3.68 (m, 1H), 2.15-2.04 (m, 1H), 1.97-1.88 (m, 0H), 1.88-1.72 (m, 1H), 1.72-1.55 (m, 1H). |
| 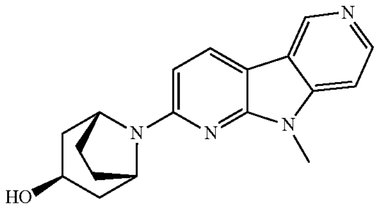 [SMILES: Cn1c2ccncc2c2ccc(N3[C@@H]4CC[C@H]3C[C@@H](O)C4)nc21] | 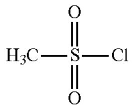 | 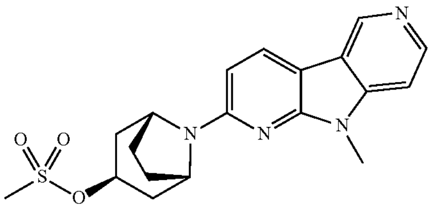<br>133 | 1. 81%<br>2. $^1$H-NMR (400 MHz, DMSO-$d_6$) δ = 9.45 (s, 1H), 8.63 (d, 1H), 8.50 (d, 1H), 8.18-8.04 (m, 1H), 7.06-6.93 (m, 1H), 4.98-4.83 (m, 1H), 4.83-4.70 (m, 2H), 3.95 (s, 3H), 3.20 (s, 3H), 2.35-2.14 (m, 4H), 2.12-1.92 (m, 4H)<br>3. 387.19 |

TABLE 15-continued
| Alcohol derivative | Alkylation reagent | Product Example | 1. Yield 2. $^1$H-NMR 3. MH$^+$ (ESI) |
|---|---|---|---|
| 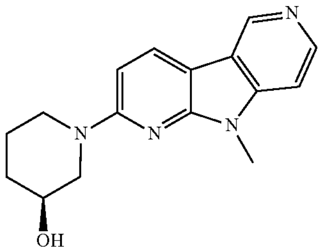 [SMILES: Cn1c2ccncc2c2ccc(N3CCC[C@H](O)C3)nc21] | 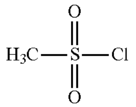 | 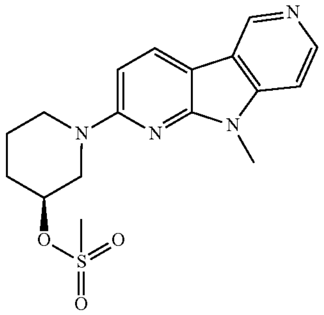 134 | 1. 42% 2. $^1$H-NMR (400 MHz, DMSO-$d_6$) δ = 9.46 (s, 1H), 8.63 (d, 1H), 8.50 (d, 1H), 8.10 (d, 1H), 7.07 (d, 1H), 4.89-4.75 (m, 1H), 4.26-3.90 (m, 5H), 3.90-3.76 (m, 1H), 3.76-3.62 (m, 1H), 3.24 (s, 3H), 2.15-2.03 (m, 1H), 2.00-1.72 (m, 2H), 1.72-1.54 (m, 1H) 3. 361.1 |
| 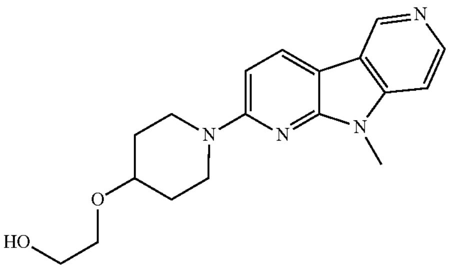 [SMILES: Cn1c2ccncc2c2ccc(N3CCC(OCCO)CC3)nc21] | 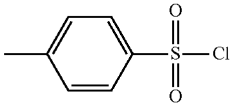 | 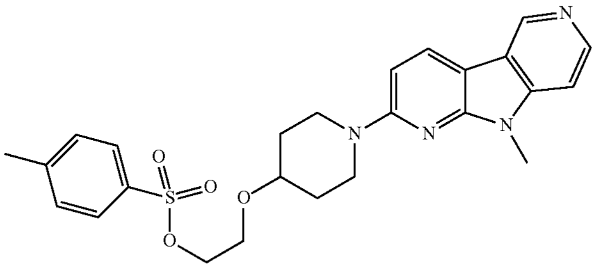 135 | 1. 82% 2. $^1$H-NMR (400 MHz, DMSO-$d_6$) δ = 9.42 (s, 1H), 8.62 (d, 1H), 8.46 (d, 1H), 8.09 (d, 1H), 7.71 (m, 2H), 7.46 (m, 1H), 7.08 (d, 2H), 4.12 (m, 3H), 3.93 (s, 3H), 3.85-3.51 (m, 4H), 3.40 (m, 2H), 2.28 (s, 3H), 1.85 (m, 2H), 1.41 (m, 2H) |
| 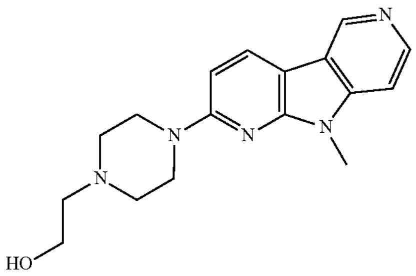 [SMILES: Cn1c2ccncc2c2ccc(N3CCN(CCO)CC3)nc21] | 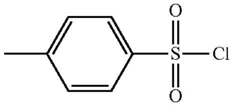 | 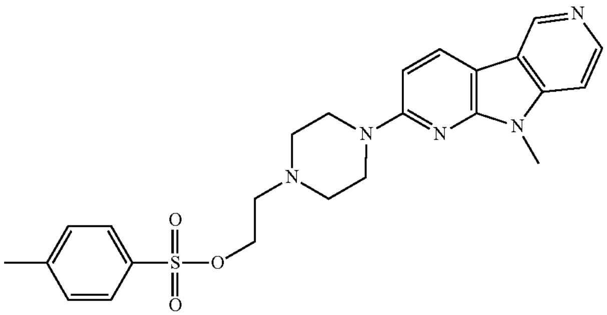 136 | 1. 18% 2. $^1$H-NMR (400 MHz, DMSO-$d_6$) δ = 9.46 (s, 1H), 8.65 (d, 1H), 8.54 (d, 1H), 8.11 (d, 1H), 7.46 (d, 2H), 7.16-7.00 (m, 3H), 4.15-3.62 (m, 9H), 3.17-2.74 (m, 6H), 2.27 (s, 3H) |

TABLE 15-continued
| Alcohol derivative | Alkylation reagent | Product Example | 1. Yield 2. $^1$H-NMR 3. $MH^+$ (ESI) |
|---|---|---|---|
| 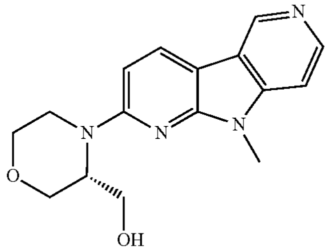 | 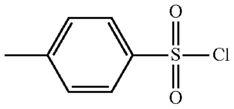 | 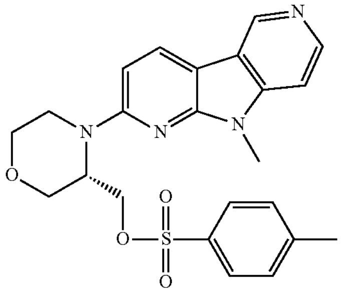 137 | 1. 60% 2. $^1$H-NMR (400 MHz, $CDCl_3$) δ = 9.20 (s, 1H), 8.55 (d, 1H), 8.24 (d, 1H), 7.87-7.64 (m, 2H), 7.43-7.31 (m, 1H), 7.33-7.13 (m, 1H), 6.64 (d, 1H), 4.76 (dd, 1H), 4.61 (dd, 1H), 4.40 (ddd, 1H), 4.07 (d, 1H), 3.93 (s, 3H), 3.87-3.79 (m, 1H), 3.68-3.61 (m, 1H), 3.59-3.47 (m, 1H), 3.47-3.41 (m, 1H), 2.39 (s, 4H), 2.13 (s, 1H) |
| 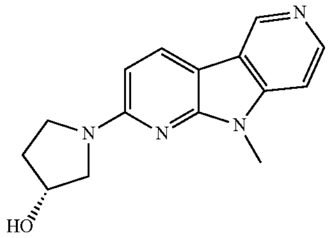 [SMILES: Cn1c2ccncc2c2ccc(N3CC[C@@H](O)C3)nc21] | 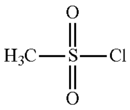 | 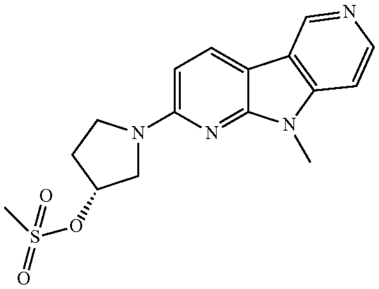 138 | 1. 23% 2. $^1$H-NMR (400 MHz, DMSO-$d_6$) δ = 9.44 (s, 1H), 8.63 (d, 1H), 8.50 (d, 1H), 8.11 (d, 1H), 6.75 (d, 1H), 5.50 (s, 1H), 4.01-3.71 (m, 6H), 3.63 (s, 1H), 3.29 (s, 3H), 2.39 (s, 2H) 3. 347.2 |

TABLE 15-continued
| Alcohol derivative | Alkylation reagent | Product Example | 1. Yield<br>2. $^{1}$H-NMR<br>3. MH$^{+}$ (ESI) |
|---|---|---|---|
| 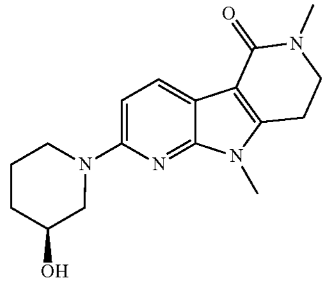 [SMILES: CN1CCc2c(c3ccc(N4CCC[C@H](O)C4)nc3n2C)C1=O] | 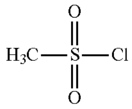 | 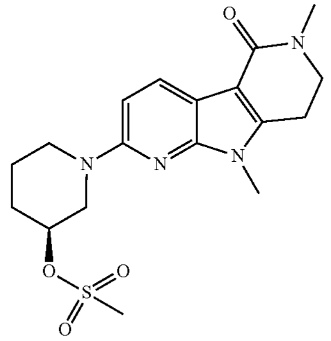<br>139 | 1. 44%<br>2. $^{1}$H-NMR (400 MHz, $CDCl_3$) δ = 8.23 (d, 1H), 6.71 (dd, 1H), 5.04-4.86 (m, 1H), 4.35-4.26 (m, 1H), 3.80-3.64 (m, 5H), 3.62-3.52 (m, 1H), 3.42-3.30 (m, 1H), 3.21-2.96 (m, 9H), 2.26-2.09 (m, 1H), 2.00-1.87 (m, 2H), 1.84-1.67 (m, 1H), |
| 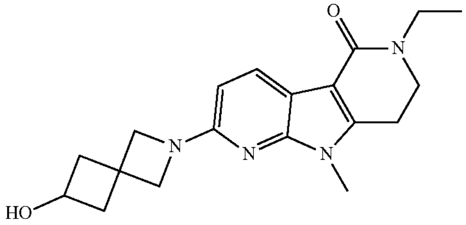 [SMILES: CCN1CCc2c(c3ccc(N4CC5(CC(O)C5)C4)nc3n2C)C1=O] | 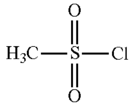 | 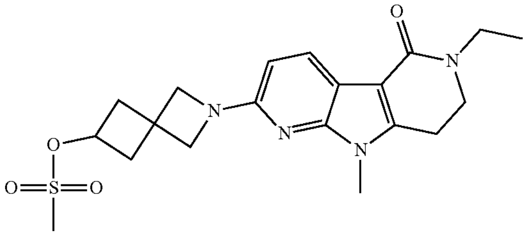<br>140 | 1. 64%<br>2. $^{1}$H-NMR (400 MHz, $CDCl_3$) δ = 8.19 (d, 1H), 6.23 (d, 1H), 5.00 (q, 1H), 4.06 (d, 4H), 3.70-3.62 (m, 5H), 3.59 (q, 2H), 3.09-2.92 (m, 5H), 2.87-2.68 (m, 2H), 2.67-2.45 (m, 2H), 1.59 (s, 0H), 1.21 (t, 3H). |
| 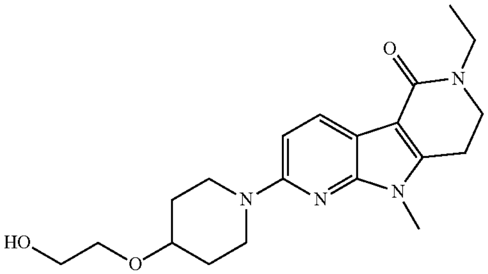 [SMILES: CCN1CCc2c(c3ccc(N4CCC(OCCO)CC4)nc3n2C)C1=O] | 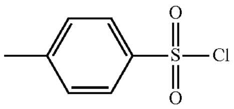 | 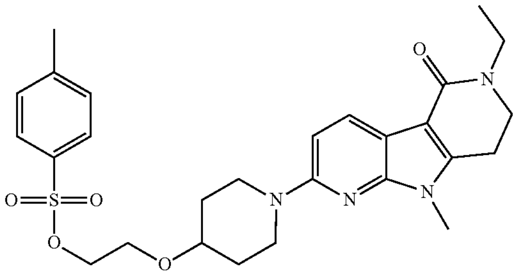<br>141 | 1. 62%<br>2. $^{1}$H-NMR (400 MHz, $CDCl_3$) δ = 8.19 (d, 1H), 7.81 (d, 2H), 7.32 (d, 2H), 6.64 (d, 1H), 4.28-4.14 (m, 2H), 4.03-3.88 (m, 2H), 3.77-3.63 (m, 7H), 3.59 (q, 2H), 3.55-3.45 (m, 1H), 3.28-3.14 (m, 2H), 3.00 (t, 2H), 2.43 (s, 3H), 1.99-1.83 (m, 2H), 1.60 (s, 2H), 1.21 (t, 3H). |

TABLE 15-continued
| Alcohol derivative | Alkylation reagent | Product Example | 1. Yield<br>2. $^{1}$H-NMR<br>3. $MH^+$ (ESI) |
|---|---|---|---|
| 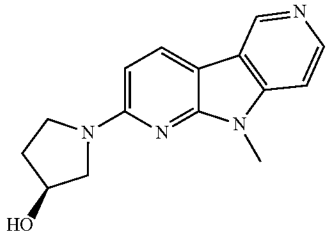 | 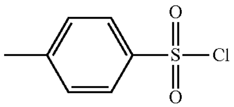 | 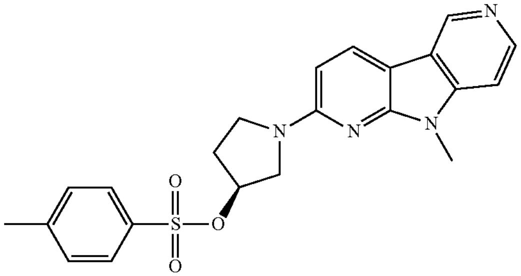<br>142 | 1. 14%<br>2. $^{1}$H-NMR (400 MHz, $CDCl_3$) δ = 9.08 (s, 1H), 8.36 (d, 1H), 8.27 (d, 1H), 7.83 (d, 2H), 7.60-7.33 (m, 3H), 6.42 (d, 1H), 5.38-5.06 (m, 1H), 3.88-3.41 (m, 7H), 2.38 (s, 3H), 2.32-2.20 (m, 1H), 2.20-2.09 (m, 1H)<br>3. 423.32 |
| 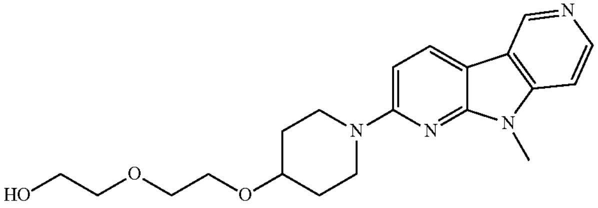 [SMILES: Cn1c2ccncc2c2ccc(N3CCC(OCCOCCO)CC3)nc21] | 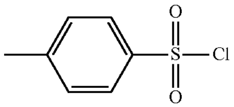 | 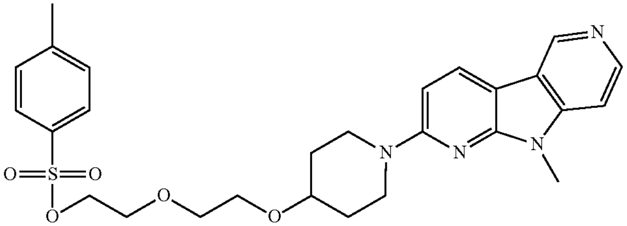<br>143 | 1. 53%<br>3. 524.9 |
| 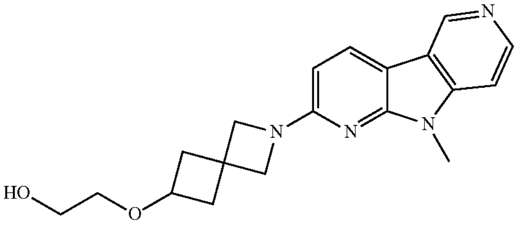 [SMILES: Cn1c2ccncc2c2ccc(N3CC4(CC(OCCO)C4)C3)nc21] | 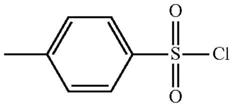 | 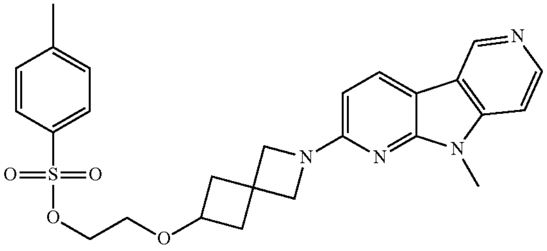<br>144 | 1. 18%<br>2. 493.20 |

Example 145

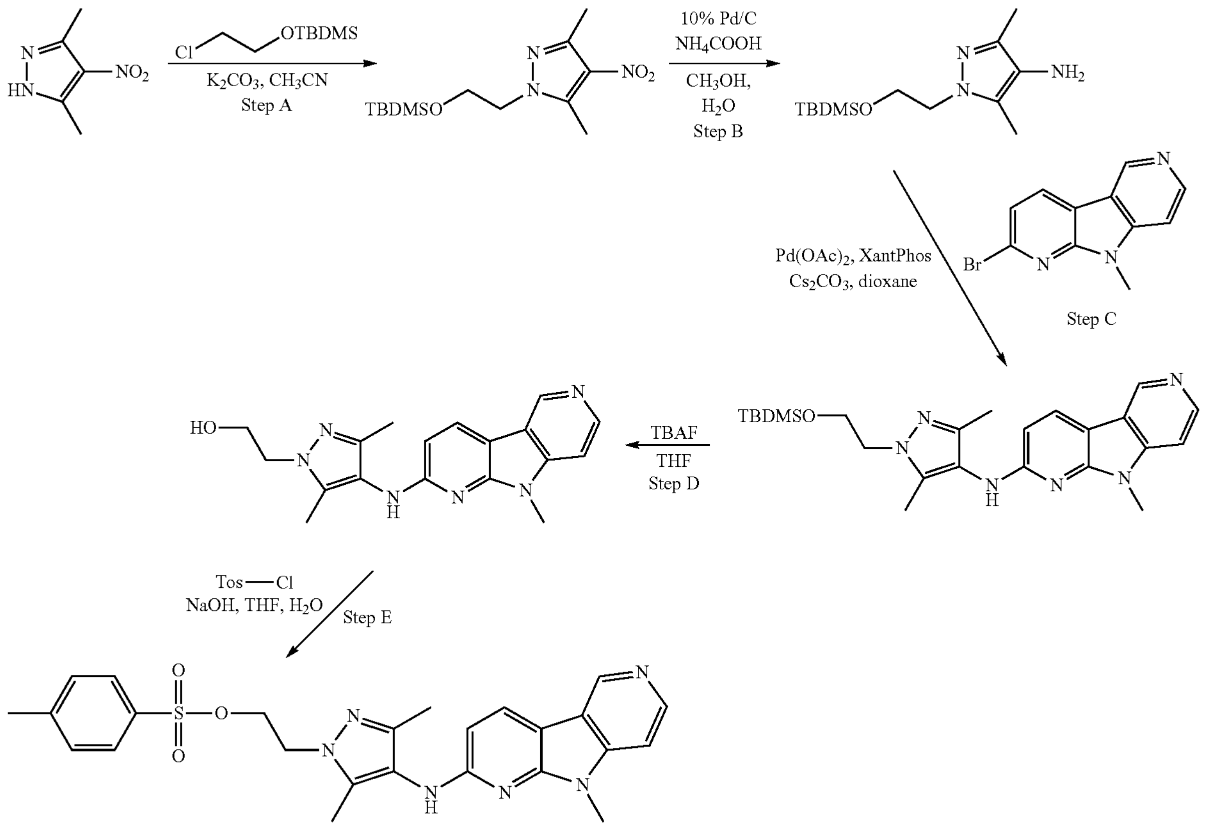

Step A

To a solution of 3,5-dimethyl-4-nitro-1H-pyrazole (0.5 g, 3.54 mmol) in acetonitrile (10 mL), $K_2CO_3$ (1.4 g, 10.62 mmol) was added and the mixture was stirred at room temperature for 30 minutes. Then tert-butyl-(2-chloroethoxy)dimethylsilane (1.2 g, 5.31 mmol) was added dropwise. The mixture was heated at reflux overnight. To the cooled reaction mixture $H_2O$ (20 ml) was added and the product was extracted with ethyl acetate (3×50 ml), the organic layers were combined, dried over $Na_2SO_4$ and evaporated under reduced pressure. The residue was purified on HP-Sil SNAP cartridges using a Biotage Isolera One purification system employing an EtOAc/n-heptane gradient (5/95->40/60) to afford the title compound which was used in the next step without further purification (0.72 g, 68%).

$^1$H-NMR (400 MHz, DMSO-d$_6$) δ=4.20 (t, 2H), 3.90 (t, 2H), 2.60 (s, 3H), 2.41 (s, 3H), 0.78 (s, 9H), −0.09 (s, 6H).

Step B

The title compound from Step A above (0.416 g, 1.38 mmol) was dissolved in methanol (10 mL) and ammonium formate was added (0.317 g, 6.9 mmol). After the addition of a suspension of 10% palladium on charcoal (0.13 g) in water (1 mL), the mixture was stirred at room temperature overnight. The reaction mixture was filtered and the catalyst was washed with methanol (5 mL). The filtrate was evaporated under reduced pressure and the residue was re-dissolved in ethyl acetate (60 mL) and water (30 mL). The organic phase was separated, dried over $Na_2SO_4$, filtered and the solvent was removed under reduced pressure. The residue was purified on HP-Sil SNAP cartridges using a Biotage Isolera One purification system employing an EtOAc/n-heptane gradient (5/95->40/60) to afford the title compound as a pale yellow oil which became an off-white solid by standing at room temperature (0.246 g, 66%).

$^1$H-NMR (400 MHz, DMSO-d$_6$) δ=3.93-3.84 (m, 2H), 3.82-3.68 (m, 2H), 2.07 (s, 3H), 1.98 (s, 3H), 0.83 (s, 9H), −0.06 (s, 6H).

MS (ESI); m/z=270.21 [M+H]$^+$.

Step C

An oven dried Schlenk flask was evacuated and back filled with argon gas. The procedure was repeated 3-4 times and the flask was cooled to room temperature. Then the title compound from Step B above (0.246 g, 0.916 mmol), the title compound from Preparative Example 1 (0.20 g, 0.763 mmol), palladium(II)-acetate (0.020 g, 0.0763 mmol), 4,5-bis(diphenylphosphino)-9,9-dimethylxanthene (0.158 g, 0.229 mmol), cesium carbonate (0.982 g, 2.52 mmol) and 1,4-dioxane (8 mL) were added and the reaction mixture was heated at 110° C. in a sand-bath for 12 h. The reaction mixture was cooled and diluted with water (20 ml) and the aqueous phase was extracted with ethyl acetate several times. The combined organics were dried over $Na_2SO_4$, filtered and concentrated in vacuo. The residue was purified on HP-Sil SNAP cartridges using a Biotage Isolera One purification system using 2 to 5% methanol in dichloromethane to afford the title compound (0.337 g, 80%).

$^1$H-NMR (400 MHz, $CDCl_3$) δ=9.10 (s, 1H), 8.51 (d, 1H), 8.07 (d, 1H), 7.34 (d, 1H), 6.22 (d, 1H), 6.01 (s, 1H), 4.16 (t, 2H), 4.02 (dd, 2H), 3.90 (d, 3H), 2.22 (s, 3H), 2.17 (s, 3H), 0.89 (s, 9H), 0.02 (s, 6H).

MS (ESI); m/z=451.44 [M+H]$^+$.

Step D

To a solution of the title compound from Step C above (0.337 g, 0.74 mmol) in tetrahydrofuran (10 mL) at 0° C. was added a 1M solution of tetrabutylammonium fluoride (2.22 mL, 2.22 mmol) in tetrahydrofuran. Then, the reaction mixture was stirred at room temperature for 16 hours. An ammonium chloride saturated solution (10 ml) and $H_2O$ (10 ml) was added and the phases were separated. The aqueous phase was extracted with dichloromethane several times. The combined organics were dried over $Na_2SO_4$, filtered and concentrated in vacuo. The residue was purified on HP-Sil SNAP cartridges using a Biotage Isolera One purification system using 2 to 20% methanol in dichloromethane to afford the title compound as a white solid (0.06 g, 25%).

$^1$H-NMR (400 MHz, DMSO-$d_6$) δ=9.07 (s, 1H), 8.37 (d, 1H), 8.28-8.07 (m, 2H), 7.52 (d, 1H), 6.27 (d, 1H), 4.88 (t, 1H), 4.03 (t, 2H), 3.85-3.58 (m, 5H), 2.13 (s, 3H), 2.02 (s, 3H).

MS (ESI): m/z=337.31 $[M+H]^+$.

Step E To a solution of the title compound from Step D above (0.06 g, 0.178 mmol) in tetrahydrofuran (4 mL) at room temperature was added a 6M solution of sodium hydroxide (1 ml). The mixture was stirred for 30 minutes and tosyl chloride (0.102 g, 0.535 mmol) was added once. The reaction mixture was stirred at room temperature for 16 hours and dichloromethane (20 ml) was added, the phases were separated and the organic layers were extracted with dichloromethane (2×20 ml). The combined organics were dried over $Na_2SO_4$, filtered and concentrated in vacuo. The residue was purified on HP-Sil SNAP cartridges using a Biotage Isolera One purification system using 2 to 20% methanol in ethyl acetate to afford the title compound as a white solid (0.05 g, 57%).

$^1$H-NMR (400 MHz, DMSO-$d_6$) δ=9.06 (s, 1H), 8.34 (d, 1H), 8.19 (d, 2H), 7.67 (d, 2H), 7.45 (dd, 4H), 4.36-4.19 (m, 4H), 3.73 (s, 3H), 2.39 (s, 3H), 2.08 (s, 3H), 1.94 (s, 3H).

MS (ESI): m/z=491.29 $[M+H]^+$.

Example 146

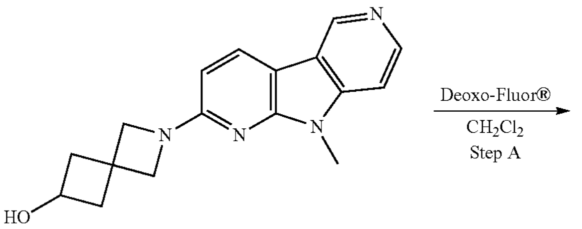

-continued

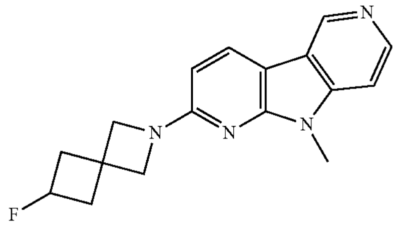

To a solution of the title compound from Example 93 (0.03 g, 0.102 mmol) in dichloromethane (1 mL) at −10° C. was added bis(2-methoxyethyl)aminosulfur trifluoride (Deoxo-Fluor®) (0.113 mL, 0.306 mmol). The reaction mixture was then stirred at −10° C. for 45 minutes, 1 hour at room temperature and 2 hours at 40° C. The reaction mixture was poured into saturated ammonium chloride aqueous solution and the aqueous phase was extracted with dichloromethane several times. The combined organics were dried over $Na_2SO_4$, filtered and concentrated in vacuo. The crude product was purified by column chromatography using 2 to 15% methanol in dichloromethane to afford the title compound (0.011 g, 35%).

1H NMR (400 MHz, DMSO-$d_6$) δ=9.10 (s, 1H), 8.37 (d, 1H), 8.29 (d, 1H), 7.52 (d, 1H), 6.30 (d, 1H), 5.05 (dt, 1H), 4.07 (d, 4H), 3.77 (s, 3H), 2.74-2.60 (m, 2H), 2.45-2.28 (m, 2H).

MS (ESI); m/z=296.68 $[M+H]^+$.

Examples 147 to 152

Following the fluorination procedure as described in Example 146, except using the alcohol derivatives and fluorination reagents indicated in the table below, the following compounds were prepared.

TABLE 16

| Alcohol derivative | Fluorination reagent | Product Example | 1. Yield<br>2. $^1$H-NMR<br>3. $MH^+$ (ESI) |
|---|---|---|---|
| 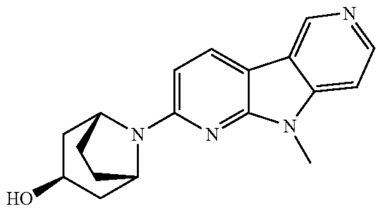 [SMILES: Cn1c2ccncc2c2ccc(N3[C@@H]4CC[C@H]3C[C@@H](O)C4)nc21] | Deoxo-Fluor ® | 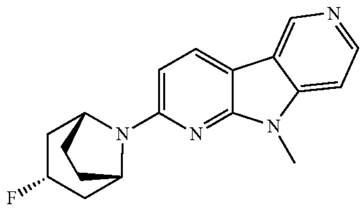<br>147 | 1. 49%<br>2. $^1$H-NMR (400 MHz, DMSO-$d_6$) δ = 9.11 (s, 1H), 8.40-8.31 (m, 2H), 7.51 (d, 1H), 6.78 (d, 1H), 5.30-5.04 (m, 1H), 4.74 (s, 2H), 3.80 (s, 3H), 2.19-1.94 (m, 4H), 1.86-1.62 (m, 4H).<br>3. 311.02 |

TABLE 16-continued

| Alcohol derivative | Fluorination reagent | Product Example | 1. Yield<br>2. $^1$H-NMR<br>3. $MH^+$ (ESI) |
|---|---|---|---|
| 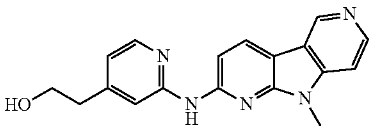 [SMILES: Cn1c2ccncc2c2ccc(Nc3cc(CCO)ccn3)nc21] | Deoxo-Fluor ® | 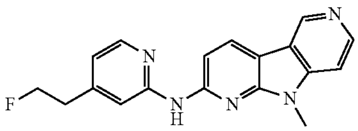<br>148 | 1. 15%<br>2. $^1$H-NMR (400 MHz, $CDCl_3$) δ = 9.15 (s, 1H), 8.52 (s, 1H), 8.33-8.10 (m, 3H), 7.32 (d, 1H), 7.09 (d, 1H), 6.83 (d, 1H), 4.02 (t, 2H), 3.91 (s, 3H), 2.95 (t, 2H) |
| 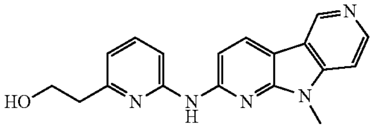 [SMILES: Cn1c2ccncc2c2ccc(Nc3cccc(CCO)n3)nc21] | Deoxo-Fluor ® | 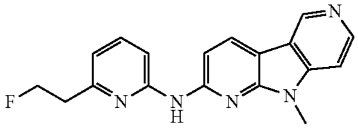<br>149 | 1. 15%<br>2. 322.2 |
| 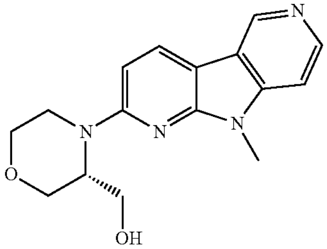 [SMILES: Cn1c2ccncc2c2ccc(N3CCOC[C@H]3CO)nc21] | Deoxo-Fluor ® | 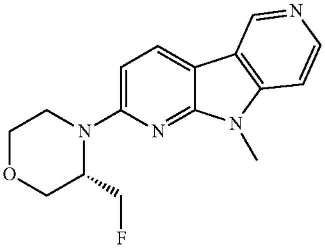<br>150 | 1. 18%<br>2. $^1$H-NMR (400 MHz, $CDCl_3$) δ = 9.12 (s, 1H), 8.48 (d, 1H), 8.25 (d, 1H), 7.35 (d, 1H), 6.72 (d, 1H), 4.55-4.28 (m, 2H), 4.02-3.81 (m, 5H), 3.63-3.58 (m, 2H), 3.56-3.45 (m, 1H), 3.01 (dd, 2H) |
| 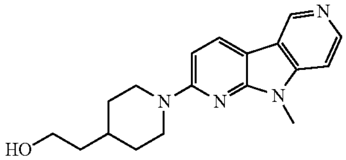 [SMILES: Cn1c2ccncc2c2ccc(N3CCC(CCO)CC3)nc21] | XtalFluor ®-M | 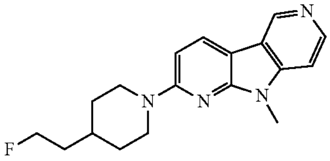<br>151 | 1. 9%<br>2. $^1$H NMR (400 MHz, DMSO-$d_6$) δ = 9.41 (s, 1H), 8.60 (d, 1H), 8.45 (d, 1H), 8.08 (d, 1H), 7.05 (d, 1H), 4.67-4.39 (m, 3H), 3.93 (s, 3H), 3.11-2.89 (m, 2H), 1.93-1.69 (m, 2H), 1.69-1.53 (m, 1H), 1.33-1.07 (m, 2H).<br>3. 312.96 |
| 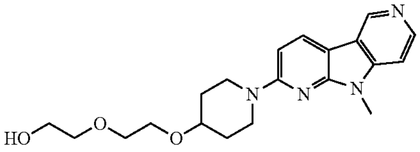 [SMILES: Cn1c2ccncc2c2ccc(N3CCC(OCCOCCO)CC3)nc21] | Deoxo-Fluor ® | 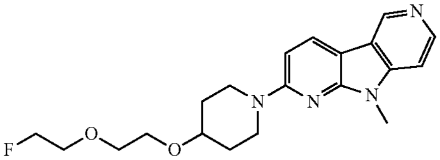<br>152 | 1. 16%<br>2. $^1$H-NMR (400 MHz, DMSO-$d_6$) δ = 9.09 (s, 1H), 8.37 (d, 1H), 8.29 (d, 1H), 7.51 (d, 1H), 6.84 (d, 1H), 4.62-4.42 (m, 2H), 4.15 (dt, 2H), 3.79 (s, 3H), 3.74-3.68 (m, 1H), 3.66-3.55 (m, 6H), 3.30-3.23 (m, 2H), 2.03-1.91 (m, 2H), 1.49 (dtd, 2H)<br>3. 372.9 |

Example 153

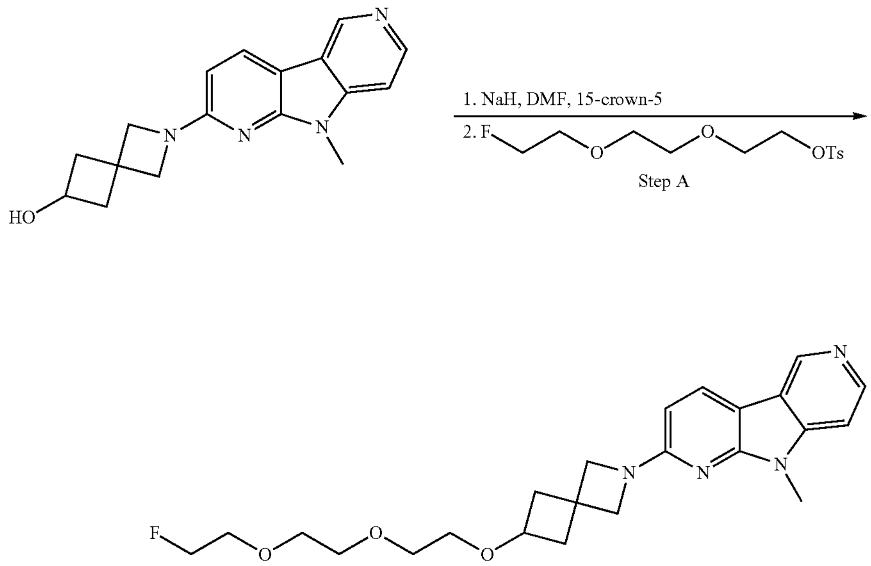

To a solution of the title compound from Example 93 (0.073 g, 0.247 mmol) in N,N' dimethylformamide (4 mL) was added sodium hydride (0.008 g, 0.297 mmol). After 30 minutes at room temperature, the reaction mixture was cooled to 0° C. and custom made 2-(2-(2-fluoroethoxy) ethoxy)ethyl 4-methylbenzenesulfonate (0.227 g, 0.742 mmol), followed by 15-CROWN-5 (0.055 g, 0.247 mmol) were added. After stirring at room temperature for 18 hours, the reaction mixture was poured into water and the aqueous phase was extracted with EtOAc several times. The combined organics were washed with brine, dried over $Na_2SO_4$, filtered and dried in vacuo. The crude product was purified by column chromatography using 2 to 10% methanol in dichloromethane to afford the title compound (0.019 g, 18%).

$^1$H-NMR (400 MHz, DMSO-$d_6$) δ=9.09 (s, 1H), 8.36 (d, 1H), 8.28 (d, 1H), 7.50 (d, 1H), 6.29 (d, 1H), 4.66-4.53 (m, 1H), 4.53-4.40 (m, 1H), 4.06 (s, 2H), 4.01 (s, 2H), 3.93 (p, 1H), 3.77 (s, 3H), 3.73-3.67 (m, 1H), 3.65-3.59 (m, 1H), 3.59-3.48 (m, 6H), 3.45-3.39 (m, 2H), 2.57-2.51 (m, 2H), 2.11 (ddd, 2H).

MS (ESI); m/z=429.65 $[M+H]^+$.

Example 154

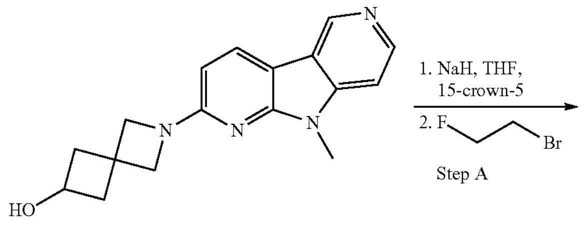

-continued

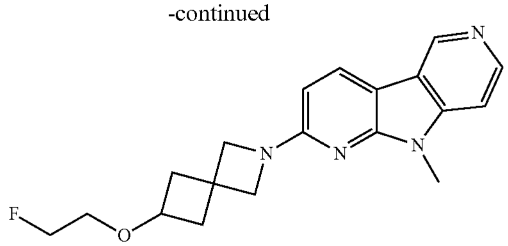

To a solution of the title compound from Example 93 (0.036 g, 0.121 mmol) in tetrahydrofuran (4 mL) was added sodium hydride (0.0039 g, 0.146 mmol), followed by 15-CROWN-5 (0.032 g, 0.146 mmol). After 15 minutes, 1-bromo-2-fluoroethane (0.046 g, 0.364 mmol) was added and the reaction mixture was heated at 55° C. for 18 hours. Water was added and the aqueous phase was extracted several times with dichloromethane. The combined organics were dried over $Na_2SO_4$, filtered and dried in vacuo. The crude product was purified by column chromatography using 2 to 15% methanol in dichloromethane to afford the title compound (0.008 g, 18%).

$^1$H-NMR (400 MHz, DMSO-$d_6$) δ=9.09 (s, 1H), 8.36 (d, 1H), 8.28 (d, 1H), 7.50 (d, 1H), 6.29 (d, 1H), 4.64-4.51 (m, 1H), 4.51-4.39 (m, 1H), 4.07 (s, 2H), 4.02 (s, 2H), 3.97 (p, 1H), 3.77 (s, 3H), 3.61-3.56 (m, 1H), 3.52-3.49 (m, 1H), 2.57-2.53 (m, 2H), 2.13 (ddd, 2H).

MS (ESI); m/z=340.86 $[M+H]^+$.

Examples 155 to 157

Following the fluorination procedure as described in Example 154, except using the alcohol derivatives and fluoroalkyl reagents indicated in the table below, the following compounds were prepared.

TABLE 17

| Alcohol derivative | Fluoroalkyl reagent | Product Example | 1. Yield<br>2. $^{1}$H-NMR<br>3. MH$^{+}$ (ESI) |
|---|---|---|---|
| 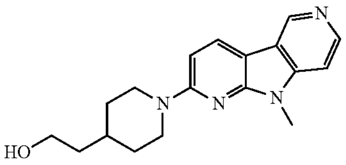 | 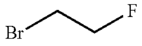 | 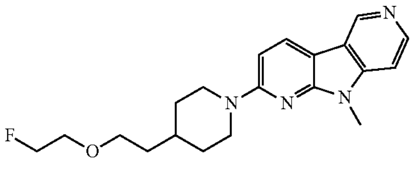<br>155 | 1. 5%<br>2. $^{1}$H-NMR (400 MHz, DMSO-d$_6$) δ = 9.42 (s, 1H), 8.60 (d, 1H), 8.45 (d, 1H), 8.08 (d, 1H), 7.05 (d, 1H), 4.67-4.37 (m, 4H), 3.94 (s, 3H), 3.73-3.41 (m, 3H), 2.99 (t, 2H), 1.78 (t, 3H), 1.50 (q, 2H), 1.31-1.06 (m, 3H).<br>3. 357.08 |
| 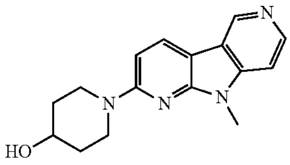 [SMILES: Cn1c2ccncc2c2ccc(N3CCC(O)CC3)nc21] | 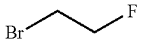 | 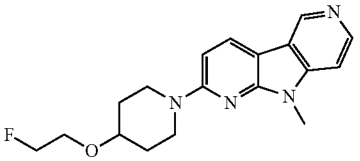<br>156 | 1. 5%<br>2. $^{1}$H-NMR (400 MHz, DMSO-d$_6$) δ = 9.19 (s, 1H), 8.45 (d, 1H), 8.34 (d, 1H), 7.68 (d, 1H), 6.91 (d, 1H), 4.70-4.54 (m, 1H), 4.54-4.42 (m, 1H), 4.17 (dt, 2H), 3.84 (s, 3H), 3.80-3.72 (m, 1H), 3.72-3.59 (m, 2H), 3.46-3.24 (m, 3H), 2.11-1.88 (m, 2H), 1.62-1.38 (m, 2H)<br>3. 328.94 |
| 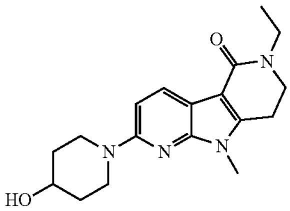 [SMILES: CCN1CCc2c(c3ccc(N4CCC(O)CC4)nc3n2C)C1=O] | 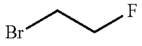 | 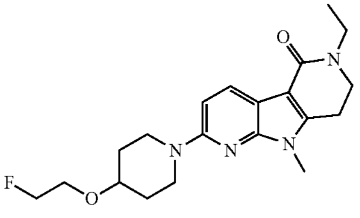<br>157 | 1. 8%<br>2. $^{1}$H-NMR (400 MHz, CDCl$_3$) δ = 8.19 (d, 1H), 6.66 (d, 1H), 4.64 (t, 1H), 4.52 (t, 1H), 4.16-4.03 (m, 2H), 3.81 (t, 1H), 3.77-3.70 (m, 1H), 3.69-3.64 (m, 5H), 3.62-3.56 (m, 2H), 3.29-3.16 (m, 2H), 3.00 (t, 2H), 2.12-1.97 (m, 1H), 1.80-1.57 (m, 4H), 1.21 (t, 3H) |

Example 158

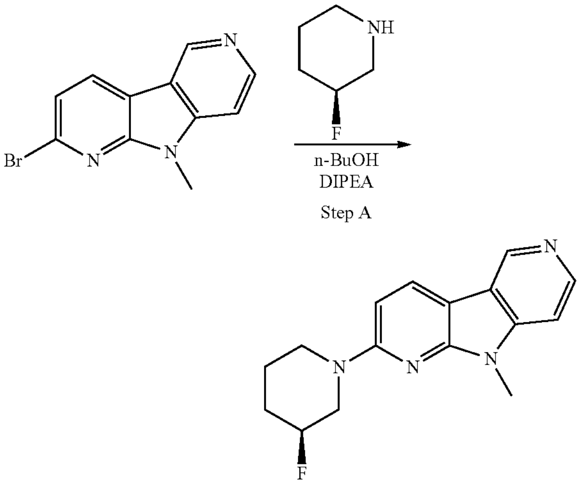

Step A

To a microwave tube were added the title compound from Preparative Example 1 (0.05 g, 0.19 mmol), (S)-3-fluoropiperidine hydrochloride (0.08 g, 0.57 mmol) and n-butanol (3 mL), followed by N,N'-diisopropylethylamine (0.231 mL, 1.33 mmol). The tube was sealed and heated at 200° C. for 2 hours using a Biotage Initiator microwave. The solvents were removed under reduced pressure and the residue was purified on HP-Sil SNAP cartridges using a Biotage Isolera One purification system employing a methanol/dichloromethane gradient (0/100->10/90) to afford the title compound (0.003 g, 5%).

$^{1}$H-NMR (400 MHz, $CD_3OD$) δ=10.75 (s, 1H), 10.00 (d, 1H), 9.90 (d, 1H), 9.49 (d, 1H), 8.55 (d, 1H), 6.35-6.22 (m, 1H), 5.85-5.69 (m, 1H), 5.69-5.59 (m, 1H), 5.56 (s, 3H), 5.52-5.29 (m, 1H), 5.24-5.11 (m, 1H), 3.67-3.50 (m, 3H), 3.33-3.19 (m, 1H).

MS (ESI); m/z=284.84 [M+H]$^{+}$.

Examples 159 to 162

Following the procedure as described in Example 158, except using the bromo derivatives and amines indicated in the table below, the following compounds were prepared.

TABLE 18
| Bromo derivative | Amines | Product Example | 1. Yield<br>2. $^1$H-NMR<br>3. MH$^+$ (ESI) |
|---|---|---|---|
| 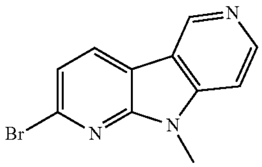 | 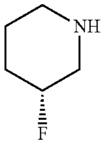 | 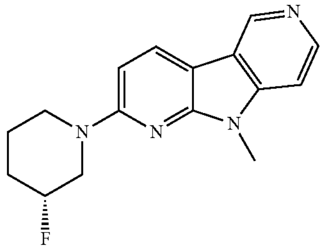<br>159 | 1. 10%<br>2. $^1$H-NMR (400 MHz, $CD_3OD$) δ = 10.50 (s, 1H), 9.87 (d, 1H), 9.71 (d, 1H), 9.01 (d, 1H), 8.31 (d, 1H), 6.40-6.16 (m, 1H), 5.54-5.43 (m, 2H), 5.43-5.35 (m, 4H), 5.23-5.08 (m, 1H), 3.70-3.34 (m, 3H), 3.29-3.09 (m, 1H) |
| 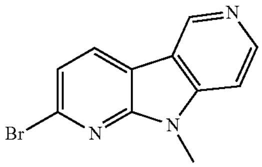 | 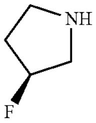 | 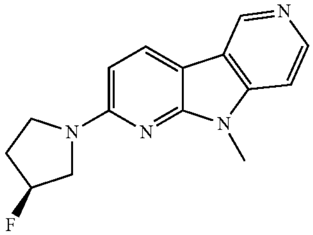<br>160 | 1. 45%<br>2. $^1$H-NMR (400 MHz, DMSO-$d_6$) δ = 9.41 (s, 1H), 8.60 (d, 1H), 8.47 (d, 1H), 8.42 (d, 0H), 8.05 (d, 1H), 6.71 (d, 1H), 5.71-5.53 (m, 1H), 5.53-5.36 (m, 1H), 3.94 (s, 3H), 3.89-3.74 (m, 1H), 3.75-3.66 (m, 1H), 3.65-3.54 (m, 1H), 2.39-2.16 (m, 2H) |
| 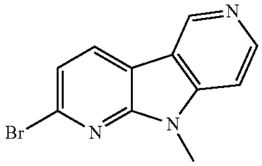 | 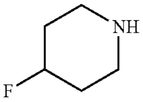 | 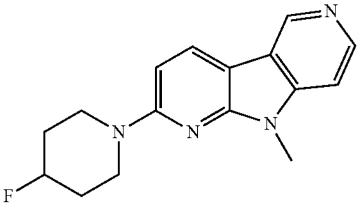<br>161 | 1. 36%<br>2. $^1$H-NMR (400 MHz, $CD_3OD$) δ = 8.96 (s, 1H), 8.32 (d, 1H), 8.20 (d, 1H), 7.46 (dd, 1H), 6.79 (d, 1H), 5.06-4.74 (m, 1H), 4.05-3.86 (m, 2H), 3.82 (s, 3H), 3.74 (m, 2H), 2.01 (m, 2H), 1.94-1.75 (m, 2H)<br>3. 285.20 |
| 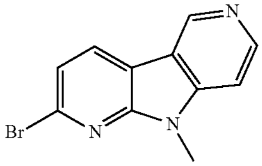 | 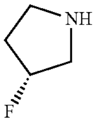 | 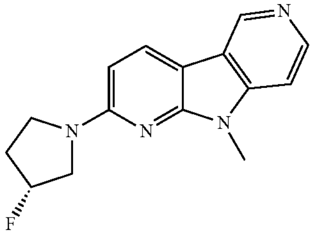<br>162 | 1. 48%<br>2. $^1$H-NMR (400 MHz, DMSO-$d_6$) δ = 9.34 (s, 1H), 8.55 (d, 1H), 8.43 (d, 1H), 7.93 (d, 1H), 6.66 (d, 1H), 5.51 (dt, 1H), 4.03-3.63 (m, 6H), 3.63-3.50 (m, 1H), 2.40-2.11 (m, 2H).<br>3. 271.30 |

Example 163

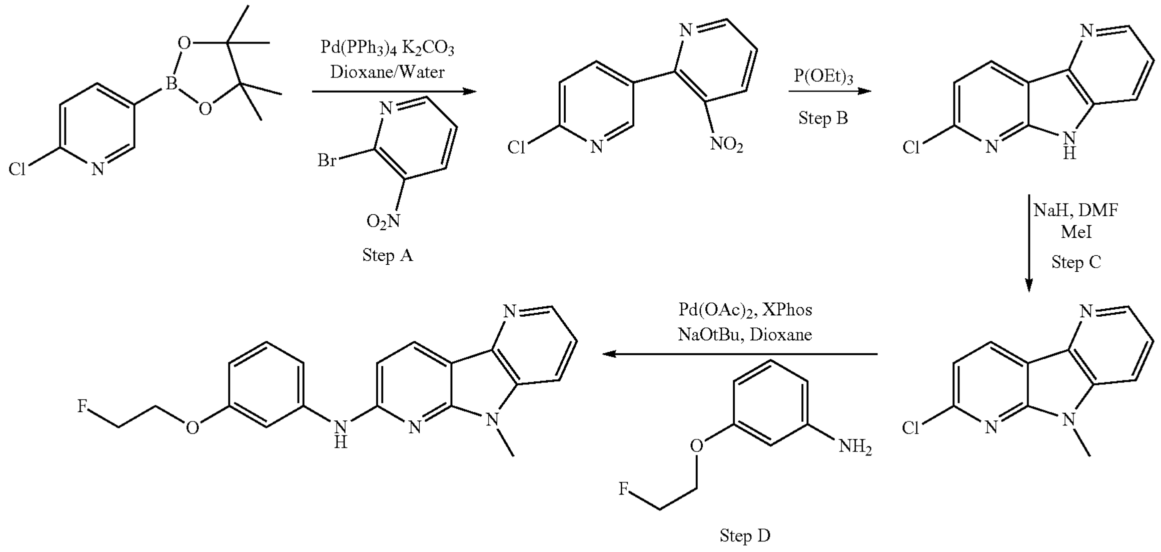

Step A

A sealed pressure tube was filled with 2-chloro-5-(4,4,5,5-tetramethyl-1,3,2-dioxaborolan-2-yl)pyridine (0.43 g, 2.7 mmol), 2-bromo-3-nitropyridine (0.5 g, 2.46 mmol), potassium carbonate (1 g, 7.38 mmol), tetrakis(triphenylphosphine)palladium(0) (0.284 g, 0.25 mmol), degassed 1,4-dioxane (16 mL) and water (4 mL). The pressure tube was filled with argon before being heated at 120° C. for 4 hours. The reaction mixture was allowed to cool to room temperature, the solvents were removed under reduced pressure. The residue was purified on HP-Sil SNAP cartridges using a Biotage Isolera One purification system employing ethyl acetate/n-heptane gradient (100/0->90/10) gradient (100/0->90/10) to afford the title compound (0.4 g, 70%).

$^{1}$H_NMR (400 MHz, DMSO-$d_6$) δ=0.99 (dd, 1H), 8.73-8.47 (m, 2H), 8.07 (dd, 1H), 7.79 (dd, 1H), 7.67 (d, 1H).

Step B

The title compound from Step A above (0.4 g, 1.7 mmol) was mixed with polyphosphoric acid (6 g) and the mixture was heated at ~150° C. in a sand-bath for 2 hours with stirring. The reaction mixture was placed in an ice-bath and made alkaline (pH~12) by the addition of a 6N solution of sodium hydroxide (exotherm). The reaction mixture was diluted with water (50 mL) to dissolve phosphate salts and was extracted with a mixture of dichloromethane/methanol (9/1; 3×50 mL). The organic phase was separated, dried over $Na_2SO_4$, filtered and the solvents were removed under reduced pressure. The residue was purified on a HP-Sil column using a Biotage Isolera One purification system employing an ethyl acetate/n-heptane gradient (100/0->50/50) to afford the crude title compound (0.025 g, 9%).

$^{1}$H-NMR (400 MHz, DMSO-$d_6$) δ=12.25 (s, 1H), 8.65-8.41 (m, 2H), 7.94 (dd, 1H), 7.49 (dd, 1H), 7.36 (d, 1H).

MS (ESI); m/z=205.79 $[M+H]^+$.

Step C

To the title compound from Step B above (0.025 g, 0.115 mmol) in N,N'-dimethylformamide (2 mL) was added sodium hydride (60% in mineral oil; 0.009 g, 0.345 mmol). The suspension was stirred at room temperature for 30 minutes, cooled at 0° C. and methyl iodide (6.6 μL, 0.161 mmol) was added. The reaction mixture was stirred at room temperature overnight. Then a saturated solution of sodium chloride (10 mL) was added and the mixture was extracted with dichloromethane (2×20 mL). The combined organic phase was dried over $Na_2SO_4$, filtered and the solvents were removed. The residue was purified by chromatography on HP-Sil SNAP cartridges using a Biotage Isolera One purification system employing an ethyl acetate/n-heptane gradient (0/100->50/50) to afford the title compound (0.019 g, 76%).

$^{1}$H-NMR (400 MHz, DMSO-$d_6$) δ=8.76-8.45 (m, 2H), 8.16 (dd, 1H), 7.57 (dd, 1H), 7.39 (d, 1H), 3.92 (s, 3H).

MS (ESI); m/z=219.59 $[M+H]^+$.

Step D An oven dried Schlenk flask was evacuated and back filled with argon gas. The procedure was repeated 3-4 times and the flask was cooled to room temperature. Then dicyclohexyl-(2',4',6'-triisopropyl-[1,1'-biphenyl]-2-yl) phosphine (0.012 g, 0.026 mmol) and palladium(II)-acetate (0.002 g, 0.0087 mmol) were dissolved in degassed 1,4-dioxane (3 mL) and heated at 110° C. for 1 minute to become a clear red solution. Then the title compound from above Step C (0.019 g, 0.087 mmol), the title compound from Preparative Example 13 (0.016 g, 0.104 mmol), and sodium tert.-butoxide (0.027 g, 0.287 mmol) were added. The reaction mixture was heated at 110° C. in a sand-bath for 4 hours, cooled to room temperature and the solvents were removed under reduced pressure. The residue was purified on HP-Sil SNAP cartridges using a Biotage Isolera One purification system employing a dichloromethane/methanol gradient (100/0->90/10) to afford the title compound (0.007 g, 24%).

$^{1}$H-NMR (400 MHz, DMSO-$d_6$) δ=9.54 (s, 1H), 8.40 (d, 1H), 8.29 (d, 1H), 7.94 (d, 1H), 7.81 (d, 1H), 7.49-7.29 (m, 2H), 7.24 (t, 1H), 6.79 (d, 1H), 6.57 (dd, 1H), 4.85 (t, 1H), 4.73 (t, 1H), 4.33 (t, 1H), 4.25 (t, 1H), 3.90 (s, 3H).

MS (ESI); m/z=337.30 $[M+H]^+$.

Example 164

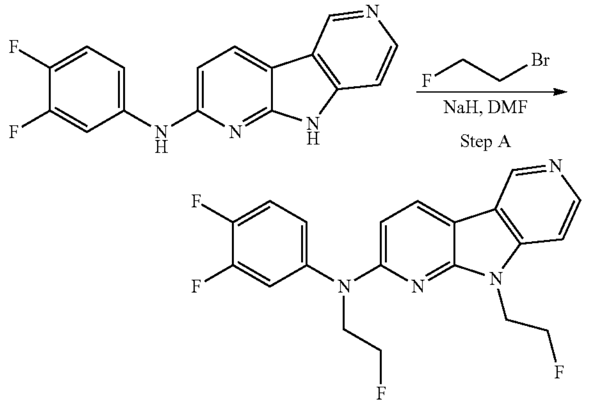

To a solution of the title compound from Example 27 (0.012 g, 0.042 mmol) in N,N'-dimethylformamide (5 mL) was added sodium hydride 60% in mineral oil (0.003 g, 0.084 mmol). After 30 minutes, 1-bromo-2-fluoroethane (5.4 µL, 0.063 mmol) was added and the reaction mixture was stirred at room temperature overnight. Water was added (50 µL) and the solvents were removed under reduced pressure. The crude product was purified by column chromatography using 2 to 15% methanol in dichloromethane to afford the title compound (0.005 g, 30%).

$^1$H-NMR (400 MHz, DMSO-$d_6$) δ=9.15 (s, 1H), 8.42 (d, 1H), 8.27 (d, 1H), 7.70-7.44 (m, 3H), 7.38-7.22 (m, 1H), 6.42 (d, 1H), 4.99-4.58 (m, 6H), 4.33 (dt, 2H).

MS (ESI); m/z=389.55 [M+H]$^+$.

Example 165

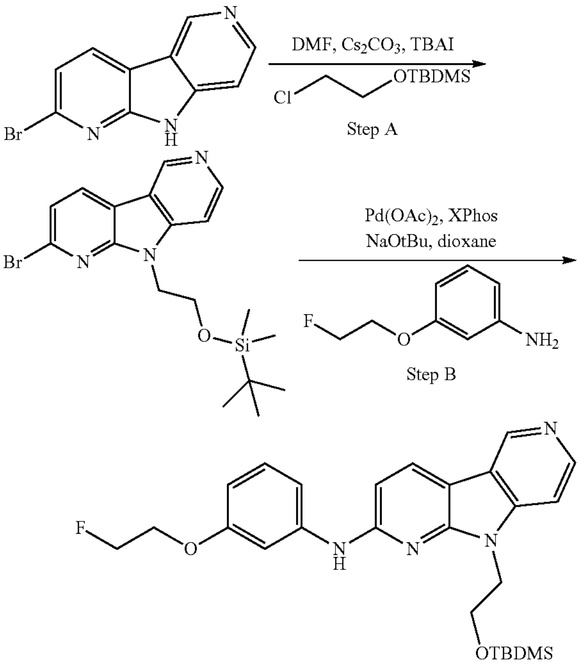

FrI

\+

-continued

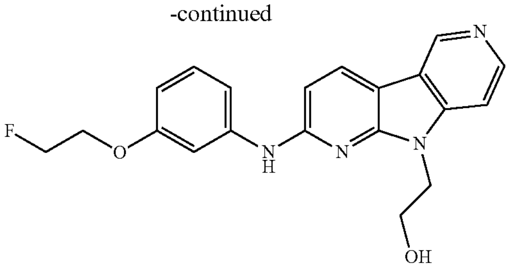

FrII

Step A

A solution of the title compound from Preparative Example 20 (0.15 g, 0.605 mmol), tert.-butyl(2-chloroethoxy)dimethylsilane (0.130 g, 0.665 mmol), cesium carbonate (0394 g, 1.209 mmol) and tetrabutylammonium iodide (0.022.g, 0.060 mmol) in N,N'-dimethylformamide (5 mL) were heated at 70° C. for 1 day. Ethyl acetate was added and the organic phase was washed several times with water, dried over $Na_2SO_4$, filtered and concentrated in vacuo. The crude product was purified by column chromatography using 2 to 10% methanol in dichloromethane. The oil was triturated in iso-propanol, filtered and dried to afford the title compound.

$^1$H-NMR (400 MHz, DMSO-$d_6$) δ=9.41 (s, 1H), 8.61 (d, 1H), 8.57 (d, 1H), 7.74 (d, 1H), 7.56 (d, 1H), 4.57 (t, 2H), 4.00 (t, 2H), 0.56 (s, 9H), −0.37 (s, 6H).

MS (ESI): m/z=406.89 [M+H]$^+$.

Step B 1,4-Dioxane (3 mL) was degassed for 10 minutes with argon and diacetoxypalladium (0.0019 g, 8.61 µmol) and dicyclohexyl-(2',4',6'-triisopropyl-[1,1'-biphenyl]-2-yl) phosphine (0.012 g, 0.026 mmol) were added. The suspension was then heated at 110° C. for 2 minutes. Then the title compound from Step A above (0.035 g, 0.086 mmol), 3-(2-fluoroethoxy)aniline (0.0147 g, 0.095 mmol) and sodium tert.-butoxide (0.025 g, 0.258 mmol) were added and the stirring was continued at 110° C. for 2 hours. The reaction mixture was diluted with water and the aqueous phase was extracted with ethyl acetate several times. The combined organics were dried over $Na_2SO_4$, filtered and concentrated in vacuo. The crude product was purified by column chromatography using 2 to 20% methanol in dichloromethane to afford the less polar FrI and the more polar FrII (0.004 g, 11%).

Less polar FrI: MS (ESI): m/z=482.07 [M+H]$^+$.

More polar FrII: $^1$H-NMR (400 MHz, DMSO-$d_6$) δ=9.54 (s, 1H), 9.19 (s, 1H), 8.47-8.31 (m, 2H), 7.87 (s, 1H), 7.66 (d, 1H), 7.29-7.16 (m, 2H), 6.84 (d, 1H), 6.62-6.41 (m, 1H), 4.94 (t, 1H), 4.88-4.79 (m, 1H), 4.76-4.67 (m, 1H), 4.50 (t, 2H), 4.38-4.29 (m, 1H), 4.29-4.18 (m, 1H), 3.93-3.81 (m, 2H).

Example 166

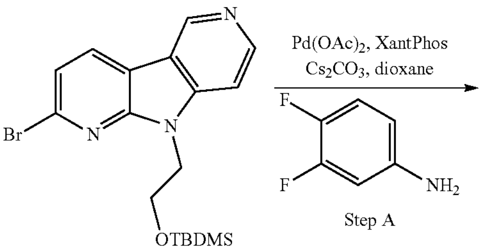

-continued

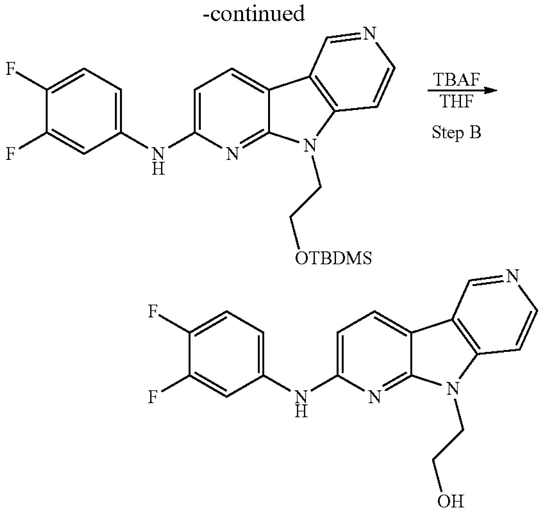

Step A 1,4-Dioxane (3 mL) was degassed for 10 min with argon and diacetoxypalladium (0.019 g, 8.61 μmol) and 4,5-bis(diphenylphosphino)-9,9-dimethylxanthene (0.015 g, 0.026 mmol) were added. The suspension was then heated at 110° C. for 2 minutes. Then the title compound from Example 165, Step A (0.035 g, 0.086 mmol), 3,4-difluoroaniline (0.012 g, 0.095 mmol) and cesium carbonate (0.084 g, 0.258 mmol) were added and stirring was continued at 110° C. for 2 hours. The reaction mixture was diluted with water and the aqueous phase was extracted with ethyl acetate several times. The combined organics were dried over $Na_2SO_4$, filtered and concentrated in vacuo. The crude product was purified by column chromatography using 2 to 5% methanol in dichloromethane to afford the title compound.

$^1$H-NMR (400 MHz, DMSO-$d_6$) δ=9.64 (s, 1H), 9.16 (s, 1H), 8.43-8.33 (m, 2H), 8.32-8.19 (m, 1H), 7.59 (d, 1H), 7.41-7.30 (m, 2H), 6.77 (d, 1H), 4.54 (t, 2H), 4.04 (t, 2H), 0.59 (s, 9H), −0.36 (s, 6H).

MS (ESI): m/z=455.27 $[M+H]^+$.

Step B

To a solution of the title compound from Step A above (0.0274 g, 0.060 mmol) in tetrahydrofuran (2 mL) at 0° C. was added a 1M solution of tetrabutylammonium fluoride (0.121 mL, 0.121 mmol) in tetrahydrofuran. Then, the reaction mixture was stirred at room temperature for 2 hours. A 1 M sodium hydroxide solution was added and the aqueous phase was extracted with dichloromethane several times. The combined organics were dried over $Na_2SO_4$, filtered and concentrated in vacuo. The crude product was purified by column chromatography using 2 to 30% methanol in dichloromethane to afford the title compound as a white solid.

$^1$H-NMR (400 MHz, DMSO-$d_6$) δ=9.67 (s, 1H), 9.17 (s, 1H), 8.40 (d, 2H), 8.18 (ddd, 1H), 7.62 (d, 1H), 7.39 (dq, 2H), 6.80 (d, 1H), 4.90 (t, 1H), 4.47 (t, 2H), 3.88 (q, 2H).

MS (ESI): m/z=341.21 $[M+H]^+$.

Example 167

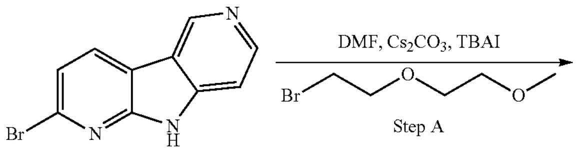

-continued

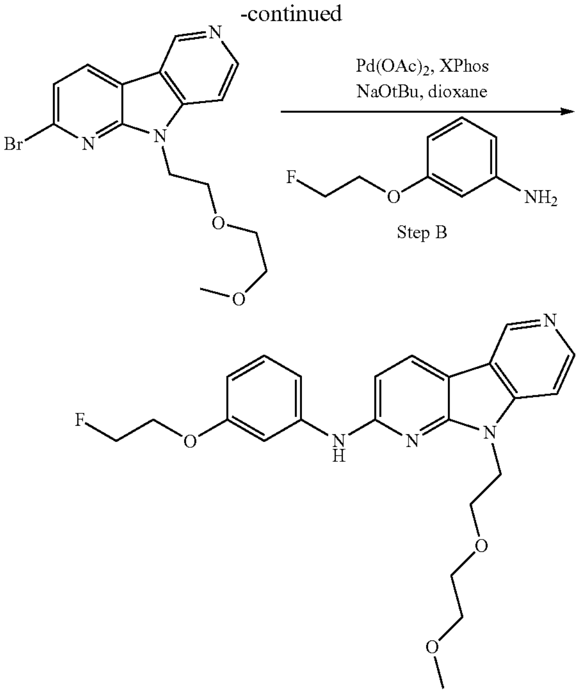

Step A

A solution of the title compound from Preparative Example 20 (0.15 g, 0.605 mmol), 1-bromo-2-(2-methoxyethoxy)ethane (0.098 mL, 0.726 mmol), cesium carbonate (0394 g, 1.209 mmol) and tetrabutylammonium iodide (0.022.g, 0.060 mmol) in N,N'-dimethylformamide (5 mL) was heated at 70° C. for 1 day. Ethyl acetate was added and the organic phase was washed several times with water, dried over $Na_2SO_4$, filtered and concentrated in vacuo. The crude product was purified by column chromatography using 2 to 8% methanol in dichloromethane. The oil was triturated in iso-propanol, filtered and dried to afford the title compound.

$^1$H-NMR (400 MHz, DMSO-$d_6$) δ=9.42 (s, 1H), 8.62 (d, 1H), 8.58 (d, 1H), 7.77 (d, 1H), 7.57 (d, 1H), 4.60 (t, 2H), 3.84 (t, 2H), 3.53-3.45 (m, 2H), 3.30-3.21 (m, 2H), 3.07 (s, 3H).

MS (ESI): m/z=350.34 $[M+H]^+$.

Step B 1,4-Dioxane (3 mL) was degassed for 10 min with argon and diacetoxypalladium (0.019 g, 8.61 μmol) and 4,5-bis(diphenylphosphino)-9,9-dimethylxanthene (0.015 g, 0.026 mmol) were added. The suspension was then heated at 110° C. for 2 minutes. Then the title compound from Step A above (0.035 g, 0.086 mmol), 3-(2-fluoroethoxy)aniline (0.014 g, 0.094 mmol) and cesium carbonate (0.084 g, 0.257 mmol) were added and stirring was continued at 110° C. for 2 hours. The reaction mixture was concentrated in vacuo to dryness. The crude product was purified by column chromatography using 2 to 10% methanol in dichloromethane to afford the title compound after trituration in ethyl acetate/n-heptane as a solid.

$^1$H-NMR (400 MHz, DMSO-$d_6$) δ=9.48 (s, 1H), 9.15 (s, 1H), 8.39 (d, 1H), 8.36 (d, 1H), 7.84 (s, 1H), 7.62 (d, 1H), 7.32-7.14 (m, 2H), 6.82 (d, 1H), 6.55 (d, 1H), 4.89-4.78 (m, 1H), 4.78-4.67 (m, 1H), 4.58 (t, 2H), 4.36-4.28 (m, 1H), 4.28-4.19 (m, 1H), 3.87 (t, 2H), 3.58-3.44 (m, 2H), 3.31-3.26 (m, 2H), 3.09 (s, 3H).

MS (ESI): m/z=425.78 $[M+H]^+$.

Example 168

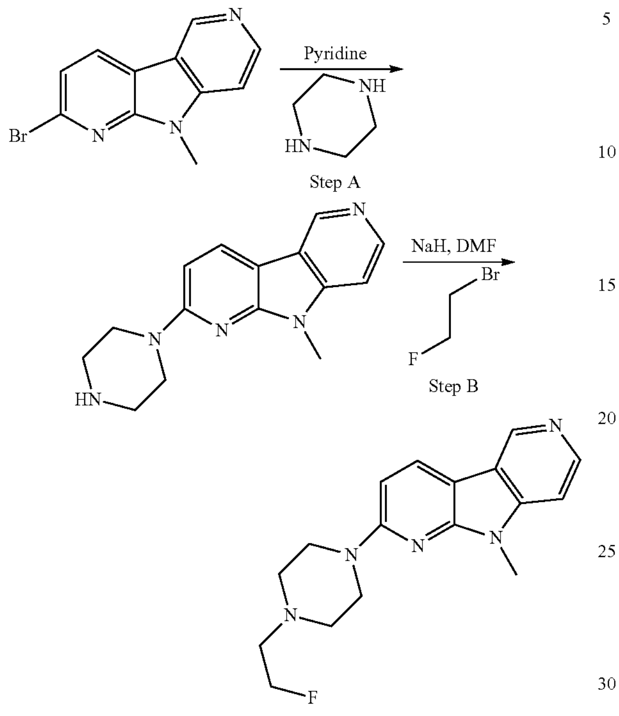

Step A

To a microwave tube were added the title compound from Preparative Example 1 (0.15 g, 0.57 mmol) and commercially available piperazine (0.054 g, 0.63 mmol) in pyridine (1 mL). The tube was sealed and heated at 150° C. for 1 hour using a Biotage Initiator microwave. The solvent was removed under reduced pressure and the residue was purified on HP-Sil SNAP cartridges using a Biotage Isolera One purification system employing a methanol/dichloromethane gradient (0/100->20/80) to afford the title compound (0.105 g; 68%).

$^1$H-NMR (400 MHz, DMSO-$d_6$) δ=9.15 (s, 1H), 8.50-8.20 (m, 2H), 7.55 (d, 1H), 6.89 (d, 1H), 3.83 (d, 7H), 3.18 (t, 4H).

Step B

To an ice-bath cooled (0° C.) suspension of the title compound from Step A above (0.030 g, 0.11 mmol) in N,N'-dimethylformamide (4 mL) was added sodium hydride (0.0054 g 1.47 mmol) portionwise. The suspension was stirred at 0° C. for 1 hour, warmed to room temperature and 1-bromo-2-fluoroethane (0.017 g, 0.137 mmol) was added. The reaction mixture was stirred at room temperature for 1 hour. The mixture was cooled again (0° C.), 1-bromo-2-fluoroethane (0.017 g, 0.137 mmol) was added and the mixture was stirred at room temperature for another hour. Then 0.5 ml of water was added and the solvent was removed under reduced pressure. The residue was dissolved in dichloromethane (10 mL) and washed with brine (2×10 mL) and water (10 mL). The organic phase was separated, dried over $Na_2SO_4$ and filtered. The solvent was removed under reduced pressure and the residue was purified on HP-Sil SNAP cartridges using a Biotage Isolera One purification system employing a methanol/dichloromethane gradient (0/100->10/90) to afford the title compound (0.006 g; 17%).

$^1$H-NMR (400 MHz, DMSO-$d_6$) δ=9.20 (s, 1H), 8.45 (d, 1H), 8.36 (d, 1H), 7.69 (d, 1H), 6.90 (d, 1H), 4.67 (t, 1H), 4.55 (t, 1H), 3.84 (s, 3H), 3.71 (t, 4H), 2.76 (t, 1H), 2.69 (t, 1H), 2.63 (t, 4H).

MS (ESI): m/z=314.00 [M+H]$^+$.

Example 169

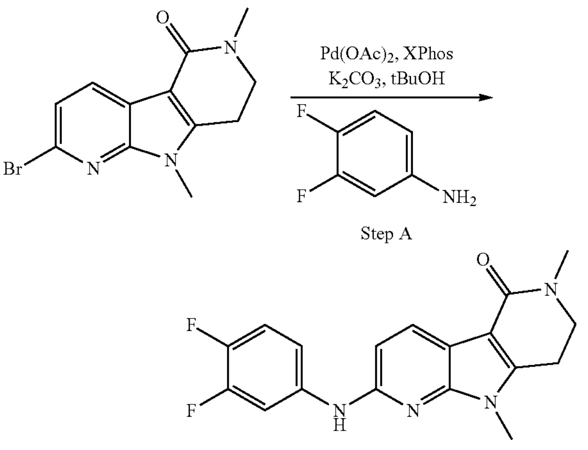

Step A

An oven dried Schlenk flask was evacuated and back filled with argon gas. To a mixture of palladium(II) acetate (0.0038 g, 0.017 mmol) and dicyclohexyl-(2',4',6'-triisopropyl-[1,1'-biphenyl]-2-yl)phosphine (0.024 g, 0.051 mmol) was added degased tert.-butanol (Ratio: 1.000, Volume: 3 ml). The mixture was warmed to 80° C. for 90 seconds. The dark red solution was transferred in a vial containing the title compound from Preparative Example 2 (0.05 g, 0.170 mmol), 3,4-difluoroaniline (0.018 ml, 0.178 mmol) and potassium carbonate (0.047 g, 0.340 mmol). The resulting mixture was stirred at 110° C. for 4 h. The reaction mixture was concentrated to dryness. The residue was purified on HP-Sil SNAP cartridges using a Biotage Isolera One purification system employing a dichloromethane/methanol gradient (99/1->95/5) to afford the title compound (0.033 g, 56%).

$^1$H-NMR (400 MHz, DMSO-$d_6$) δ=2.93 (s, 3H); 3.08 (2H); 3.61 (2H); 3.70 (s, 3H); 6.69 (d, 1H); 7.32 (q, 1H); 7.36-7.45 (m, 1H); 8.02 (d, 1H); 8.15 (ddd, 1H); 9.36 (br-s, 1H).

MS (ESI); m/z=343.62 (MH$^+$).

General Procedure Using 1,4-Dioxane as Solvent:

An oven dried Schlenk flask was evacuated and back filled with argon gas. The procedure was repeated 3-4 times and the flask was cooled to room temperature. Then dicyclohexyl-(2',4',6'-triisopropyl-[1,1-biphenyl]-2-yl)phosphine (10 mol %) and palladium(II)-acetate (10 mol %) were heated at 110° C. for 1 minute to become a clear red solution. To the catalyst solution were then added the amine (1 mmol), bromo-derivative (1 mmol), and sodium tert.-butoxide (3 mmol). The reaction mixture was heated at 110° C. in a sand-bath for 2-3 hours and cooled to room temperature and the solvents were removed under reduced pressure. The residue was purified on HP-Sil SNAP cartridges using a Biotage Isolera One purification system employing a dichloromethane/methanol gradient (100/0->90/10) to afford the title compounds.

Examples 170 to 197

Following the Pd-coupling procedure as described in Example 169 or the general procedure using 1,4-dioxane, except using the bromo-derivatives and amines indicated in the table below, the following compounds were prepared. The ligand dicyclohexyl-(2',4',6'-triisopropyl-[1,1'-biphenyl]-2-yl)phosphine (XPhos) can be replaced by 4,5-bis(diphenylphosphino)-9,9-dimethylxanthene (XantPhos) and the base sodium tert.-butoxide can be replaced by cesium carbonate.

TABLE 19

| Bromo derivative | Amine | Product Example | 1. Yield<br>2. $^1$H-NMR<br>3. MH$^+$ (ESI) |
|---|---|---|---|
| 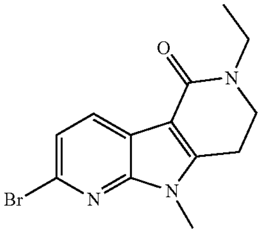 [SMILES: CCN1CCc2c(c3ccc(Br)nc3n2C)C1=O] | 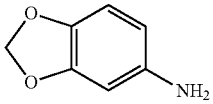 | 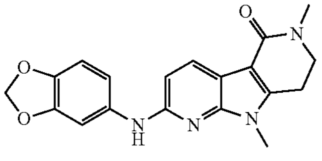<br>170 | 1. 50%<br>2. $^1$H-NMR (400 MHz, DMSO-d$_6$) δ = 2.92 (s, 3H); 3.06 (t, 2H); 3.60 (t, 2H); 3.67 (s, 3H); 5.95 (s, 2H); 6.65 (d, 1H); 6.83 (d, 1H); 7.11 (dd, 1H); 7.64 (d, 1H); 7.95 (d, 1H)<br>3. 351.59 |
| 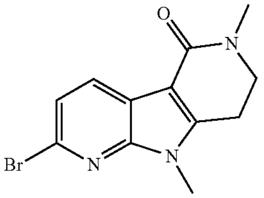 [SMILES: CN1CCc2c(c3ccc(Br)nc3n2C)C1=O] | 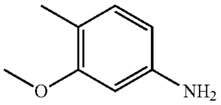 | 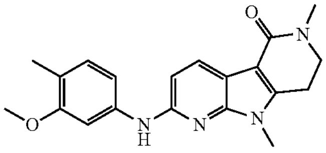<br>171 | 1. 74%<br>2. $^1$H-NMR (400 MHz, DMSO-d$_6$) δ = 2.09 (s, 3H); 2.93 (s, 3H); 3.07 (t, 2H); 3.60 (t, 2H); 3.69 (s, 3H); 3.83 (s, 3H); 6.68 (d, 1H); 6.99 (d, 1H); 7.03 (d, 1H); 7.86 (s, 1H); 7.96 (d, 1H); 9.02 (s, 1H)<br>3. 351.67 |
| 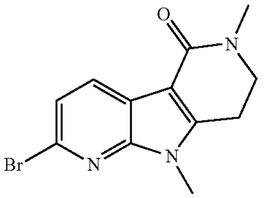 [SMILES: CN1CCc2c(c3ccc(Br)nc3n2C)C1=O] | 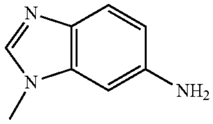 | 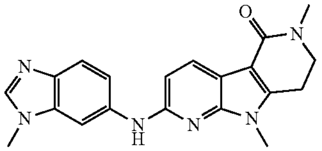<br>172 | 1. 72%<br>2. $^1$H-NMR (400 MHz, DMSO-d$_6$) δ = 2.93 (s, 3H); 3.09 (t, 2H); 3.62 (t, 2H); 3.75 (s, 3H); 3.82 (s, 3H); 6.73 (d, 1H); 7.22 (dd, 1H); 7.51 (d, 1H); 7.99 (d, 1H); 8.02 (s, 1H); 8.57 (d, 1H); 9.18 (s, 1H)<br>3. 361.38 |
| 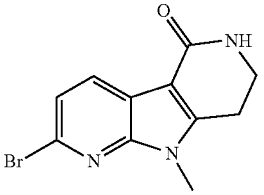 [SMILES: Cn1c2c(c3ccc(Br)nc31)C(=O)NCC2] | 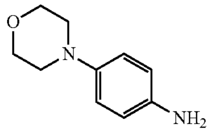 [SMILES: Nc1ccc(N2CCOCC2)cc1] | 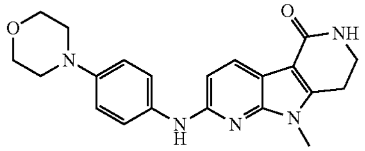<br>173 | 1. 15%<br>2. $^1$H-NMR (400 MHz, DMSO-d$_6$) δ = 2.96 (t, 2H); 3.02 (t 4H); 3.48 (t, 2H); 3.68 (s, 3H); 3.74 (t, 4H); 6.62 (d, 1H); 6.91 (d, 2H); 6.98 (br-s, 1H); 7.66 (d, 2H); 7.91 (d, 1H); 8.79 (br-s, 1H)<br>3. 378.33 |
| 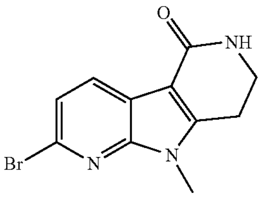 [SMILES: Cn1c2c(c3ccc(Br)nc31)C(=O)NCC2] | 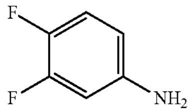 | 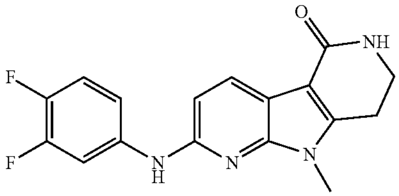<br>174 | 1. 20%<br>2. $^1$H-NMR (400 MHz, DMSO-d$_6$) δ = 9.31 (s, 1H), 8.20-8.08 (m, 1H), 8.00 (d, 1H), 7.43-7.27 (m, 2H), 7.04 (s, 1H), 6.68 (d, 1H), 3.71 (s, 1H), 3.53-3.42 (m, 2H), 3.05-2.86 (m, 2H) |

TABLE 19-continued

| Bromo derivative | Amine | Product Example | 1. Yield 2. $^1$H-NMR 3. $MH^+$ (ESI) |
|---|---|---|---|
| 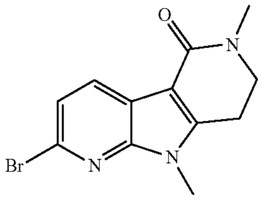 [SMILES: CN1CCc2c(c3ccc(Br)nc3n2C)C1=O] | 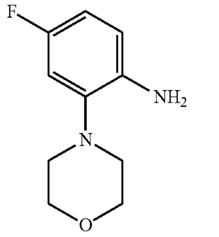 [SMILES: Nc1ccc(F)cc1N1CCOCC1] | 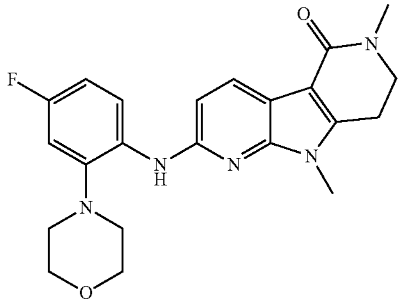 175 | 1. 10% 2. $^1$H NMR (400 MHz, Methanol-$d_4$) δ = 8.19 (d, 1H), 8.03 (dd, 1H), 7.04 (dd, 1H), 6.97-6.87 (m, 1H), 6.78 (d, 1H), 3.91-3.77 (m, 4H), 3.77-3.66 (m, 5H), 3.13 (m, 2H), 3.08 (s, 3H), 3.05-2.96 (m, 4H) 3. 410.27 |
| 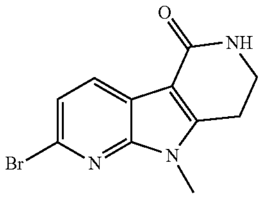 | 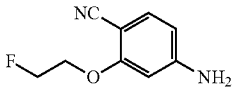 | 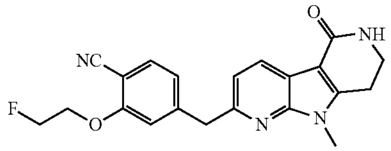 176 | 1. 17% 2. $^1$H-NMR (400 MHz, DMSO-$d_6$) δ = 9.74 (s, 1H), 8.17 (d, 1H), 8.06 (d, 1H), 7.58-7.48 (m, 1H), 7.20 (q, 1H), 7.09 (s, 1H), 6.79 (d, 1H), 4.92-4.84 (m, 1H), 4.76 (d, 1H), 4.54-4.35 (m, 2H), 3.74 (s, 3H), 3.49 (dq, 2H), 3.00 (t, 2H) |
| 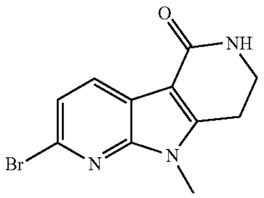 [SMILES: Cn1c2c(c3ccc(Br)nc31)C(=O)NCC2] | 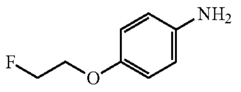 | 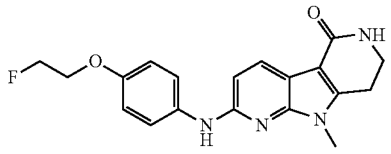 177 | 1. 28% 2. $^1$H NMR (400 MHz, DMSO-$d_6$) δ 9.74 (s, 1H), 8.16 (s, 1H), 8.06 (d, 1H), 7.54 (d, 1H), 7.20 (d, 1H), 7.09 (s, 1H), 6.79 (d, 1H), 4.94-4.81 (m, 1H), 4.83-4.67 (m, 1H), 4.51-4.42 (m, 1H), 4.46-4.34 (m, 1H), 3.74 (s, 3H), 3.54-3.39 (m, 2H), 3.11-2.89 (m, 2H). |
| 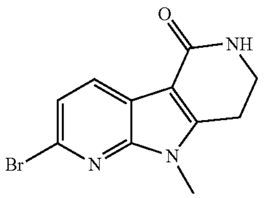 [SMILES: Cn1c2c(c3ccc(Br)nc31)C(=O)NCC2] | 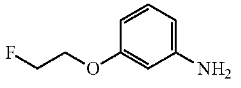 | 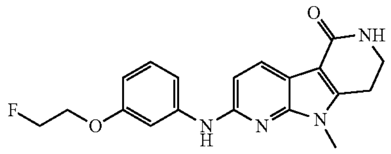 178 | 1. 39% 2. $^1$H-NMR (400 MHz, DMSO-$d_6$) δ = 9.10 (s, 1H), 7.97 (d, 1H), 7.70 (s, 1H), 7.28-7.23 (m, 1H), 7.16 (t, 1H), 7.02 (s, 1H), 6.70 (d, 1H), 6.47 (dd, 1H), 4.85-4.78 (m, 1H), 4.72-4.65 (m, 1H), 4.30-4.24 (m, 1H), 4.23-4.16 (m, 1H), 3.71 (s, 3H), 3.48 (td, 2H), 2.97 (t, 2H) |
| 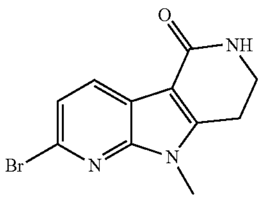 [SMILES: Cn1c2c(c3ccc(Br)nc31)C(=O)NCC2] | 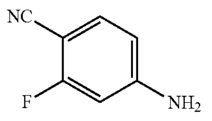 | 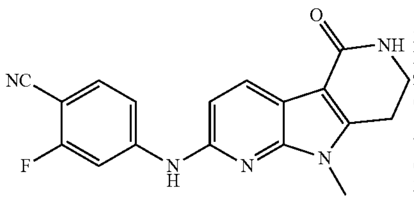 179 | 1. 9% 2. $^1$H-NMR (400 MHz, DMSO-$d_6$) δ = 9.99 (s, 1H), 8.19 (dd, 1H), 8.09 (d, 1H), 7.71 (t, 1H), 7.49 (dd, 1H), 7.10 (d, 1H), 6.81 (d, 1H), 3.74 (s, 3H), 3.49 (td, 2H), 3.01 (t, 2H) |

TABLE 19-continued

| Bromo derivative | Amine | Product Example | 1. Yield<br>2. $^1$H-NMR<br>3. $MH^+$ (ESI) |
|---|---|---|---|
| 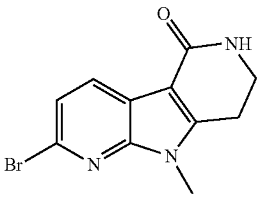 [SMILES: Cn1c2c(c3ccc(Br)nc31)C(=O)NCC2] | 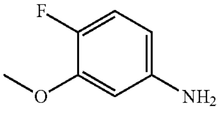 | 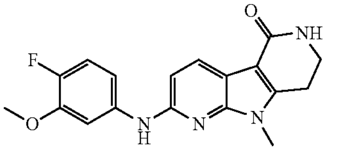<br>180 | 1. 28%<br>2. $^1$H-NMR (400 MHz, DMSO-$d_6$) δ = 9.12 (s, 1H), 8.09-8.01 (m, 1H), 7.97 (d, 1H), 7.09 (dd, 2H), 7.03 (s, 1H), 6.67 (d, 1H), 3.88 (s, 3H), 3.70 (s, 3H), 3.55-3.41 (m, 2H), 2.97 (t, 2H) |
| 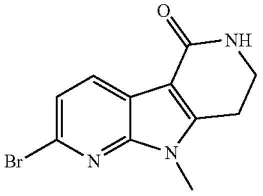 [SMILES: Cn1c2c(c3ccc(Br)nc31)C(=O)NCC2] | 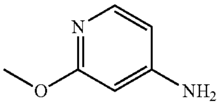 | 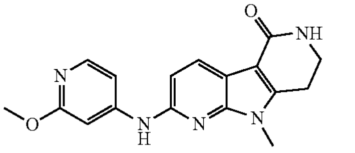<br>181 | 1. 35%<br>2. $^1$H-NMR (400 MHz, DMSO-$d_6$) δ = 10.16 (s, 1H), 8.41 (s, 1H), 8.07 (d, 1H), 7.68 (s, 1H), 7.18 (d, 1H), 7.11 (s, 1H), 3.90 (s, 3H), 3.73 (s, 3H), 3.55-3.41 (m, 2H), 3.07-2.90 (m, 2H) |
| 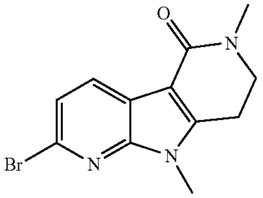 [SMILES: CN1CCc2c(c3ccc(Br)nc3n2C)C1=O] | 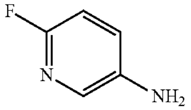 | 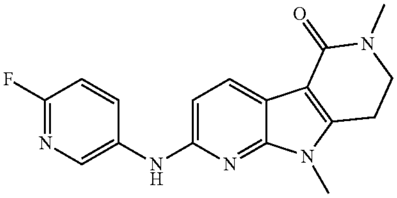<br>182 | 1. 23%<br>2. $^1$H-NMR (400 MHz, DMSO-$d_6$) δ = 9.34 (s, 1H), 8.67-8.66 (m, 1H), (ddd, 1H), 8.04 (d, 1H), 7.12 (dd, 1H), 6.71 (d, 1H), 3.70 (s, 3H), 3.61 (t, 1H), 3.08 (d, 1H), 2.93 (s, 3H)<br>3. 326.10 |
| 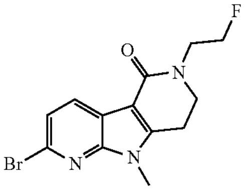 [SMILES: Cn1c2c(c3ccc(Br)nc31)C(=O)N(CCF)CC2] | 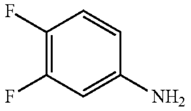 | 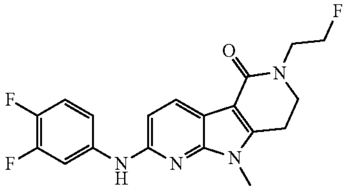<br>183 | 1. 4%<br>2. 375.1 |
| 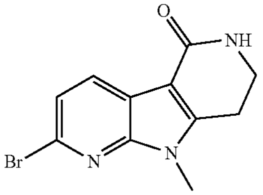 [SMILES: Cn1c2c(c3ccc(Br)nc31)C(=O)NCC2] | 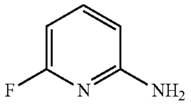 | 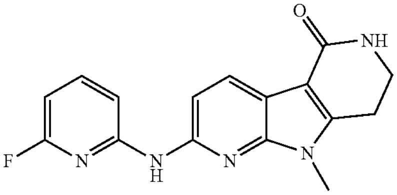<br>184 | 1. 43%<br>2. $^1$H-NMR (400 MHz, DMSO-$d_6$) δ = 9.98 (s, 1H), 8.22-8.02 (m, 2H), 8.01-7.76 (m, 1H), 7.24 (d, 1H), 7.12 (s, 1H), 6.56 (d, 1H), 5.77 (s, 1H), 3.76 (s, 3H), 3.51 (t, 2H), 3.02 (t, 2H) |
| 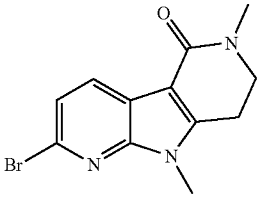 [SMILES: CN1CCc2c(c3ccc(Br)nc3n2C)C1=O] | 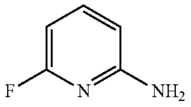 | 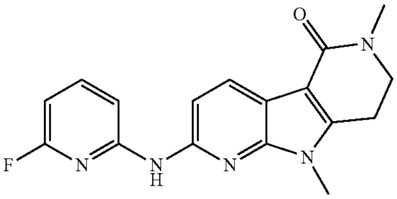<br>185 | 1. 55%<br>2. $^1$H-NMR (400 MHz, DMSO-$d_6$) δ = 9.98 (s, 1H), 8.18-8.00 (m, 2H), 7.94-7.74 (m, 1H), 7.25 (d, 1H), 6.56 (dd, 1H), 3.75 (s, 3H), 3.64 (t, 2H), 3.12 (t, 2H), 2.95 (s, 3H) |

TABLE 19-continued
| Bromo derivative | Amine | Product Example | 1. Yield 2. $^1$H-NMR 3. $MH^+$ (ESI) |
|---|---|---|---|
| 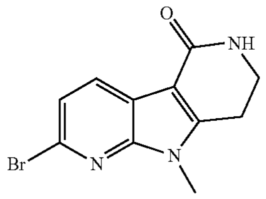 [SMILES: Cn1c2c(c3ccc(Br)nc31)C(=O)NCC2] | 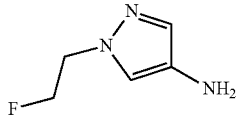 | 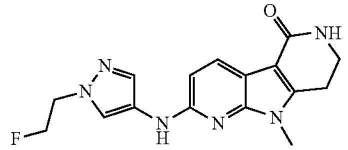 186 | 1. 19% 2. 329.25 |
| 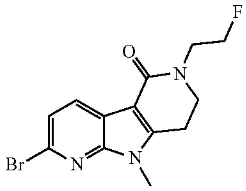 [SMILES: Cn1c2c(c3ccc(Br)nc31)C(=O)N(CCF)CC2] | 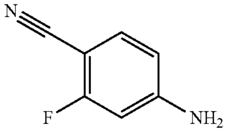 | 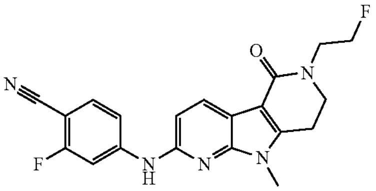 187 | 1. 29% 2. $^1$H-NMR (400 MHz, DMSO-$d_6$) δ = 10.03 (s, 1H), 8.20 (dd, 1H), 8.11 (d, 1H), 7.71 (t, 1H), 7.50 (dd, 1H), 6.83 (d, 1H), 4.66 (t, 1H), 4.54 (t, 1H), 3.81-3.61 (m, 7H), 3.32 (s, 0H), 3.10 (t, 2H) |
| 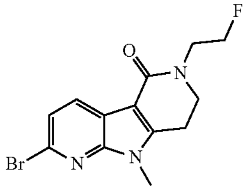 [SMILES: Cn1c2c(c3ccc(Br)nc31)C(=O)N(CCF)CC2] | 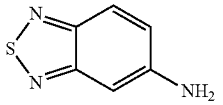 | 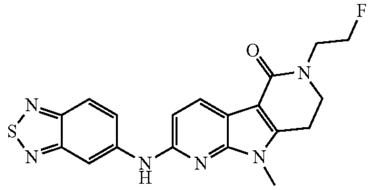 188 | 1. 64% 2. $^1$H-NMR (400 MHz, DMSO-$d_6$) δ = 9.78 (s, 1H), 9.03 (s, 1H), 8.13 (d, 1H), 7.97 (d, 1H), 7.76-7.70 (m, 1H), 6.92 (d, 1H), 4.69 (t, 1H), 4.57 (t, 1H), 3.89-3.64 (m, 7H), 3.14 (t, 2H) |
| 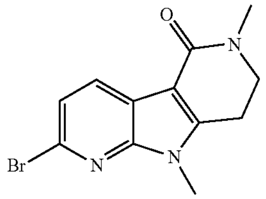 [SMILES: CN1CCc2c(c3ccc(Br)nc3n2C)C1=O] | 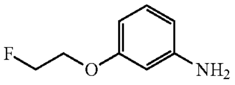 | 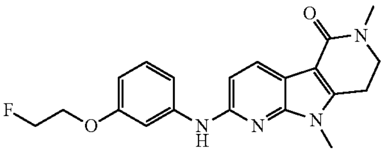 189 | 1. 9.6% 2. $^1$H-NMR (400 MHz, DMSO-$d_6$) δ = 9.10 (s, 1H), 7.99 (d, 1H), 7.70 (s, 1H), 7.25 (d, 1H), 7.16 (t, 1H), 6.70 (d, 1H), 6.47 (d, 1H), 4.88-4.74 (m, 1H), 4.69 (d, 1H), 4.28 (d, 1H), 4.20 (d, 1H), 3.67 (s, 3H), 3.66-3.53 (m, 2H), 3.31 (s, 0H), 3.07 (t, 2H), 2.93 (s, 3H) |
| 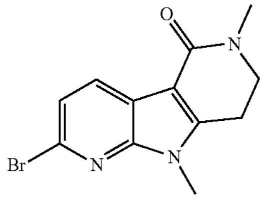 [SMILES: CN1CCc2c(c3ccc(Br)nc3n2C)C1=O] | 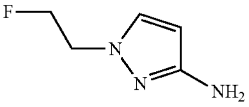 | 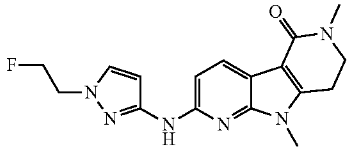 190 | 1. 61% 2. $^1$H-NMR (400 MHz, DMSO-$d_6$) δ = 9.40 (s, 1H), 7.95 (d, 1H), 7.63 (d, 1H), 6.91 (d, 1H), 6.73 (d, 1H), 4.82 (t, 1H), 4.70 (t, 1H), 4.36 (t, 1H), 4.30 (t, 1H), 3.69 (s, 3H), 3.62 (t, 2H), 3.08 (t, 2H), 2.94 (s, 3H) |
| 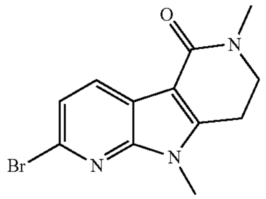 [SMILES: CN1CCc2c(c3ccc(Br)nc3n2C)C1=O] | 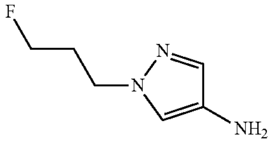 | 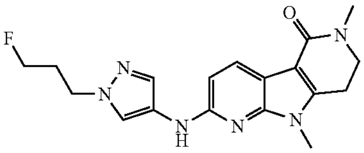 191 | 1. 21% 2. $^1$H-NMR (400 MHz, DMSO-$d_6$) δ = 8.90 (s, 1H), 8.12 (s, 1H), 7.92 (d, 1H), 7.57 (s, 1H), 6.55 (d, 1H), 4.53 (t, 1H), 4.42 (t, 1H), 4.23 (t, 2H), 3.72 (s, 3H), 3.62 (t, 2H), 3.08 (t, 2H), 2.94 (s, 3H), 2.18 (dt, 2H) |

TABLE 19-continued

| Bromo derivative | Amine | Product Example | 1. Yield<br>2. $^{1}$H-NMR<br>3. $MH^{+}$ (ESI) |
|---|---|---|---|
| 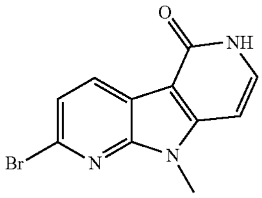 [SMILES: Cn1c2cc[nH]c(=O)c2c2ccc(Br)nc21] | 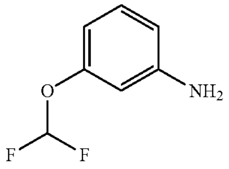 [SMILES: Nc1cccc(OC(F)F)c1] | 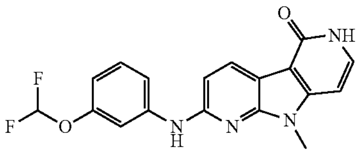<br>193 | 1. 5%<br>2. $^{1}$H-NMR (400 MHz, DMSO-$d_6$) δ 11.24 (s, 1H), 9.50 (s, 1H), 8.20 (d, 1H), 8.15 (d, 1H), 7.54-7.40 (m, 1H), 7.38-7.28 (m, 1H), 7.26 (t, 1H), 6.80 (d, 1H), 6.74-6.62 (m, 1H), 3.86 (s, 3H)<br>3. 357.16 |
| 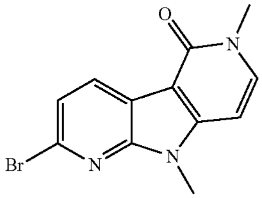 [SMILES: Cn1ccc2c(c1=O)c1ccc(Br)nc1n2C] | 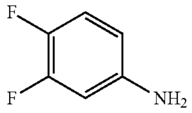 | 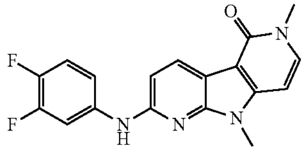<br>194 | 1. 52%<br>2. $^{1}$H-NMR (400 MHz, DMSO-$d_6$) δ = 9.52 (s, 1H), 8.30-8.13 (m, 2H), 7.68 (d, 1H), 7.45 (d, 1H), 7.36 (q, 1H), 6.78 (dd, 2H), 3.86 (s, 3H), 3.57 (s, 3H) |
| 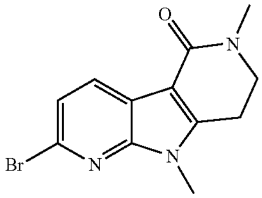 [SMILES: CN1CCc2c(c3ccc(Br)nc3n2C)C1=O] | 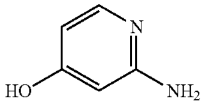 | 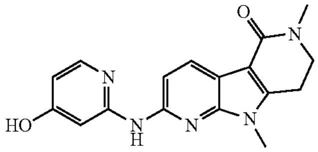<br>195 | 1. 18%<br>2. $^{1}$H-NMR (400 MHz, DMSO-$d_6$) δ = 9.46 (s, 1H), 8.01 (d, 1H), 7.94-7.83 (m, 1H), 7.67 (s, 1H), 7.22 (s, 1H), 6.29 (s, 1H), 3.74 (s, 2H), 3.62 (t, 2H), 3.09 (t, 2H), 2.93 (s, 3H). |
| 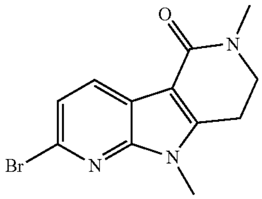 [SMILES: CN1CCc2c(c3ccc(Br)nc3n2C)C1=O] | 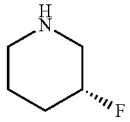 | 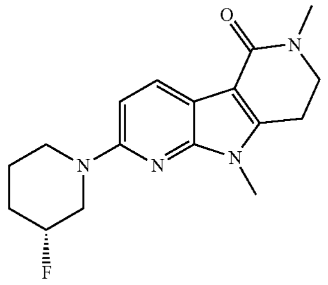<br>196 | 1. 36%<br>2. $^{1}$H-NMR (400 MHz, DMSO-$d_6$) δ =7.94 (d, 1H), 6.75 (d, 1H), 4.92-4.58 (m, 1H), 3.89-3.65 (m, 2H), 3.61 (s, 3H), 3.58 (t, 2H), 3.51-3.45 (m, 1H), 3.04 (t, 2H), 2.91 (s, 3H), 2.09-1.67 (m, 4H), 1.67-1.37 (m, 1H). |
| 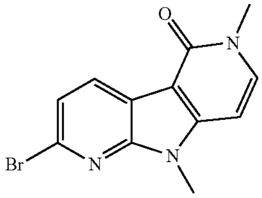 [SMILES: Cn1ccc2c(c1=O)c1ccc(Br)nc1n2C] | 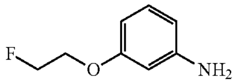 | 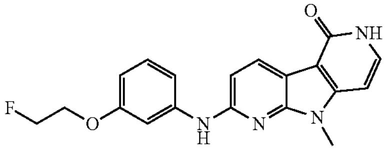<br>197 | 1. 5%<br>2. $^{1}$H NMR (400 MHz, DMSO-$d_6$) δ = 11.22 (s, 1H), 9.30 (s, 1H), 8.17 (d, 1H), 7.74 (s, 1H), 7.40-7.27 (m, 2H), 7.20 (t, 1H), 6.78 (d, 1H), 6.70 (d, 1H), 6.51 (d, 1H), 5.07-4.76 (m, 1H), 4.76-4.63 (m, 1H), 4.36-4.27 (m, 1H), 4.27-4.17 (m, 1H), 3.84 (s, 3H)<br>3. 352.80 |

Example 198

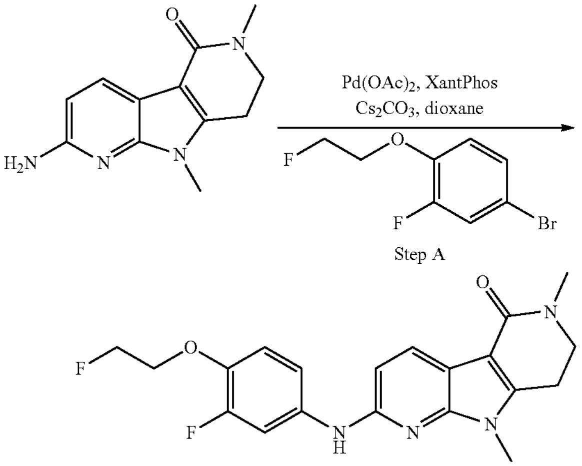

Step A

XantPhos (0.046 g, 0.09 mmol) and palladium(II)-acetate (0.008 g, 0.03 mmol) were added to degassed 1,4-dioxane (4 mL), followed by the title compound from Preparative Example 41 (0.063 g, 0.27 mmol), the title compound from Preparative Example 26 (0.075 g, 0.31 mmol), and cesium carbonate (0.3 g, 0.9 mmol). The reaction mixture was heated at 110° C. in a sand-bath for 1 hour and cooled to room temperature. The reaction mixture was dissolved in dichloromethane (150 mL), washed with water as well as brine, dried over $Na_2SO_4$ and filtered. The solvent was removed under reduced pressure and the residue was purified on KP-NH-Sil cartridges using a Biotage Isolera One purification system employing an ethyl acetate/methanol gradient (100/0->90/10) to afford the title compound (0.033 g, 28%).

$^1$H-NMR (400 MHz, DMSO-$d_6$) δ=9.13 (s, 1H), 8.07-7.66 (m, 2H), 7.50-7.33 (m, 1H), 7.12 (t, 1H), 6.65 (d, 1H), 4.84-4.71 (m, 1H), 4.74-4.59 (m, 1H), 4.34-4.23 (m, 1H), 4.24-4.14 (m, 1H), 3.69 (d, 3H), 3.60 (t, 2H), 3.07 (t, 2H), 2.92 (s, 3H).

Examples 199 to 212

Following the Pd-coupling procedure as described in Example 198, except using the amine derivatives and bromo derivatives indicated in the table below, the following compounds were prepared.

TABLE 20

| Amine derivative | Bromo derivative | Product Example | 1. Yield 2. $^1$H-NMR 3. MH$^+$ (ESI) |
|---|---|---|---|
| 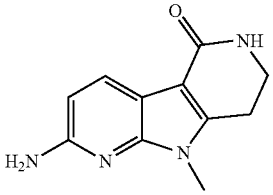 [SMILES: Cn1c2c(c3ccc(N)nc31)C(=O)NCC2] | 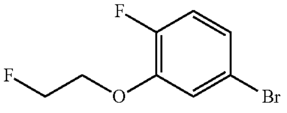 [SMILES: FCCOc1cc(Br)ccc1F] | 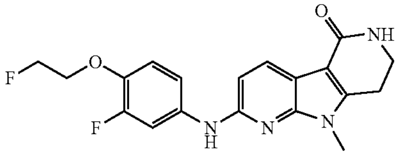 [SMILES: Cn1c2c(c3ccc(Nc4ccc(OCCF)c(F)c4)nc31)C(=O)NCC2] 199 SN | 1. 32% 2. $^1$H-NMR (400 MHz, DMSO-$d_6$) δ = 9.12 (s, 1H), 8.07-7.87 (m, 2H), 7.38 (ddd, 1H), 7.12 (t, 1H), 7.03 (t, 1H), 6.65 (d, 1H), 4.88-4.73 (m, 1H), 4.74-4.59 (m, 1H), 4.36-4.24 (m, 1H), 4.26-4.12 (m, 1H), 3.70 (s, 3H), 3.58-3.40 (m, 2H), 2.97 (t, 2H) |
| 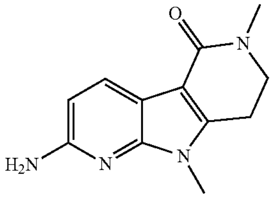 [SMILES: CN1CCc2c(c3ccc(N)nc3n2C)C1=O] | 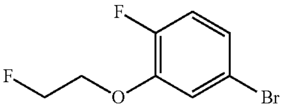 [SMILES: FCCOc1cc(Br)ccc1F] | 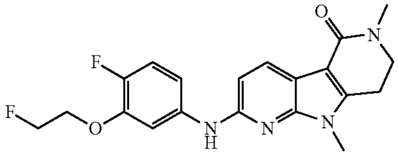 [SMILES: CN1CCc2c(c3ccc(Nc4ccc(F)c(OCCF)c4)nc3n2C)C1=O] 200 SN | 1. 49% 2. $^1$H-NMR (400 MHz, DMSO-$d_6$) δ = 9.12 (s, 1H), 7.99 (d, 1H), 7.18-7.05 (m, 2H), 6.67 (d, 1H), 4.88-4.81 (m, 1H), 4.76-4.69 (m, 1H), 4.40-4.33 (m, 1H), 4.33-4.26 (m, 1H), 3.69 (s, 3H), 3.60 (t, 2H), 3.07 (t, 2H), 2.92 (s, 3H). |
| 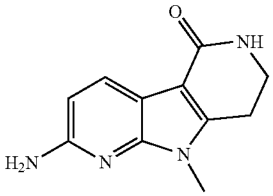 [SMILES: Cn1c2c(c3ccc(N)nc31)C(=O)NCC2] | 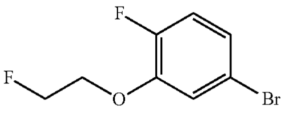 [SMILES: FCCOc1cc(Br)ccc1F] | 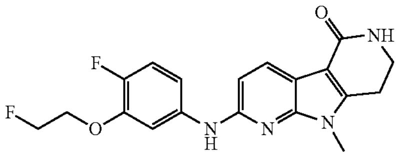 [SMILES: Cn1c2c(c3ccc(Nc4ccc(F)c(OCCF)c4)nc31)C(=O)NCC2] 201 SN | 1. 32% 2. $^1$H NMR (400 MHz, DMSO-$d_6$) δ = 9.15 (s, 1H), 8.08-7.91 (m, 2H), 7.26-7.11 (m, 2H), 7.07 (s, 1H), 6.69 (d, 1H), 5.06-4.61 (m, 2H), 4.35 (dt, 2H), 3.72 (s, 3H), 3.56-3.43 (m, 2H), 3.08-2.90 (m, 2H). |

TABLE 20-continued

| Amine derivative | Bromo derivative | Product Example | 1. Yield<br>2. $^{1}$H-NMR<br>3. MH$^{+}$ (ESI) |
| --- | --- | --- | --- |
| 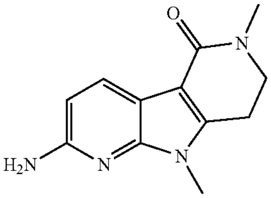 [SMILES: CN1CCc2c(c3ccc(N)nc3n2C)C1=O] | 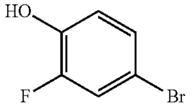 | 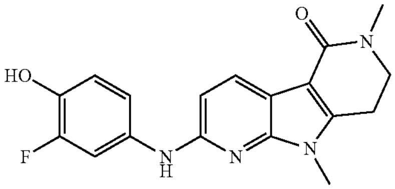 [SMILES: CN1CCc2c(c3ccc(Nc4ccc(O)c(F)c4)nc3n2C)C1=O]<br>202 | 1. 11.5%<br>2. $^{1}$H-NMR (400 MHz, DMSO-d$_{6}$) δ = 9.68 (s, 1H), 8.93 (s, 1H), 7.95 (d, 1H), 7.63 (dd, 1H), 7.16-7.05 (m, 1H), 6.99 (t, 1H), 6.65 (d, 1H), 3.71 (s, 3H), 3.60 (t, 2H), 3.07 (t, 2H), 2.92 (s, 3H) |
| 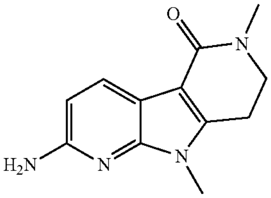 [SMILES: CN1CCc2c(c3ccc(N)nc3n2C)C1=O] | 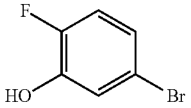 | 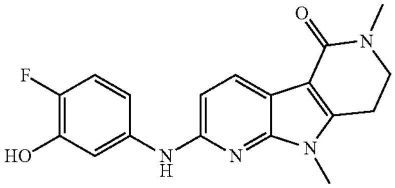 [SMILES: CN1CCc2c(c3ccc(Nc4ccc(F)c(O)c4)nc3n2C)C1=O]<br>203 | 1. 28%<br>2. $^{1}$H-NMR (400 MHz, DMSO-d$_{6}$) δ = 9.68 (s, 1H), 8.93 (s, 1H), 7.95 (d, 1H), 7.63 (dd, 1H), 7.14-7.03 (m, 1H), 7.04-6.90 (m, 1H), 6.65 (d, 1H), 3.71 (s, 3H), 3.60 (t, 2H), 3.07 (t, 2H), 2.92 (s, 3H) |
| 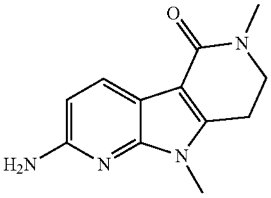 [SMILES: CN1CCc2c(c3ccc(N)nc3n2C)C1=O] | 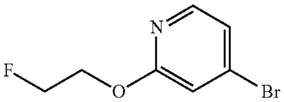 [SMILES: FCCOc1cc(Br)ccn1] | 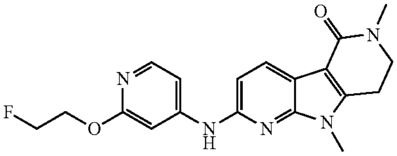 [SMILES: CN1CCc2c(c3ccc(Nc4ccnc(OCCF)c4)nc3n2C)C1=O]<br>204 | 1. 22%<br>2. $^{1}$H-NMR (400 MHz, DMSO-d$_{6}$) δ = 9.45 (s, 1H), 8.10 (d, 1H), 7.47 (d, 1H), 7.22 (d, 1H), 6.82 (d, 1H), 6.37 (dd, 1H), 4.71 (t, 1H), 4.59 (t, 1H), 4.16 (t, 1H), 4.09 (t, 1H), 3.74 (s, 3H), 3.64 (t, 2H), 3.13 (t,2H), 2.95 (s, 3H) |
| 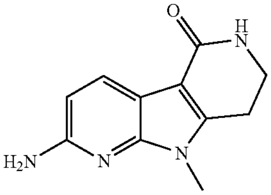 [SMILES: Cn1c2c(c3ccc(N)nc31)C(=O)NCC2] | 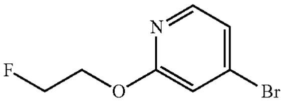 [SMILES: FCCOc1cc(Br)ccn1] | 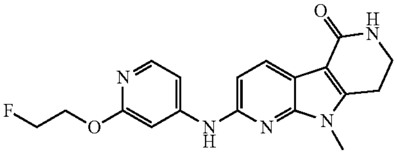 [SMILES: Cn1c2c(c3ccc(Nc4ccnc(OCCF)c4)nc31)C(=O)NCC2]<br>205 | 1. 26%<br>3. 356.2 |
| 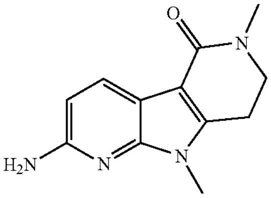 [SMILES: CN1CCc2c(c3ccc(N)nc3n2C)C1=O] | 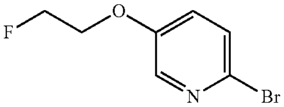 [SMILES: FCCOc1ccc(Br)nc1] | 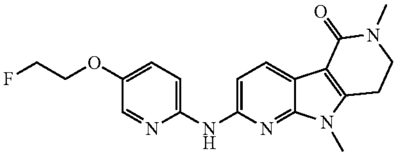 [SMILES: CN1CCc2c(c3ccc(Nc4ccc(OCCF)cn4)nc3n2C)C1=O]<br>206 | 1. 47%<br>2. $^{1}$H-NMR (400 MHz, DMSO-d$_{6}$) δ = 9.52 (s, 1H), 8.11 (d, 1H), 8.05-7.97 (m, 2H), 7.43 (dd, 1H), 7.25 (d, 1H), 4.82-4.77 (m, 1H), 4.71-4.66 (m, 1H), 4.33-4.28 (m, 1H), 4.27-4.20 (m, 1H), 3.70 (s, 3H), 3.61 (t, 2H), 3.08 (t, 2H), 2.92 (s, 3H) |
| 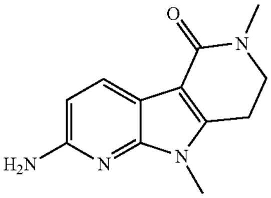 [SMILES: CN1CCc2c(c3ccc(N)nc3n2C)C1=O] | 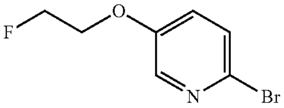 [SMILES: FCCOc1ccc(Br)nc1] | 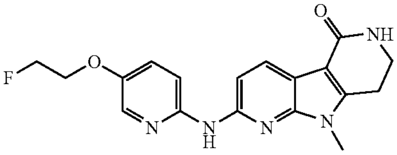 [SMILES: Cn1c2c(c3ccc(Nc4ccc(OCCF)cn4)nc31)C(=O)NCC2]<br>207 | 1. 80%<br>2. $^{1}$H-NMR (400 MHz, DMSO-d$_{6}$) δ = 9.66 (s, 1H), 8.15-7.90 (m, 2H), 7.48 (d, 1H), 7.23 (d, 1H), 7.07 (s, 1H), 4.87-4.75 (m, 1H), 4.72-4.62 (m, 1H), 4.35-4.26 (m, 1H), 4.27-4.18 (m, 1H), 3.72 |

TABLE 20-continued
| Amine derivative | Bromo derivative | Product Example | 1. Yield 2. $^1$H-NMR 3. MH$^+$ (ESI) |
|---|---|---|---|
| | | | (s, 3H), 3.49 (dt, 2H), 2.99 (t, 2H) |
| 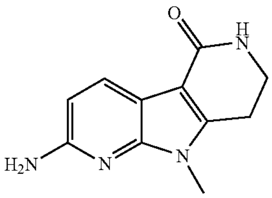 [SMILES: Cn1c2c(c3ccc(N)nc31)C(=O)NCC2] | 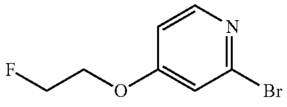 [SMILES: FCCOc1ccnc(Br)c1] | 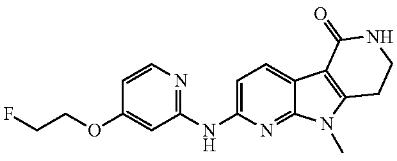 [SMILES: Cn1c2c(c3ccc(Nc4cc(OCCF)ccn4)nc31)C(=O)NCC2] 208 | 1. 40% 2. $^1$H-NMR (400 MHz, DMSO-d$_6$) δ = 9.68 (s, 1H), 8.12-7.93 (m, 2H), 7.89 (d, 1H), 7.28 (dd, 1H), 7.08 (t, 1H), 6.52 (ddd, 1H), 4.95-4.77 (m, 1H), 4.76-4.68 (m, 1H), 4.47-4.34 (m, 1H), 4.36-4.25 (m, 1H), 3.72 (d, 3H), 3.53-3.41 (m, 2H), 2.99 (t, 2H) |
| 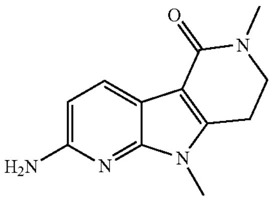 [SMILES: CN1CCc2c(c3ccc(N)nc3n2C)C1=O] | 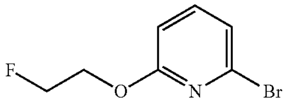 [SMILES: FCCOc1cccc(Br)n1] | 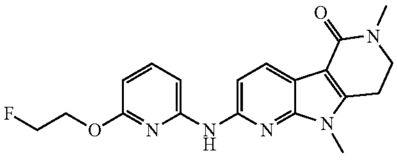 [SMILES: CN1CCc2c(c3ccc(Nc4cccc(OCCF)n4)nc3n2C)C1=O] 209 | 1. 45% 2. $^1$H-NMR (400 MHz, DMSO-d$_6$) δ = 9.54 (s, 1H), 8.06 (d, 1H), 7.69-7.51 (m, 2H), 7.40 (d, 1H), 6.30 (dd,1H), 4.86-4.76(m, 1H), 4.76-4.64 (m, 1H), 4.62-4.52 (m, 1H), 4.53-4.42 (m, 1H), 3.71 (s, 3H), 3.62 (t, 2H), 3.09 (t, 2H), 2.93 (s, 3H). 3. 370.2 (MH) |
| 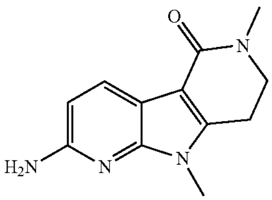 [SMILES: CN1CCc2c(c3ccc(N)nc3n2C)C1=O] | 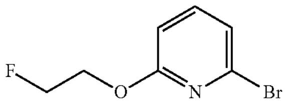 [SMILES: FCCOc1cccc(Br)n1] | 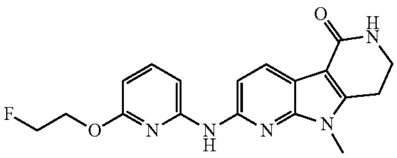 [SMILES: Cn1c2c(c3ccc(Nc4cccc(OCCF)n4)nc31)C(=O)NCC2] 210 | 1. 46% 3. 356.2 |
| 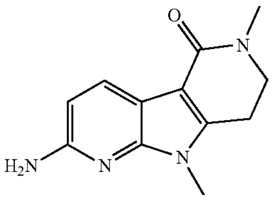 [SMILES: CN1CCc2c(c3ccc(N)nc3n2C)C1=O] | 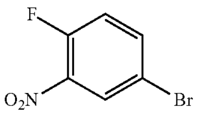 [SMILES: O=[N+]([O-])c1cc(Br)ccc1F] | 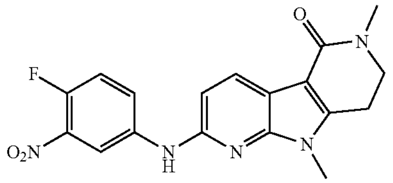 [SMILES: CN1CCc2c(c3ccc(Nc4ccc(F)c([N+](=O)[O-])c4)nc3n2C)C1=O] 211 | 1. 72% 2. $^1$H-NMR (400 MHz, DMSO-d$_6$) δ = 9.68 (s, 1H), 9.16 (dd, 1H), 8.05 (d, 1H), 7.97-7.79 (m, 1H), 7.48 (dd, 1H), 6.72 (d, 1H), 3.73 (s, 3H), 3.61 (t, 2H), 3.09 (t, 2H), 2.93 (s, 3H) |
| 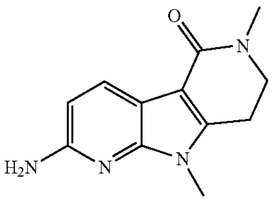 [SMILES: CN1CCc2c(c3ccc(N)nc3n2C)C1=O] | 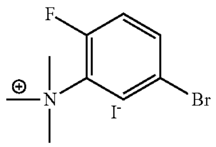 | 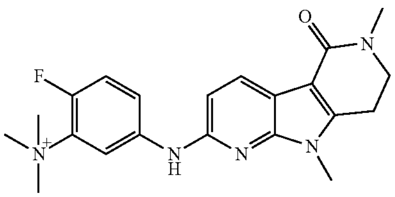 212 | 1. 12% 3. 382.1 |

Example 213
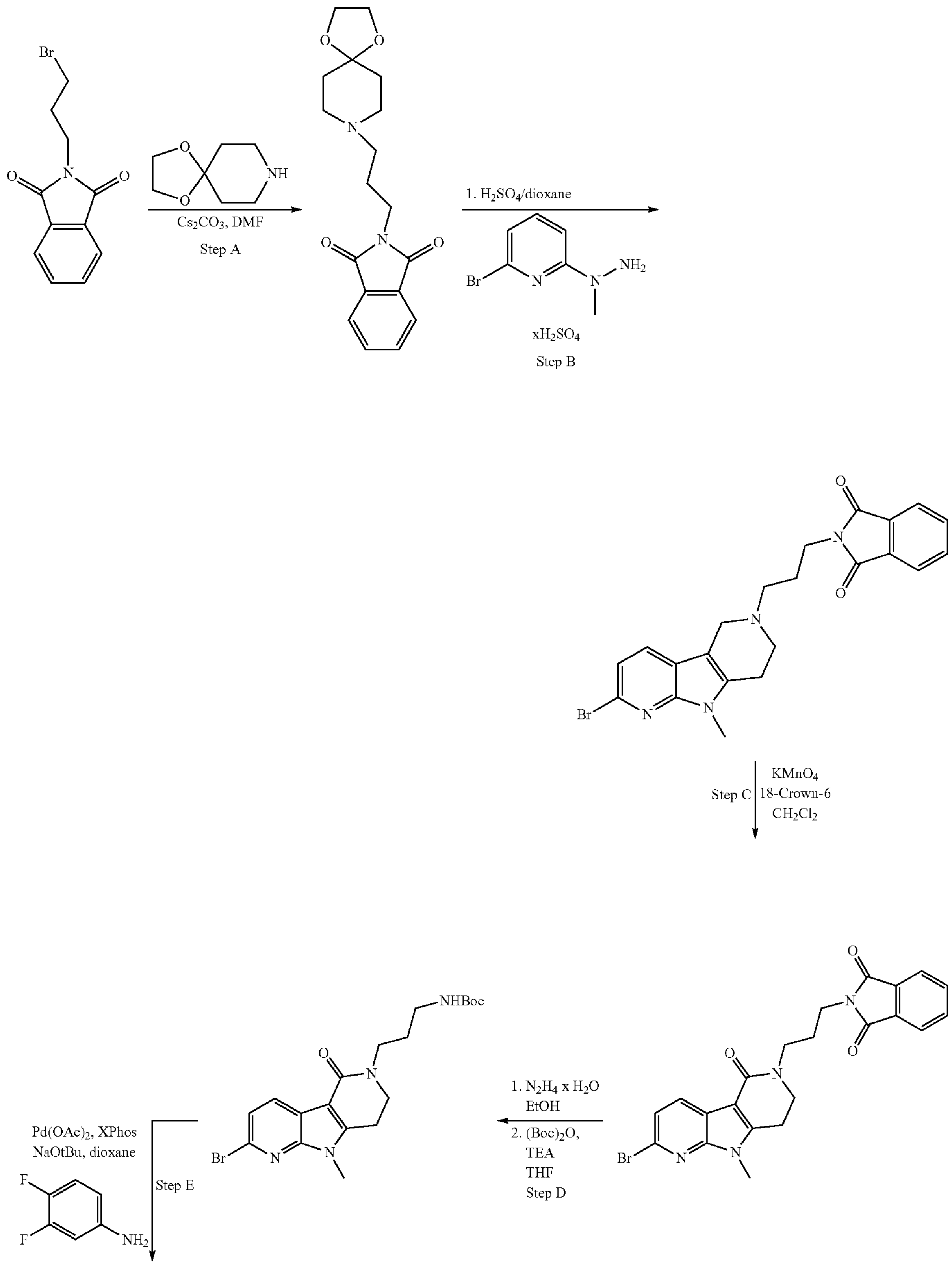

-continued

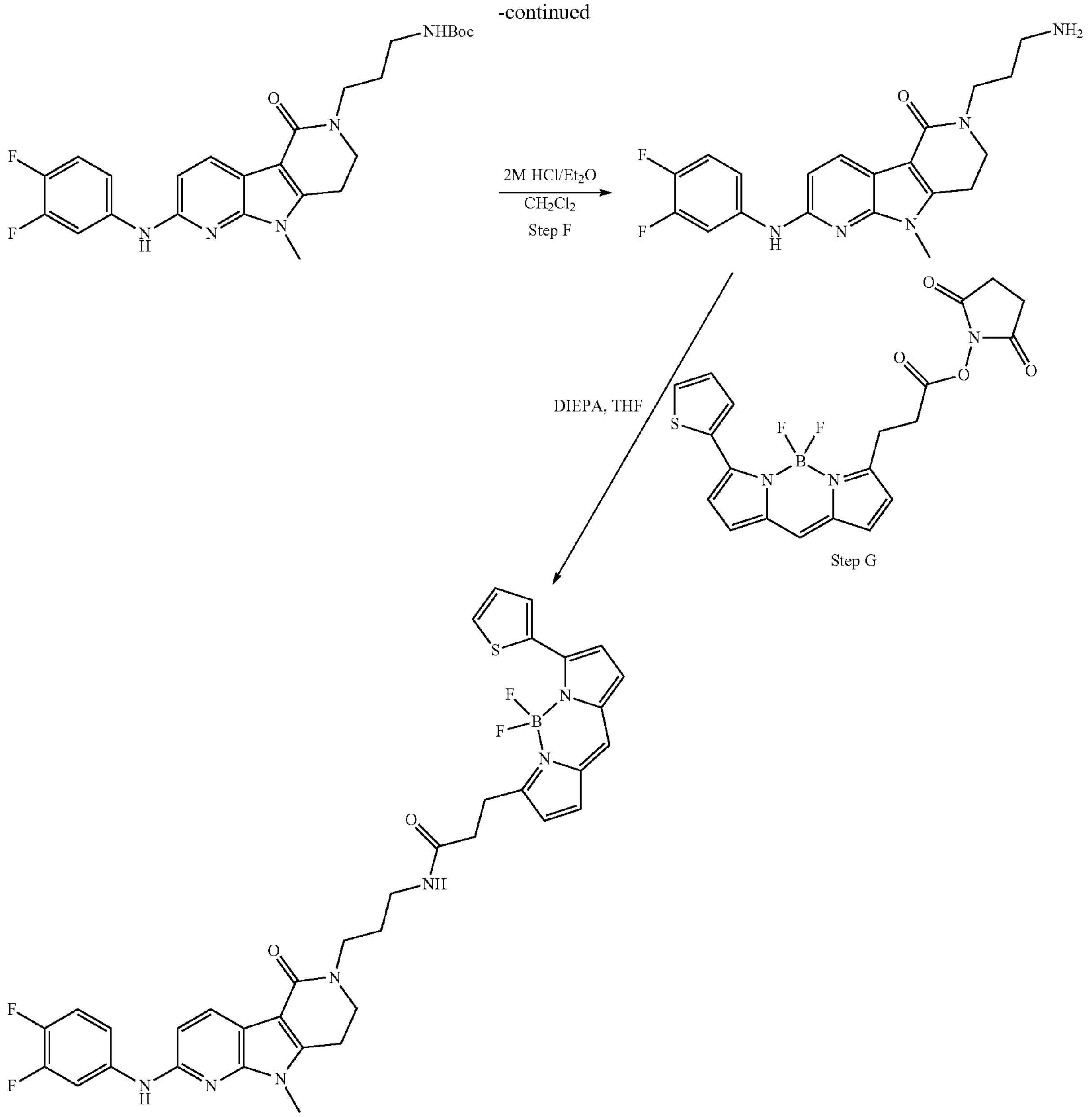

Step A

To a suspension of 1,4-dioxa-8-azaspiro[4.5]decane (2 g, 13.9 mmol) and $Cs_2CO_3$ (7 g, 21 mmol) in N,N'-dimethylformamide (10 mL) was added 2-(3-bromopropyl)isoindoline-1,3-dione (3.74 g, 13.9 mmol). The reaction mixture was then heated at 70° C. for 6 hours. Then the reaction mixture was dissolved in EtOAc (150 mL) and washed with water, brine solution and dried over $Na_2SO_4$. The solvent was removed under reduced pressure. The residue was purified on a HP-Sil cartridge using a Biotage Isolera One purification system employing an ethyl acetate/n-heptane gradient (20/80->100/0) to afford the title compound (3.21 g, 42%).

$^1$H-NMR (400 MHz, $CDCl_3$) δ=7.83 (dd, 2H), 7.71 (dd, 2H), 3.90 (s, 4H), 3.75 (t, 2H), 2.43 (q, 6H), 1.86 (p, 2H), 1.58 (t, 4H).

Step B

To mixture of the sulfate salt of Preparative Example 1, Step A (2 g, 6.6 mmol) and the title compound from Step A above (2.25 g, 6.8 mmol) was added 1,4-dioxane (9 mL). To the stirred reaction mixture concentrated $H_2SO_4$ (1 mL) was dropwise added at room temperature was (exotherm). The gummy reaction mixture was heated at reflux temperature for 6 hours using a sand-bath at ~140° C. The reaction mixture was cooled to room temperature, and the 1,4-dioxane layer discarded. Ice-water (10 mL) was added to the residue and the mixture was stirred until a clear solution was obtained. Then the pH of the reaction mixture was adjusted to pH~12 using an aqueous NaOH solution. The aqueous layer was extracted with dichloromethane (200 mL) and the organic phase was washed with water and brine. The organic phase was separated, dried over $Na_2SO_4$ and the solvent was removed, the residue was purified on HP-Sil cartridges using a Biotage Isolera One purification system employing an ethyl acetate/methanol gradient (100/0->90/10) to afford the title compound as a solid (0.51 g, 17%).

$^1$H-NMR (400 MHz, $CDCl_3$) δ=7.63 (dd, 2H), 7.51 (dd, 2H), 7.48 (d, 1H), 7.12 (d, 1H), 3.84 (t, 2H), 3.58 (s, 3H), 3.51 (s, 2H), 2.81 (t, 2H), 2.71 (t, 2H), 2.66 (d, 2H), 2.00 (t, 2H).

Step C

To a solution of the title compound from Step B above (0.43 g, 0.953 mmol) in dichloromethane (15 mL) was added 18-crown-6 (0.035 g, 0.13 mmol), followed by the addition of $KMnO_4$ (0.225 g, 1.4 mmol) in portions. The resulting reaction mixture was stirred for 6 hours at room temperature. Then the reaction mixture was diluted with saturated sodium metabisulfite solution, stirred for 30 minutes, and extracted with dichloromethane (100 mL). The organic layer was washed with water, brine, and dried over $Na_2SO_4$. The solvent was removed, the residue was purified on HP-Sil cartridges using a Biotage Isolera One purification system employing an ethyl acetate/n-heptane gradient (80/20->100/0) to afford the title compound (0.22 g, quantitative).

$^1$H-NMR (400 MHz, $CDCl_3$) δ=8.22 (d, 1H), 7.82 (dd, 2H), 7.69 (dd, 2H), 7.31 (d, 1H), 3.83-3.71 (m, 7H), 3.63 (t, 2H), 3.12 (t, 2H), 2.11-1.97 (m, 2H).

Step D

To a solution of the title compound from Step C above (0.1 g, 0.21 mmol) in ethanol (3 mL) was added hydrazine hydrate (0.5 mL). Then the reaction mixture was stirred at room temperature overnight. The white solid was filtered and discarded. The filtrate was concentrated, dissolved in ethyl acetate (100 mL) and washed with water as well as brine solution and dried over $Na_2SO_4$. The solvent was evaporated, the residue was dissolved in THF (5 mL) and $(Boc)_2O$ (0.1 g, 0.45 mmol) was added. The reaction mixture was stirred at room temperature overnight. The solvent was removed and the residue was purified on HP-Sil cartridges using a Biotage Isolera One purification system employing an ethyl acetate/n-heptane gradient (20/80->80/20) to afford the title compound (0.061 g, 67%).

$^1$H-NMR (400 MHz, $CDCl_3$) δ=8.25 (d, 1H), 7.32 (d, 1H), 3.79 (d, 3H), 3.75-3.63 (m, 5H), 3.63-3.54 (m, 2H), 3.13-3.03 (m, 2H), 1.97-1.87 (m, 1H), 1.77 (q, 1H), 1.50 (s, 9H).

Step E

An oven dried Schlenk flask was evacuated and back filled with argon gas. Then 1,4-dioxane (5 ml) was introduced and degassed with argon for 25 minutes. Then palladium(II) acetate (0.008 g, 0.03 mmol) and dicyclohexyl-(2',4',6'-triisopropyl-[1,1'-biphenyl]-2-yl)phosphine (0.051 g, 0.1 mmol) were added and heated at 110° C. for 1 minute which resulted in a dark pink solution. Then 3,4-difluoroaniline (0.03 g, 0.22 mmol), the title compound from Step D above (0.1 g, 0.22 mmol), and sodium tert.-butoxide (0.065 g, 0.66 mmol) were added. The reaction mixture was stirred at 110° C. for 1 hour. The solvent was evaporated under reduced pressure, and the residue was purified on HP-Sil cartridges using a Biotage Isolera One purification system employing an ethyl acetate/n-heptane gradient (50/50->100/0) to afford the title compound (0.075 g, 70%).

$^1$H NMR (400 MHz, $CDCl_3$) δ=8.24 (d, 1H), 7.80 (ddd, 1H), 7.18-6.94 (m, 2H), 6.62 (d, 1H), 6.45 (s, 1H), 5.49 (s, 1H), 3.75 (s, 3H), 3.68 (t, 2H), 3.61 (t, 2H), 3.17 (q, 2H), 3.05 (t, 2H), 1.81-1.72 (m, 2H), 1.45 (s, 9H).

Step F To a solution of the title compound from Step E above (0.075 g, 0.15 mmol) in dichloromethane (3 mL) was added 2M HCl in diethyl ether (0.3 mL). The reaction mixture was stirred at room temperature overnight. The solvent was evaporated to afford the title compound (0.051 g, 73%)

Step G

To a solution of the title compound from Step F above (0.0057 g, 0.016 mmol) in THF (1 mL) was added diisopropylethylamine (0.3 mL). Then a solution of commercially available BODIPY® 558/568 D2219 ester (0.005 g, 0.016 mmol) in THF (1 mL) was added. The reaction mixture was stirred at room temperature overnight while protected from light. The solvent was evaporated and the residue was on a 0.10 g KP-NH cartridge using a Biotage Isolera One purification system employing a dichloromethane/methanol gradient (100/0->90/10) to afford the title compound as a pink solid (0.006 g, 54%)

ESI-MS (m/z): 714.25 ($M^+$).

Example 214

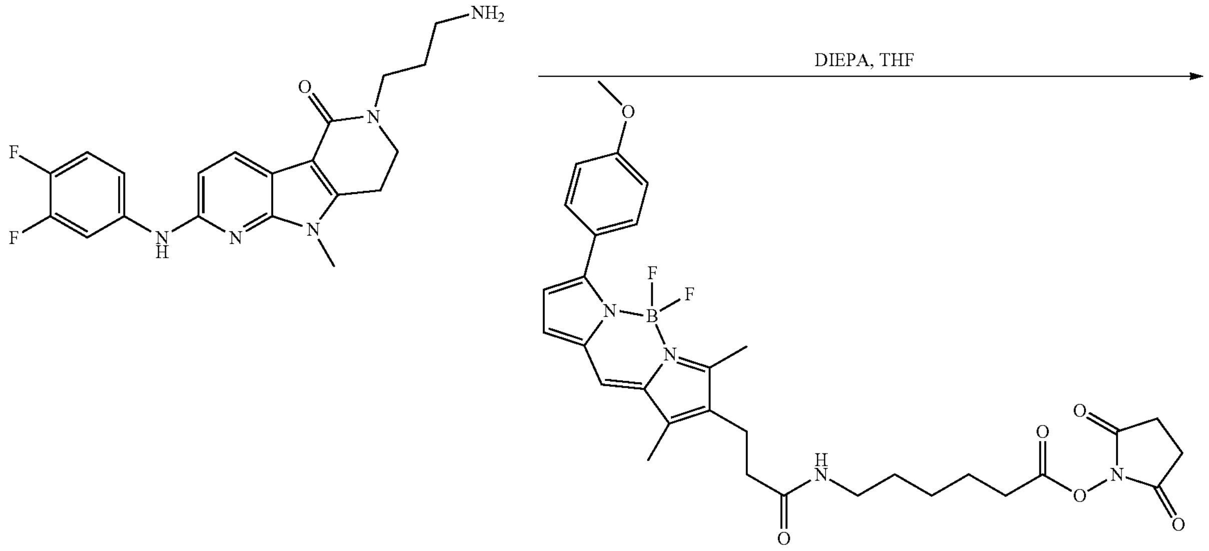

Step A

-continued

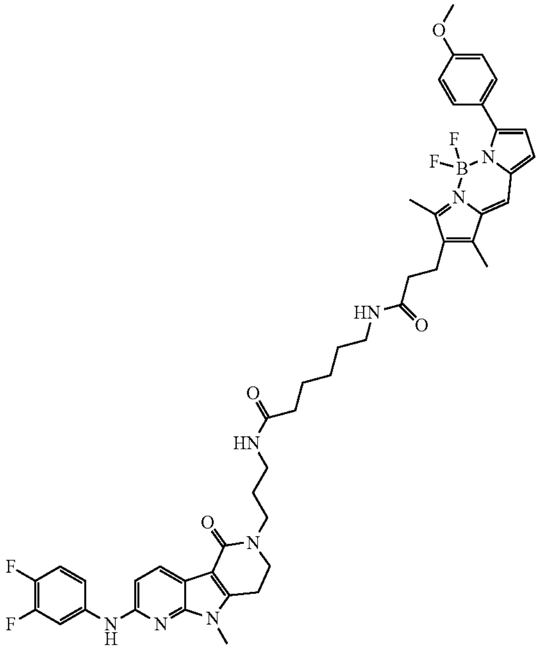

Step A

To a solution of the title compound from Example 213, Step F (0.004 g, 0.008 mmol) in THF (1 mL) was added diisopropylethylamine (0.3 mL). Then a solution of commercially available BODIPY® TMR-X D6117 ester (0.005 g, 0.008 mmol) in THF (1 mL) was added. The reaction mixture was stirred at room temperature overnight while protected from light. The solvent was evaporated and the residue was on a 10 g KP-NH cartridge using a Biotage Isolera One purification system employing an ethyl acetate/methanol gradient (100/0->98/2) to afford the title compound as a pink solid (0.004 g, 57%).

ESI-MS (m/z): 879.33 ($M^+$).

Example 215

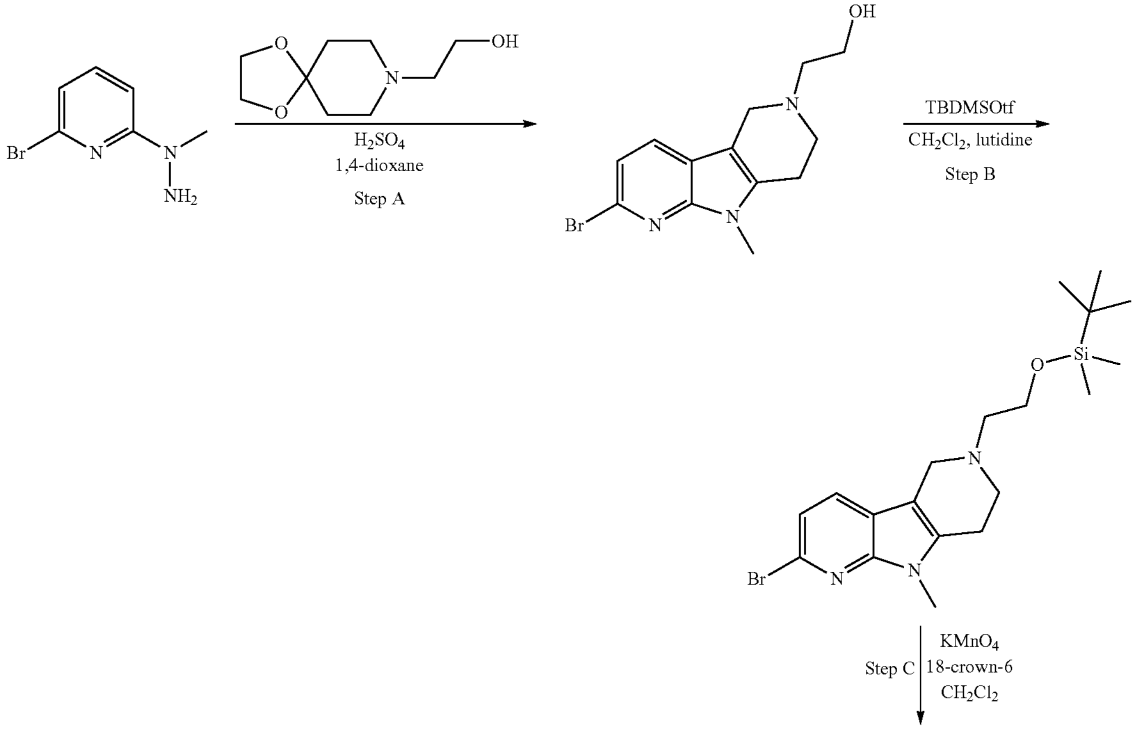

-continued

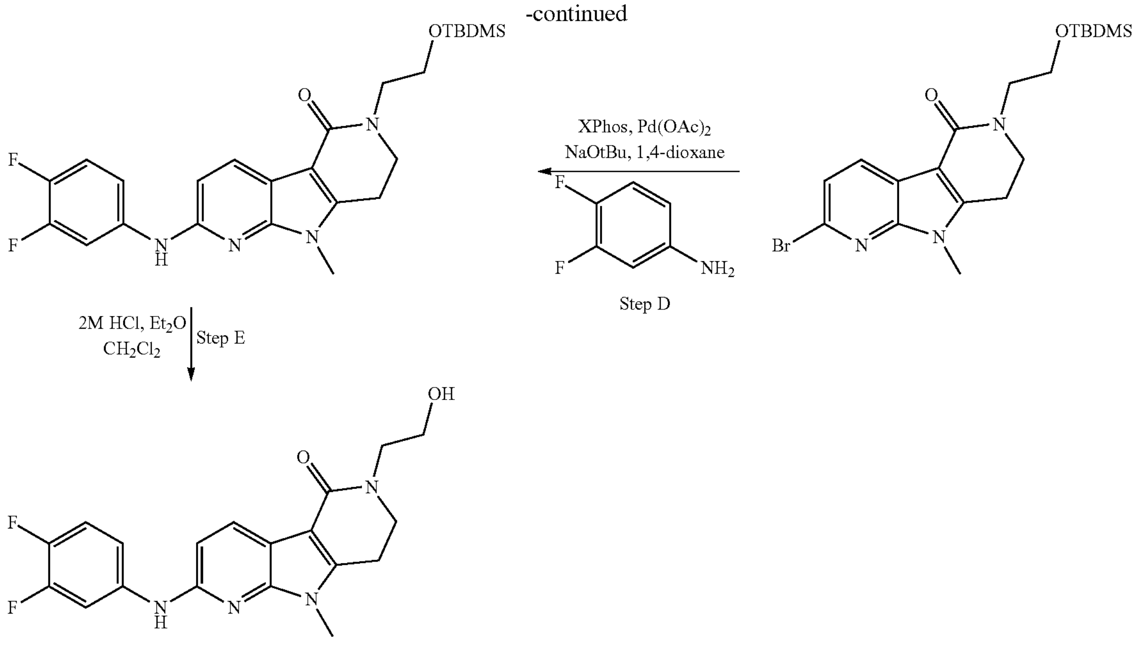

Step A

To mixture of the title compound from Preparative Example 1 Step A (1 g, 4.9 mmol) and commercially available 2-(3,3-dimethyl-1,5-dioxa-9-azaspiro[5.5]undecan-9-yl)ethanol (0.925 g, 4.9 mmol) was added 1,4-dioxane (9 mL). To the stirred mixture concentrated $H_2SO_4$ (3 mL) was added dropwise at room temperature (exotherm) to obtain a gummy material. The reaction mixture was then heated at reflux temperature for 6 hours using a sand-bath at ~140° C. The reaction mixture was cooled to room temperature, and the 1,4-dioxane layer was discarded. The residue was dissolved in ice-water (10 mL). Then the pH of the reaction mixture was adjusted to pH-12 using an aqueous NaOH solution. The aqueous layer was extracted with dichloromethane (200 mL) and the organic phase washed with water and brine. The organic phase was separated, dried over $Na_2SO_4$ and the solvent was removed under reduced pressure to afford the crude free base. The residue was purified on HP-Sil cartridges using a Biotage Isolera One purification system employing an ethyl acetate/methanol gradient (100/0->20/80) to afford the title compound as a solid (0.26 g, 17%).

$^1$H-NMR (400 MHz, $CDCl_3$) δ=7.54 (d, 1H), 7.28 (s, 1H), 7.16 (d, 1H), 3.78-3.72 (m, 7H), 3.00 (t, 2H), 2.89-2.81 (m, 4H).

Step B

To a solution of the title compound from Step A above (0.81 g, 2.6 mmol) in dichloromethane (20 mL) was added 2,6-lutidine (0.835 g, 7.8 mmol) and trifluoromethanesulfonic acid tert-butyldimethylsilyl ester (TBDMSOTf, 1.37 g, 5.2 mmol). The reaction mixture was stirred overnight, the reaction mixture diluted with dichloromethane (200 mL), washed with citric acid solution, water, and brine. The organic phase was separated, dried over $Na_2SO_4$ and filtered. The solvent was evaporated under reduced pressure, and the residue was purified on HP-Sil cartridges using a Biotage Isolera One purification system employing an ethyl acetate/n-heptane gradient (20/80->80/20) to afford the title compound as a solid (0.89 g, 81%).

$^1$H-NMR (400 MHz, $CDCl_3$) δ=7.51 (d, 1H), 7.14 (d, 1H), 3.88 (t, 2H), 3.75 (s, 2H), 3.70 (s, 3H), 3.01 (t, 2H), 2.88-2.77 (m, 4H), 0.93 (s, 9H), 0.09 (s, 6H).

Step C

To a solution of the title compound from Step B above (0.7 g, 1.65 mmol) in dichloromethane (10 mL) was added 18-crown-6 (0.045 g, 0.16 mmol) followed by the addition of $KMnO_4$ (0.39 g, 2.47 mmol) in portions. The resulting reaction mixture was stirred for 5 hours at room temperature. Then the reaction mixture was quenched with saturated sodium metabisulfite solution, stirred for 30 minutes, and extracted with dichloromethane (100 mL). The organic layer was washed with water, brine, and dried over $Na_2SO_4$. The solvent was evaporated under reduced pressure, and the residue was purified on HP-Sil cartridges using a Biotage Isolera One purification system employing an ethyl acetate/n-heptane gradient (20/80->80/20) to afford the title compound as a solid (0.4 g, 55%).

$^1$H-NMR (400 MHz, $CDCl_3$) δ=8.25 (d, 1H), 7.32 (d, 1H), 3.94-3.82 (m, 4H), 3.79 (s, 3H), 3.66 (t, 2H), 3.04 (t, 2H), 0.91 (s, 9H), 0.07 (s, 6H).

Step D

An oven dried Schlenk flask was evacuated and back filled with argon gas. Then 1,4-dioxane (5 ml) was introduced and the flask was degassed with argon for 25 minutes. Then palladium(II) acetate (0.005 g, 0.02 mmol) and dicyclohexyl-(2',4',6'-triisopropyl-[1,1-biphenyl]-2-yl)phosphine (0.03 g, 0.06 mmol) were added and the mixture was heated at 110° C. for 1 minute to become a dark pink solution. Then 3,4-difluoroaniline (0.017 g, 0.11 mmol), the title compound from Step C above (0.055 g, 0.12 mmol), and sodium tert.-butoxide (0.04 g, 0.06 mmol) were added. The reaction mixture was stirred at 110° C. for 1 hour. The solvent was evaporated under reduced pressure, and the residue was purified on HP-Sil cartridges using a Biotage Isolera One purification system employing an ethyl acetate/n-heptane gradient (50/50->100/0) to afford the title compound (0.035 g, 60%).

$^1$H-NMR (400 MHz, $CDCl_3$) δ=8.24 (d, 1H), 7.79 (ddd, 1H), 7.17-6.96 (m, 2H), 6.62 (d, 1H), 3.91-3.80 (m, 4H), 3.75 (s, 3H), 3.66 (t, 2H), 3.02 (t, 2H), 0.91 (s, 9H), 0.07 (s, 6H).

Step E

To a solution of the title compound from Step D above (0.08 g, 0.16 mmol) in dichloromethane (1 mL) was added 2M HCl in diethyl ether (0.1 mL) and the reaction mixture was stirred overnight. The reaction mixture was diluted with dichloromethane (20 mL) and the organic layer washed with sodium hydroxide solution as well as water, dried over $Na_2SO_4$, filtered and evaporated to afford the title compound (0.025 g, 40%)

$^1$H-NMR (400 MHz, $CDCl_3$) δ=8.13 (d, 1H), 7.75-7.63 (m, 1H), 7.10-6.96 (m, 2H), 6.60 (d, 1H), 3.81-3.68 (m, 7H), 3.59 (t, 2H), 3.01 (t, 2H).

Example 216

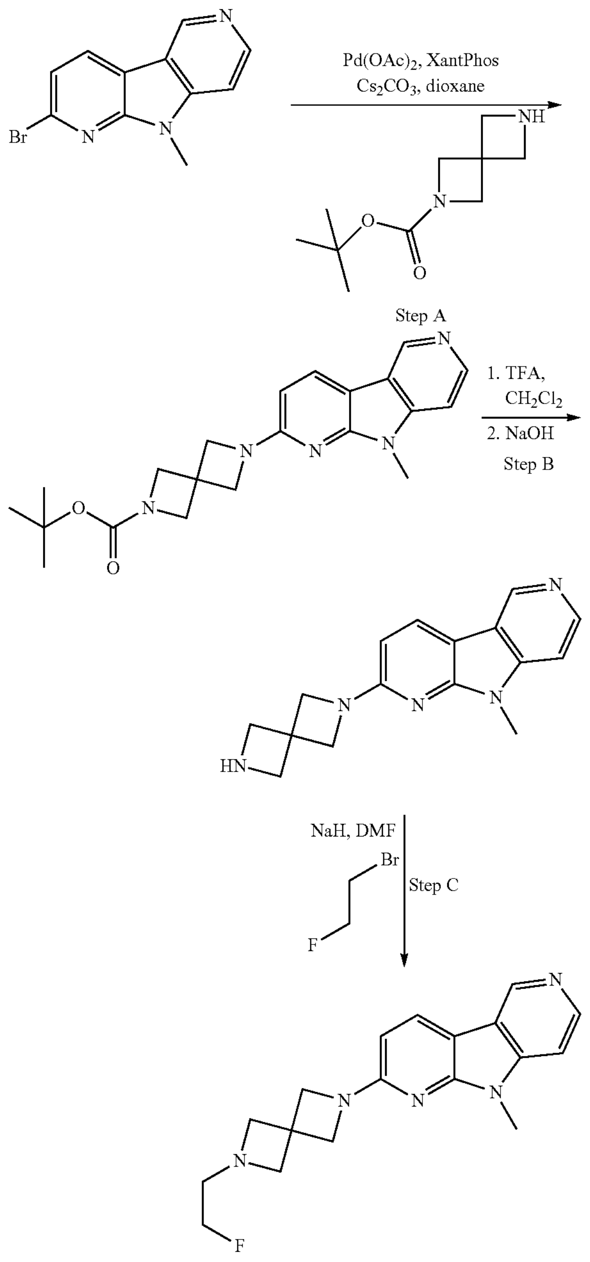

Step A

An oven dried Schlenk flask was evacuated and back filled with argon gas. The procedure was repeated 3-4 times and the flask was cooled to room temperature. Then tert-butyl 2,6-diazaspiro[3.3]heptane-2-carboxylate (0.283 g, 0.228 mmol), the title compound from Preparative Example 1 (0.312 g, 1.19 mmol), palladium(II)-acetate (0.027 g, 0.119 mmol), 4,5-bis(diphenylphosphino)-9,9-dimethylxanthene (0.206 g, 0.357 mmol), cesium carbonate (1.10 g, 3.57 mmol) and 1,4-dioxane (8 mL) were added and the reaction mixture was heated at 110° C. in a sand-bath for 12 hours. The reaction mixture was cooled and diluted with water (20 ml) and the aqueous phase was extracted with ethyl acetate several times. The combined organics were dried over $Na_2SO_4$, filtered and concentrated in vacuo. The residue was purified on HP-Sil SNAP cartridges using a Biotage Isolera One purification system using 2 to 10% methanol in dichloromethane to afford the title compound (0.380 g, 84%).

$^1$H-NMR (400 MHz, DMSO-$d_6$) δ=9.09 (s, 1H), 8.37 (d, 1H), 8.29 (d, 1H), 7.50 (d, 1H), 6.31 (d, 1H), 4.18 (s, 4H), 4.06 (s, 4H), 3.77 (s, 3H), 1.38 (s, 9H).

MS (ESI): m/z=380.36 $[M+H]^+$.

Step B

To compound from Step A above (0.38 g, 1.01 mmol) was added dichloromethane (20 mL) and trifluoroacetic acid (3 mL) and the solution was stirred at room temperature overnight. The reaction mixture was concentrated under reduced pressure and dichloromethane (20 mL) was added and the solution was washed with a water solution (1N) of sodium hydroxide (2×20 mL), dried over $Na_2SO_4$, filtered and the solvents were removed under reduced pressure. The residue was purified by chromatography on KP-NH SNAP cartridges using a Biotage Isolera One purification system employing an dichloromethane/methanol gradient (100/0->90/10) to afford the title compound (0.105 g, 37%).

$^1$H-NMR (400 MHz, $CDCl_3$) δ=9.06 (s, 1H), 8.45 (d, 1H), 8.08 (d, 1H), 7.24 (d, 1H), 6.22 (d, 1H), 4.24 (s, 4H), 3.94 (s, 4H), 3.82 (s, 3H).

MS (ESI): m/z=280.32 $[M+H]^+$.

Step C

To an ice-bath cooled (0° C.) suspension of the title compound from Step B above (0.066 g, 0.236 mmol) in N,N'-dimethylformamide (2 mL) was added sodium hydride (0.011 g 0.472 mmol) portionwise. The suspension was stirred at 0° C. for 10 minutes, warmed to room temperature and 1-bromo-2-fluoroethane (0.036 g, 0.283 mmol.) was added. The reaction mixture was stirred at room temperature for 16 hours. The mixture was cooled again (0° C.), 1-bromo-2-fluoroethane (0.017 g, 0.137 mmol) was added and the mixture was stirred at room temperature for another 1 hour. Then 0.5 ml of water was added and the solvent was removed under reduced pressure. The residue was dissolved in dichloromethane (10 mL) and washed with brine (2×10 mL) and water (10 mL). The organic phase was separated, dried over $Na_2SO_4$ and filtered. The solvent was removed under reduced pressure and the residue was purified on HP-Sil SNAP cartridges using a Biotage Isolera One purification system employing a methanol/dichloromethane gradient (0/100->20/80) to afford the title compound (0.010 g; 13%).

MS (ESI): m/z=326.16 $[M+H]^+$.

Example 217

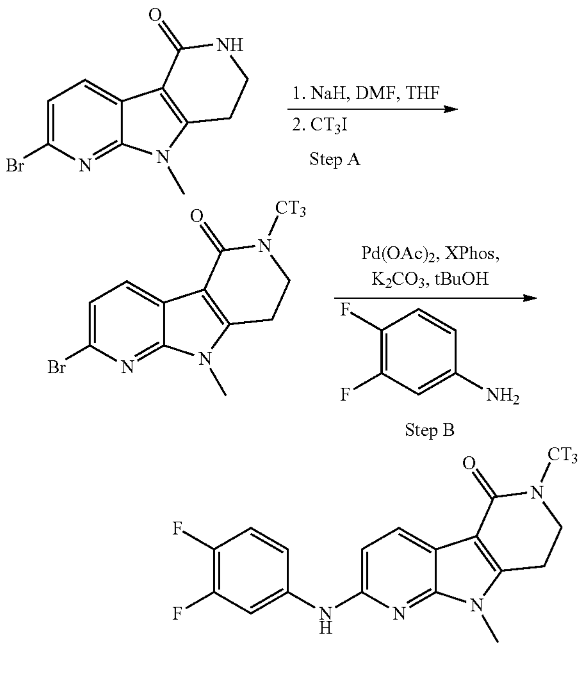

Step A

The title compound was prepared as described in Preparative Example 2, Step C with the exception that tritium labeled methyliodide was used (Moravek Biochemical and Radiochemicals (U.S.A.)).

Step B

The tritium labeled title compound from Step A above was used for a palladium coupling reaction as described in Example 169 to afford the tritium labeled title compound with a specific activity of 52.0 Ci/mmol and a radiochemical purity of 96.2% (Moravek Biochemical and Radiochemicals (U.S.A.)).

$^3$H-NMR ($CD_3OD$) δ=3.036-3.127 (m, 3T).

ESI-MS (m/z): 342.99, 345.02, 347.02, 349.03 ($MH^+$).

Synthesis of $^{18}$F-Labeled Compounds

The compounds of the preceding examples bearing a fluorine atom can also be radiolabeled to obtain the respective fluorine-18 analogs. Methods to obtain fluorine-18 radiolabeled compounds starting from corresponding precursor molecules bearing leaving groups and optionally protecting groups are well-known to a person skilled in the art. The radiolabeling of the compounds of the present invention with fluorine-18 was exemplified by the following examples.

General Method a (Direct Aromatic $^{18}$F-Fluorination)

The n.c.a [$^{18}$F]fluoride (2-5 GBq) was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, a solution of the dissolved precursor was added to the dried K[$^{18}$F]F-$K_{222}$ complex. The reaction vial was sealed and heated under conventional heating for 15 min at 130 C. Subsequently, the reaction mixture was quenched with water and the crude product was purified via semi-preparative HPLC. The isolated tracer was diluted with water (35 mL), trapped on a C-18 Plus cartridge (Waters), washed with water (5 mL), eluted with ethanol (1 mL).

General Method B (Direct $^{18}$F-Labeling)

The tracers were synthesized starting from n.c.a. [$^{18}$F] fluoride (1-10 GBq) by a $^{18}$F-direct fluorination. The aqueous [$^{18}$F]fluoride solution was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, the respective dissolved precursor was added to the dried K[$^{18}$F]F-$K_{222}$ complex. The reaction vial was sealed and heated for 15 min at 120-160° C. (heating block) and quenched with water. The crude product was purified via semi-preparative HPLC. The isolated tracer was diluted with water (25 mL), trapped on a C-18 Plus cartridge (Waters), washed with water (5 mL), and eluted with ethanol (1 mL).

Synthesis of $^{18}$F-Labeled Prosthetic Groups for Indirect Labeling

To synthesize the respective $^{18}$F-labeled prosthetic group, a general labeling procedure was applied. Briefly, n.c.a [$^{18}$F]fluoride (2-10 GBq) was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, ethylene di(p-toluenesulfonate), 1,3-propanediol di-p-tosylate, diethylene glycol di(p-toluenesulfonate), triethylene glycol di(p-toluenesulfonate) or tetraethylene glycol di(p-toluenesulfonate) (20 μmol), dissolved in acetonitrile (1 mL), were added to the dried K[$^{18}$F]F-$K_{222}$ complex. The reaction vial was sealed and heated under conventional heating for 15 min at 120° C. (heating block). Subsequently, the reaction mixture was quenched with water and the crude product was purified via semi-preparative HPLC. The isolated tracer was diluted with water (35 mL), trapped on a C-18 Plus cartridge (Waters), washed with water (5 mL), eluted with dimethyl sulfoxide (0.8 mL) and directly reacted with the phenolic labeling precursors. The respective $^{18}$F-labeled prosthetic group was obtained in a synthesis time of 60 min in radiochemical yields 50% and high radiochemical purities of >97%.

General Method C (Indirect $^{18}$F-Labeling)

The indirect labeling precursor was dissolved in dimethyl sulfoxide (0.2 mL) and base was added. The mixture was tempered at 100° C. (heating block) for 1 min. Subsequently, the respective $^{18}$F-labeled prosthetic group, synthesized according synthesis method for the syntheses of $^{18}$F-labeled prosthetic groups for indirect labeling, was eluted into a reaction vial using dimethyl sulfoxide (0.6-1 mL). The mixture was heated for 15 min at 160° C. (heating block). After cooling, the solution was diluted and purified by semi-preparative HPLC. The product fraction was diluted with water (35 mL), trapped on a C-18 Plus cartridge (Waters), washed with water (5 mL) and eluted with ethanol (1 mL).

Example $^{18}$F-169

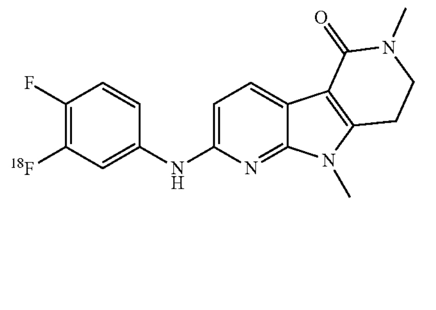 [SMILES: CN1CCc2c(c3ccc(Nc4ccc(F)c([18F])c4)nc3n2C)C1=O]

The title compound $^{18}$F-169 (83 MBq) was synthesized according to General Method A using precursor molecule from Example 211 (4 mg, 10 µmol) in dimethyl sulfoxide (0.8 mL). The radiochemical purity of 94% was determined by analytical reversed-phase HPLC ($t_R$(RAD-trace)=3.93 min). The identity of $^{18}$F-169 was confirmed by comparing the retention time with the non-radioactive reference compound from Example 169.

Example $^{18}$F-2

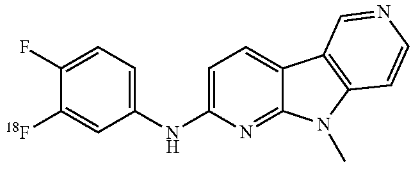 [SMILES: Cn1c2ccncc2c2ccc(Nc3ccc(F)c([18F])c3)nc21]

The title compound $^{18}$F-2 (996 MBq) was synthesized according to General Method A using precursor molecule from Example 98 (1 mg, 3 µmol) in dimethyl sulfoxide (0.5 mL). The radiochemical purity of 96% was determined by analytical reversed-phase HPLC ($t_R$(RAD-trace)=3.24 min). The identity of $^{18}$F-2 was confirmed by comparing the retention time with the non-radioactive reference compound from Example 2.

Example $^{18}$F-8

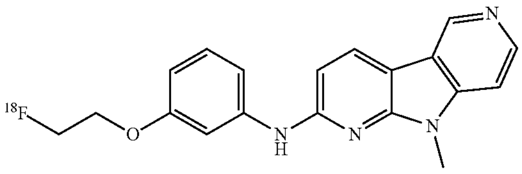 [SMILES: Cn1c2ccncc2c2ccc(Nc3cccc(OCC[18F])c3)nc21]

The title compound $^{18}$F-8 (442 MBq) was synthesized according to General Method B using precursor molecule from Example 110 (1 mg, 2 µmol) in a mixture of acetonitrile (0.5 mL) and dimethyl sulfoxide (0.3 mL). The radiochemical purity of 99% was determined by analytical reversed-phase HPLC ($t_R$(RAD-trace)=3.30 min). The identity of $^{18}$F-8 was confirmed by comparing the retention time with the non-radioactive reference compound from Example 8.

Example $^{18}$F-17

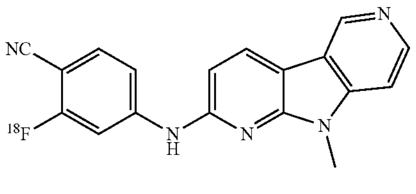 [SMILES: Cn1c2ccncc2c2ccc(Nc3ccc(C#N)c([18F])c3)nc21]

The title compound $^{18}$F-17 (219 MBq) was synthesized according to General Method A using precursor molecule from Example 102 (4.8 mg, 15 µmol) in dimethyl sulfoxide (0.6 mL). The radiochemical purity of 92% was determined by analytical reversed-phase HPLC ($t_R$(RAD-trace)=3.2 min). The identity of $^{18}$F-17 was confirmed by comparing the retention time with the non-radioactive reference compound from Example 17.

Example $^{18}$F-178

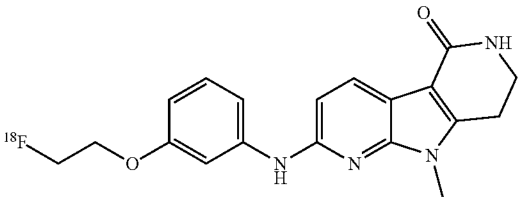 [SMILES: Cn1c2c(c3ccc(Nc4cccc(OCC[18F])c4)nc31)C(=O)NCC2]

The title compound $^{18}$F-178 (48 MBq) was synthesized according to General Method C using precursor molecule from Example 90 (4.2 mg, 13.5 µmol) and 4N sodium hydroxide (20 µmol, 5 µL) as base. The radiochemical purity of 100% was determined by analytical reversed-phase HPLC ($t_R$(RAD-trace)=4.04 min). The identity of $^{18}$F-178 was confirmed by comparing the retention time with the non-radioactive reference compound from Example 178.

Example $^{18}$F-179

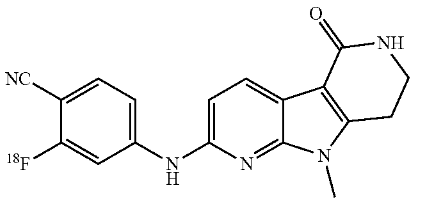 [SMILES: Cn1c2c(c3ccc(Nc4ccc(C#N)c([18F])c4)nc31)C(=O)NCC2]

$^{18}$F-179 (15 MBq) was synthesized according to General Method A using precursor molecule 103 (2.6 mg, 7.7 µmol) in dimethyl sulfoxide (500 µL). The radiochemical purity of 98% was determined by analytical reversed-phase HPLC ($t_R$(RAD-trace)=4.04 min). The identity of $^{18}$F-179 was confirmed by comparing the retention time with the non-radioactive reference from Example 179.

Example $^{18}$F-23

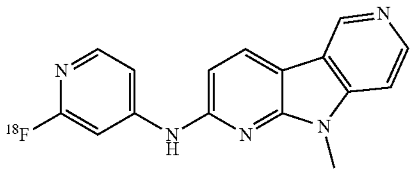 [SMILES: Cn1c2ccncc2c2ccc(Nc3ccnc([18F])c3)nc21]

The title compound $^{18}$F-23 (176 MBq) was synthesized according to General Method A using precursor molecule from Example 105 Step B (5 mg, 12 µmol) in dimethylformamide (0.5 mL). The radiochemical purity of 100% was determined by analytical reversed-phase HPLC ($t_R$(RAD-trace)=4.76 min). The identity of $^{18}$F-23 was confirmed by comparing the retention time with the non-radioactive reference compound from Example 23.

Automated Synthesis of $^{18}$F-23

$^{18}$F-23 (2624 MBq) was synthesized using a fully automated GE Tacerlab FX module. The precursor Example 105, Step B (6 mg, 14.5 μmol) was dissolved in dimethylformamide (0.5 mL). The n.c.a [$^{18}$F]fluoride (10-20 GBq) was trapped on a Sep-Pak Accell Plus QMA light cartridge (Waters) and eluted with a solution $K_2CO_3$/Kryptofix® 2.2.2. The water was removed using a stream of $N_2$ at 120° C. and vacuum to dryness with MeCN (1 mL). The dissolved precursor was added to the dried K[$^{18}$F]F-$K_{222}$ complex. The reaction mixture was heated for 15 min at 130 C, quenched with a mixture of water and MeCN and the crude product was purified via semi-preparative HPLC. The isolated tracer was diluted with water (35 mL), trapped on a C-18 Plus cartridge (Waters), washed with water (5 mL), eluted with ethanol (2 mL). The radiochemical purity of 100% was determined by analytical reversed-phase HPLC ($t_R$(RAD-trace)=4.76 min). The identity of $^{18}$F-23 was confirmed by comparing the retention time with the non-radioactive reference compound from Example 23.

Example $^{18}$F-161

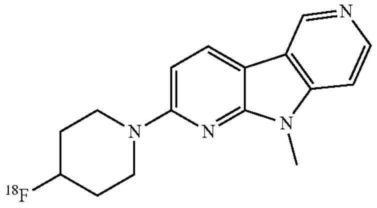 [SMILES: Cn1c2ccncc2c2ccc(N3CCC([18F])CC3)nc21]

The title compound $^{18}$F-161 (468 MBq) was synthesized according to General Method C starting using precursor molecule from Example 114 Step B (3.1 mg, 11 μmol) in dimethyl sulfoxide (0.5 mL). The radiochemical purity of 100% was determined by analytical reversed-phase HPLC ($t_R$(RAD-trace)=5.01 min). The identity of $^{18}$F-161 was confirmed by comparing the retention time with the non-radioactive reference compound from Example 161.

Example $^{18}$F-28

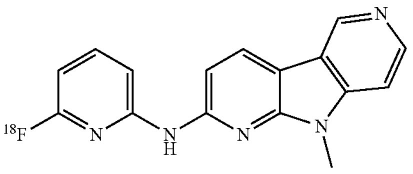 [SMILES: Cn1c2ccncc2c2ccc(Nc3cccc([18F])n3)nc21]

$^{18}$F-28 (375 MBq) was synthesized according to General Method A using precursor molecule from example 108 (5.1 mg, 12 μmol) in dimethylformamide (0.5 mL). The radiochemical purity of 98% was determined by analytical reversed-phase HPLC ($t_R$(RAD-trace)=4.09 min). The identity of $^{18}$F-28 was confirmed by comparing the retention time with the non-radioactive reference from example 28.

Example $^{18}$F-189

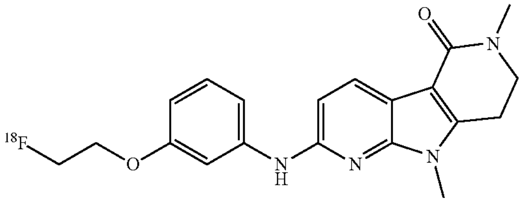

,

The title compound $^{18}$F-189 (65 MBq) was synthesized according to General Method C using precursor molecule from Example 89 (3.8 mg, 12 μmol) and 4N sodium hydroxide (20 μmol, 5 μL as base. The radiochemical purity of 99% was determined by analytical reversed-phase HPLC ($t_R$ (RAD-trace)=4.56 min). The identity of $^{18}$F-189 was confirmed by comparing the retention time with the non-radioactive reference compound from Example 189.

Example $^{18}$F-44

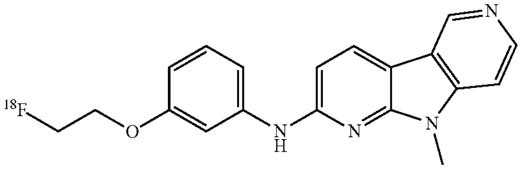 [SMILES: Cn1c2ccncc2c2ccc(Nc3cccc(OCC[18F])c3)nc21]

The title compound $^{18}$F-44 (15 MBq) was synthesized according to General Method C using precursor molecule from Example 88 (3.99 mg, 13.7 μmol) and 4N sodium hydroxide (20 μmol, 5 μL) as base. The radiochemical purity of 100% was determined by analytical reversed-phase HPLC ($t_R$(RAD-trace)=8.78 min). The identity of $^{18}$F-44 was confirmed by comparing the retention time with the non-radioactive reference compound from Example 44.

Example $^{18}$F-56

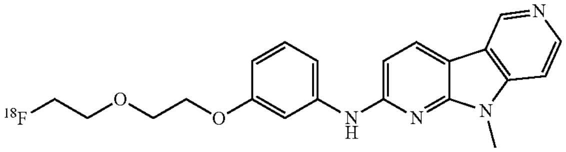 [SMILES: Cn1c2ccncc2c2ccc(Nc3cccc(OCCOCC[18F])c3)nc21]

The title compound $^{18}$F-56 (40 MBq) was synthesized according to General Method C using precursor molecule from Example 88 (3.86 mg, 13.3 μmol) and 4N sodium hydroxide (20 μmol, 5 μL) as base. The radiochemical purity of 100% was determined by analytical reversed-phase HPLC ($t_R$(RAD-trace)=8.40 min). The identity of $^{18}$F-56 was confirmed by comparing the retention time with the non-radioactive reference compound from Example 56.

Example $^{18}$F-60

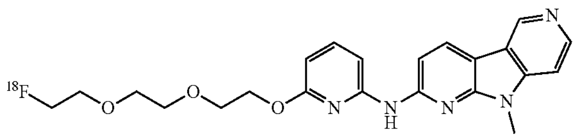 [SMILES: Cn1c2ccncc2c2ccc(Nc3cccc(OCCOCCOCC[18F])n3)nc21]

The title compound $^{18}$F-60 (53 MBq) was synthesized according to General Method C using precursor molecule from Example 88 (4.2 mg, 14 μmol) and 4N sodium hydroxide (20 μmol, 5 μL) as base. The radiochemical purity of 97% was determined by analytical reversed-phase HPLC ($t_R$(RAD-trace)=8.46 min). The identity of $^{18}$F-60 was confirmed by comparing the retention time with the non-radioactive reference compound from Example 60.

Example $^{18}$F-218

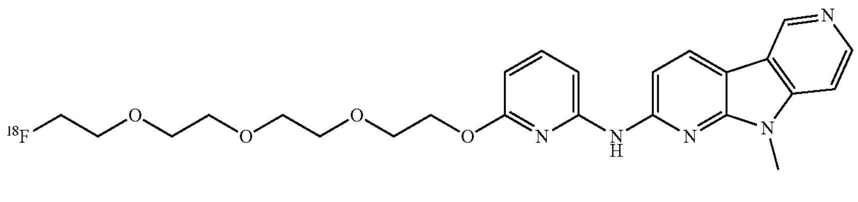 [SMILES: Cn1c2ccncc2c2ccc(Nc3cccc(OCCOCCOCCOCC[18F])n3)nc21]

The title compound $^{18}$F-218 (21 MBq) was synthesized according to General Method C using precursor molecule from Example 88 (4.1 mg, 14 μmol) and 4N sodium hydroxide (18.5 μmol, 4.6 μL) as base. The radiochemical purity of 95% was determined by analytical reversed-phase HPLC ($t_R$(RAD-trace)=8.38 min).

Example $^{18}$F-59

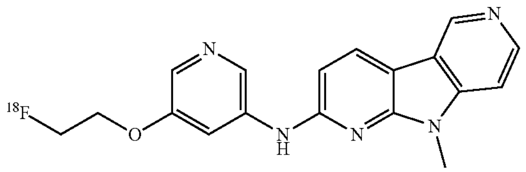 [SMILES: Cn1c2ccncc2c2ccc(Nc3cncc(OCC[18F])c3)nc21]

The title compound $^{18}$F-59 (64 MBq) was synthesized according to General Method B starting using molecule from Example 129 (0.5 mg, 1.3 μmol) in acetonitrile (500 μL). The radiochemical purity of 100% was determined by analytical reversed-phase HPLC ($t_R$(RAD-trace)=8.64 min). The identity of $^{18}$F-59 was confirmed by comparing the retention time with the non-radioactive reference compound from Example 59.

Example $^{18}$F-97

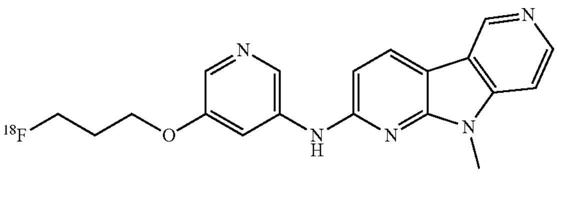 [SMILES: Cn1c2ccncc2c2ccc(Nc3cncc(OCCC[18F])c3)nc21]

The title compound $^{18}$F-97 (144 MBq) was synthesized according to General Method C using precursor molecule from Example 66 (4 mg, 13 μmol) and 4N sodium hydroxide (20 μmol, 5 μL) as base. The radiochemical purity of 98% was determined by analytical reversed-phase HPLC ($t_R$ (RAD-trace)=7.66 min. The identity of $^{18}$F-97 was confirmed by comparing the retention time with the non-radioactive reference compound from Example 97.

Example $^{18}$F-63

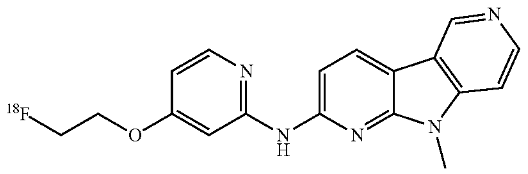 [SMILES: Cn1c2ccncc2c2ccc(Nc3cc(OCC[18F])ccn3)nc21]

The title compound $^{18}$F-63 (19 MBq) was synthesized according to General Method C using precursor molecule from Example 64 (3.1 mg, 10.5 μmol) and 4N sodium hydroxide (20 μmol, 5 μL) as base. The radiochemical purity of 100% was determined by analytical reversed-phase HPLC ($t_R$(RAD-trace)=7.28 min. The identity of $^{18}$F-63 was confirmed by comparing the retention time with the non-radioactive reference compound from Example 63.

Example $^{18}$F-219

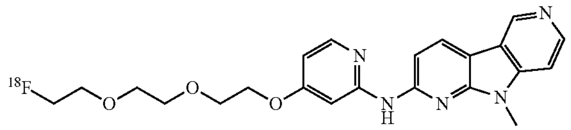 [SMILES: Cn1c2ccncc2c2ccc(Nc3cc(OCCOCCOCC[18F])ccn3)nc21]

The title compound $^{18}$F-219 (42 MBq) was synthesized according to General Method C using precursor molecule from Example 64 (3.5 mg, 12 μmol) and 4N sodium hydroxide (20 μmol, 5 μL) as base. The radiochemical purity of 100% was determined by analytical reversed-phase HPLC ($t_R$(RAD-trace)=7.47 min.

Example $^{18}$F-95

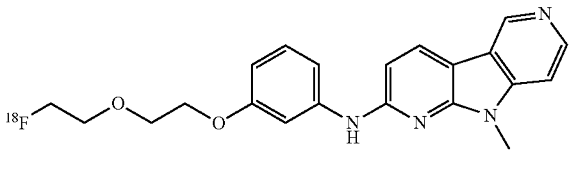 [SMILES: Cn1c2ccncc2c2ccc(Nc3cccc(OCCOCC[18F])c3)nc21]

The title compound $^{18}$F-95 (181 MBq) was synthesized according to General Method B using precursor molecule from Example 111 (1.2 mg, 2.3 μmol) in acetonitrile (0.6 mL). The radiochemical purity of 98% was determined by analytical reversed-phase HPLC ($t_R$(RAD–trace)=3.28 min). The identity of $^{18}$F-95 was confirmed by comparing the retention time with the non-radioactive reference compound from Example 95.

Example $^{18}$F-146

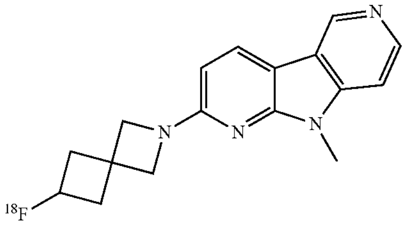 [SMILES: Cn1c2ccncc2c2ccc(N3CC4(CC([18F])C4)C3)nc21]

The title compound $^{18}$F-146 (349 MBq) was synthesized according to General Method B using precursor molecule from Example 130 (4.9 mg, 13 μmol) in dimethyl sulfoxide (0.5 mL). The radiochemical purity of 100% was determined by analytical reversed-phase HPLC ($t_R$(RAD–trace)=9.13 min). The identity of $^{18}$F-146 was confirmed by comparing the retention time with the non-radioactive reference compound from Example 146.

Example $^{18}$F-168

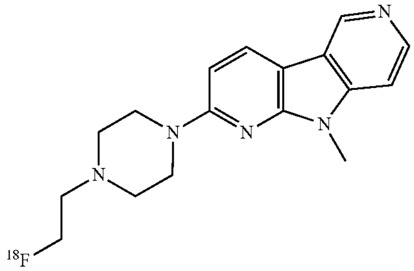 [SMILES: Cn1c2ccncc2c2ccc(N3CCN(CC[18F])CC3)nc21]

The title compound $^{18}$F-168 (165 MBq) was synthesized according to General Method B using precursor molecule from Example 136 (3 mg, 6.5 μmol) in acetonitrile (1 mL). The radiochemical purity of 100% was determined by analytical reversed-phase HPLC ($t_R$(RAD–trace)=2.31 min). The identity of $^{18}$F-168 was confirmed by comparing the retention time with the non-radioactive reference compound from Example 168 Step B.

Example $^{18}$F-156

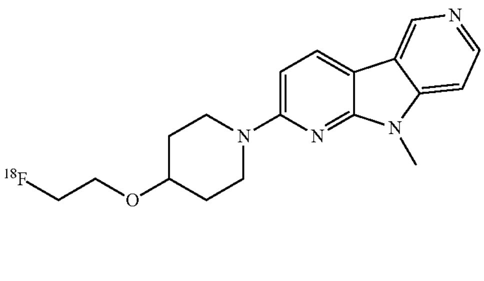 [SMILES: Cn1c2ccncc2c2ccc(N3CCC(OCC[18F])CC3)nc21]

The title compound $^{18}$F-156 (16 MBq) was synthesized according to General Method B using precursor molecule from Example 135 (3.4 mg, 7 μmol) in acetonitrile (0.5 mL). The radiochemical purity of 100% was determined by analytical reversed-phase HPLC ($t_R$(RAD–trace)=3.55 min). The identity of $^{18}$F-156 was confirmed by comparing the retention time with the non-radioactive reference compound from Example 156.

Example $^{18}$F-150

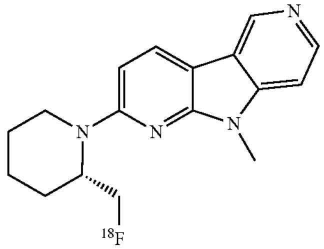 [SMILES: Cn1c2ccncc2c2ccc(N3CCCC[C@H]3C[18F])nc21]

$^{18}$F-150 4 MBq) was synthesized according to General Method B using precursor molecule of example 137 (3.9 mg, 8.6 μmol) in dimethyl sulfoxide (0.5 mL).

The radiochemical purity of 94% was determined by analytical reversed-phase HPLC ($t_R$(RAD–trace)=4.25 min). The identity of $^{18}$F-150 was confirmed by comparing the retention time with the non-radioactive reference in example 150.

Example $^{18}$F-51

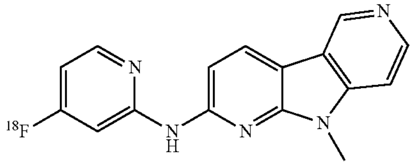 [SMILES: Cn1c2ccncc2c2ccc(Nc3cc([18F])ccn3)nc21]

The title compound $^{18}$F-51 (247 MBq) was synthesized according to General Method A using precursor molecule from Example 107 (3.2 mg, 7.7 μmol) in dimethylformamide (0.5 mL). The radiochemical purity of 100% was determined by analytical reversed-phase HPLC ($t_R$(RAD–trace)=3.75 min). The identity of $^{18}$F-51 was confirmed by comparing the retention time with the non-radioactive reference compound from Example 51.

Example $^{18}$F-158

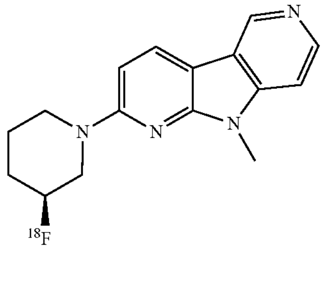 [SMILES: Cn1c2ccncc2c2ccc(N3CCC[C@H]([18F])C3)nc21]

The title compound $^{18}$F-158 (30 MBq) was synthesized according to General Method B starting form precursor molecule from Example 132 (3.7 mg, 10 μmol) in acetonitrile (0.5 mL). The radiochemical purity of 100% was determined by analytical reversed-phase HPLC ($t_R$(RAD-trace)=3.59 min). The identity of $^{18}$F-158 was confirmed by comparing the retention time with the non-radioactive reference compound from Example 158.

Example $^{18}$F-147

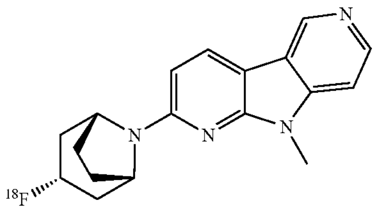 [SMILES: Cn1c2ccncc2c2ccc(N3[C@@H]4CC[C@H]3C[C@H]([18F])C4)nc21]

The title compound $^{18}$F-147 (36 MBq) was synthesized according to General Method B using precursor molecule from Example 133 (2.5 mg, 6.5 μmol) in a mixture of acetonitrile (0.5 mL) and dimethyl sulfoxide (0.2 mL). The radiochemical purity of 100% was determined by analytical reversed-phase HPLC ($t_R$(RAD-trace)=4.32 min). The identity of $^{18}$F-147 was confirmed by comparing the retention time with the non-radioactive reference compound from Example 147.

Example $^{18}$F-159

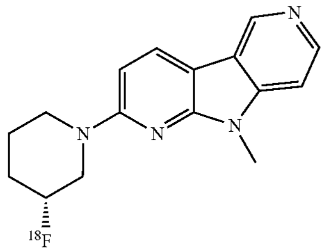 [SMILES: Cn1c2ccncc2c2ccc(N3CCC[C@@H]([18F])C3)nc21]

The title compound $^{18}$F-159 (98 MBq) was synthesized according to General Method B starting form precursor molecule from Example 134 (2.5 mg, 7 μmol) in acetonitrile (0.5 mL). The radiochemical purity of 100% was determined by analytical reversed-phase HPLC ($t_R$(RAD-trace)=3.75 min). The identity of $^{18}$F-159 was confirmed by comparing the retention time with the non-radioactive reference compound from Example 159.

Example $^{18}$F-160

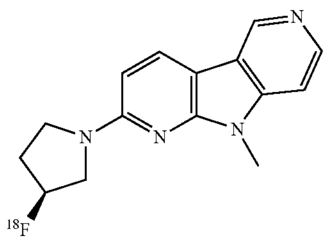 [SMILES: Cn1c2ccncc2c2ccc(N3CC[C@H]([18F])C3)nc21]

$^{18}$F-160 (34 MBq) was synthesized according to General Method B using precursor molecule from example 138 (3.3 mg, 9.5 μmol) in acetonitrile (0.5 mL). The radiochemical purity of 96% was determined by analytical reversed-phase HPLC ($t_R$(RAD-trace)=3.30 min). The identity of $^{18}$F-160 was confirmed by comparing the retention time with the non-radioactive reference from example 160.

Example $^{18}$F-196

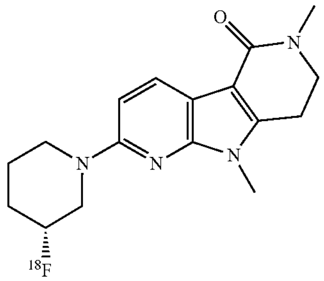 [SMILES: CN1CCc2c(c3ccc(N4CCC[C@@H]([18F])C4)nc3n2C)C1=O]

$^{18}$F-196 (32 MBq) was synthesized according to General Method B using precursor molecule from example 139 (2.4 mg, 6.2 μmol) in acetonitrile (0.5 mL). The radiochemical purity of 100% was determined by analytical reversed-phase HPLC ($t_R$(RAD-trace)=4.1 min). The identity of $^{18}$F-196 was confirmed by comparing the retention time with the non-radioactive reference from example 196.

Example $^{18}$F-152

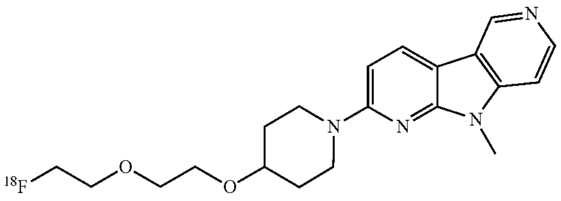 [SMILES: Cn1c2ccncc2c2ccc(N3CCC(OCCOCC[18F])CC3)nc21]

$^{18}$F-152 (99 MBq) was synthesized according to General Method B using precursor molecule from example 143 (3 mg, 5.7 μmol) in acetonitrile (0.5 mL) and dimethyl sulfoxide (100 μL). The radiochemical purity of 100% was determined by analytical reversed-phase HPLC ($t_R$(RAD-trace)=3.5 min). The identity of $^{18}$F-152 was confirmed by comparing the retention time with the non-radioactive reference from example 152.

Example $^{18}$F-157

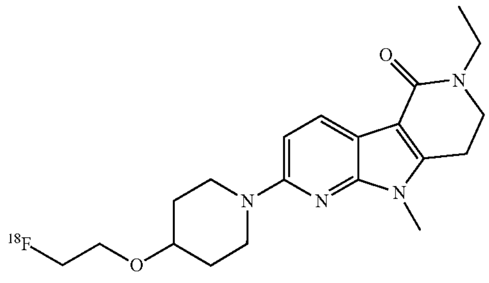 [SMILES: CCN1CCc2c(c3ccc(N4CCC(OCC[18F])CC4)nc3n2C)C1=O]

$^{18}F$-157 (1149 MBq) was synthesized according to General Method B using precursor molecule from example 141 (3.2 mg, 6 μmol) in acetonitrile (0.7 mL). The radiochemical purity of 99% was determined by analytical reversed-phase HPLC ($t_R$(RAD–trace)=4.22 min). The identity of $^{18}F$-157 was confirmed by comparing the retention time with the non-radioactive reference from example 157.

Biological Assay Description

Assay 1 (Fluorescence Based Assay):

Direct Binding of Compounds of this Invention to Human Alzheimer's Disease Brain Sections and/or Displacement of RefA and Compound B Frozen sections with a thickness of 20 μM from the amygdala of donors diagnosed with Braak stage V-VI Alzheimer's Disease (Braak, H.; Braak, E. Acta Neuropathol., 1991, 82, 239-259), were purchased from a commercial provider (Tissue Solutions) and kept at −80° C. until use.

Direct Staining of Human Alzheimer's Disease Brain Sections

Brain sections were encircled with pap pen liquid blocker to reduce the volume of solution for the different incubations. Sections were fixed for 15 min at 4° C. with 4% paraformaldehyde and washed three times 5 minutes with PBS at room temperature. Test compounds were incubated on the sections at 100 μM in 50% ethanol in water for 20 min at room temperature in the dark and then washed three times 5 minutes with PBS. To reduce the auto-fluorescence of the tissue, the sections were incubated in a solution of 0.1% Sudan Black (Sigma 199664) in 70% ethanol for 15 min at room temperature in the dark, washed four times for 5 minutes with PBS, and mounted using ProLong Gold Antifade reagent (Invitrogen P36930). Sections were then analyzed on the Nikon Eclipse Ti microscope to detect staining and imaged using Nikon DS-Fi2 camera and NIS-Element AR4.13.1 software.

Displacement of RefA and Compound B

Brain sections were mainly treated as described above. Test compounds were, however, incubated on the section at 250 μM in 50% ethanol for 20 min at room temperature, and then directly incubated with the fluorescent reference compounds RefA and Compound B, each at 1 μM in 50% ethanol for 20 min at room temperature. RefA and Compound B stainings were visualized using the 470 nm and 365 nm excitation filters, respectively. Images were acquired, and tangles and plaques quantified using the NIS-Element software. Only those compounds not directly staining tangles or plaques at the same wavelengths as RefA and Compound B were tested in the displacement assay.

Structure of RefA (Tago et al., J. Label. Compd. Radiopharm. 2013, DOI: 10.1002/jlcr.3133)

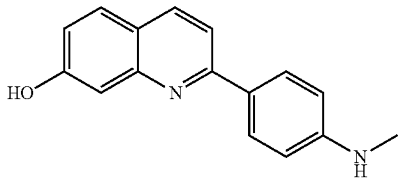 [SMILES: CNc1ccc(-c2ccc3ccc(O)cc3n2)cc1]

The direct staining of tau tangles on AD brain section by RefA at a concentration of 100 μM (green, shown in white) can be seen in FIG. 1.

Structure of Compound B (prepared by a similar procedure described for W201 in WO2010/011964):

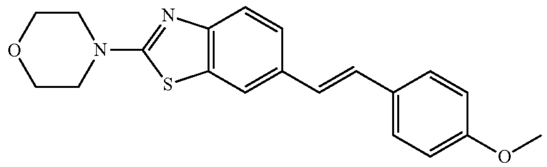 [SMILES: COc1ccc(/C=C/c2ccc3nc(N4CCOCC4)sc3c2)cc1]

Figure 2:
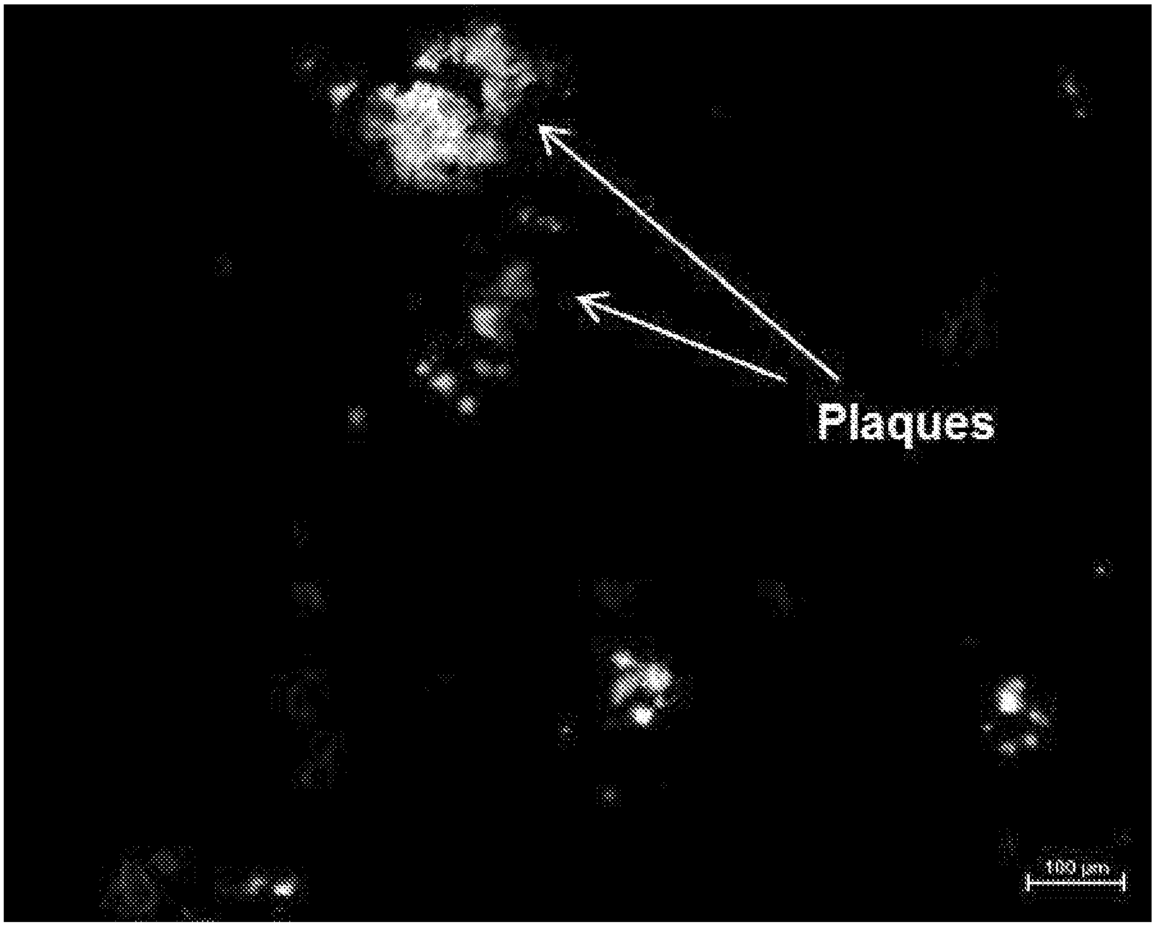
FIG. 2 shows direct staining of Aβ plaques on AD brain section by Compound B at a concentration of 100 μM (blue, here presented by white color).

Direct staining of Aβ plaques on AD brain section by Compound B at a concentration of 100 μM (blue, shown in white) is shown in FIG. 2.

Figure 3:
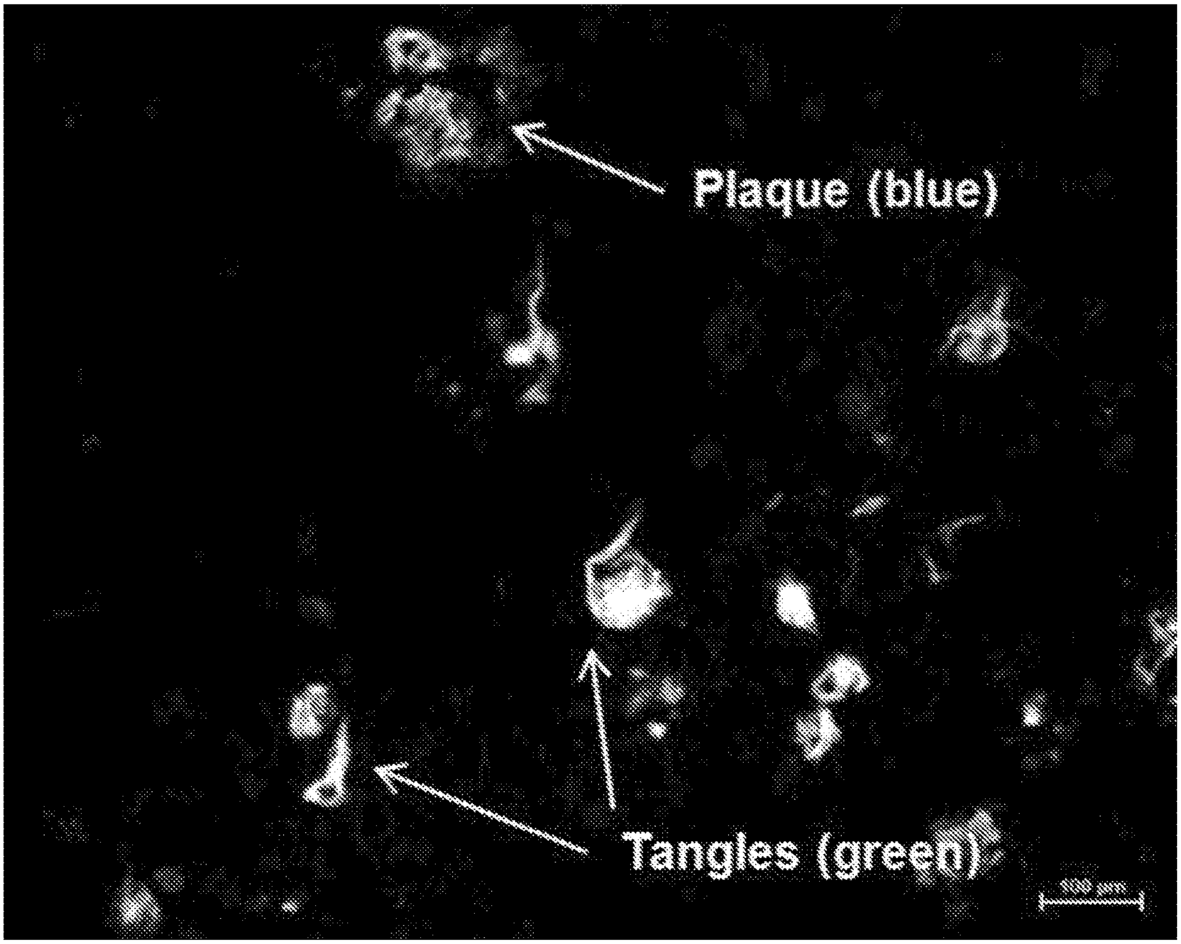
FIG. 3 shows AD brain section co-staining of tau tangles by RefA (green, here presented by white color) and AR plaques by Compound B (blue, here presented by white color) at a concentration of 100 μM.
Figure 4:
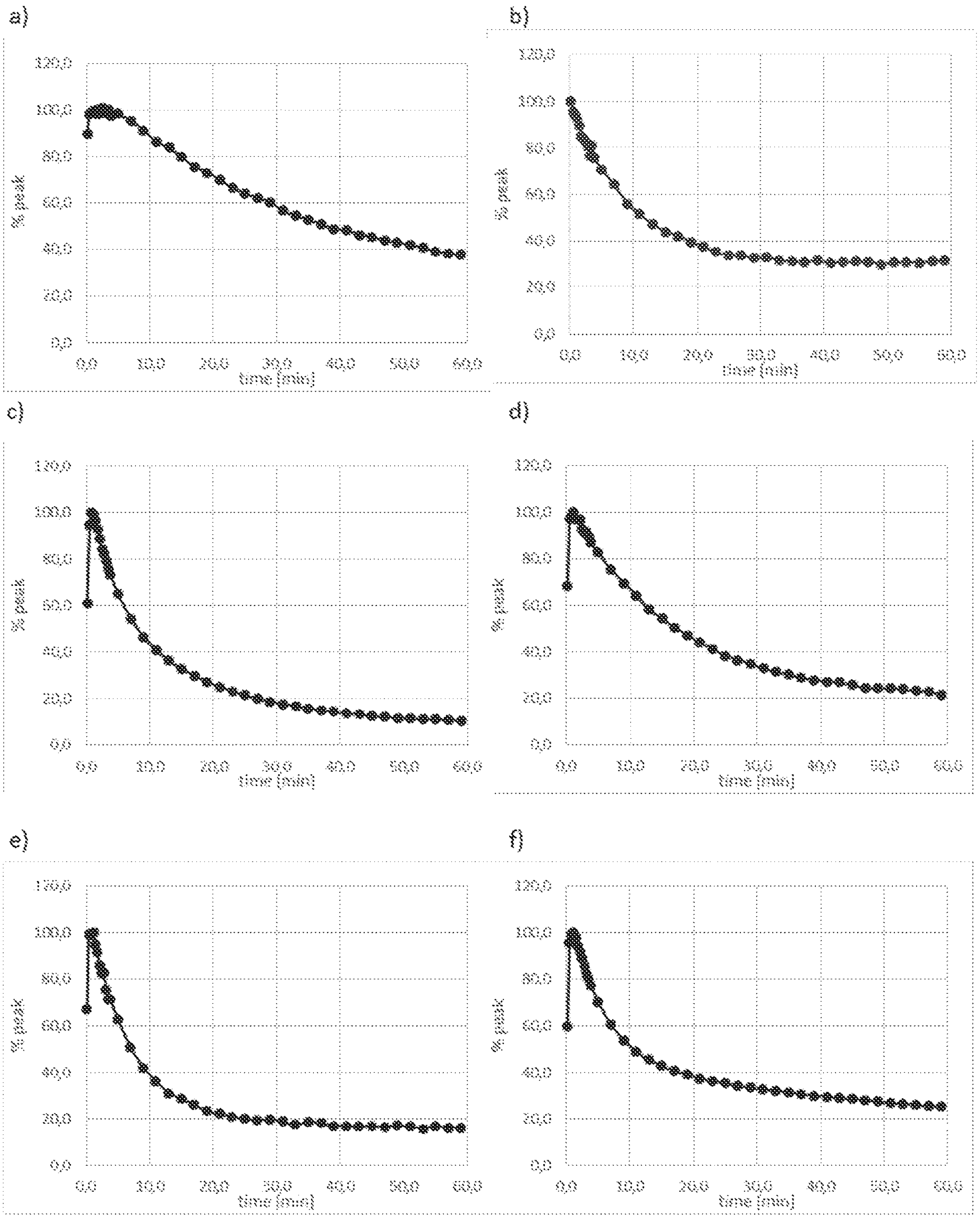
FIG. 4 shows the washout kinetics of the compounds: a) 18F-51, b) 18F-2, c) $^{18}$F-161, d) $^{18}$F-44, e) $^{18}$F-56, and f) $^{18}$F-146.
Figure 5:
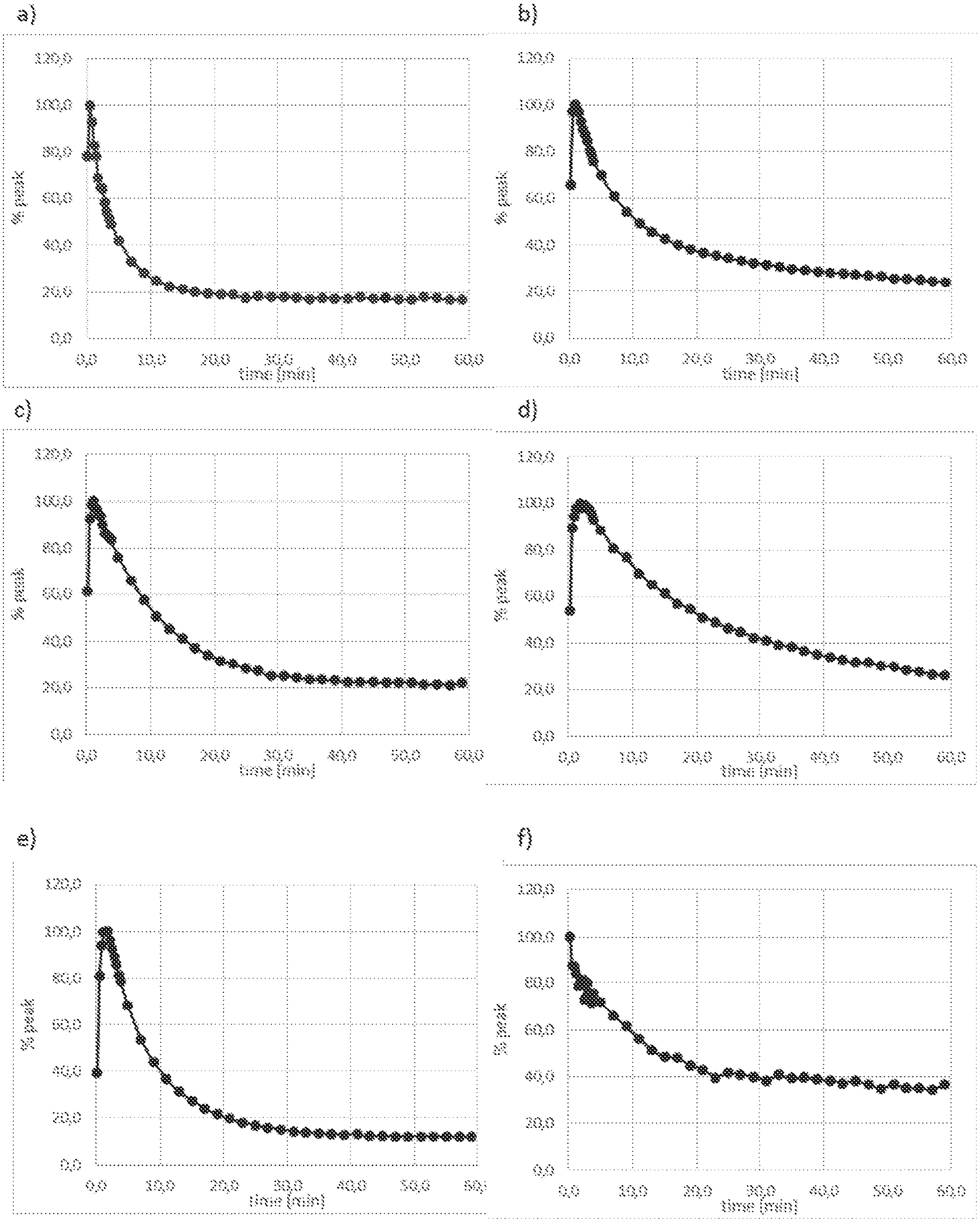
FIG. 5 shows the washout kinetics of the compounds: a) $^{18}$F-60, b) $^{18}$F-17, c) $^{18}$F-63, d) $^{18}$F-147, e) $^{18}$F-156, and f) $^{18}$F-95
Figure 6:
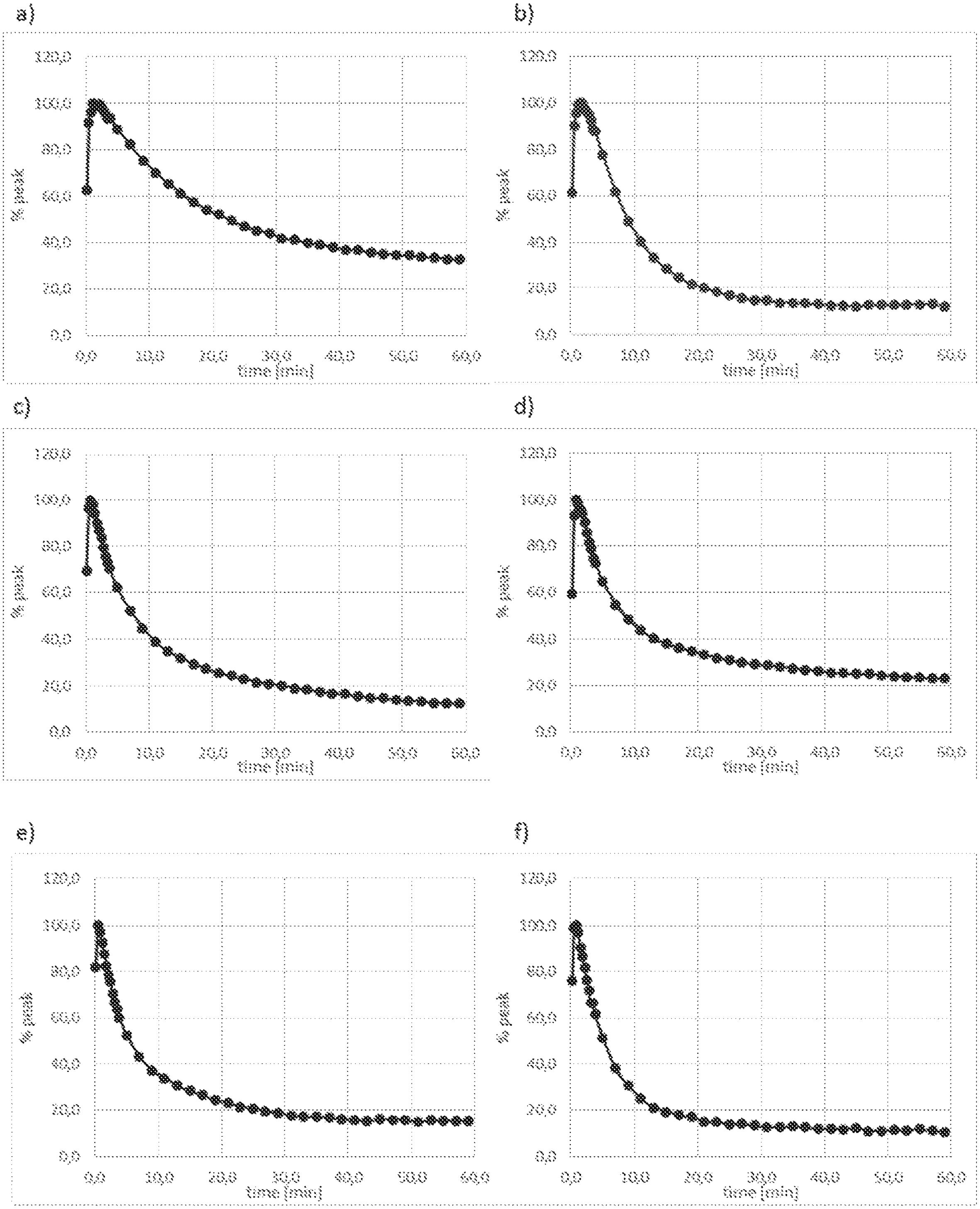
FIG. 6 shows the washout kinetics of the compounds: a) $^{18}$F-168, b) $^{18}$F-51, c) $^{18}$F-158, d) $^{18}$F-160, e) $^{18}$F-152, and f) $^{18}$F-28.

AD brain section co-staining of tau tangles by RefA (green, shown in white) and Aβ plaques by Compound B (blue, shown in white) at a concentration of 100 μM is shown in FIG. 3.

The following Example compounds were measured in Assay 1:

TABLE 21

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 1 | 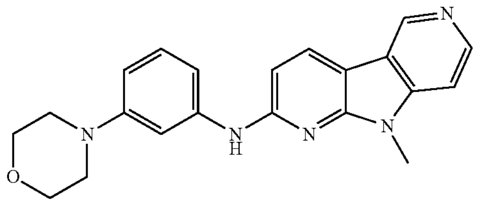 [SMILES: Cn1c2ccncc2c2ccc(Nc3cccc(N4CCOCC4)c3)nc21] | − | 84% | 32% | ~2.6 fold |
| 2 | 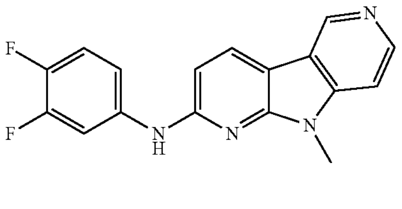 [SMILES: Cn1c2ccncc2c2ccc(Nc3ccc(F)c(F)c3)nc21] | + (tangles)[a] | 96% | 0% | >96 fold |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 3 | 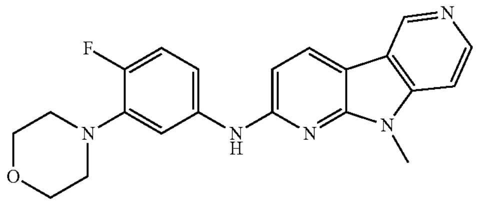 [SMILES: Cn1c2ccncc2c2ccc(Nc3ccc(F)c(N4CCOCC4)c3)nc21] | – | 78% | 8% | ~9.8 fold |
| 4 | 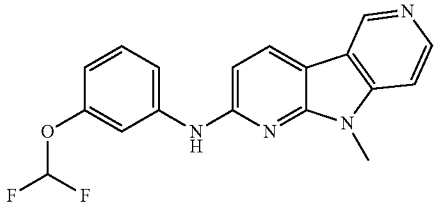 [SMILES: Cn1c2ccncc2c2ccc(Nc3cccc(OC(F)F)c3)nc21] | + (tangles)[a] | 91% | 17% | ~5.4 fold |
| 5 | 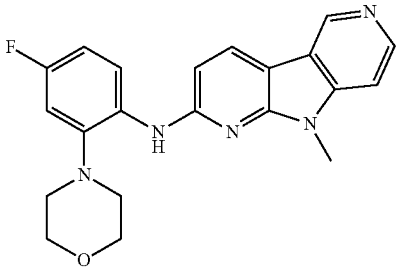 [SMILES: Cn1c2ccncc2c2ccc(Nc3ccc(F)cc3N3CCOCC3)nc21] | – | 0% | 12% | N/A |
| 6 | 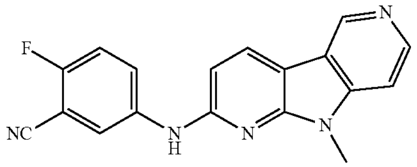 [SMILES: Cn1c2ccncc2c2ccc(Nc3ccc(F)c(C#N)c3)nc21] | +++ (tangles) | n.d. | n.d. | n.d. |
| 7 | 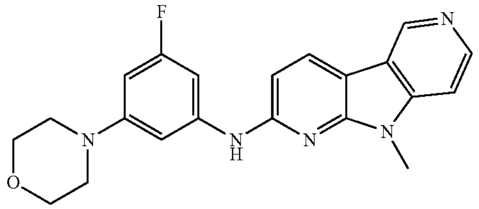 [SMILES: Cn1c2ccncc2c2ccc(Nc3cc(F)cc(N4CCOCC4)c3)nc21] | ++ (tangles) | 84% | 0% | >84 fold |
| 8 | 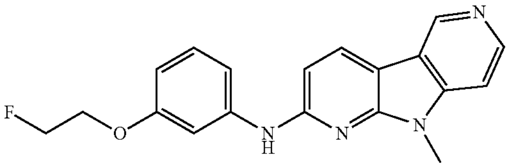 [SMILES: Cn1c2ccncc2c2ccc(Nc3cccc(OCCF)c3)nc21] | ++ (tangles) | 90% | 6% | ~15 fold |
| 9 | 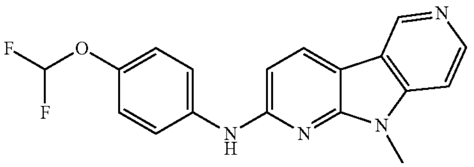 [SMILES: Cn1c2ccncc2c2ccc(Nc3ccc(OC(F)F)cc3)nc21] | ++ (tangles) | 97% | 0% | >97 fold |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
| --- | --- | --- | --- | --- | --- |
| 10 | 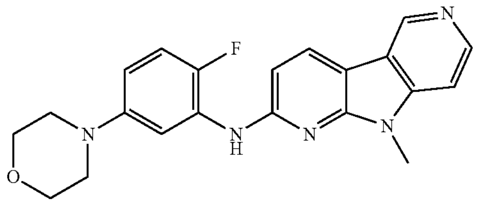 [SMILES: Cn1c2ccncc2c2ccc(Nc3cc(N4CCOCC4)ccc3F)nc21] | – | n.d. | n.d. | n.d. |
| 11 | 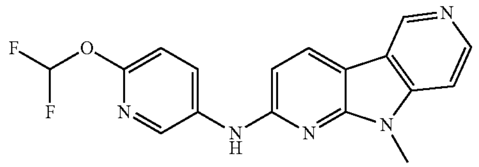 [SMILES: Cn1c2ccncc2c2ccc(Nc3ccc(OC(F)F)nc3)nc21] | ++ (tangles) | n.d. | n.d. | n.d. |
| 12 | 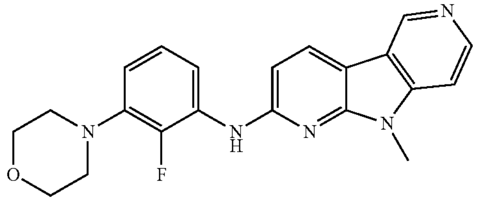 [SMILES: Cn1c2ccncc2c2ccc(Nc3cccc(N4CCOCC4)c3F)nc21] | – | 98% | 0% | >98 fold |
| 13 | 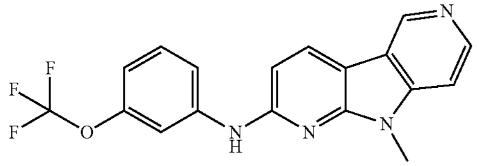 [SMILES: Cn1c2ccncc2c2ccc(Nc3cccc(OC(F)(F)F)c3)nc21] | + | n.d. | n.d. | n.d. |
| 14 | 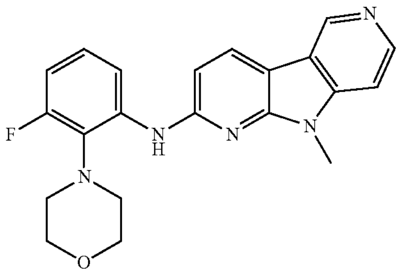 [SMILES: Cn1c2ccncc2c2ccc(Nc3cccc(F)c3N3CCOCC3)nc21] | – | n.d. | n.d. | n.d. |
| 15 | 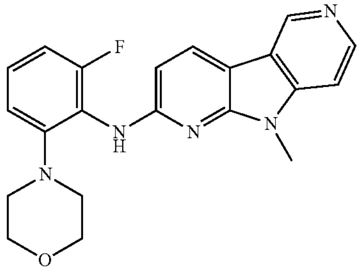 [SMILES: Cn1c2ccncc2c2ccc(Nc3c(F)cccc3N3CCOCC3)nc21] | – | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 16 | 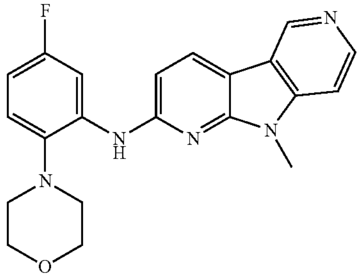 [SMILES: Cn1c2ccncc2c2ccc(Nc3cc(F)ccc3N3CCOCC3)nc21] | – | n.d. | n.d. | n.d. |
| 17 | 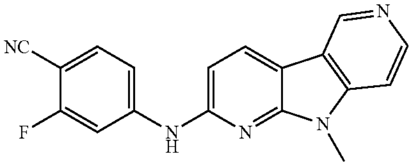 [SMILES: Cn1c2ccncc2c2ccc(Nc3ccc(C#N)c(F)c3)nc21] | +++ (tangles) | n.d. | n.d. | n.d. |
| 18 | 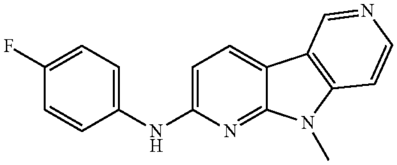 [SMILES: Cn1c2ccncc2c2ccc(Nc3ccc(F)cc3)nc21] | – | n.d. | n.d. | n.d. |
| 19 | 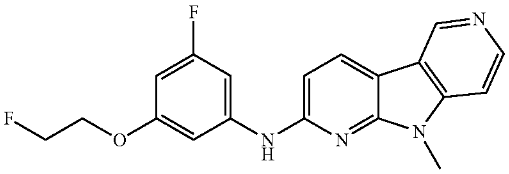 [SMILES: Cn1c2ccncc2c2ccc(Nc3cc(F)cc(OCCF)c3)nc21] | – | n.d. | n.d. | n.d. |
| 20 | 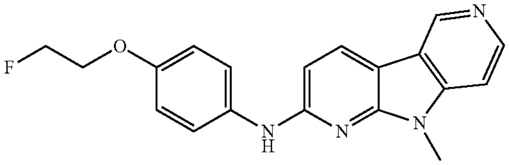 [SMILES: Cn1c2ccncc2c2ccc(Nc3ccc(OCCF)cc3)nc21] | + (plaques) | n.d. | n.d. | n.d. |
| 21 | 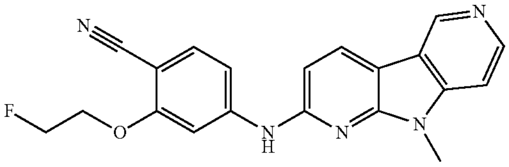 [SMILES: Cn1c2ccncc2c2ccc(Nc3ccc(C#N)c(OCCF)c3)nc21] | – | n.d. | n.d. | n.d. |
| 22 | 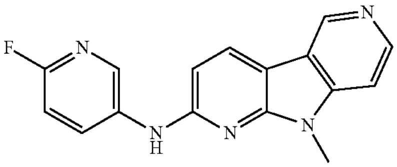 [SMILES: Cn1c2ccncc2c2ccc(Nc3ccc(F)nc3)nc21] | + (tangles) + (plaques | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 23 | 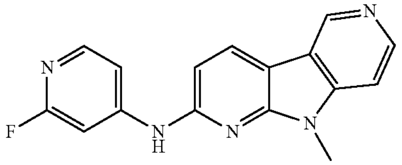 [SMILES: Cn1c2ccncc2c2ccc(Nc3ccnc(F)c3)nc21] | ++ (tangles) | 85% | 14% | ~6 fold |
| 24 | 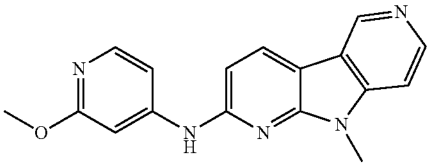 [SMILES: COc1cc(Nc2ccc3c4cnccc4n(C)c3n2)ccn1] | + (plaques) | n.d. | n.d. | n.d. |
| 25 | 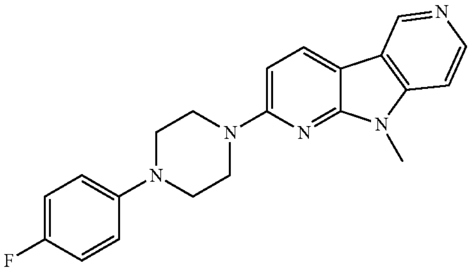 [SMILES: Cn1c2ccncc2c2ccc(N3CCN(c4ccc(F)cc4)CC3)nc21] | + (tangles) + (plaques) | n.d. | n.d. | n.d. |
| 26 | 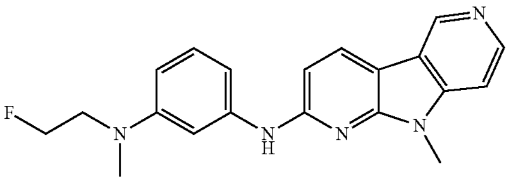 [SMILES: CN(CCF)c1cccc(Nc2ccc3c4cnccc4n(C)c3n2)c1] | +++ (plaques) | n.d. | n.d. | n.d. |
| 27 | 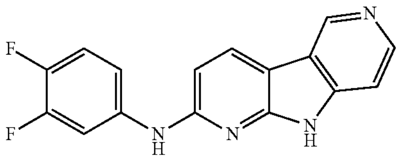 [SMILES: Fc1ccc(Nc2ccc3c(n2)[nH]c2ccncc23)cc1F] | + (tangles) + (plaques) | n.d. | n.d. | n.d. |
| 28 | 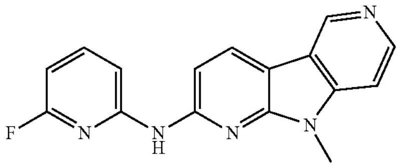 [SMILES: Cn1c2ccncc2c2ccc(Nc3cccc(F)n3)nc21] | + (tangles) | n.d. | n.d. | n.d. |
| 29 | 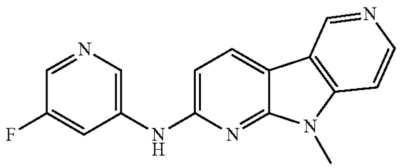 [SMILES: Cn1c2ccncc2c2ccc(Nc3cncc(F)c3)nc21] | + (tangles) | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 30 | 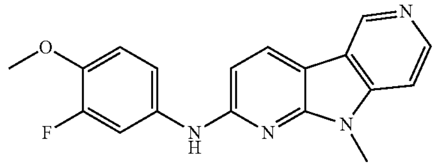 [SMILES: COc1ccc(Nc2ccc3c4cnccc4n(C)c3n2)cc1F] | + (tangles) + (plaques) | n.d. | n.d. | n.d. |
| 31 | 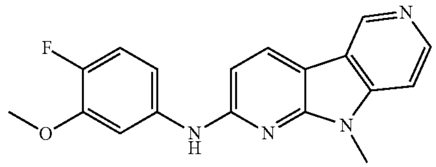 [SMILES: COc1cc(Nc2ccc3c4cnccc4n(C)c3n2)ccc1F] | + (tangles) + (plaques) | n.d. | n.d. | n.d. |
| 32 | 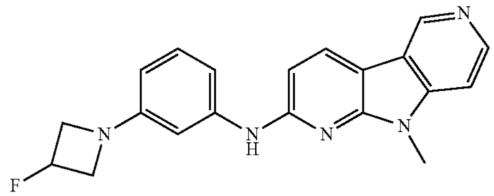 [SMILES: Cn1c2ccncc2c2ccc(Nc3cccc(N4CC(F)C4)c3)nc21] | + (tangles) + (plaques) | n.d. | n.d. | n.d. |
| 33 | 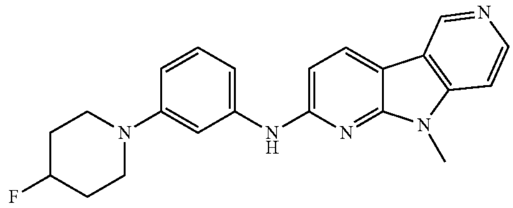 [SMILES: Cn1c2ccncc2c2ccc(Nc3cccc(N4CCC(F)CC4)c3)nc21] | + (tangles) + (plaques) | n.d. | n.d. | n.d. |
| 34 | 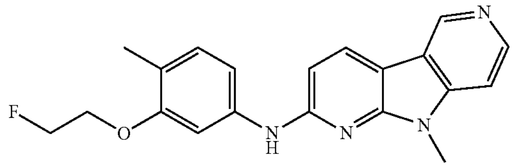 [SMILES: Cc1ccc(Nc2ccc3c4cnccc4n(C)c3n2)cc1OCCF] | +++ (tangles) | n.d. | n.d. | n.d. |
| 35 | 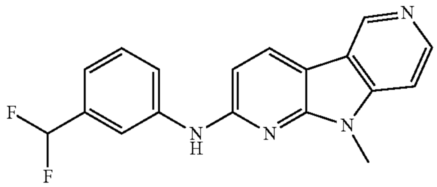 [SMILES: Cn1c2ccncc2c2ccc(Nc3cccc(C(F)F)c3)nc21] | ++ (tangles) ++ (plaques) | n.d. | n.d. | n.d. |
| 36 | 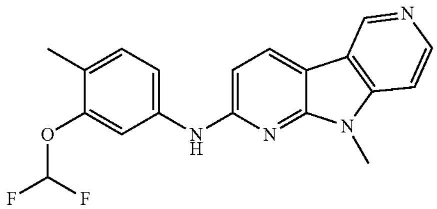 [SMILES: Cc1ccc(Nc2ccc3c4cnccc4n(C)c3n2)cc1OC(F)F] | + (plaques) | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 37 | 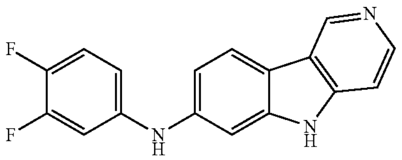 [SMILES: Fc1ccc(Nc2ccc3c(c2)[nH]c2ccncc23)cc1F] | + (tangles) | n.d. | n.d. | n.d. |
| 38 | 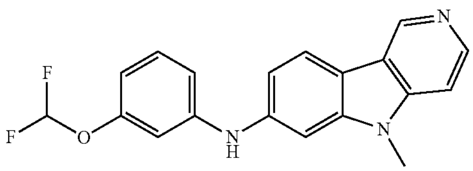 [SMILES: Cn1c2ccncc2c2ccc(Nc3cccc(OC(F)F)c3)cc21] | + (plaques) | n.d. | n.d. | n.d. |
| 39 | 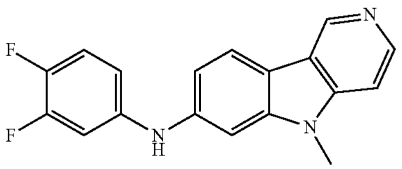 [SMILES: Cn1c2ccncc2c2ccc(Nc3ccc(F)c(F)c3)cc21] | ++ (tangles) | n.d. | n.d. | n.d. |
| 40 | 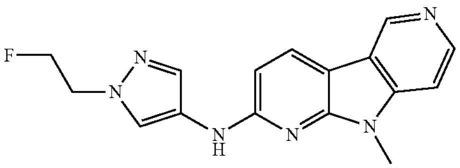 [SMILES: Cn1c2ccncc2c2ccc(Nc3cnn(CCF)c3)nc21] | +++ (tangles) | 91% | n.d. | n.d. |
| 41 | 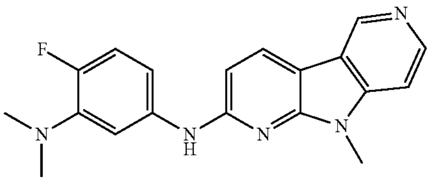 [SMILES: CN(C)c1cc(Nc2ccc3c4cnccc4n(C)c3n2)ccc1F] | – | n.d. | n.d. | n.d. |
| 42 | 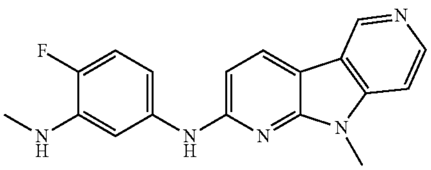 [SMILES: CNc1cc(Nc2ccc3c4cnccc4n(C)c3n2)ccc1F] | +++ (plaques) | n.d. | n.d. | n.d. |
| 43 | 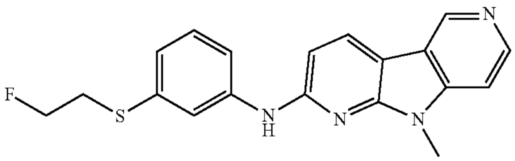 [SMILES: Cn1c2ccncc2c2ccc(Nc3cccc(SCCF)c3)nc21] | + (tangles) + (plaques) | n.d. | n.d. | n.d. |
| 44 | 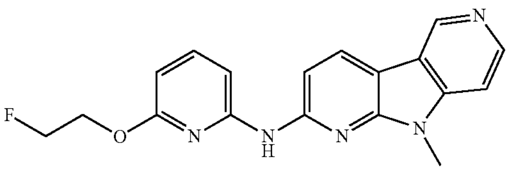 [SMILES: Cn1c2ccncc2c2ccc(Nc3cccc(OCCF)n3)nc21] | ++ (tangles) | 88% | −21% | >88 fold |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 45 | 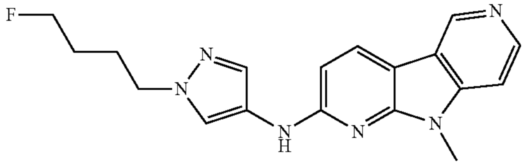 [SMILES: Cn1c2ccncc2c2ccc(Nc3cnn(CCCCF)c3)nc21] | – | 39% | n.d. | n.d. |
| 46 | 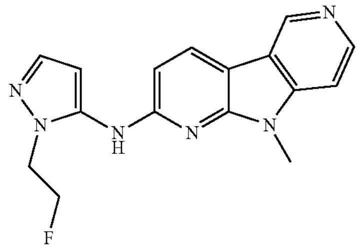 [SMILES: Cn1c2ccncc2c2ccc(Nc3ccnn3CCF)nc21] | – | 55% | n.d. | n.d. |
| 47 | 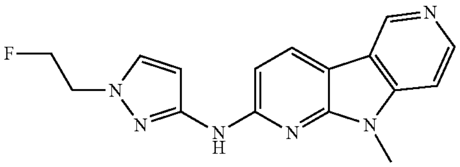 [SMILES: Cn1c2ccncc2c2ccc(Nc3ccn(CCF)n3)nc21] | ++ (tangles) | 89% | n.d. | n.d. |
| 48 | 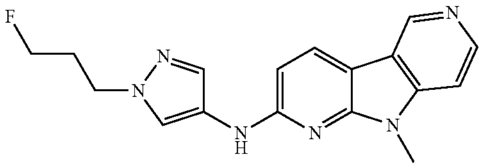 [SMILES: Cn1c2ccncc2c2ccc(Nc3cnn(CCCF)c3)nc21] | – | 96% | n.d. | n.d. |
| 49 | 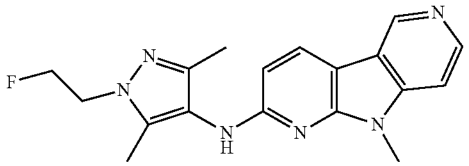 [SMILES: Cc1nn(CCF)c(C)c1Nc1ccc2c3cnccc3n(C)c2n1] | + (tangles) | n.d. | n.d. | n.d. |
| 50 | 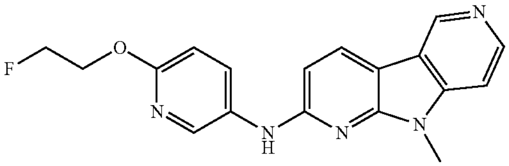 [SMILES: Cn1c2ccncc2c2ccc(Nc3ccc(OCCF)nc3)nc21] | + (tangles) + (plaques) | n.d. | n.d. | n.d. |
| 51 | 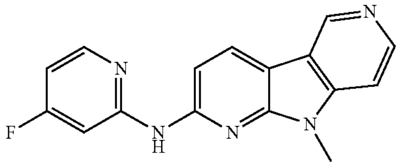 [SMILES: Cn1c2ccncc2c2ccc(Nc3cc(F)ccn3)nc21] | +++ (tangles) | n.d. | n.d. | n.d. |
| 56 | 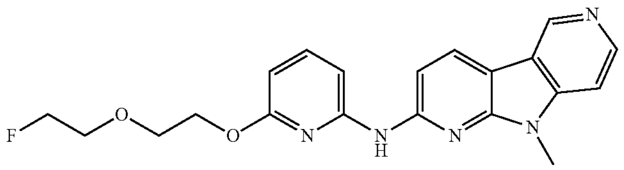 [SMILES: Cn1c2ccncc2c2ccc(Nc3cccc(OCCOCCF)n3)nc21] | ++ (tangles) | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 57 | 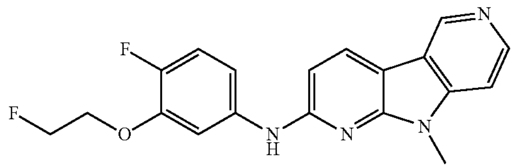 | ++ (tangles) | n.d. | n.d. | n.d. |
| 58 | 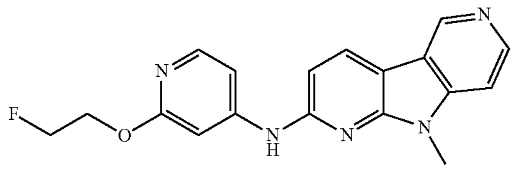 | +++ (plaques) | n.d. | n.d. | n.d. |
| 59 | 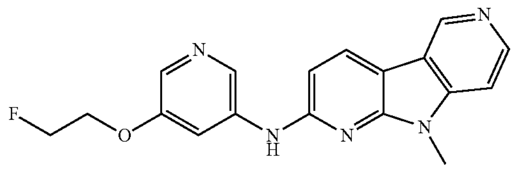 [SMILES: Cn1c2ccncc2c2ccc(Nc3cncc(OCCF)c3)nc21] | +++ (tangles) | 93%. | −9% | >93 fold |
| 60 | 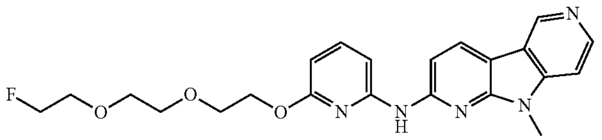 [SMILES: Cn1c2ccncc2c2ccc(Nc3cccc(OCCOCCOCCF)n3)nc21] | ++ (tangles) ++ (plaques) | n.d. | n.d. | n.d. |
| 61 | 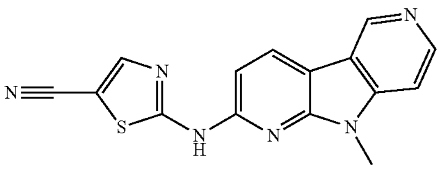 [SMILES: Cn1c2ccncc2c2ccc(Nc3ncc(C#N)s3)nc21] | − | n.d. | n.d. | n.d. |
| 62 | 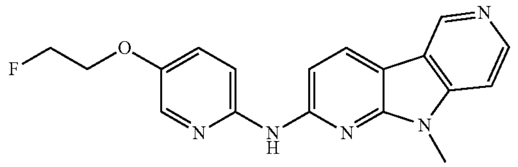 [SMILES: Cn1c2ccncc2c2ccc(Nc3ccc(OCCF)cn3)nc21] | + (tangles) | n.d. | n.d. | n.d. |
| 63 | 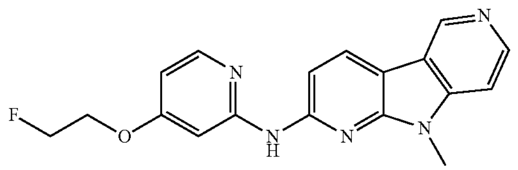 [SMILES: Cn1c2ccncc2c2ccc(Nc3cc(OCCF)ccn3)nc21] | + (tangles) | 82%. | 3% | ~27 fold |
| 65 | 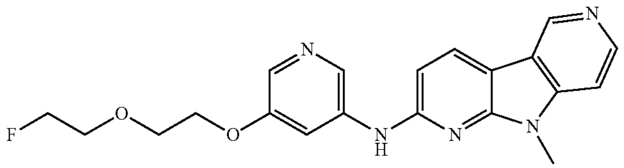 [SMILES: Cn1c2ccncc2c2ccc(Nc3cncc(OCCOCCF)c3)nc21] | ++ (tangles) | n.d. | 35% | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 69 | 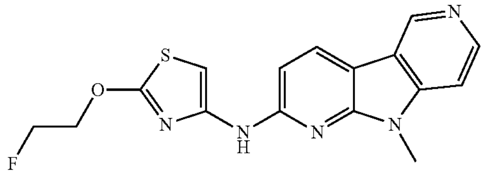 [SMILES: Cn1c2ccncc2c2ccc(Nc3csc(OCCF)n3)nc21] | ++ (tangles) | n.d. | n.d. | n.d. |
| 71 | 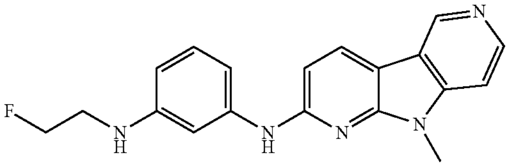 [SMILES: Cn1c2ccncc2c2ccc(Nc3cccc(NCCF)c3)nc21] | + (tangles) + (plaques) | n.d. | n.d. | n.d. |
| 78 | 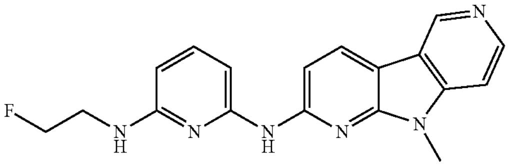 [SMILES: Cn1c2ccncc2c2ccc(Nc3cccc(NCCF)n3)nc21] | ++ (tangles) | 91% | n.d. | n.d. |
| 79 | 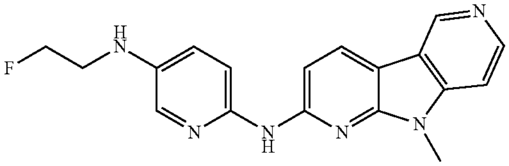 [SMILES: Cn1c2ccncc2c2ccc(Nc3ccc(NCCF)cn3)nc21] | – | n.d. | n.d. | n.d. |
| 81 | 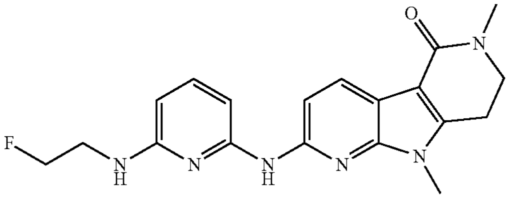 [SMILES: CN1CCc2c(c3ccc(Nc4cccc(NCCF)n4)nc3n2C)C1=O] | – | n.d. | n.d. | n.d. |
| 82 | 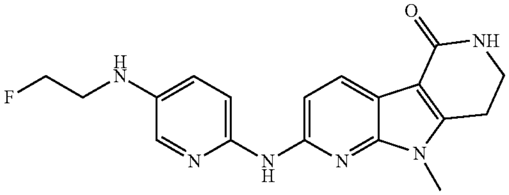 [SMILES: Cn1c2c(c3ccc(Nc4ccc(NCCF)cn4)nc31)C(=O)NCC2] | + (tangles) | n.d. | n.d. | n.d. |
| 83 | 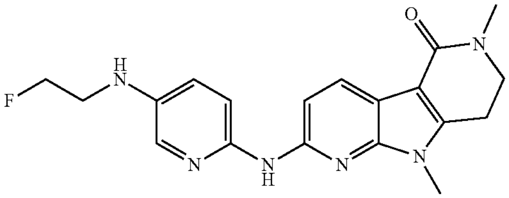 [SMILES: CN1CCc2c(c3ccc(Nc4ccc(NCCF)cn4)nc3n2C)C1=O] | + (tangles) | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 84 | 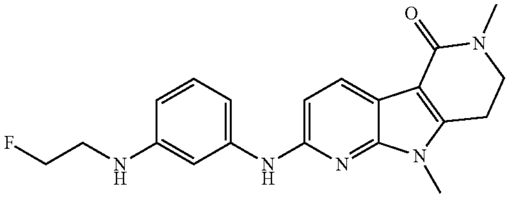 [SMILES: CN1CCc2c(c3ccc(Nc4cccc(NCCF)c4)nc3n2C)C1=O] | – | n.d. | n.d. | n.d. |
| 95 | 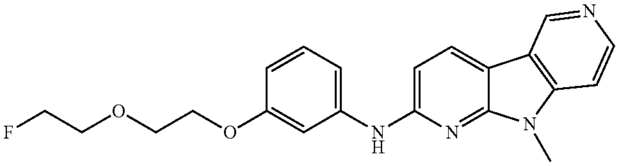 [SMILES: Cn1c2ccncc2c2ccc(Nc3cccc(OCCOCCF)c3)nc21] | ++ (tangles) | n.d. | 59% | n.d. |
| 96 | 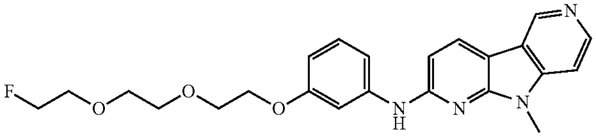 [SMILES: Cn1c2ccncc2c2ccc(Nc3cccc(OCCOCCOCCF)c3)nc21] | ++ (tangles) | n.d. | 18% | n.d. |
| 97 | 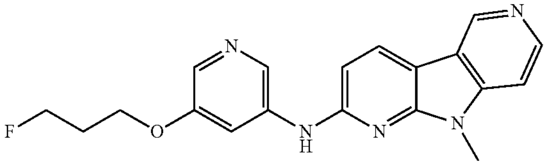 [SMILES: Cn1c2ccncc2c2ccc(Nc3cncc(OCCCF)c3)nc21] | +++ (tangles) | n.d. | n.d. | n.d. |
| 98 | 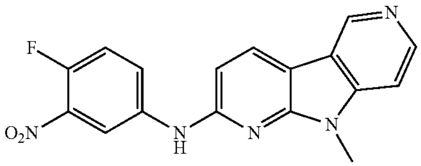 [SMILES: Cn1c2ccncc2c2ccc(Nc3ccc(F)c([N+](=O)[O-])c3)nc21] | – | n.d. | n.d. | n.d. |
| 99 | 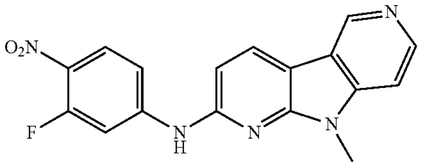 [SMILES: Cn1c2ccncc2c2ccc(Nc3ccc([N+](=O)[O-])c(F)c3)nc21] | – | n.d. | n.d. | n.d. |
| 146 | 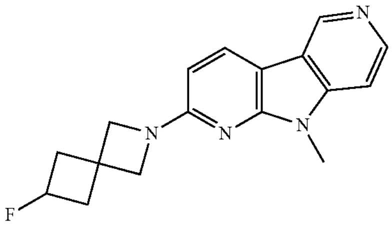 [SMILES: Cn1c2ccncc2c2ccc(N3CC4(CC(F)C4)C3)nc21] | ++ (tangles) | n.d. | 0% | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 147 | 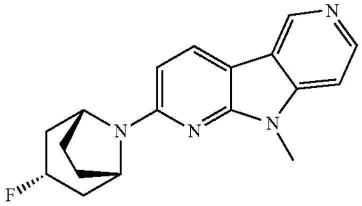 [SMILES: Cn1c2ccncc2c2ccc(N3[C@@H]4CC[C@H]3C[C@H](F)C4)nc21] | ++ (tangles) | n.d. | n.d. | n.d. |
| 148 | 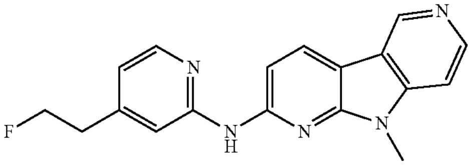 [SMILES: Cn1c2ccncc2c2ccc(Nc3cc(CCF)ccn3)nc21] | ++ (tangles) | n.d. | n.d. | n.d. |
| 149 | 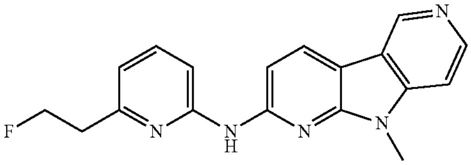 [SMILES: Cn1c2ccncc2c2ccc(Nc3cccc(CCF)n3)nc21] | ++ (tangles) | n.d. | n.d. | n.d. |
| 150 | 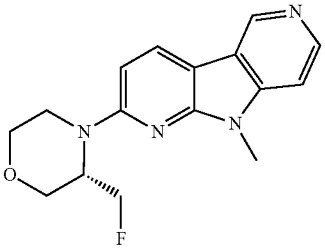 [SMILES: Cn1c2ccncc2c2ccc(N3CCOC[C@H]3CF)nc21] | + (tangles)[a] | 18% | 3% | N/A |
| 151 | 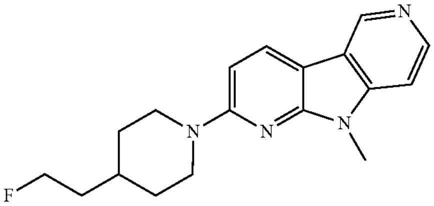 [SMILES: Cn1c2ccncc2c2ccc(N3CCC(CCF)CC3)nc21] | − | 99% | 42% | ~2.4-fold |
| 153 | 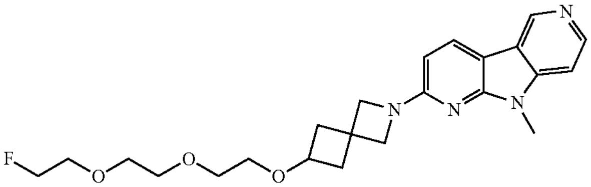 [SMILES: Cn1c2ccncc2c2ccc(N3CC4(CC(OCCOCCOCCF)C4)C3)nc21] | ++ (tangles) | n.d. | n.d. | n.d. |
| 154 | 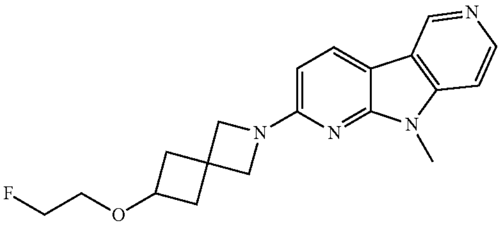 [SMILES: Cn1c2ccncc2c2ccc(N3CC4(CC(OCCF)C4)C3)nc21] | ++ (tangles) | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 155 | 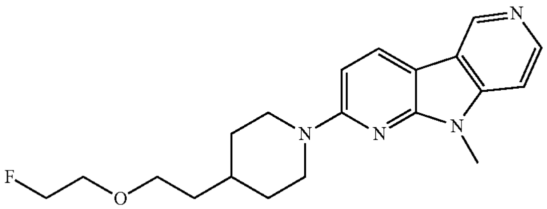 [SMILES: Cn1c2ccncc2c2ccc(N3CCC(CCOCCF)CC3)nc21] | + (tangles) + (plaques) | 90% | 15% | ~6-fold |
| 156 | 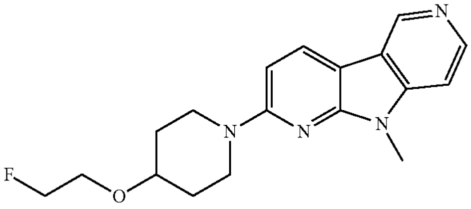 [SMILES: Cn1c2ccncc2c2ccc(N3CCC(OCCF)CC3)nc21] | + (tangles) | 72% | −8% | >72 fold |
| 158 | 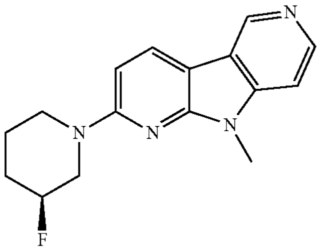 [SMILES: Cn1c2ccncc2c2ccc(N3CCC[C@H](F)C3)nc21] | ++ (tangles) | n.d. | n.d. | n.d. |
| 159 | 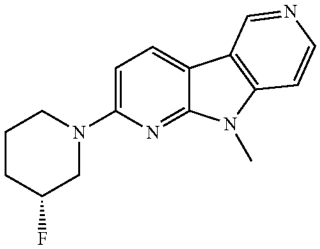 [SMILES: Cn1c2ccncc2c2ccc(N3CCC[C@@H](F)C3)nc21] | + (tangles) | n.d. | n.d. | n.d. |
| 160 | 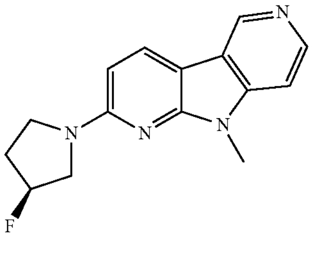 [SMILES: Cn1c2ccncc2c2ccc(N3CC[C@H](F)C3)nc21] | − | n.d. | n.d. | n.d. |
| 161 | 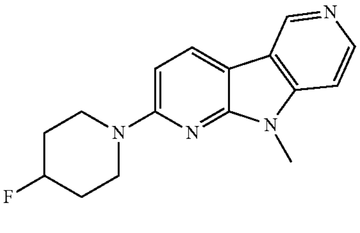 [SMILES: Cn1c2ccncc2c2ccc(N3CCC(F)CC3)nc21] | + (tangles) | 85% | 14% | ~6-fold |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 163 | 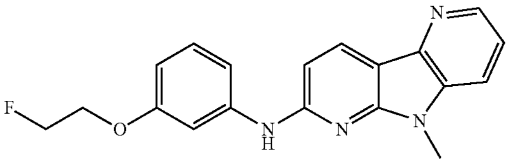 [SMILES: Cn1c2cccnc2c2ccc(Nc3cccc(OCCF)c3)nc21] | ++ (tangles) | n.d. | n.d. | n.d. |
| 164 | 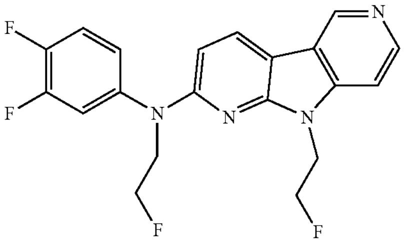 [SMILES: FCCN(c1ccc(F)c(F)c1)c1ccc2c3cnccc3n(CCF)c2n1] | + (plaques) | n.d. | n.d. | n.d. |
| 165 | 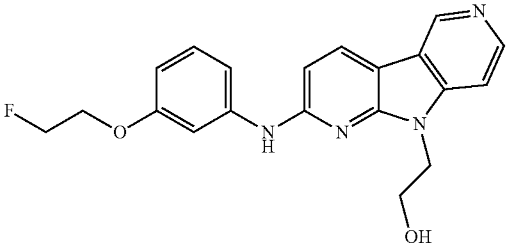 [SMILES: OCCn1c2ccncc2c2ccc(Nc3cccc(OCCF)c3)nc21] | – | n.d. | n.d. | n.d. |
| 166 | 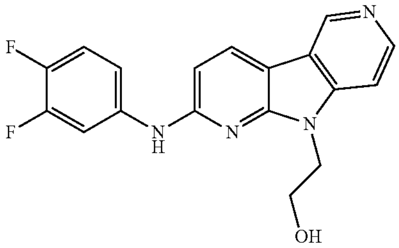 [SMILES: OCCn1c2ccncc2c2ccc(Nc3ccc(F)c(F)c3)nc21] | – | n.d. | n.d. | n.d. |
| 167 | 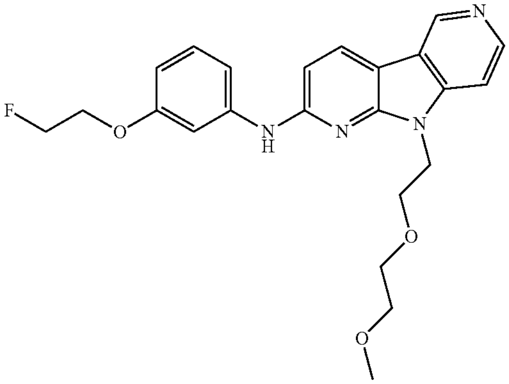 [SMILES: COCCOCCn1c2ccncc2c2ccc(Nc3cccc(OCCF)c3)nc21] | – | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 168 Step B | 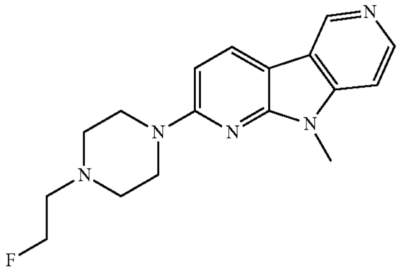 [SMILES: Cn1c2ccncc2c2ccc(N3CCN(CCF)CC3)nc21] | ++ (tangles) | n.d. | −1% | n.d. |
| 169 | 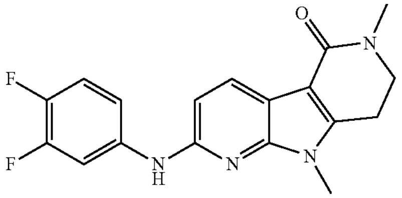 [SMILES: CN1CCc2c(c3ccc(Nc4ccc(F)c(F)c4)nc3n2C)C1=O] | − | 26% | n.d. | n.d. |
| 170 | 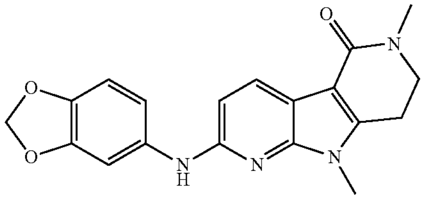 [SMILES: CN1CCc2c(c3ccc(Nc4ccc5c(c4)OCO5)nc3n2C)C1=O] | − | 20% | n.d. | n.d. |
| 171 | 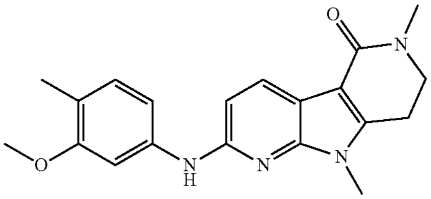 [SMILES: COc1cc(Nc2ccc3c4c(n(C)c3n2)CCN(C)C4=O)ccc1C] | − | n.d. | n.d. | n.d. |
| 172 | 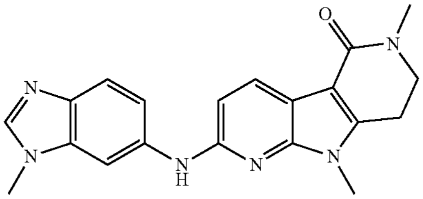 [SMILES: CN1CCc2c(c3ccc(Nc4ccc5ncn(C)c5c4)nc3n2C)C1=O] | − | 16% | n.d. | n.d. |
| 173 | 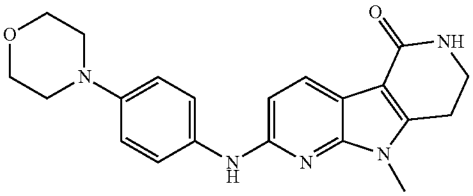 [SMILES: Cn1c2c(c3ccc(Nc4ccc(N5CCOCC5)cc4)nc31)C(=O)NCC2] | − | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 174 | 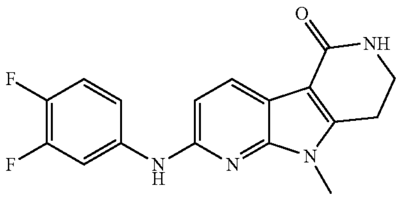 [SMILES: Cn1c2c(c3ccc(Nc4ccc(F)c(F)c4)nc31)C(=O)NCC2] | – | n.d. | n.d. | n.d. |
| 175 | 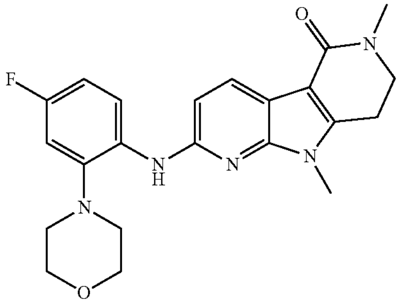 [SMILES: CN1CCc2c(c3ccc(Nc4ccc(F)cc4N4CCOCC4)nc3n2C)C1=O] | – | 6% | 0% | N/A |
| 176 | 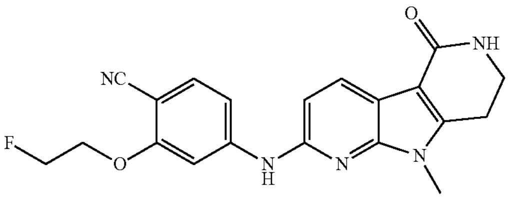 [SMILES: Cn1c2c(c3ccc(Nc4ccc(C#N)c(OCCF)c4)nc31)C(=O)NCC2] | – | n.d. | n.d. | n.d. |
| 177 | 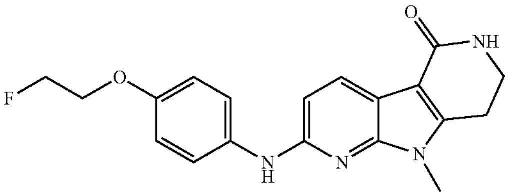 [SMILES: Cn1c2c(c3ccc(Nc4ccc(OCCF)cc4)nc31)C(=O)NCC2] | – | n.d. | n.d. | n.d. |
| 178 | 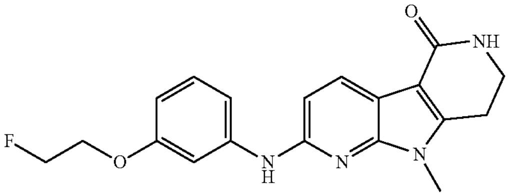 [SMILES: Cn1c2c(c3ccc(Nc4cccc(OCCF)c4)nc31)C(=O)NCC2] | – | n.d. | n.d. | n.d. |
| 179 | 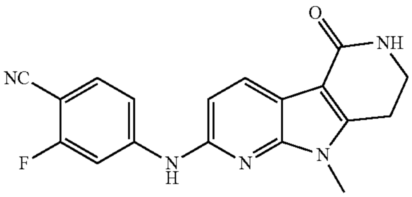 [SMILES: Cn1c2c(c3ccc(Nc4ccc(C#N)c(F)c4)nc31)C(=O)NCC2] | + (tangles) | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 180 | 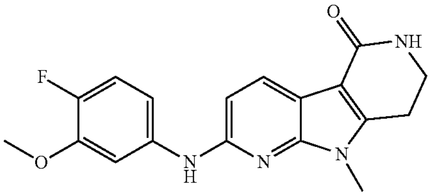 [SMILES: COc1cc(Nc2ccc3c4c(n(C)c3n2)CCNC4=O)ccc1F] | – | n.d. | n.d. | n.d. |
| 181 | 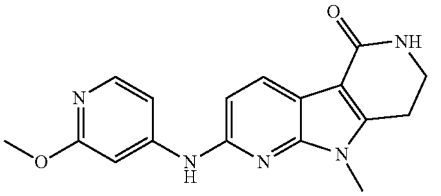 [SMILES: COc1cc(Nc2ccc3c4c(n(C)c3n2)CCNC4=O)ccn1] | + (tangles) | n.d. | n.d. | n.d. |
| 182 | 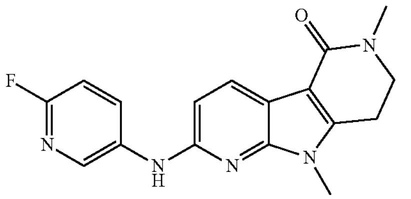 [SMILES: CN1CCc2c(c3ccc(Nc4ccc(F)nc4)nc3n2C)C1=O] | – | n.d. | n.d. | n.d. |
| 183 | 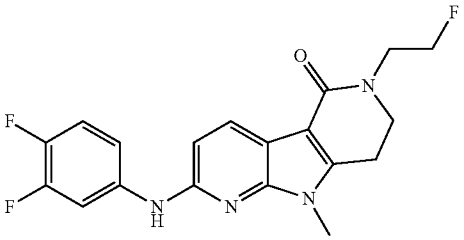 [SMILES: Cn1c2c(c3ccc(Nc4ccc(F)c(F)c4)nc31)C(=O)N(CCF)CC2] | + (plaques) | n.d. | n.d. | n.d. |
| 184 | 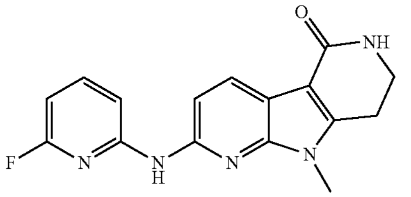 [SMILES: Cn1c2c(c3ccc(Nc4cccc(F)n4)nc31)C(=O)NCC2] | + (plaques) | n.d. | n.d. | n.d. |
| 185 | 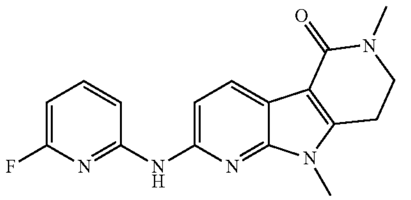 [SMILES: CN1CCc2c(c3ccc(Nc4cccc(F)n4)nc3n2C)C1=O] | + (plaques) | n.d. | n.d. | n.d. |
| 186 | 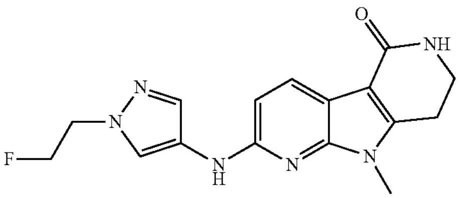 [SMILES: Cn1c2c(c3ccc(Nc4cnn(CCF)c4)nc31)C(=O)NCC2] | + (plaques) | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 187 | 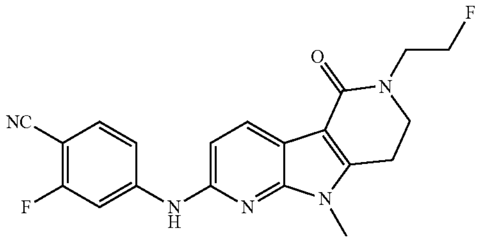 [SMILES: Cn1c2c(c3ccc(Nc4ccc(C#N)c(F)c4)nc31)C(=O)N(CCF)CC2] | + (tangles) | n.d. | n.d. | n.d. |
| 188 | 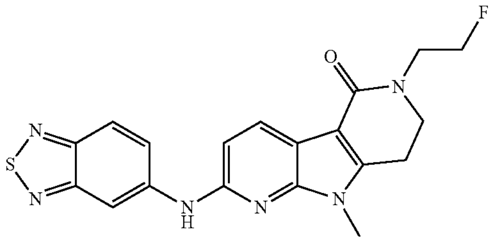 [SMILES: Cn1c2c(c3ccc(Nc4ccc5nsnc5c4)nc31)C(=O)N(CCF)CC2] | – | n.d. | n.d. | n.d. |
| 189 | 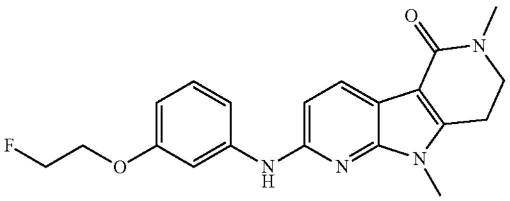 [SMILES: CN1CCc2c(c3ccc(Nc4cccc(OCCF)c4)nc3n2C)C1=O] | ++ (tangles) | n.d. | n.d. | n.d. |
| 190 | 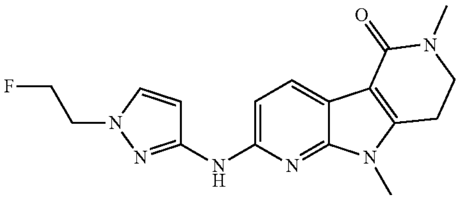 [SMILES: CN1CCc2c(c3ccc(Nc4ccn(CCF)n4)nc3n2C)C1=O] | – | n.d. | n.d. | n.d. |
| 191 | 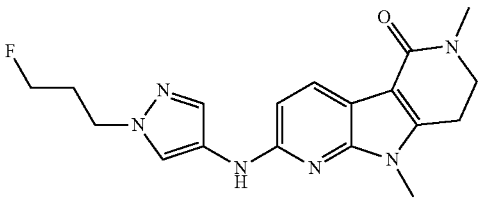 [SMILES: CN1CCc2c(c3ccc(Nc4cnn(CCCF)c4)nc3n2C)C1=O] | – | n.d. | n.d. | n.d. |
| 193 | 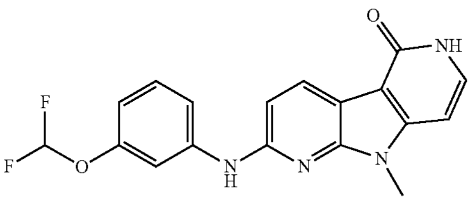 [SMILES: Cn1c2cc[nH]c(=O)c2c2ccc(Nc3cccc(OC(F)F)c3)nc21] | – | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 194 | 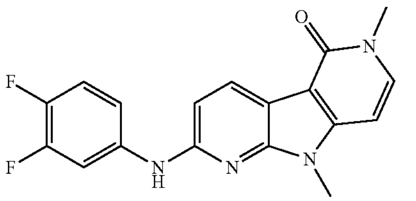 [SMILES: Cn1ccc2c(c1=O)c1ccc(Nc3ccc(F)c(F)c3)nc1n2C] | – | n.d. | n.d. | n.d. |
| 196 | 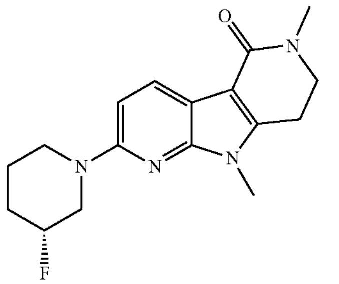 [SMILES: CN1CCc2c(c3ccc(N4CCC[C@@H](F)C4)nc3n2C)C1=O] | – | n.d. | n.d. | n.d. |
| 197 | 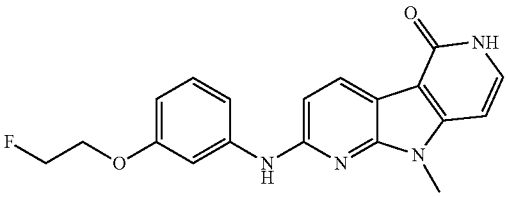 [SMILES: Cn1c2cc[nH]c(=O)c2c2ccc(Nc3cccc(OCCF)c3)nc21] | + (tangles) | n.d. | n.d. | n.d. |
| 198 | 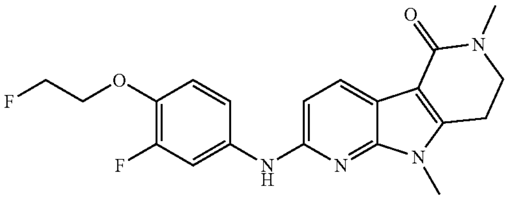 [SMILES: CN1CCc2c(c3ccc(Nc4ccc(OCCF)c(F)c4)nc3n2C)C1=O] | – | n.d. | n.d. | n.d. |
| 199 | 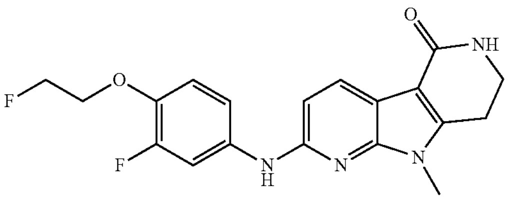 [SMILES: Cn1c2c(c3ccc(Nc4ccc(OCCF)c(F)c4)nc31)C(=O)NCC2] | + (tangles) + (plaques) | n.d. | n.d. | n.d. |
| 200 | 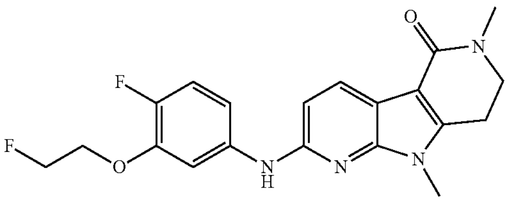 [SMILES: CN1CCc2c(c3ccc(Nc4ccc(F)c(OCCF)c4)nc3n2C)C1=O] | + (tangles) + (plaques) | n.d. | n.d. | n.d. |

TABLE 21-continued
| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 201 | 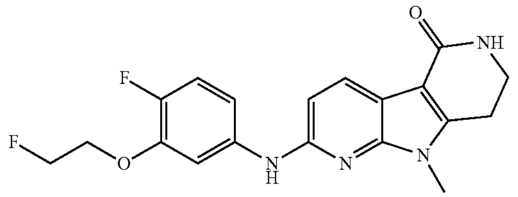 [SMILES: Cn1c2c(c3ccc(Nc4ccc(F)c(OCCF)c4)nc31)C(=O)NCC2] | – | n.d. | n.d. | n.d. |
| 202 | 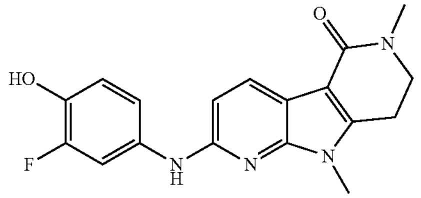 [SMILES: CN1CCc2c(c3ccc(Nc4ccc(O)c(F)c4)nc3n2C)C1=O] | – | n.d. | n.d. | n.d. |
| 203 | 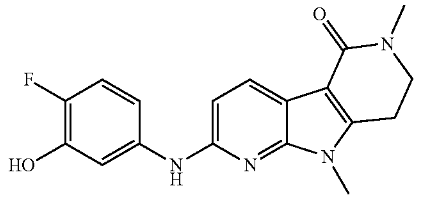 [SMILES: CN1CCc2c(c3ccc(Nc4ccc(F)c(O)c4)nc3n2C)C1=O] | – | n.d. | n.d. | n.d. |
| 204 | 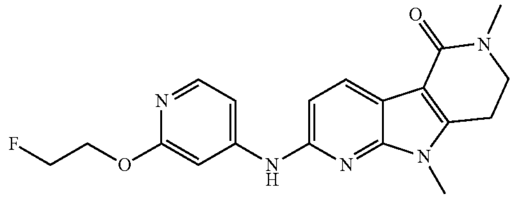 [SMILES: CN1CCc2c(c3ccc(Nc4ccnc(OCCF)c4)nc3n2C)C1=O] | – | n.d. | n.d. | n.d. |
| 205 | 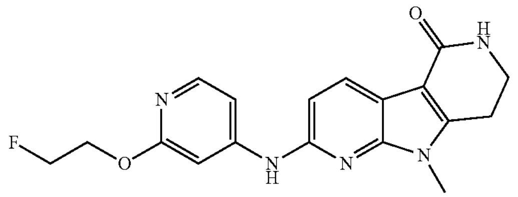 [SMILES: Cn1c2c(c3ccc(Nc4ccnc(OCCF)c4)nc31)C(=O)NCC2] | – | n.d. | n.d. | n.d. |
| 206 | 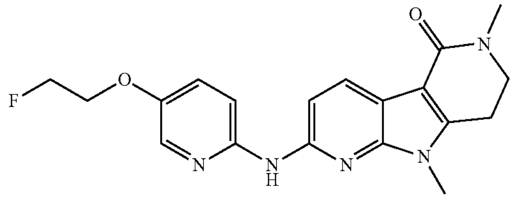 [SMILES: CN1CCc2c(c3ccc(Nc4ccc(OCCF)cn4)nc3n2C)C1=O] | – | n.d. | n.d. | n.d. |
| 207 | 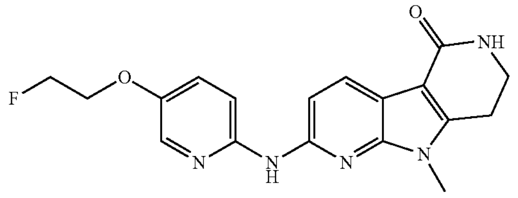 [SMILES: Cn1c2c(c3ccc(Nc4ccc(OCCF)cn4)nc31)C(=O)NCC2] | – | n.d. | n.d. | n.d. |

TABLE 21-continued

| Example | Structure | Direct staining of tau tangles/Aβ plaques on AD brain sections at 100 μM | Competition on AD brain section tau tangles (1 μM RefA vs. 250 μM compound) | Competition on AD brain section Aβ plaques (1 μM Compound B vs 250 μM compound) | Selectivity (tau/Abeta) |
|---|---|---|---|---|---|
| 208 | 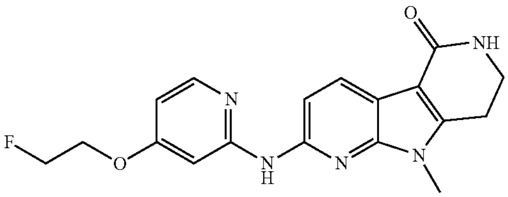 [SMILES: Cn1c2c(c3ccc(Nc4cc(OCCF)ccn4)nc31)C(=O)NCC2] | – | n.d. | n.d. | n.d. |
| 209 | 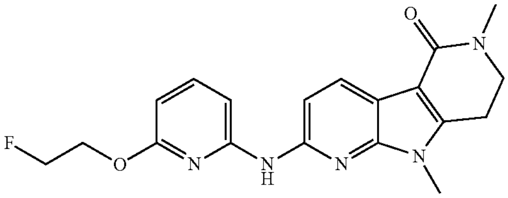 [SMILES: CN1CCc2c(c3ccc(Nc4cccc(OCCF)n4)nc3n2C)C1=O] | – | n.d. | n.d. | n.d. |
| 210 | 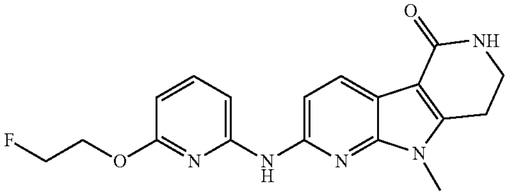 [SMILES: Cn1c2c(c3ccc(Nc4cccc(OCCF)n4)nc31)C(=O)NCC2] | – | n.d. | n.d. | n.d. |
| 211 | 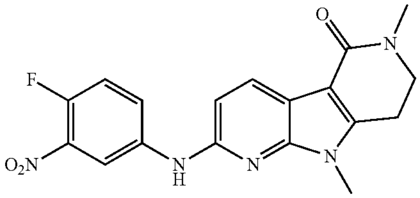 [SMILES: CN1CCc2c(c3ccc(Nc4ccc(F)c([N+](=O)[O-])c4)nc3n2C)C1=O] | – | n.d. | n.d. | n.d. |
| 212 | 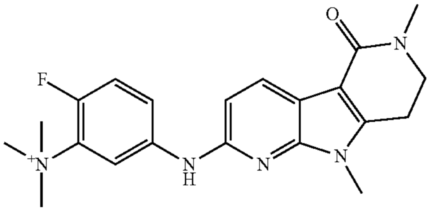 [SMILES: CN1CCc2c(c3ccc(Nc4ccc(F)c([N+](C)(C)C)c4)nc3n2C)C1=O] | – | n.d. | n.d. | n.d. |

Direct tau tangle/Aβ plaque staining:

– (No);

+++ (strong);

++ (good);

+ (weak);

n.d.: not determined;

N/A: not applicable;

[a]at 250 μM

Direct staining of human ad brain sections was also measured for the following example compounds:
TABLE 22
| Example | Structure | Direct staining of tau tangles/Aβ plaques on AD brain sections at 100 μM |
|---|---|---|
| Prep. Example 17 | 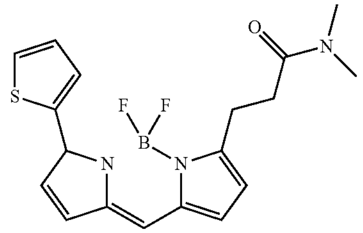 [SMILES: CN(C)C(=O)CCc1ccc(/C=C2/C=CC(c3cccs3)N2)n1B(F)F] | – |
| Prep. Example 18 | 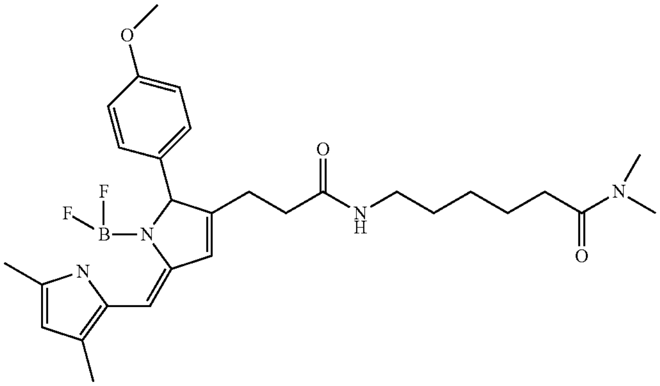 | – |
| 215 | 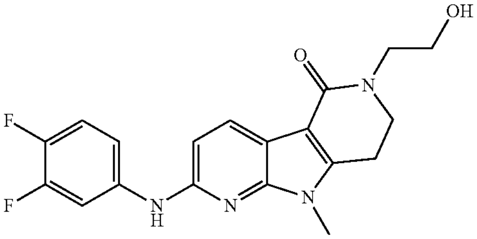 [SMILES: Cn1c2c(c3ccc(Nc4ccc(F)c(F)c4)nc31)C(=O)N(CCO)CC2] | – |
| 213 Step F | 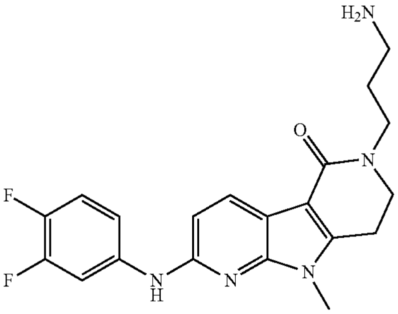 [SMILES: Cn1c2c(c3ccc(Nc4ccc(F)c(F)c4)nc31)C(=O)N(CCCN)CC2] | – |

TABLE 22-continued

| Example | Structure | Direct staining of tau tangles/Aβ plaques on AD brain sections at 100 μM |
|---|---|---|
| 213 | 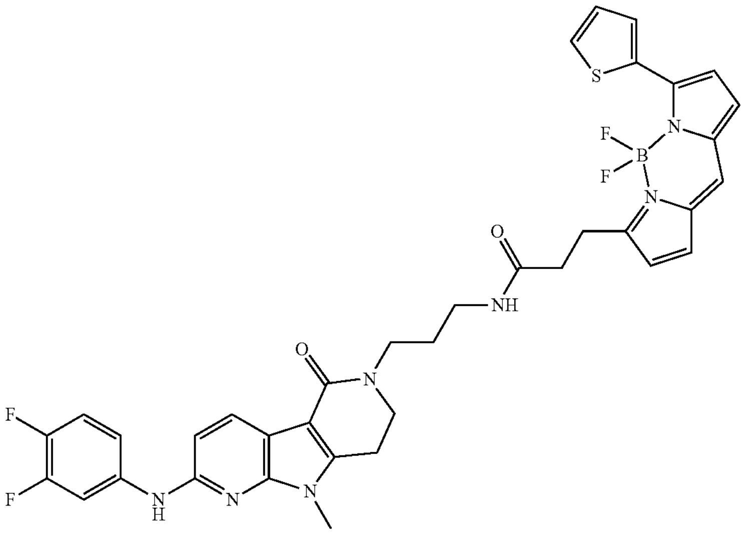 | + (tangles) |
| 214 | 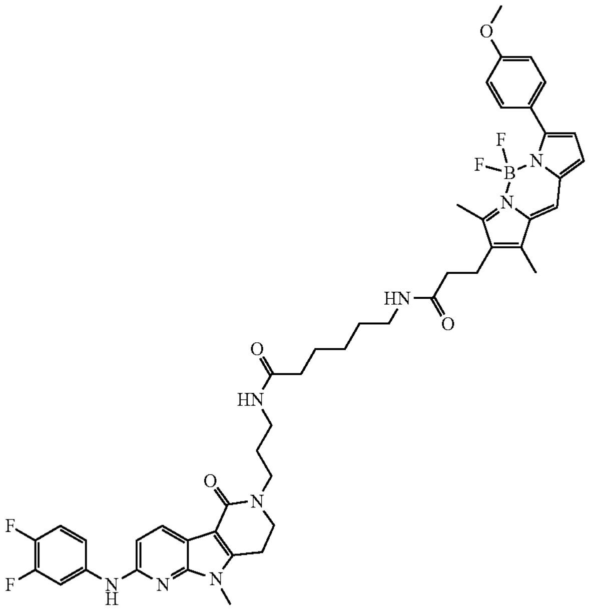 | ++ (tangles) |

Direct tau tangle/Aβ plaque staining:
− (No);
+++ (strong);
++ (good);
+ (weak)

Assay 2 (Filter Trap):

Displacement of [$^3$H]RefA by Compounds of this Invention

Enrichment of Paired Helical Filaments (PHF's) from Human Alzheimer's Disease Brain 50 g of frontal lobe tissue from post-mortem brain of an Alzheimer's disease (AD) patient were obtained from the London Tissue Bank. The patient was a Caucasian female and died at the age of 68 years. The brain sample was collected 5 hours post-mortem and characterized for Braak disease stage (Braak, H.; Braak, E. Acta Neuropathol., 1991, 82, 239-259) as stage VI. For the enrichment of PHF's, around 15 g of the AD human brain was thawed on ice and homogenized with 50 ml of homogenization buffer [0.75 M NaCl in RAB buffer (100 mM 2-(N-morpholino) ethanesulfonic acid (MES), 1 mM EGTA, 0.5 mM $MgSO_4$, 2 mM DTT, pH 6.8) supplemented with protease inhibitors (Complete; Roche 11697498001) in a glass Dounce homogenizer. The homogenate was then incubated at 4° C. for 20 min to let any residual microtubules depolymerize, before the homogenate was transferred into polycarbonate centrifuge bottles (16×76 mm; Beckman 355603) and centrifuged at 11,000 g (12,700 RPM) in an ultracentrifuge (Beckman, XL100K) for 20 min at 4° C. using the pre-cooled 70.1 rotor (Beckman, 342184). Pellets were kept on ice. Supernatants were pooled into polycarbonate bottles and centrifuged again at 100,000 g (38,000 RPM) for 1 h at 4° C. in the 70.1 Ti rotor to isolate PHF-rich pellets, whereas soluble tau remained in the supernatants. The pellets from the first and second centrifugations were re-suspended in 120 mL of extraction buffer [10 mM Tris-HCl pH 7.4, 10% sucrose, 0.85 M NaCl, 1% protease inhibitor (Calbiochem 539131), 1 mM EGTA, 1% phosphatase inhibitor (Sigma P5726 and P0044)]. The solution was then transferred into polycarbonate centrifuge bottles (16×76 mm; Beckman 355603) and centrifuged at 15,000 g (14,800 RPM) in an ultracentrifuge (Beckman, XL100K) for 20 min at 4° C. using the 70.1 Ti rotor. In the presence of 10% sucrose and at low speed centrifugation, most PHF remained in the supernatant whereas intact or fragmented NFTs and larger PHF aggregates were pelleted. The pellets were discarded. 20% Sarkosyl (Sigma L7414-10ML) was added to the supernatants to a final concentration of 1% and stirred at room temperature for 1 h. This solution was then centrifuged into polycarbonate bottles at 100,000 g (38,000 RPM) for 1 h at 4° C. in the 70.1 Ti rotor, and the pellets containing PHF-rich material were re-suspended in a total final volume of 1.5 mL of PBS, aliquoted and stored at −80° C.

Preparation of Full-Length Tau and $Abeta_{1-42}$ Aggregates

Recombinant human full-length Tau441 (flTau) was expressed in bacteria and purified in the laboratory of Professor Hilal Lashuel (EPFL, Switzerland). A solution of 8 μM (400 μg/mL) flTau in PBS, 10 μM DTT and 5 μM heparin (all from Sigma-Aldrich) was gently mixed (cradled) for 3 days at 37° C. Cradled flTau aggregates were used at a final concentration of 20 μg/mL in all binding assays. $Abeta_{1-42}$ (Bachem, Switzerland) peptide films were re-suspended in 1% DMSO and diluted in PBS to a 33 μM (150 μg/mL) suspension that was sonicated until complete dissolution. Aggregation process was done at 37° C. for 24 hours. Aggregated $Abeta_{1-42}$ was used at a concentration of 20 μg/mL in all binding assays.

Structure of [$^3$H]RefA

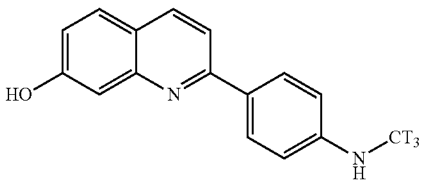

[$^3$H]RefA was prepared (Anawa Trading SA, Switzerland) by a similar procedure described for the $^{11}$C-derivative (Tago et al., J. Label. Compd. Radiopharm., 2013, DOI: 10.1002/jlcr.3133).

Structure of Example 217 ([$^3$H]Example 169)

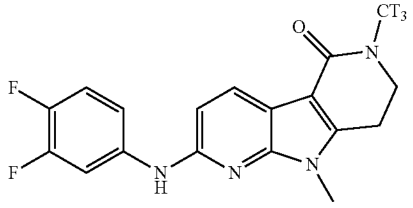

[$^3$H]RefA Radio-Binding Assay and Determination of the Dissociation Constant ($K_d$)

AD brain-enriched PHF were diluted 1/80 (with an estimated tau concentration of 62.5 ng/ml and incubated with [$^3$H]RefA at different concentrations ranging from 50 nM to 1.25 nM. The reaction was performed in a final volume of 70 μL PBS with 2.8% DMSO, for 45 min at 37° C. 30 μL of samples in duplicates were then filtered under vacuum on a GF/B filter plate (PerkinElmer 6005177) to trap the PHF with the bound radio-ligand, and washed three times with PBS. The GF/B filters were then vacuum-dried, 20 μL scintillation liquid (PerkinElmer 1200-436) was added in each well, and the filters were analyzed on a Microbeta Trilux device. To determine the non-specific signal, 10 μM non-labeled RefA was added to all concentrations of [$^3$H]RefA in controls wells. Specific binding was calculated by subtracting the non-specific signal to the total signal. In order to obtain a calibration curve to calculate the concentration of [$^3$H]RefA as a function of the radioactive counts, a serial dilution of [$^3$H]RefA was added on dry GF/B filter, vacuum dried and 20 μL scintillation liquid was added in each well. The $K_d$ values were calculated by nonlinear regression, one site specific binding using Prism V5 (GraphPad). Similar assays were performed to measure the $K_d$ of [$^3$H]RefA for in vitro aggregated recombinant human tau or $Abeta_{1-42}$. For both recombinant proteins, 20 μg/mL of aggregates were incubated with [$^3$H]RefA at different concentrations ranging from 50 nM to 1.25 nM for recombinant human tau and from 150 nM to 1.25 nM for recombinant human $Abeta_{1-42}$. The same procedure was also used to determine the $K_d$ of [$^3$H]Example 50, using Example 83 ([$^3$H]Example 50) between 50 nM and 1.25 nM and 10 μM of non-labeled RefA to determine the unspecific binding.

[$^3$H]RefA Radio-Binding Competition Assay

AD brain-enriched PHF diluted 1/80 were incubated in the presence of [$^3$H]RefA at 10 nM and the example compounds of this invention at 2.5 μM (250× excess), for 45 minutes at 37° C. Samples were then analyzed by on GF/B filter plates as described above (in the section "[$^3$H]RefA radio-binding assay and determination of the dissociation constant ($K_d$)). Non-specific signal was determined again with an excess of un-labeled RefA and specific binding calculated by subtracting the non-specific signal from the total signal. Competition was calculated as percent, where 0% was defined as the specific binding in the presence of vehicle (2.8% DMSO in PBS) and 100% as the values obtained in the presence of excess cold RefA. Similar assays were performed to determine the competition of the cold compounds on [$^3$H]RefA on in vitro aggregated recombinant human tau or $Abeta_{1-42}$ For both recombinant proteins, 20 μg/mL of aggregates were incubated with 10 nM of [$^3$H]RefA for recombinant human tau or 80 nM of [$^3$H]RefA for recombinant human $Abeta_{1-42}$.

Determination of the Binding Affinity ($K_i$)

To determine the binding affinity ($K_i$) for example compounds of this invention with at least 60% competition at the maximal concentration tested (2.5 μM, see above), a mixture of [$^3$H]RefA at 10 nM, AD brain-enriched PHF diluted 1/80 and increasing concentrations of example compounds of this invention in the range 0.12 nM to 50 μM was prepared. Samples were then analyzed on GF/B filter plates as described above and $K_i$ values calculated using Prism V5 (GraphPad).

To determine the selectivity of the compounds on tau versus Abeta, 20 μg/mL of in vitro aggregated $Abeta_{1-42}$ was mixed with 80 nM of [$^3$H]RefA in presence of increasing concentrations of example compounds of this invention, ranging from 16 nM to 50 μM. Samples were analyzed on GF/B filter plates as described above and $K_i$ values calculated using Prism V5 (GraphPad). The selectivity on tau versus Abeta is expressed as the fold increase of the $K_i$ on in vitro aggregate $Abeta_{1-42}$ versus PHF.

The $K_d$ for the Literature Compound RefA and Example 50 of this Invention were Measured in Assay 2 Using [$^3$H]RefA or Example 83 ([$^3$H]Example 50), Respectively:

TABLE 23

| Example | Structure | [$K_d$] | Fold increase on $Abeta_{1-42}$ vs PHF |
|---|---|---|---|
| RefA | 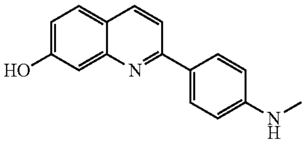 [SMILES: CNc1ccc(-c2ccc3ccc(O)cc3n2)cc1] | 35 nM | 5 |

TABLE 23-continued

| Example | Structure | [$K_d$] | Fold increase on $Abeta_{1-42}$ vs PHF |
|---|---|---|---|
| 169 | 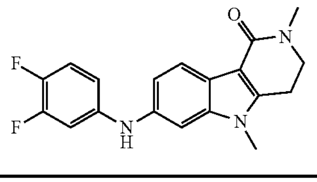 | 43 nM | n.d. |

n.d.: not determined

The Following Example Compounds were Measured in Assay 2 Using [$^3$H]RefA:

TABLE 24

| Ex. | Structure | [$^3$H]RefA competition [$K_i$] | Fold increase on $Abeta_{1-42}$ vs PHF |
|---|---|---|---|
| 1 | 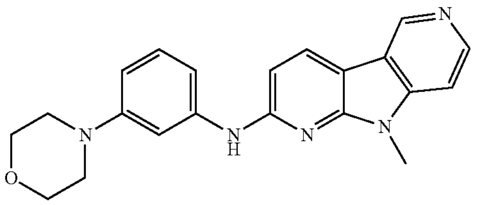 [SMILES: Cn1c2ccncc2c2ccc(Nc3cccc(N4CCOCC4)c3)nc21] | 78 nM | n.d. |
| 2 | 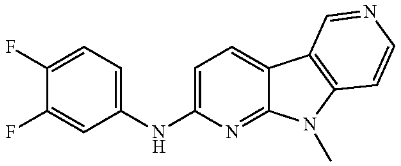 [SMILES: Cn1c2ccncc2c2ccc(Nc3ccc(F)c(F)c3)nc21] | 22 nM | N/A[1] |
| 3 | 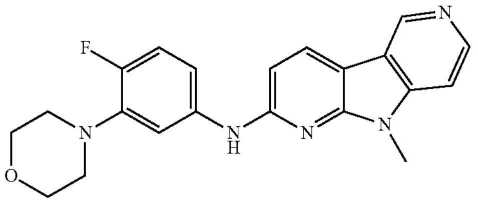 [SMILES: Cn1c2ccncc2c2ccc(Nc3ccc(F)c(N4CCOCC4)c3)nc21] | 233 nM | n.d. |
| 4 | 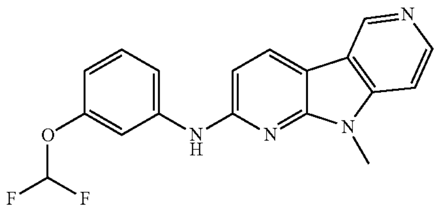 [SMILES: Cn1c2ccncc2c2ccc(Nc3cccc(OC(F)F)c3)nc21] | 3.3 nM | N/A[1] |

TABLE 24-continued
| Ex. | Structure | $[^3H]$RefA competition $[K_i]$ | Fold increase on $Abeta_{1-42}$ vs PHF |
|---|---|---|---|
| 5 | 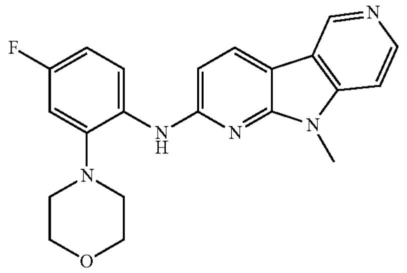 [SMILES: Cn1c2ccncc2c2ccc(Nc3ccc(F)cc3N3CCOCC3)nc21] | 305 nM | n.d. |
| 6 | 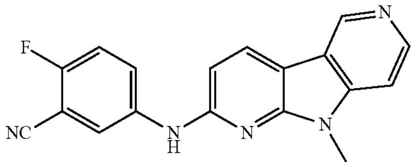 [SMILES: Cn1c2ccncc2c2ccc(Nc3ccc(F)c(C#N)c3)nc21] | N/A[2] | n.d. |
| 7 | 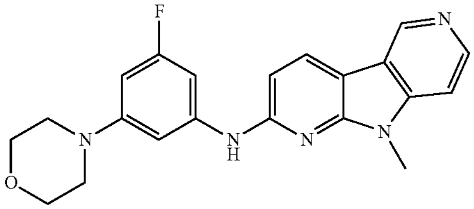 [SMILES: Cn1c2ccncc2c2ccc(Nc3cc(F)cc(N4CCOCC4)c3)nc21] | 326 nM | n.d. |
| 8 | 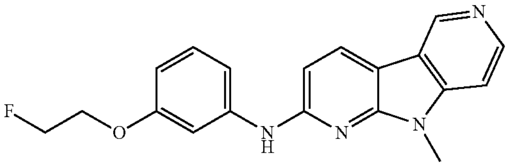 [SMILES: Cn1c2ccncc2c2ccc(Nc3cccc(OCCF)c3)nc21] | 26 nM | 0.5 |
| 9 | 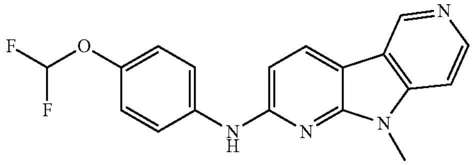 | 7.8 nM | 200 |
| 10 | 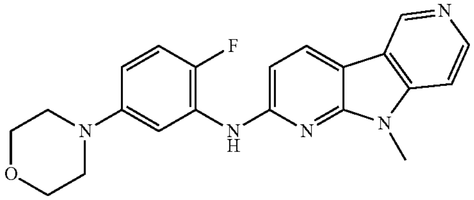 [SMILES: Cn1c2ccncc2c2ccc(Nc3cc(N4CCOCC4)ccc3F)nc21] | N/A[2] | n.d. |
| 11 | 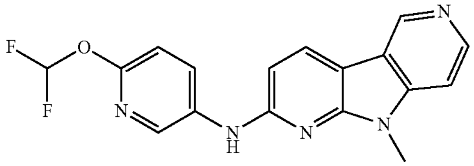 [SMILES: Cn1c2ccncc2c2ccc(Nc3ccc(OC(F)F)nc3)nc21] | 188 nM | n.d. |

TABLE 24-continued
| Ex. | Structure | [$^{3}$H]RefA competition [$K_i$] | Fold increase on $Abeta_{1-42}$ vs PHF |
|---|---|---|---|
| 12 | 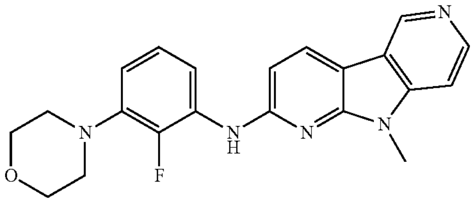 [SMILES: Cn1c2ccncc2c2ccc(Nc3cccc(N4CCOCC4)c3F)nc21] | 165 nM | n.d |
| 13 | 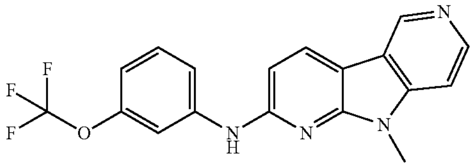 [SMILES: Cn1c2ccncc2c2ccc(Nc3cccc(OC(F)(F)F)c3)nc21] | 169 nM | n.d. |
| 14 | 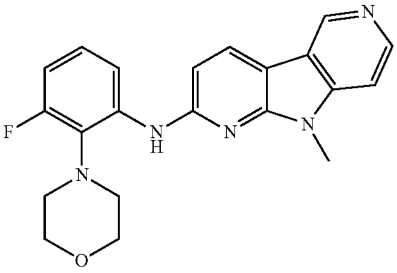 [SMILES: Cn1c2ccncc2c2ccc(Nc3cccc(F)c3N3CCOCC3)nc21] | 371 nM | n.d. |
| 15 | 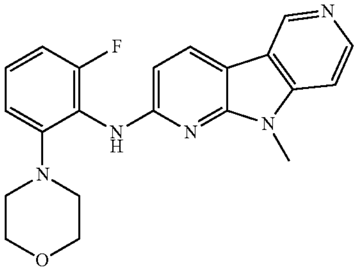 [SMILES: Cn1c2ccncc2c2ccc(Nc3c(F)cccc3N3CCOCC3)nc21] | N/A[2] | n.d. |
| 16 | 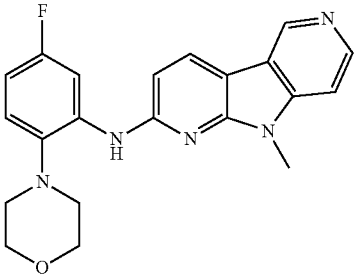 [SMILES: Cn1c2ccncc2c2ccc(Nc3cc(F)ccc3N3CCOCC3)nc21] | N/A[2] | n.d. |
| 17 | 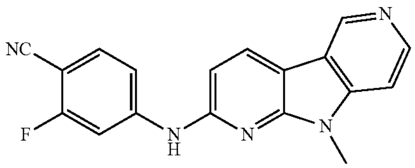 [SMILES: Cn1c2ccncc2c2ccc(Nc3ccc(C#N)c(F)c3)nc21] | N/A[2] | n.d. |

TABLE 24-continued
| Ex. | Structure | [3H]RefA competition [$K_i$] | Fold increase on $Abeta_{1-42}$ vs PHF |
|---|---|---|---|
| 169 | 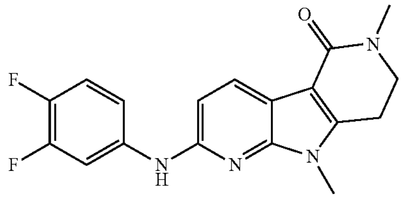 [SMILES: CN1CCc2c(c3ccc(Nc4ccc(F)c(F)c4)nc3n2C)C1=O] | 719 nM | n.d. |
| 170 | 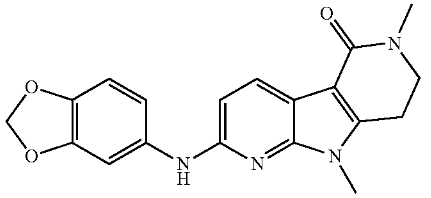 [SMILES: CN1CCc2c(c3ccc(Nc4ccc5c(c4)OCO5)nc3n2C)C1=O] | N/A[2] | n.d. |
| 171 | 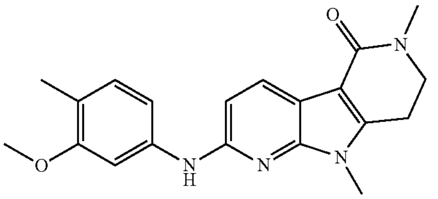 [SMILES: COc1cc(Nc2ccc3c4c(n(C)c3n2)CCN(C)C4=O)ccc1C] | N/A[2] | n.d. |
| 172 | 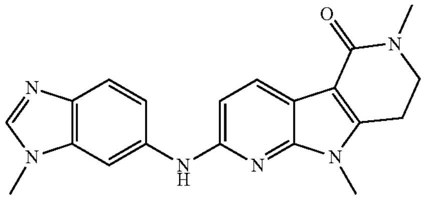 [SMILES: CN1CCc2c(c3ccc(Nc4ccc5ncn(C)c5c4)nc3n2C)C1=O] | N/A[2] | n.d. |
| 174 | 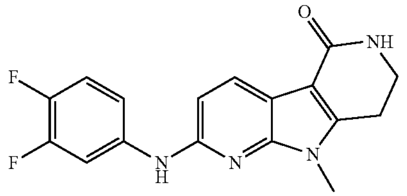 [SMILES: Cn1c2c(c3ccc(Nc4ccc(F)c(F)c4)nc31)C(=O)NCC2] | N/A[2] | n.d. |
| 175 | 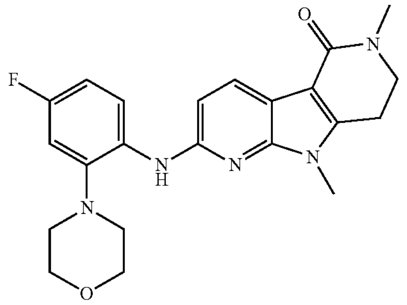 [SMILES: CN1CCc2c(c3ccc(Nc4ccc(F)cc4N4CCOCC4)nc3n2C)C1=O] | N/A[2] | n.d. |

TABLE 24-continued

| Ex. | Structure | [$^3$H]RefA competition [$K_i$] | Fold increase on $Abeta_{1-42}$ vs PHF |
|---|---|---|---|
| 212 Step F | 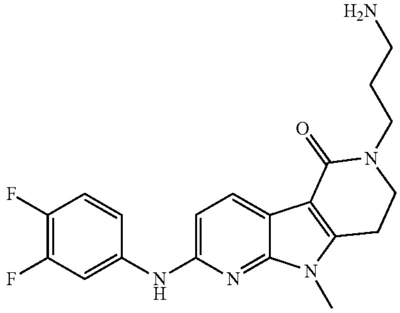 [SMILES: Cn1c2c(c3ccc(Nc4ccc(F)c(F)c4)nc31)C(=O)N(CCCN)CC2] | N/A[2] | n.d. |

n.d.: not determined
N/A[1]: not applicable because the $K_i$ for $Abeta_{1-42}$ could not be calculated
N/A[2]: not applicable because the inhibition at 2.5 μM was lower than 50%

Assay 3 (Backscattering Interferometry):

Determination of Dissociation Constants ($K_d$) of Compounds of this Invention

Enrichment of Paired Helical Filaments (PHF's) from Human Alzheimer's Disease Brains For backscattering interferometry, Tau enriched paired helical filaments (PHF) from human Alzheimer's disease (AD) brains were used as a target. Due to the limited availability of tissues, to determine dissociation constants ($K_d$) of compounds of this invention to the target, two different batches of enriched PHF were used. These batches are identified as batch 6 and 7 and were prepared as follows.

PHF batch number 6 was prepared starting from 25 g frontal cortical tissue from post-mortem brains of 25 Alzheimer's disease (AD) patients which were obtained from the London Tissue Bank. The mean age at death for the AD patients was 76 years (48% females). Brain samples were characterized for Braak disease stage (Braak and Braak, 1991), with most donors displaying a stage VI. The postmortem interval between death and brain dissection was between 6 and 65 h. Human brain homogenates were prepared by SB Drug Discovery (Glasgow, Scotland, UK) from the post-mortem cortical tissue of the 25 patients). Each tissue (1 g) was homogenized with a Dounce glass homogenizer in 1.5 mL 100 mM 2-(N-morpholino) ethanesulfonic acid (MES) pH 6.8, 0.75 M NaCl, 1 mM EGTA, 0.5 mM $MgSO_4$, 2 mM DTT containing protease inhibitors (Complete; Roche 11697498001). For each sample, two aliquots containing 0.5 g brain homogenates in 0.75 mL were shipped to AC Immune SA on dry ice and stored at −80° C. For the enrichment of PHF, 1 aliquot per donor corresponding to total 12.5 g of brain tissue were thawed on ice and then incubated at 4° C. for 20 min to depolymerize any residual microtubules. All samples were then pooled and transferred to three polycarbonate centrifuge bottles (16×76 mm; Beckman 355603).

PHF batch number 7 was prepared starting from 32 g of parietal cortex tissue from post-mortem brain of one Alzheimer's disease (AD) patient was obtained from an external provider (Tissue Solution). The patient was a Caucasian female who died at the age of 68 years for end stage AD. The brain sample was collected 5 h post-mortem and characterized for Braak disease stage (Braak and Braak, 1991) as stage VI. The method used for the PHF enrichment was modified from published procedures (Jicha et al., 1997; Rostagno and Ghiso, 2009). Around 16 g of the AD human brain was thawed on ice and homogenized with 50 ml of homogenization buffer [0.75 M NaCl in RAB buffer (100 mM 2-(N-morpholino) ethanesulfonic acid (MES), 1 mM EGTA, 0.5 mM MgSO4, 2 mM DTT, pH 6.8) supplemented with protease inhibitors (Complete; Roche 11697498001)] in a glass Dounce homogenizer. The homogenate was then incubated at 4° C. for 20 min to let depolymerize any residual microtubules, before being transferred into polycarbonate centrifuge bottles (16×76 mm; Beckman 355603). For both purifications, brain homogenates were then centrifuged at 11,000 g (12,700 RPM) in an ultracentrifuge (Beckman, XL100K) for 20 min at 4° C. using the pre-cooled 70.1 rotor (Beckman, 342184). Pellets were kept on ice. Supernatants were pooled into polycarbonate bottles and centrifuged again at 100,000 g (38,000 RPM) for 1 h at 4° C. in the 70.1 Ti rotor to isolate PHF-rich pellets, whereas soluble Tau remained in the supernatants. The pellets from the first and second centrifugations were resuspended in 120 mL of extraction buffer [10 mM Tris-HCl pH 7.4, 10% sucrose, 0.85 M NaCl, 1% protease inhibitor (Calbiochem 539131), 1 mM EGTA, 1% phosphatase inhibitor (Sigma P5726 and P0044)]. The solution was then transferred into polycarbonate centrifuge bottles (16×76 mm; Beckman 355603) and centrifuged at 15,000 g (14,800 RPM) in an ultracentrifuge (Beckman, XL100K) for 20 min at 4° C. using the 70.1 Ti rotor. In the presence of 10% sucrose and at low speed centrifugation, most PHF remained in the supernatant, whereas intact or fragmented NFTs and larger PHF aggregates were pelleted. The pellets were discarded. 20% Sarkosyl (Sigma L7414-10ML) was added to the supernatants to a final concentration of 1% and stirred at room temperature for 1 h. This solution was then centrifuged into polycarbonate bottles at 100,000 g (38,000 RPM) for 1 h at 4° C. in the 70.1 Ti rotor, and the pellets containing PHF-rich material were resuspended in a total final volume of around 1.8 mL of PBS, aliquoted and stored at −80° C.

Backscattering Interferometry

Backscattering interferometry (BSI) measurements were performed by Molecular Sensing GmbH (Idstein, Germany). Examples of this invention at 10 mM in DMSO were diluted 1:100 in PBS and then diluted again in PBS to yield 2 μM compound in PBS with 0.01% DMSO. The refractive index of the assay buffer (PBS pH 7.4 containing 0.01% DMSO) and the compound were matched and then 2× serial dilutions of the compound were done in polypropylene dilution reservoirs. A thawed aliquot of PHF Tau was diluted 1/150 in PBS, pH 7.4, and used immediately.

Examples of this invention and PHF were mixed 1:1 in 96-well PCR microplates to a final volume of 60 μL and heat sealed with foil. The assays were allowed to incubate at room temperature for 45 minutes before being run on the BSI instrument. Wells were pierced individually prior to sample injection and measurement of BSI signal (each well analyzed in triplicate).

For each assay the reference curve (without compound) was subtracted from the assay curve point by point. The final data for the difference curve was exported to Graphpad Prism® and fit with a one-site binding equation to determine a $K_d$ for the assay. Examples of this invention were run to have at least two successful experiments with good reproducibility. Success was defined as having a binding signal with a $R^2$>0.7.

The $K_d$ for the Examples of this Invention were Measured in Assay 3

TABLE 25

| Example | Structure | [$K_d$] on PHF batch 6 | [$K_d$] on PHF batch 7 |
|---|---|---|---|
| 2 | 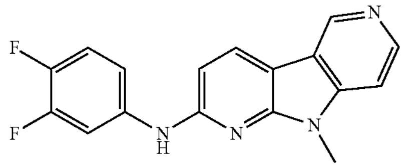 [SMILES: Cn1c2ccncc2c2ccc(Nc3ccc(F)c(F)c3)nc21] | 33 ± 5 nM | n.d. |
| 8 | 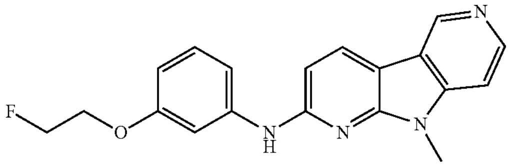 [SMILES: Cn1c2ccncc2c2ccc(Nc3cccc(OCCF)c3)nc21] | 19 ± 3 nM | n.d. |
| 23 | 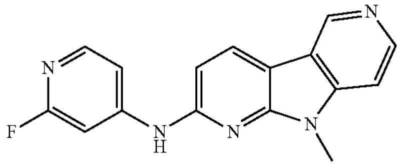 [SMILES: Cn1c2ccncc2c2ccc(Nc3ccnc(F)c3)nc21] | 38 ± 6 nM | 11 ± 2 nM |
| 28 | 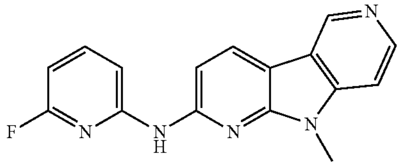 [SMILES: Cn1c2ccncc2c2ccc(Nc3cccc(F)n3)nc21] | n.d. | 400 ± 60 nM |
| 51 | 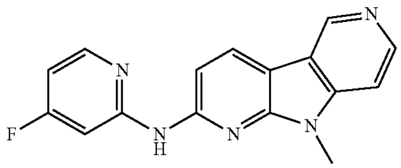 [SMILES: Cn1c2ccncc2c2ccc(Nc3cc(F)ccn3)nc21] | n.d. | 260 ± 50 nM |
| 63 | 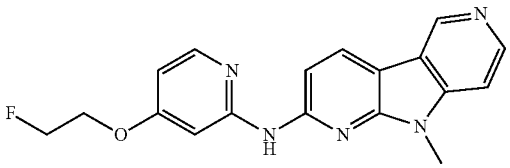 | 20 ± 3 nM | n.d. |
| 146 | 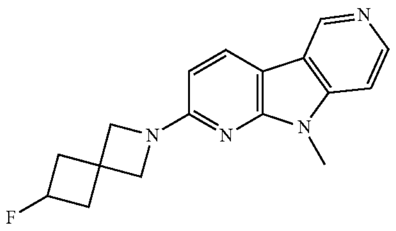 [SMILES: Cn1c2ccncc2c2ccc(N3CC4(CC(F)C4)C3)nc21] | n.d. | 40 ± 10 nM |

TABLE 25-continued
| Example | Structure | [$K_d$] on PHF batch 6 | [$K_d$] on PHF batch 7 |
|---|---|---|---|
| 147 | 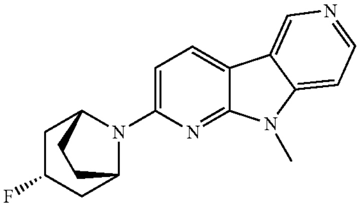 [SMILES: Cn1c2ccncc2c2ccc(N3[C@@H]4CC[C@H]3C[C@H](F)C4)nc21] | n.d. | 170 ± 40 nM |
| 153 | 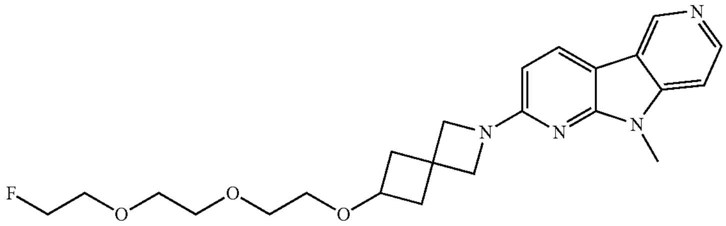 [SMILES: Cn1c2ccncc2c2ccc(N3CC4(CC(OCCOCCOCCF)C4)C3)nc21] | 20 ± 5 nM | n.d. |
| 154 | 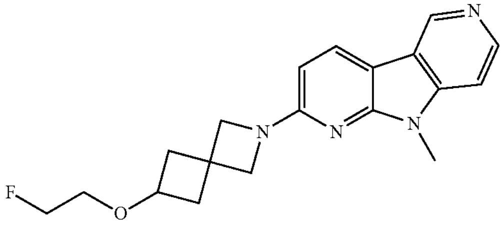 [SMILES: Cn1c2ccncc2c2ccc(N3CC4(CC(OCCF)C4)C3)nc21] | n.d. | 270 ± 50 nM |
| 156 | 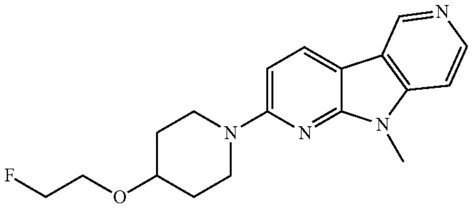 [SMILES: Cn1c2ccncc2c2ccc(N3CCC(OCCF)CC3)nc21] | 26 ± 7 nM | n.d. |
| 159 | 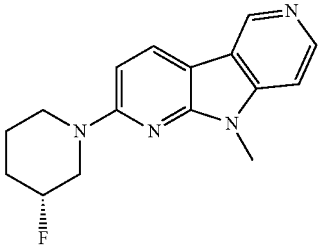 [SMILES: Cn1c2ccncc2c2ccc(N3CCC[C@@H](F)C3)nc21] | n.d. | 120 ± 20 nM |
| 161 | 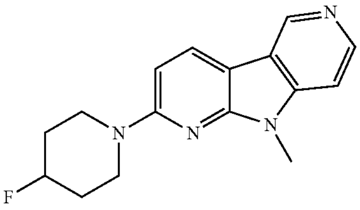 [SMILES: Cn1c2ccncc2c2ccc(N3CCC(F)CC3)nc21] | 18 ± 3 nM | N.D. |

TABLE 25-continued

| Example | Structure | $[K_d]$ on PHF batch 6 | $[K_d]$ on PHF batch 7 |
| --- | --- | --- | --- |
| 168 Step B | 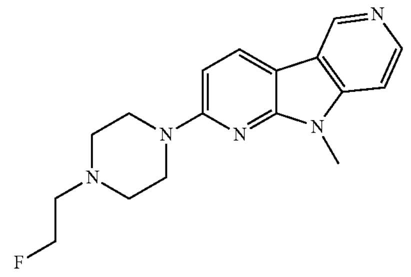 [SMILES: Cn1c2ccncc2c2ccc(N3CCN(CCF)CC3)nc21] | n.d. | 160 ± 30 nM |
| 169 | 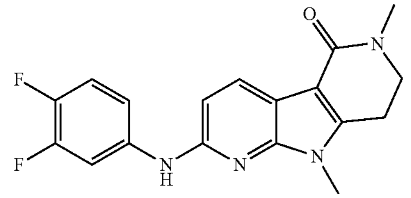 [SMILES: CN1CCc2c(c3ccc(Nc4ccc(F)c(F)c4)nc3n2C)C1=O] | 32 ± 11 nM | n.d. |
| | 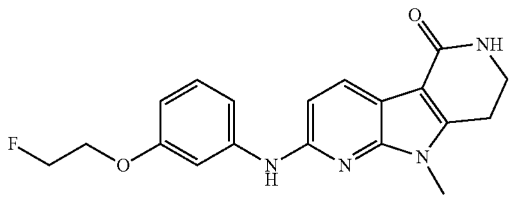 [SMILES: Cn1c2c(c3ccc(Nc4cccc(OCCF)c4)nc31)C(=O)NCC2] | 46 ± 9 nM | n.d. |
| 189 | 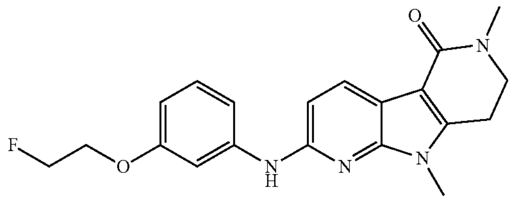 [SMILES: CN1CCc2c(c3ccc(Nc4cccc(OCCF)c4)nc3n2C)C1=O] | 16 ± 3 nM | n.d. |
| 197 | 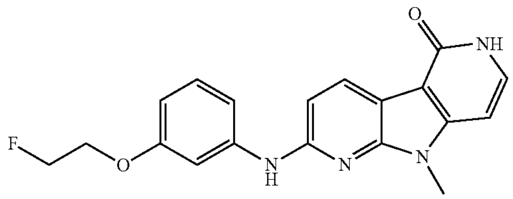 [SMILES: Cn1c2cc[nH]c(=O)c2c2ccc(Nc3cccc(OCCF)c3)nc21] | 100 ± 15 nM | n.d. |
| 201 | 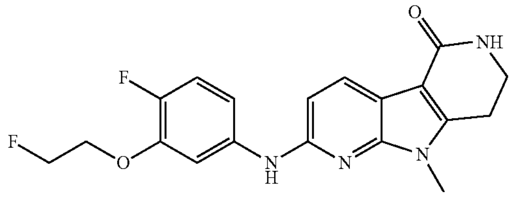 [SMILES: Cn1c2c(c3ccc(Nc4ccc(F)c(OCCF)c4)nc31)C(=O)NCC2] | 75 ± 12 nM | n.d. |

n.d.: not determined
N.D: not detected

Characterization of $^{18}$F-Labeled Compounds

Brain PK Studies in Mice Using PET Imaging

NMRI mice (weight range 25-35 g) were injected intravenously with the 18F-labeled compounds. Up to 150 μL of 1×PBS solution with 10%-15% EtOH or dilution medium (57% water for injections, 18% polyethylene glycol 400, 15% ethanol, 10% water) containing the 18F-labeled compound (2-10 MBq) were injected. Anesthesia with isoflurane was induced before injection of the tracer and maintained during the image acquisition period. PET scans were performed using a SIEMENS INVEON small animal PET/CT scanner (Siemens, Knoxville, Tenn.). PET acquisition was started immediately before the radioactive dose was injected into the animal through the tail vein. Images were generated as dynamic scans for 60 minutes. The peak uptake in the brain was set to 100% and washout curves were generated to evaluate the clearance of the activity from the normal brain. Brain wash-out curves for selected compounds ($^{18}$F-51, $^{18}$F-2; 18F-161, $^{18}$F-44, $^{18}$F-56, $^{18}$F-146, $^{18}$F-60, $^{18}$F-17, $^{18}$F-63, $^{18}$F-147, $^{18}$F-156, $^{18}$F-95, $^{18}$F-168, 18F-51, $^{18}$F-158, $^{18}$F-160, $^{18}$F-152, $^{18}$F-28, $^{18}$F-196, $^{18}$F-159, $^{18}$F-178, $^{18}$F-189, $^{18}$F-54, $^{18}$F-62, $^{18}$F-157) are illustrated in FIGS. 4-8.

Autoradiography Using Human Brain Tissue 18 micron thick frozen human brain slices and 6 micron thick human FFPE brain slices from the frontal and/or temporal lobes of AD patients were examined via autoradiography. Brain sections were equilibrated for at least 1 h in 1×PBS solution prior to use in the experiment. Each brain section was covered with a solution of the F-18 labeled tracer (200 Bq/μl, 500 μl) in 1×PBS. For blocking experiments with the corresponding 19F-labeled compound, an excess of the blocking compound was mixed with the 18F-compound to yield an end concentration of 10 μM. The brain sections were allowed to incubate with the tracer solution at room temperature for 1 h, drained afterwards and placed in a slide holder. The slides were then washed sequentially with 1×PBS for 1 min; 70% EtOH in 1×PBS for 2 min; 30% EtOH in 1×PBS for 2 min; and 1×PBS for 1 min. The slides were allowed to air-dry before being placed on Fuji imaging plates for overnight exposure. The imaging plates were scanned and the signal was measured using Fuji software to produce an autoradiographic image of the brain section. Representative examples of autoradiography studies with $^{18}$F-178, $^{18}$F-189, $^{18}$F-161, $^{18}$F-95, $^{18}$F-168, $^{18}$F-146, $^{18}$F-156, $^{18}$F-159 are shown in FIGS. 9 to 12.

Figure 13:
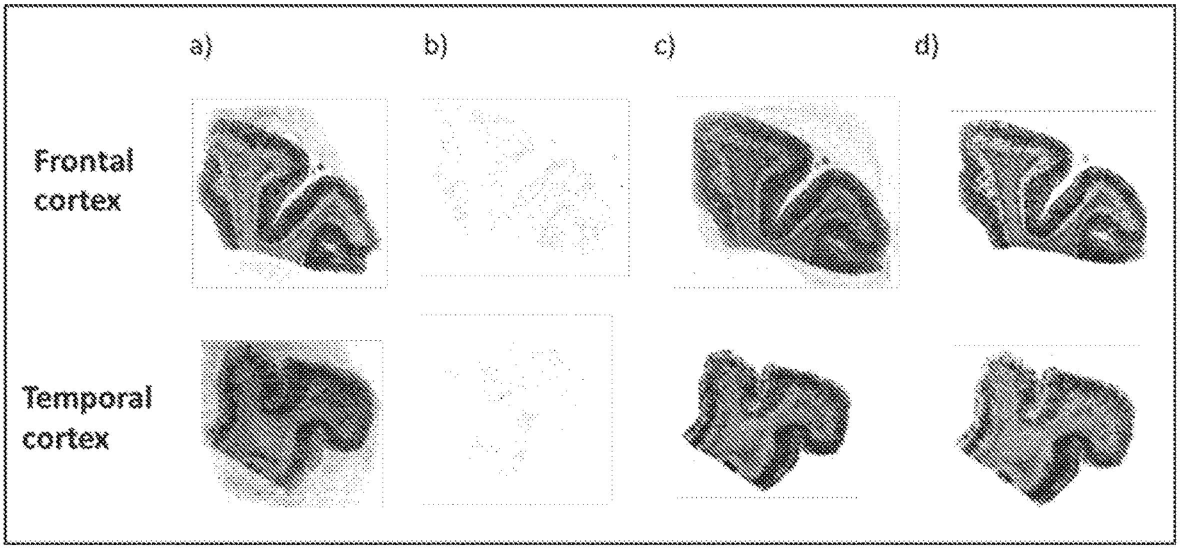
FIG. 13 shows the ex vivo autoradiograph on human brain sections with an $^{18}$F amyloid binding compound. a) $^{18}$F-amyloid binding compound, b) competition with corresponding $^{19}$F-compound, c) no competition with $^{18}$F-44, and d) no competition with $^{18}$F-59.

Strong accumulation of activity was observed in gray matter areas. The specificity of the signals were confirmed by block with an excess of the corresponding non-radioactive compounds. Additionally, selectivity was determined by using a tracer binding to amyloid-beta. No competition of selected compounds from this invention was found. Representative examples are shown in FIG. 13, which shows the ex vivo autoradiograph on human brain sections with an $^{18}$F amyloid binding compound. a) $^{18}$F-amyloid binding compound, b) competition with corresponding $^{19}$F-compound, c) no competition with $^{18}$F-44, d) no competition with $^{18}$F-59.

Figure 14:
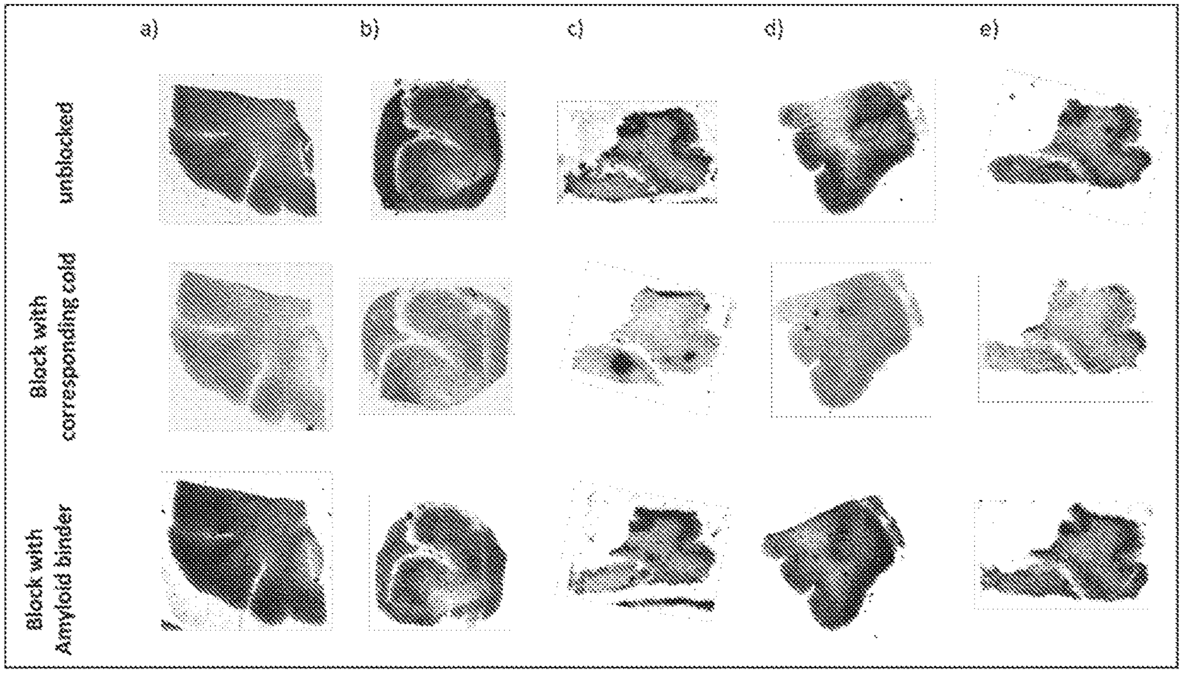
FIG. 14 shows the ex vivo autoradiograph on human brain sections. a) $^{18}$F-161, b$^{18}$F-168, c) $^{18}$F-156, d) $^{18}$F-160, and e) $^{18}$F-152, Competition observed with corresponding cold compound, no competition with amyloid binding compound.

FIG. 14 shows autoradiographies using selected compounds of this invention. Strong accumulation of activity was observed in gray matter areas. The specificity of the signals was confirmed by blocking with an excess of the corresponding non-radioactive compounds. Selectivity confirmation was performed by block with an amyloid binding compound: No competition observed in this case. FIG. 14 shows the ex vivo autoradiograph on human brain sections. a) $^{18}$F-161, b$^{18}$F-168, c) $^{18}$F-156, d) $^{18}$F-160, e) $^{18}$F-152, Competition observed with corresponding cold compound, no competition with amyloid binding compound.

Preferred compounds of the present invention are summarized in the following items:

1. A compound of formula (I):

(I)

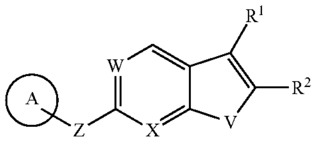

and all detectably labeled derivatives, stereoisomers, racemic mixtures, pharmaceutically acceptable salts, hydrates, solvates and polymorphs thereof;

wherein

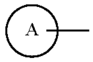

is selected from the group consisting of

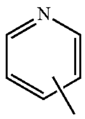

and

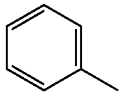

, wherein the pyridine ring

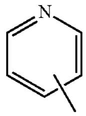

can be attached at any available position of the pyridine ring to the moiety Z, and wherein

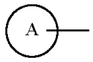

can be optionally substituted by one or more substituents $R^3$;

V is selected from the group consisting of $NR^b$, O and S;

W is selected from the group consisting of $CR^c$ and N;

X is selected from the group consisting of $CR^c$ and N;

Z is selected from the group consisting of —N($R^a$)— and —O—;

$R^a$ is selected from the group consisting of hydrogen, alkyl, and haloalkyl;

$R^b$ is selected from the group consisting of hydrogen, alkyl, and haloalkyl;

$R^c$ is selected from the group consisting of hydrogen, alkyl, haloalkyl, and halogen;

$R^d$ is selected from the group consisting of halogen or H;

$R^1$ and $R^2$ together form a 6-membered aromatic ring containing carbon atoms and optionally one or more N atoms or $R^1$ and $R^2$ together form a 6-membered ring containing an amide moiety —C(O)—N($R^{13}$)—, wherein the 6-membered aromatic ring or the 6-membered ring containing an amide moiety formed by $R^1$ and $R^2$ can be optionally substituted by $R^{12}$;

for each occurrence, $R^3$ is independently selected from the group consisting of halogen, CN, —O—$R^{10}$, —$NR^{10}R^{11}$, —$CONR^{10}R^{11}$, —N($R^{10}$)—C(O)—$R^{11}$, —C(O)O—$R^{10}$, —$(O—CH_2CH_2)_n$—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkylcarbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —$N(R^{10})$—C(O)—$R^{11}$, —C(O)O—$R^{10}$, —$(CH_2CH_2—O)_n$—$R^d$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —$(CH_2CH_2—O)_n$—$R^d$, —$(CH_2CH_2—O)_n$—$(CH_2CH_2)$—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 4.

2. The compound according to item 1 is a compound of the formula (I-1b):

(I-1b)

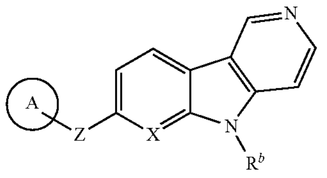

wherein A, $R^b$, X and Z are as defined in item 1.

3. The compound according to item 1 is a compound of the formula (I-1e) or (I-1f):

(I-1e)

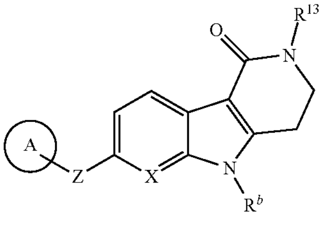

(I-1f)

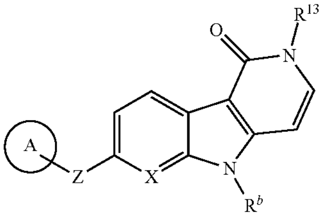

wherein A, $^b$, $R^{13}$, X and Z are as defined in item 1.

4. The compound according to any of items 1 to 3, wherein for each occurrence, $R^3$ is independently selected from the group consisting of halogen, CN, —O—$R^{10}$, —$NR^{10}R^{11}$, $(O—CH_2CH_2)_n$—$R^d$, —$(CH_2CH_2—O)_n$—$(CH_2CH_2)$—$R^d$, alkyl and heterocyclyl, wherein alkyl and heterocyclyl can be optionally substituted, and wherein $R^{10}$, $R^{11}$, n and $R^d$ are as defined in item 1; or wherein two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted.

5. The compound according to any of items 1 to 4, wherein, for each occurrence, $R^{10}$ and $R^{11}$ are each independently selected from the group consisting of hydrogen and alkyl, wherein alkyl can be optionally substituted; and/or wherein, for each occurrence, $R^{12}$ is independently selected from the group consisting of hydrogen, halogen, —$(CH_2CH_2—O)_n$—$R^d$, —$(CH_2CH_2—O)_n$—$(CH_2CH_2)$—$R^d$, and alkyl, wherein alkyl can be optionally substituted, and wherein n and $R^d$ are as defined in item 1; and/or wherein, for each occurrence, $R^{13}$ is independently selected from the group consisting of hydrogen, —$(CH_2CH_2—O)_n$—$R^d$, —$(CH_2CH_2—O)_n$—$(CH_2CH_2)$—$R^d$ and alkyl, wherein alkyl can be optionally substituted, and wherein n and $R^d$ are as defined in item 1; and/or wherein X is N; and/or wherein $R^a$ is hydrogen and/or $R^b$ is alkyl or hydrogen.

6. A compound of formula (II):

(II)

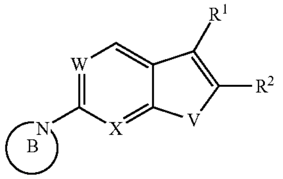

and all detectably labeled derivatives, stereoisomers, racemic mixtures, pharmaceutically acceptable salts, hydrates, solvates and polymorphs thereof;

wherein

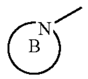

is a 5 to 8-membered ring containing carbon atoms and optionally one or more heteroatoms selected from O, S, or N or optionally one or more heteroatom (e.g., N, O and/or S)-containing moieties and wherein the 5- to 8-membered ring may be optionally substituted by one or more $R^3$;

V is selected from the group consisting of $NR^b$, O and S;

W is selected from the group consisting of $CR^c$ and N;

X is selected from the group consisting of $CR^c$ and N;

$R^b$ is selected from the group consisting of hydrogen, alkyl, and haloalkyl;

$R^c$ is selected from the group consisting of hydrogen, alkyl, haloalkyl, and halogen;

$R^d$ is selected from the group consisting of halogen or H;

$R^1$ and $R^2$ together form a 6-membered aromatic ring containing carbon atoms and optionally one or more N atoms or $R^1$ and $R^2$ together form a 6-membered saturated or unsaturated ring containing an amide moiety —C(O)—$N(R^{13})$—, wherein the 6-membered aromatic ring or the 6-membered saturated or unsaturated ring containing an amide moiety formed by $R^1$ and $R^2$ can be optionally substituted by $R^{12}$;

for each occurrence, $R^3$ is independently selected from the group consisting of halogen, CN, —O—$R^{10}$, —$NR^{10}R^{11}$, —$CONR^{10}R^{11}$, —N($R^{10}$)—C(O)—$R^{11}$, —C(O)O—$R^{10}$, —(O—$CH_2CH_2$)$_n$—$R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{12}$ is independently selected from the group consisting of halogen, —CN, —O—$R^{10}$, —$NR^{10}R^{11}$, —$CONR^{10}R^{11}$, —N($R^{10}$)—C(O)—$R^{11}$, —C(O)O—$R^{10}$, —($CH_2CH_2$—O)$_n$—$R^d$, —($CH_2CH_2$—O)$_n$—($CH_2CH_2$)—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{13}$ is independently selected from the group consisting of hydrogen, —$CONR^{10}R^{11}$, —C(O)O—$R^{10}$, —($CH_2CH_2$—O)$_n$—$R^d$, —($CH_2CH_2$—O)$_n$—($CH_2CH_2$)—$R^d$, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 4.

7. The compound according to item 6 is a compound of the formula (II-1a):

(II-1a)

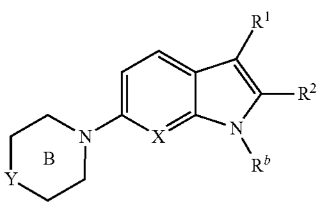

wherein

Y is $NR^{14}$ or C($R^{15}$)$_2$;

$R^{14}$ is selected from the group consisting of hydrogen, —($CH_2CH_2$—O)$_n$—$R^d$, —($CH_2CH_2$—O)$_n$—($CH_2CH_2$)—$R^d$, carbocyclyl and heterocyclyl, wherein alkyl, carbocyclyl and heterocyclyl can be optionally substituted;

$R^{15}$ is independently selected from the group consisting of hydrogen, halogen, —($CH_2CH_2$—O)$_n$—$R^d$, —($CH_2CH_2$—O)$_n$—($CH_2CH_2$)—$R^d$, carbocyclyl and heterocyclyl, wherein alkyl, carbocyclyl and heterocyclyl can be optionally substituted;

$R^1$, $R^2$, $R^b$, $R^d$, n and X are as defined in item 6 and the ring B can be optionally substituted by one or more $R^3$.

8. The compound according to item 6 or 7, wherein for each occurrence, $R^3$ is independently selected from the group consisting of halogen, CN, —O—$R^{10}$, —$NR^{10}R^{11}$, —(O—$CH_2CH_2$)$_n$—$R^d$, alkyl and heterocyclyl, wherein alkyl and heterocyclyl can be optionally substituted, and wherein $R^{10}$, $R^{11}$, n and $R^d$ are as defined in item 6; or wherein two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted.

9. The compound according to any of items 6 to 8, wherein, for each occurrence, $R^{10}$ and $R^{11}$ are each independently selected from the group consisting of hydrogen and alkyl, wherein alkyl can be optionally substituted; and/or wherein, for each occurrence, $R^{12}$ is independently selected from the group consisting of hydrogen, halogen, —($CH_2CH_2$—O)$_n$—$R^d$, —($CH_2CH_2$—O)$_n$—($CH_2CH_2$)—$R^d$, and alkyl, wherein alkyl can be optionally substituted, and wherein n and $R^d$ are as defined in item 6; and/or wherein, for each occurrence, $R^{13}$ is independently selected from the group consisting of hydrogen, —($CH_2CH_2$—O)$_n$—$R^d$, —($CH_2CH_2$—O)$_n$—($CH_2CH_2$)—$R^d$, and alkyl, wherein alkyl can be optionally substituted, and wherein n and $R^d$ are as defined in item 6; and/or wherein X is N; and/or wherein $R^b$ is alkyl or hydrogen.

10. The compound according to any one of items 1 to 9 which has been detectably labeled.

11. The compound according to item 10, wherein the detectable label is selected from the group consisting of a radionuclide, a positron emitter, a gamma emitter, or a fluorescent label such as a detectable label selected from the group consisting of $^3H$, $^{18}F$, $^{123}I$, $^{124}I$, $^{125}I$, $^{131}I$, $^{11}C$, $^{13}N$, $^{15}O$, and $^{77}Br$ or a fluorescent label.

The invention claimed is:

1. A compound of formula (II):

(II)

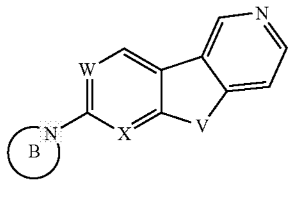

and detectably labeled derivatives, stereoisomers, racemic mixtures, pharmaceutically acceptable salts, hydrates, solvates and polymorphs thereof;

wherein

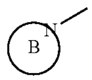

is selected from the group consisting of

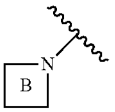 , 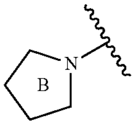 , 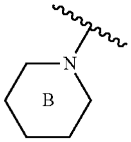 ,

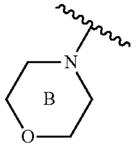 , 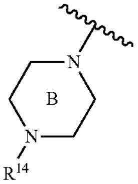 , 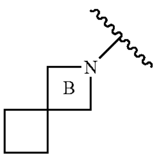 ,

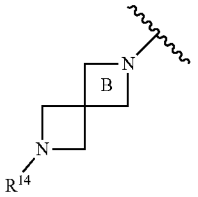 , 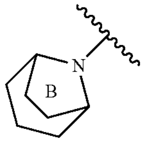 , and

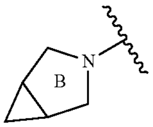 ;

wherein the ring system B can be optionally substituted in any available position of any of its rings by one or more $R^3$;

V is $NR^b$,

W is selected from the group consisting of $CR^c$ and N;

X is N;

$R^b$ is selected from the group consisting of hydrogen, alkyl, $—(CH_2CH_2—O)_n—H$ and $—(CH_2CH_2—O)_n$-alkyl, wherein alkyl can be optionally substituted;

$R^c$ is selected from the group consisting of hydrogen, alkyl, halogen, wherein alkyl can be optionally substituted;

$R^d$ is selected from the group consisting of halogen, H, OH and O-alkyl, wherein alkyl can be optionally substituted;

$R^f$ is selected from the group consisting of H and alkyl;

$R^{14}$ is selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl;

for each occurrence, $R^3$ is independently selected from the group consisting of halogen, —CN, $—O—R^{10}$, $—S—R^{10}$, $—NO_2$, $—NR^{10}R^{11}$, $—CONR^{10}R^{11}$, $—N(R^{10})—C(O)—R^{11}$, $—C(O)O—R^{10}$, $—(O—CH_2CH_2)_n—R^d$, $—(CH_2CH_2—O)_n—R^f$, $—(CH_2CH_2—O)_n—(CH_2CH_2)—R^d$, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^3$ is present and two of the groups $R^3$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ and $R^{11}$ are each independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted; and for each occurrence, n is 1 to 5, and wherein when the compound is detectably labeled, the detectable label is selected from $^2H$, $^3H$, $^{18}F$, $^{123}I$, $^{124}I$, $^{125}I$, $^{131}I$, $^{11}C$, $^{13}N$, $^{15}O$, and $^{77}Br$ or a fluorescent label.

2. The compound according to claim 1, which is a compound of the formula

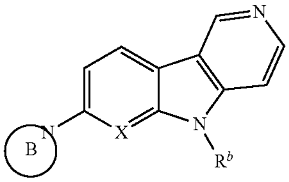

wherein B, X and $R^b$ are as defined in claim 1, and all detectably labeled derivatives, stereoisomers, racemic mixtures, pharmaceutically acceptable salts, hydrates, solvates and polymorphs thereof.

3. The compound according to claim 1, wherein for each occurrence, $R^3$ is independently selected from the group consisting of halogen, $—O—R^{10}$, $—NR^{10}R^{11}$, $—(O—CH_2CH_2)_n—R^d$, $—(CH_2CH_2—O)_n—R^f$, $—(CH_2CH_2—O)_n—(CH_2CH_2)—R^d$, and alkyl, wherein alkyl can be optionally substituted, and wherein $R^{10}$, $R^{11}$, n, $R^d$ and $R^f$ are as defined in claim 1; or wherein two groups adjacent $R^3$ are present which form a 5-membered ring containing carbon atoms and optionally one or more heteroatoms selected from O, S, or N or optionally one or more heteroatom (e.g., N, O and/or S)-containing moieties and wherein the 5-membered ring may be substituted.

4. The compound according to claim 1 which is detectably labeled.

5. The compound according to claim 4, wherein the detectable label is selected from the group consisting of $^2H$, $^3H$, or $^{18}F$.

6. The compound according to claim 5 wherein the detectable label is $^{18}F$.

7. A method of imaging amyloid and/or amyloid-like protein aggregates, wherein the method comprises the step of administering a compound according to claim 5 to a patient in need thereof.

8. A method of diagnosing a disorder associated with amyloid and/or amyloid-like protein aggregates, particularly wherein the amyloid-like protein is selected from the group consisting of tau, Abeta, alpha-synuclein, Huntingtin, prion, ATTR (transthyretin) or ADan (ADanPP), more preferably tau, wherein the method comprises the step of administering a compound according to claim 5 to a patient in need thereof.

9. The method according to claim 8, wherein the disorder is a neurological disorder.

10. The method according to claim 8, wherein the disorder is selected from the group consisting of Alzheimer' s disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, tau panencephalopathy, AD-like with astrocytes, certain prion diseases (GS S with tau), mutations in LRRK2, Hallervorden-Spatz disease, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy.

11. A compound which is detectably labeled with $^{18}F$ and which is selected from

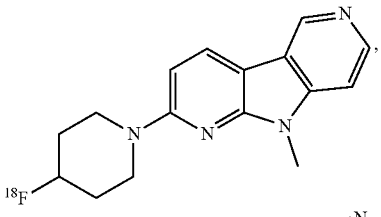
,

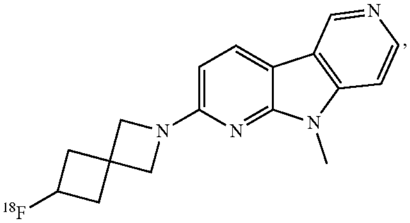
,

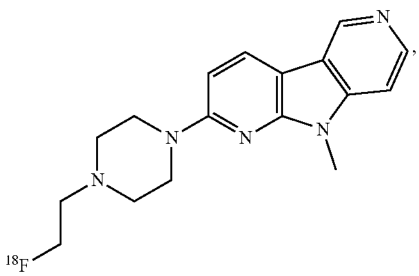
,

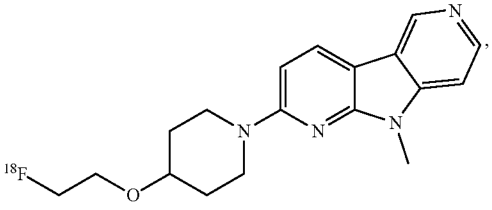
,

-continued

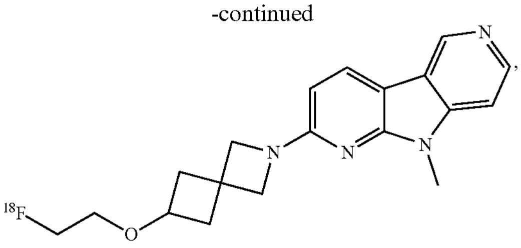
,

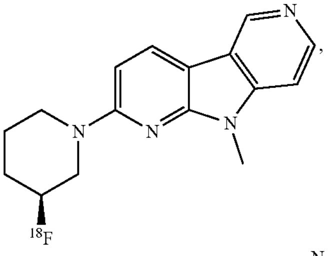
,

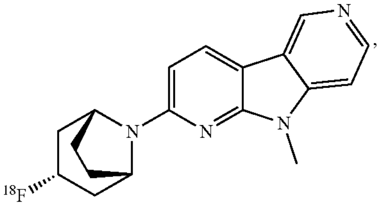
,

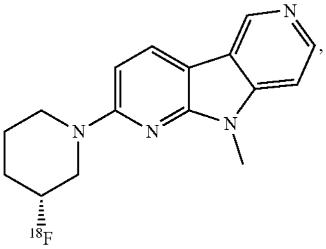
,

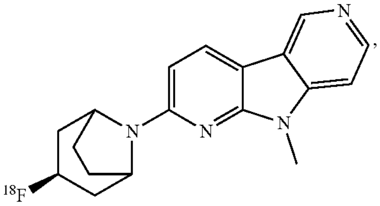
,

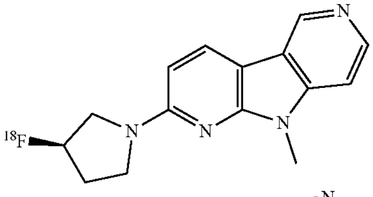
,

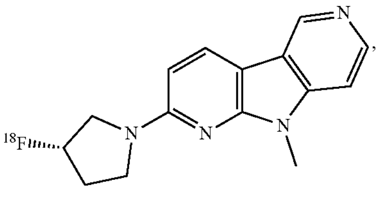
, and

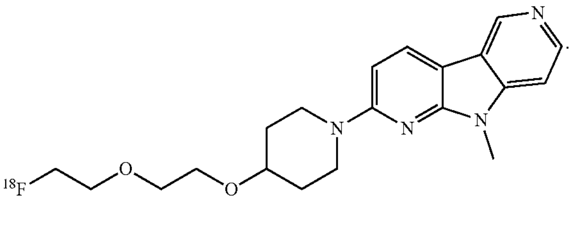
.

12. A method of imaging amyloid and/or amyloid-like protein aggregates, wherein the method comprises the step of administering a compound according to claim 6 to a patient in need thereof.

13. The method of claim 7, wherein the imaging amyloid and/or amyloid-like protein aggregates is in the brain or in the eye.

14. The method of claim 12, wherein the imaging amyloid and/or amyloid-like protein aggregates is in the brain or in the eye.

* * * * *